US010370715B2

(12) United States Patent
Staudt et al.

(10) Patent No.: US 10,370,715 B2
(45) Date of Patent: Aug. 6, 2019

(54) METHODS FOR IDENTIFYING, DIAGNOSING, AND PREDICTING SURVIVAL OF LYMPHOMAS

(71) Applicant: The United States of America, as represented by the Secretary, Department of Health and Human Services, Washington, DC (US)

(72) Inventors: Louis M. Staudt, Bethesda, MD (US); George W. Wright, Rockville, MD (US); Sandeep Dave, Chapel Hill, NC (US); Bruce K. Tan, Chicago, IL (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 783 days.

(21) Appl. No.: 14/570,316

(22) Filed: Dec. 15, 2014

(65) Prior Publication Data

US 2015/0167088 A1  Jun. 18, 2015

Related U.S. Application Data

(60) Continuation of application No. 13/008,403, filed on Jan. 18, 2011, now abandoned, which is a continuation-in-part of application No. 12/592,778, filed on Dec. 2, 2009, now abandoned, which is a division of application No. 10/934,930, filed on Sep. 3, 2004, now Pat. No. 7,711,492.

(60) Provisional application No. 60/500,377, filed on Sep. 3, 2003.

(51) Int. Cl.
| | | |
|---|---|---|
| G01N 33/48 | (2006.01) | |
| G01N 33/00 | (2006.01) | |
| C12Q 1/6883 | (2018.01) | |
| C12Q 1/6886 | (2018.01) | |
| G01N 33/574 | (2006.01) | |

(52) U.S. Cl.
CPC ......... *C12Q 1/6883* (2013.01); *C12Q 1/6886* (2013.01); *G01N 33/57407* (2013.01); *C12Q 2600/112* (2013.01); *C12Q 2600/118* (2013.01); *C12Q 2600/158* (2013.01); *G01N 2800/60* (2013.01)

(58) Field of Classification Search
None
See application file for complete search history.

(56) References Cited

U.S. PATENT DOCUMENTS

| 2004/0152651 A1* | 8/2004 | Rana ................... C12N 15/113 514/44 A |
| 2005/0112630 A1 | 5/2005 | Shaughnessy et al. |
| 2007/0072178 A1* | 3/2007 | Haferlach ............ C12Q 1/6886 435/6.16 |
| 2007/0248659 A1* | 10/2007 | Shanahan .......... A61K 31/7105 424/450 |

FOREIGN PATENT DOCUMENTS

| WO | WO 02/024956 A2 | 3/2002 |
| WO | WO 03/021229 A2 | 3/2003 |

OTHER PUBLICATIONS

U.S. Appl. No. 13/008,403, filed Jan. 18, 2011.
U.S. Appl. No. 10/934,930, filed Sep. 3, 2004.
Alizadeh et al., "The lymphochip: a specialized cDNA microarray for the genomic-scale analysis of gene expression in normal and malignant lymphocytes," *Cold Spring Harbor Symp. Quant. Biol.*, 64, 71-78 (1999).
Alizadeh et al., "Distinct types of diffuse large B-cell lymphoma identified by gene expression profiling," *Nature*, 403 (6769), 503-511 (Feb. 2000).
Alon et al., "Broad patterns of gene expression revealed by clustering analysis of tumor and normal colon tissues probed by oligonucleotide arrays," *Proc. Natl. Acad. Sci. USA*, 96 (12) 6745-6750 (1999).
Ando et al., "Fuzzy neural network applied to gene expression profiling for predicting the prognosis of diffuse large B-cell lymphoma," *Jpn. J. Cancer Res.*, 93 (11), 1207-1212 (Nov. 2002).
Andreasson et al., "Genomic amplification of CCND2 is rare in non-Hodgkin lymphomas," *Cancer Genet. Cytogenet.*, 102 (1), 81-82 (1998).
Basso et al., "Tracking CD40 signaling during germinal center development," *Blood*, 104 (13), 4088-4096 (2004).
Bea et al., "Diffuse large B-cell lymphoma subgroups have distinct genetic profiles that influence tumor biology and improve gene-expression-based survival prediction," *Blood*, 106 (9), 3183-3190 (Nov. 1, 2005).

(Continued)

*Primary Examiner* — Anna Skibinsky
(74) *Attorney, Agent, or Firm* — Leydig, Voit & Mayer, Ltd.

(57) ABSTRACT

The invention provides methods for identifying, diagnosing, and predicting survival in a lymphoma or lymphoproliferative disorder on the basis of gene expression patterns. The invention provides a microarray for obtaining gene expression data from a lymphoma sample. The invention also provides a variety of methods for utilizing lymphoma gene expression data to determine the identity of a particular lymphoma and to predict survival in a subject diagnosed with a particular lymphoma, which is useful in developing an appropriate therapeutic approach.

5 Claims, 28 Drawing Sheets

(56) References Cited

OTHER PUBLICATIONS

Bea et al., "Increased number of chromosomal imbalances and high-level DNA amplifications in mantle cell lymphoma are associated with blastoid variants," *Blood*, 93 (12), 4365-4374 (1999).
Bea et al., "Clinicopathologic significance and prognostic value of chromosomal imbalances in diffuse large B-cell lymphomas," *J. Clin. Oncol.*, 22 (17), 3498-3506 (2004).
Berglund et al., "Chromosomal imbalances in diffuse large B-cell lymphoma detected by comparative genomic hybridization," *Mod. Pathol.*, 15 (8), 807-816 (2002).
Bergsagel et al., "Critical roles for immunoglobulin translocations and cyclin D dysregulation in multiple myeloma," *Immunol. Rev.*, 194, 96-104 (2003).
Bishop et al., "Burkitt's lymphoma: molecular pathogenesis and treatment," *Cancer Invest.*, 18 (6), 574-583 (2000).
Boxer et al., "Translocations involving c-myc and c-myc function," *Oncogene*, 20 (40), 5595-5610 (2001).
Chiarle et al., "Increased proteasome degradation of cyclin-dependent kinase inhibitor p27 is associated with a decreased overall survival in mantle cell lymphoma," *Blood*, 95 (2), 619-626 (2000).
Cigudosa et al., "Cytogenetic analysis of 363 consecutively ascertained diffuse large B-cell lymphomas," *Genes Chromosomes Cancer*, 25 (2), 123-133 (1999).
Copie-Bergman et al., "Interleukin 4-induced gene 1 is activated in primary mediastinal large B-cell lymphoma," *Blood*, 101 (7), 2756-2761 (2003).
Copie-Bergman et al., "MAL expression in lymphoid cells: further evidence for MAL as a distinct molecular marker of primary mediastinal large B-cell lymphomas," *Mod. Pathol.*, 15 (11), 1172-1180 (2002).
Dave et al., "Cytogenetic characterization of diffuse large cell lymphoma using multi-color fluorescence in situ hybridization," *Cancer Genet. Cytogenet.*, 132 (2), 125-132 (2002).
Dave et al., "Molecular diagnosis of Burkitt's lymphoma," *N. Engl. J. Med.*, 354 (23), 2431-2442 (Jun. 8, 2006).
Delmer et al., "Overexpression of cyclin D2 in chronic B-cell malignancies," *Blood*, 85 (10), 2870-2876 (1995).
Derisi et at., "Use of a cDNA microarray to analyse gene expression patterns in human cancer," *Nat. Genet.*, 14 (4), 457-460 (1996).
Doglioni et al., "Cyclin D3 expression in normal, reactive and neoplastic tissues," *J. Pathol.*, 185 (2), 159-166 (1998).
Dudoit et al., "Comparison of Discrimination Methods for the Classification of Tumors Using Gene Expression Data," *J. Am. Stat. Assoc.*, 97 (457), 77-87 (2002).
Dybkaer et al., "Molecular diagnosis and outcome prediction in diffuse large B-cell lymphoma and other subtypes of lymphoma," *Clinical Lymphoma*, 5 (1), 19-28 (Jun. 2004).
Eisen et al., "Cluster analysis and display of genome-wide expression patterns," *Proc. Natl. Acad. Ci. USA*, 95 (25), 14863-14868 (Dec. 1998).
EP 09170243.1 Partial European Search Report dated Jun. 24, 2010.
European Patent Office, European Search Report in European Patent Application No. 10014565.5 (dated Feb. 16, 2011).
European Patent Office, European Search Report in European Patent Application No. 09170243.1 (dated Nov. 10, 2010).
European Patent Office, Supplementary European Search Report in European Patent Application No. 04783330.6 (dated Jul. 10, 2008).
Feuerhake et al., "NFkappaB activity, function, and target-gene signatures in primary mediastinal large B-cell lymphoma and diffuse large B-cell lymphoma subtypes," *Blood*, 106 (4) 1392-1399 (2005).
Fu et al., "Cyclin D1-negative mantle cell lymphoma: a clinicopathologic study based on gene expression profiling," *Blood*, 106 (13), 4315-4321 (Dec. 15, 2005).
Gerbitz et al., "Deregulation of the proto-oncogene c-myc through t(8;22) translocation in Burkitt's lymphoma," *Oncogene*, 18 (19), 1745-1753 (1999).

Goff et al., "The use of real-time quantitative polymerase chain reaction and comparative genomic hybridization to identify amplification of the REL gene in follicular lymphoma," *Br. J. Haematol.*, 111 (2), 618-625 (2000).
Golub et al., "Molecular classification of cancer: class discovery and class prediction by gene expression monitoring," *Science*, 286 (5439), 531-537 (1999).
Gress et al., "A pancreatic cancer-specific expression profile," *Oncogene*, 13 (8), 1819-1830 (1996).
Haralambieva et al., "Clinical, immunophenotypic, and genetic analysis of adult lymphomas with morphologic features of Burkitt lymphoma," *Am. J. Surg. Pathol.*, 29 (8), 1086-1094 (2005).
Harpole et al., A Prognostic Model of Recurrence and Death in Stage 1 Non-Small Cell Lung Cancer Utilizing Presentation, Histopathology, and Oncoprotein Expression, *Cancer Research*, 55, 51-56 (1995).
Huang et al., "The t(14;18) defines a unique subset of diffuse large B-cell lymphoma with a germinal center B-cell gene expression profile," *Blood*, 99 (7), 2285-2290 (2002).
Hummel et al., "A biologic definition of Burkitt's lymphoma from transcriptional and genomic profiling," *N. Engl. J. Med.*, 354 (23), 2419-2430 (Jun. 2006).
Huvalé, "The gene for human thioredoxin maps on the short arm of chromosome 3 at bands 3p11-p12," *FEBS Letters*, 255 (1), 89-91 (Sep. 1989).
Hyman et al., "Impact of DNA amplification on gene expression patterns in breast cancer," *Cancer Res.*, 62 (21), 6240-6245 (2002).
Iqbal et al., "BCL2 translocation defines a unique tumor subset within the germinal center B-cell-like diffuse large B-cell lymphoma," *Am. J. Pathol.*, 165 (1), 159-166 (2004).
Jares et al., "Expression of retinoblastoma gene product (pRb) in mantle cell lymphomas. Correlation with cyclin D1 (PRAD1/CCND1) mRNA levels and proliferative activity," *Am. J. Pathol.*, 148 (5), 1591-1600 (1996).
Khan et al., "Classification and diagnostic prediction of cancers using gene expression profiling and artificial neural networks," *Nature Medicine*, 7 (6), 673-679 (Jun. 2001).
Kovacs, "Consistent chromosome 3p deletion and loss of heterozygosity in renal cell carcinoma," *Proc. Natl. Acad. Sci., USA*, 85, 1571-1573 (Mar. 1988).
Kramer et al., "Clinical relevance of BCL2, BCL6, and MYC rearrangements in diffuse large B-cell lymphoma," *Blood*, 92 (9), 3152-3162 (1998).
Li, "Survival prediction of diffuse large-B-cell lymphoma based on both clinical and gene expression information," *Bioinformatics*, 22 (4), 466-471 (2006).
Martinez et al., "The Molecular Signature of Mantle Cell Lymphoma Reveals Multiple Signals Favoring Cell Survival," *Cancer Research*, 63, 6226-8232 (2003).
Monni et al., "DNA copy number changes in diffuse large B-cell lymphoma—comparative genomic hybridization study," *Blood*, 87 (12), 5269-5278 (1996).
Neri et al., "Different regions of the immunoglobulin heavy-chain locus are involved in chromosomal translocations in distinct pathogenetic forms of Burkitt lymphoma," *Proc. Natl. Acad. Sci. USA*, 85 (8), 2748-2752 (1988).
Orsetti et al., "Genomic and expression profiling of chromosome 17 in breast cancer reveals complex patterns of alterations and novel candidate genes," *Cancer Res.*, 64 (8), 6453-6460 (2004).
Ott et al., "Cyclin D1 expression in mantle cell lymphoma is accompanied by downregulation of cyclin D3 and is not related to the proliferative activity," *Blood*, 90 (8), 3154-3159 (1997).
Pruneri et al., "Immunoreactivity for cyclin D3 is frequently detectable in high-grade primary gastric lymphomas in the absence of the t(6;14)(p21.1;q32.3) chromosomal translocation," *J. Pathol.*, 200 (5), 596-601 (2003).
Quintanilla-Martinez et al., "Mantle cell lymphomas lack expression of p27Kip1, a cyclin-dependent kinase inhibitor," *Am. J. Pathol.*, 153 (1), 175-182 (1998).
Radmacher et al., "A Paradigm for Class Prediction Using Gene Expression Profiles," *J. Comput. Biol.*, 9 (3), 505-511 (2002).
Ramaswamy et al., "Multiclass cancer diagnosis using tumor gene expression signatures," *Proc. Natl. Acad Sci. USA*, 98 (26), 15149-15154 (2001).

(56) References Cited

OTHER PUBLICATIONS

Ransohoff, "Rules of evidence for cancer molecular-marker discovery and validation," *Nat. Rev. Cancer*, 4 (4), 309-314 (2004).

Rao et al., "Chromosomal and gene amplification in diffuse large B-cell lymphoma," *Blood*, 92 (1), 234-240 (1998).

Rosenwald et al., "Gene Expression Profiling of Diffuse Large B-Cell Lymphoma," *Leukemia & Lymphoma*, 44 (Supp. 3), S41-S47 (2003).

Rosenwald et al., "The proliferation gene expression signature is a quantitative integrator of oncogenic events that predicts survival in mantle cell lymphoma," *Cancer Cell*, 3 (2), 185-197 (2003).

Rosenwald et al., "Molecular diagnosis of primary mediastinal B cell lymphoma identifies a clinically favorable subgroup of diffuse large B cell lymphoma related to Hodgkin lymphoma," *J. Exp. Med.*, 198 (6), 851-862 (2003).

Rosenwald et al., "The use of molecular profiling to predict survival after chemotherapy for diffuse large-B-cell lymphoma," *New Engl. J. Med.*, 346 (25), 1937-1947 (2002).

Savage et al., "The molecular signature of mediastinal large B-cell lymphoma differs from that of other diffuse large B-cell lymphomas and shares features with classical Hodgkin lymphoma," *Blood*, 102 (12), 3871-3879 (2003).

Shipp et al., "Diffuse large B-cell lymphoma outcome prediction by gene-expression profiling and supervised machine learning," *Nat. Med.*, 8 (1), 68-74 (Jan. 2002).

Sonoki et al., "Cyclin D3 is a target gene of t(6;14)(p21.1;q32.3) of mature B-cell malignancies," *Blood*, 98 (9), 2837-2844 (2001).

Supplementary European Search Report, European Patent Office, dated Jul. 10, 2018.

Tibshirani et al., "Diagnosis of multiple cancer types by shrunken centroids of gene expression," *Proc. Natl. Acad. Sci. USA*, 99 (10), 6567-6572 (2002).

Wright et al., "A gene expression-based method to diagnose clinically distinct subgroups of diffuse large B cell lymphoma," *Proc. Natl. Acad. Sci. USA*, 100 (17), 9991-9996 (2003).

Wuthrich et al., "MHC class II, antigen presentation and tumor necrosis factor in renal tubular epithelial cells," *Kidney International*, 37, 783-792 (1990).

Yatabe et al., "Significance of cyclin D1 overexpression for the diagnosis of mantle cell lymphoma: a clinicopathologic comparison of cyclin D1-positive MCL and cyclin D1-negative MCL-like B-cell lymphoma," *Blood*, 95 (7), 2253-2261 (2000).

Ye et al., "Variable frequencies of t(11;18)(q21;q21) in MALT lymphomas of different sites: significant association with CagA strains of H pylori in gastric MALT lymphoma," *Blood*, 102 (3), 1012-1018 (2003).

Zeller et al., "An integrated database of genes responsive to the Myc oncogenic transcription factor: identification of direct genomic targets," *Genome Biol.*, 4 (10), R69 (2003).

\* cited by examiner

Figure 16

| Lymphoma Subtype | Model Prediction | | | | | |
|---|---|---|---|---|---|---|
| | ABC | MCL | GCB | MCL | SLL | MCL |
| ABC | 42 | 0 | | | | |
| MCL | 0 | 46 | | | | |
| GCB | | | 67 | 0 | | |
| MCL | | | 0 | 46 | | |
| SLL | | | | | 11 | 0 |
| MCL | | | | | 0 | 46 |

Training Set

| | ABC | MCL | GCB | MCL | SLL | MCL |
|---|---|---|---|---|---|---|
| ABC | 41 | 1 | | | | |
| MCL | 0 | 45 | | | | |
| GCB | | | 66 | 0 | | |
| MCL | | | 0 | 46 | | |
| SLL | | | | | 11 | 0 |
| MCL | | | | | 0 | 46 |

Validation Set

MCL vs. ABC Model | MCL vs. GCB Model | MCL vs. SLL Model

Figure 18

DLBCL Subgroup by Hierarchical Clustering

Training Set

|  | Model Prediction | | |
|---|---|---|---|
|  | ABC | GCB | Other |
| ABC | 37 | 1 | 4 |
| GCB | 1 | 58 | 8 |

Validation Set

|  | ABC | GCB | Other |
|---|---|---|---|
| ABC | 38 | 1 | 2 |
| GCB | 2 | 57 | 8 |
| Type 3 | 14 | 18 | 25 |

All Samples

|  | ABC | GCB | Other |
|---|---|---|---|
| ABC | 75 | 2 | 6 |
| GCB | 3 | 115 | 16 |
| Type 3 | 14 | 18 | 25 |

METHODS FOR IDENTIFYING, DIAGNOSING, AND PREDICTING SURVIVAL OF LYMPHOMAS

CROSS-REFERENCE TO RELATED APPLICATIONS

This patent application is a continuation of copending U.S. patent application Ser. No. 13/008,403, filed Jan. 18, 2011, which is a continuation-in-part of U.S. patent application Ser. No. 12/592,778, filed Dec. 2, 2009, now abandoned, which is a divisional of U.S. patent application Ser. No. 10/934,930, filed Sep. 3, 2004, issued as U.S. Pat. No. 7,711,492, which claims the benefit of U.S. Provisional Patent Application No. 60/500,377, filed Sep. 3, 2003, which are incorporated by reference in their entirety herein.

STATEMENT REGARDING FEDERALLY SPONSORED RESEARCH AND DEVELOPMENT

This invention was made with Government support under project number Z1A BC 011006 by the National Institutes of Health, National Cancer Institute. The Government has certain rights in the invention.

REFERENCE TO TABLES AND COMPUTER PROGRAM LISTING APPENDIX PREVIOUSLY SUBMITTED ON COMPACT DISC

Tables 2-1723 and 1725-2358 are contained on 21 CD-ROMs submitted with U.S. patent application Ser. No. 10/934,930, now issued as U.S. Pat. No. 7,711,492, and U.S. patent application Ser. No. 12/592,778, filed Dec. 2, 2009. These CD-ROMs are numbered 1-21 of 22. The name, size, and date of creation for each file is presented in the file entitled "Tableofcontents.txt," located on CD number 21 of 22. The name of each file incorporates the number of the corresponding table. Any reference to a table or file should be considered an incorporation by reference of the contents of the table and/or file at that particular place in the specification.

A computer program listing appendix is contained on one CD-ROM numbered 22 of 22 submitted with U.S. patent application Ser. No. 10/934,930, now issued U.S. as U.S. Pat. No. 7,711,492, and U.S. patent application Ser. No. 12/592,778, filed Dec. 2, 2009. The computer program listing appendix contains files related to the implementation of an algorithm for determining lymphoma type. The name, size, and date of creation for each file in the computer program listing appendix is presented in the file entitled "Table_of_contents.txt," located on CD-ROM 22. Any reference to a file contained in the computer program listing appendix should be considered an incorporation by reference of the contents of that file at that particular place in the specification.

BACKGROUND OF INVENTION

A variety of systems for identifying and classifying lymphomas have been proposed over the last 20 years. In the 1980's, the Working Formulation was introduced as a method of classifying lymphomas based on morphological and clinical characteristics. In the 1990's, the Revised European-American Lymphoma (REAL) system was introduced in an attempt to take into account immunophenotypic and genetic characteristics in classifying lymphomas (Harris 1994). The most recent standard, set forth by the World Health Organization (WHO), attempts to build on these previous systems (Jaffe 2001). The WHO classification of lymphomas is based on several factors, including tumor morphology, immunophenotype, recurrent genetic abnormalities, and clinical features. Table 1, below, contains a list of the B and T cell neoplasms that have been recognized by the WHO classification. Each malignancy is listed according to its WHO classification nomenclature, followed by a WHO classification number.

TABLE 1

| Category | Name | WHO ID # |
|---|---|---|
| B-cell neoplasms | | |
| Precursor B-cell neoplasms | Precursor B-cell lymphoblastic leukemia | 9835/3 |
| | Precursor B-cell lymphoblastic lymphoma | 9728/3 |
| Mature B-cell neoplasms | Chronic lymphocytic leukemia | 9823/3 |
| | Small lymphocytic lymphoma | 9670/3 |
| | B-cell prolymphocytic leukemia | 9833/3 |
| | Lymphoplasmacytic lymphoma | 9671/3 |
| | Splenic marginal zone lymphoma | 9689/3 |
| | Hairy cell leukemia | 9940/3 |
| | Plasma cell myeloma | 9732/3 |
| | Solitary plasmacytoma of bone | 9731/3 |
| | Extraosseous plasmacytoma | 9734/3 |
| | Extranodal marginal zone B-cell lymphoma of mucosa-associated lymphoid tissue (MALT lymphoma) | 9699/3 |
| | Nodal marginal zone B-cell lymphoma | 9699/3 |
| | Follicular lymphoma (Grade 1, 2, 3a, 3b) | 9690/3 |
| | Mantle cell lymphoma | 9673/3 |
| | Diffuse large B-cell lymphoma | 9680/3 |
| | Mediastinal (thymic) large B-cell lymphoma | 9679/3 |
| | Intravascular large B-cell lymphoma | 9680/3 |
| | Primary effusion lymphoma | 9678/3 |
| | Burkitt lymphoma | 9687/3 |
| | Burkitt leukemia | 9826/3 |
| B-cell proliferations of uncertain malignant potential | Lymphomatoid granulomatosis | 9766/1 |
| | Post-transplant lymphoproliferative disorder, polymorphic | 9970/1 |
| T-cell and NK-cell neoplasms | | |
| Precursor T-cell and NK-cell neoplasms | Precursor T lymphoblastic leukemia | 9837/3 |
| | Precursor T lymphoblastic lymphoma | 9729/3 |
| | Blastic NK-cell lymphoma | 9727/3 |
| Mature T-cell and NK-cell neoplasms | T-cell prolymphocytic leukemia | 9834/3 |
| | T-cell large granular lymphocytic leukemia | 9831/3 |
| | Aggressive NK-cell leukemia | 9948/3 |
| | Adult T-cell leukemia/lymphoma | 9827/3 |
| | Extranodal NK-/T-cell lymphoma, nasal type | 9719/3 |
| | Enteropathy-type T-cell lymphoma | 9717/3 |
| | Hepatosplenic T-cell lymphoma | 9716/3 |
| | Subcutaneous panniculitis-like T-cell lymphoma | 9708/3 |
| | Mycosis fungoides | 9700/3 |
| | Sezary syndrome (9701/3) | 9701/3 |
| | Primary cutaneous anaplastic large cell lymphoma (C-ALCL) | 9718/3 |
| | Peripheral T-cell lymphoma, unspecified | 9702/3 |
| | Angioimmunoblastic T-cell lymphoma | 9705/3 |
| | Anaplastic large cell lymphoma | 9714/3 |

TABLE 1-continued

| Category | Name | WHO ID # |
|---|---|---|
| T-cell proliferation of uncertain malignant potential | Lymphomatoid papulosis | 9718/3 |
| Hodgkin lymphoma | Nodular lymphocyte predominant Hodgkin lymphoma | 9659/3 |
| | Classical Hodgkin lymphoma | 9650/3 |
| | Classical Hodgkin lymphoma, nodular sclerosis | 9663/3 |
| | Classical Hodgkin lymphoma, lymphocyte-rich | 9651/3 |
| | Classical Hodgkin lymphoma, mixed cellularity | 9652/3 |
| | Classical Hodgkin lymphoma, lymphocyte depleted | 9653/3 |

Other diagnoses that have not been given WHO diagnostic numbers include HIV-associated lymphoma, germinal center B cell-like subtype of diffuse large B cell lymphoma, activated B cell-like subtype of diffuse large B-cell lymphoma, follicular hyperplasia (non-malignant), and infectious mononucleosis (non-malignant).

Although the WHO classification has proven useful in patient management and treatment, patients assigned to the same WHO diagnostic category often have noticeably different clinical outcomes. In many cases, these different outcomes appear to be due to molecular differences between tumors that cannot be readily observed by analyzing tumor morphology. More precise methods are needed for identifying and classifying lymphomas based on their molecular characteristics.

SUMMARY OF THE INVENTION

Accurate identification of lymphoma type or subtype in a subject suffering from a lymphoproliferative disorder is important for developing an appropriate therapeutic strategy. Previous attempts have been made to identify lymphomas using gene expression data obtained using a microarray. However, there is a need in the art for more accurate and predictive methods of analyzing this gene expression data. In addition, there is a need for more specific and efficient methods of obtaining gene expression data.

The present invention discloses a novel microarray for obtaining gene expression data to be used in identifying lymphoma types and predicting survival in a subject. The present invention further discloses a variety of methods for analyzing gene expression data obtained from a lymphoma sample, and specific algorithms for predicting survival and clinical outcome in a subject suffering from a lymphoma.

One embodiment of the present invention provides a composition comprising the set of probes listed in Table 2, which is set forth below and contained in the file entitled "Tableb.-0002_LymphDx_Probe_List.txt." Preferably, this composition comprises a microarray.

In another embodiment, the present invention provides a method of generating a survival predictor for a particular lymphoma type. In this method, one or more biopsy samples that have been diagnosed as belonging to a particular lymphoma type are obtained. Gene expression data is obtained for these samples, and genes with expression patterns associated with longer or shorter survival are identified. Hierarchical clustering is performed to group these genes into gene expression signatures, and the expression of all genes within each signature are averaged to obtain a gene expression signature value for each signature. These gene expression signature values are then used to generate a multivariate survival predictor.

In another embodiment, the present invention provides a method for predicting survival in a follicular lymphoma (FL) subject. In this method, a biopsy sample is obtained from the subject and gene expression data is obtained from the biopsy sample. The expression level of those genes belonging to an immune response-1 or immune response-2 gene expression signature are averaged to generate gene expression signature values for each signature. A survival predictor score is then calculated using an equation: [2.71*(immune response-2 gene expression signature value)]−[2.36*(immune response-1 gene expression signature value)]. A higher survival predictor score is associated with a less favorable outcome. In one embodiment, the gene expression data used in this method is obtained using a microarray.

In another embodiment, the present invention provides another method for predicting survival in a follicular lymphoma (FL) subject. In this method, a biopsy sample is obtained from the subject and gene expression data is obtained from the biopsy sample. The expression level of those genes belonging to a B cell differentiation, T-cell, or macrophage gene expression signature are averaged to generate gene expression signature values for each signature. A survival predictor score is then calculated using an equation: [2.053*(macrophage gene expression signature value)]−[2.344*(T-cell gene expression signature value)]−[0.729*(B-cell gene expression signature value)]. A higher survival predictor score is associated with a less favorable outcome. In one embodiment, the gene expression data used in this method is obtained using a microarray.

In another embodiment, the present invention provides yet another method for predicting survival in a follicular lymphoma (FL) subject. In this method, a biopsy sample is obtained from the subject and gene expression data is obtained from the biopsy sample. The expression level of those genes belonging to a macrophage, T-cell, or B-cell differentiation gene expression signature are averaged to generate gene expression signature values for each signature. A survival predictor score is then calculated using an equation: [1.51*(macrophage gene expression signature value)]−[2.11*(T-cell gene expression signature value)]−[0.505*(B-cell differentiation gene expression signature value)]. A higher survival predictor score is associated with a less favorable outcome. In one embodiment, the gene expression data used in this method is obtained using a microarray.

In another embodiment, the present invention provides a method for predicting survival in a diffuse large B cell lymphoma (DLBCL) subject. In this method, a biopsy sample is obtained from the subject and gene expression data is obtained from the biopsy sample. The expression level of those genes belonging to an ABC DLBCL high, lymph node, or MHC class II gene expression signature are averaged to generate gene expression signature values for each signature. A survival predictor score is then calculated using an equation: [0.586*(ABC DLBCL high gene expression signature value)]−[0.468*(lymph node gene expression signature value)]−[0.336*(MHC class II gene expression signature value)]. A higher survival predictor score is associated with a less favorable outcome. In one embodiment, the gene expression data used in this method is obtained using a microarray.

In another embodiment, the present invention provides another method for predicting survival in a diffuse large B cell lymphoma (DLBCL) subject. In this method, a biopsy sample is obtained from the subject and gene expression data is obtained from the biopsy sample. The expression level of those genes belonging to a lymph node, germinal B cell, proliferation, or MHC class II gene expression signature are averaged to generate gene expression signature values for each signature. A survival predictor score is then calculated using an equation: [−0.4337*(lymph node gene expression signature)]+[0.09*(proliferation gene expression signature)]−[0.4144*(germinal center B-cell gene expression signature)]−[0.2006*(MHC class II gene expression signature)]. A higher survival predictor score is associated with a less favorable outcome. In one embodiment, the gene expression data used in this method is obtained using a microarray.

In another embodiment, the present invention provides yet another method for predicting survival in a diffuse large B cell lymphoma (DLBCL) subject. In this method, a biopsy sample is obtained from the subject and gene expression data is obtained from the biopsy sample. The expression level of those genes belonging to a lymph node, germinal B cell, or MHC class II gene expression signature are averaged to generate gene expression signature values for each signature. A survival predictor score is then calculated using an equation: [−0.32*(lymph node gene expression signature)]−[0.176*(germinal B cell gene expression signature)]−[0.206*(MHC class II gene expression signature)]. A higher survival predictor score is associated with a less favorable outcome. In one embodiment, the gene expression data used in this method is obtained using a microarray. In another embodiment, the gene expression data is obtained using RT-PCR.

In another embodiment, the present invention provides a method for predicting survival in a mantle cell lymphoma (MCL) subject. In this method, a biopsy sample is obtained from the subject and gene expression data is obtained from the biopsy sample. The expression level of those genes belonging to a proliferation gene expression signature are averaged to generate a gene expression signature value. A survival predictor score is then calculated using an equation: [1.66*(proliferation gene expression signature value)]. A higher survival predictor score is associated with a less favorable outcome. In one embodiment, the gene expression data used in this method is obtained using a microarray.

In another embodiment, the present invention provides a method for determining the probability that a sample X belongs to a first lymphoma type or a second lymphoma type. In this method, a set of genes is identified that is differentially expressed between the two lymphoma types in question, and a set of scale factors representing the difference in expression between the lymphoma types for each of these genes are calculated. A series of linear predictor scores are generated for samples belonging to either of the two lymphoma types based on expression of these genes. Gene expression data is then obtained for sample X, and a linear predictor score is calculated for this sample. The probability that sample X belongs to the first lymphoma type is calculated using an equation that incorporates the linear predictor score of sample X and the mean and variance of the linear predictor scores for the known samples of either lymphoma type.

In another embodiment, the present invention provides a method for determining the lymphoma type of a sample X In this method, a set of genes is identified that is differentially expressed between a first lymphoma type and a second lymphoma type, and a set of scale factors representing the difference in expression of each of these genes between the two lymphoma types are calculated. A series of linear predictor scores are generated for samples belonging to either of the two lymphoma types based on expression of these genes. Gene expression data is then obtained for sample X, and a linear predictor score is calculated for this sample. The probability that sample X belongs to the first lymphoma type is calculated using an equation that incorporates the linear predictor score of sample X and the mean and variance of the linear predictor scores for the known samples of either lymphoma type. This entire process is then repeated with various lymphoma types being substituted for the first lymphoma type, the second lymphoma type, or both.

In another embodiment, the present invention provides another method for determining the lymphoma type of a sample X. In this method, a series of lymphoma type pairs are created, with each pair consisting of a first lymphoma type and a second lymphoma type. For each type pair, gene expression data is obtained for a set of genes, and a series of scale factors representing the difference in expression of each of these genes between the two lymphoma types are calculated. A subset of z genes with the largest scale factors are identified, and a series of linear predictor scores are generated for samples belonging to either of the two lymphoma types. Linear predictor scores are calculated for anywhere from 1 to z of these genes. The number of genes from 1 to z that results in the largest difference in linear predictor scores between the two lymphoma types is selected, and gene expression data for these genes is obtained for sample X. A linear predictor score is generated for sample X, and the probability that the sample belongs to the first lymphoma type is calculated using an equation that incorporates the linear predictor score for sample X and the mean and variance of the linear predictor scores for the known samples of either lymphoma type.

In another embodiment, the present invention provides another method for determining the lymphoma type of a sample X. In this method, a series of lymphoma type pairs are created, with each pair consisting of a first lymphoma type and a second lymphoma type. For each type pair, gene expression data is obtained for a set of genes, and a series of scale factors representing the difference in expression of each of these genes between the two lymphoma types are calculated. The set of genes is divided into gene-list categories indicating correlation with a gene expression signature. Within each gene-list category, a subset of z genes with the largest scale factors are identified, and a series of linear predictor scores are generated for samples belonging to either of the two lymphoma types. Linear predictor scores are calculated for anywhere from 1 to z of these genes. The number of genes from 1 to z that results in the largest difference in linear predictor scores between the two lymphoma types is selected, and gene expression data for these genes is obtained for sample X. A linear predictor score is generated for sample X, and the probability q that the sample belongs to the first lymphoma type is calculated using an equation that incorporates the linear predictor score for sample X and the mean and variance of the linear predictor scores for the known samples of either lymphoma type. A high probability q indicates that sample X belongs to the first lymphoma type, a low probability q indicates that sample X belongs to the second lymphoma type, and a middle probability q indicates that sample X belongs to neither lymphoma type. The cut-off point between high, middle, and low probability values is determined by ranking samples of known lymphoma type according to their probability values, then analyzing every possible cut-off point between adjacent samples using the equation: 3.99*[(% of first lymphoma type misidentified as second lymphoma type)+(% of second lymphoma type misidentified as a first lymphoma type)]+[(% of first lymphoma type identified as belonging to neither lymphoma type)+(% of second lymphoma type identified as belonging to neither lymphoma type)]. The final cut-off points are those that minimize the value of this equation.

BRIEF DESCRIPTION OF THE DRAWINGS

FIG. 16: Performance of MCL predictor model. Results of the gene-expression based predictor model for MCL are shown for three models (MCL vs. ABC, MCL vs. GCB, MCL vs. SLL). Performance is shown for both the training set and the validation set.

FIG. 18: Performance of DLBCL subtype predictor model. Assignments of DLBCL samples to the ABC or GCB subtypes based on hierarchical clustering vs. the predictor model disclosed herein are compared within the training, validation, and total set of samples.

DETAILED DESCRIPTION

Figure 1:
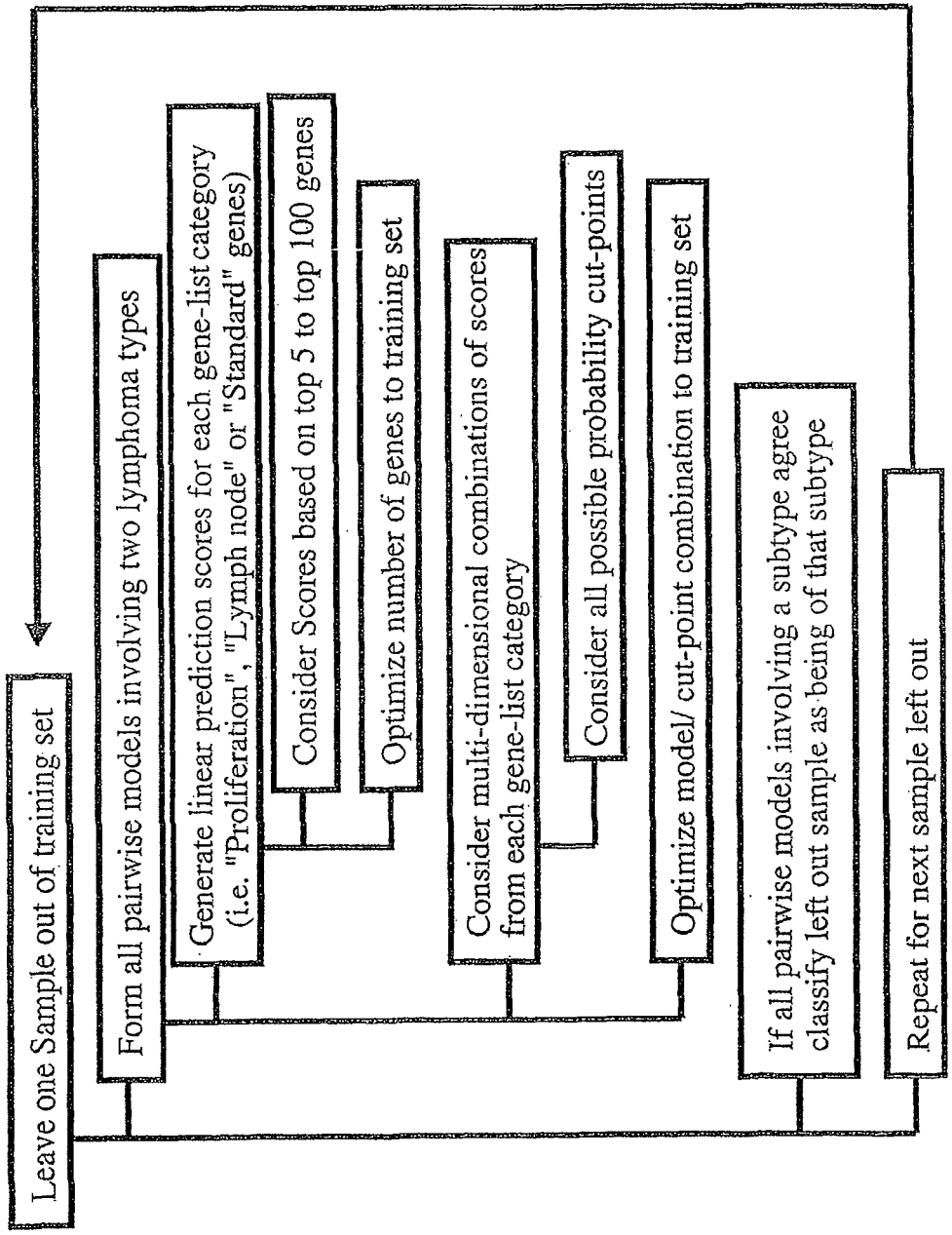
FIG. 1: Method for identifying lymphoma type. Flow chart depicts a general method for identifying lymphoma type using gene expression data.

The following description is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such embodiments are to be included herein.

Gene expression profiling of a cancer cell or biopsy reflects the molecular phenotype of a cancer at the time of diagnosis. As a consequence, the detailed picture provided by the genomic expression pattern provides the basis for a new systematic classification of cancers and more accurate predictors of survival and response to treatment. The present invention discloses methods for identifying, diagnosing, and/or classifying a lymphoma, lymphoid malignancy, or lymphoproliferative disorder based on its gene expression patterns. The present invention also discloses methods for predicting survival in a subject diagnosed with a particular lymphoma type or subtype using gene expression data. The information obtained using these methods will be useful in evaluating the optimal therapeutic approach to be employed with regards to a particular subject.

The term "lymphoproliferative disorder" as used herein refers to any tumor of lymphocytes, and may refer to both malignant and benign tumors. The terms "lymphoma" and "lymphoid malignancy" as used herein refer specifically to malignant tumors derived from lymphocytes and lymphoblasts. Examples of lymphomas include, but are not limited to, follicular lymphoma (FL), Burkitt lymphoma (BL), mantle cell lymphoma (MCL), follicular hyperplasia (FH), small cell lymphocytic lymphoma (SLL), mucosa-associated lymphoid tissue lymphoma (MALT), splenic lymphoma, multiple myeloma, lymphoplasmacytic lymphoma, post-transplant lymphoproliferative disorder (PTLD), lymphoblastic lymphoma, nodal marginal zone lymphoma (NMZ), germinal center B cell-like diffuse large B cell lymphoma (GCB), activated B cell-like diffuse large B cell lymphoma (ABC) and primary mediastinal B cell lymphoma (PMBL).

The phrase "lymphoma type" (or simply "type") as used herein refers to a diagnostic classification of a lymphoma. The phrase may refer to a broad lymphoma class (e.g., DLBCL, FL, MCL, etc.) or to a subtype or subgroup falling within a broad lymphoma class (e.g., GCB DLBCL, ABC DLBCL).

The phrase "gene expression data" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. "Gene expression data" may be acquired for an individual cell, or for a group of cells such as a tumor or biopsy sample.

The term "microarray," "array," or "chip" refers to a plurality of nucleic acid probes coupled to the surface of a substrate in different known locations. The substrate is preferably solid. Microarrays have been generally described in the art in, for example, U.S. Pat. No. 5,143,854 (Pirrung), U.S. Pat. No. 5,424,186 (Fodor), U.S. Pat. No. 5,445,934

(Fodor), U.S. Pat. No. 5,677,195 (Winkler), U.S. Pat. No. 5,744,305 (Fodor), U.S. Pat. No. 5,800,992 (Fodor), U.S. Pat. No. 6,040,193 (Winkler), and Fodor et al. 1991. Light-directed, spatially addressable parallel chemical synthesis. Science, 251:767-777. Each of these references is incorporated by reference herein in their entirety.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer (Shaffer 2001). Examples of gene expression signatures include lymph node (Shaffer 2001), proliferation (Rosenwald 2002), MHC class II, ABC DLBCL high, B-cell differentiation, T-cell, macrophage, immune response-1, immune response-2, and germinal center B cell.

The phrase "survival predictor score" as used herein refers to a score generated by a multivariate model used to predict survival based on gene expression. A subject with a higher survival predictor score is predicted to have poorer survival than a subject with a lower survival predictor score.

The term "survival" as used herein may refer to the probability or likelihood of a subject surviving for a particular period of time. Alternatively, it may refer to the likely term of survival for a subject, such as expected mean or median survival time for a subject with a particular gene expression pattern.

The phrase "linear predictor score" or "LPS" as used herein refers to a score that denotes the probability that a sample belongs to a particular lymphoma type. An LPS may be calculated using an equation such as:

$$LPS(S) = \sum_{j \in G} t_j S_j,$$

where $S_j$ is the expression of gene j from gene set G in a sample S, and $t_j$ is a scale factor representing the difference in expression of gene j between a first lymphoma type and a second lymphoma type. Alternatively, a linear predictor score may be generated by other methods including but not limited to linear discriminant analysis (Dudoit 2002), support vector machines (Furey 2000), or shrunken centroids (Tibshirani 2002)

The phrase "scale factor" as used herein refers to a factor that defines the relative difference in expression of a particular gene between two samples. An example of a scale factor is a t-score generated by a Student's t-test.

The phrase "lymphoma subject," wherein "lymphoma" is a specific lymphoma type (e.g., "follicular lymphoma subject"), may refer to a subject that has been diagnosed with a particular lymphoma by any method known in the art or discussed herein. This phrase may also refer to a subject with a known or suspected predisposition or risk of developing a particular lymphoma type.

The pattern of expression of a particular gene is closely connected to the biological role and effect of its gene product. For this reason, the systematic study of variations in gene expression provides an alternative approach for linking specific genes with specific diseases and for recognizing heritable gene variations that are important for immune function. For example, allelic differences in the regulatory region of a gene may influence the expression levels of that gene. An appreciation for such quantitative traits in the immune system may help elucidate the genetics of autoimmune diseases and lymphoproliferative disorders.

Genes that encode components of the same multi-subunit protein complex are often coordinately regulated. Coordinate regulation is also observed among genes whose products function in a common differentiation program or in the same physiological response pathway. Recent application of gene expression profiling to the immune system has shown that lymphocyte differentiation and activation are accompanied by parallel changes in expression among hundreds of genes. Gene expression databases may be used to interpret the pathological changes in gene expression that accompany autoimmunity, immune deficiencies, cancers of immune cells and of normal immune responses.

Scanning and interpreting large bodies of relative gene expression data is a formidable task. This task is greatly facilitated by algorithms designed to organize the data in a way that highlights systematic features, and by visualization tools that represent the differential expression of each gene as varying intensities and hues of color (Eisen 1998). The development of microarrays, which are capable of generating massive amounts of expression data in a single experiment, has greatly increased the need for faster and more efficient methods of analyzing large-scale expression data sets. In order to effectively utilize microarray gene expression data for the identification and diagnosis of lymphoma and for the prediction of survival in lymphoma patients, new algorithms must be developed to identify important information and convert it to a more manageable format. In addition, the microarrays used to generate this data should be streamlined to incorporate probe sets that are useful for diagnosis and survival prediction. Disclosed herein are various methods and compositions that address both of these issues.

Mathematical analysis of gene expression data is a rapidly evolving science based on a rich mathematics of pattern recognition developed in other contexts (Kohonen 1997). Mathematical analysis of gene expression generally has three goals. First, it may be used to identify groups of genes that are coordinately regulated within a biological system. Second, it may be used to recognize and interpret similarities between biological samples on the basis of similarities in gene expression patterns. Third, it may be used to recognize and identify those features of a gene expression pattern that are related to distinct biological processes or phenotypes.

Mathematical analysis of gene expression data often begins by establishing the expression pattern for each gene on an array across n experimental samples. The expression pattern of each gene can be represented by a point in n-dimensional space, with each coordinate specified by an expression measurement in one of the n samples (Eisen 1998). A clustering algorithm that uses distance metrics can then be applied to locate clusters of genes in this n-dimensional space. These clusters indicate genes with similar patterns of variation in expression over a series of experiments. Clustering methods that have been applied to microarray data in the past include hierarchical clustering (Eisen 1998), self-organizing maps (SOMs) (Tamayo 1999), k-means (Tavazoie 1999), and deterministic annealing (Alon 1999). A variety of different algorithms, each emphasizing distinct orderly features of the data, may be required to glean the maximal biological insight from a set of samples (Alizadeh 1998). One such algorithm, hierarchical clustering, begins by determining the gene expression correlation coefficients for each pair of the n genes studied. Genes with similar gene expression correlation coefficients are grouped next to one another in a hierarchical fashion. Generally, genes with similar expression patterns under a particular set of conditions encode protein products that play related roles in the physiological adaptation to those conditions. Novel genes of unknown function that are clustered with a large group of functionally related genes are likely to participate in the same biological process. Likewise, the other clustering methods mentioned herein may also group genes together that encode proteins with related biological function.

Gene expression maps may be constructed by organizing gene expression data from multiple samples using any of the various clustering algorithms outlined herein. The ordered tables of data may then be displayed graphically in a way that allows researchers and clinicians to assimilate both the choreography of gene expression on a broad scale and the fine distinctions in expression of individual genes.

In such a gene expression map, genes that are clustered together reflect a particular biological function, and are termed gene expression signatures (Shaffer 2001). One general type of gene expression signature includes genes that are characteristically expressed in a particular cell type or at a particular stage of cellular differentiation or activation. Another general type of gene expression signature includes genes that are regulated in their expression by a particular biological process such as proliferation, or by the activity of a particular transcription factor or signaling pathway.

The pattern of gene expression in a biological sample provides a distinctive and accessible molecular picture of its functional state and identity (DeRisi 1997; Cho 1998; Chu 1998; Holstege 1998; Spellman 1998). Each cell transduces variations in its environment, internal state, and developmental state into readily measured and recognizable variations in its gene expression patterns. Two different samples that have related gene expression patterns are therefore likely to be biologically and functionally similar to one another. Some biological processes are reflected by the expression of genes in a specific gene expression signature, as described above. The expression of a specific gene expression signature in a sample can provide important biological insights into its cellular composition and the function of various intracellular pathways within those cells.

The present invention discloses a variety of gene expression signatures related to the clinical outcome of lymphoma patients. While several of these signatures share a name with a previously disclosed signature, each of the gene expression signatures disclosed herein comprises a novel combination of genes. For example, the lymph node signature disclosed herein includes genes encoding extracellular matrix components and genes that are characteristically expressed in macrophage, NK, and T cells (e.g., α-Actinin, collagen type III α 1, connective tissue growth factor, fibronectin, KIAA0233, urokinase plasminogen activator). The proliferation signature includes genes that are characteristically expressed by cells that are rapidly multiplying or proliferating (e.g., c-myc, E21G3, NPM3, BMP6). The MHC class II signature includes genes that interact with lymphocytes in order to allow the recognition of foreign antigens (e.g., HLA-DPα, HLA-DQα, HLA-DRα, HLA-DRβ). The immune response-1 signature includes genes encoding T cell markers (e.g., CD7, CD8B1, ITK, LEF1, STAT4), as well as genes that are highly expressed in macrophages (e.g., ACTN1, TNFSF13B). The immune response-2 signature includes genes known to be preferentially expressed in macrophages and/or dendritic cells (e.g., TLR5, FCGR1A, SEPT10, LGMN, C3AR1). The germinal center B cell signature includes genes known to be overexpressed at this stage of B cell differentiation (e.g., MME, MEF2C, BCL6, LMO2, PRSPAP2, MBD4, EBF, MYBL1).

Databases of gene expression signatures have proven quite useful in elucidating the complex gene expression patterns of various cancers. For example, expression of genes from the germinal center B-cell signature in a lymphoma biopsy suggests that the lymphoma is derived from this stage of B cell differentiation. In the same lymphoma biopsy, the expression of genes from the T cell signature can be used to estimate the degree of infiltration of the tumor by host T cells, while the expression of genes from the proliferation signature can be used to quantitate the tumor cell proliferation rate. In this manner, gene expression signatures provide an "executive summary" of the biological properties of a tumor specimen. Gene expression signatures can also be helpful in interpreting the results of a supervised analysis of gene expression data. Supervised analysis generates a long list of genes with expression patterns that are correlated with survival. Gene expression signatures can be useful in assigning these "predictive" genes to functional categories. In building a multivariate model of survival based on gene expression data, this functional categorization helps to limit the inclusion of multiple genes in the model that measure the same aspect of tumor biology.

Gene expression profiles can be used to create multivariate models for predicting survival. The methods for creating these models are called "supervised" because they use clinical data to guide the selection of genes to be used in the prognostic classification. For example, a supervised method might identify genes with expression patterns that correlate with the length of overall survival following chemotherapy. The general method used to create a multivariate model for predicting survival may utilize the following steps:

1. Identify genes with expression patterns that are univariately associated with a particular clinical outcome using a Cox proportional hazards model. Generally, a univariate p-value of <0.01 is considered the cut-off for significance. These genes are termed "predictor" genes.
2. Within a set of predictor genes, identify gene expression signatures.
3. For each gene expression signature that is significantly associated with survival, average the expression of the component genes within this signature to generate a gene expression signature value.
4. Build a multivariate Cox model of clinical outcome using the gene expression signature values.
5. If possible, include additional genes in the model that do not belong to a gene expression signature but which add to the statistical power of the model.

This approach has been utilized in the present invention to create novel survival prediction models for FL, DLBCL, and MCL. Each of these models generates a survival predictor score, with a higher score being associated with worse clinical outcome. Each of these models may be used separately to predict survival. Alternatively, these models may be used in conjunction with one or more other models, disclosed herein or in other references, to predict survival.

A first FL survival predictor was generated using gene expression data obtained using Affymetrix U133A and U133B microarrays. This predictor incorporated immune response-1 and immune response-2 gene expression signatures. Fitting the Cox proportional hazards model to the gene expression signature values obtained from these signatures resulted in the following model:

Survival predictor score=[(2.71*immune response-2 gene expression signature value)]−[(2.36×immune response-1 gene expression signature value)].

A second FL survival predictor was generated using gene expression data obtained using Affymetrix U133A and U133B microarrays. This predictor incorporated macrophage, T-cell, and B-cell differentiation gene expression signatures. Fitting the Cox proportional hazards model to the gene expression signature values obtained from these signatures resulted in the following model:

Survival predictor score=[2.053*(macrophage gene expression signature value)]−[2.344*(T-cell gene expression signature value)]−[0.729*(B-cell differentiation gene expression signature value)].

A third FL survival predictor was generated using gene expression data obtained using the Lymph Dx microarray. This predictor incorporated macrophage, T-cell, and B-cell differentiation gene expression signatures. Fitting the Cox proportional hazards model to the gene expression signature values obtained from these signatures resulted in the following model:

Survival predictor score=[1.51*(macrophage gene expression signature value)]−[2.11*(T-cell gene expression signature value)]−[0.505*(B-cell differentiation gene expression signature value)].

A first DLBCL survival predictor was generated using gene expression data obtained using Affymetrix U133A and U133B microarrays. This predictor incorporated ABC DLBCL high, lymph node, and MHC class II gene expression signatures. Fitting the Cox proportional hazards model to the gene expression signature values obtained from these signatures resulted in the following model:

Survival predictor score=[0.586*(ABC DLBCL high gene expression signature value)]−[0.468*(lymph node gene expression signature value)]−0.336*(MHC class II gene expression signature value)].

A second DLBCL survival predictor was generated using gene expression data obtained using the Lymph Dx microarray. This predictor incorporated lymph node, proliferation, germinal center B-cell, and MHC class II gene expression signatures. Fitting the Cox proportional hazards model to the gene expression signature values obtained from these signatures resulted in the following model:

Survival predictor score=[−0.4337*(lymph node gene expression signature value)]+[0.09*(proliferation gene expression signature value)]−[0.4144*(germinal center B-cell gene expression signature value)]−[0.2006*(MHC class II gene expression signature value)].

A third DLBCL survival predictor was generated using gene expression data obtained using the Lymph Dx microarray. This predictor incorporated lymph node, germinal center B cell, and MHC class II gene expression signatures. Fitting the Cox proportional hazards model to the gene expression signature values obtained from these signatures resulted in the following model:

Survival predictor score=[−0.32*(lymph node gene expression signature value)]−[0.176*(germinal center B-cell gene expression signature value)]−[0.206*(MHC class II gene expression signature value)].

An MCL survival predictor was generated using gene expression data obtained using Affymetrix U133A, Affymetrix U133B, and Lymph Dx microarrays. This predictor incorporated a proliferation gene expression signature. Fitting the Cox proportional hazards model to the gene expression signature values obtained from these signatures resulted in the following model:

Survival predictor score=[1.66*(proliferation gene expression signature value)].

Gene expression data can also be used to diagnose and identify lymphoma types. In an embodiment of the present invention, a statistical method based on Bayesian analysis was developed to classify lymphoma specimens according to their gene expression profiles. This method does not merely assign a tumor to a particular lymphoma type, but also determines the probability that the tumor belongs to that lymphoma type. Many different methods have been formulated to predict cancer subgroups (Golub 1999; Ramaswamy 2001; Dudoit 2002; Radmacher 2002). These methods assign tumors to one of two subgroups based on expression of a set of differentially expressed genes. However, they do not provide a probability of membership in a subgroup. By contrast, the method disclosed herein used Bayes' rule to estimate this probability, thus allowing one to vary the probability cut-off for assignment of a tumor to a particular subgroup. In tumor types in which unknown additional subgroups may exist, the present method allows samples that do not meet the gene expression criteria of known subgroups to fall into an unclassified group with intermediate probability. A cancer subgroup predictor of the type described herein may be used clinically to provide quantitative diagnostic information for an individual cancer patient. This information can in turn be used to provide a predictor of treatment outcome for a particular cancer patient.

For any two lymphoma types A and B, there is a set of genes with significantly higher expression in type A than type B, and a set of genes with significantly lower expression in type A than in type B. By observing the expression of these genes in an unknown sample, it is possible to determine to which of the two types the sample belongs. Evaluating the likelihood that a particular sample belongs to one or the other lymphoma type by Bayesian analysis may be done using the following steps:

1. Identify those genes that are most differentially expressed between the two lymphoma types. This can be done by selecting those genes with the largest t-statistic between the two lymphoma types. The genes in this step may be subdivided into gene expression signatures in certain cases, with genes from each signature analyzed separately.
2. Create a series of linear predictor score (LPS) for samples belonging to either lymphoma type.
3. Evaluate the LPS for each sample in a training set, and estimate the distribution of these scores within each lymphoma type according to a normal distribution.
4. Use Bayes' rule to evaluate the probability that each subsequent sample belongs to one or the other lymphoma type.

If only two types of lymphoma are being distinguished, then a single probability score is sufficient to discriminate between the two types. However, if more than two lymphoma types are being distinguished, multiple scores will be needed to highlight specific differences between the types.

A novel microarray termed the Lymph Dx microarray is disclosed herein for the identification and diagnosis of various lymphoma types. The Lymph Dx microarray contains cDNA probes corresponding to approximately 2,653 genes, fewer than the number seen on microarrays that have been used previously for lymphoma diagnosis. The reduced number of probes on the Lymph Dx microarray is the result of eliminating genes that are less useful for the identification of lymphoma types and predicting clinical outcome. This reduction allows for simplified analysis of gene expression data. The genes represented on the Lymph Dx microarray can be divided into four broad categories: 1,101 lymphoma predictor genes identified previously using the Affymetrix 0133 microarray, 171 outcome predictor genes, 167 new genes not found on the Affymetrix U133 microarray, and 1,121 named genes. A list of the probe sets on the Lymph Dx microarray is presented in Table 2, contained in the file "Table_0002_LymphDx_Probe_List.txt."

Gene expression data obtained using the Lymph Dx microarray may be used to identify and classify lymphomas using Bayesian analysis using a strategy similar to that set forth above. In certain embodiments, this strategy may include additional steps designed to optimize the number of genes used and the cut-off points between lymphoma types. A general overview of such a method is presented in FIG. 1. In one example of the method, each gene represented on the Lymph Dx microarray was placed into one of three gene-list categories based on its correlation with the lymph node or proliferation gene expression signatures: lymph node, proliferation, or standard. These signatures were identified by clustering of the DLBCL cases using hierarchical clustering and centroid-correlation of 0.35. Standard genes were those with expression patterns that did not correlate highly with expression of the lymph node or proliferation signatures. Lymph Dx gene expression data was first used to identify samples as FL, MCL, SLL, FH, or DLBCL/BL, then to identify DLBCL/BL samples as ABC, GCB, PMBL, or BL. For each stage, a series of pair-wise models was created, with each model containing a different pair of lymphoma types (e.g., FL vs. MCL, SLL vs. FH, etc.). For each pair, the difference in expression of each gene on the microarray was measured, and a t-statistic was generated representing this difference. Genes from each gene-list category were ordered based on their t-statistic, and those with the largest t-statistics were used to generate a series of LPSs for samples belonging to either lymphoma type. The number of genes used to generate the LPSs was optimized by repeating the calculation using between five and 100 genes from each gene-list category. The number of genes from each category used in the final LPS calculation was that which gave rise to the largest difference in LPS between the two lymphoma types. Once the number of genes in each gene-list category was optimized, four different LPSs were calculated for each sample. The first included genes from the standard gene-list category only, the second included genes from the proliferation and standard gene-list categories, the third included genes from the lymph node and standard gene-list categories, and the fourth included genes from all three categories. The probability q that a sample X belongs to the first lymphoma type of a pair-wise model can then be calculated using an equation:

$$q = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

LPS(X) is the LPS for sample X, $\phi(x; \mu, \sigma)$ is the normal density function with mean $\mu$ and standard deviation $\sigma$, $\hat{\mu}_1$ and $\hat{\sigma}_1$ are the mean and variance of the LPSs for samples belonging to the first lymphoma type, and $\hat{\mu}_2$ and $\hat{\sigma}_2$ are the mean and variance of the LPSs for samples belonging to the second lymphoma type. Samples with high q values were classified as the first lymphoma type, samples with low q values were classified as the second lymphoma type, and samples with middle range q values were deemed unclassified. To determine the proper cut-off point between high, low, and middle q values, every possible cut-off point between adjacent samples was analyzed by an equation:

$$3.99*[(\% \text{ of type 1 misidentified as type 2}) + (\% \text{ of type 2 misidentified as type 1})] + [(\% \text{ of type 1 unclassified}) + (\% \text{ of type 2 misidentified})].$$

This equation was used to favor the assignment of a sample to an "unclassified" category rather than to an incorrect lymphoma type. The final cut-off points were those which minimized this equation. The coefficient of 3.99 was chosen arbitrarily to allow an additional classification error only if the adjustment resulted in four or more unclassified samples becoming correctly classified. The coefficient can be varied to achieve a different set of trade-offs between the number of unclassified and misidentified samples.

To ensure that the accuracy of the model was not a result of overfitting, each model was validated by leave-one-out cross-validation. This entailed removing each sample of known lymphoma type from the data one at a time, and then determining whether the model could predict the missing sample. This process confirmed the accuracy of the prediction method.

The classification of a lymphoproliferative disorder in accordance with embodiments of the present invention may be used in combination with any other effective classification feature or set of features. For example, a disorder may be classified by a method of the present invention in conjunction with WHO suggested guidelines, morphological properties, histochemical properties, chromosomal structure, genetic mutation, cellular proliferation rates, immunoreactivity, clinical presentation, and/or response to chemical, biological, or other agents. Embodiments of the present invention may be used in lieu of or in conjunction with other methods for lymphoma diagnosis, such as immunohistochemistry, flow cytometry, FISH for translocations, or viral diagnostics.

Accurate determination of lymphoma type in a subject allows for better selection and application of therapeutic methods. Knowledge about the exact lymphoma affecting a subject allows a clinician to select therapies or treatments that are most appropriate and useful for that subject, while avoiding therapies that are nonproductive or even counterproductive. For example, CNS prophylaxis may be useful for treating BL but not DLBCL, CHOP treatment may be useful for treating DLBCL but not blastic MCL (Fisher 1993; Khouri 1998), and subjects with follicular lymphoma frequently receive treatment while subjects with follicular hyperplasia do not. In each of these situations, the lymphoma types or subtypes in question can be difficult to distinguish using prior art diagnostic methods. The diagnostic and identification methods of the present invention allow for more precise delineation between these lymphomas, which simplifies the decision of whether to pursue a particular therapeutic option. Likewise, the survival prediction methods disclosed in the present invention also allow for better selection of therapeutic options. A subject with a very low survival predictor score (i.e., very good prognosis) may not receive treatment, but may instead be subjected to periodic check-ups and diligent observation. As survival predictor scores increase (i.e., prognosis gets worse), subjects may receive more intensive treatments. Those subjects with the highest survival predictor scores (i.e., very poor prognosis) may receive experimental treatments or treatments with novel agents. Accurate survival prediction using the methods disclosed herein provides an improved tool for selecting treatment options and for predicting the likely clinical outcome of those options.

Any effective method of quantifying the expression of at least one gene, gene set, or group of gene sets may be used to acquire gene expression data for use in embodiments of the present invention. For example, gene expression data may be measured or estimated using one or more microarrays. The microarrays may be of any effective type, including but not limited to nucleic acid based or antibody based. Gene expression may also be measured by a variety of other techniques, including but not limited to PCR, quantitative RT-PCR, real-time PCR, RNA amplification, in situ hybridization, immunohistochemistry, immunocytochemistry, FACS, serial analysis of gene expression (SAGE) (Velculescu 1995), Northern blot hybridization, or western blot hybridization.

Nucleic acid microarrays generally comprise nucleic acid probes derived from individual genes and placed in an ordered array on a support. This support may be, for example, a glass slide, a nylon membrane, or a silicon wafer. Gene expression patterns in a sample are obtained by hybridizing the microarray with the gene expression product from the sample. This gene expression product may be, for example, total cellular mRNA, rRNA, or cDNA obtained by reverse transcription of total cellular mRNA. The gene expression product from a sample is labeled with a radioactive, fluorescent, or other label to allow for detection. Following hybridization, the microarray is washed, and hybridization of gene expression product to each nucleic acid probe on the microarray is detected and quantified using a detection device such as a phosphorimager or scanning confocal microscope.

There are two broad classes of microarrays: cDNA and oligonucleotide arrays. cDNA arrays consist of hundreds or thousands of cDNA probes immobilized on a solid support. These cDNA probes are usually 100 nucleotides or greater in size. There are two commonly used designs for cDNA arrays. The first is the nitrocellulose filter array, which is generally prepared by robotic spotting of purified DNA fragments or lysates of bacteria containing cDNA clones onto a nitrocellulose filter (Southern 1992; Southern 1994; Gress 1996; Pietu 1996). The other commonly used cDNA arrays is fabricated by robotic spotting of PCR fragments from cDNA clones onto glass microscope slides (Schena 1995; DeRisi 1996; Schena 1996; Shalon 1996; DeRisi 1997; Heller 1997; Lashkari 1997). These cDNA microarrays are simultaneously hybridized with two fluorescent cDNA probes, each labeled with a different fluorescent dye (typically Cy3 or Cy5). In this format, the relative mRNA expression in two samples is directly compared for each gene on the microarray. Oligonucleotide arrays differ from cDNA arrays in that the probes are 20- to 25-mer oligonucleotides. Oligonucleotide arrays are generally produced by in situ oligonucleotide synthesis in conjunction with photolithographic masking techniques (Pease 1994; Lipshutz 1995; Chee 1996; Lockhart 1996; Wodicka 1997). The solid support for oligonucleotide arrays is typically a glass or silicon surface.

Methods and techniques applicable to array synthesis and use have been described in, for example, U.S. Pat. No. 5,143,854 (Pirrung), U.S. Pat. No. 5,242,974 (Holmes), U.S. Pat. No. 5,252,743 (Barrett), U.S. Pat. No. 5,324,633 (Fodor), U.S. Pat. No. 5,384,261 (Winkler), U.S. Pat. No. 5,424,186 (Fodor), U.S. Pat. No. 5,445,934 (Fodor), U.S. Pat. No. 5,451,683 (Barrett), U.S. Pat. No. 5,482,867 (Barrett), U.S. Pat. No. 5,491,074 (Aldwin), U.S. Pat. No. 5,527,681 (Holmes), U.S. Pat. No. 5,550,215 (Holmes), U.S. Pat. No. 5,571,639 (Hubbell), U.S. Pat. No. 5,578,832 (Trulson), U.S. Pat. No. 5,593,839 (Hubbell), U.S. Pat. No. 5,599,695 (Pease), U.S. Pat. No. 5,624,711 (Sundberg), U.S. Pat. No. 5,631,734 (Stern), U.S. Pat. No. 5,795,716 (Chee), U.S. Pat. No. 5,831,070 (Pease), U.S. Pat. No. 5,837,832 (Chee), U.S. Pat. No. 5,856,101 (Hubbell), U.S. Pat. No. 5,858,659 (Sapolsky), U.S. Pat. No. 5,936,324 (Montagu), U.S. Pat. No. 5,968,740 (Fodor), U.S. Pat. No. 5,974,164 (Chee), U.S. Pat. No. 5,981,185 (Matson), U.S. Pat. No. 5,981,956 (Stern), U.S. Pat. No. 6,025,601 (Trulson), U.S. Pat. No. 6,033,860 (Lockhart), U.S. Pat. No. 6,040,193 (Winkler), U.S. Pat. No. 6,090,555 (Fiekowsky), and U.S. Pat. No. 6,410,229 (Lockhart), and U.S. Patent Application Publication No. 20030104411 (Fodor). Each of the above patents and applications is incorporated by reference herein in its entirety.

Microarrays may generally be produced using a variety of techniques, such as mechanical or light directed synthesis methods that incorporate a combination of photolithographic methods and solid phase synthesis methods. Techniques for the synthesis of microarrays using mechanical synthesis methods are described in, for example, U.S. Pat. No. 5,384,261 (Winkler) and U.S. Pat. No. 6,040,193 (Winkler). Although a planar array surface is preferred, the microarray may be fabricated on a surface of virtually any shape, or even on a multiplicity of surfaces. Microarrays may be nucleic acids on beads, gels, polymeric surfaces, fibers such as fiber optics, glass or any other appropriate substrate. See, for example, U.S. Pat. No. 5,708,153 (Dower); U.S. Pat. No. 5,770,358 (Dower); U.S. Pat. No. 5,789,162 (Dower); U.S. Pat. No. 5,800,992 (Fodor); and U.S. Pat. No. 6,040,193 (Winkler), each of which is incorporated by reference herein in its entirety.

Microarrays may be packaged in such a manner as to allow for diagnostic use, or they can be an all-inclusive device. See, for example, U.S. Pat. No. 5,856,174 (Lipshutz) and U.S. Pat. No. 5,922,591 (Anderson), both of which are incorporated by reference herein in their entirety.

Microarrays directed to a variety of purposes are commercially available from Affymetrix (Affymetrix, Santa Clara, Calif.). For instance, these microarrays may be used for genotyping and gene expression monitoring for a variety of eukaryotic and prokaryotic species.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Collection and Analysis of Gene Expression Data Using Affymetrix U133A and U133B Microarrays 568 cell samples representing various forms of human lymphoid malignancies were obtained by biopsy using known methods described in the literature. The samples were reviewed by a panel of hematopathologists and classified into the following lymphoma types based on current diagnostic criteria:
  231 diffuse large B cell lymphomas (DLBCL)
  191 follicular lymphomas (FL)
  26 Burkitt lymphomas (BL)
  21 mantle cell lymphoma (MCL)
  18 follicular hyperplasias (FH)
  17 small cell lymphocytic lymphomas (SLL)
  16 mucosa-associated lymphoid tissue lymphomas (MALT)
  13 splenic lymphomas (Splenic)
  10 cyclin-D1 negative lymphomas with MCL morphology (CD1 negMCL)
  9 multiple myeloma (Mult_Myeloma)
  6 lymphoplasmacytic lymphomas (LPC)
  4 post-transplant lymphoproliferative disorders (PTLD)
  3 lymphoblastic lymphomas (Lymbl)
  3 nodal marginal zone lymphomas (NMZ)
The 231 DLBCL samples were subdivided into the following lymphoma types based on gene expression (see below):
  88 germinal center B cell-like (GCB)
  78 activated B cell-like (ABC)
  33 primary mediastinal B cell lymphoma (PMBL)
  32 samples for which the subtype could not be determined (UC_DLBCL)
The 16 MALT samples were subdivided into the following four group based on tumor origin:
  9 from the gastric region (MALT_gastric)
  1 from the salivary gland (MALT_salivary)
  1 from the lung (MALT_lung)
  1 from the tonsil (MALT tonsil)
  4 of unknown origin (MALT_unk)

Each of the 568 cell samples was given a unique sample ID number consisting of the lymphoma type followed by a unique numerical identifier. For example, "ABC_304" refers to an ABC DLBCL sample numbered 304. Cells were purified and RNA was isolated from the purified cells according to known methods described in the literature.

Aliquots of RNA from each sample were applied to Affymetrix U133A and Affymetrix U133B microarrays according to standard Affymetrix protocol. The U133A and U133B microarrays are divided into probe sets, with each probe set consisting of up to 69 oligonucleotide probes 25 nucleotides in length. Each probe set represents a distinct human gene. Information pertaining to these microarrays is available at the Affymetrix company web site. Each microarray was scanned using an Affymetrix scanner, which records signal intensity for every probe on the microarray. This information can be transformed into summary signal values for each probe set using a number of different algorithms, including MAS 5.0, D-chip (Li 2001), or Bioconductor's RMA algorithms (Irizarry 2003). The images produced by the scanner were evaluated by Affymetrix MAS 5.0 software and stored as tables in .txt format. Since each sample was scanned on both microarrays, there are two .txt files for each sample. Each .txt file was given a unique name consisting of the table number, sample ID number (discussed above), and a letter denoting the microarray used. For example, Table_0588_ABC_304_A.txt is the .txt file for Table 588, which contains data for sample ID number ABC_304 from the U133A array. The data for each sample tested is contained in Tables 3-1138.

The signal value for each probe on the U133A and U133B microarrays was normalized to a target value of 500, and the base-2 log of the normalized values was used for the following analyses. Log-signal values for each probe set are presented in Tables 1139-1706, contained in files with the title format "Table_No._NAME_Jog_signal.txt," where NAME refers to the sample ID number (e.g., ABC_304). The first column provides the UNIQID for the probe set, while the second column provides the log-signal value.

Log-signal files were statistically analyzed using S+ software and the S+ subtype predictor script contained in the file entitled "Subtype_Predictor.txt," located in the computer program listing appendix contained on CD number 22 of 22. Although the log-signal values were analyzed using S+ software and the above algorithm, any effective software/algorithm combination may be used. Tables 1707-1721 provide descriptive statistical characteristics for each of the lymphoma types tested except for CD1 negMCL, non-gastric MALT, and UC_DLBCL. Table 1722 provides statistical characteristics for all MALT samples combined, while Table 1723 does likewise for all DLBCL samples.

The files containing Tables 1707-1723 have the title format "Table_No._TYPE_Stats.txt," where TYPE refers to the lymphoma type. Each row of these tables represents a particular probe set. The first column of each table provides the UNIQID for the probe set, while the second column provides the average log-signal for the probe set over all samples of a particular lymphoma type. The third column provides the log-fold change in expression of the probe set between the lymphoma type in question and a second lymphoma type. For example, if logfold.ABC.vs.GCB is −0.21 for gene X, expression of gene X in the ABC samples is, on average, 0.86 (i.e., $2^{-0.21}$) times greater than expression of gene X in the GCB samples. The fourth column provides a two-sided P-value derived from a t-test of the log signals of the two lymphoma types compared in column three. If, for example, P.value.ABC.vs.GCB was 0.00001 for gene X, this would indicate that the observed difference in expression of gene X between ABC and GCB would only occur approximately one time in 100,000 if there was no actual difference in gene X expression between the two lymphoma types. The remainder of the columns can be read as pairs that repeat the pattern of columns three and four, presenting the log-fold change and P-value of the difference in expression of the probe set for the lymphoma type in question versus all other lymphoma types being tested. Tables 1710, 1715, and 1723 (corresponding to FL, MCL, and DLBCL, respectively) contain two additional columns entitled "TYPE_Cox_coefficient" and "TYPE_Cox_P_value." The content of these columns is discussed in the following examples.

Example 2

Collection of Gene Expression Data Using the Novel Lymph Dx Microarray

The novel Lymph Dx microarray contains cDNA probes corresponding to approximately 2,734 genes. 174 of these are "housekeeping" genes present for quality control, since they represent genes that are most variably expressed across all lymphoma samples. Other genes represented on the microarray were selected for their utility in identifying particular lymphoma samples and predicting survival in those samples. The genes represented on the Lymph Dx microarray can be divided into four broad categories: 1,101 lymphoma predictor genes identified previously using the Affymetrix 0133 microarray, 171 outcome predictor genes identified using the Affymetrix U133 microarray, 167 genes not found on the Affymetrix U133 microarray but represented on the Lymphochip microarray (Alizadeh 1999), and 1,121 named genes. The types of genes making up each of these broad categories are summarized in Table 1724, below, while the specific genes represented on the Lymph Dx microarray are listed in Table 2 and contained in the file "Table_0002_LymphDx_Probe_List.txt."

TABLE 2

| UNIQID | Probe Set | Genbank Accession No. | Unigene ID Build 167 | Unigene Symbol |
|---|---|---|---|---|
| 1119003 | 200004_at | NM_001418 | 183684 | EIF4G2 |
| 1119007 | 200009_at | NM_001494 | 56845 | GDI2 |
| 1119015 | 200024_at | NM_001009 | 378103 | RPS5 |
| 1130426 | 200039_s_at | NM_002794 | 432607 | PSMB2 |
| 1130429 | 200048_s_at | NM_006694 | 6396 | JTB |
| 1130430 | 200052_s_at | NM_004515 | 75117 | ILF2 |
| 1130433 | 200058_s_at | NM_014014 | 246112 | U5-200KD |
| 1130446 | 200076_s_at | NM_024069 | 369785 | MGC2749 |
| 1130447 | 200077_s_at | NM_004152 | 446427 | OAZ1 |
| 1119039 | 200084_at | NM_014267 | 447513 | SMAP |
| 1130465 | 200098_s_at | NM_016237 | 7101 | ANAPC5 |
| 1130468 | 200594_x_at | NM_004501 | 166463 | HNRPU |
| 1130472 | 200599_s_at | NM_003299 | 192374 | TRA1 |
| 1119046 | 200606_at | NM_004415 | 349499 | DSP |
| 1130482 | 200616_s_at | NM_014730 | 181418 | KIAA0152 |
| 1130483 | 200622_x_at | NM_005184 | 334330 | CALM3 |
| 1119056 | 200633_at | NM_018955 | 356190 | UBB |
| 1119061 | 200644_at | NM_023009 | 75061 | MLP |
| 1130501 | 200650_s_at | NM_005566 | 2795 | LDHA |
| 1119068 | 200660_at | NM_005620 | 417004 | S100A11 |
| 1119070 | 200663_at | NM_001780 | 445570 | CD63 |
| 1130509 | 200665_s_at | NM_003118 | 111779 | SPARC |
| 1119071 | 200667_at | NM_003340 | 411826 | UBE2D3 |
| 1119072 | 200670_at | NM_005080 | 437638 | XBP1 |
| 1119074 | 200675_at | NM_004356 | 54457 | CD81 |
| 1130518 | 200679_x_at | NM_002128 | 434102 | HMGB1 |
| 1119076 | 200681_at | NM_006708 | 268849 | GLO1 |
| 1130527 | 200692_s_at | NM_004134 | 184233 | HSPA9B |
| 1130533 | 200706_s_at | NM_004862 | 76507 | LITAF |
| 1119090 | 200709_at | NM_000801 | 374638 | FKBP1A |
| 1130588 | 200775_s_at | NM_002140 | 307544 | HNRPK |
| 1130603 | 200797_s_at | NM_021960 | 86386 | MCL1 |
| 1119111 | 200804_at | NM_003217 | 35052 | TEGT |
| 1130618 | 200822_x_at | NM_000365 | 83848 | GRCC9 |
| 1130622 | 200829_x_at | NM_003457 | 97128 | ZNF207 |
| 1130624 | 200832_s_at | NM_005063 | 119597 | SCD |
| 1130629 | 200839_s_at | NM_001908 | 135226 | CTSB |
| 1130631 | 200842_s_at | NM_004446 | 171292 | EPRS |
| 1130645 | 200860_s_at | NM_016284 | 279949 | KIAA1007 |
| 1130653 | 200875_s_at | NM_006392 | 376064 | NOL5A |
| 1119139 | 200880_at | NM_001539 | 388392 | DNAJA1 |
| 1130658 | 200886_s_at | NM_002629 | 447492 | PGAM1 |
| 1130668 | 200897_s_at | NM_016081 | 194431 | KIAA0992 |
| 1130674 | 200905_x_at | NM_005516 | 381008 | HLA-E |
| 1130676 | 200907_s_at | NM_016081 | 194431 | KIAA0992 |
| 1130680 | 200912_s_at | NM_001967 | 511904 | EIF4A2 |
| 1130687 | 200924_s_at | NM_002394 | 79748 | SLC3A2 |
| 1119155 | 200934_at | NM_003472 | 110713 | DEK |
| 1130704 | 200951_s_at | NM_001759 | 376071 | CCND2 |
| 1130707 | 200956_s_at | NM_003146 | 79162 | SSRP1 |
| 1130712 | 200965_s_at | NM_002313 | 442540 | ABLIM1 |
| 1119171 | 200974_at | NM_001613 | 208641 | ACTA2 |
| 1119173 | 200978_at | NM_005917 | 75375 | MDH1 |
| 1119183 | 200997_at | NM_002896 | 211203 | RBM4 |
| 1130732 | 201002_s_at | NM_021988 | 381025 | UBE2V1 |
| 1119186 | 201005_at | NM_001769 | 387579 | CD9 |
| 1130735 | 201009_s_at | NM_006472 | 179526 | TXNIP |
| 1130744 | 201027_s_at | NM_015904 | 158688 | EIF5B |
| 1130746 | 201029_s_at | NM_002414 | 283477 | CD99 |
| 1130747 | 201030_x_at | NM_002300 | 234489 | LDHB |
| 1119202 | 201042_at | NM_004613 | 512708 | TGM2 |
| 1130755 | 201043_s_at | NM_006305 | 356089 | ANP32A |
| 1119209 | 201063_at | NM_002901 | 167791 | RCN1 |
| 1130771 | 201068_s_at | NM_002803 | 61153 | PSMC2 |
| 1119212 | 201069_at | NM_004530 | 367877 | MMP2 |
| 1130799 | 201114_x_at | NM_002792 | 233952 | PSMA7 |
| 1130812 | 201131_s_at | NM_004360 | 194657 | CDH1 |
| 1119237 | 201141_at | NM_002510 | 389964 | GPNMB |
| 1130820 | 201144_s_at | NM_004094 | 151777 | EIF2S1 |
| 1119239 | 201145_at | NM_006118 | 199625 | HAX1 |
| 1130835 | 201163_s_at | NM_001553 | 435795 | IGFBP7 |
| 1130839 | 201167_x_at | NM_004309 | 159161 | ARHGDIA |

TABLE 2-continued

| UNIQID | Probe Set | Genbank Accession No. | Unigene ID Build 167 | Unigene Symbol |
|---|---|---|---|---|
| 1119243 | 201171_at | NM_003945 | 440165 | ATP6V0E |
| 1119245 | 201178_at | NM_012179 | 5912 | FBXO7 |
| 1130852 | 201184_s_at | NM_001273 | 74441 | CHD4 |
| 1130855 | 201189_s_at | NM_002224 | 77515 | ITPR3 |
| 1119251 | 201194_at | NM_003009 | 433941 | SEPW1 |
| 1119258 | 201209_at | NM_004964 | 88556 | HDAC1 |
| 1119260 | 201212_at | NM_005606 | 18069 | LGMN |
| 1119263 | 201216_at | NM_006817 | 511762 | C12orf8 |
| 1130871 | 201222_s_at | NM_002874 | 159087 | RAD23B |
| 1130879 | 201231_s_at | NM_001428 | 433455 | ENO1 |
| 1119268 | 201234_at | NM_004517 | 6196 | ILK |
| 1130882 | 201236_s_at | NM_006763 | 75462 | BTG2 |
| 1130888 | 201244_s_at | NM_002880 | 257266 | RAF1 |
| 1130898 | 201260_s_at | NM_006754 | 80919 | SYPL |
| 1130900 | 201262_s_at | NM_001711 | 821 | BGN |
| 1130906 | 201277_s_at | NM_004499 | 81361 | HNRPAB |
| 1130910 | 201284_s_at | NM_001640 | 221589 | APEH |
| 1130911 | 201287_s_at | NM_002997 | 82109 | SDC1 |
| 1119294 | 201292_at | NM_001067 | 156346 | TOP2A |
| 1130914 | 201294_s_at | NM_015626 | 315379 | WSB1 |
| 1130922 | 201305_x_at | NM_006401 | 459987 | ANP32B |
| 1130923 | 201306_s_at | NM_006401 | 459987 | ANP32B |
| 1130926 | 201310_s_at | NM_004772 | 508741 | C5orf13 |
| 1119300 | 201314_at | NM_006374 | 155206 | STK25 |
| 1130936 | 201331_s_at | NM_003153 | 437475 | STAT6 |
| 1130942 | 201338_x_at | NM_002097 | 445977 | GTF3A |
| 1119311 | 201341_at | NM_003633 | 104925 | ENC1 |
| 1119317 | 201349_at | NM_004252 | 396783 | SLC9A3R1 |
| 1119325 | 201365_at | NM_002537 | 74563 | OAZ2 |
| 1119334 | 201389_at | NM_002205 | 149609 | ITGA5 |
| 1130972 | 201393_s_at | NM_000876 | 76473 | IGF2R |
| 1130977 | 201401_s_at | NM_001619 | 83636 | ADRBK1 |
| 1119350 | 201425_at | NM_000690 | 331141 | ALDH2 |
| 1130994 | 201431_s_at | NM_001387 | 150358 | DPYSL3 |
| 1119361 | 201448_at | NM_022037 | 391858 | TIA1 |
| 1119365 | 201460_at | NM_004759 | 75074 | MAPKAPK2 |
| 1131012 | 201464_x_at | NM_002228 | 78465 | JUN |
| 1119369 | 201473_at | NM_002229 | 25292 | JUNB |
| 1131019 | 201474_s_at | NM_002204 | 265829 | ITGA3 |
| 1119375 | 201489_at | NM_005729 | 381072 | PPIF |
| 1131038 | 201502_s_at | NM_020529 | 81328 | NFKBIA |
| 1119383 | 201508_at | NM_001552 | 1516 | IGFBP4 |
| 1119390 | 201518_at | NM_006807 | 77254 | CBX1 |
| 1119400 | 201536_at | NM_004090 | 181046 | DUSP3 |
| 1119401 | 201540_at | NM_001449 | 421383 | FHL1 |
| 1131068 | 201564_s_at | NM_003088 | 118400 | FSCN1 |
| 1131069 | 201565_s_at | NM_002166 | 180919 | ID2 |
| 1131074 | 201572_x_at | NM_001921 | 76894 | DCTD |
| 1119417 | 201579_at | NM_005245 | 166994 | FAT |
| 1131081 | 201586_s_at | NM_005066 | 180610 | SFPQ |
| 1131082 | 201587_s_at | NM_001569 | 182018 | IRAK1 |
| 1119424 | 201599_at | NM_000274 | 75485 | OAT |
| 1131107 | 201628_s_at | NM_006570 | 432330 | RRAGA |
| 1131110 | 201631_s_at | NM_003897 | 76095 | IER3 |
| 1119438 | 201641_at | NM_004335 | 118110 | BST2 |
| 1131119 | 201647_s_at | NM_005506 | 349656 | SCARB2 |
| 1119443 | 201648_at | NM_002227 | 436004 | JAK1 |
| 1119445 | 201650_at | NM_002276 | 309517 | KRT19 |
| 1119448 | 201656_at | NM_000210 | 212296 | ITGA6 |
| 1131140 | 201684_s_at | NM_014828 | 194035 | C14orf92 |
| 1131149 | 201694_s_at | NM_001964 | 326035 | EGR1 |
| 1131150 | 201695_s_at | NM_000270 | 75514 | NP |
| 1119460 | 201696_at | NM_005626 | 76122 | SFRS4 |
| 1119462 | 201700_at | NM_001760 | 83173 | CCND3 |
| 1119466 | 201710_at | NM_002466 | 179718 | MYBL2 |
| 1119467 | 201714_at | NM_001070 | 21635 | TUBG1 |
| 1119475 | 201739_at | NM_005627 | 296323 | SGK |
| 1119477 | 201743_at | NM_000591 | 163867 | CD14 |
| 1131181 | 201744_s_at | NM_002345 | 406475 | LUM |
| 1119479 | 201746_at | NM_000546 | 408312 | TP53 |
| 1119488 | 201761_at | NM_006636 | 154672 | MTHFD2 |
| 1131197 | 201778_s_at | NM_014774 | 269902 | KIAA0494 |
| 1119503 | 201803_at | NM_000938 | 149353 | POLR2B |
| 1131218 | 201809_s_at | NM_000118 | 76753 | ENG |
| 1131219 | 201810_s_at | NM_004844 | 109150 | SH3BP5 |
| 1119510 | 201820_at | NM_000424 | 433845 | KRT5 |
| 1119515 | 201833_at | NM_001527 | 3352 | HDAC2 |

TABLE 2-continued

| UNIQID | Probe Set | Genbank Accession No. | Unigene ID Build 167 | Unigene Symbol |
|---|---|---|---|---|
| 1119516 | 201834_at | NM_006253 | 6061 | PRKAB1 |
| 1119519 | 201849_at | NM_004052 | 79428 | BNIP3 |
| 1131246 | 201853_s_at | NM_004358 | 153752 | CDC25B |
| 1131260 | 201872_s_at | NM_002940 | 12013 | ABCE1 |
| 1131263 | 201877_s_at | NM_002719 | 249955 | PPP2R5C |
| 1119533 | 201886_at | NM_025230 | 283976 | WDR23 |
| 1131268 | 201888_s_at | NM_001560 | 285115 | IL13RA1 |
| 1119537 | 201895_at | NM_001654 | 446641 | TIMP1 |
| 1131274 | 201897_s_at | NM_001826 | 374378 | CKS1B |
| 1119541 | 201910_at | NM_005766 | 207428 | FARP1 |
| 1119546 | 201921_at | NM_001017998 | 433898 | GNG10 |
| 1131290 | 201925_s_at | NM_000574 | 408864 | DAF |
| 1119557 | 201939_at | NM_006622 | 398157 | PLK2 |
| 1119559 | 201941_at | NM_001304 | 5057 | CPD |
| 1119561 | 201945_at | NM_002569 | 59242 | FURIN |
| 1119564 | 201952_at | NM_001627 | 10247 | ALCAM |
| 1119565 | 201953_at | NM_006384 | 135471 | CIB1 |
| 1119566 | 201954_at | NM_005720 | 433506 | ARPC1B |
| 1119568 | 201957_at | NM_002481 | 269777 | PPP1R12B |
| 1131321 | 201983_s_at | NM_005228 | 77432 | EGFR |
| 1131325 | 201990_s_at | NM_001310 | 13313 | CREBL2 |
| 1119582 | 201998_at | NM_003032 | 2554 | SIAT1 |
| 1131336 | 202010_s_at | NM_021188 | 405945 | ZNF410 |
| 1131340 | 202018_s_at | NM_002343 | 437457 | LTF |
| 1131342 | 202020_s_at | NM_006055 | 13351 | LANCL1 |
| 1131379 | 202075_s_at | NM_006227 | 439312 | PLTP |
| 1119611 | 202076_at | NM_001166 | 289107 | BIRC2 |
| 1131395 | 202102_s_at | NM_014299 | 278675 | BRD4 |
| 1131401 | 202119_s_at | NM_003909 | 14158 | CPNE3 |
| 1131405 | 202123_s_at | NM_005157 | 446504 | ABL1 |
| 1131407 | 202125_s_at | NM_015049 | 154248 | ALS2CR3 |
| 1119633 | 202126_at | NM_003913 | 198891 | PRPF4B |
| 1119636 | 202130_at | NM_003831 | 209061 | RIOK3 |
| 1131411 | 202135_s_at | NM_005735 | 2477 | ACTR1B |
| 1119639 | 202136_at | NM_006624 | 145894 | BS69 |
| 1131414 | 202140_s_at | NM_003992 | 511790 | CLK3 |
| 1119647 | 202161_at | NM_002741 | 2499 | PRKCL1 |
| 1119652 | 202175_at | NM_024536 | 458374 | CHPF |
| 1119655 | 202178_at | NM_002744 | 407181 | |
| 1131450 | 202200_s_at | NM_003137 | 369358 | SRPK1 |
| 1119667 | 202206_at | NM_005737 | 111554 | ARL7 |
| 1119680 | 202237_at | NM_006169 | 364345 | NNMT |
| 1119683 | 202241_at | NM_025195 | 444947 | C8FW |
| 1119684 | 202242_at | NM_004615 | 439586 | TM4SF2 |
| 1131473 | 202243_s_at | NM_002796 | 89545 | PSMB4 |
| 1131474 | 202246_s_at | NM_000075 | 95577 | CDK4 |
| 1119694 | 202265_at | NM_005180 | 380403 | COMMD3 |
| 1119699 | 202273_at | NM_002609 | 307783 | PDGFRB |
| 1119706 | 202281_at | NM_005255 | 153227 | GAK |
| 1119708 | 202283_at | NM_002615 | 173594 | SERPINF1 |
| 1131490 | 202284_s_at | NM_000389 | 370771 | CDKN1A |
| 1119709 | 202288_at | NM_004958 | 338207 | FRAP1 |
| 1131497 | 202295_s_at | NM_004390 | 114931 | CTSH |
| 1131503 | 202303_x_at | NM_003601 | 135705 | SMARCA5 |
| 1131507 | 202311_s_at | NM_000088 | 172928 | COL1A1 |
| 1119725 | 202329_at | NM_004383 | 77793 | CSK |
| 1119729 | 202338_at | NM_003258 | 164457 | TK1 |
| 1131531 | 202350_s_at | NM_002380 | 153647 | MATN2 |
| 1119734 | 202351_at | NM_002210 | 436873 | ITGAV |
| 1131541 | 202369_s_at | NM_012288 | 310230 | TRAM2 |
| 1119752 | 202391_at | NM_006317 | 511745 | BASP1 |
| 1131561 | 202403_s_at | NM_000089 | 232115 | COL1A2 |
| 1119765 | 202421_at | NM_001542 | 81234 | IGSF3 |
| 1119766 | 202423_at | NM_006766 | 93231 | MYST3 |
| 1131578 | 202431_s_at | NM_002467 | 202453 | MYC |
| 1131584 | 202439_s_at | NM_000202 | 303154 | IDS |
| 1131592 | 202450_s_at | NM_000396 | 83942 | CTSK |
| 1131594 | 202454_s_at | NM_001982 | 306251 | ERBB3 |
| 1119775 | 202455_at | NM_005474 | 9028 | HDAC5 |
| 1119780 | 202472_at | NM_002435 | 75694 | MPI |
| 1119782 | 202478_at | NM_021643 | 155418 | TRB2 |
| 1131614 | 202483_s_at | NM_002882 | 24763 | RANBP1 |
| 1119799 | 202518_at | NM_001707 | 408219 | BCL7B |
| 1119802 | 202522_at | NM_012399 | 7370 | PITPNB |
| 1131636 | 202524_s_at | NM_014767 | 436193 | SPOCK2 |
| 1131637 | 202527_s_at | NM_005359 | 75862 | MADH4 |
| 1119807 | 202530_at | NM_001315 | 79107 | MAPK14 |

TABLE 2-continued

| UNIQID | Probe Set | Genbank Accession No. | Unigene ID Build 167 | Unigene Symbol |
|---|---|---|---|---|
| 1119808 | 202531_at | NM_002198 | 80645 | IRF1 |
| 1131640 | 202534_x_at | NM_000791 | 83765 | DHFR |
| 1131645 | 202542_s_at | NM_004757 | 105656 | SCYE1 |
| 1119813 | 202545_at | NM_006254 | 155342 | PRKCD |
| 1131654 | 202555_s_at | NM_053025 | 386078 | MYLK |
| 1119817 | 202561_at | NM_003747 | 409194 | TNKS |
| 1131663 | 202568_s_at | NM_002376 | 437625 | MARK3 |
| 1119820 | 202573_at | NM_001319 | 181390 | CSNK1G2 |
| 1119826 | 202589_at | NM_001071 | 87491 | TYMS |
| 1131687 | 202606_s_at | NM_012290 | 369280 | TLK1 |
| 1119838 | 202615_at | NM_002072 | 469951 | GNAQ |
| 1119841 | 202625_at | NM_002350 | 80887 | LYN |
| 1119846 | 202634_at | NM_005034 | 351475 | POLR2K |
| 1131705 | 202638_s_at | NM_000201 | 386467 | ICAM1 |
| 1131710 | 202644_s_at | NM_006290 | 211600 | TNFAIP3 |
| 1119860 | 202670_at | NM_002755 | 132311 | MAP2K1 |
| 1131733 | 202686_s_at | NM_001699 | 83341 | AXL |
| 1119868 | 202688_at | NM_003810 | 387871 | TNFSF10 |
| 1131737 | 202693_s_at | NM_004760 | 9075 | STK17A |
| 1119872 | 202696_at | NM_005109 | 95220 | OSR1 |
| 1119873 | 202697_at | NM_007006 | 446393 | CPSF5 |
| 1119876 | 202703_at | NM_003584 | 14611 | DUSP11 |
| 1119878 | 202705_at | NM_004701 | 194698 | CCNB2 |
| 1119880 | 202709_at | NM_002023 | 442844 | FMOD |
| 1119884 | 202716_at | NM_002827 | 418004 | PTPN1 |
| 1131752 | 202724_s_at | NM_002015 | 170133 | FOXO1A |
| 1131753 | 202727_s_at | NM_000416 | 180866 | IFNGR1 |
| 1131755 | 202729_s_at | NM_000627 | 241257 | LTBP1 |
| 1119889 | 202731_at | NM_014456 | 257697 | PDCD4 |
| 1131757 | 202736_s_at | NM_012321 | 76719 | LSM4 |
| 1119894 | 202740_at | NM_000666 | 334707 | ACY1 |
| 1119895 | 202741_at | NM_002731 | 156324 | PRKACB |
| 1119903 | 202753_at | NM_014814 | 350939 | p44S10 |
| 1131767 | 202758_s_at | NM_003721 | 296776 | RFXANK |
| 1119906 | 202762_at | NM_004850 | 58617 | ROCK2 |
| 1119907 | 202763_at | NM_004346 | 141125 | CASP3 |
| 1131778 | 202779_s_at | NM_014501 | 396393 | UBE2S |
| 1119916 | 202780_at | NM_000436 | 177584 | OXCT |
| 1119919 | 202786_at | NM_013233 | 199263 | STK39 |
| 1119920 | 202788_at | NM_004635 | 234521 | MAPKAPK3 |
| 1119924 | 202794_at | NM_002194 | 32309 | INPP1 |
| 1119928 | 202799_at | NM_006012 | 317335 | CLPP |
| 1131786 | 202803_s_at | NM_000211 | 375957 | ITGB2 |
| 1119936 | 202811_at | NM_006463 | 407994 | STAMBP |
| 1119939 | 202820_at | NM_001621 | 170087 | AHR |
| 1119946 | 202834_at | NM_000029 | 19383 | AGT |
| 1119950 | 202840_at | NM_003487 | 402752 | TAF15 |
| 1131806 | 202842_s_at | NM_012328 | 6790 | DNAJB9 |
| 1131808 | 202845_s_at | NM_006788 | 75447 | RALBP1 |
| 1131813 | 202853_s_at | NM_002958 | 285346 | RYK |
| 1131815 | 202856_s_at | NM_004207 | 386678 | SLC16A3 |
| 1131816 | 202859_x_at | NM_000584 | 624 | IL8 |
| 1131827 | 202880_s_at | NM_004762 | 1050 | PSCD1 |
| 1131835 | 202888_s_at | NM_001150 | 1239 | ANPEP |
| 1119972 | 202894_at | NM_004444 | 437008 | EPHB4 |
| 1131839 | 202899_s_at | NM_003017 | 405144 | SFRS3 |
| 1131845 | 202906_s_at | NM_002485 | 25812 | NBS1 |
| 1131847 | 202910_s_at | NM_001784 | 3107 | CD97 |
| 1119979 | 202911_at | NM_000179 | 445052 | MSH6 |
| 1119983 | 202920_at | NM_001148 | 409783 | ANK2 |
| 1131854 | 202923_s_at | NM_001498 | 414985 | GCLC |
| 1131861 | 202933_s_at | NM_005433 | 194148 | YES1 |
| 1131863 | 202936_s_at | NM_000346 | 2316 | SOX9 |
| 1131868 | 202947_s_at | NM_002101 | 81994 | GYPC |
| 1119995 | 202948_at | NM_000877 | 82112 | IL1R1 |
| 1119997 | 202951_at | NM_007271 | 367811 | STK38 |
| 1131870 | 202952_s_at | NM_003474 | 8850 | ADAM12 |
| 1119998 | 202953_at | NM_000491 | 8986 | C1QB |
| 1131875 | 202965_s_at | NM_014289 | 169172 | CAPN6 |
| 1120008 | 202969_at | NM_003583 | 173135 | DYRK2 |
| 1120011 | 202983_at | NM_003071 | 3068 | SMARCA3 |
| 1120016 | 202991_at | NM_006804 | 77628 | STARD3 |
| 1120023 | 203005_at | NM_002342 | 1116 | LTBR |
| 1120024 | 203006_at | NM_005539 | 408063 | INPP5A |
| 1120026 | 203010_at | NM_003152 | 437058 | STAT5A |
| 1131916 | 203035_s_at | NM_006099 | 435761 | PIAS3 |
| 1131918 | 203037_s_at | NM_014751 | 77694 | MTSS1 |

TABLE 2-continued

| UNIQID | Probe Set | Genbank Accession No. | Unigene ID Build 167 | Unigene Symbol |
|---|---|---|---|---|
| 1120038 | 203044_at | NM_014918 | 110488 | CHSY1 |
| 1120044 | 203053_at | NM_005872 | 22960 | BCAS2 |
| 1131925 | 203054_s_at | NM_022171 | 250894 | TCTA |
| 1120053 | 203073_at | NM_007357 | 82399 | COG2 |
| 1120055 | 203075_at | NM_005901 | 110741 | MADH2 |
| 1120059 | 203083_at | NM_003247 | 458354 | THBS2 |
| 1131940 | 203085_s_at | NM_000660 | 1103 | TGFB1 |
| 1120063 | 203090_at | NM_006923 | 118684 | SDF2 |
| 1120069 | 203104_at | NM_005211 | 174142 | CSF1R |
| 1120072 | 203110_at | NM_004103 | 405474 | PTK2B |
| 1131955 | 203112_s_at | NM_005663 | 21771 | WHSC2 |
| 1120079 | 203126_at | NM_014214 | 5753 | IMPA2 |
| 1131964 | 203130_s_at | NM_004522 | 6641 | KIF5C |
| 1120081 | 203131_at | NM_006206 | 74615 | PDGFRA |
| 1120082 | 203132_at | NM_000321 | 408528 | RB1 |
| 1120088 | 203138_at | NM_003642 | 13340 | HAT1 |
| 1120089 | 203139_at | NM_004938 | 244318 | DAPK1 |
| 1120090 | 203140_at | NM_001706 | 155024 | BCL6 |
| 1131972 | 203154_s_at | NM_005884 | 20447 | PAK4 |
| 1131975 | 203160_s_at | NM_003958 | 24439 | RNF8 |
| 1120108 | 203175_at | NM_001665 | 75082 | ARHG |
| 1120120 | 203196_at | NM_005845 | 307915 | ABCC4 |
| 1120121 | 203198_at | NM_001261 | 150423 | CDK9 |
| 1131998 | 203210_s_at | NM_007370 | 443227 | RFC5 |
| 1120127 | 203213_at | NM_001786 | 334562 | CDC2 |
| 1132004 | 203217_s_at | NM_003896 | 415117 | SIAT9 |
| 1120128 | 203218_at | NM_002752 | 348446 | MAPK9 |
| 1120129 | 203221_at | NM_005077 | 406491 | TLE1 |
| 1132011 | 203229_s_at | NM_003993 | 73986 | CLK2 |
| 1132013 | 203232_s_at | NM_000332 | 434961 | SCA1 |
| 1120134 | 203233_at | NM_000418 | 75545 | IL4R |
| 1132016 | 203238_s_at | NM_000435 | 8546 | NOTCH3 |
| 1120137 | 203240_at | NM_003890 | 111732 | FCGBP |
| 1132022 | 203247_s_at | NM_006965 | 173911 | ZNF24 |
| 1120145 | 203256_at | NM_001793 | 191842 | CDH3 |
| 1132031 | 203266_s_at | NM_003010 | 134106 | MAP2K4 |
| 1132034 | 203271_s_at | NM_005148 | 410455 | UNC119 |
| 1132035 | 203272_s_at | NM_007275 | 8186 | TUSC2 |
| 1120152 | 203275_at | NM_002199 | 83795 | IRF2 |
| 1120153 | 203276_at | NM_005573 | 89497 | LMNB1 |
| 1120160 | 203288_at | NM_014686 | 436976 | KIAA0355 |
| 1120163 | 203302_at | NM_000788 | 709 | DCK |
| 1132058 | 203313_s_at | NM_003244 | 161999 | TGIF |
| 1120191 | 203373_at | NM_003877 | 405946 | SOCS2 |
| 1120194 | 203379_at | NM_002953 | 149957 | RPS6KA1 |
| 1120196 | 203386_at | NM_014832 | 173802 | TBC1D4 |
| 1132104 | 203387_s_at | NM_014832 | 173802 | TBC1D4 |
| 1120205 | 203405_at | NM_003720 | 5198 | DSCR2 |
| 1120214 | 203416_at | NM_000560 | 443057 | CD53 |
| 1120216 | 203418_at | NM_001237 | 85137 | CCNA2 |
| 1132122 | 203434_s_at | NM_000902 | 307734 | MME |
| 1132132 | 203454_s_at | NM_004045 | 279910 | ATOX1 |
| 1120254 | 203485_at | NM_021136 | 99947 | RTN1 |
| 1120261 | 203499_at | NM_004431 | 171596 | EPHA2 |
| 1120266 | 203507_at | NM_001251 | 246381 | CD68 |
| 1120267 | 203508_at | NM_001066 | 256278 | TNFRSF1B |
| 1120269 | 203510_at | NM_000245 | 419124 | MET |
| 1120272 | 203514_at | NM_002401 | 29282 | MAP3K3 |
| 1120274 | 203517_at | NM_006554 | 31584 | MTX2 |
| 1132159 | 203521_s_at | NM_014345 | 147868 | ZNF318 |
| 1120278 | 203528_at | NM_006378 | 511748 | SEMA4D |
| 1120288 | 203547_at | NM_000616 | 17483 | CD4 |
| 1120289 | 203552_at | NM_006575 | 246970 | MAP4K5 |
| 1132178 | 203554_x_at | NM_004219 | 350966 | PTTG1 |
| 1120299 | 203574_at | NM_005384 | 79334 | NFIL3 |
| 1120300 | 203575_at | NM_001896 | 82201 | CSNK2A2 |
| 1132196 | 203591_s_at | NM_000760 | 381027 | CSF3R |
| 1120316 | 203611_at | NM_005652 | 63335 | TERF2 |
| 1120317 | 203612_at | NM_004053 | 106880 | BYSL |
| 1120324 | 203627_at | NM_000875 | 239176 | IGF1R |
| 1132220 | 203632_s_at | NM_016235 | 448805 | GPRC5B |
| 1132223 | 203638_s_at | NM_000141 | 404081 | FGFR2 |
| 1132230 | 203649_s_at | NM_000300 | 76422 | PLA2G2A |
| 1120335 | 203652_at | NM_002419 | 432787 | MAP3K11 |
| 1132236 | 203661_s_at | NM_003275 | 374849 | TMOD1 |
| 1120350 | 203679_at | NM_006858 | 446686 | IL1RL1LG |
| 1120353 | 203685_at | NM_000633 | 79241 | BCL2 |

TABLE 2-continued

| UNIQID | Probe Set | Genbank Accession No. | Unigene ID Build 167 | Unigene Symbol |
|---|---|---|---|---|
| 1120355 | 203687_at | NM_002996 | 80420 | CX3CL1 |
| 1120356 | 203688_at | NM_000297 | 458291 | PKD2 |
| 1120359 | 203697_at | NM_001463 | 128453 | FRZB |
| 1132256 | 203702_s_at | NM_014640 | 169910 | KIAA0173 |
| 1132260 | 203706_s_at | NM_003507 | 173859 | FZD7 |
| 1120361 | 203708_at | NM_002600 | 188 | PDE4B |
| 1120362 | 203709_at | NM_000294 | 196177 | PHKG2 |
| 1120366 | 203717_at | NM_001935 | 44926 | DPP4 |
| 1120370 | 203723_at | NM_002221 | 78877 | ITPKB |
| 1120373 | 203728_at | NM_001188 | 93213 | BAK1 |
| 1120378 | 203738_at | NM_018356 | 151046 | FLJ11193 |
| 1120385 | 203755_at | NM_001211 | 36708 | BUB1B |
| 1120387 | 203758_at | NM_001334 | 75262 | CTSO |
| 1120389 | 203761_at | NM_006748 | 75367 | SLA |
| 1132288 | 203767_s_at | NM_000351 | 79876 | STS |
| 1132292 | 203771_s_at | NM_000712 | 435726 | BLVRA |
| 1132294 | 203777_s_at | NM_003952 | 32156 | RPS6KB2 |
| 1120400 | 203787_at | NM_012446 | 152207 | SSBP2 |
| 1120402 | 203794_at | NM_003607 | 18586 | CDC42BPA |
| 1132306 | 203795_s_at | NM_020993 | 371758 | BCL7A |
| 1120417 | 203827_at | NM_017983 | 9398 | FLJ10055 |
| 1120419 | 203830_at | NM_022344 | 9800 | NJMU-R1 |
| 1120422 | 203835_at | NM_005512 | 151641 | GARP |
| 1120423 | 203837_at | NM_005923 | 151988 | MAP3K5 |
| 1132329 | 203839_s_at | NM_005781 | 528296 | ACK1 |
| 1120425 | 203843_at | NM_004586 | 188361 | RPS6KA3 |
| 1132336 | 203853_s_at | NM_012296 | 30687 | GAB2 |
| 1120433 | 203856_at | NM_003384 | 422662 | VRK1 |
| 1132345 | 203868_s_at | NM_001078 | 109225 | VCAM1 |
| 1120438 | 203870_at | NM_022832 | 109268 | USP46 |
| 1132349 | 203881_s_at | NM_000109 | 169470 | DMD |
| 1132353 | 203887_s_at | NM_000361 | 2030 | THBD |
| 1132354 | 203890_s_at | NM_001348 | 153908 | DAPK3 |
| 1120465 | 203915_at | NM_002416 | 77367 | CXCL9 |
| 1120477 | 203934_at | NM_002253 | 12337 | KDR |
| 1120478 | 203935_at | NM_001105 | 150402 | ACVR1 |
| 1132375 | 203942_s_at | NM_004954 | 157199 | MARK2 |
| 1132376 | 203944_x_at | NM_007049 | 169963 | BTN2A1 |
| 1120483 | 203947_at | NM_001326 | 180034 | CSTF3 |
| 1120484 | 203949_at | NM_000250 | 458272 | MPO |
| 1120494 | 203967_at | NM_001254 | 405958 | CDC6 |
| 1120500 | 203979_at | NM_000784 | 82568 | CYP27A1 |
| 1132396 | 203988_s_at | NM_004480 | 118722 | FUT8 |
| 1120509 | 204000_at | NM_006578 | 155090 | GNB5 |
| 1132407 | 204005_s_at | NM_002583 | 406074 | PAWR |
| 1120520 | 204023_at | NM_002916 | 35120 | RFC4 |
| 1120524 | 204033_at | NM_004237 | 436187 | TRIP13 |
| 1120529 | 204039_at | NM_004364 | 76171 | CEBPA |
| 1132426 | 204049_s_at | NM_014721 | 102471 | C6orf56 |
| 1132428 | 204051_s_at | NM_003014 | 105700 | SFRP4 |
| 1120538 | 204057_at | NM_002163 | 14453 | ICSBP1 |
| 1132433 | 204059_s_at | NM_002395 | 14732 | ME1 |
| 1132434 | 204060_s_at | NM_005044 | 147996 | PRKX |
| 1132435 | 204062_s_at | NM_014683 | 168762 | ULK2 |
| 1120544 | 204068_at | NM_006281 | 166684 | STK3 |
| 1120553 | 204086_at | NM_006115 | 30743 | PRAME |
| 1120555 | 204090_at | NM_004197 | 444 | STK19 |
| 1132449 | 204092_s_at | NM_003600 | 250822 | STK6 |
| 1120562 | 204103_at | XM_003960674 | 75703 | CCL4 |
| 1120564 | 204106_at | NM_006285 | 79358 | TESK1 |
| 1120572 | 204116_at | NM_000206 | 84 | IL2RG |
| 1120574 | 204118_at | NM_001778 | 901 | CD48 |
| 1132460 | 204126_s_at | NM_003504 | 114311 | CDC45L |
| 1120580 | 204127_at | NM_002915 | 115474 | RFC3 |
| 1120581 | 204129_at | NM_004326 | 415209 | BCL9 |
| 1132462 | 204131_s_at | NM_001455 | 14845 | FOXO3A |
| 1120583 | 204133_at | NM_004704 | 153768 | RNU3IP2 |
| 1120588 | 204140_at | NM_003596 | 421194 | TPST1 |
| 1132468 | 204147_s_at | NM_007111 | 79353 | TFDP1 |
| 1120593 | 204150_at | NM_015136 | 301989 | STAB1 |
| 1120594 | 204154_at | NM_001801 | 442378 | CDO1 |
| 1120595 | 204156_at | NM_025164 | 444909 | KIAA0999 |
| 1120596 | 204159_at | NM_001262 | 4854 | CDKN2C |
| 1120601 | 204166_at | NM_014963 | 441129 | KIAA0963 |
| 1132479 | 204170_s_at | NM_001827 | 83758 | CKS2 |
| 1120605 | 204171_at | NM_003161 | 86858 | RPS6KB1 |
| 1132485 | 204183_s_at | NM_005160 | 445563 | ADRBK2 |

TABLE 2-continued

| UNIQID | Probe Set | Genbank Accession No. | Unigene ID Build 167 | Unigene Symbol |
|---|---|---|---|---|
| 1120615 | 204191_at | NM_000629 | 181315 | IFNAR1 |
| 1120616 | 204192_at | NM_001774 | 166556 | CD37 |
| 1120617 | 204193_at | NM_005198 | 439777 | CPT1B |
| 1120625 | 204208_at | NM_003800 | 27345 | RNGTT |
| 1132498 | 204211_x_at | NM_002759 | 439523 | PRKR |
| 1120630 | 204218_at | NM_014042 | 38044 | DKFZP564M082 |
| 1132504 | 204222_s_at | NM_006851 | 511765 | GLIPR1 |
| 1120633 | 204225_at | NM_006037 | 222874 | HDAC4 |
| 1120637 | 204232_at | NM_004106 | 433300 | FCER1G |
| 1132519 | 204247_s_at | NM_004935 | 166071 | CDK5 |
| 1132520 | 204249_s_at | NM_005574 | 283063 | LMO2 |
| 1120643 | 204252_at | NM_001798 | 19192 | CDK2 |
| 1132525 | 204255_s_at | NM_000376 | 2062 | VDR |
| 1120645 | 204257_at | NM_021727 | 21765 | FADS3 |
| 1132529 | 204265_s_at | NM_022107 | 288316 | GPSM3 |
| 1132531 | 204267_x_at | NM_004203 | 77783 | PKMYT1 |
| 1120651 | 204269_at | NM_006875 | 80205 | PIM2 |
| 1132536 | 204285_s_at | NM_021127 | 96 | PMAIP1 |
| 1120673 | 204301_at | NM_014867 | 5333 | KIAA0711 |
| 1132545 | 204306_s_at | NM_004357 | 512857 | CD151 |
| 1132547 | 204310_s_at | NM_003995 | 78518 | NPR2 |
| 1120695 | 204352_at | NM_004619 | 385685 | TRAF5 |
| 1120697 | 204355_at | NM_014966 | 323462 | DHX30 |
| 1132572 | 204357_s_at | NM_002314 | 36566 | LIMK1 |
| 1120700 | 204362_at | NM_003930 | 410745 | SCAP2 |
| 1120703 | 204368_at | NM_005630 | 83974 | SLCO2A1 |
| 1132584 | 204379_s_at | NM_000142 | 1420 | FGFR3 |
| 1120716 | 204392_at | NM_003656 | 512804 | CAMK1 |
| 1120717 | 204394_at | NM_003627 | 444159 | SLC43A1 |
| 1132592 | 204396_s_at | NM_005308 | 211569 | GRK5 |
| 1120720 | 204401_at | NM_002250 | 10082 | KCNN4 |
| 1120730 | 204415_at | NM_002038 | 287721 | G1P3 |
| 1120743 | 204440_at | NM_004233 | 79197 | CD83 |
| 1132614 | 204446_s_at | NM_000698 | 89499 | ALOX5 |
| 1120750 | 204454_at | NM_012317 | 45231 | LDOC1 |
| 1132628 | 204468_s_at | NM_005424 | 78824 | TIE |
| 1120755 | 204470_at | NM_001511 | 789 | CXCL1 |
| 1120765 | 204484_at | NM_002646 | 343329 | PIK3C2B |
| 1132636 | 204490_s_at | NM_000610 | 306278 | CD44 |
| 1120770 | 204493_at | NM_001196 | 300825 | BID |
| 1120779 | 204510_at | NM_003503 | 28853 | CDC7 |
| 1120780 | 204511_at | NM_014808 | 301283 | FARP2 |
| 1120785 | 204517_at | NM_000943 | 110364 | PPIC |
| 1120789 | 204524_at | NM_002613 | 154729 | PDPK1 |
| 1132651 | 204529_s_at | NM_014729 | 439767 | TOX |
| 1120792 | 204533_at | NM_001565 | 413924 | CXCL10 |
| 1120803 | 204549_at | NM_014002 | 321045 | IKBKE |
| 1120808 | 204562_at | NM_002460 | 127686 | IRF4 |
| 1120809 | 204563_at | NM_000655 | 82848 | SELL |
| 1120813 | 204568_at | NM_014924 | 414809 | KIAA0831 |
| 1120814 | 204569_at | NM_014920 | 417022 | ICK |
| 1120818 | 204579_at | NM_002011 | 165950 | FGFR4 |
| 1120824 | 204589_at | NM_014840 | 200598 | ARK5 |
| 1120825 | 204591_at | NM_006614 | 388344 | CHL1 |
| 1120828 | 204600_at | NM_004443 | 2913 | EPHB3 |
| 1120832 | 204604_at | NM_012395 | 57856 | PFTK1 |
| 1120834 | 204606_at | NM_002989 | 57907 | CCL21 |
| 1120838 | 204612_at | NM_006823 | 433700 | PKIA |
| 1120839 | 204613_at | NM_002661 | 512298 | PLCG2 |
| 1120846 | 204632_at | NM_003942 | 105584 | RPS6KA4 |
| 1132700 | 204633_s_at | NM_004755 | 109058 | RPS6KA5 |
| 1120847 | 204634_at | NM_003157 | 433008 | NEK4 |
| 1120853 | 204641_at | NM_002497 | 153704 | NEK2 |
| 1120854 | 204642_at | NM_001400 | 154210 | EDG1 |
| 1120858 | 204647_at | NM_004838 | 410683 | HOMER3 |
| 1120863 | 204655_at | NM_002985 | 489044 | CCL5 |
| 1120875 | 204674_at | NM_006152 | 124922 | LRMP |
| 1120880 | 204682_at | NM_000428 | 105689 | LTBP2 |
| 1120881 | 204683_at | NM_000873 | 433303 | ICAM2 |
| 1132726 | 204707_s_at | NM_002747 | 433728 | MAPK4 |
| 1120900 | 204718_at | NM_004445 | 380089 | EPHB6 |
| 1132734 | 204724_s_at | NM_001853 | 126248 | COL9A3 |
| 1120918 | 204754_at | NM_002126 | 250692 | HLF |
| 1120923 | 204765_at | NM_005435 | 334 | ARHGEF5 |
| 1120925 | 204773_at | NM_001142784 | 204891 | IL11RA |
| 1132762 | 204777_s_at | NM_002371 | 80395 | MAL |
| 1132766 | 204781_s_at | NM_000043 | 82359 | TNFRSF6 |

TABLE 2-continued

| UNIQID | Probe Set | Genbank Accession No. | Unigene ID Build 167 | Unigene Symbol |
|---|---|---|---|---|
| 1132768 | 204785_x_at | NM_000874 | 512211 | IFNAR2 |
| 1132775 | 204803_s_at | NM_004165 | 1027 | RRAD |
| 1132780 | 204811_s_at | NM_006030 | 389415 | CACNA2D2 |
| 1120946 | 204813_at | NM_002753 | 25209 | MAPK10 |
| 1120952 | 204822_at | NM_003318 | 169840 | TTK |
| 1120955 | 204825_at | NM_014791 | 184339 | MELK |
| 1120958 | 204831_at | NM_001260 | 397734 | CDK8 |
| 1132787 | 204832_s_at | NM_004329 | 2534 | BMPR1A |
| 1132799 | 204859_s_at | NM_001160 | 373575 | APAF1 |
| 1120976 | 204867_at | NM_005258 | 245644 | GCHFR |
| 1120980 | 204872_at | NM_007005 | 494269 | TLE4 |
| 1132809 | 204878_s_at | NM_004783 | 291623 | PSK |
| 1120986 | 204886_at | NM_014264 | 172052 | PLK4 |
| 1132818 | 204891_s_at | NM_005356 | 1765 | LCK |
| 1132825 | 204900_x_at | NM_003864 | 512813 | SAP30 |
| 1132830 | 204908_s_at | NM_005178 | 31210 | BCL3 |
| 1120993 | 204912_at | NM_001558 | 327 | IL10RA |
| 1132834 | 204914_s_at | NM_003108 | 432638 | SOX11 |
| 1121000 | 204924_at | NM_003264 | 519033 | TLR2 |
| 1121005 | 204932_at | NM_002546 | 81791 | TNFRSF11B |
| 1121007 | 204936_at | NM_004579 | 440835 | SF1 |
| 1121012 | 204947_at | NM_005225 | 96055 | E2F1 |
| 1121013 | 204949_at | NM_002162 | 353214 | ICAM3 |
| 1132850 | 204954_s_at | NM_004714 | 130988 | DYRK1B |
| 1121021 | 204958_at | NM_004073 | 153640 | PLK3 |
| 1132851 | 204961_s_at | NM_000265 | 1583 | |
| 1132852 | 204962_s_at | NM_001809 | 1594 | CENPA |
| 1121028 | 204968_at | NM_021184 | 247323 | APOM |
| 1121029 | 204971_at | NM_005213 | 412999 | CSTA |
| 1121033 | 204975_at | NM_001424 | 356835 | EMP2 |
| 1132860 | 204986_s_at | NM_016151 | 291623 | PSK |
| 1132862 | 204990_s_at | NM_000213 | 85266 | ITGB4 |
| 1132866 | 204998_s_at | NM_012068 | 9754 | ATF5 |
| 1132874 | 205013_s_at | NM_000675 | 197029 | ADORA2A |
| 1121054 | 205016_at | NM_003236 | 170009 | TGFA |
| 1121057 | 205026_at | NM_012448 | 434992 | STAT5B |
| 1132883 | 205027_s_at | NM_005204 | 432453 | MAP3K8 |
| 1121061 | 205032_at | NM_002203 | 387725 | ITGA2 |
| 1121062 | 205034_at | NM_057749 | 408658 | CCNE2 |
| 1132890 | 205049_s_at | NM_001783 | 79630 | CD79A |
| 1132892 | 205051_s_at | NM_000222 | 81665 | KIT |
| 1121073 | 205052_at | NM_001698 | 81886 | AUH |
| 1121076 | 205055_at | NM_002208 | 389133 | ITGAE |
| 1121082 | 205067_at | NM_000576 | 126256 | IL1B |
| 1121100 | 205098_at | NM_001295 | 301921 | CCR1 |
| 1121102 | 205101_at | NM_000246 | 126714 | MHC2TA |
| 1132918 | 205114_s_at | NM_002983 | 73817 | CCL3 |
| 1132920 | 205119_s_at | NM_002029 | 753 | FPR1 |
| 1121115 | 205124_at | NM_005919 | 78881 | MEF2B |
| 1121117 | 205126_at | NM_006296 | 82771 | VRK2 |
| 1121120 | 205130_at | NM_014226 | 104119 | RAGE |
| 1121129 | 205159_at | NM_000395 | 285401 | CSF2RB |
| 1121136 | 205168_at | NM_006182 | 440905 | DDR2 |
| 1132953 | 205180_s_at | NM_001109 | 86947 | ADAM8 |
| 1121143 | 205184_at | NM_004485 | 447973 | GNG4 |
| 1121149 | 205192_at | NM_003954 | 440315 | MAP3K14 |
| 1132959 | 205198_s_at | NM_000052 | 606 | ATP7A |
| 1121159 | 205205_at | NM_006509 | 307905 | RELB |
| 1121161 | 205207_at | NM_000600 | 512234 | IL6 |
| 1132961 | 205212_s_at | NM_014716 | 337242 | CENTB1 |
| 1121166 | 205214_at | NM_004226 | 88297 | STK17B |
| 1121170 | 205220_at | NM_006018 | 458425 | HM74 |
| 1121186 | 205242_at | NM_006419 | 100431 | CXCL13 |
| 1121190 | 205247_at | NM_004557 | 436100 | NOTCH4 |
| 1121195 | 205253_at | NM_002585 | 408222 | PBX1 |
| 1132973 | 205255_x_at | NM_003202 | 169294 | TCF7 |
| 1121201 | 205263_at | NM_003921 | 193516 | BCL10 |
| 1121203 | 205266_at | NM_002309 | 2250 | LIF |
| 1121205 | 205269_at | NM_005565 | 2488 | LCP2 |
| 1132979 | 205271_s_at | NM_012119 | 26322 | CCRK |
| 1121217 | 205291_at | NM_000878 | 75596 | IL2RB |
| 1121220 | 205296_at | NM_002895 | 87 | RBL1 |
| 1132990 | 205297_s_at | NM_000626 | 89575 | CD79B |
| 1132994 | 205301_s_at | NM_002542 | 380271 | OGG1 |
| 1132996 | 205306_x_at | NM_003679 | 409081 | KMO |
| 1121228 | 205312_at | NM_003120 | 157441 | SPI1 |
| 1133004 | 205327_s_at | NM_001616 | 389846 | ACVR2 |

TABLE 2-continued

| UNIQID | Probe Set | Genbank Accession No. | Unigene ID Build 167 | Unigene Symbol |
|---|---|---|---|---|
| 1121248 | 205345_at | NM_000465 | 54089 | BARD1 |
| 1133011 | 205347_s_at | NM_021992 | 56145 | TMSNB |
| 1121265 | 205372_at | NM_002655 | 14968 | PLAG1 |
| 1133021 | 205377_s_at | NM_000665 | 154495 | ACHE |
| 1133024 | 205383_s_at | NM_015642 | 436987 | ZNF288 |
| 1133030 | 205392_s_at | NM_032962 | 272493 | CCL15 |
| 1121276 | 205394_at | NM_001274 | 24529 | CHEK1 |
| 1121278 | 205399_at | NM_004734 | 21355 | DCAMKL1 |
| 1121281 | 205403_at | NM_004633 | 25333 | 1L1R2 |
| 1121287 | 205411_at | NM_006282 | 35140 | STK4 |
| 1121290 | 205418_at | NM_002005 | 7636 | FES |
| 1121291 | 205419_at | NM_004951 | 784 | EBI2 |
| 1133042 | 205422_s_at | NM_004791 | 311054 | ITGBL1 |
| 1133047 | 205434_s_at | NM_014911 | 528338 | AAK1 |
| 1133049 | 205436_s_at | NM_002105 | 147097 | H2AFX |
| 1121301 | 205437_at | NM_006385 | 449971 | ZNF134 |
| 1121306 | 205443_at | NM_003082 | 179312 | SNAPC1 |
| 1121309 | 205449_at | NM_013299 | 23642 | HSU79266 |
| 1121315 | 205455_at | NM_002447 | 2942 | MST1R |
| 1121316 | 205456_at | NM_000733 | 3003 | CD3E |
| 1121322 | 205467_at | NM_001230 | 5353 | CASP10 |
| 1121326 | 205476_at | NM_004591 | 75498 | CCL20 |
| 1133065 | 205479_s_at | NM_002658 | 77274 | PLAU |
| 1133068 | 205483_s_at | NM_005101 | 458485 | G1P2 |
| 1121329 | 205484_at | NM_014450 | 88012 | SIT |
| 1121331 | 205486_at | NM_007170 | 8980 | TESK2 |
| 1121343 | 205504_at | NM_000061 | 159494 | BTK |
| 1133076 | 205512_s_at | NM_004208 | 18720 | PDCD8 |
| 1133080 | 205526_s_at | NM_007044 | 440341 | KATNA1 |
| 1133091 | 205544_s_at | NM_001877 | 73792 | CR2 |
| 1133093 | 205546_s_at | NM_003331 | 75516 | TYK2 |
| 1121368 | 205551_at | NM_014848 | 8071 | SV2B |
| 1133099 | 205554_s_at | NM_004944 | 88646 | DNASE1L3 |
| 1121371 | 205558_at | NM_004620 | 444172 | TRAF6 |
| 1133102 | 205565_s_at | NM_000144 | 360041 | FRDA |
| 1121380 | 205569_at | NM_014398 | 10887 | LAMP3 |
| 1121383 | 205572_at | NM_001147 | 115181 | ANGPT2 |
| 1121387 | 205578_at | NM_004560 | 208080 | ROR2 |
| 1133111 | 205593_s_at | NM_002606 | 389777 | PDE9A |
| 1121400 | 205599_at | NM_005658 | 223474 | TRAF1 |
| 1133117 | 205607_s_at | NM_020423 | 435560 | PACE-1 |
| 1121404 | 205609_at | NM_001146 | 2463 | ANGPT1 |
| 1121406 | 205611_at | NM_003809 | | TNFSF12 |
| 1121408 | 205613_at | NM_016524 | 258326 | LOC51760 |
| 1133119 | 205614_x_at | NM_020998 | 512587 | MST1 |
| 1121414 | 205621_at | NM_006020 | 94542 | ALKBH |
| 1121436 | 205659_at | NM_014707 | 487662 | HDAC9 |
| 1121444 | 205668_at | NM_002349 | 153563 | LY75 |
| 1133138 | 205671_s_at | NM_002120 | 1802 | HLA-DOB |
| 1133141 | 205677_s_at | NR_002605 | 344524 | DLEU1 |
| 1121452 | 205681_at | NM_004049 | 227817 | BCL2A1 |
| 1133148 | 205692_s_at | NM_001775 | 174944 | CD38 |
| 1133150 | 205698_s_at | NM_002758 | 256924 | MAP2K6 |
| 1121468 | 205707_at | NM_014339 | 129751 | IL17R |
| 1133156 | 205713_s_at | NM_000095 | 1584 | COMP |
| 1121473 | 205718_at | NM_000889 | 1741 | ITGB7 |
| 1121482 | 205729_at | NM_003999 | 238648 | OSMR |
| 1121497 | 205758_at | NM_001768 | 85258 | CD8A |
| 1121511 | 205780_at | NM_001197 | 155419 | BIK |
| 1133184 | 205786_s_at | NM_000632 | 172631 | ITGAM |
| 1121516 | 205789_at | NM_001766 | 1799 | CD1D |
| 1121518 | 205792_at | NM_003881 | 194679 | WISP2 |
| 1133192 | 205801_s_at | NM_015376 | 24024 | RASGRP3 |
| 1133195 | 205805_s_at | NM_005012 | 274243 | ROR1 |
| 1121533 | 205821_at | NM_007360 | 387787 | KLRK1 |
| 1121542 | 205831_at | NM_001767 | 89476 | CD2 |
| 1133210 | 205842_s_at | NM_004972 | 434374 | JAK2 |
| 1121546 | 205844_at | NM_004666 | 12114 | VNN1 |
| 1121554 | 205854_at | NM_003324 | 437046 | TULP3 |
| 1121558 | 205858_at | NM_002507 | 415768 | NGFR |
| 1121559 | 205859_at | NM_004271 | 184018 | LY86 |
| 1121560 | 205861_at | NM_003121 | 437905 | SPIB |
| 1121564 | 205865_at | NM_005224 | 437783 | ARID3A |
| 1133216 | 205872_x_at | XM_003846520 | 502577 | PDE4DIP |
| 1121572 | 205876_at | NM_002310 | 446501 | LIFR |
| 1121573 | 205878_at | NM_002702 | 2815 | POU6F1 |
| 1133219 | 205879_x_at | NM_020630 | 350321 | RET |

TABLE 2-continued

| UNIQID | Probe Set | Genbank Accession No. | Unigene ID Build 167 | Unigene Symbol |
|---|---|---|---|---|
| 1121574 | 205880_at | NM_002742 | 2891 | PRKCM |
| 1133227 | 205895_s_at | NM_004741 | 75337 | NOLC1 |
| 1121584 | 205898_at | NM_001337 | 78913 | CX3CR1 |
| 1121585 | 205899_at | NM_003914 | 417050 | CCNA1 |
| 1121587 | 205901_at | NM_006228 | 371809 | PNOC |
| 1121589 | 205904_at | NM_000247 | 90598 | MICA |
| 1133232 | 205910_s_at | NM_001807 | 406160 | CEL |
| 1121629 | 205965_at | NM_006399 | 41691 | BATF |
| 1133252 | 205977_s_at | NM_005232 | 89839 | EPHA1 |
| 1121643 | 205986_at | NM_004920 | 514575 | AATK |
| 1121645 | 205988_at | NM_003874 | 398093 | CD84 |
| 1133260 | 205992_s_at | NM_000585 | 528402 | IL15 |
| 1121650 | 206002_at | NM_005756 | 421137 | GPR64 |
| 1121655 | 206009_at | NM_002207 | 222 | ITGA9 |
| 1133272 | 206028_s_at | NM_006343 | 306178 | MERTK |
| 1133275 | 206036_s_at | NM_002908 | 44313 | REL |
| 1121680 | 206049_at | NM_003005 | 73800 | SELP |
| 1133296 | 206070_s_at | NM_005233 | 123642 | EPHA3 |
| 1133299 | 206075_s_at | NM_001895 | 446484 | CSNK2A1 |
| 1121689 | 206076_at | NM_006992 | 155586 | B7 |
| 1121693 | 206080_at | NM_014638 | 170156 | KIAA0450 |
| 1121695 | 206082_at | NR_040662 | 511759 | HCP5 |
| 1133300 | 206085_s_at | NM_001902 | 19904 | CTH |
| 1121711 | 206106_at | NM_002969 | 432642 | MAPK12 |
| 1121717 | 206114_at | NM_004438 | 73964 | EPHA4 |
| 1121720 | 206118_at | NM_003151 | 80642 | STAT4 |
| 1121722 | 206120_at | NM_001772 | 83731 | CD33 |
| 1121726 | 206126_at | NM_001716 | 113916 | BLR1 |
| 1121739 | 206142_at | NM_003436 | 85863 | ZNF135 |
| 1121743 | 206148_at | NM_002183 | 460433 | IL3RA |
| 1121745 | 206150_at | NM_001242 | 355307 | TNFRSF7 |
| 1121757 | 206170_at | NM_000024 | 2551 | ADRB2 |
| 1121759 | 206172_at | NM_000640 | 336046 | IL13RA2 |
| 1121760 | 206176_at | NM_001718 | 285671 | BMP6 |
| 1121762 | 206181_at | NM_003037 | 32970 | SLAMF1 |
| 1121767 | 206187_at | NM_000960 | 458324 | PTGIR |
| 1121780 | 206206_at | NM_005582 | 87205 | LY64 |
| 1121783 | 206211_at | NM_000450 | 89546 | SELE |
| 1121788 | 206216_at | NM_014370 | 104865 | STK23 |
| 1121792 | 206222_at | NM_003841 | 119684 | TNFRSF10C |
| 1121793 | 206223_at | NM_014916 | 122708 | LMTK2 |
| 1121809 | 206247_at | NM_005931 | 211580 | MICB |
| 1121814 | 206255_at | NM_001715 | 389900 | BLK |
| 1133355 | 206267_s_at | NM_002378 | 437808 | MATK |
| 1121828 | 206271_at | NM_003265 | 29499 | TLR3 |
| 1121834 | 206279_at | NR_028062 | 183165 | PRKY |
| 1133358 | 206283_s_at | NM_003189 | 73828 | TAL1 |
| 1121841 | 206291_at | NM_006183 | 80962 | NTS |
| 1121844 | 206295_at | NM_001562 | 83077 | IL18 |
| 1121848 | 206301_at | NM_003215 | 278005 | TEC |
| 1121853 | 206310_at | NM_021114 | 98243 | SPINK2 |
| 1121854 | 206312_at | NM_004963 | 171470 | GUCY2C |
| 1121857 | 206315_at | NM_004750 | 114948 | CRLF1 |
| 1133376 | 206324_s_at | NM_014326 | 129208 | DAPK2 |
| 1121869 | 206336_at | NM_002993 | 164021 | CXCL6 |
| 1121870 | 206337_at | NM_001838 | 1652 | CCR7 |
| 1121874 | 206341_at | NM_000417 | 130058 | IL2RA |
| 1133388 | 206362_x_at | NM_002446 | 435014 | MAP3K10 |
| 1121887 | 206363_at | NM_005360 | 134859 | MAF |
| 1133389 | 206366_x_at | NM_003175 | 174228 | XCL1 |
| 1133392 | 206380_s_at | NM_002621 | 53155 | RFC |
| 1133397 | 206390_x_at | NM_002619 | 81564 | PF4 |
| 1133400 | 206398_s_at | NM_001770 | 96023 | CD19 |
| 1133405 | 206407_s_at | NM_005408 | 414629 | CCL13 |
| 1133406 | 206411_s_at | NM_005158 | 159472 | ABL2 |
| 1121918 | 206412_at | NM_005246 | 121558 | FER |
| 1133407 | 206413_s_at | NM_004918 | 144519 | TCL6 |
| 1133408 | 206414_s_at | NM_003887 | 12802 | DDEF2 |
| 1121947 | 206464_at | NM_001721 | 27372 | BMX |
| 1133430 | 206467_x_at | NM_003823 | 348183 | TNFRSF6B |
| 1121953 | 206478_at | NR_026800 | 38365 | KIAA0125 |
| 1121956 | 206482_at | NM_005975 | 51133 | PTK6 |
| 1121959 | 206486_at | NM_002286 | 409523 | LAG3 |
| 1121963 | 206493_at | NM_000419 | 411312 | ITGA2B |
| 1121966 | 206498_at | NM_000275 | 82027 | OCA2 |
| 1133445 | 206499_s_at | NM_001269 | 196769 | CHC1 |
| 1121970 | 206508_at | NM_001252 | 99899 | TNFSF7 |

TABLE 2-continued

| UNIQID | Probe Set | Genbank Accession No. | Unigene ID Build 167 | Unigene Symbol |
|---|---|---|---|---|
| 1133453 | 206518_s_at | NM_003835 | 117149 | RGS9 |
| 1121996 | 206545_at | NM_006139 | 1987 | CD28 |
| 1122007 | 206569_at | NM_006850 | 411311 | IL24 |
| 1133476 | 206571_s_at | NM_004834 | 3628 | MAP4K4 |
| 1122009 | 206575_at | NM_003159 | 50905 | CDKL5 |
| 1122021 | 206591_at | NM_000448 | 73958 | RAG1 |
| 1122036 | 206618_at | NM_003855 | 159301 | IL18R1 |
| 1122051 | 206637_at | NM_014879 | 2465 | GPR105 |
| 1122053 | 206641_at | NM_001192 | 2556 | TNFRSF17 |
| 1122065 | 206660_at | NM_020070 | 348935 | IGLL1 |
| 1122075 | 206674_at | NM_004119 | 385 | FLT3 |
| 1133515 | 206687_s_at | NM_002831 | 63489 | PTPN6 |
| 1122087 | 206693_at | NM_000880 | 72927 | IL7 |
| 1122091 | 206702_at | NM_000459 | 89640 | TEK |
| 1122104 | 206718_at | NM_002315 | 1149 | LMO1 |
| 1122112 | 206729_at | NM_001243 | 1314 | TNFRSF8 |
| 1122131 | 206756_at | NM_019886 | 138155 | CHST7 |
| 1133538 | 206760_s_at | NM_002002 | 1416 | FCER2 |
| 1122139 | 206766_at | NM_003637 | 158237 | ITGA10 |
| 1122156 | 206794_at | NM_005235 | 1939 | ERBB4 |
| 1122165 | 206804_at | NM_000073 | 2259 | CD3G |
| 1122181 | 206828_at | NM_003328 | 29877 | TXK |
| 1133565 | 206846_s_at | NM_006044 | 6764 | HDAC6 |
| 1133568 | 206854_s_at | NM_003188 | 290346 | MAP3K7 |
| 1133569 | 206855_s_at | NM_003773 | 76873 | HYAL2 |
| 1133576 | 206864_s_at | NM_003806 | 87247 | HRK |
| 1133577 | 206874_s_at | NM_014720 | 105751 | SLK |
| 1133580 | 206881_s_at | NM_006865 | 113277 | LILRA3 |
| 1122215 | 206887_at | NM_001296 | 528317 | CCBP2 |
| 1122217 | 206890_at | NM_005535 | 223894 | IL12RB1 |
| 1122219 | 206892_at | NM_020547 | 437877 | AMHR2 |
| 1122230 | 206907_at | NM_003811 | 1524 | TNFSF9 |
| 1122241 | 206923_at | NM_002737 | 349611 | PRKCA |
| 1133595 | 206926_s_at | NM_000641 | 1721 | IL11 |
| 1122253 | 206943_at | NM_004612 | 28005 | TGFBR1 |
| 1122274 | 206974_at | NM_006564 | 34526 | CXCR6 |
| 1122275 | 206975_at | NM_000595 | 36 | LTA |
| 1122277 | 206978_at | NM_001123041 | 511794 | CCR2 |
| 1122281 | 206983_at | NM_004367 | 46468 | CCR6 |
| 1122284 | 206988_at | NM_005624 | 310511 | CCL25 |
| 1133618 | 206991_s_at | NM_000579 | 511796 | CCR5 |
| 1122288 | 206999_at | NM_001559 | 413608 | IL12RB2 |
| 1122292 | 207008_at | NM_001557 | 846 | IL8RB |
| 1133629 | 207011_s_at | NM_002821 | 90572 | PTK7 |
| 1122304 | 207029_at | NM_000899 | 1048 | KITLG |
| 1122327 | 207061_at | NM_001433 | 137575 | ERN1 |
| 1122335 | 207073_at | NM_003948 | 143241 | CDKL2 |
| 1133652 | 207076_s_at | NM_000050 | 160786 | ASS |
| 1122344 | 207094_at | NM_000634 | 194778 | IL8RA |
| 1122353 | 207111_at | NM_001974 | 2375 | EMR1 |
| 1133672 | 207113_s_at | NM_000594 | 241570 | TNF |
| 1133676 | 207121_s_at | NM_002748 | 271980 | MAPK6 |
| 1122380 | 207160_at | NM_000882 | 673 | IL12A |
| 1133694 | 207163_s_at | NM_005163 | 368861 | AKT1 |
| 1122382 | 207165_at | NM_012484 | 72550 | HMMR |
| 1133700 | 207173_x_at | NM_001797 | 443435 | CDH11 |
| 1133701 | 207176_s_at | NM_005191 | 838 | CD80 |
| 1133702 | 207178_s_at | NM_002031 | 89426 | FRK |
| 1122388 | 207179_at | NM_005521 | 89583 | TLX1 |
| 1133704 | 207181_s_at | NM_001227 | 9216 | CASP7 |
| 1122394 | 207188_at | NM_001258 | 100009 | CDK3 |
| 1133708 | 207194_s_at | NM_001544 | 512159 | ICAM4 |
| 1122400 | 207199_at | NM_198253 | 439911 | TERT |
| 1122412 | 207216_at | NM_001244 | 177136 | TNFSF8 |
| 1122420 | 207228_at | NM_002732 | 158029 | PRKACG |
| 1133724 | 207239_s_at | NM_006201 | 171834 | PCTK1 |
| 1122428 | 207245_at | NM_001077 | 183596 | UGT2B17 |
| 1133731 | 207253_s_at | NM_016936 | 21479 | UBN1 |
| 1122449 | 207277_at | NM_021155 | 278694 | CD209 |
| 1122471 | 207312_at | NM_006213 | 512612 | PHKG1 |
| 1133753 | 207314_x_at | NM_006737 | 380156 | KIR3DL1 |
| 1133755 | 207318_s_at | NM_003718 | 404501 | CDC2L5 |
| 1133757 | 207320_x_at | NM_004602 | 6113 | STAU |
| 1133766 | 207339_s_at | NM_002341 | 376208 | LTB |
| 1122491 | 207354_at | NM_004590 | 10458 | CCL16 |
| 1133778 | 207375_s_at | NM_002189 | 12503 | IL15RA |
| 1133786 | 207396_s_at | NM_005787 | 153591 | ALG3 |

TABLE 2-continued

| UNIQID | Probe Set | Genbank Accession No. | Unigene ID Build 167 | Unigene Symbol |
|---|---|---|---|---|
| 1133801 | 207426_s_at | NM_003326 | 181097 | TNFSF4 |
| 1133802 | 207428_x_at | NM_033486 | 454861 | CDC2L2 |
| 1122537 | 207433_at | NM_000572 | 193717 | IL10 |
| 1122541 | 207442_at | NM_000759 | 2233 | CSF3 |
| 1133810 | 207445_s_at | NM_006641 | 225946 | CCR9 |
| 1122544 | 207446_at | NM_006068 | 366986 | TLR6 |
| 1133829 | 207497_s_at | NM_000139 | 386748 | MS4A2 |
| 1122581 | 207505_at | NM_006259 | 41749 | PRKG2 |
| 1133834 | 207509_s_at | NM_002288 | 43803 | LAIR2 |
| 1122596 | 207533_at | NM_002981 | 72918 | CCL1 |
| 1133846 | 207536_s_at | NM_001561 | 528403 | TNFRSF9 |
| 1122599 | 207538_at | NM_000589 | 73917 | IL4 |
| 1133848 | 207540_s_at | NM_003177 | 192182 | SYK |
| 1122602 | 207550_at | NM_005373 | 82906 | CDC20 |
| 1122609 | 207568_at | NM_004198 | 103128 | CHRNA6 |
| 1122610 | 207569_at | NM_002944 | 1041 | ROS1 |
| 1133867 | 207571_x_at | NM_004848 | 10649 | C1orf38 |
| 1133869 | 207574_s_at | NM_015675 | 110571 | GADD45B |
| 1133901 | 207633_s_at | NM_005592 | 156465 | MUSK |
| 1122640 | 207634_at | NM_005018 | 158297 | PDCD1 |
| 1122645 | 207641_at | NM_012452 | 158341 | TNFRSF13B |
| 1133904 | 207643_s_at | NM_001065 | 159 | TNFRSF1A |
| 1133910 | 207655_s_at | NM_013314 | 167746 | BLNK |
| 1122664 | 207681_at | NM_001504 | 198252 | CXCR3 |
| 1133931 | 207697_x_at | NM_005874 | 306230 | LILRB2 |
| 1122680 | 207709_at | NM_006252 | 256067 | PRKAA2 |
| 1122710 | 207766_at | NM_004196 | 380788 | CDKL1 |
| 1133998 | 207826_s_at | NM_002167 | 76884 | ID3 |
| 1122738 | 207840_at | NM_007053 | 81743 | CD160 |
| 1122740 | 207844_at | NM_002188 | 845 | IL13 |
| 1122743 | 207849_at | NM_000586 | 89679 | IL2 |
| 1122744 | 207850_at | NM_002090 | 89690 | CXCL3 |
| 1122749 | 207861_at | NM_002990 | 80420 | CX3CL1 |
| 1122763 | 207884_at | NM_000180 | 309958 | GUCY2D |
| 1122767 | 207892_at | NM_000074 | 652 | TNFSF5 |
| 1122772 | 207900_at | NM_002987 | 66742 | CCL17 |
| 1122773 | 207901_at | NM_002187 | 674 | IL12B |
| 1122774 | 207902_at | NM_000564 | 68876 | IL5RA |
| 1122775 | 207906_at | NM_000588 | 694 | IL3 |
| 1122776 | 207907_at | NM_003807 | 129708 | TNFSF14 |
| 1122796 | 207952_at | NM_000879 | 2247 | IL5 |
| 1134069 | 207979_s_at | NM_004931 | 405667 | CD8B1 |
| 1134076 | 207988_s_at | NM_005731 | 83583 | ARPC2 |
| 1134083 | 207996_s_at | NM_181481 | 285091 | C18orf1 |
| 1134095 | 208018_s_at | NM_002110 | 89555 | HCK |
| 1134109 | 208037_s_at | NM_130760 | 102598 | MADCAM1 |
| 1122824 | 208038_at | NM_003854 | 416814 | IL1RL2 |
| 1122834 | 208059_at | NM_005201 | 113222 | CCR8 |
| 1134133 | 208075_s_at | NM_006273 | 251526 | CCL7 |
| 1134145 | 208091_s_at | NM_030796 | 4750 | DKFZP564K0822 |
| 1134200 | 208161_s_at | NM_003786 | 90786 | ABCC3 |
| 1134212 | 208178_x_at | NM_007118 | 367689 | TRIO |
| 1134220 | 208189_s_at | NM_000260 | 370421 | MYO7A |
| 1122863 | 208193_at | NM_000590 | 960 | IL9 |
| 1122864 | 208195_at | NM_003319 | 434384 | TTN |
| 1122865 | 208200_at | NM_000575 | 1722 | IL1A |
| 1134230 | 208206_s_at | NM_153819 | 99491 | RASGRP2 |
| 1134233 | 208212_s_at | NM_004304 | 410680 | ALK |
| 1134270 | 208284_x_at | NM_005265 | 352119 | GGT1 |
| 1134271 | 208286_x_at | NM_002701 | 249184 | POU5F1 |
| 1134280 | 208303_s_at | NM_022148 | 287729 | CRLF2 |
| 1122914 | 208304_at | NM_001837 | 506190 | CCR3 |
| 1134296 | 208335_s_at | NM_002036 | 183 | FY |
| 1134316 | 208365_s_at | NM_182982 | 32959 | GRK4 |
| 1122939 | 208376_at | NM_005508 | 184926 | CCR4 |
| 1134361 | 208426_x_at | NM_002255 | 515605 | KIR2DL4 |
| 1134370 | 208438_s_at | NM_005248 | 1422 | FGR |
| 1122956 | 208450_at | NM_006498 | 113987 | LGALS2 |
| 1134379 | 208451_s_at | NM_007293 | 150833 | C4A |
| 1122983 | 208495_at | NM_021025 | 249125 | TLX3 |
| 1122994 | 208524_at | NM_005290 | 159900 | GPR15 |
| 1134422 | 208536_s_at | NM_006538 | 84063 | BCL2L11 |
| 1134424 | 208540_x_at | NM_020672 |  | S100A14 |
| 1123026 | 208578_at | NM_006514 | 250443 | SCN10A |
| 1134457 | 208605_s_at | NM_002529 | 406293 | NTRK1 |
| 1134480 | 208634_s_at | NM_012090 | 372463 | MACF1 |
| 1123038 | 208636_at | NM_001102 | 119000 | ACTN1 |

TABLE 2-continued

| UNIQID | Probe Set | Genbank Accession No. | Unigene ID Build 167 | Unigene Symbol |
|---|---|---|---|---|
| 1123039 | 208638_at | NM_005742 | 212102 | P5 |
| 1134494 | 208657_s_at | NM_006640 | 288094 | MSF |
| 1123052 | 208680_at | NM_002574 | 180909 | PRDX1 |
| 1123053 | 208683_at | NM_001748 | 350899 | CAPN2 |
| 1134517 | 208690_s_at | NM_020992 | 75807 | PDLIM1 |
| 1123055 | 208691_at | NM_003234 | 185726 | TFRC |
| 1134523 | 208700_s_at | NM_001064 | 89643 | TKT |
| 1134532 | 208711_s_at | NM_053056 | 371468 | CCND1 |
| 1134533 | 208716_s_at | NM_019026 | 93832 | LOC54499 |
| 1134542 | 208729_x_at | NM_005514 | 77961 | HLA-B |
| 1123086 | 208774_at | NM_001893 | 378918 | CSNK1D |
| 1134582 | 208794_s_at | NM_003072 | 78202 | SMARCA4 |
| 1134593 | 208812_x_at | NM_002117 | 274485 | HLA-C |
| 1123105 | 208820_at | NM_005607 | 434281 | PTK2 |
| 1123108 | 208828_at | NM_017443 | 108112 | POLE3 |
| 1134615 | 208851_s_at | NM_006288 | 134643 | THY1 |
| 1134618 | 208854_s_at | NM_003576 | 168913 | STK24 |
| 1134647 | 208892_s_at | NM_001946 | 298654 | DUSP6 |
| 1123127 | 208894_at | NM_019111 | 409805 | HLA-DRA |
| 1134653 | 208901_s_at | NM_003286 | 253536 | TOP1 |
| 1134665 | 208921_s_at | NM_003130 | 422340 | SRI |
| 1134674 | 208937_s_at | NM_002165 | 410900 | ID1 |
| 1134676 | 208942_s_at | NM_003262 | 158193 | TLOC1 |
| 1123148 | 208944_at | NM_003242 | 82028 | TGFBR2 |
| 1134679 | 208946_s_at | NM_003766 | 12272 | BECN1 |
| 1134682 | 208949_s_at | NM_002306 | 411701 | LGALS3 |
| 1134687 | 208959_s_at | NM_015051 | 154023 | TXNDC4 |
| 1134699 | 208974_x_at | NM_002265 | 439683 | KPNB1 |
| 1123160 | 208982_at | NM_000442 | 78146 | PECAM1 |
| 1134706 | 208987_s_at | NM_012308 | 219614 | FBXL11 |
| 1123163 | 208991_at | NM_003150 | 421342 | STAT3 |
| 1134710 | 208993_s_at | NM_004792 | 77965 | PPIG |
| 1134727 | 209018_s_at | NM_032409 | 439600 | PINK1 |
| 1134738 | 209033_s_at | NM_001396 | 75842 | DYRK1A |
| 1134753 | 209053_s_at | NM_133330 | 110457 | WHSC1 |
| 1134778 | 209085_x_at | NM_002913 | 166563 | RFC1 |
| 1123188 | 209089_at | NM_004162 | 73957 | RAB5A |
| 1123192 | 209100_at | NM_006764 | 315177 | IFRD2 |
| 1123193 | 209101_at | NM_001901 | 410037 | CTGF |
| 1123198 | 209112_at | NM_004064 | 238990 | CDKN1B |
| 1134797 | 209118_s_at | NM_006009 | 433394 | TUBA3 |
| 1123213 | 209154_at | NM_014604 | 12956 | TIP-1 |
| 1123223 | 209173_at | NM_006408 | 226391 | AGR2 |
| 1134837 | 209185_s_at | NM_003749 | 143648 | IRS2 |
| 1123231 | 209189_at | NM_005252 | 25647 | FOS |
| 1123233 | 209193_at | NM_002648 | 81170 | PIM1 |
| 1123235 | 209196_at | NM_005452 | 436930 | C6orf11 |
| 1134843 | 209199_s_at | NM_002397 | 368950 | MEF2C |
| 1134850 | 209210_s_at | NM_006832 | 270411 | PLEKHC1 |
| 1134852 | 209214_s_at | NM_005243 | 374477 | EWSR1 |
| 1134858 | 209226_s_at | NM_002270 | 405954 | TNPO1 |
| 1123250 | 209233_at | NM_006331 | 135643 | C2F |
| 1123255 | 209239_at | NM_003998 | 160557 | NFKB1 |
| 1134865 | 209241_x_at | NM_015716 | 112028 | MINK |
| 1134880 | 209265_s_at | NM_019852 | 168799 | METTL3 |
| 1134888 | 209278_s_at | NM_006528 | 438231 | TFPI2 |
| 1123278 | 209295_at | NM_003842 | 51233 | TNFRSF10B |
| 1134903 | 209306_s_at | NM_015055 | 153026 | SWAP70 |
| 1123286 | 209311_at | NM_004050 | 410026 | BCL2L2 |
| 1123289 | 209317_at | NM_203290 | 5409 | POLR1C |
| 1123293 | 209333_at | NM_003565 | 47061 | ULK1 |
| 1123298 | 209339_at | NM_005067 | 20191 | SIAH2 |
| 1134921 | 209341_s_at | NM_001556 | 413513 | IKBKB |
| 1134928 | 209352_s_at | NM_015260 | 13999 | SIN3B |
| 1123304 | 209354_at | NM_003820 | 279899 | TNFRSF14 |
| 1134933 | 209360_s_at | NM_001754 | 410774 | RUNX1 |
| 1123308 | 209364_at | NM_004322 | 76366 | BAD |
| 1123310 | 209368_at | NM_001979 | 212088 | EPHX2 |
| 1134945 | 209379_s_at | NM_018999 | 81897 | KIAA1128 |
| 1123317 | 209386_at | NM_014220 | 351316 | TM4SF1 |
| 1123321 | 209392_at | NM_006209 | 23719 | ENPP2 |
| 1123331 | 209409_at | NM_005311 | 512118 | GRB10 |
| 1134961 | 209417_s_at | NM_005533 | 50842 | IFI35 |
| 1123346 | 209443_at | NM_000624 | 76353 | SERPINA3 |
| 1123358 | 209464_at | NM_004217 | 442658 | AURKB |
| 1134988 | 209467_s_at | NM_003684 | 79516 | MKNK1 |
| 1134991 | 209474_s_at | NM_001776 | 444105 | ENTPD1 |

TABLE 2-continued

| UNIQID | Probe Set | Genbank Accession No. | Unigene ID Build 167 | Unigene Symbol |
|---|---|---|---|---|
| 1123369 | 209481_at | NM_017719 | 79025 | SNRK |
| 1123372 | 209487_at | NM_001008712 | 195825 | RBPMS |
| 1123376 | 209496_at | NM_002889 | 37682 | RARRES2 |
| 1135002 | 209500_x_at | NM_003808 | 54673 | TNFSF13 |
| 1123399 | 209541_at | NM_000618 | 308053 | 1GF1 |
| 1135023 | 209543_s_at | NM_001773 | 374990 | CD34 |
| 1135024 | 209545_s_at | NM_003821 | 103755 | RIPK2 |
| 1123401 | 209550_at | NM_002487 | 50130 | NDN |
| 1135028 | 209555_s_at | NM_001001548 | 443120 | CD36 |
| 1123413 | 209575_at | NM_000628 | 418291 | IL10RB |
| 1135042 | 209582_s_at | NM_005944 | 79015 | MOX2 |
| 1135047 | 209589_s_at | NM_004442 | 125124 | EPHB2 |
| 1123419 | 209590_at | NM_001719 | 170195 | BMP7 |
| 1135056 | 209604_s_at | NM_002051 | 169946 | GATA3 |
| 1123429 | 209619_at | NM_004355 | 446471 | CD74 |
| 1135068 | 209621_s_at | NM_014476 | 71719 | PDLIM3 |
| 1123430 | 209622_at | NM_001008910 | 153003 | STK16 |
| 1123437 | 209636_at | NM_002502 | 73090 | NFKB2 |
| 1123439 | 209642_at | NM_004336 | 287472 | BUB1 |
| 1135080 | 209644_x_at | NM_058195 | 421349 | CDKN2A |
| 1135085 | 209650_s_at | NM_014346 | 505862 | C22orf4 |
| 1135088 | 209656_s_at | NM_031442 | 8769 | TM4SF10 |
| 1135093 | 209666_s_at | NM_001278 | 198998 | CHUK |
| 1135101 | 209680_s_at | NM_002263 | 20830 | KIFC1 |
| 1123455 | 209682_at | NM_170662 | 436986 | CBLB |
| 1123457 | 209684_at | NM_018993 | 446304 | RIN2 |
| 1135102 | 209685_s_at | NM_002738 | 349845 | PRKCB1 |
| 1123459 | 209687_at | NM_199168 | 436042 | CXCL12 |
| 1123470 | 209704_at | NM_007358 | 31016 | M96 |
| 1123476 | 209711_at | NM_015139 | 82635 | SLC35D1 |
| 1123479 | 209716_at | NM_000757 | 173894 | CSF1 |
| 1123490 | 209732_at | NM_005127 | 85201 | CLECSF2 |
| 1123497 | 209747_at | NM_003239 | 2025 | TGFB3 |
| 1135130 | 209757_s_at | NM_005378 | 25960 | MYCN |
| 1123502 | 209760_at | NM_015196 | 511944 | KIAA0922 |
| 1123507 | 209770_at | NM_007048 | 284283 | BTN3A1 |
| 1135138 | 209771_x_at | NM_013230 | 375108 | CD24 |
| 1135141 | 209774_x_at | NM_002089 | 75765 | CXCL2 |
| 1135151 | 209790_s_at | NM_001226 | 3280 | CASP6 |
| 1123529 | 209815_at | NM_000264 | 159526 | PTCH |
| 1135164 | 209825_s_at | NM_012474 | 458360 | UMPK |
| 1135165 | 209827_s_at | NM_004513 | 170359 | IL16 |
| 1123535 | 209829_at | NM_014722 | 389488 | C6orf32 |
| 1135168 | 209831_x_at | NM_001375 | 118243 | DNASE2 |
| 1135173 | 209841_s_at | NM_018334 | 3781 | LRRN3 |
| 1135186 | 209860_s_at | NM_001156 | 386741 | ANXA7 |
| 1135189 | 209863_s_at | NM_003722 | 137569 | TP73L |
| 1123552 | 209879_at | NM_003006 | 423077 | SELPLG |
| 1135209 | 209899_s_at | NM_014281 | 74562 | SIAHBP1 |
| 1123566 | 209906_at | NM_004054 | 155935 | C3AR1 |
| 1135214 | 209908_s_at | NM_003238 | 169300 | TGFB2 |
| 1123573 | 209924_at | NM_002988 | 16530 | CCL18 |
| 1135226 | 209929_s_at | NM_003639 | 43505 | IKBKG |
| 1135227 | 209930_s_at | NM_006163 | 75643 | NFE2 |
| 1135229 | 209932_s_at | NM_001948 | 367676 | DUT |
| 1123581 | 209941_at | NM_003804 | 390758 | RIPK1 |
| 1135234 | 209945_s_at | NM_002093 | 282359 | GSK3B |
| 1123584 | 209946_at | NM_005429 | 79141 | VEGFC |
| 1123586 | 209948_at | NM_004137 | 93841 | KCNMB1 |
| 1123587 | 209949_at | NM_000433 | 949 | NCF2 |
| 1135240 | 209955_s_at | NM_004460 | 436852 | FAR |
| 1135251 | 209969_s_at | NM_139266 | 21486 | STAT1 |
| 1135253 | 209971_x_at | NM_006303 | 301613 | JTV1 |
| 1135267 | 209995_s_at | NM_021966 | 2484 | TCL1A |
| 1135270 | 209999_x_at | NM_003745 | 50640 | SOCS1 |
| 1123608 | 210017_at | NM_006785 | 180566 | MALT1 |
| 1135285 | 210024_s_at | NM_006357 | 449501 | UBE2E3 |
| 1123611 | 210029_at | NM_002164 | 840 | INDO |
| 1123613 | 210031_at | NM_000734 | 97087 | CD32 |
| 1123614 | 210038_at | NM_006257 | 408049 | PRKCQ |
| 1135299 | 210044_s_at | NM_005583 | 46446 | LYL1 |
| 1123622 | 210051_at | NM_006105 | 8578 | EPAC |
| 1123628 | 210058_at | NM_002754 | 178695 | MAPK13 |
| 1123634 | 210072_at | NM_006274 | 50002 | CCL19 |
| 1123635 | 210073_at | NM_003034 | 408614 | SIAT8A |
| 1123643 | 210092_at | NM_002370 | 421576 | MAGOH |
| 1135322 | 210095_s_at | NM_000598 | 450230 | IGFBP3 |

TABLE 2-continued

| UNIQID | Probe Set | Genbank Accession No. | Unigene ID Build 167 | Unigene Symbol |
|---|---|---|---|---|
| 1135328 | 210105_s_at | NM_002037 | 390567 | FYN |
| 1123663 | 210133_at | NM_002986 | 54460 | CCL11 |
| 1123671 | 210148_at | NM_005734 | 30148 | HIPK3 |
| 1135350 | 210151_s_at | NM_003582 | 164267 | DYRK3 |
| 1123672 | 210152_at | NM_001278426 | 67846 | LILRB4 |
| 1123679 | 210163_at | NM_005409 | 103982 | CXCL11 |
| 1123680 | 210164_at | NM_004131 | 1051 | GZMB |
| 1123682 | 210166_at | NM_003268 | 114408 | TLR5 |
| 1123690 | 210176_at | NM_003263 | 111805 | TLR1 |
| 1123694 | 210184_at | NM_000887 | 385521 | ITGAX |
| 1135374 | 210214_s_at | NM_001204 | 53250 | BMPR2 |
| 1135379 | 210225_x_at | NM_001081450 | 511766 | LILRB3 |
| 1135380 | 210229_s_at | NM_000758 | 1349 | CSF2 |
| 1135383 | 210240_s_at | NM_001800 | 435051 | CDKN2D |
| 1123731 | 210258_at | NM_002927 | 17165 | RGS13 |
| 1135395 | 210260_s_at | NM_014350 | 17839 | TNFAIP8 |
| 1135399 | 210275_s_at | NM_006007 | 406096 | ZNF216 |
| 1123744 | 210279_at | NM_005292 | 88269 | GPR18 |
| 1123760 | 210313_at | NM_012276 | 406708 | ILT7 |
| 1123762 | 210316_at | NM_002020 | 415048 | FLT4 |
| 1123778 | 210349_at | NM_001744 | 440638 | CAMK4 |
| 1123780 | 210354_at | NM_000619 | 856 | IFNG |
| 1135467 | 210404_x_at | NM_001220 | 321572 | CAMK2B |
| 1135475 | 210416_s_at | NM_007194 | 146329 | CHEK2 |
| 1135487 | 210432_s_at | NM_006922 | 300717 | SCN3A |
| 1135489 | 210438_x_at | NM_001042369 | 288178 | SSA2 |
| 1123814 | 210439_at | NM_012092 | 56247 | ICOS |
| 1123816 | 210442_at | NM_016232 | 66 | IL1RL1 |
| 1135492 | 210448_s_at | NM_002561 | 408615 | P2RX5 |
| 1135513 | 210481_s_at | NM_014257 | 421437 | CD209L |
| 1123833 | 210487_at | NM_001017520 | 397294 | DNTT |
| 1123842 | 210506_at | NM_004479 | 457 | FUT7 |
| 1135526 | 210512_s_at | NM_003376 | 73793 | VEGF |
| 1135529 | 210517_s_at | NM_005100 | 197081 | AKAP12 |
| 1123847 | 210523_at | NM_001203 | 87223 | BMPR1B |
| 1135541 | 210538_s_at | NM_001165 | 127799 | BIRC3 |
| 1135549 | 210549_s_at | NM_005064 | 169191 | CCL23 |
| 1135550 | 210550_s_at | NM_002891 | 221811 | RASGRF1 |
| 1135571 | 210582_s_at | NM_005569 | 278027 | LIMK2 |
| 1135583 | 210606_x_at | NM_002262 | 41682 | KLRD1 |
| 1123875 | 210607_at | NM_001204502 | 428 | FLT3LG |
| 1135592 | 210621_s_at | NM_002890 | 758 | RASA1 |
| 1135593 | 210622_x_at | NM_052988 | 77313 | CDK10 |
| 1123889 | 210643_at | NM_003701 | 333791 | TNFSF11 |
| 1135606 | 210644_s_at | NM_002287 | 407964 | LAIR1 |
| 1123890 | 210654_at | NM_003840 | 129844 | TNFRSF10D |
| 1123892 | 210659_at | NM_004072 | 159553 | CMKLR1 |
| 1135622 | 210671_x_at | NM_002750 | 445864 | MAPK8 |
| 1135645 | 210715_s_at | NM_021102 | 31439 | SPINT2 |
| 1135665 | 210749_x_at | NM_001954 | 423573 | DDR1 |
| 1135673 | 210759_s_at | NM_002786 | 82159 | PSMA1 |
| 1123938 | 210772_at | NM_001462 | 99855 | FPRL1 |
| 1135684 | 210775_x_at | NM_001229 | 329502 | CASP9 |
| 1135685 | 210776_x_at | NM_003200 | 371282 | TCF3 |
| 1135735 | 210838_s_at | NM_000020 | 410104 | ACVRL1 |
| 1135743 | 210847_x_at | NM_003790 | 299558 | TNFRSF25 |
| 1123954 | 210865_at | NM_000639 | 2007 | TNFSF6 |
| 1135755 | 210869_s_at | NM_006500 | 511397 | MCAM |
| 1135773 | 210889_s_at | NM_004001 | 126384 | FCGR2B |
| 1135778 | 210895_s_at | NM_006889 | 27954 | CD86 |
| 1135795 | 210933_s_at | NM_003088 | 55923 | Lin10 |
| 1135801 | 210943_s_at | NM_000081 | 130188 | CHS1 |
| 1135802 | 210944_s_at | NM_000070 | 439343 | CAPN3 |
| 1135826 | 210976_s_at | NM_000289 | 75160 | PFKM |
| 1135830 | 210981_s_at | NM_002082 | 235116 | GRK6 |
| 1135835 | 210986_s_at | NM_001018004 | 133892 | TPM1 |
| 1123988 | 211005_at | NM_014387 | 498997 | LAT |
| 1135852 | 211008_s_at | NM_194259 | 302903 | UBE2I |
| 1135858 | 211015_s_at | NM_002154 | 90093 | HSPA4 |
| 1135866 | 211026_s_at | NM_007283 | 409826 | MGLL |
| 1135871 | 211031_s_at | NM_003388 | 104717 | CYLN2 |
| 1135899 | 211070_x_at | NM_001079862 | 78888 | DBI |
| 1135925 | 211100_x_at | NM_001130917 | 149924 | LILRB1 |
| 1135929 | 211105_s_at | NM_006162 | 96149 | NFATC1 |
| 1135930 | 211107_s_at | NM_003160 | 98338 | AURKC |
| 1135966 | 211155_s_at | NM_000460 | 1166 | THPO |
| 1135968 | 211160_x_at | NM_001102 | 119000 | ACTN1 |

TABLE 2-continued

| UNIQID | Probe Set | Genbank Accession No. | Unigene ID Build 167 | Unigene Symbol |
|---|---|---|---|---|
| 1135974 | 211168_s_at | NM_002911 | 388125 | RENT1 |
| 1135982 | 211178_s_at | NM_003978 | 129758 | PSTPIP1 |
| 1135994 | 211197_s_at | NM_015259 | 14155 | ICOSL |
| 1136002 | 211208_s_at | NM_003688 | 288196 | CASK |
| 1124049 | 211276_at | NM_080390 | 401835 | my048 |
| 1136048 | 211282_x_at | NM_003790 | 299558 | TNFRSF25 |
| 1136051 | 211286_x_at | NM_172246 | 520937 | CSF2RA |
| 1136055 | 211296_x_at | NM_021009 | 183704 | UBC |
| 1136056 | 211297_s_at | NM_001799 | 184298 | CDK7 |
| 1136087 | 211339_s_at | NM_005546 | 211576 | ITK |
| 1136109 | 211370_s_at | NM_002757 | 436145 | MAP2K5 |
| 1136150 | 211432_s_at | NM_006293 | 381282 | TYRO3 |
| 1136152 | 211434_s_at | NM_003965 | 458436 | CCRL2 |
| 1136162 | 211453_s_at | NM_001626 | 326445 | AKT2 |
| 1136172 | 211470_s_at | NM_001056 | 38084 | SULT1C1 |
| 1136185 | 211488_s_at | NM_002214 | 355722 | ITGB8 |
| 1136193 | 211499_s_at | NM_002751 | 57732 | MAPK11 |
| 1136216 | 211528_x_at | NM_002127 | 512152 | HLA-G |
| 1136269 | 211593_s_at | NM_015112 | 101474 | MAST2 |
| 1136273 | 211597_s_at | NM_032495 | 13775 | HOP |
| 1136285 | 211615_s_at | NM_133259 | 182490 | LRPPRC |
| 1124132 | 211658_at | NM_005809 | 432121 | PRDX2 |
| 1136329 | 211675_s_at | NM_199072 | 132739 | HIC |
| 1136337 | 211685_s_at | NM_032041 | 90063 | NCALD |
| 1136343 | 211692_s_at | NM_014417 | 87246 | BBC3 |
| 1124137 | 211693_at | T29661 | 366 | MGC27165 |
| 1136357 | 211709_s_at | NM_002975 | 512680 | SCGF |
| 1136362 | 211714_x_at | NM_178014 | 356729 | OK/SW-cl.56 |
| 1136369 | 211724_x_at | NM_019005 | 387140 | FLJ20323 |
| 1136371 | 211726_s_at | NM_001460 | 361155 | FMO2 |
| 1136379 | 211734_s_at | NM_002001 | 897 | FCER1A |
| 1136391 | 211748_x_at | NM_000954 | 446429 | PTGDS |
| 1136393 | 211750_x_at | NM_032704 | 406578 | TUBA6 |
| 1136401 | 211761_s_at | NM_014412 | 27258 | SIP |
| 1136408 | 211771_s_at | NM_002698 | 1101 | POU2F2 |
| 1136427 | 211795_s_at | NM_001465 | 276506 | FYB |
| 1136430 | 211798_x_at | AA570353 | 102950 | IGLJ3 |
| 1136459 | 211828_s_at | NM_015028 | 252550 | KIAA0551 |
| 1136464 | 211833_s_at | NM_004324 | 159428 | BAX |
| 1136540 | 211924_s_at | NM_002659 | 179657 | PLAUR |
| 1124176 | 211966_at | NM_001846 | 407912 | COL4A2 |
| 1124177 | 211967_at | NM_052932 | 172089 | PORIMIN |
| 1124178 | 211969_at | NM_005348 | 446579 | HSPCA |
| 1124187 | 211986_at | NM_001620 | 378738 | MGC5395 |
| 1124188 | 211987_at | NM_001068 | 282346 | TOP2B |
| 1136573 | 211991_s_at | NM_033554 | 914 | HLA-DPA1 |
| 1124192 | 211992_at | NM_014823 | 275999 | PRKWNK1 |
| 1124195 | 211998_at | NM_005324 | 180877 | H3F3B |
| 1136585 | 212022_s_at | NM_002417 | 80976 | MKI67 |
| 1124215 | 212037_at | NM_002687 | 409965 | PNN |
| 1136595 | 212038_s_at | NM_003374 | 404814 | VDAC1 |
| 1136599 | 212046_x_at | NM_002746 | 861 | MAPK3 |
| 1136601 | 212048_s_at | NM_003680 | 322735 | YARS |
| 1136605 | 212064_x_at | NM_002383 | 448398 | MAZ |
| 1124237 | 212080_at | NM_005933 | 258855 | MLL |
| 1136620 | 212091_s_at | NM_001848 | 415997 | COL6A1 |
| 1124254 | 212110_at | NM_015359 | 301743 | SLC39A14 |
| 1124266 | 212123_at | NM_015631 | 438991 | DKFZP564D116 |
| 1124283 | 212144_at | NM_015374 | 406612 | UNC84B |
| 1124296 | 212158_at | NM_002998 | 1501 | SDC2 |
| 1124304 | 212168_at | NM_006047 | 166887 | CPNE1 |
| 1124316 | 212186_at | NM_198834 | 449863 | ACACA |
| 1124318 | 212190_at | NM_006216 | 21858 | SERPINE2 |
| 1124321 | 212196_at | NM_002184 | 529772 | |
| 1136655 | 212218_s_at | NM_004104 | 388387 | FBXO9 |
| 1124342 | 212230_at | NM_003713 | 432840 | PPAP2B |
| 1136662 | 212240_s_at | NM_181504 | 6241 | PIK3R1 |
| 1124357 | 212247_at | NM_015135 | 413636 | NUP205 |
| 1124362 | 212252_at | NM_006549 | 297343 | CAMKK2 |
| 1124365 | 212261_at | NM_015575 | 334871 | TNRC15 |
| 1124377 | 212282_at | NM_014573 | 199695 | MAC30 |
| 1124381 | 212288_at | NM_015033 | 440808 | FNBP1 |
| 1124384 | 212291_at | NM_181358 | 12259 | HIPK1 |
| 1124391 | 212299_at | NM_033116 | 7200 | NEK9 |
| 1136681 | 212303_x_at | NM_003685 | 91142 | KHSRP |
| 1124400 | 212312_at | NM_001191 | 305890 | BCL2L1 |
| 1124411 | 212326_at | NM_015378 | 194737 | VPS13D |

TABLE 2-continued

| UNIQID | Probe Set | Genbank Accession No. | Unigene ID Build 167 | Unigene Symbol |
|---|---|---|---|---|
| 1124416 | 212331_at | NM_005611 | 283604 | RBL2 |
| 1124429 | 212344_at | NM_015170 | 409602 | SULF1 |
| 1136687 | 212345_s_at | NM_194071 | 59943 | CREB3L2 |
| 1124438 | 212358_at | NM_015526 | 7357 | CLiPR-59 |
| 1136692 | 212359_s_at | NM_015037 | 65135 | KIAA0913 |
| 1124456 | 212382_at | NM_003199 | 359289 | TCF4 |
| 1136702 | 212399_s_at | NM_014667 | 155584 | KIAA0121 |
| 1136710 | 212429_s_at | NM_001521 | 75782 | GTF3C2 |
| 1136712 | 212442_s_at | NM_203463 | 503941 | LOC253782 |
| 1136718 | 212459_x_at | NM_003848 | 446476 | SUCLG2 |
| 1136722 | 212481_s_at | NM_003290 | 250641 | TPM4 |
| 1136724 | 212491_s_at | NM_014280 | 433540 | DNAJC8 |
| 1124539 | 212494_at | NM_015319 | 6147 | TENC1 |
| 1124543 | 212500_at | NM_032804 | 99821 | C10orf22 |
| 1124549 | 212508_at | NM_022151 | 24719 | MOAP1 |
| 1124561 | 212530_at | NM_133494 | 24119 | NEK7 |
| 1124563 | 212533_at | NM_003390 | 249441 | WEE1 |
| 1124577 | 212552_at | NM_002149 | 3618 | HPCAL1 |
| 1124583 | 212558_at | NM_005841 | 20977 | GDAP1L1 |
| 1124594 | 212572_at | NM_015000 | 184523 | STK38L |
| 1124606 | 212588_at | NM_002838 | 444324 | PTPRC |
| 1124610 | 212592_at | NM_144646 | 381568 | IGJ |
| 1124613 | 212599_at | NM_015570 | 296720 | AUTS2 |
| 1124616 | 212603_at | NM_005830 | 154655 | MRPS31 |
| 1136759 | 212605_s_at | NM_006703 | 188882 | |
| 1124620 | 212610_at | NM_002834 | 83572 | PTPN11 |
| 1136762 | 212624_s_at | NM_001822 | 380138 | CHN1 |
| 1136765 | 212629_s_at | NM_006256 | 69171 | PRKCL2 |
| 1124646 | 212646_at | NM_015150 | 436432 | RAFTLIN |
| 1136774 | 212657_s_at | NM_000577 | 81134 | IL1RN |
| 1124655 | 212658_at | NM_005779 | 79299 | LHFPL2 |
| 1124658 | 212663_at | NM_015258 | 522351 | KIAA0674 |
| 1136777 | 212671_s_at | NM_002122 | 387679 | HLA-DQA1 |
| 1124666 | 212672_at | NM_000051 | 526394 | ATM |
| 1136781 | 212680_x_at | NM_138689 | 120197 | PPP1R14B |
| 1136784 | 212689_s_at | NM_018433 | 321707 | JMJD1 |
| 1136786 | 212694_s_at | NM_000532 | 63788 | PCCB |
| 1136788 | 212698_s_at | NM_144710 | 355455 | 9/10/2004 |
| 1124692 | 212713_at | NM_002404 | 296049 | MFAP4 |
| 1124705 | 212730_at | NM_015286 | 381347 | DMN |
| 1124712 | 212738_at | NM_032900 | 80305 | ARHGAP19 |
| 1124713 | 212740_at | NM_014602 | 306747 | PIK3R4 |
| 1124723 | 212753_at | NM_006315 | 435065 | RNF3 |
| 1124733 | 212771_at | NM_001010924 | 66762 | LOC221061 |
| 1124734 | 212774_at | NM_006352 | 446677 | ZNF238 |
| 1124745 | 212789_at | NM_015261 | 438550 | KIAA0056 |
| 1136819 | 212798_s_at | NM_020319 | 112605 | DKFZP564O043 |
| 1124753 | 212801_at | NM_007174 | 528307 | CIT |
| 1124755 | 212805_at | NM_015225 | 23311 | KIAA0367 |
| 1124760 | 212813_at | NM_032801 | 419149 | JAM3 |
| 1124768 | 212824_at | NM_003934 | 98751 | FUBP3 |
| 1124770 | 212827_at | T29654 | 153261 | IGHM |
| 1136831 | 212841_s_at | NM_003621 | 12953 | PPFIBP2 |
| 1136832 | 212842_x_at | NM_005054 | 434959 | RANBP2L1 |
| 1124782 | 212843_at | NM_000615 | 78792 | NCAM1 |
| 1124786 | 212847_at | NM_144573 | 22370 | NEXN |
| 1124798 | 212867_at | NM_006540 | 446678 | NCOA2 |
| 1124800 | 212871_at | NM_003668 | 413901 | MAPKAPK5 |
| 1136844 | 212875_s_at | NM_015500 | 16007 | C21orf25 |
| 1124806 | 212881_at | NM_015897 | 105779 | PIASY |
| 1124820 | 212899_at | NM_015076 | 129836 | CDK11 |
| 1124830 | 212911_at | NM_015291 | 9059 | KIAA0962 |
| 1124831 | 212912_at | NM_021135 | 301664 | RPS6KA2 |
| 1124833 | 212914_at | NM_175709 | 356416 | CBX7 |
| 1136853 | 212922_s_at | NM_020197 | 66170 | SMYD2 |
| 1136859 | 212942_s_at | NM_018689 | 212584 | KIAA1199 |
| 1124862 | 212954_at | NM_003845 | 439530 | DYRK4 |
| 1136865 | 212959_s_at | NM_024312 | 412128 | MGC4170 |
| 1124864 | 212960_at | NM_015130 | 411317 | KIAA0882 |
| 1124875 | 212975_at | NM_014957 | 18166 | KIAA0870 |
| 1124889 | 212993_at | NM_144653 | 244847 | BTBD14A |
| 1136876 | 212997_s_at | NM_006852 | 445078 | TLK2 |
| 1136877 | 212998_x_at | NM_002123 | 409934 | HLA-DQB1 |
| 1124893 | 213002_at | NM_002356 | 318603 | MARCKS |
| 1124913 | 213027_at | NM_001173524 | 288178 | SSA2 |
| 1124920 | 213039_at | NM_015318 | 6150 | ARHGEF18 |
| 1124921 | 213044_at | NM_005406 | 306307 | ROCK1 |

TABLE 2-continued

| UNIQID | Probe Set | Genbank Accession No. | Unigene ID Build 167 | Unigene Symbol |
|---|---|---|---|---|
| 1124922 | 213045_at | NM_015016 | 173864 | MAST3 |
| 1124941 | 213068_at | NM_001937 | 80552 | DPT |
| 1124942 | 213069_at | NM_020733 | 433452 | HEG |
| 1124948 | 213075_at | NM_182487 | 357004 | LOC169611 |
| 1124953 | 213083_at | NM_007001 | 386278 | SLC35D2 |
| 1136902 | 213086_s_at | NM_001892 | 442592 | |
| 1136903 | 213087_s_at | NR_026868 | 334798 | EEF1D |
| 1124967 | 213108_at | NM_015981 | 143535 | CAMK2A |
| 1136913 | 213113_s_at | NM_014096 | 99962 | SLC43A3 |
| 1124972 | 213116_at | NM_002498 | 2236 | NEK3 |
| 1136925 | 213154_s_at | NM_015250 | 436939 | BICD2 |
| 1125001 | 213158_at | BC016962 | 16193 | |
| 1125009 | 213169_at | NM_003966 | 27621 | |
| 1125010 | 213170_at | NM_015696 | 43728 | GPX7 |
| 1125013 | 213174_at | NM_015351 | 79170 | TTC9 |
| 1136938 | 213188_s_at | NM_032778 | 23294 | MINA53 |
| 1136939 | 213193_x_at | NM_002769 | 419777 | |
| 1125025 | 213196_at | NM_001080417 | 301094 | |
| 1125027 | 213198_at | NM_004302 | 371974 | ACVR1B |
| 1125058 | 213238_at | NM_020453 | 437241 | ATP10D |
| 1125079 | 213264_at | NM_005016 | 211601 | MAP3K12 |
| 1125122 | 213324_at | NM_005417 | 436015 | SRC |
| 1125124 | 213326_at | NM_014231 | 20021 | VAMP1 |
| 1136971 | 213330_s_at | NM_006819 | 257827 | STIP1 |
| 1136972 | 213331_s_at | NM_012224 | 414410 | NEK1 |
| 1125130 | 213338_at | NM_015444 | 35861 | RIS1 |
| 1125132 | 213341_at | NM_020177 | 47367 | FEM1C |
| 1125136 | 213348_at | NM_000076 | 106070 | CDKN1C |
| 1136983 | 213360_s_at | NM_172020 | 450237 | LOC340318 |
| 1136984 | 213364_s_at | NM_003099 | 498154 | SNX1 |
| 1136987 | 213370_s_at | NM_016329 | 21695 | SFMBT1 |
| 1136988 | 213373_s_at | NM_001228 | 243491 | CASP8 |
| 1136996 | 213397_x_at | NM_002937 | 283749 | RNASE4 |
| 1125181 | 213418_at | NM_002155 | 3268 | HSPA6 |
| 1125195 | 213438_at | NM_015090 | 7309 | |
| 1137022 | 213475_s_at | NM_002209 | 174103 | ITGAL |
| 1125231 | 213489_at | NM_014268 | 446375 | MAPRE2 |
| 1137026 | 213490_s_at | NM_030662 | 366546 | MAP2K2 |
| 1125245 | 213517_at | NM_005016 | 132977 | PCBP2 |
| 1125246 | 213518_at | NM_002740 | 496511 | PRKCI |
| 1125249 | 213523_at | NM_001238 | 244723 | CCNE1 |
| 1137042 | 213524_s_at | NM_015714 | 432132 | G0S2 |
| 1125279 | 213575_at | NM_013293 | 445652 | TRA2A |
| 1125305 | 213627_at | NM_201222 | 376719 | MAGED2 |
| 1137097 | 213656_s_at | NM_182923 | 20107 | KNS2 |
| 1137109 | 213689_x_at | NM_001006605 | 469653 | RPL5 |
| 1137112 | 213693_s_at | NM_002456 | 89603 | MUC1 |
| 1137137 | 213746_s_at | NM_001456 | 195464 | FLNA |
| 1125377 | 213748_at | NM_014818 | 196966 | KIAA0298 |
| 1125397 | 213784_at | NM_001177701 | 415172 | RABL4 |
| 1137158 | 213794_s_at | NM_015514 | 9043 | C14orf120 |
| 1137201 | 213877_x_at | NM_007108 | 433343 | SRRM2 |
| 1137202 | 213881_x_at | NM_006937 | 380973 | SMT3H2 |
| 1125456 | 213906_at | NM_001080416 | 300592 | MYBL1 |
| 1125459 | 213909_at | NM_130830 | 288467 | LRRC15 |
| 1125462 | 213915_at | NM_005601 | 10306 | NKG7 |
| 1125485 | 213958_at | NM_006725 | 436949 | CD6 |
| 1137247 | 213975_s_at | NM_000239 | 234734 | LYZ |
| 1137273 | 214020_x_at | NM_002213 | 149846 | ITGB5 |
| 1125516 | 214032_at | NM_001079 | 234569 | ZAP70 |
| 1125520 | 214038_at | NM_005623 | 271387 | CCL8 |
| 1137289 | 214049_x_at | NM_006137 | 36972 | CD7 |
| 1125527 | 214051_at | NM_194324 | 422848 | MGC39900 |
| 1137291 | 214055_x_at | NM_015172 | 446197 | XTP2 |
| 1125532 | 214058_at | NM_001033081 | 437922 | MYCL1 |
| 1125546 | 214081_at | NM_020405 | 125036 | PLXDC1 |
| 1137308 | 214093_s_at | NM_003902 | 118962 | FUBP1 |
| 1137328 | 214130_s_at | NM_014644 | 502577 | PDE4DIP |
| 1137332 | 214146_s_at | NM_002704 | 2164 | PPBP |
| 1137343 | 214170_x_at | NM_000143 | 391168 | FH |
| 1125593 | 214180_at | NM_020379 | 8910 | MAN1C1 |
| 1137360 | 214196_s_at | NM_000391 | 429658 | CLN2 |
| 1137378 | 214228_x_at | NM_003327 | 129780 | TNFRSF4 |
| 1125634 | 214265_at | NM_003638 | 171025 | ITGA8 |
| 1125658 | 214322_at | NM_001222 | 12436 | CAMK2G |
| 1137439 | 214339_s_at | NM_007181 | 95424 | MAP4K1 |
| 1137447 | 214359_s_at | NM_007355 | 74335 | HSPCB |

TABLE 2-continued

| UNIQID | Probe Set | Genbank Accession No. | Unigene ID Build 167 | Unigene Symbol |
|---|---|---|---|---|
| 1137449 | 214363_s_at | NM_018834 | 223745 | MATR3 |
| 1125685 | 214371_at | NM_053006 | 103978 | STK22B |
| 1137481 | 214428_x_at | NM_007293 | 150833 | C4A |
| 1137486 | 214442_s_at | NM_004671 | 441069 | MIZ1 |
| 1137488 | 214448_x_at | NR_040515 | 9731 | NFKBIB |
| 1137492 | 214459_x_at | NM_001243042 | 274485 | HLA-C |
| 1125742 | 214470_at | NM_002258 | 169824 | KLRB1 |
| 1137506 | 214501_s_at | NM_004893 | 75258 | H2AFY |
| 1137512 | 214512_s_at | NM_006713 | 229641 | PC4 |
| 1137534 | 214551_s_at | NM_006137 | 36972 | CD7 |
| 1125789 | 214560_at | NM_002030 | 511953 | FPRL2 |
| 1137539 | 214567_s_at | NM_002995 | 458346 | XCL2 |
| 1125818 | 214607_at | NM_002578 | 152663 | PAK3 |
| 1125826 | 214617_at | NM_005041 | 2200 | PRF1 |
| 1137561 | 214639_s_at | NM_005522 | 67397 | HOXA1 |
| 1125852 | 214660_at | NM_181501 | 439320 | ITGA1 |
| 1125854 | 214663_at | NM_015375 | 6874 | DustyPK |
| 1137582 | 214683_s_at | NM_004071 | 433732 | CLK1 |
| 1137583 | 214687_x_at | NM_000034 | 273415 | ALDOA |
| 1125872 | 214696_at | NR_028502 | 417157 | MGC14376 |
| 1137594 | 214710_s_at | NM_031966 | 23960 | CCNB1 |
| 1137597 | 214721_x_at | NM_012121 | 3903 | CDC42EP4 |
| 1137601 | 214730_s_at | NM_012201 | 78979 | GLG1 |
| 1125901 | 214745_at | NM_014996 | 193143 | KIAA1069 |
| 1125916 | 214764_at | NM_016052 | 497770 | |
| 1125917 | 214769_at | NM_001830 | 417091 | CLCN4 |
| 1125919 | 214772_at | NM_012194 | 432369 | G2 |
| 1125921 | 214777_at | AK092753 | 512003 | |
| 1125927 | 214787_at | NM_005848 | 511742 | IRLB |
| 1125928 | 214790_at | NM_015571 | 435628 | SUSP1 |
| 1137626 | 214797_s_at | NM_002596 | 445402 | PCTK3 |
| 1137643 | 214864_s_at | NM_012203 | 155742 | GRHPR |
| 1137663 | 214909_s_at | NM_013974 | 247362 | DDAH2 |
| 1126047 | 214969_at | NM_033141 | 437214 | MAP3K9 |
| 1137687 | 214974_x_at | NM_002994 | 89714 | CXCL5 |
| 1137698 | 215001_s_at | NM_002065 | 442669 | GLUL |
| 1126081 | 215030_at | NM_002092 | 309763 | GRSF1 |
| 1137742 | 215111_s_at | NM_006022 | 114360 | TSC22 |
| 1126131 | 215117_at | NM_000536 | 159376 | RAG2 |
| 1137751 | 215127_s_at | NM_002897 | 241567 | RBMS1 |
| 1126148 | 215143_at | NM_173812 | 408264 | FLJ36166 |
| 1137760 | 215158_s_at | NM_032998 | 169681 | DEDD |
| 1137771 | 215193_x_at | XM_003846462 | 308026 | HLA-DRB3 |
| 1137782 | 215223_s_at | NM_000636 | 384944 | SOD2 |
| 1137806 | 215313_x_at | NM_002116 | 181244 | HLA-A |
| 1137809 | 215332_s_at | NM_172101 | 405667 | CD8B1 |
| 1126293 | 215346_at | NM_152854 | 504816 | TNFRSF5 |
| 1137838 | 215411_s_at | NM_147686 | 437508 | C6orf4 |
| 1137868 | 215493_x_at | NM_007049 | 169963 | BTN2A1 |
| 1126387 | 215499_at | NM_002756 | 180533 | MAP2K3 |
| 1126408 | 215528_at | NM_002410 | 22689 | |
| 1137908 | 215603_x_at | NR_003267 | 454906 | |
| 1137955 | 215722_s_at | NM_003090 | 434901 | SNRPA1 |
| 1126540 | 215750_at | NM_020831 | 474916 | KIAA1659 |
| 1126554 | 215767_at | NM_194250 | 159528 | LOC91752 |
| 1126559 | 215776_at | NM_014215 | 248138 | INSRR |
| 1138030 | 215925_s_at | NM_001782 | 116481 | CD72 |
| 1138048 | 215967_s_at | NM_002348 | 403857 | LY9 |
| 1138120 | 216178_x_at | NM_033668 | 287797 | ITGB1 |
| 1138128 | 216199_s_at | NM_005922 | 390428 | MAP3K4 |
| 1138132 | 216207_x_at | H42883 | 390427 | IGKV1D-13 |
| 1138136 | 216215_s_at | NM_014309 | 433574 | RBM9 |
| 1138147 | 216234_s_at | NM_002730 | 194350 | PRKACA |
| 1138150 | 216237_s_at | NM_006739 | 77171 | MCM5 |
| 1138157 | 216251_s_at | NM_015140 | 82563 | KIAA0153 |
| 1126858 | 216261_at | NM_000212 | 87149 | ITGB3 |
| 1138192 | 216321_s_at | NM_000176 | 126608 | NR3C1 |
| 1126892 | 216331_at | NM_002206 | 74369 | ITGA7 |
| 1138244 | 216442_x_at | NM_002026 | 418138 | FN1 |
| 1138259 | 216484_x_at | NM_004494 | 89525 | HDGF |
| 1138279 | 216520_s_at | NM_003295 | 374596 | TPT1 |
| 1138312 | 216598_s_at | NM_002982 | 303649 | CCL2 |
| 1138331 | 216640_s_at | NM_005742 | 212102 | P5 |
| 1138355 | 216705_s_at | NM_000022 | 407135 | ADA |
| 1138379 | 216836_s_at | NM_004448 | 446352 | ERBB2 |
| 1127214 | 216837_at | NM_004439 | 201920 | EPHA5 |
| 1138392 | 216862_s_at | NM_001018024 | 3548 | MTCP1 |

TABLE 2-continued

| UNIQID | Probe Set | Genbank Accession No. | Unigene ID Build 167 | Unigene Symbol |
|---|---|---|---|---|
| 1138400 | 216876_s_at | NM_002190 | 41724 | IL17 |
| 1138417 | 216905_s_at | NM_021978 | 56937 | ST14 |
| 1138421 | 216913_s_at | NM_015179 | 434251 | KIAA0690 |
| 1138441 | 216945_x_at | NM_015148 | 397891 | PASK |
| 1138443 | 216950_s_at | NM_000566 | 74424 | FCGR1A |
| 1127290 | 217019_at | NM_013271 | 447032 | |
| 1127294 | 217028_at | NM_003467 | 421986 | CXCR4 |
| 1138507 | 217066_s_at | NM_004409 | 898 | DMPK |
| 1138515 | 217080_s_at | NM_004839 | 93564 | HOMER2 |
| 1138532 | 217128_s_at | NM_020439 | 199068 | CAMK1G |
| 1138537 | 217140_s_at | NM_003374 | | |
| 1138538 | 217143_s_at | AI355686 | 2014 | TRD@ |
| 1138541 | 217149_x_at | NM_003985 | 203420 | TNK1 |
| 1127371 | 217164_at | NM_022037 | 391858 | TIA1 |
| 1138555 | 217184_s_at | NM_002344 | 434481 | LTK |
| 1138567 | 217200_x_at | NM_001915 | 355264 | CYB561 |
| 1138645 | 217373_x_at | NM_002392 | 212217 | MDM2 |
| 1138647 | 217377_x_at | NM_002530 | 171262 | ETV6 |
| 1138652 | 217388_s_at | NM_003937 | 444471 | KYNU |
| 1138670 | 217422_s_at | NM_001771 | 262150 | CD22 |
| 1138671 | 217427_s_at | NM_003325 | 415735 | HIRA |
| 1138677 | 217436_x_at | NR_024240 | 390440 | |
| 1127567 | 217529_at | NM_032831 | 440667 | FLJ20013 |
| 1127576 | 217544_at | AA960755 | 529751 | |
| 1138721 | 217552_x_at | NM_000573 | 334019 | CR1 |
| 1138759 | 217707_x_at | NM_003070 | 396404 | SMARCA2 |
| 1138765 | 217716_s_at | NM_013336 | 306079 | SEC61A1 |
| 1138778 | 217736_s_at | NM_014413 | 434986 | HRI |
| 1138780 | 217739_s_at | NM_005746 | 293464 | PBEF1 |
| 1138783 | 217742_s_at | NM_016628 | 370152 | WAC |
| 1138789 | 217750_s_at | NM_023079 | 369120 | FLJ13855 |
| 1127720 | 217765_at | NM_013392 | 272736 | NRBP |
| 1138801 | 217774_s_at | NM_016404 | 333579 | HSPC152 |
| 1127742 | 217814_at | NM_020198 | 8207 | GK001 |
| 1127744 | 217817_at | NM_005718 | 323342 | ARPC4 |
| 1138832 | 217829_s_at | NM_006590 | 12820 | USP39 |
| 1138845 | 217849_s_at | NM_006035 | 436985 | CDC42BPB |
| 1127756 | 217850_at | NM_014366 | 313544 | NS |
| 1127761 | 217863_at | NM_016166 | 75251 | PIAS1 |
| 1138858 | 217871_s_at | NM_002415 | 407995 | MIF |
| 1127775 | 217886_at | NM_001981 | 79095 | EPS15 |
| 1138867 | 217892_s_at | NM_016357 | 10706 | EPLIN |
| 1138874 | 217910_x_at | NM_170607 | 383019 | TCFL4 |
| 1138878 | 217917_s_at | NM_014183 | 100002 | DNCL2A |
| 1138887 | 217937_s_at | NM_015401 | 200063 | HDAC7A |
| 1127805 | 217947_at | NM_017801 | 380627 | CKLFSF6 |
| 1127807 | 217950_at | NM_015953 | 7236 | NOSIP |
| 1127813 | 217962_at | NM_018648 | 14317 | NOLA3 |
| 1138905 | 217970_s_at | NM_015455 | 437844 | K1AA1194 |
| 1127822 | 217977_at | NM_016332 | 279623 | SEPX1 |
| 1138910 | 217982_s_at | NM_006791 | 374503 | MORF4L1 |
| 1127833 | 218001_at | NM_016034 | 382044 | MRPS2 |
| 1138920 | 218002_s_at | NM_004887 | 24395 | CXCL14 |
| 1127838 | 218012_at | NM_022117 | 136164 | SE20-4 |
| 1127849 | 218032_at | NM_003498 | 76691 | SNN |
| 1138944 | 218051_s_at | NM_022908 | 84753 | FLJ12442 |
| 1127864 | 218066_at | NM_006598 | 172613 | SLC12A7 |
| 1138959 | 218076_s_at | NM_018054 | 203605 | RICH1 |
| 1127873 | 218089_at | NM_015511 | 11314 | C20orf4 |
| 1138973 | 218097_s_at | NM_024040 | 11270 | C10orf66 |
| 1127885 | 218113_at | NM_013390 | 160417 | TMEM2 |
| 1138994 | 218143_s_at | NM_005697 | 238030 | SCAMP2 |
| 1138995 | 218144_s_at | NM_022489 | 24956 | FLJ22056 |
| 1127901 | 218145_at | NM_021158 | 344378 | C20orf97 |
| 1139005 | 218168_s_at | NM_020247 | 273186 | CABC1 |
| 1139017 | 218189_s_at | NM_018946 | 274424 | NANS |
| 1139026 | 218205_s_at | NM_017572 | 512094 | MKNK2 |
| 1127931 | 218208_at | NM_025078 | 288284 | PQLC1 |
| 1139037 | 218223_s_at | NM_016274 | 173380 | CKIP-1 |
| 1127940 | 218227_at | NM_012225 | 256549 | NUBP2 |
| 1139039 | 218228_s_at | NM_025235 | 280776 | TNKS2 |
| 1127943 | 218232_at | NM_015991 | 9641 | C1QA |
| 1139048 | 218250_s_at | NM_013354 | 170553 | CNOT7 |
| 1139054 | 218263_s_at | NM_021211 | 25726 | LOC58486 |
| 1139076 | 218306_s_at | NM_003922 | 133411 | HERC1 |
| 1139100 | 218350_s_at | NM_015895 | 234896 | GMNN |
| 1139105 | 218367_x_at | NM_012475 | 8015 | USP21 |

TABLE 2-continued

| UNIQID | Probe Set | Genbank Accession No. | Unigene ID Build 167 | Unigene Symbol |
|---|---|---|---|---|
| 1139106 | 218368_s_at | NM_016639 | 355899 | TNFRSF12A |
| 1139127 | 218409_s_at | NM_022365 | 13015 | DNAJC1 |
| 1128042 | 218436_at | NM_022464 | 297875 | SIL1 |
| 1128066 | 218475_at | NM_022727 | 63609 | HTF9C |
| 1128070 | 218481_at | NM_020158 | 283741 | RRP46 |
| 1128079 | 218499_at | NM_016542 | 23643 | MST4 |
| 1128095 | 218520_at | NM_013254 | 432466 | TBK1 |
| 1128099 | 218529_at | NM_016579 | 333427 | 8D6A |
| 1128100 | 218530_at | NM_013241 | 95231 | FHOD1 |
| 1139185 | 218535_s_at | NM_018343 | 27021 | RIOK2 |
| 1128106 | 218542_at | NM_018131 | 14559 | C10orf3 |
| 1128111 | 218552_at | NM_018281 | 170915 | FLJ10948 |
| 1139196 | 218559_s_at | NM_005461 | 169487 | MAFB |
| 1139202 | 218569_s_at | NM_016506 | 440695 | KBTBD4 |
| 1128125 | 218581_at | NM_022060 | 445665 | ABHD4 |
| 1139215 | 218597_s_at | NM_018464 | 43549 | C10orf70 |
| 1128144 | 218613_at | NM_015310 | 236438 | DKFZp761K1423 |
| 1128151 | 218625_at | NM_016588 | 103291 | NRN1 |
| 1128157 | 218631_at | NM_021732 | 23918 | VIP32 |
| 1139226 | 218633_x_at | NM_018394 | 266514 | FLJ11342 |
| 1139230 | 218640_s_at | NM_024613 | 29724 | PLEKHF2 |
| 1128164 | 218646_at | NM_017867 | 44344 | FLJ20534 |
| 1139235 | 218651_s_at | NM_018357 | 416755 | FLJ11196 |
| 1128167 | 218653_at | NM_014252 | 78457 | SLC25A15 |
| 1128174 | 218665_at | NM_012193 | 19545 | FZD4 |
| 1128192 | 218696_at | NM_004836 | 102506 | EIF2AK3 |
| 1128195 | 218699_at | NM_003929 | 115325 | RAB7L1 |
| 1139265 | 218722_s_at | NM_024661 | 187657 | FLJ12436 |
| 1139266 | 218723_s_at | NM_014059 | 76640 | RGC32 |
| 1128214 | 218734_at | NM_024771 | 408443 | FLJ13848 |
| 1139274 | 218740_s_at | NM_176096 | 20157 | CDK5RAP3 |
| 1139277 | 218747_s_at | NM_018009 | 267993 | TAPBP-R |
| 1139280 | 218751_s_at | NM_018315 | 312503 | FBXW7 |
| 1128223 | 218753_at | NM_018053 | 55024 | FLJ10307 |
| 1128231 | 218764_at | NM_006255 | 315366 | PRKCH |
| 1139301 | 218792_s_at | NM_017688 | 108502 | BSPRY |
| 1139303 | 218794_s_at | NM_017853 | 134406 | FLJ20511 |
| 1128248 | 218802_at | NM_017918 | 234149 | FLJ20647 |
| 1139314 | 218831_s_at | NM_004107 | 111903 | FCGRT |
| 1128283 | 218856_at | NM_014452 | 159651 | TNFRSF21 |
| 1128287 | 218862_at | NM_024701 | 300063 | ASB13 |
| 1128298 | 218887_at | NM_015950 | 55041 | MRPL2 |
| 1128311 | 218909_at | NM_012424 | 30352 | RPS6KC1 |
| 1128321 | 218921_at | NM_021805 | 433036 | SIGIRR |
| 1139360 | 218947_s_at | NM_018109 | 173946 | FLJ10486 |
| 1128341 | 218955_at | NM_018310 | 274136 | BRF2 |
| 1128356 | 218983_at | NM_016546 | 415792 | C1RL |
| 1128360 | 218988_at | NM_018656 | 445043 | SLC35E3 |
| 1128377 | 219014_at | NM_016619 | 371003 | PLAC8 |
| 1128386 | 219025_at | NM_020404 | 195727 | CD164L1 |
| 1128387 | 219028_at | NM_022740 | 397465 | HIPK2 |
| 1139393 | 219032_x_at | NM_014322 | 170129 | OPN3 |
| 1128395 | 219039_at | NM_017789 | 7188 | SEMA4C |
| 1128401 | 219049_at | NM_018371 | 341073 | ChGn |
| 1139411 | 219073_s_at | NM_017784 | 368238 | OSBPL10 |
| 1128418 | 219082_at | NM_015944 | 433499 | CGI-14 |
| 1128435 | 219109_at | NM_001025436 | 6783 | PF20 |
| 1128439 | 219118_at | NM_016594 | 438695 | FKBP11 |
| 1128447 | 219130_at | NM_019083 | 40337 | FLJ10287 |
| 1128457 | 219148_at | NM_018492 | 104741 | TOPK |
| 1139444 | 219151_s_at | NM_007081 | 355874 | RABL2B |
| 1128469 | 219173_at | NR_003587 | 390817 | FLJ22686 |
| 1128471 | 219176_at | NM_024520 | 3592 | FLJ22555 |
| 1139461 | 219191_s_at | NM_016293 | 14770 | BIN2 |
| 1128494 | 219209_at | NM_022168 | 389539 | MDA5 |
| 1139466 | 219210_s_at | NM_016530 | 365655 | RAB8B |
| 1128506 | 219226_at | NM_015083 | 416108 | CRK7 |
| 1139483 | 219249_s_at | NM_021939 | 3849 | FKBP10 |
| 1128535 | 219278_at | NM_004672 | 194694 | MAP3K6 |
| 1128536 | 219279_at | NM_014689 | 21126 | DOCK10 |
| 1139526 | 219356_s_at | NM_016410 | 415534 | C9orf83 |
| 1139528 | 219360_s_at | NM_017636 | 31608 | TRPM4 |
| 1139531 | 219365_s_at | NM_024046 | 145156 | MGC8407 |
| 1128585 | 219366_at | NM_020371 | 63168 | AVEN |
| 1139542 | 219396_s_at | NM_024608 | 512732 | NEIL1 |
| 1128615 | 219410_at | NM_018004 | 104800 | FLJ10134 |
| 1128626 | 219424_at | NM_005755 | 501452 | EBI3 |

TABLE 2-continued

| UNIQID | Probe Set | Genbank Accession No. | Unigene ID Build 167 | Unigene Symbol |
|---|---|---|---|---|
| 1139552 | 219441_s_at | NM_024652 | 413386 | LRRK1 |
| 1128648 | 219452_at | NM_022355 | 499331 | DPEP2 |
| 1139556 | 219457_s_at | NM_024832 | 413374 | RIN3 |
| 1128653 | 219461_at | NM_020168 | 21420 | PAK6 |
| 1128655 | 219463_at | NM_012261 | 22920 | C20orf103 |
| 1128660 | 219471_at | NM_025113 | 413071 | C13orf18 |
| 1128681 | 219500_at | NM_013246 | 191548 | CLC |
| 1128688 | 219509_at | NM_021245 | 238756 | MYOZ1 |
| 1139572 | 219511_s_at | NM_005460 | 24948 | SNCAIP |
| 1128694 | 219517_at | NM_025165 | 171466 | ELL3 |
| 1139575 | 219519_s_at | NM_023068 | 31869 | SN |
| 1139579 | 219528_s_at | NM_022898 | 57987 | BCL11B |
| 1128705 | 219535_at | NM_014586 | 109437 | HUNK |
| 1128710 | 219542_at | NM_024800 | 159146 | NEK11 |
| 1128713 | 219545_at | NM_023930 | 17296 | KCTD14 |
| 1128733 | 219572_at | NM_017954 | 489847 | CADPS2 |
| 1128738 | 219581_at | NM_025265 | 335550 | MGC2776 |
| 1139603 | 219603_s_at | NM_015919 | 145956 | ZNF226 |
| 1128757 | 219618_at | NM_016123 | 142295 | IRAK4 |
| 1128781 | 219648_at | NM_018000 | 79741 | FLJ10116 |
| 1128786 | 219654_at | NM_014241 | 114062 | PTPLA |
| 1128787 | 219655_at | NM_024728 | 114611 | C7orf10 |
| 1139623 | 219667_s_at | NM_017935 | 193736 | BANK1 |
| 1128801 | 219676_at | NM_025231 | 288539 | ZNF435 |
| 1128807 | 219686_at | NM_018401 | 58241 | HSA250839 |
| 1128845 | 219734_at | NM_017699 | 272416 | FLJ20174 |
| 1128860 | 219753_at | NM_012447 | 323634 | STAG3 |
| 1139645 | 219757_s_at | NM_017799 | 134051 | C14orf101 |
| 1139654 | 219787_s_at | NM_018098 | 293257 | ECT2 |
| 1139661 | 219806_s_at | NM_020179 | 416456 | FN5 |
| 1128900 | 219812_at | NM_024070 | 323634 | STAG3 |
| 1128901 | 219813_at | NM_004690 | 487239 | LATS1 |
| 1139663 | 219816_s_at | NM_018107 | 4997 | RNPC4 |
| 1128915 | 219831_at | NM_016508 | 105818 | CDKL3 |
| 1139669 | 219837_s_at | NM_018659 | 13872 | C17 |
| 1128965 | 219901_at | NM_018351 | 170623 | FGD6 |
| 1128969 | 219906_at | NM_018029 | 446590 | FLJ10213 |
| 1129024 | 220005_at | NM_176894 | 13040 | GPR86 |
| 1129026 | 220007_at | NM_024770 | 135146 | FLJ13984 |
| 1129043 | 220028_at | NM_001106 | 23994 | ACVR2B |
| 1129049 | 220034_at | NM_007199 | 268552 | IRAK3 |
| 1129059 | 220054_at | NM_016584 | 98309 | IL23A |
| 1129061 | 220056_at | NM_021258 | 110915 | IL22RA1 |
| 1129064 | 220059_at | NM_012108 | 121128 | BRDG1 |
| 1129071 | 220068_at | NM_013378 | 136713 | VPREB3 |
| 1129085 | 220088_at | NM_001736 | 2161 | C5R1 |
| 1129103 | 220118_at | NM_014383 | 99430 | TZFP |
| 1139767 | 220127_s_at | NM_017703 | 12439 | FBXL12 |
| 1139774 | 220140_s_at | NM_013323 | 15827 | SNX11 |
| 1129120 | 220146_at | NM_016562 | 179152 | TLR7 |
| 1129151 | 220196_at | NM_024690 | 432676 | MUC16 |
| 1139805 | 220230_s_at | NM_016229 | 414362 | CYB5R2 |
| 1129203 | 220273_at | NM_014443 | 110040 | IL17B |
| 1129223 | 220296_at | NM_198321 | 13785 | GALNT10 |
| 1129228 | 220302_at | NM_005906 | 148496 | MAK |
| 1129232 | 220307_at | NM_016382 | 157872 | CD244 |
| 1129245 | 220322_at | NM_019618 | 211238 | IL1F9 |
| 1139830 | 220330_s_at | NM_022136 | 221851 | SAMSN1 |
| 1139831 | 220335_x_at | NM_024922 | 268700 | FLJ21736 |
| 1129265 | 220351_at | NM_016557 | 310512 | CCRL1 |
| 1139839 | 220357_s_at | NM_016276 | 62863 | SGK2 |
| 1129269 | 220358_at | NM_018664 | 62919 | SNFT |
| 1139842 | 220367_s_at | NM_024545 | 133523 | SAP130 |
| 1129281 | 220377_at | NR_026800 | 395486 | C14orf110 |
| 1129310 | 220415_at | NM_015978 | 414091 | TNNI3K |
| 1129336 | 220448_at | NM_022055 | 252617 | KCNK12 |
| 1129419 | 220565_at | NM_016602 | 278446 | GPR2 |
| 1139925 | 220643_s_at | NM_018147 | 173438 | FAIM |
| 1129495 | 220684_at | NM_013351 | 272409 | TBX21 |
| 1129517 | 220712_at | NM_014957 | | |
| 1139949 | 220725_x_at | NM_017539 | 528684 | FLJ23558 |
| 1139950 | 220731_s_at | NM_018090 | 437385 | FLJ10420 |
| 1129535 | 220737_at | NM_014496 | 368153 | RPS6KA6 |
| 1139955 | 220740_s_at | NM_005135 | 4876 | SLC12A6 |
| 1139957 | 220742_s_at | NM_018297 | 63657 | NGLY1 |
| 1129537 | 220745_at | NM_013371 | 71979 | IL19 |
| 1139962 | 220751_s_at | NM_032385 | 10235 | C5orf4 |

TABLE 2-continued

| UNIQID | Probe Set | Genbank Accession No. | Unigene ID Build 167 | Unigene Symbol |
|---|---|---|---|---|
| 1139969 | 220761_s_at | NM_016281 | 12040 | JIK |
| 1139971 | 220765_s_at | NM_017980 | 127273 | LIMS2 |
| 1140007 | 220865_s_at | NM_014317 | 279865 | TPRT |
| 1140018 | 220917_s_at | NM_025132 | 438482 | PWDMP |
| 1140027 | 220933_s_at | NM_024617 | 12742 | ZCCHC6 |
| 1140031 | 220937_s_at | NM_175039 | 3972 | SIAT7D |
| 1129661 | 220971_at | NM_022789 | 302036 | IL17E |
| 1140072 | 220984_s_at | NM_030958 | 199750 | SLCO5A1 |
| 1140075 | 220987_s_at | NM_030952 | 172012 | SNARK |
| 1140088 | 221002_s_at | NM_030927 | 509050 | DC-TM4F2 |
| 1140127 | 221044_s_at | NM_021616 | 125300 | TRIM34 |
| 1140151 | 221080_s_at | NM_024898 | 236449 | FAM31C |
| 1129681 | 221085_at | NM_005118 | 241382 | TNFSF15 |
| 1129694 | 221111_at | NM_018402 | 272350 | IL26 |
| 1129743 | 221191_at | NM_001002840 | 429531 | DKFZP434A0131 |
| 1140214 | 221215_s_at | NM_020639 | 55565 | ANKRD3 |
| 1140236 | 221239_s_at | NM_030764 | 194976 | SPAP1 |
| 1140238 | 221241_s_at | NM_030766 | 11962 | BCL2L14 |
| 1129754 | 221271_at | NM_021803 | 302014 | IL21 |
| 1129760 | 221287_at | NM_021133 | 404277 | RNASEL |
| 1129812 | 221355_at | NM_005199 | 248101 | CHRNG |
| 1129821 | 221367_at | NM_005372 | 248146 | MOS |
| 1129825 | 221371_at | NM_005092 | 248197 | TNFSF18 |
| 1129874 | 221463_at | NM_002991 | 247838 | CCL24 |
| 1129879 | 221468_at | NM_005283 | 248116 | XCR1 |
| 1140344 | 221479_s_at | NM_004331 | 132955 | BNIP3L |
| 1129887 | 221485_at | NM_004776 | 107526 | B4GALT5 |
| 1140370 | 221520_s_at | NM_018101 | 48855 | CDCA8 |
| 1140378 | 221530_s_at | NM_030762 | 437282 | BHLHB3 |
| 1129907 | 221539_at | NM_004095 | 406408 | EIF4EBP1 |
| 1129911 | 221549_at | NM_031485 | 400625 | GRWD1 |
| 1140391 | 221558_s_at | NM_016269 | 44865 | LEF1 |
| 1129917 | 221560_at | NM_031417 | 118843 | MARK4 |
| 1129923 | 221571_at | NM_003300 | 297660 | TRAF3 |
| 1140399 | 221577_x_at | NM_004864 | 296638 | GDF15 |
| 1140404 | 221584_s_at | NM_002247 | 354740 | KCNMA1 |
| 1140416 | 221601_s_at | NM_005449 | 58831 | TOSO |
| 1129943 | 221626_at | NM_001099269 | 512828 | ZNF506 |
| 1140457 | 221658_s_at | NM_021798 | 210546 | IL21R |
| 1140464 | 221667_s_at | NM_014365 | 111676 | HSPB8 |
| 1140473 | 221676_s_at | NM_014325 | 17377 | CORO1C |
| 1140491 | 221696_s_at | NM_018423 | 24979 | DKFZp761P1010 |
| 1140497 | 221704_s_at | NM_024667 | 77870 | FLJ12750 |
| 1129967 | 221739_at | NM_019107 | 10927 | C19orf10 |
| 1140520 | 221741_s_at | NM_017798 | 11747 | C20orf21 |
| 1129978 | 221753_at | NM_018984 | 60377 | SSH1 |
| 1140524 | 221766_s_at | NM_017633 | 10784 | C6orf37 |
| 1129993 | 221777_at | NM_032848 | 412981 | FLJ14827 |
| 1140534 | 221790_s_at | NM_015627 | 184482 | ARM |
| 1130007 | 221796_at | NM_001007097 | 439109 | NTRK2 |
| 1130030 | 221834_at | NR_040677 | 301872 | LONP |
| 1130040 | 221855_at | NM_001042631 | 356460 | |
| 1130054 | 221872_at | NM_206963 | 82547 | RARRES1 |
| 1140565 | 221875_x_at | NM_018950 | 411958 | HLA-F |
| 1140567 | 221881_s_at | NM_013943 | 25035 | CLIC4 |
| 1140570 | 221891_x_at | NM_006597 | 180414 | HSPA8 |
| 1140571 | 221893_s_at | NM_052853 | 210397 | ADCK2 |
| 1130072 | 221898_at | NM_006474 | 468675 | T1A-2 |
| 1130078 | 221905_at | NM_015247 | 386952 | CYLD |
| 1140574 | 221912_s_at | NM_024296 | 17987 | MGC1203 |
| 1130088 | 221918_at | NM_002595 | 258536 | PCTK2 |
| 1130090 | 221922_at | NM_013296 | 278338 | GPSM2 |
| 1140584 | 221932_s_at | NM_016417 | 294083 | C14orf87 |
| 1140589 | 221942_s_at | NM_000856 | 433488 | GUCY1A3 |
| 1130114 | 221965_at | NM_022782 | 445084 | MPHOSPH9 |
| 1130117 | 221969_at | NM_016734 | 22030 | PAX5 |
| 1130121 | 221978_at | NM_001098479 | 411958 | HLA-F |
| 1140613 | 221998_at | NM_016440 | 443330 | VRK3 |
| 1140630 | 222033_s_at | NM_002019 | 347713 | FLT1 |
| 1140632 | 222036_s_at | NM_005914 | 460184 | MCM4 |
| 1130155 | 222043_at | NM_001831 | 436657 | CLU |
| 1130168 | 222061_at | NM_001144822 | 75626 | CD58 |
| 1130169 | 222062_at | NM_004843 | 132781 | IL27RA |
| 1130201 | 222126_at | NM_006076 | 278502 | HRBL |
| 1140729 | 222223_s_at | NM_012275 | 207224 | IL1F5 |
| 1140745 | 222245_s_at | NR_024377 | 72222 | FER1L4 |
| 1130293 | 222315_at | XR_159169 | 292853 | |

TABLE 2-continued

| UNIQID | Probe Set | Genbank Accession No. | Unigene ID Build 167 | Unigene Symbol |
|---|---|---|---|---|
| 1130337 | 222368_at | AK096778 | 491069 | |
| 1095985 | 222450_at | NM_020182 | 83883 | TMEPAI |
| 1095996 | 222482_at | NM_018070 | 288801 | SSBP3 |
| 1114679 | 222503_s_at | NM_018268 | 16470 | FLJ10904 |
| 1096028 | 222557_at | NM_015894 | 285753 | STMN3 |
| 1114715 | 222565_s_at | NM_005813 | 434387 | PRKCN |
| 1096035 | 222569_at | NM_020120 | 105794 | UGCGL1 |
| 1096038 | 222572_at | NM_018444 | 22265 | PPM2C |
| 1114726 | 222590_s_at | NM_016231 | 3532 | NLK |
| 1096054 | 222606_at | NM_017975 | 21331 | FLJ10036 |
| 1096070 | 222640_at | NM_022552 | 241565 | DNMT3A |
| 1096077 | 222659_at | NM_016338 | 441043 | IPO11 |
| 1096078 | 222661_at | NM_018046 | 284216 | HSU84971 |
| 1114766 | 222666_s_at | NM_005772 | 113052 | RCL1 |
| 1096085 | 222674_at | NM_016390 | 224137 | HSPC109 |
| 1096108 | 222731_at | NM_016353 | 292871 | ZDHHC2 |
| 1114824 | 222762_x_at | NM_014240 | 193370 | LIMD1 |
| 1114853 | 222812_s_at | NM_019034 | 512618 | ARHF |
| 1096149 | 222824_at | NM_014142 | 410205 | NUDT5 |
| 1096152 | 222828_at | NM_014432 | 288240 | IL20RA |
| 1096158 | 222838_at | NM_021181 | 132906 | SLAMF7 |
| 1096163 | 222848_at | NM_022145 | 164018 | FKSG14 |
| 1114877 | 222862_s_at | NM_012093 | 18268 | AK5 |
| 1096172 | 222880_at | NM_005465 | 300642 | AKT3 |
| 1096180 | 222890_at | NM_014157 | 11614 | HSPC065 |
| 1114893 | 222891_s_at | NM_022893 | 314623 | BCL11A |
| 1096182 | 222899_at | NM_001004439 | 256297 | ITGA11 |
| 1114913 | 222920_s_at | NM_014796 | 33187 | KIAA0748 |
| 1096220 | 222974_at | NM_020525 | 287369 | IL22 |
| 1114967 | 223028_s_at | NM_016224 | 7905 | SNX9 |
| 1114970 | 223032_x_at | NM_013237 | 279529 | PX19 |
| 1096248 | 223040_at | NM_016100 | 109253 | NAT5 |
| 1096251 | 223044_at | NM_014585 | 409875 | SLC40A1 |
| 1114977 | 223052_x_at | NM_014188 | 30026 | HSPC182 |
| 1114981 | 223057_s_at | NM_020750 | 203206 | XPO5 |
| 1114988 | 223075_s_at | NM_031426 | 4944 | C9orf58 |
| 1115008 | 223117_s_at | NM_017944 | 441028 | USP47 |
| 1115012 | 223122_s_at | NM_003013 | 31386 | SFRP2 |
| 1096297 | 223141_at | NM_031432 | 9597 | UCK1 |
| 1096300 | 223151_at | NM_032299 | 74284 | MGC2714 |
| 1115034 | 223158_s_at | NM_014397 | 387222 | NEK6 |
| 1115052 | 223190_s_at | NM_018682 | 380021 | MLL5 |
| 1115071 | 223218_s_at | NM_031419 | 390476 | MAIL |
| 1115073 | 223220_s_at | NM_031458 | 131315 | BAL |
| 1096341 | 223241_at | NM_013321 | 12169 | SNX8 |
| 1096356 | 223266_at | NM_018571 | 259230 | ALS2CR2 |
| 1096357 | 223267_at | NM_017819 | 57898 | FLJ20432 |
| 1096362 | 223274_at | NM_007109 | 512706 | TCF19 |
| 1096364 | 223276_at | NM_032947 | 29444 | NID67 |
| 1096369 | 223286_at | NM_015362 | 417029 | DERP6 |
| 1096378 | 223303_at | NM_031471 | 180535 | URP2 |
| 1096379 | 223304_at | NM_032295 | 439590 | SLC37A3 |
| 1115128 | 223349_s_at | NM_032515 | 293753 | BOK |
| 1096406 | 223361_at | NM_021243 | 238205 | C6orf115 |
| 1096429 | 223405_at | NM_030769 | 64896 | NPL |
| 1115160 | 223413_s_at | NM_017816 | 425427 | LYAR |
| 1096440 | 223423_at | NM_014373 | 231320 | GPR160 |
| 1096442 | 223430_at | NM_015191 | 306864 | SIK2 |
| 1096446 | 223434_at | NM_018284 | 92287 | GBP3 |
| 1115176 | 223451_s_at | NM_016951 | 15159 | CKLF |
| 1096456 | 223454_at | NM_022059 | 82407 | CXCL16 |
| 1096460 | 223460_at | NM_032294 | 8417 | CAMKK1 |
| 1096466 | 223467_at | NM_016084 | 25829 | RASD1 |
| 1096469 | 223471_at | NM_022456 | 103267 | RAB3IP |
| 1115186 | 223480_s_at | NM_020409 | 283734 | MRPL47 |
| 1115194 | 223502_s_at | NM_006573 | 270737 | TNFSF13B |
| 1096499 | 223514_at | NM_032415 | 293867 | CARD11 |
| 1096503 | 223522_at | NR_026677 | 21379 | C9orf45 |
| 1115203 | 223534_s_at | NM_031464 | 414481 | RPS6KL1 |
| 1096530 | 223565_at | NM_016459 | 409563 | PACAP |
| 1115226 | 223600_s_at | NM_025249 | 279718 | KIAA1683 |
| 1096570 | 223624_at | NM_174890 | 409813 | ANUBL1 |
| 1096579 | 223640_at | NM_014266 | 117339 | HCST |
| 1115253 | 223664_x_at | NM_015367 | 310922 | BCL2L13 |
| 1096609 | 223696_at | NM_001669 | 528631 | ARSD |
| 1115271 | 223705_s_at | NM_022913 | 71252 | DKFZp761C169 |
| 1096615 | 223707_at | NM_000990 | 356342 | RPL27A |

TABLE 2-continued

| UNIQID | Probe Set | Genbank Accession No. | Unigene ID Build 167 | Unigene Symbol |
|---|---|---|---|---|
| 1096616 | 223708_at | NM_031909 | 119302 | C1QTNF4 |
| 1096617 | 223710_at | NM_006072 | 131342 | CCL26 |
| 1096621 | 223715_at | NM_003957 | 170819 | STK29 |
| 1115286 | 223750_s_at | NM_030956 | 120551 | TLR10 |
| 1115290 | 223759_s_at | NM_031965 | 193666 | GSG2 |
| 1115303 | 223787_s_at | NM_016474 | 236257 | LOC51244 |
| 1115309 | 223804_s_at | NM_015453 | 443081 | DKFZP434F091 |
| 1096690 | 223827_at | NM_148957 | 334174 | TNFRSF19 |
| 1096693 | 223834_at | NM_014143 | 443271 | PDCD1LG1 |
| 1115329 | 223852_s_at | NM_032017 | 439658 | MGC4796 |
| 1096719 | 223874_at | NM_001164458 | 250153 | ARP3BETA |
| 1115338 | 223883_s_at | NM_031414 | 224355 | STK31 |
| 1096738 | 223903_at | NM_017442 | 87968 | TLR9 |
| 1115347 | 223909_s_at | NM_018486 | 112272 | HDAC8 |
| 1096742 | 223910_at | NM_033266 | 114905 | ERN2 |
| 1115360 | 223940_x_at | NR_002819 | 187199 | PRO1073 |
| 1096805 | 224027_at | NM_148672 | 334633 | CCL28 |
| 1096829 | 224071_at | NM_018724 | 272373 | IL20 |
| 1096834 | 224079_at | NM_013278 | 278911 | IL17C |
| 1096877 | 224132_at | AA992036 | 326732 | MGC13008 |
| 1115441 | 224156_x_at | NM_018725 | 5470 | IL17RB |
| 1096903 | 224185_at | NM_018081 | 437460 | FLJ10385 |
| 1096936 | 224262_at | NM_032556 | 306974 | IL1F10 |
| 1115519 | 224302_s_at | NM_033281 | 408914 | MRPS36 |
| 1096965 | 224346_at | NM_000146 | 433466 | PRO1853 |
| 1115566 | 224369_s_at | NM_030793 | 163825 | SP329 |
| 1096981 | 224399_at | NM_025239 | 61929 | PDCD1LG2 |
| 1115587 | 224402_s_at | NM_031282 | 120260 | IRTA1 |
| 1115589 | 224406_s_at | NM_031281 | 415950 | IRTA2 |
| 1115591 | 224409_s_at | NM_032037 | 367871 | SSTK |
| 1115607 | 224428_s_at | NM_031942 | 435733 | CDCA7 |
| 1115621 | 224450_s_at | NM_031480 | 437474 | RIOK1 |
| 1115646 | 224481_s_at | NM_015382 | 210850 | HECTD1 |
| 1115668 | 224509_s_at | NM_032730 | 155839 | RTN4IP1 |
| 1115673 | 224514_x_at | NM_032732 | 129959 | IL17RC |
| 1115679 | 224523_s_at | NM_032359 | 8345 | MGC4308 |
| 1115695 | 224553_s_at | NM_004195 | 212680 | TNFRSF18 |
| 1115696 | 224555_x_at | NM_014439 | 166371 | IL1F7 |
| 1115704 | 224569_s_at | NM_182972 | 350268 | IRF2BP2 |
| 1097030 | 224574_at | NM_174893 | 511801 | |
| 1097065 | 224621_at | NM_002745 | 324473 | MAPK1 |
| 1097096 | 224659_at | NM_020451 | 8518 | SEPN1 |
| 1097107 | 224673_at | NM_052925 | 502378 | LENG8 |
| 1097109 | 224675_at | NM_015154 | 78871 | MESDC2 |
| 1097126 | 224694_at | NM_032208 | 274520 | ANTXR1 |
| 1097143 | 224716_at | NM_178148 | 74335 | HSPCB |
| 1097156 | 224733_at | NM_144601 | 298198 | CKLFSF3 |
| 1097161 | 224740_at | NM_001048249 | 5064 | |
| 1097172 | 224753_at | NM_080668 | 434886 | CDCA5 |
| 1097177 | 224761_at | NM_006572 | 9691 | GNA13 |
| 1097195 | 224785_at | NM_182565 | 149931 | MGC29814 |
| 1097202 | 224796_at | NM_018482 | 386779 | DDEF1 |
| 1097229 | 224830_at | NM_007006 | 446393 | CPSF5 |
| 1097236 | 224837_at | NM_032682 | 235860 | FOXP1 |
| 1115763 | 224839_s_at | NM_133443 | 355862 | GPT2 |
| 1097247 | 224851_at | NM_001259 | 388761 | CDK6 |
| 1097253 | 224859_at | NM_025240 | 77873 | B7H3 |
| 1097255 | 224861_at | NM_002072 | 380144 | |
| 1097271 | 224880_at | NM_005402 | 6906 | RALA |
| 1097280 | 224891_at | NM_001455 | 423523 | |
| 1097281 | 224892_at | NM_012388 | 7037 | PLDN |
| 1097282 | 224893_at | NM_015459 | 356719 | LOC283241 |
| 1097290 | 224903_at | NM_032830 | 151001 | CIRH1A |
| 1097297 | 224917_at | NM_030938 | 166254 | VMP1 |
| 1097307 | 224929_at | NM_198282 | 379754 | LOC340061 |
| 1097310 | 224934_at | NM_030799 | 5672 | SMAP-5 |
| 1097325 | 224951_at | NM_147190 | 458450 | LASS5 |
| 1097329 | 224955_at | NM_021961 | 528675 | TEAD1 |
| 1097334 | 224960_at | NM_017988 | 71573 | FLJ10074 |
| 1097359 | 224990_at | NM_174921 | 518723 | |
| 1097365 | 224998_at | NM_178818 | 325825 | CKLFSF4 |
| 1097371 | 225005_at | NM_153812 | 7299 | PHF13 |
| 1097383 | 225019_at | NM_001221 | 111460 | CAMK2D |
| 1097388 | 225024_at | NM_021215 | 278839 | C20orf77 |
| 1097395 | 225032_at | NM_022763 | 299883 | FAD104 |
| 1115800 | 225040_s_at | NM_006916 | 282260 | RPE |
| 1097424 | 225067_at | NM_001099436 | 7978 | DKFZP434C131 |

TABLE 2-continued

| UNIQID | Probe Set | Genbank Accession No. | Unigene ID Build 167 | Unigene Symbol |
|---|---|---|---|---|
| 1097441 | 225086_at | NM_173611 | 6799 | FLJ38426 |
| 1097448 | 225093_at | NM_007124 | 250607 | UTRN |
| 1115812 | 225164_s_at | NM_001013703 | 412102 | EIF2AK4 |
| 1115813 | 225175_s_at | NM_020428 | 105509 | CTL2 |
| 1097540 | 225195_at | NM_001047434 | 388087 | |
| 1097553 | 225214_at | NR_027406 | 197071 | PSMB7 |
| 1097561 | 225224_at | NM_080616 | 19221 | DKFZP566G1424 |
| 1097563 | 225226_at | NM_033088 | 169577 | FLJ14743 |
| 1097564 | 225227_at | NM_005414 | 272108 | SKIL |
| 1115829 | 225253_s_at | NM_181725 | 433213 | METTL2 |
| 1097600 | 225272_at | NM_133491 | 10846 | SAT2 |
| 1097609 | 225283_at | NM_183376 | 6093 | ARRDC4 |
| 1097610 | 225284_at | NM_006260 | 6019 | DNAJC3 |
| 1097611 | 225285_at | NM_005504 | 438993 | BCAT1 |
| 1097614 | 225289_at | NM_003150 | 410491 | MGC16063 |
| 1115840 | 225308_s_at | NM_033394 | 437362 | KIAA1728 |
| 1097637 | 225317_at | NM_032360 | 63220 | ACBD6 |
| 1097665 | 225351_at | NM_207009 | 434241 | HT011 |
| 1097676 | 225366_at | NM_018290 | 23363 | PGM2 |
| 1097683 | 225373_at | NM_022153 | 132569 | PP2135 |
| 1097684 | 225374_at | NM_152464 | 368878 | MGC45714 |
| 1097704 | 225399_at | NM_052965 | 440663 | C1orf19 |
| 1097707 | 225402_at | NM_033550 | 440263 | C20orf64 |
| 1097717 | 225412_at | NM_032824 | 23317 | FLJ14681 |
| 1097735 | 225436_at | NM_021214 | 26765 | LOC58489 |
| 1097804 | 225519_at | NM_018029 | 446590 | FLJ10213 |
| 1097814 | 225529_at | NM_030649 | 21446 | CENTB5 |
| 1115876 | 225535_s_at | NM_006327 | 11866 | TIMM23 |
| 1097824 | 225540_at | NM_002374 | 167 | MAP2 |
| 1115877 | 225552_x_at | NM_017900 | 76239 | MGC3047 |
| 1097887 | 225611_at | NM_015183 | 212787 | KIAA0303 |
| 1097897 | 225622_at | NM_018440 | 266175 | PAG |
| 1097899 | 225624_at | NM_032167 | 145047 | LOC92017 |
| 1097901 | 225626_at | NM_018440 | 266175 | PAG |
| 1115888 | 225629_s_at | NM_020899 | 35096 | ZBTB4 |
| 1097902 | 225630_at | NM_030636 | 412318 | KIAA1706 |
| 1115892 | 225649_s_at | NM_080836 | 100057 | STK35 |
| 1097918 | 225650_at | NM_138352 | 140309 | LOC90378 |
| 1097928 | 225660_at | NM_020796 | 443012 | SEMA6A |
| 1097930 | 225662_at | NM_133646 | 115175 | ZAK |
| 1097940 | 225673_at | NM_138373 | 380906 | MYADM |
| 1115895 | 225682_s_at | NM_138338 | 202505 | RPC8 |
| 1097948 | 225684_at | NM_182620 | 69476 | LOC348235 |
| 1097961 | 225699_at | NR_003697 | 25892 | |
| 1097966 | 225704_at | NM_001142641 | 127270 | KIAA1545 |
| 1097976 | 225715_at | NM_020761 | 218017 | raptor |
| 1098012 | 225756_at | NM_001894 | 355669 | CSNK1E |
| 1115905 | 225757_s_at | NM_024734 | 301478 | CLMN |
| 1098023 | 225773_at | NM_133368 | 181161 | KIAA1972 |
| 1098065 | 225817_at | NM_032866 | 10119 | FLJ14957 |
| 1098069 | 225823_at | NM_205767 | 356626 | |
| 1115916 | 225836_s_at | NM_001252499 | 157148 | MGC13204 |
| 1115917 | 225849_s_at | NM_145169 | 284265 | C6orf83 |
| 1098095 | 225852_at | NM_032217 | 131059 | ANKRD17 |
| 1098103 | 225864_at | NM_174911 | 124951 | NSE2 |
| 1098145 | 225913_at | NM_024776 | 9587 | KIAA2002 |
| 1098152 | 225922_at | NM_020840 | 377588 | KIAA1450 |
| 1098156 | 225927_at | NM_005921 | 170610 | MAP3K1 |
| 1098168 | 225943_at | NM_020726 | 22151 | NLN |
| 1098174 | 225949_at | NM_178564 | 274401 | LOC340371 |
| 1098179 | 225956_at | NM_153607 | 163725 | LOC153222 |
| 1098186 | 225964_at | NM_001040653 | 288697 | MGC11349 |
| 1098195 | 225974_at | NM_001008495 | 88594 | DKFZp762C1112 |
| 1098204 | 225984_at | NM_006251 | 43322 | PRKAA1 |
| 1098220 | 226002_at | NM_002039 | 80720 | GAB1 |
| 1098234 | 226016_at | NM_001777 | 446414 | CD47 |
| 1098235 | 226017_at | NM_138410 | 440494 | CKLFSF7 |
| 1098242 | 226025_at | NM_015199 | 273104 | KIAA0379 |
| 1098252 | 226035_at | NM_020718 | 16953 | USP31 |
| 1098256 | 226041_at | NM_198990 | 431871 | SVH |
| 1098258 | 226043_at | NM_001145638 | 239370 | GPSM1 |
| 1098268 | 226053_at | NM_145185 | 110299 | MAP2K7 |
| 1098271 | 226056_at | NM_020754 | 300670 | CDGAP |
| 1098277 | 226065_at | NM_153026 | 6786 | PRICKLE1 |
| 1098278 | 226066_at | NM_000248 | 166017 | MITF |
| 1098303 | 226096_at | NM_153756 | 15463 | FNDC5 |
| 1115953 | 226111_s_at | NM_015481 | 278422 | ZNF385 |

TABLE 2-continued

| UNIQID | Probe Set | Genbank Accession No. | Unigene ID Build 167 | Unigene Symbol |
|---|---|---|---|---|
| 1115955 | 226132_s_at | NM_152496 | 7988 | FLJ31434 |
| 1098338 | 226136_at | NM_006851 | 269857 | HRB2 |
| 1115960 | 226145_s_at | NM_025074 | 15420 | FRAS1 |
| 1115965 | 226166_x_at | NM_015690 | 26996 | STK36 |
| 1098405 | 226218_at | NM_002185 | 362807 | IL7R |
| 1098412 | 226225_at | NM_002387 | 409515 | MCC |
| 1098415 | 226230_at | NM_001122964 | 130900 | KIAA1387 |
| 1098433 | 226250_at | AK091904 | 202577 | |
| 1098447 | 226267_at | NM_130469 | 154095 | JDP2 |
| 1098459 | 226279_at | NM_007173 | 25338 | SPUVE |
| 1098461 | 226281_at | NM_139072 | 234074 | DNER |
| 1098476 | 226299_at | NM_013355 | 300485 | pknbeta |
| 1098495 | 226318_at | NM_032811 | 443668 | TBRG1 |
| 1098506 | 226333_at | NM_000565 | 193400 | IL6R |
| 1098521 | 226350_at | NM_001821 | 170129 | OPN3 |
| 1098548 | 226377_at | NM_005597 | 436639 | NFIC |
| 1098550 | 226381_at | XR_109878 | 355655 | |
| 1098553 | 226384_at | NM_001102559 | 437179 | HTPAP |
| 1098574 | 226410_at | NM_001012759 | 79077 | KIAA0233 |
| 1098592 | 226431_at | NM_173511 | 283707 | ALS2CR13 |
| 1098604 | 226444_at | NM_020342 | 32793 | SLC39A10 |
| 1098607 | 226448_at | NM_198552 | 38516 | MGC15887 |
| 1098611 | 226452_at | NM_002610 | 433611 | PDK1 |
| 1098613 | 226454_at | NM_138396 | 388125 | RENT1 |
| 1098618 | 226459_at | NM_152309 | 374836 | PIK3AP1 |
| 1116001 | 226465_s_at | NM_032195 | 430541 | SON |
| 1098629 | 226473_at | NM_005189 | 103305 | |
| 1116006 | 226491_x_at | NM_002819 | 172550 | PTBP1 |
| 1098658 | 226507_at | NM_002576 | 64056 | PAK1 |
| 1098668 | 226517_at | NM_005504 | 438993 | BCAT1 |
| 1098669 | 226518_at | NM_031954 | 302746 | KCTD10 |
| 1098678 | 226530_at | NM_033503 | 386140 | BMF |
| 1098683 | 226535_at | NM_000888 | 57664 | ITGB6 |
| 1098694 | 226548_at | NM_001024401 | 97837 | |
| 1098718 | 226574_at | NM_001042414 | 16364 | PSPC1 |
| 1116022 | 226611_s_at | NM_181716 | 433422 | p30 |
| 1098771 | 226638_at | NM_001199417 | 374446 | KIAA1501 |
| 1098784 | 226653_at | NM_018650 | 12808 | MARK1 |
| 1098809 | 226682_at | NM_002943 | 359394 | |
| 1098821 | 226694_at | NM_001004065 | 42322 | PALM2 |
| 1098822 | 226695_at | NM_006902 | 443452 | PRRX1 |
| 1098832 | 226705_at | NM_015850 | 748 | FGFR1 |
| 1098840 | 226713_at | NM_174908 | 55098 | C3orf6 |
| 1098862 | 226737_at | NM_178526 | 303669 | MGC26694 |
| 1098865 | 226741_at | NM_005135 | 250905 | LOC51234 |
| 1098883 | 226760_at | NM_015884 | 412014 | MBTPS2 |
| 1098893 | 226771_at | NM_020452 | 43577 | ATP8B2 |
| 1098898 | 226777_at | NM_003474 | 8850 | ADAM12 |
| 1098909 | 226789_at | NM_198449 | 446408 | |
| 1098918 | 226799_at | NM_018351 | 170623 | FGD6 |
| 1098927 | 226811_at | NM_017709 | 356216 | FLJ20202 |
| 1116045 | 226828_s_at | NM_014571 | 23823 | HEYL |
| 1098946 | 226834_at | NM_024769 | 135121 | ASAM |
| 1098951 | 226840_at | NM_138610 | 75258 | H2AFY |
| 1098952 | 226841_at | NM_001039396 | 62264 | KIAA0937 |
| 1098954 | 226844_at | NM_024761 | 128905 | MOBKL2B |
| 1098962 | 226853_at | NM_198892 | 20137 | BMP2K |
| 1098978 | 226869_at | NM_001409 | 124863 | |
| 1098987 | 226879_at | NM_032369 | 412559 | FLJ21127 |
| 1098991 | 226884_at | NM_020873 | 126085 | LRRN1 |
| 1116056 | 226913_s_at | NM_014587 | 243678 | SOX8 |
| 1099028 | 226930_at | NM_032532 | 334838 | FNDC1 |
| 1099032 | 226936_at | NM_001012507 | 35962 | |
| 1099040 | 226944_at | NM_053044 | 390421 | HTRA3 |
| 1116063 | 226957_x_at | NM_006788 | 75447 | RALBP1 |
| 1099053 | 226959_at | NR_027322 | 376041 | |
| 1099058 | 226964_at | NM_173500 | 425116 | |
| 1099072 | 226979_at | NM_006609 | 28827 | MAP3K2 |
| 1099088 | 226996_at | NM_182551 | 14355 | |
| 1099105 | 227013_at | NM_014572 | 78960 | LATS2 |
| 1099112 | 227020_at | NM_001005404 | 368672 | |
| 1099120 | 227030_at | NM_012481 | 371680 | |
| 1099124 | 227034_at | NM_023016 | 355455 | 9/10/2004 |
| 1099128 | 227039_at | NM_006738 | 350631 | AKAP13 |
| 1099135 | 227046_at | NM_139177 | 3402 | SLC39A11 |
| 1099140 | 227052_at | NM_174921 | 500350 | |
| 1099148 | 227060_at | NM_032871 | 434975 | TNFRSF19L |

TABLE 2-continued

| UNIQID | Probe Set | Genbank Accession No. | Unigene ID Build 167 | Unigene Symbol |
|---|---|---|---|---|
| 1099150 | 227062_at | NR_028272 | 240443 | |
| 1099152 | 227064_at | NM_052855 | 351247 | MGC15396 |
| 1099154 | 227066_at | NM_145279 | 97927 | MOBKL2C |
| 1116071 | 227067_x_at | NM_203458 | 502564 | FLJ20719 |
| 1099167 | 227080_at | NM_001080470 | 381105 | MGC45731 |
| 1116073 | 227103_s_at | NM_032331 | 146161 | MGC2408 |
| 1099204 | 227121_at | AL110204 | 193784 | |
| 1116085 | 227173_s_at | NM_021813 | 88414 | BACH2 |
| 1099265 | 227193_at | AK056686 | 375762 | |
| 1099291 | 227222_at | NM_012166 | 130774 | FBXO10 |
| 1099292 | 227223_at | NM_004902 | 282901 | RNPC2 |
| 1099299 | 227232_at | NM_016337 | 241471 | EVL |
| 1099318 | 227255_at | NM_152835 | 29911 | LOC149420 |
| 1099328 | 227267_at | NM_152408 | 432726 | FLJ35779 |
| 1099332 | 227272_at | NM_207380 | 32433 | |
| 1099358 | 227300_at | NM_181724 | 93135 | |
| 1116103 | 227308_x_at | NM_021070 | 289019 | LTBP3 |
| 1099377 | 227324_at | NM_024876 | 130712 | ADCK4 |
| 1099388 | 227336_at | NM_004416 | 124024 | DTX1 |
| 1099396 | 227346_at | NM_006060 | 435949 | ZNFN1A1 |
| 1099403 | 227354_at | NM_018440 | 266175 | PAG |
| 1099418 | 227370_at | NM_177454 | 172792 | KIAA1946 |
| 1099444 | 227407_at | NM_153365 | 434489 | FLJ90013 |
| 1116122 | 227408_s_at | NM_031953 | 42768 | DKFZp761O0113 |
| 1116126 | 227432_s_at | NM_000208 | 438669 | INSR |
| 1099510 | 227482_at | NM_020421 | 15251 | ADCK1 |
| 1099526 | 227502_at | NM_001080392 | 521240 | LCHN |
| 1099539 | 227520_at | NM_018360 | 201624 | CXorf15 |
| 1099549 | 227533_at | NM_152663 | 446665 | |
| 1099563 | 227550_at | NM_005264 | 388347 | |
| 1099598 | 227590_at | NM_207327 | 511859 | |
| 1116150 | 227606_s_at | NM_020799 | 16229 | AMSH-LP |
| 1099631 | 227624_at | NM_001127208 | 367639 | FLJ20032 |
| 1099633 | 227627_at | NM_013257 | 380877 | SGKL |
| 1099651 | 227646_at | NM_024007 | 120785 | EBF |
| 1099669 | 227666_at | NM_001040260 | 45057 | MGC45428 |
| 1099680 | 227677_at | NM_000215 | 210387 | JAK3 |
| 1099686 | 227684_at | NM_004230 | 117721 | |
| 1099699 | 227697_at | NM_003955 | 436943 | SOCS3 |
| 1099711 | 227713_at | NM_032116 | 243596 | |
| 1099734 | 227740_at | NM_144624 | 127310 | KIS |
| 1099743 | 227750_at | NM_001142571 | 162189 | TRAD |
| 1099748 | 227755_at | AK124426 | 356481 | |
| 1099760 | 227767_at | NM_004384 | 129206 | CSNK1G3 |
| 1099798 | 227811_at | NM_033086 | 411081 | FGD3 |
| 1099826 | 227842_at | NM_014488 | 445862 | RAB30 |
| 1099830 | 227847_at | NM_014805 | 28020 | EPM2AIP1 |
| 1099847 | 227867_at | NM_001080824 | 36723 | LOC129293 |
| 1099857 | 227877_at | NM_001014279 | 119768 | |
| 1116181 | 227891_s_at | NM_003487 | 402752 | TAF15 |
| 1099886 | 227917_at | NR_040092 | 511708 | |
| 1099900 | 227934_at | NM_002269 | 444508 | |
| 1099939 | 227983_at | NM_145058 | 488173 | MGC7036 |
| 1099951 | 227999_at | NM_138499 | 157728 | LOC170394 |
| 1099953 | 228001_at | NR_040016 | 433668 | C21orf4 |
| 1099960 | 228008_at | NM_001033026 | 144583 | |
| 1099965 | 228014_at | NM_001002913 | 71962 | LOC138428 |
| 1099978 | 228035_at | NM_030906 | 148135 | STK33 |
| 1116219 | 228056_s_at | NR_002798 | 322854 | NAP1L |
| 1099995 | 228057_at | NM_145244 | 107515 | DDIT4L |
| 1100005 | 228069_at | NM_138419 | 121536 | DUFD1 |
| 1100027 | 228094_at | NM_153206 | 16291 | AMICA |
| 1100040 | 228109_at | NM_006909 | 410953 | RASGRF2 |
| 1100042 | 228113_at | NM_175738 | 351413 | RAB37 |
| 1116233 | 228128_x_at | NM_002581 | 440769 | PAPPA |
| 1100054 | 228130_at | NM_001112734 | 125353 | |
| 1100060 | 228139_at | NM_006871 | 268551 | RIPK3 |
| 1100071 | 228153_at | NM_182757 | 432653 | IBRDC2 |
| 1100130 | 228224_at | NM_002725 | 76494 | PRELP |
| 1100136 | 228231_at | NM_013321 | 413078 | NUDT1 |
| 1100138 | 228234_at | NM_021649 | 278391 | TIRP |
| 1100144 | 228240_at | NM_014914 | 436379 | |
| 1100150 | 228248_at | NM_152756 | 9343 | MGC39830 |
| 1100159 | 228258_at | NM_198517 | 32156 | RPS6KB2 |
| 1100161 | 228261_at | NM_080875 | 135805 | LOC142678 |
| 1100171 | 228273_at | NM_018304 | 528654 | FLJ11029 |
| 1100183 | 228286_at | NM_182625 | 180582 | FLJ40869 |

TABLE 2-continued

| UNIQID | Probe Set | Genbank Accession No. | Unigene ID Build 167 | Unigene Symbol |
|---|---|---|---|---|
| 1100249 | 228367_at | NM_052947 | 388674 | HAK |
| 1100258 | 228377_at | NM_020805 | 88442 | KIAA1384 |
| 1100263 | 228382_at | NM_138348 | 406335 | LOC90268 |
| 1116277 | 228384_s_at | NM_032709 | 118210 | C10orf33 |
| 1100288 | 228411_at | NM_057177 | 26981 | ALS2CR19 |
| 1100290 | 228414_at | NM_001014797 | 4241 | |
| 1100301 | 228426_at | NM_001004419 | 356250 | LLT1 |
| 1100311 | 228437_at | NM_014184 | 445890 | HSPC163 |
| 1100335 | 228464_at | CR590554 | 268474 | |
| 1100339 | 228468_at | NM_032844 | 276905 | MASTL |
| 1100384 | 228524_at | NM_174922 | 283374 | ADCK5 |
| 1100405 | 228549_at | NM_014698 | 119387 | KIAA0792 |
| 1100420 | 228565_at | NM_032435 | 50883 | KIAA1804 |
| 1100423 | 228568_at | NM_152451 | 50841 | FLJ30973 |
| 1100433 | 228580_at | NM_053044 | 390421 | HTRA3 |
| 1100443 | 228592_at | NM_021950 | 438040 | MS4A1 |
| 1100496 | 228654_at | NM_001012968 | 111496 | LOC139886 |
| 1116317 | 228661_s_at | XR_110481 | 526415 | |
| 1100538 | 228709_at | NM_003292 | 432458 | PRG4 |
| 1100561 | 228736_at | NM_133636 | 194109 | HEL308 |
| 1100562 | 228737_at | NM_032883 | 26608 | C20orf100 |
| 1100581 | 228758_at | NM_001130845 | 155024 | BCL6 |
| 1100585 | 228762_at | NM_002304 | 159142 | LFNG |
| 1100591 | 228769_at | NM_181846 | 388162 | HKR2 |
| 1100598 | 228776_at | NM_005497 | 531058 | |
| 1100609 | 228788_at | NM_013313 | 447045 | PPIL2 |
| 1100625 | 228806_at | NM_005060 | 232803 | |
| 1100721 | 228918_at | NM_152346 | 18713 | |
| 1100750 | 228955_at | NM_004631 | 280387 | |
| 1100753 | 228958_at | NM_006961 | 512717 | ZNF19 |
| 1100770 | 228976_at | NM_015259 | 65578 | |
| 1100847 | 229070_at | NM_032744 | 97411 | C6orf105 |
| 1100849 | 229072_at | AK092185 | 184430 | |
| 1100851 | 229074_at | NM_139265 | 55058 | EHD4 |
| 1100871 | 229101_at | NM_014339 | 48353 | |
| 1100873 | 229103_at | NM_030753 | 445884 | |
| 1100879 | 229111_at | NM_006610 | 119983 | MASP2 |
| 1100904 | 229145_at | NM_173473 | 426296 | LOC119504 |
| 1100911 | 229152_at | NM_152997 | 320147 | C4orf7 |
| 1100916 | 229158_at | NM_032387 | 105448 | PRKWNK4 |
| 1100977 | 229233_at | NM_001010848 | 444783 | NRG3 |
| 1100995 | 229256_at | NM_173582 | 26612 | PGM2L1 |
| 1101004 | 229265_at | NM_003036 | 2969 | SKI |
| 1101023 | 229288_at | NM_004440 | 73962 | EPHA7 |
| 1101054 | 229322_at | NM_006246 | 173328 | PPP2R5E |
| 1116432 | 229356_x_at | NM_017553 | 409362 | KIAA1259 |
| 1101096 | 229373_at | BQ711516 | 527236 | |
| 1101119 | 229401_at | NM_001193380 | 390823 | IL17RE |
| 1101128 | 229411_at | NM_001039582 | 436667 | MGC45419 |
| 1116445 | 229436_x_at | NM_024332 | 301927 | C6.1A |
| 1101149 | 229437_at | NR_001458 | 517226 | BIC |
| 1101211 | 229513_at | NM_018387 | 287659 | STRBP |
| 1101272 | 229584_at | NM_198578 | 179089 | DKFZp434H2111 |
| 1101276 | 229588_at | NM_018981 | 1098 | ERdj5 |
| 1101291 | 229606_at | NM_000944 | 272458 | PPP3CA |
| 1101295 | 229610_at | NM_152515 | 99807 | FLJ40629 |
| 1101305 | 229623_at | NM_001080506 | 112742 | |
| 1101322 | 229645_at | NM_001044369 | 227699 | |
| 1101354 | 229686_at | NM_178129 | 111377 | P2RY8 |
| 1101416 | 229764_at | NM_198485 | 338851 | FLJ41238 |
| 1101430 | 229779_at | NM_000092 | 418040 | |
| 1101439 | 229790_at | NM_005652 | 63335 | TERF2 |
| 1101477 | 229838_at | NM_005013 | 423095 | NUCB2 |
| 1101478 | 229839_at | NM_173833 | 146246 | MGC45780 |
| 1101514 | 229886_at | NM_198566 | 88801 | FLJ32363 |
| 1101566 | 229947_at | NM_015886 | 98558 | |
| 1101582 | 229967_at | NM_144673 | 195685 | CKLFSF2 |
| 1101586 | 229971_at | NM_153837 | 187884 | GPR114 |
| 1101628 | 230021_at | NM_152259 | 441708 | MGC45866 |
| 1101634 | 230028_at | NM_014949 | 510588 | |
| 1101687 | 230086_at | NM_015033 | 440808 | FNBP1 |
| 1101708 | 230110_at | NM_153259 | 459526 | MCOLN2 |
| 1101758 | 230170_at | NM_020530 | 248156 | OSM |
| 1101775 | 230191_at | NM_032538 | 343820 | TTBK1 |
| 1101777 | 230193_at | NM_144668 | 359981 | MGC33630 |
| 1101829 | 230252_at | NM_020400 | 155538 | GPR92 |
| 1101892 | 230327_at | XR_108937 | 225948 | |

TABLE 2-continued

| UNIQID | Probe Set | Genbank Accession No. | Unigene ID Build 167 | Unigene Symbol |
|---|---|---|---|---|
| 1116593 | 230329_s_at | NM_007083 | 422889 | NUDT6 |
| 1101905 | 230345_at | NM_003612 | 170843 | |
| 1101944 | 230391_at | NM_003874 | 439064 | |
| 1101948 | 230395_at | NM_016025 | 14411 | |
| 1101974 | 230425_at | NM_004441 | 272311 | EPHB1 |
| 1102027 | 230489_at | NM_014207 | 58685 | CD5 |
| 1102030 | 230494_at | NM_005415 | 110855 | SLC20A1 |
| 1102081 | 230551_at | NM_173598 | 506977 | |
| 1102165 | 230650_at | AK022971 | 152460 | |
| 1102193 | 230680_at | NM_173078 | 22668 | |
| 1102282 | 230788_at | NM_001491 | 934 | GCNT2 |
| 1116666 | 230803_s_at | NM_031305 | 442801 | DKFZP564B1162 |
| 1102350 | 230864_at | NM_153361 | 25845 | MGC42105 |
| 1116676 | 230894_s_at | NM_138962 | 185084 | MSI2 |
| 1102408 | 230934_at | XR_109030 | 306327 | RAB3GAP |
| 1102415 | 230942_at | NM_138460 | 99272 | CKLFSF5 |
| 1102437 | 230966_at | NM_152899 | 437023 | IL4I1 |
| 1102470 | 231007_at | DB311024 | 292915 | |
| 1102471 | 231008_at | NM_173561 | 158357 | UNC5CL |
| 1102479 | 231017_at | NM_000455 | 301772 | STK11 |
| 1102537 | 231087_at | NM_018157 | 202151 | |
| 1102540 | 231093_at | NM_052939 | 434881 | FCRH3 |
| 1116715 | 231149_s_at | NM_017886 | 123427 | FLJ20574 |
| 1102633 | 231198_at | NM_001145306 | 511124 | |
| 1102652 | 231219_at | NM_181268 | 343717 | CKLFSF1 |
| 1102654 | 231221_at | NM_001243403 | 380599 | KIAA0350 |
| 1102725 | 231303_at | NR_024027 | 234016 | C21orf42 |
| 1102744 | 231324_at | NM_003073 | 198671 | |
| 1102821 | 231412_at | XR_108862 | 202024 | |
| 1102859 | 231455_at | NR_038369 | 446195 | |
| 1102885 | 231481_at | NM_033031 | 130310 | CCNB3 |
| 1102898 | 231496_at | NM_032029 | 145519 | FKSG87 |
| 1102912 | 231514_at | NM_032884 | 194610 | MGC15882 |
| 1103054 | 231690_at | BX118843 | 341531 | |
| 1103107 | 231759_at | NM_005421 | 247978 | TAL2 |
| 1103111 | 231763_at | NM_007055 | 436896 | RPC155 |
| 1103120 | 231775_at | NM_003844 | 401745 | TNFRSF10A |
| 1103124 | 231779_at | NM_001570 | 424542 | IRAK2 |
| 1103134 | 231792_at | NM_033118 | 86092 | MYLK2 |
| 1103137 | 231796_at | NM_020526 | 283613 | EPHA8 |
| 1103139 | 231798_at | NM_005450 | 248201 | NOG |
| 1116826 | 231823_s_at | NM_001017995 | 26204 | KIAA1295 |
| 1116829 | 231840_x_at | NM_181705 | 115467 | LOC90624 |
| 1103224 | 231906_at | NM_019558 | 301963 | HOXD8 |
| 1116844 | 231920_s_at | NM_022048 | 405789 | CSNK1G1 |
| 1103264 | 231954_at | NR_033797 | 142307 | DKFZP434I0714 |
| 1103272 | 231964_at | AL117598 | 137206 | |
| 1103284 | 231978_at | NM_139075 | 186655 | TPCN2 |
| 1116854 | 231992_x_at | NR_002933 | 438623 | |
| 1103303 | 232000_at | NM_152574 | 49605 | C9orf52 |
| 1103304 | 232001_at | NR_036502 | 46919 | |
| 1116863 | 232068_s_at | NM_003266 | 174312 | TLR4 |
| 1103390 | 232103_at | NM_006085 | 271752 | BPNT1 |
| 1103398 | 232112_at | NM_152663 | 220745 | FLJ10244 |
| 1103420 | 232138_at | NM_144778 | 372571 | MBNL2 |
| 1116879 | 232160_s_at | NM_024309 | 325630 | TNIP2 |
| 1103475 | 232204_at | NM_024007 | 120785 | EBF |
| 1103497 | 232231_at | NM_001015051 | 50115 | |
| 1103504 | 232239_at | NR_038382 | 142517 | |
| 1103540 | 232282_at | NM_020922 | 92423 | PRKWNK3 |
| 1103639 | 232399_at | NM_033403 | 388304 | KIAA1765 |
| 1103711 | 232478_at | NM_033334 | 288718 | |
| 1103766 | 232546_at | NM_005427 | 192132 | TP73 |
| 1103855 | 232645_at | NR_015447 | 259625 | LOC153684 |
| 1103858 | 232648_at | NM_002788 | 246240 | PSMA3 |
| 1116958 | 232693_s_at | NM_018660 | 27410 | PBF |
| 1103921 | 232724_at | NM_152852 | 371612 | MS4A6A |
| 1103932 | 232741_at | NM_012084 | 31330 | |
| 1116966 | 232744_x_at | NM_000332 | 301124 | |
| 1103982 | 232798_at | NM_033105 | 142926 | MGC26226 |
| 1104072 | 232906_at | NM_014458 | 287429 | |
| 1104175 | 233029_at | NM_001271223 | 287383 | KIAA1639 |
| 1104195 | 233052_at | NM_001206927 | 172101 | DNAH8 |
| 1117023 | 233110_s_at | NM_138639 | 289052 | BCL2L12 |
| 1104254 | 233121_at | NM_014943 | 492700 | |
| 1104373 | 233271_at | NR_003611 | | |
| 1104545 | 233476_at | AK000189 | 254477 | |

TABLE 2-continued

| UNIQID | Probe Set | Genbank Accession No. | Unigene ID Build 167 | Unigene Symbol |
|---|---|---|---|---|
| 1104552 | 233483_at | XM_002347724 | 193857 | LOC96597 |
| 1104840 | 233867_at | NM_152789 | 482250 | |
| 1104870 | 233916_at | NM_020864 | 210958 | KIAA1486 |
| 1117211 | 233955_x_at | NM_016463 | 356509 | HSPC195 |
| 1104905 | 233964_at | NM_032558 | 13453 | FLJ14753 |
| 1104910 | 233969_at | NM_080926 | 458262 | IGL@ |
| 1105001 | 234088_at | AK022149 | 527386 | |
| 1117245 | 234107_s_at | NM_080820 | 527974 | HARS2 |
| 1105178 | 234284_at | NM_033258 | 283961 | GNG8 |
| 1117278 | 234312_s_at | NM_018677 | 14779 | ACAS2 |
| 1117298 | 234366_x_at | AA634638 | 449586 | |
| 1105248 | 234403_at | NM_001004713 | | |
| 1117343 | 234643_x_at | NM_052956 | 306812 | BUCS1 |
| 1117350 | 234672_s_at | NM_018087 | 435982 | FLJ10407 |
| 1117373 | 234725_s_at | NM_020210 | 416077 | SEMA4B |
| 1117394 | 234792_x_at | BQ711772 | | |
| 1117403 | 234863_x_at | NM_012177 | 272027 | FBXO5 |
| 1105668 | 234954_at | NG_007007 | | |
| 1105684 | 234973_at | NM_033518 | 195155 | SLC38A5 |
| 1105728 | 235022_at | NM_152352 | 13034 | MGC24180 |
| 1105732 | 235026_at | NM_152440 | 396626 | FLJ32549 |
| 1105751 | 235046_at | BM450047 | 176376 | |
| 1105759 | 235056_at | NM_001987 | 171262 | ETV6 |
| 1105798 | 235099_at | NM_178868 | 154986 | CKLFSF8 |
| 1105814 | 235117_at | NM_001008708 | 105223 | |
| 1105832 | 235136_at | NM_139280 | 306777 | GSDML |
| 1105838 | 235142_at | NM_001040441 | 129837 | ZBTB8 |
| 1105842 | 235146_at | NM_020698 | 173392 | KIAA1145 |
| 1105854 | 235158_at | NM_032842 | 267245 | FLJ14803 |
| 1105866 | 235170_at | NM_007139 | 9521 | ZNF92 |
| 1105900 | 235211_at | BX505282 | 525015 | |
| 1105915 | 235229_at | AV687243 | 332649 | |
| 1105935 | 235251_at | AK124776 | 444290 | |
| 1105936 | 235252_at | NM_014238 | 276238 | KSR |
| 1105959 | 235278_at | NM_080676 | 399982 | |
| 1105986 | 235310_at | NM_152785 | 49614 | GCET2 |
| 1106013 | 235341_at | NM_006260 | 6019 | DNAJC3 |
| 1106015 | 235343_at | NM_024749 | 96885 | FLJ12505 |
| 1106025 | 235353_at | NM_015187 | 49500 | KIAA0746 |
| 1106030 | 235359_at | NM_198565 | 162185 | UNQ3030 |
| 1106043 | 235372_at | NM_032738 | 266331 | FREB |
| 1106053 | 235383_at | NM_001080527 | 154578 | MYO7B |
| 1106088 | 235421_at | NM_005204 | 499235 | |
| 1106110 | 235444_at | NM_032682 | 235860 | FOXP1 |
| 1106124 | 235458_at | NM_032782 | 155111 | HAVCR2 |
| 1106126 | 235460_at | NM_024798 | 434937 | PPIB |
| 1106159 | 235496_at | NM_001039792 | 208081 | |
| 1106196 | 235536_at | NM_173647 | 142074 | |
| 1106204 | 235545_at | NM_017779 | 445098 | SDP35 |
| 1106230 | 235572_at | NM_182513 | 381225 | Spc24 |
| 1106279 | 235626_at | NM_153498 | 130065 | CAMK1D |
| 1106306 | 235657_at | CA942841 | 14204 | |
| 1106317 | 235668_at | NM_001198 | 381140 | PRDM1 |
| 1106323 | 235674_at | NM_015196 | 442690 | |
| 1106394 | 235750_at | NR_049729 | 126932 | |
| 1106401 | 235758_at | NM_001170944 | 11849 | MGC15827 |
| 1106415 | 235774_at | XR_110207 | 169071 | |
| 1117517 | 235816_s_at | NM_153615 | 148656 | Rgr |
| 1106478 | 235843_at | NM_001346 | 119898 | |
| 1106522 | 235890_at | CA314011 | 31903 | |
| 1106589 | 235965_at | NM_177455 | 22627 | MIST1 |
| 1106722 | 236109_at | NM_032795 | 150458 | FLJ14494 |
| 1106781 | 236172_at | NM_181657 | 445013 | LTB4R |
| 1106855 | 236255_at | NM_052909 | 455101 | KIAA1909 |
| 1117555 | 236295_s_at | NM_178844 | 128357 | NOD3 |
| 1106908 | 236313_at | NM_004936 | 72901 | CDKN2B |
| 1106935 | 236341_at | NM_005214 | 247824 | CTLA4 |
| 1106990 | 236401_at | NM_130759 | 369561 | |
| 1107044 | 236458_at | AW978486 | 163426 | |
| 1107076 | 236491_at | NM_020396 | 283672 | BCL2L10 |
| 1107124 | 236543_at | NM_001145065 | 130203 | |
| 1107190 | 236614_at | NR_046273 | 50601 | MGC10986 |
| 1107197 | 236621_at | NM_025164 | 40838 | |
| 1107329 | 236761_at | NM_199000 | 439124 | LHFPL3 |
| 1107348 | 236782_at | NM_001017373 | 440508 | SAMD3 |
| 1107369 | 236805_at | NM_153710 | 512466 | |
| 1107457 | 236901_at | NM_014244 | 120330 | ADAMTS2 |

TABLE 2-continued

| UNIQID | Probe Set | Genbank Accession No. | Unigene ID Build 167 | Unigene Symbol |
|---|---|---|---|---|
| 1117599 | 236918_s_at | NM_153353 | 120277 | MGC27085 |
| 1107527 | 236981_at | NM_001163075 | 14706 | |
| 1107575 | 237033_at | NM_001042693 | 424589 | MGC52498 |
| 1107637 | 237104_at | NM_004079 | | |
| 1107762 | 237244_at | XR_110401 | 58597 | |
| 1107838 | 237322_at | NR_003491 | 355618 | |
| 1117644 | 237451_x_at | NM_015849 | 34174 | |
| 1107997 | 237493_at | NM_052962 | 126891 | IL22RA2 |
| 1108088 | 237591_at | NR_027345 | 441601 | |
| 1108200 | 237710_at | AI954795 | 156135 | |
| 1108237 | 237753_at | NM_021798 | 126232 | |
| 1108323 | 237849_at | NM_005907 | 526982 | |
| 1108347 | 237880_at | NM_001261427 | 121476 | |
| 1108467 | 238018_at | NM_001002919 | 346333 | LOC285016 |
| 1108473 | 238025_at | NM_152649 | 119878 | FLJ34389 |
| 1108515 | 238071_at | NM_001001712 | 98132 | LCN6 |
| 1108745 | 238323_at | NM_003598 | 528776 | TEAD2 |
| 1117747 | 238365_s_at | NM_001145636 | 158272 | |
| 1108776 | 238376_at | XR_158888 | 513346 | |
| 1108910 | 238536_at | AI633551 | 351848 | |
| 1108925 | 238552_at | NM_015070 | 136102 | KIAA0853 |
| 1108961 | 238593_at | NM_024650 | 292088 | FLJ22531 |
| 1108970 | 238604_at | NM_030796 | 140489 | |
| 1108988 | 238624_at | NM_016231 | 3532 | NLK |
| 1117800 | 238701_x_at | NR_034154 | 125166 | |
| 1109058 | 238706_at | NM_001114394 | 220277 | FLJ38499 |
| 1109107 | 238759_at | NM_001135597 | 292925 | KIAA1212 |
| 1109188 | 238846_at | NM_003839 | 204044 | TNFRSF11A |
| 1109195 | 238853_at | NM_022456 | 416155 | |
| 1109210 | 238870_at | NM_016601 | 117010 | KCNK9 |
| 1109220 | 238880_at | NM_002097 | 445977 | GTF3A |
| 1109505 | 239186_at | NR_033851 | 8162 | MGC39372 |
| 1109519 | 239201_at | NM_139158 | 348711 | ALS2CR7 |
| 1117835 | 239205_s_at | NM_000573 | 89688 | CR1L |
| 1109530 | 239214_at | XR158846 | 123244 | |
| 1109545 | 239231_at | AK123904 | 63187 | |
| 1109557 | 239243_at | NM_014497 | 444548 | NP220 |
| 1109560 | 239246_at | NM_005766 | 207428 | FARP1 |
| 1109603 | 239292_at | DB317658 | | |
| 1109732 | 239427_at | AA131524 | 374124 | |
| 1109756 | 239453_at | NM_015033 | 530304 | |
| 1117853 | 239479_x_at | NM_000740 | 268724 | |
| 1109827 | 239533_at | NM_152529 | 127196 | GPR155 |
| 1109913 | 239629_at | NM_001202518 | 355724 | CFLAR |
| 1110019 | 239744_at | NM_130795 | | |
| 1110070 | 239803_at | NM_022141 | | |
| 1110099 | 239835_at | NM_032505 | 116665 | TA-KRP |
| 1110198 | 239946_at | NM_015196 | 189046 | |
| 1110214 | 239964_at | NR_028288 | 144519 | TCL6 |
| 1110223 | 239973_at | CR613326 | 212709 | |
| 1110284 | 240038_at | NM_012081 | 192221 | ELL2 |
| 1110309 | 240066_at | NM_176814 | 105623 | |
| 1110313 | 240070_at | NM_173799 | 421750 | FLJ39873 |
| 1110486 | 240260_at | NM_002827 | 445054 | |
| 1110608 | 240392_at | NM_001257970 | 306227 | CARD14 |
| 1110610 | 240394_at | NR_015430 | 436906 | |
| 1110740 | 240538_at | BX105952 | 416810 | |
| 1110852 | 240661_at | XR_110492 | 196026 | |
| 1110871 | 240681_at | BG429817 | 431753 | |
| 1117977 | 240854_x_at | BF514007 | | |
| 1111070 | 240899_at | AA827683 | 202201 | |
| 1111478 | 241357_at | NM_139021 | 133017 | ERK8 |
| 1111486 | 241365_at | AK124253 | 33024 | |
| 1111494 | 241373_at | NM_000884 | 75432 | IMPDH2 |
| 1111503 | 241383_at | NM_001242704 | 502910 | KBRAS2 |
| 1111694 | 241592_at | XR_110327 | 157302 | |
| 1111807 | 241751_at | NM_003611 | 6483 | OFD1 |
| 1111946 | 241928_at | NM_004196 | 280881 | |
| 1112019 | 242013_at | NM_001010922 | 196484 | |
| 1118148 | 242020_s_at | NM_030776 | 302123 | ZBP1 |
| 1112052 | 242052_at | NM_001714 | 525361 | |
| 1112061 | 242064_at | NM_001144952 | 43410 | |
| 1112256 | 242293_at | NM_019071 | 143198 | ING3 |
| 1112344 | 242406_at | NM_001007544 | 163242 | |
| 1118228 | 242520_s_at | NM_001145636 | 173679 | |
| 1112510 | 242595_at | NM_174944 | 314432 | C14orf20 |
| 1112521 | 242611_at | NM_033407 | 244818 | |

TABLE 2-continued

| UNIQID | Probe Set | Genbank Accession No. | Unigene ID Build 167 | Unigene Symbol |
|---|---|---|---|---|
| 1112552 | 242650_at | NM_174890 | 89029 | |
| 1112674 | 242794_at | NM_018717 | 310320 | MAML3 |
| 1112689 | 242814_at | NM_004155 | 104879 | SERPINB9 |
| 1118286 | 242866_x_at | NM_002698 | 147381 | |
| 1112762 | 242901_at | NM_015559 | 208179 | |
| 1112764 | 242903_at | NM_000416 | 180866 | IFNGR1 |
| 1112837 | 242994_at | NM_002525 | 4099 | NRD1 |
| 1112849 | 243006_at | NM_002037 | 208965 | |
| 1112871 | 243030_at | NM_005921 | 269493 | |
| 1112935 | 243099_at | NM_145912 | 436677 | NFAM1 |
| 1112981 | 243154_at | AA215381 | 86650 | |
| 1113020 | 243198_at | NM_198524 | 373484 | LOC161577 |
| 1118347 | 243366_s_at | NM_000885 | 528404 | ITGA4 |
| 1113263 | 243467_at | BM548358 | 435736 | |
| 1113435 | 243659_at | NM_012081 | 100636 | |
| 1113488 | 243717_at | NM_173641 | 129435 | |
| 1113500 | 243729_at | NM_024764 | 165900 | |
| 1113545 | 243780_at | BM548358 | 435736 | |
| 1113555 | 243791_at | AW979261 | 291993 | |
| 1113589 | 243829_at | NM_004333 | 162967 | BRAF |
| 1118414 | 243968_x_at | NM_052938 | 415473 | FCRH1 |
| 1113730 | 243993_at | NM_002595 | 293771 | |
| 1113769 | 244035_at | NM_000633 | 46996 | |
| 1113783 | 244052_at | NM_032783 | 71616 | FLJ14431 |
| 1113930 | 244214_at | NM_145065 | 24725 | MGC35521 |
| 1113972 | 244261_at | NM_170743 | 386334 | IL28RA |
| 1113993 | 244286_at | NM_015033 | 131811 | |
| 1114017 | 244313_at | NM_000573 | 133255 | |
| 1114064 | 244364_at | NM_017433 | 148228 | MYO3A |
| 1114109 | 244413_at | NM_172004 | 203041 | DCAL1 |
| 1114162 | 244467_at | NM_001207020 | 526942 | |
| 1114351 | 244677_at | NM_002616 | 445534 | PER1 |
| 1114503 | 244845_at | NM_032682 | 170577 | |
| 1114543 | 244887_at | NM_002927 | 156189 | |
| 1118612 | 32625_at | NM_000906 | | |
| 1118621 | 33307_at | NM_015703 | | |
| 1130354 | 33323_r_at | NM_006142 | 184510 | SFN |
| 1118659 | 35617_at | NM_002749 | | |
| 1118681 | 36711_at | NM_012323 | | |
| 1118684 | 36830_at | NM_005932 | | |
| 1118708 | 37408_at | NM_006039 | | |
| 1118736 | 38340_at | NM_003959 | | |
| 1118772 | 40420_at | NM_005990 | | |
| 1130378 | 44783_s_at | NM_012258 | 234434 | HEY1 |
| 1118835 | 47069_at | NM_015366 | | |
| 1118861 | 49878_at | NM_004813 | | |
| 1130387 | 50314_i_at | NM_001039140 | 274422 | C20orf27 |
| 1130393 | 58780_s_at | NM_018071 | 22451 | FLJ10357 |
| 1118939 | 60528_at | NM_005090 | | |
| 1118573 | 632_at | NM_019884 | | |
| 1118949 | 64064_at | NM_018384 | | |
| 1118963 | 65472_at | NM_001013649 | | |
| 1130400 | 74694_s_at | NM_024816 | 170253 | FRA |
| 1140788 | AFFX-DapX-3_at | Affymetrix control sequence | | |
| 1140834 | AFFX-HSAC07/X00351_3_at | NM_001101 | 426930 | ACTB |
| 1140835 | AFFX-HSAC07/X00351_5_at | NM_001101 | 426930 | ACTB |
| 1140836 | AFFX-HSAC07/X00351_M_at | NM_001101 | 426930 | ACTB |
| 1140842 | AFFX-HUMGAPDH/M33197_3_at | NM_002046 | 169476 | GAPD |
| 1140843 | AFFX-HUMGAPDH/M33197_5_at | NM_002046 | 169476 | GAPD |
| 1140844 | AFFX-HUMGAPDH/M33197_M_at | NM_002046 | 169476 | GAPD |
| 1140845 | AFFX-HUMISGF3A/M97935_3_at | NM_007315 | 21486 | STAT1 |
| 1140846 | AFFX-HUMISGF3A/M97935_5_at | NM_007315 | 21486 | STAT1 |
| 1140847 | AFFX-HUMISGF3A/M97935_MA_at | NM_007315 | 21486 | STAT1 |
| 1140848 | AFFX-HUMISGF3A/M97935_MB_at | NM_007315 | 21486 | STAT1 |
| 1140837 | AFFX-HUMRGE/M10098_3_at | NR_003286 | | RNA18S5 |

TABLE 2-continued

| UNIQID | Probe Set | Genbank Accession No. | Unigene ID Build 167 | Unigene Symbol |
|---|---|---|---|---|
| 1140838 | AFFX-HUMRGE/M10098_5_at | NR_003286 | | RNA18S5 |
| 1140839 | AFFX-HUMRGE/M10098_M_at | NR_003286 | | RNA18S5 |
| 1140791 | AFFX-LysX-3_at | Affymetrix control sequence | | |
| 1140792 | AFFX-LysX-5_at | Affymetrix control sequence | | |
| 1140793 | AFFX-LysX-M_at | Affymetrix control sequence | | |
| 1140806 | AFFX-M27830_3_at | Affymetrix control sequence | | |
| 1140807 | AFFX-M27830_5_at | NR_003287 | | |
| 1140808 | AFFX-M27830_M_at | Affymetrix control sequence | | |
| 1140794 | AFFX-PheX-3_at | Affymetrix control sequence | | |
| 1140795 | AFFX-PheX-5_at | Affymetrix control sequence | | |
| 1140796 | AFFX-PheX-M_at | Affymetrix control sequence | | |
| 1140797 | AFFX-ThrX-3_at | Affymetrix control sequence | | |
| 1140798 | AFFX-ThrX-5_at | Affymetrix control sequence | | |
| 1140799 | AFFX-ThrX-M_at | Affymetrix control sequence | | |
| 1140802 | AFFX-TrpnX-3_at | Affymetrix control sequence | | |
| 1140803 | AFFX-TrpnX-5_at | Affymetrix control sequence | | |
| 1140804 | AFFX-TrpnX-M_at | Affymetrix control sequence | | |
| 1140805 | AFFX-hum_alu_at | Affymetrix control sequence | | |
| 1140809 | AFFX-r2-Bs-dap-3_at | Affymetrix control sequence | | |
| 1140810 | AFFX-r2-Bs-dap-5_at | Affymetrix control sequence | | |
| 1140811 | AFFX-r2-Bs-dap-M_at | Affymetrix control sequence | | |
| 1140812 | AFFX-r2-Bs-lys-3_at | Affymetrix control sequence | | |
| 1140813 | AFFX-r2-Bs-lys-5_at | Affymetrix control sequence | | |
| 1140814 | AFFX-r2-Bs-lys-M_at | Affymetrix control sequence | | |
| 1140815 | AFFX-r2-Bs-phe-3_at | Affymetrix control sequence | | |
| 1140816 | AFFX-r2-Bs-phe-5_at | Affymetrix control sequence | | |
| 1140817 | AFFX-r2-Bs-phe-M_at | Affymetrix control sequence | | |
| 1140827 | AFFX-r2-Bs-thr-3_s_at | Affymetrix control sequence | | |
| 1140828 | AFFX-r2-Bs-thr-5_s_at | Affymetrix control sequence | | |
| 1140829 | AFFX-r2-Bs-thr-M_s_at | Affymetrix control sequence | | |
| 1140820 | AFFX-r2-Ec-bioB-3_at | Affymetrix control sequence | | |
| 1140821 | AFFX-r2-Ec-bioB-5_at | Affymetrix control sequence | | |
| 1140822 | AFFX-r2-Ec-bioB-M_at | Affymetrix control sequence | | |
| 1140823 | AFFX-r2-Ec-bioC-3_at | Affymetrix control sequence | | |
| 1140824 | AFFX-r2-Ec-bioC-5_at | Affymetrix control sequence | | |
| 1140825 | AFFX-r2-Ec-bioD-3_at | Affymetrix control sequence | | |
| 1140826 | AFFX-r2-Ec-bioD-5_at | Affymetrix control sequence | | |
| 1140818 | AFFX-r2-P1-cre-3_at | Affymetrix control sequence | | |
| 1140819 | AFFX-r2-P1-cre-5_at | Affymetrix control sequence | | |

TABLE 2-continued

| UNIQID | Probe Set | Genbank Accession No. | Unigene ID Build 167 | Unigene Symbol |
|---|---|---|---|---|
| 1529284 | Lymph_Dx_001_at | NM_002387 | 409515 | MCC |
| 1529285 | Lymph_Dx_002_at | NM_020336 | 348929 | KIAA1219 |
| 1529286 | Lymph_Dx_003_at | NM_005903 | 167700 | MADH5 |
| 1529287 | Lymph_Dx_004_s_at | NM_198828 | 212787 | KIAA0303 |
| 1529288 | Lymph_Dx_005_at | NM_004354 | 13291 | CCNG2 |
| 1529443 | Lymph_Dx_006_at | NM_006304 | 88886 | |
| 1529289 | Lymph_Dx_007_at | NM_005079 | 96557 | |
| 1529290 | Lymph_Dx_008_at | NM_015111 | 101761 | N4BP3 |
| 1529291 | Lymph_Dx_009_at | AI476422 | 104450 | |
| 1529292 | Lymph_Dx_010_at | AW968764 | | |
| 1529293 | Lymph_Dx_011_at | AA767493 | 113117 | |
| 1529294 | Lymph_Dx_011_s_at | AA767493 | 113117 | |
| 1529295 | Lymph_Dx_012_at | NM_207506 | 116441 | |
| 1529296 | Lymph_Dx_013_at | NM_001144 | 122428 | |
| 1529444 | Lymph_Dx_014_at | NM_006959 | 126905 | |
| 1529297 | Lymph_Dx_015_at | NM_032682 | 132335 | |
| 1529298 | Lymph_Dx_016_at | NM_021813 | 136707 | |
| 1529299 | Lymph_Dx_017_at | H18495 | 444290 | |
| 1529300 | Lymph_Dx_018_at | AA911599 | 449608 | |
| 1529301 | Lymph_Dx_019_at | AI281566 | | |
| 1529445 | Lymph_Dx_020_at | NM_002285 | | |
| 1529302 | Lymph_Dx_021_at | NM_004433 | 67928 | ELF3 |
| 1529303 | Lymph_Dx_022_at | W22811 | | |
| 1529304 | Lymph_Dx_022_s_at | W22811 | | |
| 1529305 | Lymph_Dx_023_at | AA761222 | 173957 | |
| 1529306 | Lymph_Dx_024_at | NM_152581 | 190043 | MGC26706 |
| 1529446 | Lymph_Dx_025_at | NM_002643 | 190626 | |
| 1529307 | Lymph_Dx_026_at | AA262473 | 435736 | |
| 1529308 | Lymph_Dx_027_x_at | AI478915 | 193014 | |
| 1529309 | Lymph_Dx_028_at | NM_032855 | 512797 | HSH2 |
| 1529310 | Lymph_Dx_029_x_at | NM_002733 | 3136 | PRKAG1 |
| 1529311 | Lymph_Dx_030_at | NM_002927 | 251214 | |
| 1529312 | Lymph_Dx_031_s_at | NM_001010855 | 255809 | |
| 1529313 | Lymph_Dx_032_at | BX343240 | 271998 | |
| 1529314 | Lymph_Dx_033_at | NM_025146 | | |
| 1529315 | Lymph_Dx_034_at | AW976624 | 530912 | |
| 1529316 | Lymph_Dx_035_at | NM_003453 | 315241 | ZNF198 |
| 1529447 | Lymph_Dx_036_at | AA828269 | 291886 | |
| 1529317 | Lymph_Dx_037_at | NM_181780 | | |
| 1529318 | Lymph_Dx_038_at | AW978724 | 291954 | |
| 1529319 | Lymph_Dx_039_at | H84296 | 103329 | KIAA0970 |
| 1529320 | Lymph_Dx_040_at | AI392661 | 309149 | |
| 1529321 | Lymph_Dx_041_s_at | NM_006850 | 411311 | IL24 |
| 1529322 | Lymph_Dx_042_x_at | BQ694724 | 514291 | |
| 1529323 | Lymph_Dx_043_at | NM_000397 | | |
| 1529324 | Lymph_Dx_044_at | NM_033423 | 348264 | GZMH |
| 1529325 | Lymph_Dx_045_at | NM_004271 | | |
| 1529326 | Lymph_Dx_046_s_at | NM_015401 | 200063 | HDAC7A |
| 1529327 | Lymph_Dx_047_s_at | AA732879 | 288986 | SMN2 |
| 1529328 | Lymph_Dx_048_s_at | NM_001206702 | 369056 | |
| 1529448 | Lymph_Dx_049_at | NM_022166 | 369101 | |
| 1529329 | Lymph_Dx_049_s_at | NM_022166 | 369101 | |
| 1529330 | Lymph_Dx_050_at | NR_015447 | 259625 | LOC153684 |
| 1529331 | Lymph_Dx_051_s_at | NM_052938 | 374126 | |
| 1529332 | Lymph_Dx_052_at | NM_145266 | 140443 | LOC134492 |
| 1529333 | Lymph_Dx_053_at | NM_020845 | 378849 | |
| 1529334 | Lymph_Dx_054_at | NM_003242 | 529494 | |
| 1529335 | Lymph_Dx_055_s_at | NM_152419 | 400872 | |
| 1529336 | Lymph_Dx_056_at | NM_004103 | 405474 | PTK2B |
| 1529337 | Lymph_Dx_057_at | NM_018064 | 201864 | C6orf166 |
| 1529338 | Lymph_Dx_058_s_at | NM_002577 | 284275 | PAK2 |
| 1529339 | Lymph_Dx_059_s_at | NM_152436 | | |
| 1529449 | Lymph_Dx_060_s_at | NM_014964 | | |
| 1529340 | Lymph_Dx_061_at | AA827872 | | |
| 1529341 | Lymph_Dx_062_at | NM_002349 | 153563 | LY75 |
| 1529342 | Lymph_Dx_063_at | NM_017554 | | |
| 1529343 | Lymph_Dx_064_at | NM_004036 | 521948 | |
| 1529344 | Lymph_Dx_065_at | NM_001080451 | 317970 | SERPINA11 |
| 1529450 | Lymph_Dx_066_at | AA255658 | | |
| 1529345 | Lymph_Dx_067_s_at | BF891110 | 443475 | |
| 1529346 | Lymph_Dx_068_at | NM_145755 | 443935 | |
| 1529347 | Lymph_Dx_069_at | NM_004271 | 444019 | |
| 1529348 | Lymph_Dx_070_s_at | NM_005633 | 326392 | SOS1 |
| 1529349 | Lymph_Dx_071_at | AI225238 | 445500 | |
| 1529451 | Lymph_Dx_072_at | NM_152405 | 396853 | JMY |
| 1529350 | Lymph_Dx_073_at | NM_030753 | 445884 | |
| 1529351 | Lymph_Dx_074_s_at | NM_001080416 | 445898 | |

TABLE 2-continued

| UNIQID | Probe Set | Genbank Accession No. | Unigene ID Build 167 | Unigene Symbol |
|---|---|---|---|---|
| 1529352 | Lymph_Dx_075_at | NR_038369 | 446195 | |
| 1529353 | Lymph_Dx_076_at | NM_207506 | 446198 | |
| 1529354 | Lymph_Dx_077_at | NM_018014 | 314623 | BCL11A |
| 1529452 | Lymph_Dx_078_at | NM_001624 | 422550 | AIM1 |
| 1529355 | Lymph_Dx_079_at | NM_175852 | 370675 | |
| 1529356 | Lymph_Dx_080_at | NM_019589 | 303775 | C14orf170 |
| 1529357 | Lymph_Dx_081_at | AA910231 | 444651 | |
| 1529358 | Lymph_Dx_082_at | NM_002349 | 127178 | |
| 1529359 | Lymph_Dx_083_at | AA832388 | | |
| 1529360 | Lymph_Dx_084_at | NM_016562 | 443036 | |
| 1529453 | Lymph_Dx_085_at | NM_000569 | 372679 | FCGR3A |
| 1529361 | Lymph_Dx_086_s_at | NM_003883 | 388681 | HDAC3 |
| 1529362 | Lymph_Dx_087_at | NM_005030 | 329989 | PLK1 |
| 1529363 | Lymph_Dx_088_at | NM_017617 | 311559 | NOTCH1 |
| 1529364 | Lymph_Dx_089_at | NM_000051 | 526394 | ATM |
| 1529365 | Lymph_Dx_090_at | NM_052945 | 344088 | TNFRSF13C |
| 1529366 | Lymph_Dx_091_at | X01995 | | |
| 1529367 | Lymph_Dx_092_at | X01995 | | |
| 1529368 | Lymph_Dx_093_at | K03333 | | |
| 1529369 | Lymph_Dx_095_at | U21195 | | |
| 1529370 | Lymph_Dx_096_at | M4212 | | |
| 1529371 | Lymph_Dx_097_at | M17293 | | |
| 1529372 | Lymph_Dx_098_at | M17547 | | |
| 1529373 | Lymph_Dx_099_at | X04060 | | |
| 1529374 | Lymph_Dx_100_at | M23028 | | |
| 1529454 | Lymph_Dx_101_at | AJ507799 | | |
| 1529375 | Lymph_Dx_102_at | U90534 | | |
| 1529376 | Lymph_Dx_103_at | U66522 | | |
| 1529377 | Lymph_Dx_104_at | U66521 | | |
| 1529378 | Lymph_Dx_105_at | U52064 | | |
| 1529455 | Lymph_Dx_107_at | U67773 | | |
| 1529379 | Lymph_Dx_108_at | AF367767 | | |
| 1529380 | Lymph_Dx_109_at | U67774 | | |
| 1529381 | Lymph_Dx_110_at | AF178799 | | |
| 1529382 | Lymph_Dx_111_at | NM_053056 | 371468 | CCND1 |
| 1529383 | Lymph_Dx_112_at | NM_053056 | 371468 | CCND1 |
| 1529456 | Lymph_Dx_113_at | NM_053056 | 371468 | CCND1 |
| 1529384 | Lymph_Dx_114_at | NM_053056 | 371468 | CCND1 |
| 1529385 | Lymph_Dx_115_at | NM_053056 | 371468 | CCND1 |
| 1529386 | Lymph_Dx_116_at | NM_053056 | 371468 | CCND1 |
| 1529387 | Lymph_Dx_117_at | NM_000633 | 79241 | BCL2 |
| 1529388 | Lymph_Dx_118_at | NM_000633 | 79241 | BCL2 |
| 1529389 | Lymph_Dx_119_at | NM_000633 | 79241 | BCL2 |
| 1529390 | Lymph_Dx_120_at | NM_000633 | 79241 | BCL2 |
| 1529391 | Lymph_Dx_121_at | NM_000633 | 79241 | BCL2 |
| 1529392 | Lymph_Dx_122_at | NM_145259 | 352338 | ACVR1C |
| 1529393 | Lymph_Dx_123_s_at | NM_032430 | 182081 | KIAA1811 |
| 1529394 | Lymph_Dx_124_s_at | NM_182493 | 339846 | LOC91807 |
| 1529395 | Lymph_Dx_125_at | NM_001009565 | 403201 | |
| 1529396 | Lymph_Dx_126_at | NM_145203 | 512897 | MGC33182 |
| 1529397 | Lymph_Dx_127_s_at | NM_020666 | 406557 | CLK4 |
| 1529398 | Lymph_Dx_128_at | NM_017525 | 293590 | HSMDPKIN |
| 1529399 | Lymph_Dx_129_at | NM_001080448 | 256916 | LOC203806 |
| 1529457 | Lymph_Dx_130_at | NM_139209 | 351818 | GRK7 |
| 1529400 | Lymph_Dx_131_s_at | NM_144685 | 210697 | HIPK4 |
| 1529401 | Lymph_Dx_132_at | NM_003618 | 399752 | MAP4K3 |
| 1529402 | Lymph_Dx_133_at | NM_173598 | 375836 | KSR2 |
| 1529403 | Lymph_Dx_134_s_at | NM_001080434 | 511780 | LMTK3 |
| 1529404 | Lymph_Dx_135_at | NM_005921 | 170610 | MAP3K1 |
| 1529405 | Lymph_Dx_136_s_at | NM_014975 | 227489 | SAST |
| 1529406 | Lymph_Dx_137_s_at | NM_138995 | 409066 | MYO3B |
| 1529458 | Lymph_Dx_138_at | NM_178170 | 448468 | NEK8 |
| 1529407 | Lymph_Dx_139_s_at | NM_002577 | 284275 | PAK2 |
| 1529408 | Lymph_Dx_141_at | NM_033126 | 336929 | PSKH2 |
| 1529409 | Lymph_Dx_142_s_at | NM_001174103 | 351173 | FLJ25006 |
| 1529410 | Lymph_Dx_143_s_at | NM_173354 | 380991 | SNF1LK |
| 1529411 | Lymph_Dx_144_at | NM_005876 | 80181 | APEG1 |
| 1529459 | Lymph_Dx_145_at | NM_080823 | 411061 | SRMS |
| 1529412 | Lymph_Dx_146_at | NM_052841 | 512763 | STK22C |
| 1529413 | Lymph_Dx_147_at | NM_006648 | 232116 | PRKWNK2 |
| 1529414 | Lymph_Dx_148_s_at | NM_145001 | 352370 | MGC22688 |
| 1529415 | Lymph_Dx_149_at | NM_198465 | 369523 | DKFZp686A17109 |
| 1529416 | Lymph_Dx_150_s_at | NM_000077 | 421349 | CDKN2A |
| 1529417 | Lymph_Dx_151_at | NM_000077 | 421349 | CDKN2A |
| 1529418 | Lymph_Dx_152_at | NM_000077 | 421349 | CDKN2A |
| 1529419 | Lymph_Dx_153_s_at | NM_030764 | 104182 | |
| 1529420 | Lymph_Dx_154_at | NM_052872 | 272295 | IL17F |

TABLE 2-continued

| UNIQID | Probe Set | Genbank Accession No. | Unigene ID Build 167 | Unigene Symbol |
|---|---|---|---|---|
| 1529421 | Lymph_Dx_156_at | NM_145659 | 375043 | IL27 |
| 1529422 | Lymph_Dx_157_s_at | NM_144701 | 375184 | IL23R |
| 1529423 | Lymph_Dx_158_at | NM_005353 | 381264 | ITGAD |
| 1529424 | Lymph_Dx_159_s_at | AI282844 | 512683 | CCL3L1 |
| 1529425 | Lymph_Dx_160_at | NM_002186 | 406228 | IL9R |
| 1529426 | Lymph_Dx_162_at | NM_172139 | 406744 | IL28B |
| 1529427 | Lymph_Dx_163_at | NM_172140 | 406745 | IL29 |
| 1529428 | Lymph_Dx_164_at | NM_002507 | 415768 | NGFR |
| 1529429 | Lymph_Dx_165_at | NM_138284 | 434103 | IL17D |
| 1529430 | Lymph_Dx_166_at | NM_020126 | 444484 | SPHK2 |
| 1529431 | Lymph_Dx_167_at | NM_052938 | | |
| 1529432 | Lymph_Dx_168_at | J00228 | | |
| 1529433 | Lymph_Dx_168_x_at | J00228 | | |
| 1529434 | Lymph_Dx_171_at | AI351797 | 103995 | FLJ27099 |
| 1529435 | Lymph_Dx_172_s_at | J00220 | | |
| 1529436 | Lymph_Dx_174_at | J00222 | | |
| 1529437 | Lymph_Dx_175_at | NM_181780 | 445162 | BTLA |

TABLE 1724

| Gene type | Number of genes |
|---|---|
| Lymphoma predictor genes | 1101 |
| Subtype specific | 763 |
| Lymph node signature | 178 |
| Proliferation signature | 160 |
| Outcome predictor genes | 171 |
| DLBCL | 79 |
| FL | 81 |
| MCL | 11 |
| New genes not on U133 | 167 |
| Lymphochip lymphoma predictor genes | 84 |
| EBV and HHV8 viral genes | 18 |
| BCL-2/cyclin D1/INK4a specialty probes | 14 |
| Named genes missing from U133 | 51 |
| Named genes | 1121 |
| Protein kinase | 440 |
| Interleukin | 35 |
| Interleukin receptor | 29 |
| Chemokine | 51 |
| Chemokine receptor | 29 |
| TNF family | 26 |
| TNF receptor family | 51 |
| Adhesion | 45 |
| Surface marker | 264 |
| Oncogene/tumor suppressor | 49 |
| Apoptosis | 46 |
| Drug target | 10 |
| Regulatory | 46 |

Cell samples representing various forms of human lymphoid malignancy were obtained by biopsy using known methods described in the literature. These 634 biopsy samples were reviewed by a panel of hematopathologists and classified into the following lymphoma types based on current diagnostic criteria:
  201 diffuse large B-cell lymphomas (DLBCL)
  191 follicular lymphomas (FL)
  60 Burkitt lymphomas (BL)
  21 mantle cell lymphomas (MCL)
  30 primary mediastinal B cell lymphoma (PMBL)
  18 follicular hyperplasias (FH)
  18 small cell lymphocytic lymphomas (SLL)
  17 mucosa-associated lymphoid tissue lymphomas (MALT), including 9 gastric MALTs (GMALT)
  16 chronic lymphocytic leukemias (CLL)
  13 splenic lymphomas (SPL)
  11 lymphoplasmacytic lymphomas (LPC)
  11 transformed DLBCL (trDLBCL) (DLBCL that arose from an antecedent FL)
  10 cyclin D1 negative lymphomas with MCL morphology (CD1 N)
  6 peripheral T-cell lymphoma (PTCL)
  4 post-transplant lymphoproliferative disorders (PTLD)
  4 nodal marginal zone lymphomas (NMZ)
  3 lymphoblastic lymphomas (LBL)

Each of the 634 samples was given a unique sample ID number consisting of the lymphoma type followed by a unique numerical identifier. For example, "BL_2032_52748" refers to a Burkitt lymphoma sample with the numerical identifier 2032_52748. Cells were purified and RNA was isolated from the purified cells according to known methods described in the literature.

Aliquots of purified RNA from each sample were applied to the Lymph Dx microarrays according to standard Affymetrix microarray protocol. Each microarray was scanned on an Affymetrix scanner. This scanner produced an image of the microarray, which was then evaluated by Affymetrix MAS 5.0 software. This information was stored in tables in .txt format. Each of these .txt files was given a unique name consisting of the table number, the sample ID number (discussed above), and the UNIQID for identifying the array data in the National Cancer Institute Database. For example, Table_1725_BL_2032_52748. txt is the .txt file for Table 1725, which contains data for sample ID number BL_2032. The data for each sample analyzed is contained in Tables 1725-2358. The signal intensity for each probe on the microarray can be transformed into summary signal values for each probe set through a number of different algorithms, including but not limited to MAS 5.0, D-chip (Li 2001), or Bioconductor's RMA algorithms (Irizarry 2003).

Example 3

Figure 2:
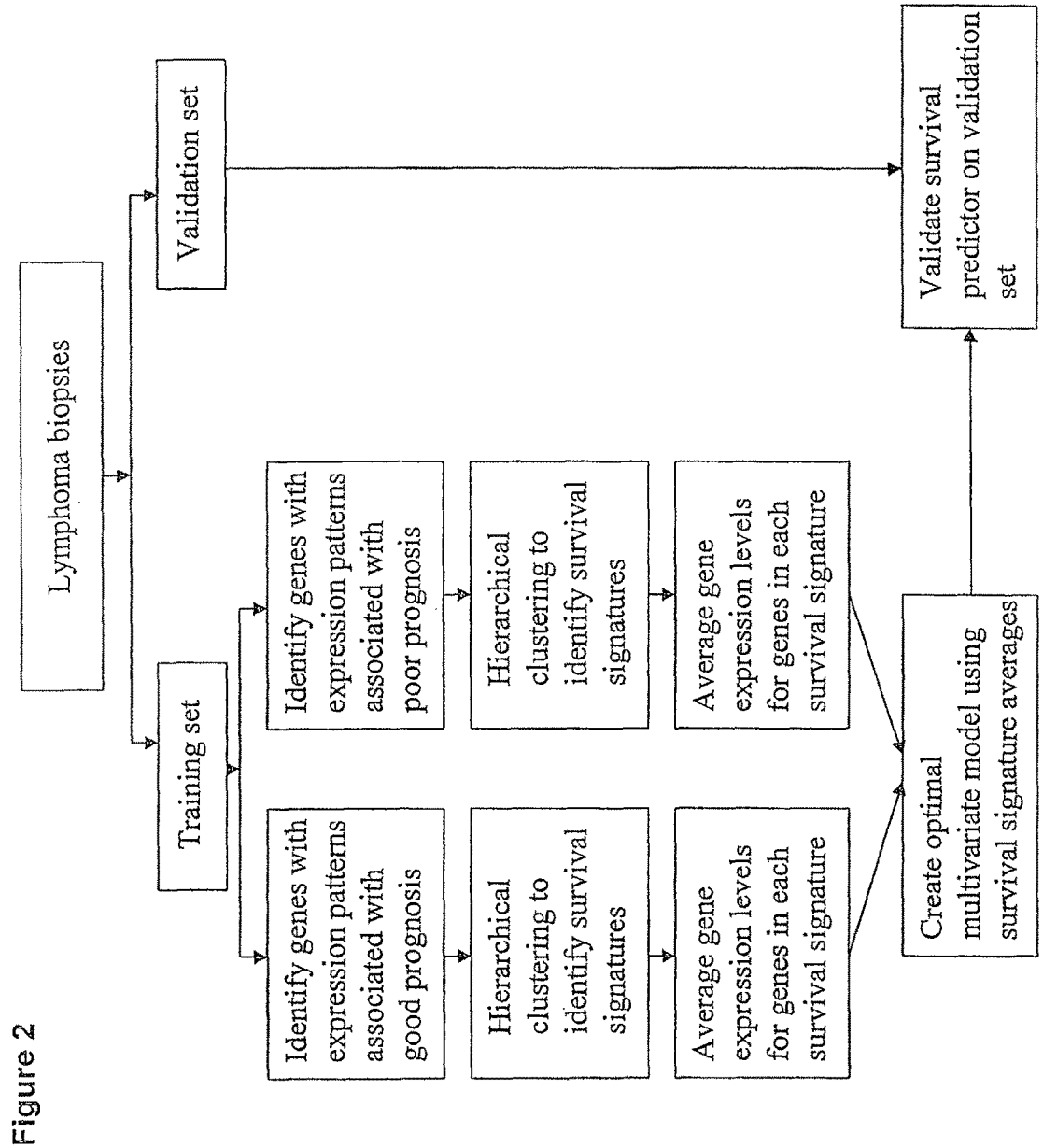
FIG. 2: Survival signature analysis. Flow chart depicts method for developing a lymphoma survival predictor based on gene expression patterns.

Development of a First FL Survival Predictor Using Gene Expression Data from Affymetrix U133A and U133B Microarrays An analytical method entitled Survival Signature Analysis was developed to create survival prediction models for lymphoma. This method is summarized in FIG. 2. The key feature of this method is the identification of gene expression signatures. Survival Signature Analysis begins by identifying genes whose expression patterns are statistically associated with survival. A hierarchical clustering algorithm is then used to identify subsets of these genes with correlated expression patterns across the lymphoma samples. These subsets are operationally defined as "survival-associated signatures." Evaluating a limited number of survival-associated signatures mitigates the multiple comparison problems that are inherent in the use of large-scale gene expression data sets to create statistical models of survival (Ransohoff 2004).

Figure 3:
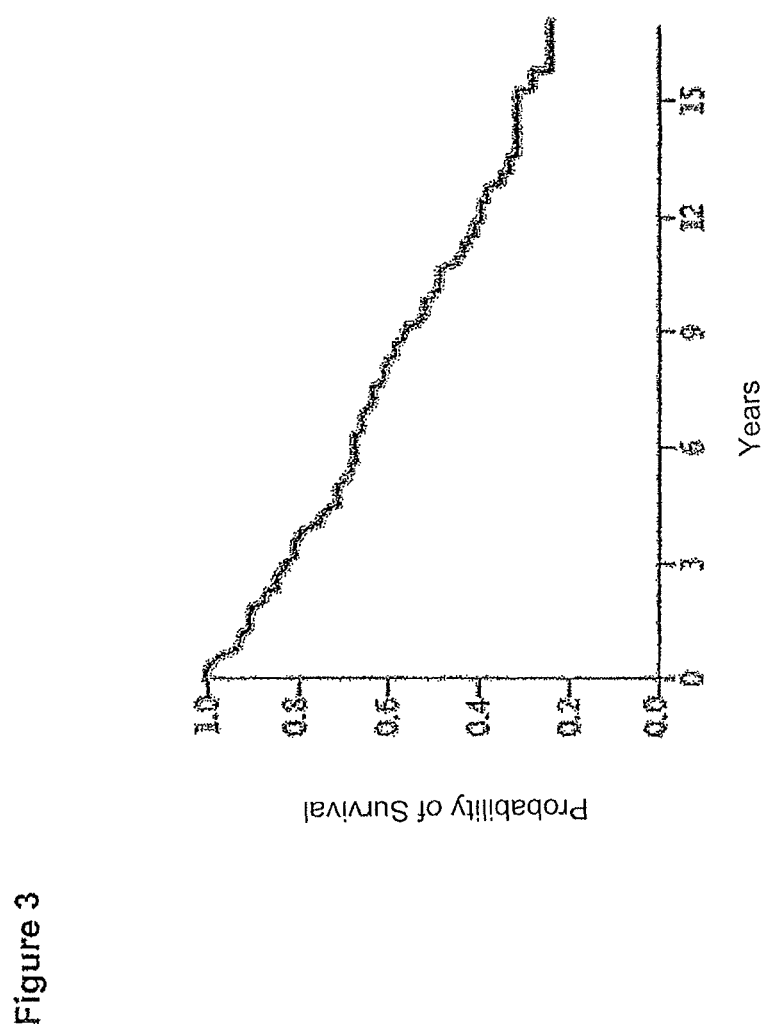
FIG. 3: FL survival data. Survival data for 191 subjects diagnosed with FL. Median age at diagnosis was 51 years (ranging from 23 to 81 years), and the subjects had a median follow-up of 6.6 years (8.1 years for survivors, with a range of <1 to 28.2 years).
Figure 4:
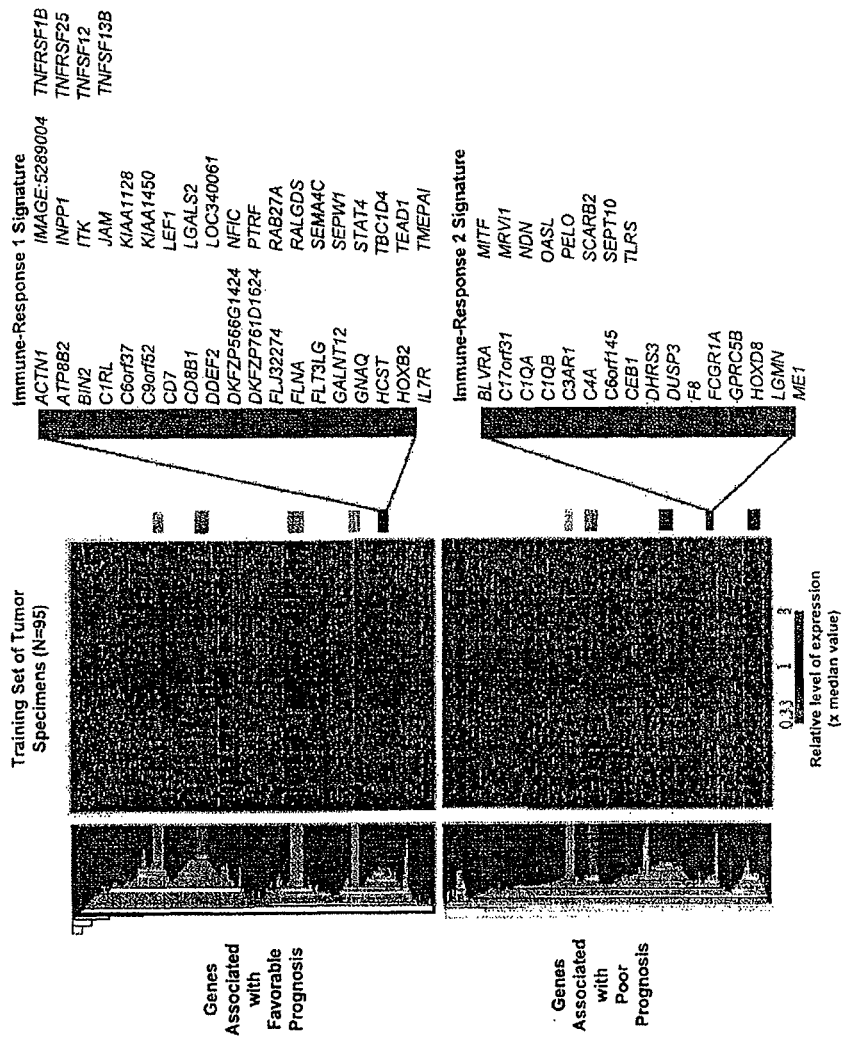
FIG. 4: Hierarchical clustering of survival associated genes in FL samples. Each column represents a single FL sample, while each row represents a single gene. Relative gene expression is depicted according to the scale at the bottom of the figure. The dendrogram to the left indicates the degree to which the expression pattern of each gene is correlated with that of the other genes. The colored bars indicate sets of coordinately regulated genes defined as gene expression signatures. Genes comprising the immune response-1 and immune response-2 gene expression signature are listed on the right.

FL samples were divided into two equivalent groups: a training set (95 samples) for developing the survival prediction model, and a validation set (96 samples) for evaluating the reproducibility of the model. The overall survival of this cohort is depicted in FIG. 3. The median age at diagnosis was 51 years (ranging from 23 to 81 years), and the patients had a median follow-up of 6.6 years (8.1 years for survivors, with a range of <1 to 28.2 years). Gene expression data from Affymetrix U133A and U133B microarrays was obtained for each sample. Within the training set, a Cox proportional hazards model was used to identify "survival predictor" genes, which were genes whose expression levels were associated with long survival (good prognosis genes) or short survival (poor prognosis genes). A hierarchical clustering algorithm (Eisen 1998) was used to identify gene expression signatures within the good and poor prognosis genes according to their expression pattern across all samples. Ten gene expression signatures were observed within either the good prognosis or poor prognosis gene sets (FIG. 4). The expression level of every component gene in each of these ten gene expression signatures was averaged to create a gene expression signature value.

To create a multivariate model of survival, different combinations of the ten gene expression signature values were generated and evaluated for their ability to predict survival within the training set. Among models consisting of two signatures, an exceptionally strong statistical synergy was observed between one signature from the good prognosis group and one signature from the poor prognosis group. These signatures were deemed "immune response-1" and "immune response-2," respectively, based on the biological function of certain genes within each signature. The immune response-1 gene expression signature included genes encoding T cell markers (e.g., CD7, CD8B1, ITK, LEF1, STAT4) and genes that are highly expressed in macrophages (e.g., ACTN1, TNFSF13B). The immune response-1 signature is not merely a surrogate for the number of T cells in the FL biopsy sample because many other standard T cell genes (e.g., CD2, CD4, LAT, TRIM, SH2D1A) were not associated with survival. The immune response-2 gene expression signature included genes known to be preferentially expressed in macrophages and/or dendritic cells (e.g., TLR5, FCGR1A, SEPT10, LGMN, C3AR1). Table 2359 lists the genes that were used to generate the gene expression signature values for the immune response-1 and immune response-2 signatures. The Unigene ID Build database referenced in the following tables is hosted by the hosted by the National Center for Biotechnology Information (NCBI) web site

TABLE 2359

| Signature | UNIQID | Unigene ID Build 167 | Gene symbol |
|---|---|---|---|
| Immune response-1 | 1095985 | 83883 | TMEPAI |
| Immune response-1 | 1096579 | 117339 | HCST |
| Immune response-1 | 1097255 | 380144 | |
| Immune response-1 | 1097307 | 379754 | LOC340061 |
| Immune response-1 | 1097329 | 528675 | TEAD1 |
| Immune response-1 | 1097561 | 19221 | C20orf112 |
| Immune response-1 | 1098152 | 377588 | KIAA1450 |

TABLE 2359-continued

| Signature | UNIQID | Unigene ID Build 167 | Gene symbol |
|---|---|---|---|
| Immune response-1 | 1098405 | 362807 | IL7R |
| Immune response-1 | 1098548 | 436639 | NFIC |
| Immune response-1 | 1098893 | 43577 | ATP8B2 |
| Immune response-1 | 1099053 | 376041 | |
| Immune response-1 | 1100871 | 48353 | |
| Immune response-1 | 1101004 | 2969 | SKI |
| Immune response-1 | 1103303 | 49605 | C9orf52 |
| Immune response-1 | 1107713 | 171806 | |
| Immune response-1 | 1115194 | 270737 | TNFSF13B |
| Immune response-1 | 1119251 | 433941 | SEPW1 |
| Immune response-1 | 1119838 | 469951 | GNAQ |
| Immune response-1 | 1119924 | 32309 | INPP1 |
| Immune response-1 | 1120196 | 173802 | TBC1D4 |
| Immune response-1 | 1120267 | 256278 | TNFRSF1B |
| Immune response-1 | 1121313 | 290432 | HOXB2 |
| Immune response-1 | 1121406 | NA | TNFSF12 |
| Immune response-1 | 1121720 | 80642 | STAT4 |
| Immune response-1 | 1122956 | 113987 | LGALS2 |
| Immune response-1 | 1123038 | 119000 | ACTN1 |
| Immune response-1 | 1123092 | 437191 | PTRF |
| Immune response-1 | 1123875 | 428 | FLT3LG |
| Immune response-1 | 1124760 | 419149 | JAM3 |
| Immune response-1 | 1128356 | 415792 | C1RL |
| Immune response-1 | 1128395 | 7188 | SEMA4C |
| Immune response-1 | 1132104 | 173802 | TBC1D4 |
| Immune response-1 | 1133408 | 12802 | DDEF2 |
| Immune response-1 | 1134069 | 405667 | CD8B1 |
| Immune response-1 | 1134751 | 106185 | RALGDS |
| Immune response-1 | 1134945 | 81897 | KIAA1128 |
| Immune response-1 | 1135743 | 299558 | TNFRSF25 |
| Immune response-1 | 1135968 | 119000 | ACTN1 |
| Immune response-1 | 1136048 | 299558 | TNFRSF25 |
| Immune response-1 | 1136087 | 211576 | ITK |
| Immune response-1 | 1137137 | 195464 | FLNA |
| Immune response-1 | 1137289 | 36972 | CD7 |
| Immune response-1 | 1137534 | 36972 | CD7 |
| Immune response-1 | 1139339 | 47099 | GALNT12 |
| Immune response-1 | 1139461 | 14770 | BIN2 |
| Immune response-1 | 1140391 | 44865 | LEF1 |
| Immune response-1 | 1140524 | 10784 | C6orf37 |
| Immune response-1 | 1140759 | 298530 | RAB27A |
| Immune response-2 | 1118755 | 127826 | EPOR |
| Immune response-2 | 1118966 | 19196 | LOC51619 |
| Immune response-2 | 1121053 | 1690 | FGFBP1 |
| Immune response-2 | 1121267 | 334629 | SLN |
| Immune response-2 | 1121331 | 8980 | TESK2 |
| Immune response-2 | 1121766 | 396566 | MPP3 |
| Immune response-2 | 1121852 | 421391 | LECT1 |
| Immune response-2 | 1122624 | 126378 | ABCG4 |
| Immune response-2 | 1122679 | 232770 | ALOXE3 |
| Immune response-2 | 1122770 | 66578 | CRHR2 |
| Immune response-2 | 1123767 | 1309 | CD1A |
| Immune response-2 | 1123841 | 389 | ADH7 |
| Immune response-2 | 1126097 | 498015 | |
| Immune response-2 | 1126380 | 159408 | |
| Immune response-2 | 1126628 | 254321 | CTNNA1 |
| Immune response-2 | 1126836 | 414410 | NEK1 |
| Immune response-2 | 1127277 | 121494 | SPAM1 |
| Immune response-2 | 1127519 | NA | |
| Immune response-2 | 1127648 | 285050 | |
| Immune response-2 | 1128483 | 444359 | SEMA4G |
| Immune response-2 | 1128818 | 115830 | HS3ST2 |
| Immune response-2 | 1129012 | 95497 | SLC2A9 |
| Immune response-2 | 1129582 | 272236 | C21orf77 |
| Immune response-2 | 1129658 | 58356 | PGLYRP4 |
| Immune response-2 | 1129705 | 289368 | ADAM19 |
| Immune response-2 | 1129867 | 283963 | G6PC2 |
| Immune response-2 | 1130003 | 432799 | |
| Immune response-2 | 1130388 | 19196 | LOC51619 |
| Immune response-2 | 1131837 | 156114 | PTPNS1 |
| Immune response-2 | 1133843 | 6682 | SLC7A11 |
| Immune response-2 | 1133949 | 502092 | PSG9 |
| Immune response-2 | 1134447 | 417628 | CRHR1 |
| Immune response-2 | 1135117 | 512646 | PSG6 |
| Immune response-2 | 1136017 | 1645 | CYP4A11 |
| Immune response-2 | 1137478 | 315235 | ALDOB |
| Immune response-2 | 1137745 | 26776 | NTRK3 |
| Immune response-2 | 1137768 | 479985 | |

TABLE 2359-continued

| Signature | UNIQID | Unigene ID Build 167 | Gene symbol |
|---|---|---|---|
| Immune response-2 | 1138476 | 351874 | HLA-DOA |
| Immune response-2 | 1138529 | 407604 | CRSP2 |
| Immune response-2 | 1138601 | 149473 | PRSS7 |
| Immune response-2 | 1139862 | 251383 | CHST4 |
| Immune response-2 | 1140189 | 287369 | IL22 |
| Immune response-2 | 1140389 | 22116 | CDC14B |

Although the immune response-1 and immune response-2 gene expression signatures taken individually were not ideal predictors of survival, the binary model formed by combining the two was more predictive of survival in the training set than any other binary model (p<0.001). Using this binary model as an anchor, other signatures were added to the model using a step up procedure (Drapner 1966). Of the remaining eight signatures, only one signature contributed significantly to the model in the training set (p<0.01), resulting in a three-variable model for survival. This model was associated with survival in a highly statistically significant fashion in both the training (p<0.001) and validation sets (p=0.003). However, only the immune response-1 and immune response-2 gene expression signatures contributed to the predictive power of the model in both the training set and the validation set. The predictive power of each of these signatures is summarized in Table 2360.

TABLE 2360

| Gene expression signature | Contribution of signature to model in validation set (p-value) | Relative risk of death among patients in validation set (95% C.I.) | Effect of increased expression on survival |
|---|---|---|---|
| Immune response-1 | <0.001 | 0.15 (0.05-0.46) | Favorable |
| Immune response-2 | <0.001 | 9.35 (3.02-28.9) | Poor |

Based on this information, the third signature was removed from the model and the two-signature model was used to generate a survival predictor score using the following equation:

Survival predictor score=[(2.71*immune response-2 gene expression signature value)]−[(2.36×immune response-1 gene expression signature value)].

A higher survival predictor score was associated with worse outcome. The two-signature model was associated with survival in a statistically significant fashion in both the training set (p<0.001) and the validation set (p<0.001), which demonstrated that the model was reproducible. For the 187 FL samples with available clinical data, the survival predictor score had a mean of 1.6 and a standard deviation of 0.894, with each unit increase in the predictor score corresponding to a 2.5 fold increase in the relative risk of death. Data for all 191 samples is shown in Table 2361.

TABLE 2361

| Sample ID # | Set | Length of follow-up (years) | Status at follow-up | Immune response-1 signature value | Immune response-2 signature value | Survival predictor score |
|---|---|---|---|---|---|---|
| FL__1073 | Training | 7.68 | Dead | 9.20 | 8.67 | 1.77 |
| FL__1074 | Training | 4.52 | Dead | 9.10 | 8.57 | 1.74 |
| FL__1075 | Validation | 4.52 | Dead | 8.97 | 8.69 | 2.38 |
| FL__1076 | Training | 3.22 | Dead | 9.20 | 8.55 | 1.44 |
| FL__1077 | Training | 7.06 | Alive | 9.80 | 8.46 | −0.20 |
| FL__1078 | Training | 4.95 | Alive | 9.32 | 8.23 | 0.30 |
| FL__1080 | Training | 6.05 | Alive | 9.45 | 8.94 | 1.93 |
| FL__1081 | Validation | 6.61 | Alive | 9.00 | 8.22 | 1.05 |
| FL__1083 | Training | 10.01 | Alive | 9.82 | 8.72 | 0.47 |
| FL__1085 | Validation | 8.84 | Alive | 9.31 | 8.58 | 1.29 |
| FL__1086 | Validation | 1.98 | Dead | 9.49 | 9.09 | 2.22 |
| FL__1087 | Training | 8.19 | Alive | 9.98 | 9.27 | 1.57 |
| FL__1088 | Validation | 5.30 | Alive | 9.22 | 8.47 | 1.20 |
| FL__1089 | Training | 10.72 | Alive | 9.42 | 8.35 | 0.40 |
| FL__1090 | Validation | 10.20 | Alive | 9.27 | 8.37 | 0.82 |
| FL__1097 | Validation | 8.79 | Dead | 9.87 | 8.92 | 0.87 |
| FL__1098 | Validation | 5.34 | Dead | 9.33 | 8.81 | 1.87 |
| FL__1099 | Training | 7.65 | Alive | 9.73 | 9.04 | 1.54 |
| FL__1102 | Validation | 13.20 | Dead | 9.45 | 8.89 | 1.79 |
| FL__1104 | Training | 8.42 | Dead | 9.30 | 8.27 | 0.48 |
| FL__1106 | Validation | 7.94 | Alive | 9.13 | 9.19 | 3.36 |
| FL__1107 | Training | 5.01 | Dead | 9.41 | 9.32 | 3.07 |
| FL__1183 | Training | 11.56 | Dead | 9.31 | 8.53 | 1.16 |
| FL__1184 | Training | 6.93 | Dead | 9.66 | 8.83 | 1.13 |
| FL__1185 | Validation | 7.02 | Dead | 9.23 | 9.09 | 2.86 |
| FL__1186 | Training | 1.34 | Dead | 9.01 | 8.84 | 2.68 |
| FL__1416 | Validation | 6.21 | Alive | 9.50 | 8.67 | 1.08 |
| FL__1417 | Training | 2.40 | Dead | 8.47 | 8.39 | 2.73 |
| FL__1418 | Validation | 3.59 | Alive | 8.94 | 8.42 | 1.72 |
| FL__1419 | Training | 3.85 | Alive | 9.82 | 8.56 | 0.03 |
| FL__1422 | Training | 5.72 | Alive | 9.46 | 8.49 | 0.68 |
| FL__1425 | Validation | 4.26 | Alive | 8.93 | 8.50 | 1.98 |
| FL__1426 | Training | 7.32 | Alive | 9.08 | 8.26 | 0.97 |
| FL__1427 | Training | 5.22 | Alive | 8.57 | 8.28 | 2.22 |
| FL__1428 | Validation | 5.41 | Dead | 9.22 | 8.44 | 1.10 |
| FL__1432 | Training | 3.66 | Alive | 9.22 | 8.95 | 2.51 |
| FL__1436 | Training | 9.08 | Dead | 9.48 | 8.63 | 1.02 |
| FL__1440 | Training | 7.85 | Alive | 9.07 | 8.35 | 1.22 |
| FL__1445 | Training | 9.24 | Dead | 8.67 | 8.66 | 3.01 |
| FL__1450 | Validation | 0.65 | Dead | 9.83 | 9.99 | 3.86 |

TABLE 2361-continued

| Sample ID # | Set | Length of follow-up (years) | Status at follow-up | Immune response-1 signature value | Immune response-2 signature value | Survival predictor score |
|---|---|---|---|---|---|---|
| FL_1472 | Validation | 16.72 | Alive | 8.85 | 8.49 | 2.10 |
| FL_1473 | Training | 15.07 | Alive | 9.75 | 8.50 | 0.02 |
| FL_1474 | Validation | 2.75 | Dead | 9.34 | 9.10 | 2.62 |
| FL_1476 | Validation | 4.08 | Dead | 9.51 | 8.87 | 1.60 |
| FL_1477 | Training | 0.59 | Dead | 9.64 | 9.06 | 1.83 |
| FL_1478 | Training | 12.47 | Dead | 9.60 | 8.87 | 1.39 |
| FL_1479 | Training | 2.29 | Dead | 8.71 | 9.07 | 4.01 |
| FL_1480 | Training | 16.29 | Alive | 9.40 | 8.67 | 1.30 |
| FL_1579 | Training | 8.22 | Dead | 8.81 | 8.44 | 2.10 |
| FL_1580 | Training | 19.30 | Alive | 9.58 | 8.52 | 0.49 |
| FL_1581 | Training | 9.52 | Dead | 9.08 | 9.02 | 3.00 |
| FL_1582 | Validation | 1.30 | Dead | 8.40 | 8.18 | 2.36 |
| FL_1583 | Training | 15.26 | Dead | 9.47 | 8.79 | 1.48 |
| FL_1584 | Training | 15.73 | Dead | 9.44 | 8.55 | 0.89 |
| FL_1585 | Validation | 0.01 | Alive | 8.96 | 8.53 | 1.96 |
| FL_1586 | Validation | 3.11 | Alive | 9.38 | 8.55 | 1.03 |
| FL_1588 | Training | 0.49 | Dead | 9.52 | 9.06 | 2.08 |
| FL_1589 | Training | 3.15 | Alive | 9.72 | 8.74 | 0.72 |
| FL_1591 | Training | 11.22 | Alive | 9.49 | 8.62 | 0.97 |
| FL_1594 | Validation | 11.19 | Alive | 9.25 | 8.59 | 1.47 |
| FL_1595 | Training | 8.03 | Alive | 9.75 | 9.60 | 3.01 |
| FL_1598 | Validation | 2.80 | Dead | 8.81 | 8.33 | 1.79 |
| FL_1599 | Validation | 6.17 | Alive | 9.48 | 8.65 | 1.06 |
| FL_1603 | Training | 5.17 | Dead | 9.66 | 9.75 | 3.63 |
| FL_1604 | Training | 3.98 | Dead | 9.24 | 8.86 | 2.20 |
| FL_1606 | Validation | 4.22 | Dead | 9.45 | 9.18 | 2.57 |
| FL_1607 | Validation | 8.12 | Alive | 9.40 | 8.60 | 1.13 |
| FL_1608 | Validation | 9.70 | Alive | 8.92 | 8.41 | 1.72 |
| FL_1610 | Validation | 2.05 | Dead | 9.33 | 9.35 | 3.32 |
| FL_1611 | Validation | 10.15 | Alive | 9.42 | 8.69 | 1.31 |
| FL_1616 | Training | 2.36 | Dead | 9.38 | 8.82 | 1.78 |
| FL_1617 | Validation | 7.85 | Alive | 8.96 | 8.49 | 1.87 |
| FL_1619 | Validation | 9.24 | Dead | 9.43 | 8.56 | 0.94 |
| FL_1620 | Validation | 9.36 | Dead | 9.14 | 8.35 | 1.04 |
| FL_1622 | Training | 14.01 | Alive | 9.23 | 8.53 | 1.33 |
| FL_1623 | Training | 9.72 | Alive | 9.67 | 8.93 | 1.38 |
| FL_1624 | Validation | 3.98 | Dead | 9.05 | 8.50 | 1.70 |
| FL_1625 | Validation | 11.16 | Alive | 8.98 | 8.47 | 1.75 |
| FL_1626 | Validation | 6.47 | Dead | 8.59 | 8.14 | 1.76 |
| FL_1628 | Validation | 0.82 | Dead | 9.80 | 8.72 | 0.51 |
| FL_1637 | Validation | 18.81 | Alive | 9.95 | 9.58 | 2.48 |
| FL_1638 | Validation | 4.06 | Alive | 9.13 | 8.88 | 2.51 |
| FL_1639 | Training | 4.75 | Alive | 9.53 | 8.89 | 1.62 |
| FL_1643 | Training | 0.77 | Dead | 9.73 | 9.06 | 1.58 |
| FL_1644 | Validation | 3.84 | Alive | 9.55 | 8.68 | 0.98 |
| FL_1645 | Training | 3.56 | Alive | 9.49 | 8.70 | 1.18 |
| FL_1646 | Training | 1.97 | Dead | 9.25 | 8.61 | 1.50 |
| FL_1647 | Training | 1.22 | Dead | 9.12 | 8.89 | 2.55 |
| FL_1648 | Training | 11.01 | Alive | 9.13 | 8.12 | 0.46 |
| FL_1652 | Training | 3.72 | Dead | 9.50 | 9.14 | 2.35 |
| FL_1654 | Validation | 0.30 | Dead | 8.74 | 8.28 | 1.82 |
| FL_1655 | Training | 8.45 | Alive | 9.51 | 8.85 | 1.53 |
| FL_1656 | Validation | 9.36 | Alive | 9.06 | 8.58 | 1.87 |
| FL_1657 | Training | 10.09 | Alive | 9.53 | 8.46 | 0.44 |
| FL_1660 | Training | 2.32 | Alive | 8.81 | 8.38 | 1.91 |
| FL_1661 | Validation | 1.48 | Alive | 9.86 | 8.90 | 0.85 |
| FL_1662 | Validation | 0.74 | Dead | 9.57 | 9.15 | 2.21 |
| FL_1664 | Validation | 4.53 | Dead | 9.34 | 8.62 | 1.31 |
| FL_1669 | Training | 4.40 | Dead | 8.87 | 8.58 | 2.30 |
| FL_1670 | Training | 1.88 | Alive | 9.64 | 9.45 | 2.86 |
| FL_1675 | Training | 4.57 | Alive | 9.36 | 8.46 | 0.84 |
| FL_1681 | Validation | 4.23 | Alive | 9.52 | 8.63 | 0.91 |
| FL_1683 | Validation | 4.03 | Dead | 9.95 | 9.10 | 1.19 |
| FL_1684 | Training | 2.88 | Dead | 9.53 | 8.73 | 1.18 |
| FL_1716 | Validation | 9.69 | Alive | 8.95 | 8.35 | 1.50 |
| FL_1717 | Validation | 2.01 | Dead | 9.35 | 8.88 | 1.98 |
| FL_1718 | Training | 10.35 | Alive | 9.23 | 8.13 | 0.26 |
| FL_1719 | Validation | 7.70 | Dead | 9.13 | 8.50 | 1.49 |
| FL_1720 | Training | 3.91 | Dead | 8.78 | 8.88 | 3.33 |
| FL_1729 | Training | 8.06 | Alive | 9.35 | 8.65 | 1.39 |
| FL_1732 | Validation | 0.71 | Dead | 7.81 | 8.59 | 4.86 |
| FL_1761 | Validation | 10.83 | Alive | 9.31 | 8.55 | 1.22 |
| FL_1764 | Training | 0.42 | Dead | 9.25 | 8.87 | 2.21 |
| FL_1768 | Training | 13.04 | Alive | 9.42 | 8.47 | 0.72 |
| FL_1771 | Training | 9.26 | Dead | 9.09 | 8.67 | 2.06 |

TABLE 2361-continued

| Sample ID # | Set | Length of follow-up (years) | Status at follow-up | Immune response-1 signature value | Immune response-2 signature value | Survival predictor score |
|---|---|---|---|---|---|---|
| FL__1772 | Validation | 13.64 | Dead | 9.49 | 8.49 | 0.61 |
| FL__1788 | Training | 1.00 | Dead | 9.09 | 9.13 | 3.29 |
| FL__1790 | Training | 1.42 | Alive | 9.85 | 9.40 | 2.22 |
| FL__1792 | Validation | 2.01 | Dead | 9.33 | 8.72 | 1.61 |
| FL__1795 | Training | 0.71 | Dead | 10.19 | 9.27 | 1.08 |
| FL__1797 | Validation | 7.17 | Alive | 9.34 | 8.92 | 2.14 |
| FL__1799 | Training | 14.18 | Alive | 9.32 | 8.63 | 1.38 |
| FL__1810 | Validation | 9.91 | Alive | 8.66 | 8.41 | 2.35 |
| FL__1811 | Validation | 3.04 | Alive | 9.38 | 8.27 | 0.29 |
| FL__1825 | Training | 2.98 | Alive | 9.46 | 9.07 | 2.25 |
| FL__1827 | Training | 3.66 | Alive | 9.80 | 8.84 | 0.83 |
| FL__1828 | Validation | 11.51 | Alive | 8.99 | 8.09 | 0.72 |
| FL__1829 | Validation | 4.11 | Alive | 9.57 | 8.73 | 1.08 |
| FL__1830 | Validation | 5.65 | Dead | 9.01 | 8.68 | 2.25 |
| FL__1833 | Training | 11.95 | Alive | 9.74 | 8.67 | 0.51 |
| FL__1834 | Validation | 15.92 | Alive | 9.22 | 8.72 | 1.88 |
| FL__1835 | Validation | 12.49 | Alive | 9.26 | 8.83 | 2.10 |
| FL__1836 | Validation | 12.24 | Alive | 9.55 | 8.64 | 0.85 |
| FL__1837 | Validation | 0.55 | Dead | 9.47 | 8.84 | 1.62 |
| FL__1838 | Validation | 2.54 | Alive | 9.90 | 9.12 | 1.34 |
| FL__1839 | Training | 4.48 | Alive | 8.56 | 8.32 | 2.34 |
| FL__1841 | Training | 0.88 | Dead | 9.32 | 9.10 | 2.66 |
| FL__1842 | Validation | 4.56 | Alive | 9.73 | 8.87 | 1.07 |
| FL__1844 | Validation | 13.39 | Alive | 9.41 | 8.55 | 0.98 |
| FL__1845 | Training | 12.92 | Dead | 9.89 | 9.04 | 1.16 |
| FL__1846 | Validation | 1.80 | Dead | 9.79 | 9.61 | 2.93 |
| FL__1848 | Training | 12.52 | Alive | 9.76 | 8.81 | 0.82 |
| FL__1851 | Training | 4.08 | Dead | 9.43 | 9.01 | 2.18 |
| FL__1853 | Validation | 12.50 | Alive | 9.28 | 8.54 | 1.25 |
| FL__1854 | Validation | 13.81 | Alive | 9.32 | 8.84 | 1.98 |
| FL__1855 | Validation | 9.96 | Dead | 9.31 | 8.39 | 0.75 |
| FL__1857 | Validation | 8.39 | Dead | 9.80 | 9.14 | 1.65 |
| FL__1861 | Validation | 3.19 | Dead | 9.47 | 8.57 | 0.88 |
| FL__1862 | Validation | 7.22 | Dead | 8.96 | 8.33 | 1.44 |
| FL__1863 | Validation | 10.77 | Dead | 9.31 | 8.85 | 2.00 |
| FL__1864 | Training | 14.25 | Alive | 9.98 | 9.12 | 1.17 |
| FL__1866 | Training | 10.72 | Dead | 9.93 | 8.94 | 0.79 |
| FL__1870 | Validation | 6.41 | Dead | 10.01 | 9.22 | 1.36 |
| FL__1873 | Training | 7.78 | Dead | 9.39 | 8.66 | 1.30 |
| FL__1874 | Validation | 3.15 | Dead | 9.38 | 8.74 | 1.53 |
| FL__1876 | Validation | 15.07 | Alive | 9.59 | 8.72 | 0.98 |
| FL__1879 | Training | 7.13 | Dead | 9.25 | 8.62 | 1.53 |
| FL__1880 | Validation | 12.84 | Dead | 8.82 | 8.35 | 1.82 |
| FL__1882 | Training | 8.84 | Dead | 9.43 | 8.76 | 1.49 |
| FL__1884 | Validation | 11.92 | Dead | 9.48 | 9.14 | 2.41 |
| FL__1885 | Validation | 15.49 | Alive | 9.70 | 8.85 | 1.11 |
| FL__1887 | Training | 5.14 | Dead | 9.47 | 8.57 | 0.87 |
| FL__1888 | Training | 15.08 | Alive | 9.83 | 8.97 | 1.11 |
| FL__1890 | Training | 3.03 | Dead | 9.29 | 9.05 | 2.60 |
| FL__1894 | Training | 11.37 | Dead | 9.01 | 8.64 | 2.13 |
| FL__1896 | Training | 12.03 | Alive | 9.80 | 8.56 | 0.08 |
| FL__1897 | Training | 9.63 | Alive | 9.02 | 8.33 | 1.29 |
| FL__1898 | Training | 5.20 | Alive | 8.82 | 8.25 | 1.54 |
| FL__1900 | Validation | 7.38 | Alive | 9.13 | 8.26 | 0.85 |
| FL__1903 | Validation | 28.25 | Alive | 9.07 | 8.46 | 1.54 |
| FL__1904 | Validation | 7.36 | Alive | 9.16 | 8.53 | 1.50 |
| FL__1905 | Validation | 3.68 | Dead | 9.25 | 8.38 | 0.87 |
| FL__1906 | Training | 2.35 | Dead | 8.04 | 8.69 | 4.56 |
| FL__1907 | Validation | 2.35 | Dead | 8.11 | 8.21 | 3.11 |
| FL__1910 | Training | 13.84 | Alive | 9.36 | 8.72 | 1.56 |
| FL__1912 | Validation | 0.73 | Dead | 9.30 | 9.21 | 3.02 |
| FL__1913 | Training | 2.57 | Alive | 9.77 | 8.51 | 0.01 |
| FL__1916 | Validation | 11.61 | Alive | 9.22 | 8.49 | 1.24 |
| FL__1918 | Validation | 9.95 | Dead | 9.54 | 8.77 | 1.26 |
| FL__1919 | Training | 10.84 | Dead | 9.51 | 8.81 | 1.44 |
| FL__735 | Validation | 11.05 | Dead | 8.81 | 8.23 | 1.53 |
| FL__738 | Validation | 10.15 | Dead | 9.19 | 8.79 | 2.13 |
| FL__739 | Training | 10.80 | Dead | 9.29 | 8.77 | 1.85 |
| FL__878 | Validation | 3.87 | Dead | 8.85 | 8.54 | 2.26 |
| FL__879 | Training | 4.34 | Dead | 8.95 | 8.74 | 2.56 |
| FL__886 | Validation | 3.29 | Alive | 9.43 | 8.72 | 1.40 |
| FL__888 | Validation | 1.32 | Dead | 8.76 | 8.49 | 2.34 |
| FL__1627 | Training | NA | NA | 9.60 | 8.51 | 0.40 |
| FL__1429 | Training | NA | NA | 8.69 | 8.28 | 1.93 |
| FL__1850 | Validation | NA | NA | 9.75 | 8.83 | 0.92 |

TABLE 2361-continued

| Sample ID # | Set | Length of follow-up (years) | Status at follow-up | Immune response-1 signature value | Immune response-2 signature value | Survival predictor score |
|---|---|---|---|---|---|---|
| FL__1735 | Validation | NA | NA | 7.32 | 8.30 | 5.24 |

Figure 5:
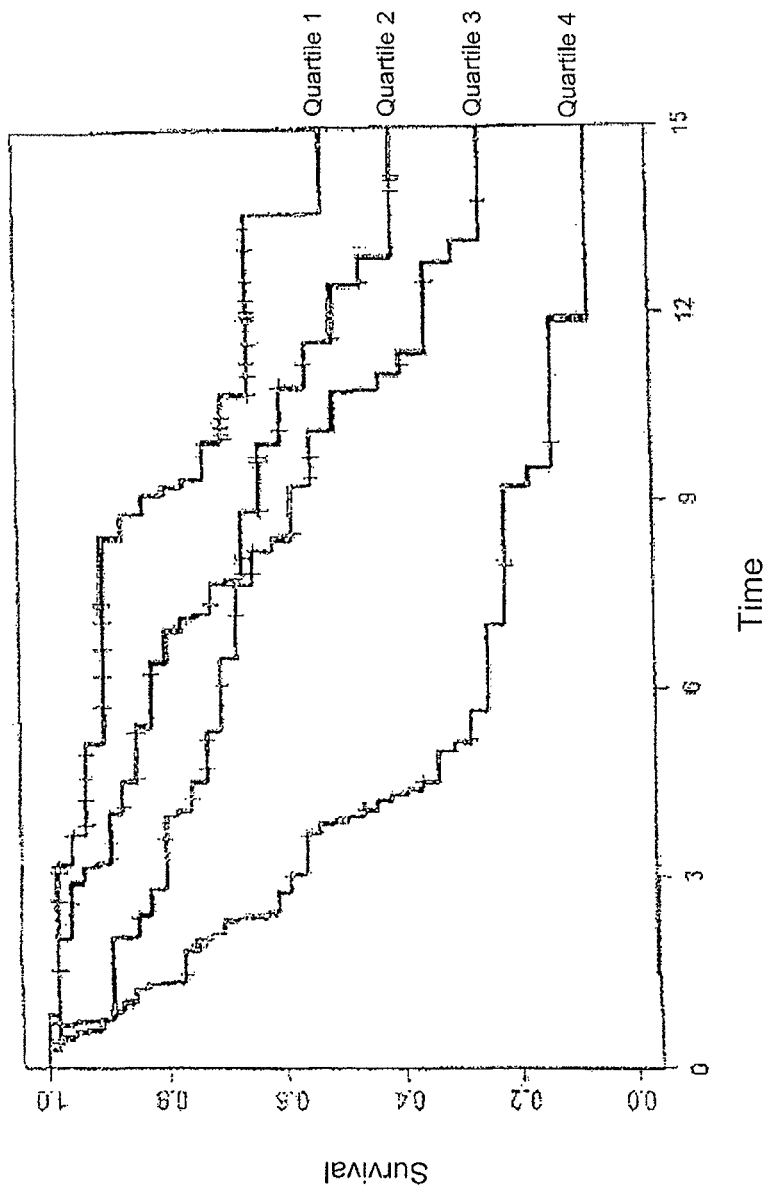
FIG. 5: Kaplan-Meier plot of survival in FL samples based on survival predictor scores. 191 FL samples were divided into quartiles based on their survival predictor scores. The survival predictor scores were calculated by: [(2.71*immune response-2 gene expression signature value)]−[(2.36×immune response-1 gene expression signature value)].

In order to visualize the predictive power of the model, the FL samples were ranked according to their survival predictor scores and divided into four quartiles. Kaplan-Meier plots of overall survival showed clear differences in survival rate in the validation set (FIG. 5). The median survival for each of the four quartiles is set forth in Table 2362.

TABLE 2362

| Quartile | Median survival (years) |
|---|---|
| 1 | 13.6 |
| 2 | 11.1 |
| 3 | 10.8 |
| 4 | 3.9 |

Various clinical variables were found to be significantly associated with survival, including the IPI and some of its components and the presence of B-symptoms. The gene expression-based model was independent of each of these variables at predicting survival. These clinical variables and the relative risk of death associated with each are summarized in Table 2363.

TABLE 2363

| Clinical variable | Criteria | % of patients[1] Training set | % of patients[1] Validation set | Univariate (clinical variable only) relative risk of death among patients in validation set | | Multivariate (clinical variable + survival predictor score) relative risk of death among patients in validation set | |
|---|---|---|---|---|---|---|---|
| | | | | RR[2] (95% C.I.) | p-value | RR[2] (95% C.I.) | p-value |
| Age | 60 | 64.5 | 70.2 | 1.90 (1.02-3.56) | 0.044 | 2.21 (1.48-3.29) | <0.001 |
| | >60 | 35.5 | 29.8 | | | | |
| Stage | I-II | 33.3 | 25 | 1.31 (0.65-2.64) | 0.447 | 2.31 (1.51-3.52) | <0.001 |
| | III-IV | 66.7 | 75 | | | | |
| Extranodal sites (#) | 2 | 5.4 | 20.2 | 1.58 (0.83-2.99) | 0.163 | 2.21 (1.48-3.30) | <0.001 |
| | <2 | 94.6 | 79.8 | | | | |
| LDH | Normal | 77.1 | 66.2 | 1.77 (0.97-3.24) | 0.065 | 2.40 (1.57-3.67) | <0.001 |
| | Greater than normal | 22.9 | 33.8 | | | | |
| ECOG performance status | 2 | 9.4 | 12.5 | 2.05 (0.89-4.71) | 0.090 | 2.17 (1.40-3.35) | <0.001 |
| | <2 | 90.6 | 87.5 | | | | |
| Gender | Male | 42 | 65 | 1.62 (0.90-2.90) | 0.105 | 2.17 (1.45-3.25) | <0.001 |
| | Female | 58 | 35 | | | | |
| B-symptoms | Present | 17.2 | 21.3 | 2.05 (1.08-3.89) | 0.029 | 2.10 (1.37-3.23) | <0.001 |
| | Absent | 82.8 | 78.7 | | | | |
| Grade[3] | 1 | 45 | 43.4 | N/A | 0.118 | 2.55 (1.63-3.99) | <0.001 |
| | 2 | 34.8 | 33.3 | 2.03 (1.04-3.96) | | | |
| | 3 | 20.2 | 23.3 | 1.39 (0.65-2.98) | | | |
| Int'l. Prognostic Index[4] | Scores 0-1 | 63.1 | 47.5 | N/A | 0.029 | 2.28 (1.46-3.57) | <0.001 |
| | Scores 2-3 | 33.3 | 45 | 2.07 (1.07-4.00) | | | |
| | Scores 4-5 | 3.6 | 7.5 | 3.73 (1.18-11.18) | | | |

[1]Due to rounding, percentages may not total 100
[2]Relative risk of death (RR) based on 2-fold increase in expression
[3]RR for grades 2 and 3 calculated with respect to risk of death for grade 1. The p-value is calculated for all grades.
[4]RR for scores 2-3 and 4-5 calculated with respect to risk of death for scores 0-1. The p-value is calculated for all grades.

Figure 6:
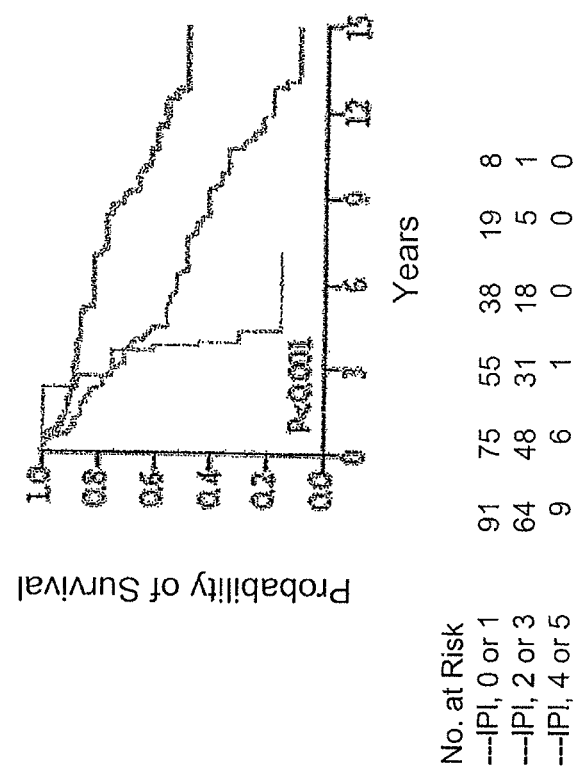
FIG. 6: Kaplan-Meier plot of survival in FL samples based on IPI score. 96 FL samples were divided into three groups based on their IPI scores.
Figure 7:
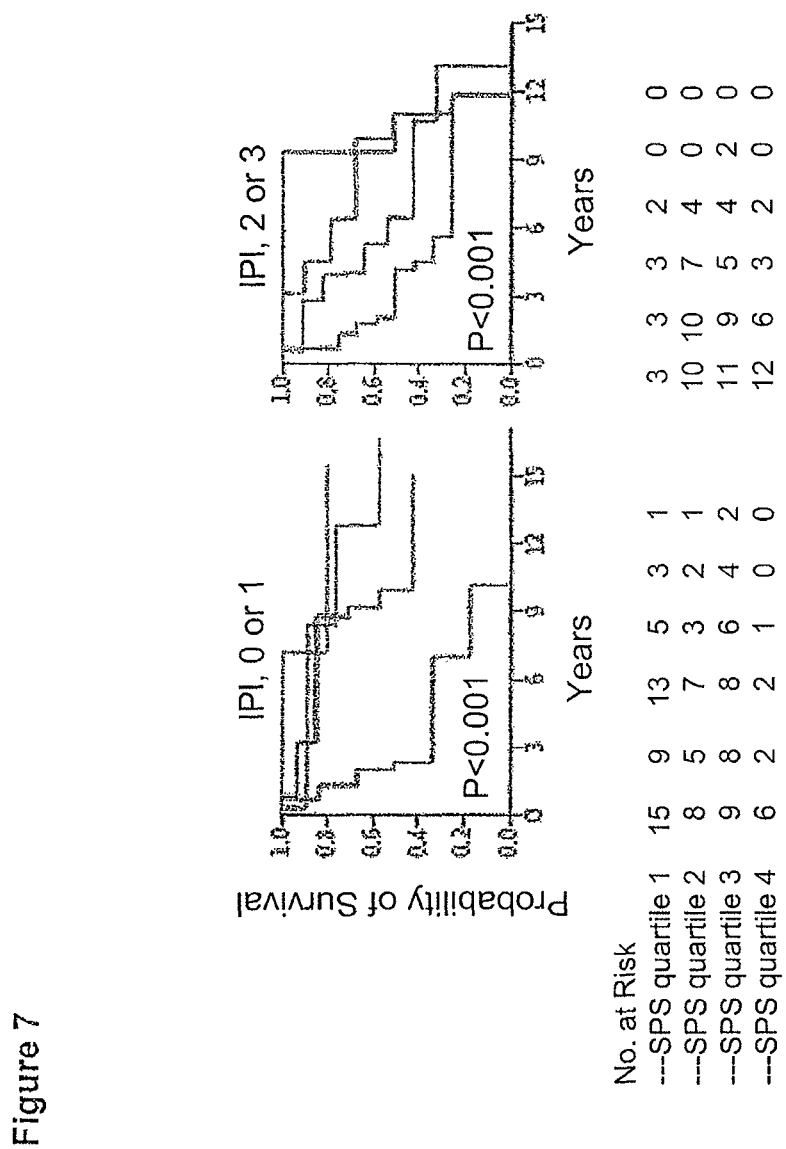
FIG. 7: Kaplan-Meier plot of survival in FL samples with low or high risk IPI scores based on survival predictor scores. 96 FL samples with low risk (left panel) or intermediate risk (right panel) IPI scores were divided into quartiles based on their survival predictor scores. The survival predictor scores were calculated by: [(2.71*immune response-2 gene expression signature value)]−[(2.36×immune response-1 gene expression signature value)].

The samples in the validation set were divided into three groups based on their IPI score, and the relationship between survival and IPI score was visualized by Kaplan-Meier plot (FIG.6). Among validation set samples from the low-risk (IPI 0-1) and intermediate risk (IPI 2-3) IPI groups, the gene-expression-based survival predictor could stratify patients into groups differing by more than 5 years with regards to median survival (FIG. 7). The high-risk IPI group (IPI 4-5) comprised less than 5% of the samples, and was omitted from this analysis. These results demonstrate that the gene expression-based model is not merely acting as a surrogate for clinical variables that are known to predict survival in FL, but rather it identifies distinct biological attributes of the tumors that are associated with survival.

Example 4

Development of a Second FL Survival Predictor Using Gene Expression Data from Affymetrix U133A and U133B Microarrays 191 FL were divided into two equivalent groups: a training set (95 samples) for developing the survival prediction model, and a validation set (96 samples) for evaluating the reproducibility of the model. Gene expression data from Affymetrix U133A and U133B microarrays was obtained for each of the samples. A Cox proportional hazards model was used to identify survival predictor genes whose expression levels were associated with long survival (good prognosis genes) or short survival (poor prognosis genes) in the training set. The correlation between expression and survival for each gene on the microarrays is provided in the final two columns of Table 1710. The first of these two columns ("FL_Cox_coefficient") provides a Cox coefficient indicating the extent to which a 2-fold increase in expression of a particular gene affects mortality. A positive Cox coefficient indicates increasing mortality with increasing expression of the gene, while a negative Cox coefficient indicates decreasing mortality with increasing expression of the gene. The second of these two columns provides a Cox p-value indicating the estimated probability that the increase or decrease in survival associated with the gene would occur by chance if there was no connection between the expression of the gene and survival.

A hierarchical clustering algorithm (Eisen 1998) was used to identify gene expression signatures within the good and poor prognosis genes according to their expression pattern across all samples. Eight clusters of coordinately regulated genes were observed within the good prognosis gene set and six clusters were observed in the poor prognosis gene sets. The expression level of every component gene in each of these gene expression signatures was averaged to create a gene expression signature value. After averaging, only ten of the gene expression signatures were found to be significantly associated with survival in the training set (p<0.01). To create a multivariate model of survival, different combinations of these ten gene expression signature averages were generated and evaluated for their ability to predict survival within the training set. Among models consisting of two signatures, an exceptionally strong statistical synergy was noted between one signature from the good prognosis group and one from the poor prognosis group. These gene expression signatures were termed "T-cell" and "macrophage" based on the biological function of certain genes within each signature. The T-cell gene expression signature included genes that were typically expressed in T-cells, while the macrophage gene expression signature included a number of genes typically expressed in macrophages. Although these two signatures taken individually were not the best predictors of survival, the binary model formed by combining the two was more predictive than any combination of three signatures that did not contain these two signatures. Using these two signatures as an anchor, other signatures were added to the model using a step up procedure (Drapner 1966). Only one of the remaining eight signatures, termed the B-cell differentiation signature, contributed significantly to the model in the training set (p=0.054). The B-cell differentiation signature included a number of genes that appear to be involved in B-cell signal transduction. Table 2364 lists the genes that were used to generate the gene expression signature values for the T-cell, macrophage, and B-cell differentiation gene expression signatures.

TABLE 2364

| Signature | UNIQID | Unigene ID Build 167 | Gene symbol |
|---|---|---|---|
| B-cell differentiation | 1119350 | 331141 | ALDH2 |
| B-cell differentiation | 1130922 | 459987 | ANP32B |
| B-cell differentiation | 1130923 | 459987 | ANP32B |
| B-cell differentiation | 1099291 | 130774 | C9orf105 |
| B-cell differentiation | 1102859 | 446195 | FLJ42418 |
| B-cell differentiation | 1120976 | 245644 | GCHFR |
| B-cell differentiation | 1098862 | 303669 | MGC26694 |
| B-cell differentiation | 1111070 | 202201 | |
| B-cell differentiation | 1105935 | | |
| B-cell differentiation | 1139017 | 274424 | NANS |
| B-cell differentiation | 1108988 | 3532 | NLK |
| B-cell differentiation | 1114726 | 3532 | NLK |
| B-cell differentiation | 1097897 | 266175 | PAG |
| B-cell differentiation | 1097901 | 266175 | PAG |
| B-cell differentiation | 1119813 | 155342 | PRKCD |
| B-cell differentiation | 1123298 | 20191 | SIAH2 |
| B-cell differentiation | 1101439 | 63335 | TERF2 |
| B-cell differentiation | 1120316 | 63335 | TERF2 |
| B-cell differentiation | 1096035 | 105794 | UGCGL1 |
| T-cell | 1134945 | 81897 | KIAA1128 |
| T-cell | 1134069 | 405667 | CD8B1 |
| T-cell | 1137809 | 405667 | CD8B1 |
| T-cell | 1119251 | 433941 | SEPW1 |
| T-cell | 1096579 | 117339 | HCST |
| T-cell | 1101004 | 2969 | SKI |
| T-cell | 1137137 | 195464 | FLNA |
| T-cell | 1100871 | 48353 | |
| T-cell | 1139461 | 14770 | BIN2 |
| T-cell | 1128395 | 7188 | SEMA4C |
| T-cell | 1119880 | 442844 | FMOD |
| T-cell | 1130676 | 194431 | KIAA0992 |
| T-cell | 1130668 | 194431 | KIAA0992 |
| T-cell | 1135968 | 119000 | ACTN1 |
| T-cell | 1097329 | 528675 | TEAD1 |
| T-cell | 1098548 | 436639 | NFIC |
| T-cell | 1123038 | 119000 | ACTN1 |
| T-cell | 1128356 | 415792 | C1RL |
| T-cell | 1133408 | 12802 | DDEF2 |
| T-cell | 1140524 | 10784 | C6orf37 |
| T-cell | 1119838 | 469951 | GNAQ |
| T-cell | 1097255 | 380144 | |
| T-cell | 1098152 | 377588 | KIAA1450 |
| T-cell | 1115194 | 270737 | TNFSF13B |
| T-cell | 1124760 | 419149 | JAM3 |
| T-cell | 1120267 | 256278 | TNFRSF1B |
| T-cell | 1137289 | 36972 | CD7 |
| T-cell | 1137534 | 36972 | CD7 |
| T-cell | 1097307 | 379754 | LOC340061 |
| T-cell | 1123613 | 97087 | CD3Z |
| T-cell | 1121720 | 80642 | STAT4 |
| T-cell | 1120196 | 173802 | TBC1D4 |
| T-cell | 1136087 | 211576 | ITK |
| T-cell | 1132104 | 173802 | TBC1D4 |
| T-cell | 1140391 | 44865 | LEF1 |
| T-cell | 1098405 | 362807 | IL7R |
| T-cell | 1135743 | 299558 | TNFRSF25 |
| T-cell | 1136048 | 299558 | TNFRSF25 |
| T-cell | 1123875 | 428 | FLT3LG |
| T-cell | 1098893 | 43577 | ATP8B2 |
| T-cell | 1097561 | 19221 | C20orf112 |
| T-cell | 1122956 | 113987 | LGALS2 |
| T-cell | 1121406 | | TNFSF12 |
| T-cell | 1125532 | | |
| T-cell | 1138538 | 2014 | TRD |
| T-cell | 1103303 | 49605 | C9orf52 |
| T-cell | 1119924 | 32309 | INPP1 |
| Macrophage | 1123682 | 114408 | TLR5 |
| Macrophage | 1099124 | 355455 | SEPT10 |
| Macrophage | 1123401 | 50130 | NDN |
| Macrophage | 1134379 | 150833 | C4A |
| Macrophage | 1137481 | 150833 | C4A |
| Macrophage | 1132220 | 448805 | GPRC5B |
| Macrophage | 1119400 | 181046 | DUSP3 |
| Macrophage | 1131119 | 349656 | SCARB2 |
| Macrophage | 1123566 | 155935 | C3AR1 |
| Macrophage | 1138443 | 77424 | FCGR1A |
| Macrophage | 1127943 | 9641 | C1QA |
| Macrophage | 1119998 | 8986 | C1QB |

TABLE 2364-continued

| Signature | UNIQID | Unigene ID Build 167 | Gene symbol |
|---|---|---|---|
| Macrophage | 1132433 | 14732 | ME1 |
| Macrophage | 1119260 | 18069 | LGMN |
| Macrophage | 1098278 | 166017 | MITF |

The three signatures were used to generate a survival predictor score using the following equation:

Survival predictor score=[2.053*(macrophage gene expression signature value)]−[2.344*(T-cell gene expression signature value)]−[0.729*(B-cell differentiation gene expression signature value)].

A higher survival predictor score was associated with worse outcome. According to a likelihood ratio test adjusted for the number of variables included, this model was significant in predicting survival in both the training set ($p=1.8\times10^{-8}$) and the validation set ($p=2.0\times10^{-5}$). For the 187 FL samples with available clinical data, the survival predictor score had a mean of −11.9 and a standard deviation of 0.9418, with each unit increase in the predictor score corresponding to a 2.5 fold increase in the relative risk of death. Data for all 191 samples is shown in Table 2365.

TABLE 2365

| Sample ID # | Set | B cell differentiation signature value | T-cell signature value | Macrophage signature value | Survival predictor score |
|---|---|---|---|---|---|
| FL_1073 | Training | 9.70 | 9.14 | 8.58 | −10.89 |
| FL_1074 | Training | 11.11 | 9.06 | 8.52 | −11.84 |
| FL_1075 | Validation | 11.23 | 8.92 | 8.75 | −11.15 |
| FL_1076 | Training | 10.02 | 9.21 | 8.59 | −11.25 |
| FL_1077 | Training | 9.94 | 9.77 | 8.44 | −12.82 |
| FL_1078 | Training | 10.67 | 9.32 | 8.21 | −12.76 |
| FL_1080 | Training | 10.62 | 9.44 | 8.88 | −11.64 |
| FL_1081 | Validation | 10.38 | 9.00 | 8.09 | −12.04 |
| FL_1083 | Training | 10.29 | 9.77 | 8.74 | −12.47 |
| FL_1085 | Validation | 9.87 | 9.24 | 8.43 | −11.55 |
| FL_1086 | Validation | 10.03 | 9.50 | 9.02 | −11.06 |
| FL_1087 | Training | 9.83 | 9.98 | 9.37 | −11.31 |
| FL_1088 | Validation | 10.57 | 9.21 | 8.29 | −12.27 |
| FL_1089 | Training | 10.30 | 9.38 | 8.27 | −12.53 |
| FL_1090 | Validation | 9.74 | 9.24 | 8.20 | −11.93 |
| FL_1097 | Validation | 9.57 | 9.82 | 8.80 | −11.93 |
| FL_1098 | Validation | 11.08 | 9.40 | 8.97 | −11.69 |
| FL_1099 | Training | 10.23 | 9.70 | 9.12 | −11.46 |
| FL_1102 | Validation | 9.66 | 9.46 | 8.90 | −10.93 |
| FL_1104 | Training | 10.72 | 9.19 | 8.20 | −12.53 |
| FL_1106 | Validation | 11.11 | 9.17 | 9.57 | −9.96 |
| FL_1107 | Training | 9.70 | 9.42 | 9.55 | −9.54 |
| FL_1183 | Training | 9.85 | 9.25 | 8.44 | −11.54 |
| FL_1184 | Training | 10.12 | 9.57 | 8.86 | −11.63 |
| FL_1185 | Validation | 10.75 | 9.21 | 9.13 | −10.68 |
| FL_1186 | Training | 9.76 | 8.88 | 8.83 | −9.80 |
| FL_1416 | Validation | 9.94 | 9.45 | 8.59 | −11.77 |
| FL_1417 | Training | 10.12 | 8.53 | 8.43 | −10.08 |
| FL_1418 | Validation | 9.35 | 8.86 | 8.27 | −10.59 |
| FL_1419 | Training | 10.20 | 9.76 | 8.53 | −12.81 |
| FL_1422 | Training | 10.22 | 9.48 | 8.40 | −12.43 |
| FL_1425 | Validation | 9.61 | 8.89 | 8.58 | −10.23 |
| FL_1426 | Training | 10.80 | 9.06 | 8.13 | −12.41 |
| FL_1427 | Training | 10.27 | 8.56 | 8.13 | −10.87 |
| FL_1428 | Validation | 10.76 | 9.25 | 8.38 | −12.32 |
| FL_1432 | Training | 10.51 | 9.17 | 9.04 | −10.59 |
| FL_1436 | Training | 9.69 | 9.40 | 8.61 | −11.42 |
| FL_1440 | Training | 9.82 | 9.04 | 8.21 | −11.50 |
| FL_1445 | Training | 9.24 | 8.69 | 8.62 | −9.41 |
| FL_1450 | Validation | 9.70 | 9.88 | 10.37 | −8.93 |
| FL_1472 | Validation | 10.78 | 8.96 | 8.51 | −11.40 |
| FL_1473 | Training | 9.99 | 9.70 | 8.41 | −12.75 |

TABLE 2365-continued

| Sample ID # | Set | B cell differentiation signature value | T-cell signature value | Macrophage signature value | Survival predictor score |
|---|---|---|---|---|---|
| FL_1474 | Validation | 10.21 | 9.27 | 9.05 | −10.59 |
| FL_1476 | Validation | 9.82 | 9.44 | 8.78 | −11.27 |
| FL_1477 | Training | 9.32 | 9.61 | 9.03 | −10.78 |
| FL_1478 | Training | 10.19 | 9.60 | 8.81 | −11.83 |
| FL_1479 | Training | 10.69 | 8.78 | 9.09 | −9.71 |
| FL_1480 | Training | 10.10 | 9.42 | 8.70 | −11.57 |
| FL_1579 | Training | 10.15 | 8.82 | 8.24 | −11.15 |
| FL_1580 | Training | 10.31 | 9.59 | 8.50 | −12.54 |
| FL_1581 | Training | 9.91 | 8.96 | 9.05 | −9.66 |
| FL_1582 | Validation | 9.73 | 8.31 | 8.06 | −10.03 |
| FL_1583 | Training | 10.95 | 9.45 | 8.86 | −11.95 |
| FL_1584 | Training | 9.98 | 9.38 | 8.46 | −11.89 |
| FL_1585 | Validation | 10.53 | 8.88 | 8.46 | −11.11 |
| FL_1586 | Validation | 10.00 | 9.30 | 8.42 | −11.81 |
| FL_1588 | Training | 9.59 | 9.41 | 8.94 | −10.68 |
| FL_1589 | Training | 10.29 | 9.68 | 8.73 | −12.27 |
| FL_1591 | Training | 10.44 | 9.45 | 8.56 | −12.18 |
| FL_1594 | Validation | 10.01 | 9.25 | 8.56 | −11.41 |
| FL_1595 | Training | 9.61 | 9.75 | 9.65 | −10.07 |
| FL_1598 | Validation | 11.18 | 8.80 | 8.31 | −11.71 |
| FL_1599 | Validation | 10.55 | 9.48 | 8.60 | −12.24 |
| FL_1603 | Training | 9.40 | 9.60 | 9.77 | −9.31 |
| FL_1604 | Training | 9.92 | 9.21 | 8.90 | −10.54 |
| FL_1606 | Validation | 9.87 | 9.45 | 9.17 | −10.52 |
| FL_1607 | Validation | 9.76 | 9.37 | 8.50 | −11.63 |
| FL_1608 | Validation | 9.92 | 8.90 | 8.39 | −10.85 |
| FL_1610 | Validation | 10.02 | 9.38 | 9.74 | −9.30 |
| FL_1611 | Validation | 10.18 | 9.41 | 8.69 | −11.64 |
| FL_1616 | Training | 9.62 | 9.33 | 8.85 | −10.71 |
| FL_1617 | Validation | 9.90 | 8.95 | 8.39 | −10.98 |
| FL_1619 | Validation | 9.98 | 9.37 | 8.47 | −11.85 |
| FL_1620 | Validation | 9.43 | 8.95 | 8.12 | −11.19 |
| FL_1622 | Training | 9.84 | 9.15 | 8.31 | −11.56 |
| FL_1623 | Training | 9.95 | 9.61 | 8.97 | −11.37 |
| FL_1624 | Validation | 10.55 | 9.06 | 8.43 | −11.61 |
| FL_1625 | Validation | 10.00 | 8.89 | 8.23 | −11.22 |
| FL_1626 | Validation | 11.05 | 8.62 | 8.10 | −11.62 |
| FL_1628 | Validation | 10.08 | 9.81 | 8.66 | −12.57 |
| FL_1637 | Validation | 9.77 | 9.95 | 9.59 | −10.76 |
| FL_1638 | Validation | 10.25 | 9.20 | 9.07 | −10.41 |
| FL_1639 | Training | 10.29 | 9.52 | 8.99 | −11.35 |
| FL_1643 | Training | 9.80 | 9.72 | 9.00 | −11.46 |
| FL_1644 | Validation | 9.51 | 9.46 | 8.61 | −11.43 |
| FL_1645 | Training | 9.39 | 9.46 | 8.70 | −11.15 |
| FL_1646 | Training | 9.90 | 9.25 | 8.52 | −11.42 |
| FL_1647 | Training | 9.51 | 9.12 | 8.95 | −9.92 |
| FL_1648 | Training | 10.02 | 9.18 | 7.86 | −12.67 |
| FL_1652 | Training | 9.62 | 9.39 | 9.19 | −10.16 |
| FL_1654 | Validation | 10.32 | 8.59 | 8.10 | −11.02 |
| FL_1655 | Training | 10.12 | 9.53 | 8.75 | −11.74 |
| FL_1656 | Validation | 10.54 | 9.08 | 8.55 | −11.42 |
| FL_1657 | Training | 10.53 | 9.53 | 8.55 | −12.46 |
| FL_1660 | Training | 10.24 | 8.75 | 8.27 | −10.99 |
| FL_1661 | Validation | 10.08 | 9.85 | 9.00 | −11.97 |
| FL_1662 | Validation | 9.85 | 9.56 | 9.49 | −10.11 |
| FL_1664 | Validation | 10.16 | 9.35 | 8.48 | −11.92 |
| FL_1669 | Training | 9.48 | 8.76 | 8.28 | −10.45 |
| FL_1670 | Training | 9.76 | 9.66 | 9.66 | −9.92 |
| FL_1675 | Training | 10.57 | 9.28 | 8.41 | −12.18 |
| FL_1681 | Validation | 10.48 | 9.52 | 8.66 | −12.19 |
| FL_1683 | Training | 9.88 | 9.92 | 9.07 | −11.83 |
| FL_1684 | Training | 9.64 | 9.53 | 8.85 | −11.20 |
| FL_1716 | Validation | 9.90 | 8.91 | 8.22 | −11.23 |
| FL_1717 | Validation | 9.87 | 9.34 | 8.95 | −10.71 |
| FL_1718 | Training | 10.00 | 9.21 | 7.98 | −12.49 |
| FL_1719 | Validation | 9.87 | 9.06 | 8.42 | −11.14 |
| FL_1720 | Training | 10.70 | 8.77 | 8.92 | −10.05 |
| FL_1729 | Training | 10.50 | 9.23 | 8.65 | −11.53 |
| FL_1732 | Validation | 9.91 | 7.68 | 8.54 | −7.69 |
| FL_1761 | Validation | 9.81 | 9.22 | 8.39 | −11.54 |
| FL_1764 | Training | 9.81 | 9.24 | 8.77 | −10.80 |
| FL_1768 | Training | 10.12 | 9.36 | 8.50 | −11.86 |
| FL_1771 | Training | 9.92 | 9.12 | 8.68 | −10.79 |
| FL_1772 | Validation | 9.72 | 9.42 | 8.43 | −11.87 |

TABLE 2365-continued

| Sample ID # | Set | B cell differentiation signature value | T-cell signature value | Macrophage signature value | Survival predictor score |
|---|---|---|---|---|---|
| FL_1788 | Training | 9.65 | 9.05 | 9.12 | -9.51 |
| FL_1790 | Training | 9.58 | 9.83 | 9.48 | -10.56 |
| FL_1792 | Validation | 9.79 | 9.29 | 8.67 | -11.11 |
| FL_1795 | Training | 9.58 | 10.18 | 9.33 | -11.69 |
| FL_1797 | Validation | 9.93 | 9.26 | 8.79 | -10.90 |
| FL_1799 | Training | 10.49 | 9.28 | 8.64 | -11.65 |
| FL_1810 | Validation | 10.06 | 8.55 | 8.21 | -10.52 |
| FL_1811 | Validation | 9.84 | 9.37 | 8.08 | -12.56 |
| FL_1825 | Training | 10.49 | 9.44 | 9.03 | -11.24 |
| FL_1827 | Training | 10.06 | 9.76 | 8.84 | -12.08 |
| FL_1828 | Validation | 10.55 | 8.93 | 7.67 | -12.87 |
| FL_1829 | Validation | 9.85 | 9.58 | 8.65 | -11.87 |
| FL_1830 | Validation | 10.80 | 8.99 | 8.67 | -11.15 |
| FL_1833 | Training | 10.41 | 9.83 | 8.82 | -12.52 |
| FL_1834 | Validation | 10.81 | 9.25 | 8.63 | -11.85 |
| FL_1835 | Validation | 9.36 | 9.25 | 8.91 | -10.21 |
| FL_1836 | Validation | 10.58 | 9.58 | 8.61 | -12.50 |
| FL_1837 | Validation | 10.22 | 9.47 | 8.76 | -11.68 |
| FL_1838 | Validation | 10.51 | 9.89 | 9.19 | -11.98 |
| FL_1839 | Training | 10.79 | 8.54 | 8.19 | -11.09 |
| FL_1841 | Training | 10.32 | 9.31 | 9.18 | -10.48 |
| FL_1842 | Validation | 10.36 | 9.69 | 8.92 | -11.95 |
| FL_1844 | Validation | 10.92 | 9.43 | 8.49 | -12.65 |
| FL_1845 | Training | 9.87 | 9.87 | 9.06 | -11.73 |
| FL_1846 | Validation | 9.66 | 9.81 | 9.93 | -9.63 |
| FL_1848 | Training | 9.82 | 9.74 | 8.70 | -12.14 |
| FL_1851 | Training | 9.89 | 9.47 | 9.03 | -10.87 |
| FL_1853 | Validation | 9.96 | 9.28 | 8.54 | -11.49 |
| FL_1854 | Validation | 9.97 | 9.29 | 8.73 | -11.12 |
| FL_1855 | Validation | 9.95 | 9.33 | 8.42 | -11.85 |
| FL_1857 | Validation | 10.35 | 9.81 | 9.28 | -11.50 |
| FL_1861 | Validation | 9.73 | 9.46 | 8.43 | -11.96 |
| FL_1862 | Validation | 10.42 | 8.94 | 8.22 | -11.69 |
| FL_1863 | Validation | 10.79 | 9.29 | 8.82 | -11.54 |
| FL_1864 | Training | 9.67 | 9.97 | 9.07 | -11.80 |
| FL_1866 | Training | 10.19 | 9.88 | 8.89 | -12.33 |
| FL_1870 | Validation | 9.78 | 10.07 | 9.30 | -11.63 |
| FL_1873 | Training | 10.09 | 9.41 | 8.77 | -11.40 |
| FL_1874 | Validation | 10.05 | 9.33 | 8.69 | -11.37 |
| FL_1876 | Validation | 10.15 | 9.59 | 8.67 | -12.08 |
| FL_1879 | Training | 9.73 | 9.21 | 8.58 | -11.06 |
| FL_1880 | Validation | 10.02 | 8.79 | 8.35 | -10.77 |
| FL_1882 | Training | 9.59 | 9.44 | 8.80 | -11.05 |
| FL_1884 | Validation | 9.76 | 9.51 | 9.26 | -10.38 |
| FL_1885 | Validation | 10.48 | 9.66 | 8.75 | -12.32 |
| FL_1887 | Training | 9.98 | 9.42 | 8.47 | -11.96 |
| FL_1888 | Training | 9.73 | 9.83 | 8.99 | -11.67 |
| FL_1890 | Training | 10.06 | 9.33 | 8.98 | -10.76 |
| FL_1894 | Training | 9.85 | 8.99 | 8.75 | -10.29 |
| FL_1896 | Training | 10.21 | 9.80 | 8.51 | -12.94 |
| FL_1897 | Training | 10.67 | 8.99 | 8.26 | -11.90 |
| FL_1898 | Training | 9.59 | 8.77 | 8.21 | -10.68 |
| FL_1900 | Validation | 10.12 | 9.10 | 8.10 | -12.08 |
| FL_1903 | Validation | 11.08 | 8.99 | 8.39 | -11.93 |
| FL_1904 | Validation | 10.20 | 9.16 | 8.30 | -11.87 |
| FL_1905 | Validation | 9.73 | 9.21 | 8.22 | -11.80 |
| FL_1906 | Training | 9.95 | 8.15 | 8.44 | -9.01 |
| FL_1907 | Validation | 10.12 | 7.95 | 7.99 | -9.62 |
| FL_1910 | Training | 11.03 | 9.38 | 8.74 | -12.10 |
| FL_1912 | Validation | 9.83 | 9.38 | 9.36 | -9.95 |
| FL_1913 | Training | 9.81 | 9.75 | 8.43 | -12.69 |
| FL_1916 | Validation | 9.83 | 9.18 | 8.40 | -11.43 |
| FL_1918 | Validation | 9.86 | 9.52 | 8.79 | -11.45 |
| FL_1919 | Training | 9.87 | 9.53 | 8.79 | -11.48 |
| FL_735 | Validation | 10.48 | 8.73 | 8.23 | -11.20 |
| FL_738 | Validation | 11.05 | 9.10 | 8.75 | -11.43 |
| FL_739 | Training | 9.66 | 9.25 | 8.74 | -10.78 |
| FL_878 | Validation | 10.61 | 8.92 | 8.65 | -10.89 |
| FL_879 | Training | 9.92 | 8.94 | 8.78 | -10.14 |
| FL_886 | Validation | 10.16 | 9.41 | 8.63 | -11.73 |
| FL_888 | Validation | 9.35 | 8.76 | 8.38 | -10.15 |
| FL_1627 | Training | 9.82 | 9.48 | 8.49 | -11.94 |
| FL_1429 | Training | 10.06 | 8.70 | 8.14 | -11.01 |
| FL_1850 | Validation | 9.58 | 9.73 | 8.70 | -11.93 |
| FL_1735 | Validation | 9.60 | 7.46 | 8.42 | -7.19 |

Figure 8:
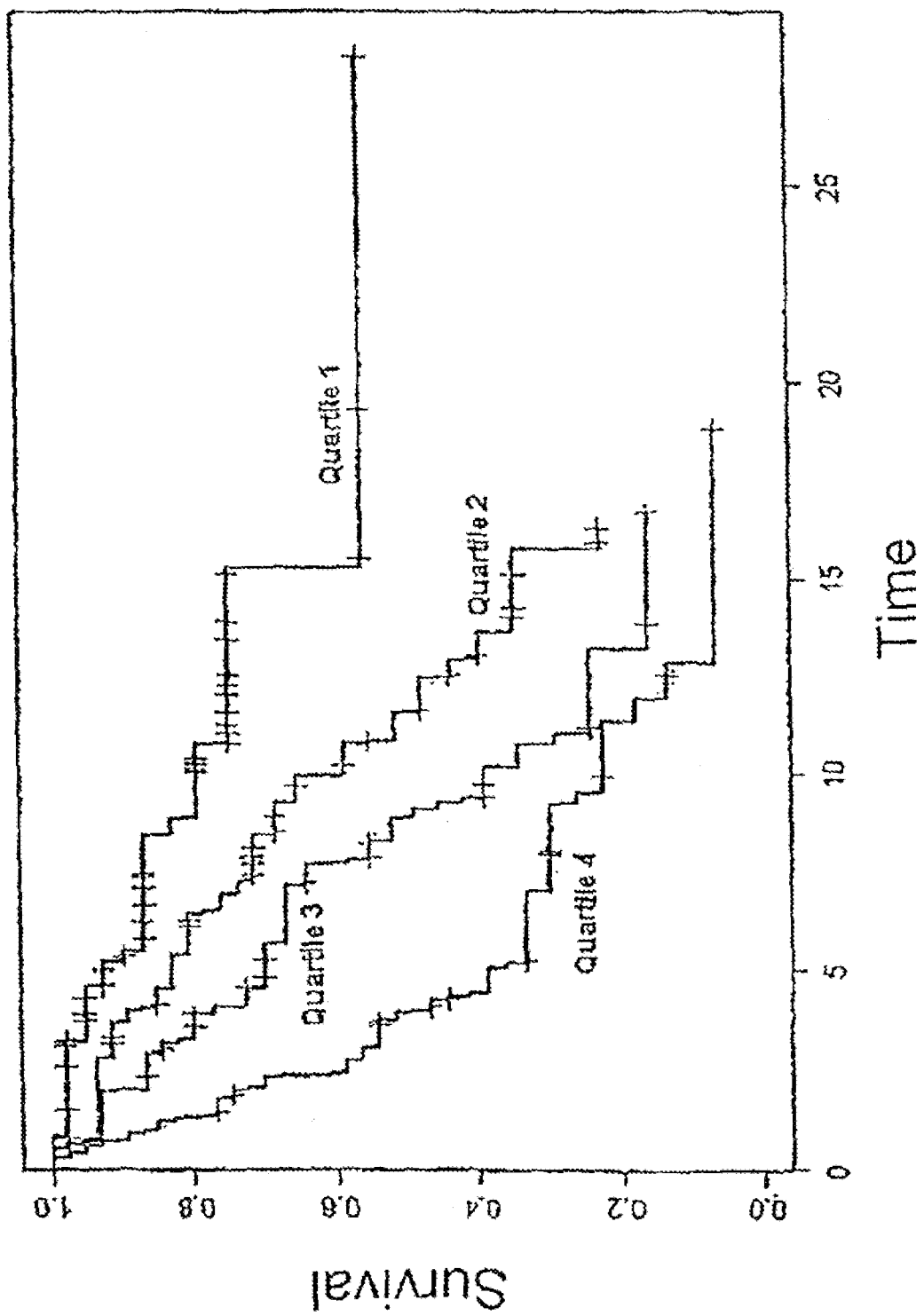
FIG. 8: Kaplan-Meier plot of survival in FL samples based on survival predictor scores. 191 FL samples were divided into quartiles based on their survival predictor scores. The survival predictor scores were calculated by: [2.053*(macrophage gene expression signature value)]−[2.344*(T-cell gene expression signature value)]−[0.729*(B-cell differentiation gene expression signature value)].

In order to visualize the predictive power of the model, the FL samples were ranked according to their survival predictor scores and divided into four quartiles. Kaplan-Meier plots of overall survival showed clear differences in survival rate in the validation set (FIG. 8). The median survival for each of the four quartiles is set forth in Table 2366.

TABLE 2366

| Quartile | Median survival (yrs.) | 5-year survival | 10-year survival |
|---|---|---|---|
| 1 | NR | 94% | 79% |
| 2 | 11.6 | 82% | 62% |
| 3 | 8.8 | 69% | 39% |
| 4 | 3.9 | 38% | 22% |

Example 5

Development of a Third FL Survival Predictor Using Gene Expression Data from the Lymph Dx Microarray 191 FL samples were divided into two equivalent groups: a training set for developing the survival prediction model, and a validation set for evaluating the reproducibility of the model. Gene expression data from the Lymph Dx microarray was obtained for those genes listed in Table 2364, above. This gene expression data was used to calculate gene expression signature values for the macrophage, T-cell, and B-cell differentiation gene expression signatures, and these signature values were used to generate a survival predictor score using the following equation:

Survival predictor score=[1.51*(macrophage gene expression signature value)]−[2.11*(T-cell gene expression signature value)]−[0.505*(B-cell differentiation gene expression signature value)].

A higher survival predictor score was associated with worse outcome. For the 187 FL samples with available clinical data, the survival predictor score had a mean of −10.1 and a standard deviation of 0.69, with each unit increase in the predictor score corresponding to a 2.7 fold increase in the relative risk of death. Data for all 191 samples is shown in Table 2367.

TABLE 2367

| Sample ID # | Set | B cell differentiation signature value | T-cell signature value | Macrophage signature value | Survival predictor score |
|---|---|---|---|---|---|
| FL_1073 | Training | 8.26 | 8.17 | 7.36 | -10.30 |
| FL_1074 | Training | 9.53 | 8.12 | 7.56 | -10.53 |
| FL_1075 | Validation | 9.81 | 8.00 | 7.99 | -9.77 |
| FL_1076 | Training | 8.46 | 8.10 | 7.62 | -9.86 |
| FL_1077 | Training | 8.45 | 8.66 | 7.32 | -11.49 |

TABLE 2367-continued

| Sample ID # | Set | B cell differentiation signature value | T-cell signature value | Macrophage signature value | Survival predictor score |
|---|---|---|---|---|---|
| FL_1078 | Training | 9.23 | 8.32 | 7.32 | −11.18 |
| FL_1080 | Training | 9.18 | 8.37 | 7.86 | −10.42 |
| FL_1081 | Validation | 8.96 | 8.01 | 6.94 | −10.96 |
| FL_1083 | Training | 8.72 | 8.65 | 7.89 | −10.75 |
| FL_1085 | Validation | 8.34 | 8.17 | 7.54 | −10.07 |
| FL_1086 | Validation | 8.50 | 8.35 | 7.94 | −9.94 |
| FL_1087 | Training | 8.02 | 8.88 | 8.48 | −10.00 |
| FL_1088 | Validation | 9.10 | 8.15 | 7.38 | −10.65 |
| FL_1089 | Training | 8.76 | 8.31 | 7.35 | −10.86 |
| FL_1090 | Validation | 8.18 | 8.23 | 7.43 | −10.28 |
| FL_1097 | Validation | 8.07 | 8.81 | 7.90 | −10.73 |
| FL_1098 | Validation | 9.53 | 8.30 | 8.09 | −10.11 |
| FL_1099 | Training | 8.44 | 8.56 | 8.26 | −9.86 |
| FL_1102 | Validation | 7.92 | 8.43 | 7.94 | −9.80 |
| FL_1104 | Training | 9.17 | 8.07 | 7.21 | −10.78 |
| FL_1106 | Validation | 9.71 | 8.15 | 8.77 | −8.85 |
| FL_1107 | Training | 8.16 | 8.44 | 8.60 | −8.95 |
| FL_1183 | Training | 8.49 | 8.15 | 7.23 | −10.56 |
| FL_1184 | Training | 8.81 | 8.49 | 7.91 | −10.43 |
| FL_1185 | Validation | 9.31 | 8.19 | 8.06 | −9.80 |
| FL_1186 | Training | 8.43 | 7.87 | 7.83 | −9.04 |
| FL_1416 | Validation | 8.42 | 8.34 | 7.63 | −10.34 |
| FL_1417 | Training | 8.65 | 7.51 | 7.05 | −9.58 |
| FL_1418 | Validation | 7.96 | 7.82 | 7.22 | −9.62 |
| FL_1419 | Training | 8.80 | 8.71 | 7.55 | −11.43 |
| FL_1422 | Training | 8.63 | 8.35 | 7.39 | −10.83 |
| FL_1425 | Validation | 8.21 | 7.92 | 7.62 | −9.36 |
| FL_1426 | Training | 9.39 | 8.09 | 7.15 | −11.01 |
| FL_1427 | Training | 8.66 | 7.51 | 7.00 | −9.65 |
| FL_1428 | Validation | 9.33 | 8.18 | 7.39 | −10.81 |
| FL_1432 | Training | 8.98 | 8.17 | 7.93 | −9.81 |
| FL_1436 | Training | 8.04 | 8.17 | 7.35 | −10.20 |
| FL_1440 | Training | 8.29 | 7.82 | 7.15 | −9.89 |
| FL_1445 | Training | 8.04 | 7.78 | 7.63 | −8.94 |
| FL_1450 | Validation | 8.25 | 8.81 | 9.52 | −8.39 |
| FL_1472 | Validation | 9.29 | 7.88 | 7.33 | −10.26 |
| FL_1473 | Training | 8.49 | 8.57 | 7.52 | −11.03 |
| FL_1474 | Validation | 8.59 | 8.09 | 8.53 | −8.54 |
| FL_1476 | Validation | 8.25 | 8.39 | 7.71 | −10.23 |
| FL_1477 | Training | 7.94 | 8.57 | 7.88 | −10.21 |
| FL_1478 | Training | 8.57 | 8.40 | 7.88 | −10.16 |
| FL_1479 | Training | 9.15 | 7.83 | 7.87 | −9.27 |
| FL_1480 | Training | 8.25 | 8.38 | 7.44 | −10.63 |
| FL_1579 | Training | 8.70 | 7.73 | 7.43 | −9.48 |
| FL_1580 | Training | 8.86 | 8.46 | 7.64 | −10.79 |
| FL_1581 | Training | 8.41 | 7.89 | 8.08 | −8.69 |
| FL_1582 | Validation | 8.20 | 7.42 | 6.99 | −9.24 |
| FL_1583 | Training | 9.34 | 8.34 | 7.94 | −10.32 |
| FL_1584 | Training | 8.50 | 8.33 | 7.75 | −10.17 |
| FL_1585 | Validation | 9.08 | 7.96 | 7.72 | −9.72 |
| FL_1586 | Validation | 8.52 | 8.25 | 7.36 | −10.61 |
| FL_1588 | Training | 7.97 | 8.35 | 7.73 | −9.98 |
| FL_1589 | Training | 8.85 | 8.48 | 7.76 | −10.66 |
| FL_1591 | Training | 8.92 | 8.36 | 7.77 | −10.42 |
| FL_1594 | Validation | 8.54 | 8.22 | 7.74 | −9.96 |
| FL_1595 | Training | 8.05 | 8.82 | 8.68 | −9.57 |
| FL_1598 | Validation | 9.74 | 7.81 | 6.97 | −10.88 |
| FL_1599 | Validation | 9.13 | 8.42 | 7.69 | −10.77 |
| FL_1603 | Training | 7.97 | 8.66 | 8.90 | −8.86 |
| FL_1604 | Training | 8.47 | 8.14 | 7.75 | −9.75 |
| FL_1606 | Validation | 8.34 | 8.32 | 8.11 | −9.51 |
| FL_1607 | Validation | 8.33 | 8.30 | 7.39 | −10.57 |
| FL_1608 | Validation | 8.35 | 7.88 | 6.98 | −10.31 |
| FL_1610 | Validation | 8.48 | 8.35 | 8.86 | −8.52 |
| FL_1611 | Validation | 8.54 | 8.33 | 7.64 | −10.37 |
| FL_1616 | Training | 8.03 | 8.39 | 7.67 | −10.18 |
| FL_1617 | Validation | 8.30 | 7.85 | 7.52 | −9.40 |
| FL_1619 | Validation | 8.53 | 8.31 | 7.64 | −10.32 |
| FL_1620 | Validation | 8.09 | 7.99 | 7.17 | −10.11 |
| FL_1622 | Training | 8.14 | 8.10 | 7.36 | −10.09 |
| FL_1623 | Training | 8.45 | 8.52 | 8.15 | −9.93 |
| FL_1624 | Validation | 9.13 | 8.12 | 7.46 | −10.49 |
| FL_1625 | Validation | 8.53 | 7.94 | 7.17 | −10.23 |
| FL_1626 | Validation | 9.63 | 7.67 | 7.17 | −10.22 |
| FL_1628 | Validation | 8.63 | 8.76 | 7.95 | −10.86 |
| FL_1637 | Validation | 8.07 | 8.81 | 8.79 | −9.38 |
| FL_1638 | Validation | 8.52 | 8.18 | 8.19 | −9.18 |
| FL_1639 | Training | 8.70 | 8.33 | 7.89 | −10.06 |
| FL_1643 | Training | 8.26 | 8.62 | 8.01 | −10.26 |
| FL_1644 | Validation | 8.28 | 8.33 | 7.77 | −10.02 |
| FL_1645 | Training | 7.84 | 8.32 | 7.68 | −9.91 |
| FL_1646 | Training | 8.40 | 8.26 | 7.71 | −10.01 |
| FL_1647 | Training | 8.10 | 8.04 | 7.92 | −9.10 |
| FL_1648 | Training | 8.33 | 8.08 | 6.87 | −10.90 |
| FL_1652 | Training | 8.15 | 8.33 | 8.37 | −9.07 |
| FL_1654 | Validation | 8.67 | 7.62 | 7.03 | −9.85 |
| FL_1655 | Training | 8.53 | 8.41 | 7.75 | −10.36 |
| FL_1656 | Validation | 9.09 | 8.09 | 7.62 | −10.16 |
| FL_1657 | Training | 8.95 | 8.44 | 7.58 | −10.89 |
| FL_1660 | Training | 8.82 | 7.79 | 7.26 | −9.93 |
| FL_1661 | Validation | 8.56 | 8.79 | 8.17 | −10.53 |
| FL_1662 | Validation | 8.30 | 8.47 | 8.69 | −8.93 |
| FL_1664 | Validation | 8.62 | 8.23 | 7.56 | −10.31 |
| FL_1669 | Training | 7.89 | 7.67 | 7.39 | −9.02 |
| FL_1670 | Training | 8.01 | 8.54 | 8.64 | −9.03 |
| FL_1675 | Training | 9.00 | 8.21 | 7.36 | −10.76 |
| FL_1681 | Validation | 8.83 | 8.39 | 7.59 | −10.72 |
| FL_1683 | Validation | 8.14 | 8.85 | 7.97 | −10.74 |
| FL_1684 | Training | 7.99 | 8.42 | 7.84 | −9.97 |
| FL_1716 | Validation | 8.28 | 7.90 | 7.26 | −9.88 |
| FL_1717 | Validation | 8.27 | 8.21 | 7.89 | −9.60 |
| FL_1718 | Training | 8.50 | 8.17 | 7.15 | −10.75 |
| FL_1719 | Validation | 8.35 | 8.02 | 7.21 | −10.26 |
| FL_1720 | Training | 9.03 | 7.65 | 8.01 | −8.61 |
| FL_1729 | Training | 8.97 | 8.27 | 7.69 | −10.37 |
| FL_1732 | Validation | 8.49 | 6.82 | 7.71 | −7.02 |
| FL_1761 | Validation | 8.36 | 8.19 | 7.29 | −10.49 |
| FL_1764 | Training | 8.52 | 8.24 | 7.94 | −9.69 |
| FL_1768 | Training | 8.70 | 8.25 | 7.63 | −10.28 |
| FL_1771 | Training | 8.55 | 8.19 | 7.65 | −10.04 |
| FL_1772 | Validation | 8.30 | 8.38 | 7.41 | −10.71 |
| FL_1788 | Training | 8.14 | 8.06 | 8.11 | −8.87 |
| FL_1790 | Training | 7.95 | 8.69 | 8.36 | −9.74 |
| FL_1792 | Validation | 8.16 | 8.20 | 7.64 | −9.88 |
| FL_1795 | Training | 7.94 | 9.08 | 8.37 | −10.54 |
| FL_1797 | Validation | 8.17 | 8.21 | 7.87 | −9.57 |
| FL_1799 | Training | 9.02 | 8.21 | 7.77 | −10.14 |
| FL_1810 | Validation | 8.43 | 7.52 | 7.06 | −9.47 |
| FL_1811 | Validation | 8.33 | 8.24 | 7.07 | −10.93 |
| FL_1825 | Training | 8.90 | 8.39 | 7.97 | −10.18 |
| FL_1827 | Training | 8.47 | 8.77 | 7.96 | −10.76 |
| FL_1828 | Validation | 9.13 | 7.87 | 6.76 | −11.01 |
| FL_1829 | Validation | 8.34 | 8.51 | 7.59 | −10.71 |
| FL_1830 | Validation | 9.26 | 8.04 | 7.62 | −10.13 |
| FL_1833 | Training | 8.82 | 8.86 | 7.88 | −11.26 |
| FL_1834 | Validation | 9.25 | 8.17 | 7.62 | −10.39 |
| FL_1835 | Validation | 7.71 | 8.16 | 8.01 | −9.02 |
| FL_1836 | Validation | 9.06 | 8.52 | 7.59 | −11.09 |
| FL_1837 | Validation | 8.57 | 8.33 | 7.37 | −10.79 |
| FL_1838 | Validation | 8.78 | 8.72 | 8.04 | −10.69 |
| FL_1839 | Training | 9.27 | 7.36 | 7.37 | −9.08 |
| FL_1841 | Training | 8.66 | 8.35 | 8.17 | −9.64 |
| FL_1842 | Validation | 8.62 | 8.50 | 8.02 | −10.19 |
| FL_1844 | Validation | 9.37 | 8.40 | 7.47 | −11.18 |
| FL_1845 | Validation | 8.33 | 8.84 | 8.30 | −10.32 |
| FL_1846 | Validation | 8.11 | 8.75 | 9.06 | −8.89 |
| FL_1848 | Training | 8.19 | 8.60 | 7.91 | −10.33 |
| FL_1851 | Training | 8.37 | 8.50 | 8.15 | −9.84 |
| FL_1853 | Validation | 8.37 | 8.14 | 7.43 | −10.19 |
| FL_1854 | Validation | 8.50 | 8.29 | 7.96 | −9.78 |
| FL_1855 | Validation | 8.63 | 8.34 | 7.54 | −10.58 |
| FL_1857 | Validation | 8.73 | 8.82 | 8.45 | −10.26 |
| FL_1861 | Validation | 8.21 | 8.50 | 7.50 | −10.77 |
| FL_1862 | Validation | 8.98 | 7.96 | 7.31 | −10.28 |
| FL_1863 | Validation | 9.30 | 8.22 | 7.86 | −10.18 |
| FL_1864 | Training | 8.13 | 8.93 | 8.27 | −10.46 |
| FL_1866 | Training | 8.62 | 8.78 | 7.91 | −10.93 |
| FL_1870 | Validation | 8.16 | 8.97 | 8.52 | −10.18 |

TABLE 2367-continued

| Sample ID # | Set | B cell differentiation signature value | T-cell signature value | Macrophage signature value | Survival predictor score |
|---|---|---|---|---|---|
| FL_1873 | Training | 8.55 | 8.30 | 8.00 | −9.74 |
| FL_1874 | Validation | 8.43 | 8.20 | 7.59 | −10.10 |
| FL_1876 | Validation | 8.48 | 8.52 | 7.70 | −10.64 |
| FL_1879 | Training | 8.29 | 8.21 | 7.66 | −9.94 |
| FL_1880 | Validation | 8.56 | 7.76 | 7.34 | −9.61 |
| FL_1882 | Training | 8.02 | 8.40 | 7.71 | −10.14 |
| FL_1884 | Validation | 8.14 | 8.46 | 8.42 | −9.24 |
| FL_1885 | Validation | 8.88 | 8.57 | 7.78 | −10.81 |
| FL_1887 | Training | 8.38 | 8.39 | 7.38 | −10.78 |
| FL_1888 | Training | 8.14 | 8.74 | 8.07 | −10.37 |
| FL_1890 | Training | 8.45 | 8.24 | 8.11 | −9.41 |
| FL_1894 | Training | 8.38 | 7.97 | 7.82 | −9.25 |
| FL_1896 | Training | 8.63 | 8.71 | 7.52 | −11.37 |
| FL_1897 | Training | 9.01 | 7.91 | 6.93 | −10.78 |
| FL_1898 | Training | 8.08 | 7.75 | 7.09 | −9.74 |
| FL_1900 | Validation | 8.61 | 7.94 | 6.84 | −10.77 |
| FL_1903 | Validation | 9.63 | 7.96 | 7.30 | −10.64 |
| FL_1904 | Validation | 8.79 | 8.14 | 7.15 | −10.82 |
| FL_1905 | Validation | 8.22 | 8.24 | 7.36 | −10.43 |
| FL_1906 | Training | 8.40 | 7.40 | 7.24 | −8.93 |
| FL_1907 | Validation | 8.61 | 7.11 | 6.59 | −9.40 |
| FL_1910 | Training | 9.47 | 8.28 | 7.63 | −10.73 |
| FL_1912 | Validation | 8.32 | 8.45 | 8.52 | −9.18 |
| FL_1913 | Training | 8.24 | 8.60 | 7.23 | −11.41 |
| FL_1916 | Validation | 8.31 | 8.04 | 7.27 | −10.19 |
| FL_1918 | Validation | 8.30 | 8.49 | 7.78 | −10.37 |
| FL_1919 | Training | 8.05 | 8.42 | 8.00 | −9.75 |
| FL_735 | Validation | 9.03 | 7.83 | 7.41 | −9.88 |
| FL_738 | Validation | 9.54 | 8.07 | 7.65 | −10.30 |
| FL_739 | Training | 8.14 | 8.09 | 7.69 | −9.57 |
| FL_878 | Validation | 9.17 | 7.91 | 7.70 | −9.69 |
| FL_879 | Training | 8.37 | 7.96 | 7.67 | −9.45 |
| FL_886 | Validation | 8.59 | 8.38 | 7.67 | −10.44 |
| FL_888 | Validation | 7.85 | 7.71 | 7.07 | −9.56 |
| FL_1627 | Training | 8.26 | 8.17 | 7.36 | −10.30 |
| FL_1429 | Training | 9.53 | 8.12 | 7.56 | −10.53 |
| FL_1850 | Validation | 9.81 | 8.00 | 7.99 | −9.77 |
| FL_1735 | Validation | 8.46 | 8.10 | 7.62 | −9.86 |

Figure 9:
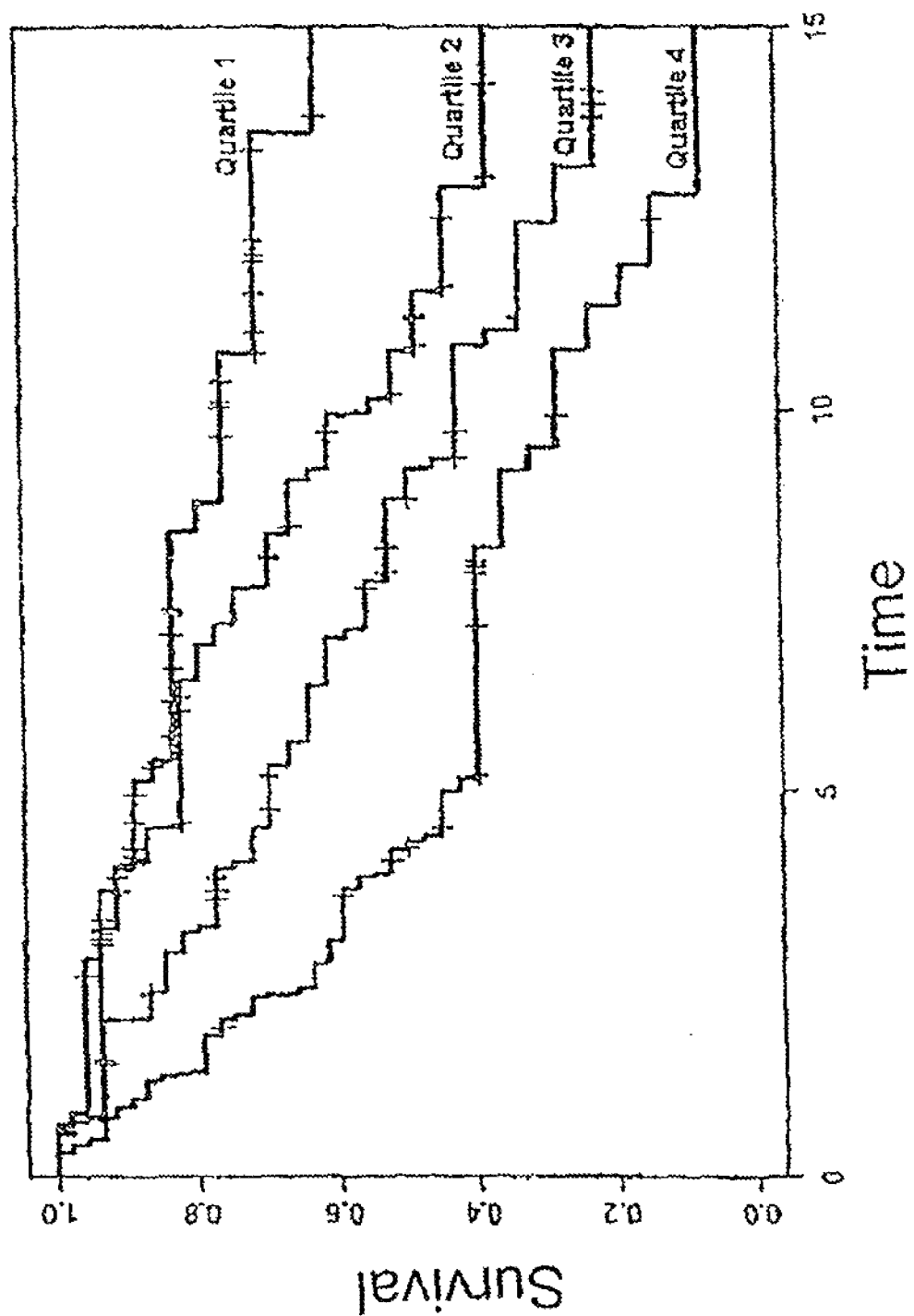
FIG. 9: Kaplan-Meier plot of survival in FL samples based on survival predictor scores. 191 FL samples were divided into quartiles based on their survival predictor scores. The survival predictor scores were calculated by: [1.51*(macrophage gene expression signature value)]−[2.11*(T-cell gene expression signature value)]−[0.505*(B-cell differentiation gene expression signature value)].

In order to visualize the predictive power of the model, the FL samples were ranked according to their survival predictor scores and divided into four quartiles. Kaplan-Meier plots of overall survival showed clear differences in survival rate in the validation set (FIG. 9).

Example 6

Development of a First DLBCL Survival Predictor Using Gene Expression Data from Affymetrix U133A and U133B Microarrays Gene expression data from Affymetrix U133A and U133B microarrays was obtained for 231 DLBCL samples. The follow-up time and status at follow-up for each of the subjects from whom these samples were acquired is listed in Table 2368. Table 2368 also indicates which samples were used in creating the survival predictor.

TABLE 2368

| Sample ID # | Length of follow-up (years) | Status at follow-up | Used in creating survival predictor? |
|---|---|---|---|
| ABC_1000 | 0.69 | Dead | Yes |
| ABC_1002 | 0.28 | Dead | Yes |
| ABC_1023 | 5.57 | Dead | Yes |
| ABC_1027 | 0.25 | Dead | Yes |
| ABC_1031 | 6.64 | Dead | Yes |
| ABC_1034 | 2.31 | Dead | Yes |
| ABC_1038 | 0.71 | Dead | Yes |
| ABC_1043 | 2.31 | Dead | Yes |
| ABC_1045 | 2.26 | Dead | Yes |
| ABC_1055 | 7.81 | Alive | Yes |
| ABC_1057 | 2.13 | Dead | Yes |
| ABC_1059 | 2.00 | Dead | Yes |
| ABC_1061 | 1.04 | Dead | Yes |
| ABC_1946 | 0.68 | Dead | No |
| ABC_1994 | 1.21 | Dead | No |
| ABC_2001 | 1.32 | Dead | No |
| ABC_304 | 1.31 | Dead | Yes |
| ABC_305 | 0.82 | Alive | Yes |
| ABC_309 | 2.80 | Alive | Yes |
| ABC_413 | 0.60 | Dead | Yes |
| ABC_428 | 11.38 | Alive | Yes |
| ABC_432 | 0.38 | Dead | Yes |
| ABC_446 | 2.82 | Dead | Yes |
| ABC_462 | 7.49 | Dead | Yes |
| ABC_477 | 1.70 | Dead | Yes |
| ABC_481 | 10.75 | Alive | Yes |
| ABC_482 | 7.72 | Alive | Yes |
| ABC_538 | 0.34 | Dead | Yes |
| ABC_541 | 4.11 | Alive | Yes |
| ABC_544 | 1.31 | Dead | Yes |
| ABC_547 | 0.05 | Dead | Yes |
| ABC_577 | 1.65 | Alive | Yes |
| ABC_616 | 0.99 | Dead | Yes |
| ABC_626 | 2.49 | Dead | Yes |
| ABC_633 | 2.02 | Alive | Yes |
| ABC_642 | 0.34 | Dead | Yes |
| ABC_644 | 0.31 | Dead | Yes |
| ABC_645 | 6.08 | Dead | Yes |
| ABC_646 | 2.59 | Dead | Yes |
| ABC_651 | 2.34 | Alive | Yes |
| ABC_652 | 0.01 | Dead | Yes |
| ABC_660 | 0.20 | Dead | Yes |
| ABC_663 | 0.62 | Dead | Yes |
| ABC_668 | 6.44 | Alive | Yes |
| ABC_676 | 1.00 | Dead | Yes |
| ABC_678 | 0.06 | Dead | Yes |
| ABC_687 | 0.94 | Dead | Yes |
| ABC_689 | 2.54 | Dead | Yes |
| ABC_692 | 10.53 | Alive | Yes |
| ABC_694 | 4.83 | Alive | Yes |
| ABC_700 | 5.40 | Dead | Yes |
| ABC_702 | 4.13 | Dead | Yes |
| ABC_704 | 9.67 | Alive | Yes |
| ABC_709 | 0.47 | Dead | Yes |
| ABC_712 | 3.26 | Dead | Yes |
| ABC_714 | 2.45 | Dead | Yes |
| ABC_717 | 0.42 | Dead | Yes |
| ABC_725 | 0.96 | Dead | Yes |
| ABC_726 | 7.62 | Alive | Yes |
| ABC_730 | 1.03 | Dead | Yes |
| ABC_753 | 0.04 | Dead | Yes |
| ABC_756 | 7.21 | Alive | Yes |
| ABC_771 | 6.80 | Dead | Yes |
| ABC_779 | 0.35 | Dead | Yes |
| ABC_800 | 0.33 | Dead | Yes |
| ABC_807 | 0.31 | Dead | Yes |
| ABC_809 | 0.51 | Dead | Yes |
| ABC_816 | 1.86 | Dead | Yes |
| ABC_820 | 1.59 | Dead | Yes |
| ABC_823 | 0.16 | Dead | Yes |
| ABC_835 | 1.22 | Dead | Yes |
| ABC_839 | 0.29 | Dead | Yes |
| ABC_841 | 10.14 | Alive | Yes |
| ABC_858 | 3.58 | Dead | Yes |
| ABC_872 | 5.00 | Alive | Yes |
| ABC_875 | 8.45 | Alive | Yes |
| ABC_912 | 16.79 | Alive | Yes |
| ABC_996 | 0.21 | Dead | Yes |
| GCB_1005 | 5.77 | Alive | Yes |
| GCB_1008 | 6.46 | Alive | Yes |

TABLE 2368-continued

| Sample ID # | Length of follow-up (years) | Status at follow-up | Used in creating survival predictor? |
|---|---|---|---|
| GCB_1009 | 9.68 | Alive | Yes |
| GCB_1021 | 14.59 | Alive | Yes |
| GCB_1025 | 2.86 | Dead | Yes |
| GCB_1026 | 6.94 | Dead | Yes |
| GCB_1037 | 0.23 | Dead | Yes |
| GCB_1039 | 2.05 | Dead | Yes |
| GCB_1049 | 1.33 | Dead | Yes |
| GCB_1051 | 0.12 | Dead | Yes |
| GCB_1058 | 0.42 | Dead | Yes |
| GCB_1060 | 6.45 | Alive | Yes |
| GCB_1990 | 0.06 | Dead | No |
| GCB_1991 | 1.01 | Dead | No |
| GCB_2017 | 0.08 | Dead | No |
| GCB_2018 | 0.17 | Dead | No |
| GCB_2095 | 0.97 | Alive | No |
| GCB_412 | 12.12 | Alive | Yes |
| GCB_415 | 5.38 | Dead | Yes |
| GCB_421 | 1.24 | Dead | Yes |
| GCB_424 | 10.62 | Dead | Yes |
| GCB_433 | 0.76 | Dead | Yes |
| GCB_434 | 10.53 | Alive | Yes |
| GCB_438 | 8.15 | Alive | Yes |
| GCB_459 | 9.65 | Alive | Yes |
| GCB_470 | 11.17 | Alive | Yes |
| GCB_479 | 7.24 | Alive | Yes |
| GCB_492 | 11.29 | Alive | Yes |
| GCB_517 | 3.03 | Dead | Yes |
| GCB_523 | 8.36 | Alive | Yes |
| GCB_524 | 5.88 | Alive | Yes |
| GCB_529 | 1.06 | Dead | Yes |
| GCB_533 | 0.71 | Dead | Yes |
| GCB_537 | 4.99 | Dead | Yes |
| GCB_543 | 3.47 | Alive | Yes |
| GCB_545 | 1.10 | Dead | Yes |
| GCB_549 | 2.68 | Dead | Yes |
| GCB_550 | 21.78 | Alive | Yes |
| GCB_553 | 0.82 | Dead | Yes |
| GCB_565 | 9.11 | Dead | Yes |
| GCB_572 | 14.24 | Alive | Yes |
| GCB_617 | 5.88 | Alive | Yes |
| GCB_618 | 5.65 | Alive | Yes |
| GCB_619 | 8.76 | Alive | Yes |
| GCB_623 | 2.43 | Alive | Yes |
| GCB_627 | 1.27 | Dead | Yes |
| GCB_654 | 7.37 | Alive | Yes |
| GCB_661 | 0.56 | Alive | Yes |
| GCB_669 | 7.11 | Alive | Yes |
| GCB_672 | 6.78 | Alive | Yes |
| GCB_674 | 7.22 | Alive | Yes |
| GCB_675 | 6.02 | Alive | Yes |
| GCB_681 | 9.70 | Alive | Yes |
| GCB_688 | 0.33 | Dead | Yes |
| GCB_695 | 0.15 | Dead | Yes |
| GCB_698 | 3.88 | Alive | Yes |
| GCB_701 | 3.90 | Alive | Yes |
| GCB_710 | 1.08 | Dead | Yes |
| GCB_711 | 3.93 | Dead | Yes |
| GCB_722 | 3.32 | Alive | Yes |
| GCB_724 | 1.40 | Dead | Yes |
| GCB_731 | 10.18 | Alive | Yes |
| GCB_742 | 4.09 | Alive | Yes |
| GCB_744 | 8.86 | Alive | Yes |
| GCB_745 | 1.33 | Dead | Yes |
| GCB_747 | 15.41 | Alive | Yes |
| GCB_749 | 10.40 | Alive | Yes |
| GCB_758 | 1.10 | Dead | Yes |
| GCB_772 | 2.48 | Alive | Yes |
| GCB_777 | 4.27 | Dead | Yes |
| GCB_792 | 5.53 | Alive | Yes |
| GCB_795 | 3.43 | Alive | Yes |
| GCB_797 | 6.87 | Dead | Yes |
| GCB_803 | 1.45 | Dead | Yes |
| GCB_810 | 11.72 | Alive | Yes |
| GCB_817 | 2.76 | Dead | Yes |
| GCB_818 | 0.10 | Dead | Yes |
| GCB_819 | 0.72 | Dead | Yes |
| GCB_821 | 9.47 | Alive | Yes |
| GCB_832 | 4.01 | Alive | Yes |
| GCB_836 | 4.29 | Alive | Yes |
| GCB_840 | 3.40 | Alive | Yes |
| GCB_847 | 4.16 | Alive | Yes |
| GCB_860 | 3.03 | Dead | Yes |
| GCB_871 | 0.41 | Dead | Yes |
| GCB_874 | 0.12 | Dead | Yes |
| GCB_995 | 6.65 | Alive | Yes |
| PMBL_1006 | 7.12 | Alive | Yes |
| PMBL_1024 | 19.83 | Alive | Yes |
| PMBL_1048 | 7.70 | Alive | Yes |
| PMBL_1053 | 1.04 | Dead | Yes |
| PMBL_1920 | 1.97 | Alive | No |
| PMBL_1921 | 4.16 | Alive | No |
| PMBL_1923 | 1.60 | Alive | No |
| PMBL_1924 | 6.11 | Alive | No |
| PMBL_1935 | 12.42 | Alive | No |
| PMBL_1941 | 0.71 | Alive | No |
| PMBL_1942 | 0.88 | Alive | No |
| PMBL_1943 | 8.96 | Alive | No |
| PMBL_1945 | 0.84 | Dead | No |
| PMBL_1948 | 7.96 | Alive | No |
| PMBL_1949 | 4.28 | Alive | No |
| PMBL_1989 | 1.33 | Dead | No |
| PMBL_1992 | 1.00 | Dead | No |
| PMBL_1993 | 1.33 | Dead | No |
| PMBL_2002 | 6.62 | Alive | No |
| PMBL_2019 | 0.99 | Dead | No |
| PMBL_2020 | 2.08 | Alive | No |
| PMBL_2092 | 1.27 | Alive | No |
| PMBL_484 | 1.40 | Dead | Yes |
| PMBL_546 | 0.78 | Dead | Yes |
| PMBL_570 | 14.40 | Alive | Yes |
| PMBL_621 | 8.14 | Alive | Yes |
| PMBL_638 | 0.70 | Dead | Yes |
| PMBL_691 | 0.32 | Dead | Yes |
| PMBL_791 | 1.33 | Dead | Yes |
| PMBL_824 | 12.24 | Alive | Yes |
| PMBL_906 | 16.80 | Alive | Yes |
| PMBL_994 | 4.79 | Alive | Yes |
| PMBL_998 | 9.11 | Alive | Yes |
| UC_DLBCL_1001 | 0.33 | Dead | Yes |
| UC_DLBCL_1004 | 6.72 | Alive | Yes |
| UC_DLBCL_1007 | 2.26 | Dead | Yes |
| UC_DLBCL_1018 | 0.03 | Dead | Yes |
| UC_DLBCL_1041 | 3.13 | Dead | Yes |
| UC_DLBCL_1054 | 12.34 | Alive | Yes |
| UC_DLBCL_306 | 2.69 | Alive | Yes |
| UC_DLBCL_310 | 0.97 | Alive | Yes |
| UC_DLBCL_449 | 9.16 | Alive | Yes |
| UC_DLBCL_452 | 9.17 | Alive | Yes |
| UC_DLBCL_458 | 1.18 | Dead | Yes |
| UC_DLBCL_460 | 9.02 | Alive | Yes |
| UC_DLBCL_491 | 4.47 | Dead | Yes |
| UC_DLBCL_528 | 1.64 | Alive | Yes |
| UC_DLBCL_615 | 4.94 | Alive | Yes |
| UC_DLBCL_625 | 5.24 | Alive | Yes |
| UC_DLBCL_664 | 0.62 | Dead | Yes |
| UC_DLBCL_671 | 3.35 | Alive | Yes |
| UC_DLBCL_682 | 0.11 | Dead | Yes |
| UC_DLBCL_683 | 7.42 | Alive | Yes |
| UC_DLBCL_684 | 1.92 | Dead | Yes |
| UC_DLBCL_748 | 1.01 | Dead | Yes |
| UC_DLBCL_751 | 9.99 | Alive | Yes |
| UC_DLBCL_808 | 0.37 | Dead | Yes |
| UC_DLBCL_831 | 11.02 | Dead | Yes |
| UC_DLBCL_834 | 1.64 | Dead | Yes |
| UC_DLBCL_838 | 0.00 | Dead | Yes |
| UC_DLBCL_851 | 0.05 | Dead | Yes |
| UC_DLBCL_854 | 1.51 | Dead | Yes |
| UC_DLBCL_855 | 1.67 | Alive | Yes |
| UC_DLBCL_856 | 0.60 | Dead | Yes |

The correlation between expression of each gene represented on the microarrays and survival was estimated using a Cox proportional hazards model. The results of this survival analysis are provided in the final two columns of Table 1723. The first of these two columns ("DLBCL_Cox_coefficient") provides a Cox coefficient indicating the extent to which a 2-fold increase in expression of a particular gene affects mortality. A positive Cox coefficient indicates increasing mortality with increasing expression of the gene, while a negative Cox coefficient indicates decreasing mortality with increasing expression of the gene. The second of these two columns ("DLBCL_Cox_P_value") provides a Cox p-value indicating the estimated probability that the increase or decrease in survival associated with the gene would occur by chance if there was no connection between the expression of the gene and survival.

Genes that were significantly correlated with survival (p<0.001) were grouped into gene expression signatures using a hierarchical clustering algorithm. The expression level of every component gene in each of these gene expression signatures was averaged for each sample to create a gene expression signature value. A step-up procedure (Drapner 1966) was applied to determine the optimal number of gene signatures to use in the survival predictor model. First, the gene expression signature that was most significantly associated with survival was included in the model. Next, the gene expression signature with the second highest association with survival was added to the model to form a two-component model. This procedure was repeated until there was no gene expression signature to add to the model with a p-value of <0.05.

The final prediction model incorporated gene expression signature values from three gene expression signatures. The first gene expression signature added to the model was termed "ABC DLBCL high," because it included genes that were more highly expressed in ABC than in GCB (Rosenwald 2002). The second gene expression signature added to the model was termed "lymph node," because it reflected the response of non-tumor cells in the lymph node to the malignant lymphoma cells. The final gene expression signature added to the model was termed "MHC class II," because it included all of the genes encoding the MHC class II alpha and beta chains. Table 2369 shows the genes that were averaged to form each of these signatures.

TABLE 2369

| Signature | UNIQID | Gene symbol | Survival p-value |
|---|---|---|---|
| ABC DLBCL high | 1134271 | POU5F1 | 3.09E−05 |
| ABC DLBCL high | 1121564 | DRIL1 | 4.06E−05 |
| ABC DLBCL high | 1119889 | PDCD4 | 7.28E−05 |
| ABC DLBCL high | 1133300 | CTH | 1.23E−04 |
| ABC DLBCL high | 1106030 | MGC: 50789 | 1.70E−04 |
| ABC DLBCL high | 1139301 | FLJ20150 | 4.49E−04 |
| ABC DLBCL high | 1122131 | CHST7 | 5.18E−04 |
| ABC DLBCL high | 1114824 | LIMD1 | 5.20E−04 |
| ABC DLBCL high | 1100161 | LOC142678 | 6.24E−04 |
| ABC DLBCL high | 1120129 | TLE1 | 6.95E−04 |
| Lymph node | 1097126 | TEM8 | 5.14E−09 |
| Lymph node | 1120880 | LTBP2 | 9.80E−07 |
| Lymph node | 1098898 | FLJ31066 | 1.09E−06 |
| Lymph node | 1123376 | RARRES2 | 1.68E−06 |
| Lymph node | 1128945 | SLC12A8 | 2.90E−06 |
| Lymph node | 1130994 | DPYSL3 | 3.37E−06 |
| Lymph node | 1124429 | SULF1 | 3.53E−06 |
| Lymph node | 1099358 | FLJ39971 | 4.09E−06 |
| Lymph node | 1130509 | SPARC | 6.23E−06 |
| Lymph node | 1095985 | TMEPAI | 7.07E−06 |
| Lymph node | 1123038 | ACTN1 | 7.90E−06 |
| Lymph node | 1133700 | CDH11 | 8.20E−06 |
| Lymph node | 1122101 | TFEC | 9.66E−06 |
| Lymph node | 1124296 | SDC2 | 9.99E−06 |

TABLE 2369-continued

| Signature | UNIQID | Gene symbol | Survival p-value |
|---|---|---|---|
| MHC Class II | 1123127 | HLA-DRA | 1.21E−06 |
| MHC Class II | 1136777 | HLA-DQA1 | 3.45E−06 |
| MHC Class II | 1137771 | HLA-DRB1 | 3.95E−06 |
| MHC Class II | 1134281 | HLA-DRB4 | 2.70E−05 |
| MHC Class II | 1136573 | HLA-DPA1 | 2.92E−05 |
| MHC Class II | 1132710 | HLA-DRB3 | 7.09E−05 |

Fitting the Cox proportional hazards model to the three gene expression signature values resulted in the following model:

Survival predictor score=[0.586*(ABC DLBCL high gene expression signature value)]−[0.468* (lymph node gene expression signature value)]− [0.336*(MHC Class II gene expression signature value)].

Figure 10:
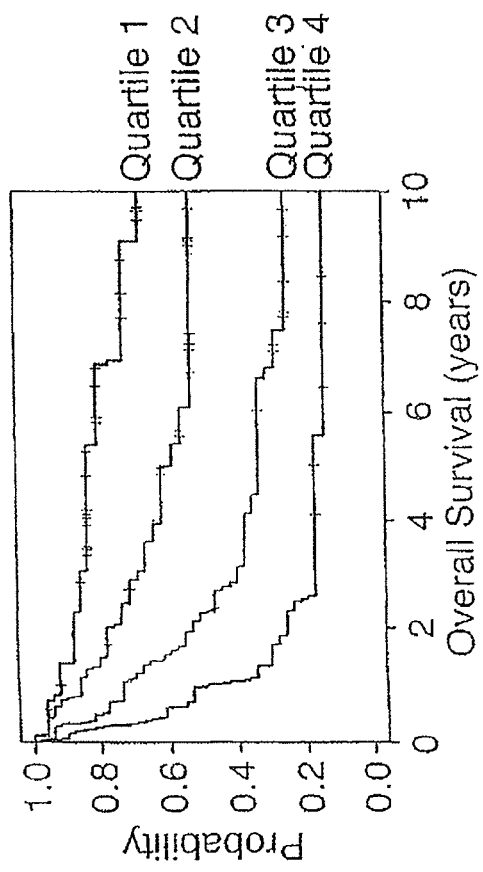
FIG. 10: Kaplan-Meier plot of survival in DLBCL samples based on survival predictor scores. 231 DLBCL samples were divided into quartiles based on their survival predictor scores. The survival predictor scores were calculated by: [0.586*(ABC DLBCL high gene expression signature value)]−[0.468*(lymph node gene expression signature value)]−[(0.336*MHC Class II gene expression signature value)].

A higher survival predictor score was associated with worse outcome. According to a likelihood ratio test adjusted for the number of variables included, this model was significant in predicting survival at p=2.13×10$^{-13}$. In order to visualize the predictive power of the model, the 205 samples used to create the model were ranked according to their survival predictor scores and divided into four quartiles. Kaplan-Meier plots of overall survival probability show clear differences in survival rate between these four quartiles (FIG. 10). The five-year survival probabilities for each quartile are set forth in Table 2370.

TABLE 2370

| Quartile | 5-year survival |
|---|---|
| 1 | 83% |
| 2 | 59% |
| 3 | 33% |
| 4 | 17% |

Example 7

Development of a Second DLBCL Survival Predictor Using Gene Expression Data from the Lymph Dx Microarray A DLBCL survival model based on gene expression had been developed previously using proliferation, germinal center B-cell, lymph node, and MHC class II gene expression signatures and the expression of the single gene BMP-6 (Rosenwald 2002). BMP-6 expression was poorly measured on the Lymph Dx microarray, but genes associated with each of these four gene expression signatures exhibited associations with survival similar to those observed using Lymphochip microarrays. DLBCL samples were divided into two groups: a training set (100 samples) for developing the survival prediction model, and a validation set (100 samples) for evaluating the reproducibility of the model. Gene expressed in the training set samples were clustered, and lymph node, germinal center B-cell, MHC class II, and proliferation gene expression signatures were identified. Within each signature, expression of genes that were associated with survival (p<0.01) was averaged to generate a gene expression signature value for each signature. Table 2371 lists the genes that were used to generate the gene expression signature value for each signature.

TABLE 2371

| Signature | UNIQID | Unigene ID Build 167 | Gene symbol |
|---|---|---|---|
| Germinal center B-cell | 1099686 | 117721 | |
| Germinal center B-cell | 1099711 | 243596 | |
| Germinal center B-cell | 1103390 | 271752 | BPNT1 |
| Germinal center B-cell | 1106025 | 49500 | KIAA0746 |
| Germinal center B-cell | 1128287 | 300063 | ASB13 |
| Germinal center B-cell | 1132520 | 283063 | LMO2 |
| Germinal center B-cell | 1138192 | 126608 | NR3C1 |
| Germinal center B-cell | 1529318 | 291954 | |
| Germinal center B-cell | 1529344 | 317970 | SERPINA11 |
| Germinal center B-cell | 1529352 | 446195 | |
| Germinal center B-cell | 1096570 | 409813 | ANUBL1 |
| Germinal center B-cell | 1097897 | 266175 | PAG |
| Germinal center B-cell | 1097901 | 266175 | PAG |
| Germinal center B-cell | 1098611 | 433611 | PDK1 |
| Germinal center B-cell | 1100581 | 155024 | BCL6 |
| Germinal center B-cell | 1115034 | 387222 | NEK6 |
| Germinal center B-cell | 1120090 | 155024 | BCL6 |
| Germinal center B-cell | 1120946 | 25209 | MAPK10 |
| Germinal center B-cell | 1121248 | 54089 | BARD1 |
| Germinal center B-cell | 1123105 | 434281 | PTK2 |
| Germinal center B-cell | 1125456 | 300592 | MYBL1 |
| Germinal center B-cell | 1128694 | 171466 | ELL3 |
| Germinal center B-cell | 1128787 | 114611 | C7orf10 |
| Germinal center B-cell | 1132122 | 307734 | MME |
| Germinal center B-cell | 1136269 | 101474 | MAST2 |
| Germinal center B-cell | 1136702 | 155584 | KIAA0121 |
| Germinal center B-cell | 1139230 | 29724 | PLEKHF2 |
| Germinal center B-cell | 1529292 | NA | |
| Germinal center B-cell | 1529295 | 116441 | |
| Lymph node | 1097126 | 274520 | ANTXR1 |
| Lymph node | 1099028 | 334838 | FNDC1 |
| Lymph node | 1099358 | 93135 | |
| Lymph node | 1101478 | 146246 | MGC45780 |
| Lymph node | 1103497 | 50115 | |
| Lymph node | 1121029 | 412999 | CSTA |
| Lymph node | 1124429 | 409602 | SULF1 |
| Lymph node | 1135068 | 71719 | PDLIM3 |
| Lymph node | 1136051 | 520937 | CSF2RA |
| Lymph node | 1136172 | 38084 | SULT1C1 |
| MHC class II | 1136777 | 387679 | HLA-DQA1 |
| MHC class II | 1136877 | 409934 | HLA-DQB1 |
| Proliferation | 1096903 | 437460 | FLJ10385 |
| Proliferation | 1120583 | 153768 | RNU3IP2 |
| Proliferation | 1123289 | 5409 | POLR1C |
| Proliferation | 1131808 | 75447 | RALBP1 |
| Proliferation | 1133102 | 360041 | FRDA |
| Proliferation | 1136595 | 404814 | VDAC1 |

Table 2372 lists p-values for the association of each signature with survival in the training set, the validation set, and overall.

TABLE 2372

| Signature | Training set | Validation set | Overall |
|---|---|---|---|
| Lymph node | $4.0 \times 10^{-5}$ | $2.3 \times 10^{-6}$ | $6.8 \times 10^{-10}$ |
| Proliferation | $8.1 \times 10^{-5}$ | $3.4 \times 10^{-3}$ | $2.1 \times 10^{-6}$ |
| Germinal center B-cell | $6.2 \times 10^{-6}$ | $2.1 \times 10^{-3}$ | $5.0 \times 10^{-8}$ |
| MHC class II | $2.4 \times 10^{-2}$ | $2.7 \times 10^{-3}$ | $3.1 \times 10^{-4}$ |

The four gene expression signatures were used to generate a survival predictor score using the following equation:

Survival predictor score = $[-0.4337*$(lymph node gene expression signature value)$] + [0.09*$(proliferation gene expression signature value)$] - [0.4144*$(germinal center B-cell gene expression signature value)$] - [0.2006*$(MHC class II gene expression signature value)$]$.

A higher survival predictor score was associated with worse outcome. For the 200 DLBCL samples used to generate the model, the survival predictor score had a mean of 5.7 and a standard deviation of 0.78, with each unit increase in the predictor score corresponding to an approximately 2.7 fold increase in the relative risk of death. Data for all 200 samples is presented in Table 2373.

TABLE 2373

| Sample ID # | Set | Lymph node signature value | Proliferation signature value | Germinal center B-cell signature value | MHC class II signature value | Survival predictor score |
|---|---|---|---|---|---|---|
| ABC_1000 | Validation | 6.50 | 8.92 | 7.60 | 11.50 | −5.08 |
| ABC_1002 | Validation | 7.00 | 8.58 | 7.27 | 12.54 | −5.50 |
| ABC_1023 | Validation | 7.43 | 8.99 | 6.80 | 11.42 | −5.05 |
| ABC_1027 | Training | 5.68 | 9.00 | 6.87 | 12.31 | −4.70 |
| ABC_1031 | Validation | 8.02 | 9.00 | 7.17 | 11.68 | −5.53 |
| ABC_1034 | Validation | 6.06 | 9.61 | 6.72 | 11.83 | −4.58 |
| ABC_1038 | Training | 6.83 | 8.97 | 7.17 | 12.30 | −5.23 |
| ABC_1043 | Training | 6.96 | 9.01 | 6.77 | 12.29 | −5.11 |
| ABC_1045 | Validation | 8.18 | 8.21 | 6.77 | 12.07 | −5.66 |
| ABC_1055 | Validation | 5.58 | 9.16 | 7.30 | 13.05 | −4.76 |
| ABC_1057 | Training | 7.33 | 8.94 | 7.74 | 12.05 | −5.53 |
| ABC_1059 | Validation | 9.02 | 8.46 | 7.15 | 11.35 | −6.08 |
| ABC_1061 | Training | 7.13 | 9.18 | 7.09 | 12.28 | −5.21 |
| ABC_304 | Validation | 5.92 | 8.80 | 6.76 | 12.76 | −4.84 |
| ABC_305 | Training | 5.92 | 8.74 | 7.50 | 11.89 | −4.91 |
| ABC_309 | Validation | 8.86 | 8.39 | 7.62 | 12.53 | −6.46 |
| ABC_413 | Validation | 6.45 | 9.32 | 6.55 | 9.04 | −4.16 |
| ABC_428 | Training | 7.52 | 9.19 | 7.98 | 10.25 | −5.51 |
| ABC_432 | Validation | 6.48 | 9.33 | 7.45 | 9.56 | −4.56 |
| ABC_446 | Training | 7.91 | 9.42 | 7.41 | 10.55 | −5.46 |
| ABC_462 | Validation | 6.41 | 8.85 | 6.67 | 13.36 | −5.03 |
| ABC_477 | Validation | 6.26 | 9.02 | 6.69 | 12.45 | −4.89 |
| ABC_481 | Training | 8.18 | 8.30 | 7.35 | 11.98 | −5.91 |
| ABC_482 | Training | 8.59 | 9.01 | 7.66 | 12.35 | −6.16 |
| ABC_538 | Validation | 8.06 | 8.84 | 7.17 | 11.83 | −5.69 |
| ABC_541 | Training | 6.14 | 8.52 | 7.42 | 10.59 | −4.71 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| ABC_544 | Training | 6.91 | 9.03 | 6.82 | 11.87 | −4.89 |
| ABC_547 | Validation | 5.80 | 8.96 | 7.14 | 11.38 | −4.60 |
| ABC_577 | Validation | 7.84 | 8.65 | 8.16 | 11.95 | −5.94 |
| ABC_616 | Validation | 6.03 | 9.05 | 7.36 | 12.64 | −4.84 |
| ABC_626 | Validation | 7.48 | 9.22 | 7.25 | 11.11 | −5.27 |
| ABC_633 | Training | 7.74 | 8.35 | 7.39 | 12.45 | −5.80 |
| ABC_642 | Training | 5.71 | 8.82 | 6.41 | 13.80 | −4.62 |
| ABC_644 | Validation | 6.64 | 9.15 | 7.05 | 13.28 | −5.20 |
| ABC_645 | Training | 8.44 | 8.81 | 7.93 | 13.39 | −6.43 |
| ABC_646 | Validation | 5.94 | 9.11 | 6.71 | 11.60 | −4.63 |
| ABC_652 | Validation | 5.87 | 8.85 | 6.88 | 12.73 | −4.77 |
| ABC_660 | Training | 5.19 | 9.34 | 6.64 | 10.17 | −3.86 |
| ABC_663 | Training | 5.69 | 9.02 | 7.33 | 12.82 | −4.91 |
| ABC_668 | Validation | 7.12 | 9.28 | 7.03 | 10.57 | −4.91 |
| ABC_676 | Training | 4.95 | 8.90 | 7.09 | 13.32 | −4.61 |
| ABC_678 | Training | 5.84 | 9.11 | 7.34 | 11.26 | −4.41 |
| ABC_687 | Validation | 5.15 | 9.89 | 6.56 | 10.46 | −3.76 |
| ABC_689 | Training | 6.49 | 8.86 | 7.10 | 12.56 | −4.88 |
| ABC_692 | Validation | 7.32 | 8.96 | 7.25 | 11.57 | −5.32 |
| ABC_694 | Validation | 8.28 | 9.21 | 8.01 | 12.41 | −6.23 |
| ABC_700 | Training | 7.29 | 8.97 | 7.55 | 12.10 | −5.48 |
| ABC_702 | Validation | 7.60 | 8.66 | 6.86 | 12.55 | −5.45 |
| ABC_704 | Training | 7.07 | 8.92 | 7.03 | 12.83 | −5.35 |
| ABC_709 | Validation | 5.92 | 8.58 | 6.37 | 13.40 | −4.66 |
| ABC_712 | Validation | 5.79 | 9.12 | 6.34 | 12.02 | −4.23 |
| ABC_714 | Training | 7.49 | 8.88 | 7.49 | 11.97 | −5.54 |
| ABC_717 | Training | 7.17 | 9.45 | 7.01 | 11.34 | −5.05 |
| ABC_725 | Training | 6.71 | 9.01 | 6.52 | 12.76 | −4.86 |
| ABC_726 | Validation | 6.91 | 8.72 | 6.71 | 11.91 | −4.90 |
| ABC_730 | Validation | 6.28 | 9.22 | 7.28 | 12.14 | −4.88 |
| ABC_753 | Training | 6.84 | 9.64 | 7.05 | 13.00 | −5.22 |
| ABC_756 | Training | 7.67 | 8.45 | 7.59 | 12.48 | −5.85 |
| ABC_771 | Training | 6.98 | 8.76 | 6.91 | 12.20 | −5.18 |
| ABC_779 | Training | 6.73 | 9.32 | 6.78 | 9.82 | −4.44 |
| ABC_800 | Validation | 8.75 | 8.31 | 7.45 | 11.91 | −6.04 |
| ABC_807 | Training | 5.50 | 9.53 | 6.92 | 7.56 | −3.79 |
| ABC_809 | Training | 7.40 | 8.70 | 7.68 | 10.83 | −5.50 |
| ABC_816 | Training | 5.20 | 9.91 | 7.65 | 10.64 | −4.14 |
| ABC_820 | Training | 6.71 | 8.94 | 6.55 | 11.98 | −4.85 |
| ABC_823 | Validation | 5.58 | 9.26 | 6.44 | 10.09 | −3.97 |
| ABC_835 | Validation | 6.95 | 8.68 | 8.04 | 12.31 | −5.59 |
| ABC_839 | Training | 6.63 | 9.17 | 7.23 | 11.89 | −5.04 |
| ABC_841 | Validation | 6.35 | 9.51 | 7.52 | 13.19 | −5.28 |
| ABC_858 | Training | 7.63 | 8.51 | 7.12 | 11.74 | −5.42 |
| ABC_872 | Training | 6.78 | 8.73 | 7.41 | 12.47 | −5.44 |
| ABC_875 | Training | 7.59 | 8.81 | 7.20 | 11.26 | −5.25 |
| ABC_912 | Validation | 7.01 | 8.55 | 7.45 | 12.79 | −5.64 |
| ABC_996 | Validation | 5.00 | 9.53 | 6.70 | 10.02 | −3.94 |
| GCB_1005 | Validation | 8.28 | 8.67 | 9.11 | 13.27 | −6.98 |
| GCB_1008 | Training | 8.17 | 8.59 | 9.83 | 12.83 | −7.06 |
| GCB_1009 | Training | 6.63 | 9.02 | 10.07 | 12.28 | −6.19 |
| GCB_1021 | Validation | 6.44 | 8.83 | 9.34 | 13.20 | −6.15 |
| GCB_1025 | Validation | 7.87 | 8.48 | 9.27 | 12.37 | −6.57 |
| GCB_1026 | Training | 7.71 | 8.30 | 9.81 | 13.52 | −6.85 |
| GCB_1037 | Training | 4.95 | 8.83 | 9.35 | 12.57 | −5.22 |
| GCB_1039 | Training | 7.63 | 8.65 | 9.01 | 13.28 | −6.47 |
| GCB_1049 | Validation | 8.54 | 8.61 | 8.12 | 12.60 | −6.41 |
| GCB_1051 | Validation | 6.26 | 9.09 | 9.48 | 12.76 | −5.97 |
| GCB_1058 | Validation | 7.12 | 8.89 | 8.34 | 12.80 | −5.85 |
| GCB_1060 | Validation | 8.27 | 8.84 | 8.94 | 12.96 | −6.75 |
| GCB_412 | Training | 7.22 | 8.33 | 8.50 | 13.09 | −6.09 |
| GCB_415 | Training | 9.01 | 8.62 | 8.38 | 11.99 | −6.47 |
| GCB_421 | Training | 7.59 | 7.89 | 7.49 | 12.20 | −5.80 |
| GCB_424 | Training | 9.29 | 8.42 | 8.51 | 12.44 | −6.79 |
| GCB_433 | Training | 8.45 | 8.34 | 8.02 | 12.64 | −6.54 |
| GCB_434 | Training | 8.46 | 8.55 | 9.17 | 12.54 | −6.98 |
| GCB_438 | Validation | 8.14 | 8.71 | 9.13 | 12.51 | −6.67 |
| GCB_459 | Validation | 8.98 | 8.39 | 8.42 | 11.37 | −6.49 |
| GCB_470 | Validation | 7.72 | 8.57 | 8.67 | 12.23 | −6.12 |
| GCB_479 | Validation | 6.86 | 8.25 | 7.13 | 13.07 | −5.35 |
| GCB_492 | Training | 8.01 | 8.61 | 9.51 | 12.34 | −6.63 |
| GCB_517 | Validation | 8.57 | 8.73 | 7.99 | 12.76 | −6.48 |
| GCB_523 | Training | 5.96 | 8.56 | 8.74 | 12.77 | −5.72 |
| GCB_524 | Training | 8.51 | 8.09 | 8.76 | 12.51 | −6.57 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| GCB_529 | Training | 5.12 | 9.17 | 8.88 | 10.77 | −4.86 |
| GCB_533 | Training | 8.88 | 8.81 | 8.36 | 12.44 | −6.60 |
| GCB_537 | Validation | 7.42 | 8.19 | 9.73 | 13.29 | −6.68 |
| GCB_543 | Validation | 8.49 | 8.02 | 8.66 | 12.06 | −6.45 |
| GCB_545 | Training | 8.65 | 8.28 | 6.90 | 12.90 | −6.13 |
| GCB_549 | Validation | 6.87 | 8.24 | 8.65 | 12.15 | −6.00 |
| GCB_550 | Validation | 8.98 | 8.29 | 8.76 | 12.24 | −6.94 |
| GCB_553 | Validation | 8.51 | 8.64 | 8.62 | 12.63 | −6.69 |
| GCB_565 | Validation | 7.97 | 8.79 | 9.79 | 13.42 | −6.98 |
| GCB_572 | Training | 7.61 | 8.60 | 9.39 | 12.58 | −6.42 |
| GCB_617 | Validation | 8.31 | 7.89 | 7.54 | 13.17 | −6.12 |
| GCB_618 | Training | 5.66 | 8.97 | 9.20 | 13.32 | −5.54 |
| GCB_619 | Validation | 7.83 | 8.65 | 9.34 | 12.12 | −6.36 |
| GCB_623 | Training | 7.16 | 8.88 | 9.26 | 12.35 | −6.21 |
| GCB_627 | Validation | 8.13 | 8.83 | 8.62 | 11.85 | −6.31 |
| GCB_654 | Training | 6.30 | 9.60 | 8.45 | 10.00 | −4.88 |
| GCB_661 | Validation | 8.46 | 8.51 | 8.18 | 12.66 | −6.33 |
| GCB_669 | Training | 7.88 | 8.65 | 8.59 | 12.32 | −6.19 |
| GCB_672 | Training | 8.29 | 8.61 | 8.14 | 12.41 | −6.21 |
| GCB_674 | Validation | 8.36 | 8.62 | 7.76 | 12.33 | −6.14 |
| GCB_675 | Validation | 6.01 | 9.52 | 8.90 | 10.12 | −5.09 |
| GCB_681 | Training | 9.25 | 8.72 | 8.72 | 12.59 | −6.89 |
| GCB_688 | Validation | 6.97 | 9.01 | 9.90 | 9.94 | −5.99 |
| GCB_695 | Validation | 8.80 | 8.73 | 9.23 | 12.45 | −6.84 |
| GCB_698 | Validation | 9.27 | 8.35 | 8.85 | 11.99 | −6.96 |
| GCB_701 | Training | 7.77 | 7.93 | 8.68 | 13.10 | −6.33 |
| GCB_710 | Validation | 6.12 | 8.78 | 7.65 | 13.19 | −5.24 |
| GCB_711 | Training | 7.57 | 8.80 | 8.43 | 11.44 | −5.84 |
| GCB_722 | Training | 7.78 | 8.31 | 8.93 | 12.61 | −6.51 |
| GCB_724 | Training | 7.88 | 9.08 | 8.74 | 11.53 | −6.21 |
| GCB_731 | Validation | 7.72 | 8.92 | 9.08 | 12.20 | −6.46 |
| GCB_742 | Validation | 8.33 | 8.55 | 8.58 | 12.95 | −6.70 |
| GCB_744 | Training | 8.02 | 8.64 | 9.36 | 11.85 | −6.52 |
| GCB_745 | Training | 8.47 | 8.34 | 8.93 | 11.95 | −6.67 |
| GCB_747 | Validation | 7.64 | 8.48 | 8.32 | 13.06 | −6.27 |
| GCB_749 | Training | 7.57 | 8.61 | 9.40 | 12.55 | −6.56 |
| GCB_758 | Validation | 5.66 | 8.77 | 7.89 | 12.51 | −4.63 |
| GCB_772 | Validation | 8.52 | 7.81 | 7.95 | 12.25 | −6.34 |
| GCB_777 | Validation | 7.52 | 8.65 | 8.57 | 11.69 | −6.10 |
| GCB_792 | Training | 8.14 | 8.64 | 9.21 | 12.08 | −6.65 |
| GCB_795 | Validation | 9.19 | 8.17 | 8.81 | 11.60 | −6.92 |
| GCB_797 | Validation | 7.50 | 8.62 | 8.08 | 12.84 | −6.09 |
| GCB_803 | Validation | 6.19 | 8.65 | 9.49 | 13.18 | −6.11 |
| GCB_810 | Training | 8.46 | 8.32 | 8.10 | 13.13 | −6.50 |
| GCB_817 | Training | 6.93 | 8.51 | 9.49 | 11.09 | −6.04 |
| GCB_818 | Training | 7.18 | 8.96 | 8.08 | 12.23 | −5.76 |
| GCB_819 | Validation | 7.16 | 8.97 | 8.06 | 13.22 | −5.79 |
| GCB_821 | Validation | 8.13 | 8.59 | 8.90 | 12.41 | −6.61 |
| GCB_832 | Training | 7.83 | 8.35 | 8.71 | 12.47 | −6.37 |
| GCB_836 | Validation | 7.84 | 8.99 | 8.50 | 11.46 | −5.85 |
| GCB_840 | Training | 8.24 | 7.75 | 7.40 | 11.74 | −5.77 |
| GCB_847 | Training | 7.82 | 8.17 | 8.97 | 12.55 | −6.51 |
| GCB_860 | Training | 7.12 | 8.39 | 9.34 | 11.54 | −6.10 |
| GCB_871 | Training | 5.59 | 9.60 | 7.28 | 11.16 | −4.23 |
| GCB_874 | Training | 8.53 | 9.14 | 8.95 | 11.65 | −6.47 |
| GCB_995 | Validation | 6.98 | 8.68 | 8.54 | 12.22 | −5.76 |
| PMBL_1006 | Validation | 7.34 | 8.51 | 7.66 | 10.94 | −5.33 |
| PMBL_1024 | Validation | 7.62 | 8.48 | 8.56 | 10.89 | −5.96 |
| PMBL_1048 | Validation | 8.68 | 8.16 | 7.23 | 12.18 | −6.08 |
| PMBL_1053 | Training | 7.02 | 8.28 | 8.24 | 11.12 | −5.31 |
| PMBL_484 | Training | 7.15 | 8.45 | 7.01 | 13.62 | −5.41 |
| PMBL_546 | Validation | 8.19 | 7.88 | 7.66 | 11.73 | −6.06 |
| PMBL_570 | Training | 9.34 | 8.21 | 8.48 | 12.70 | −6.86 |
| PMBL_621 | Training | 8.08 | 8.60 | 9.14 | 12.96 | −6.72 |
| PMBL_638 | Training | 7.56 | 8.26 | 8.00 | 11.37 | −5.75 |
| PMBL_691 | Validation | 6.48 | 8.92 | 8.40 | 10.17 | −5.04 |
| PMBL_791 | Validation | 7.72 | 8.65 | 8.94 | 11.56 | −6.16 |
| PMBL_824 | Validation | 8.06 | 8.01 | 7.76 | 13.28 | −6.11 |
| PMBL_994 | Validation | 9.15 | 8.36 | 7.46 | 12.43 | −6.29 |
| PMBL_998 | Training | 6.70 | 8.35 | 9.24 | 13.19 | −6.20 |
| UC_DLBCL_1001 | Validation | 6.74 | 8.43 | 7.10 | 12.76 | −5.31 |
| UC_DLBCL_1004 | Validation | 7.54 | 8.75 | 8.01 | 13.09 | −6.10 |
| UC_DLBCL_1007 | Training | 9.97 | 8.44 | 7.64 | 12.97 | −6.85 |
| UC_DLBCL_1018 | Training | 6.42 | 8.38 | 6.97 | 12.71 | −5.03 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| UC_DLBCL_1041 | Validation | 5.76 | 8.69 | 6.78 | 13.38 | −4.71 |
| UC_DLBCL_1054 | Training | 8.92 | 8.65 | 8.51 | 11.48 | −6.59 |
| UC_DLBCL_306 | Validation | 7.85 | 8.90 | 8.31 | 12.36 | −6.23 |
| UC_DLBCL_310 | Training | 8.14 | 8.80 | 7.63 | 12.27 | −6.03 |
| UC_DLBCL_449 | Validation | 9.03 | 8.48 | 7.07 | 12.17 | −6.01 |
| UC_DLBCL_458 | Training | 5.92 | 8.53 | 8.28 | 9.60 | −4.96 |
| UC_DLBCL_460 | Validation | 7.92 | 9.08 | 8.30 | 12.29 | −6.13 |
| UC_DLBCL_491 | Training | 7.65 | 8.33 | 7.35 | 12.39 | −5.53 |
| UC_DLBCL_528 | Validation | 6.99 | 8.56 | 7.36 | 11.63 | −5.35 |
| UC_DLBCL_615 | Validation | 7.11 | 8.32 | 8.77 | 12.80 | −6.10 |
| UC_DLBCL_625 | Training | 8.93 | 7.78 | 7.85 | 12.62 | −6.46 |
| UC_DLBCL_664 | Training | 7.62 | 8.15 | 8.17 | 12.72 | −6.04 |
| UC_DLBCL_671 | Training | 8.09 | 8.48 | 7.61 | 11.53 | −5.78 |
| UC_DLBCL_682 | Training | 7.38 | 8.35 | 7.14 | 12.33 | −5.43 |
| UC_DLBCL_683 | Training | 7.91 | 8.36 | 7.78 | 12.57 | −6.02 |
| UC_DLBCL_684 | Validation | 8.06 | 8.63 | 8.29 | 12.76 | −6.29 |
| UC_DLBCL_748 | Validation | 5.38 | 8.57 | 7.45 | 9.55 | −4.23 |
| UC_DLBCL_751 | Training | 6.33 | 8.65 | 8.88 | 13.14 | −5.74 |
| UC_DLBCL_808 | Training | 7.42 | 9.01 | 7.44 | 13.09 | −5.63 |
| UC_DLBCL_831 | Validation | 8.33 | 8.30 | 7.46 | 11.58 | −5.84 |
| UC_DLBCL_834 | Training | 6.98 | 9.09 | 8.61 | 11.77 | −5.66 |
| UC_DLBCL_838 | Validation | 7.25 | 8.40 | 7.23 | 12.56 | −5.36 |
| UC_DLBCL_851 | Validation | 6.28 | 9.05 | 6.78 | 8.19 | −4.10 |
| UC_DLBCL_854 | Validation | 7.36 | 8.50 | 7.39 | 12.59 | −5.53 |
| UC_DLBCL_855 | Training | 8.31 | 7.94 | 7.49 | 12.08 | −6.07 |
| UC_DLBCL_856 | Validation | 5.65 | 9.01 | 8.52 | 9.32 | −4.68 |

Figure 11:
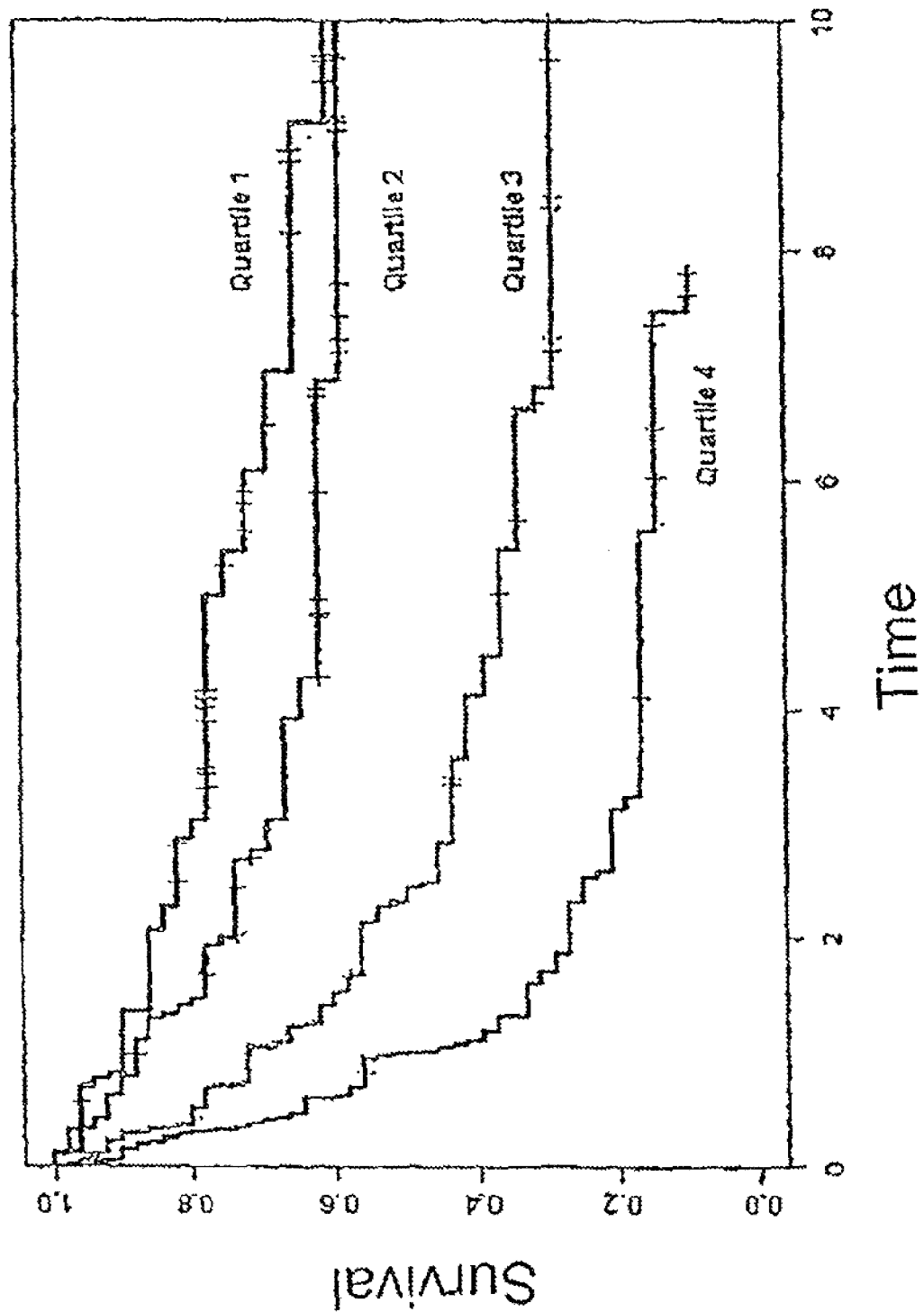
FIG. 11: Kaplan-Meier plot of survival in DLBCL samples based on survival predictor scores. 200 DLBCL samples were divided into quartiles based on their survival predictor scores. The survival predictor scores were calculated by: [−0.4337*(lymph node gene expression signature value)]+[0.09*(proliferation gene expression signature value)]−[0.4144*(germinal center B-cell gene expression signature value)]−[0.2006*(MHC class II gene expression signature value)].

In order to visualize the predictive power of the model, the 200 samples were ranked according to their survival predictor scores and divided into four quartiles. Kaplan-Meier plots of overall survival probability show clear differences in survival rate between these four quartiles (FIG. 11).

Example 8

Development of a Third DLBCL Survival Predictor Using Gene Expression Data from the Lymph Dx Microarray The number of genes used to generate the DLBCL survival predictor in Example 7 was reduced in order to create a survival predictor compatible with RT-PCR. The list of genes from the lymph node and germinal center B-cell gene expression signatures was narrowed to those three genes from each signature that were most closely correlated with the lymph node and germinal center B-cell gene expression signature values, respectively. The genes from the proliferation gene expression signature did not add significantly to the reduced gene survival prediction model, so they were removed entirely. The expression of the genes within each signature was averaged on the $\log_2$ scale to generate a gene expression signature value for each signature. Table 2374 lists the genes that were used to generate these gene expression signature values.

TABLE 2374

| Signature | UNIQID | Unigene ID Build 167 | Gene symbol |
|---|---|---|---|
| Germinal center B-cell | 1099686 | 117721 | |
| Germinal center B-cell | 1529318 | 291954 | |
| Germinal center B-cell | 1529344 | 317970 | SERPINA11 |

TABLE 2374-continued

| Signature | UNIQID | Unigene ID Build 167 | Gene symbol |
|---|---|---|---|
| Lymph node | 1097126 | 274520 | ANTXR1 |
| Lymph node | 1099358 | 93135 | |
| Lymph node | 1121029 | 412999 | CSTA |
| MHC class II | 1136777 | 387679 | HLA-DQA1 |
| MHC class II | 1136877 | 409934 | HLA-DQB1 |

Table 2375 lists p-values for the association of each signature with survival in the training set, the validation set, and overall.

TABLE 2375

| Signature | Training set | Validation set | Overall |
|---|---|---|---|
| Lymph node | $6.1 \times 10^{-6}$ | 0.0021 | $2.1 \times 10^{-17}$ |
| Germinal center B-cell | $3.5 \times 10^{-4}$ | 0.0099 | $2.7 \times 10^{-5}$ |
| MHC class II | 0.024 | 0.0026 | 0.00031 |

The three gene expression signatures were used to generate a survival predictor score using the following equation:

Survival predictor score=[−0.32*(lymph node gene expression signature value)]−[0.176*(germinal center B-cell gene expression signature value)]−[0.206*(MHC class II gene expression signature value)].

A higher survival predictor score was associated with worse outcome. For the 200 DLBCL samples used to generate the model, the survival predictor score had a mean of 6.54 and a standard deviation of 0.69, with each unit increase in the predictor score corresponding to an approximately 2.7 fold increase in the relative risk of death. Data for all 200 samples is presented in Table 2376.

TABLE 2376

| Sample ID # | Set | Lymph node signature value | Germinal center B-cell signature value | MHC class II signature value | Survival predictor score |
|---|---|---|---|---|---|
| ABC_1000 | Validation | 8.08 | 5.68 | 11.50 | −5.96 |
| ABC_1002 | Validation | 8.32 | 6.06 | 12.54 | −6.31 |
| ABC_1023 | Validation | 9.36 | 4.74 | 11.42 | −6.18 |
| ABC_1027 | Training | 7.41 | 4.90 | 12.31 | −5.77 |
| ABC_1031 | Validation | 9.40 | 5.23 | 11.68 | −6.33 |
| ABC_1034 | Validation | 7.47 | 4.92 | 11.83 | −5.69 |
| ABC_1038 | Training | 7.89 | 5.84 | 12.30 | −6.09 |
| ABC_1043 | Training | 7.84 | 4.66 | 12.29 | −5.86 |
| ABC_1045 | Validation | 9.31 | 4.66 | 12.07 | −6.29 |
| ABC_1055 | Validation | 6.46 | 6.38 | 13.05 | −5.88 |
| ABC_1057 | Training | 9.13 | 7.93 | 12.05 | −6.80 |
| ABC_1059 | Validation | 10.93 | 4.82 | 11.35 | −6.68 |
| ABC_1061 | Training | 8.18 | 5.04 | 12.28 | −6.04 |
| ABC_304 | Validation | 7.31 | 6.47 | 12.76 | −6.10 |
| ABC_305 | Training | 7.02 | 6.60 | 11.89 | −5.86 |
| ABC_309 | Validation | 10.47 | 7.00 | 12.53 | −7.16 |
| ABC_413 | Validation | 7.99 | 4.80 | 9.04 | −5.26 |
| ABC_428 | Training | 9.43 | 7.59 | 10.25 | −6.47 |
| ABC_432 | Validation | 7.29 | 8.16 | 9.56 | −5.74 |
| ABC_446 | Training | 9.49 | 5.46 | 10.55 | −6.17 |
| ABC_462 | Validation | 7.72 | 4.97 | 13.36 | −6.10 |
| ABC_477 | Validation | 7.16 | 3.69 | 12.45 | −5.51 |
| ABC_481 | Training | 9.75 | 6.89 | 11.98 | −6.80 |
| ABC_482 | Training | 10.51 | 7.64 | 12.35 | −7.25 |
| ABC_538 | Validation | 8.79 | 5.00 | 11.83 | −6.13 |
| ABC_541 | Training | 7.70 | 5.80 | 10.59 | −5.67 |
| ABC_544 | Training | 8.90 | 3.98 | 11.87 | −5.99 |
| ABC_547 | Validation | 7.05 | 5.18 | 11.38 | −5.51 |
| ABC_577 | Validation | 9.93 | 8.05 | 11.95 | −7.06 |
| ABC_616 | Validation | 7.34 | 4.54 | 12.64 | −5.75 |
| ABC_626 | Validation | 8.78 | 6.77 | 11.11 | −6.29 |
| ABC_633 | Training | 9.63 | 5.02 | 12.45 | −6.53 |
| ABC_642 | Training | 7.31 | 4.95 | 13.80 | −6.05 |
| ABC_644 | Validation | 7.77 | 5.35 | 13.28 | −6.15 |
| ABC_645 | Training | 9.77 | 6.21 | 13.39 | −6.98 |
| ABC_646 | Validation | 7.39 | 3.75 | 11.60 | −5.41 |
| ABC_652 | Validation | 7.51 | 4.53 | 12.73 | −5.82 |
| ABC_660 | Training | 5.85 | 3.55 | 10.17 | −4.59 |
| ABC_663 | Training | 7.04 | 5.06 | 12.82 | −5.78 |
| ABC_668 | Validation | 8.00 | 5.65 | 10.57 | −5.73 |
| ABC_676 | Training | 6.53 | 4.29 | 13.32 | −5.59 |
| ABC_678 | Training | 6.87 | 7.48 | 11.26 | −5.83 |
| ABC_687 | Validation | 6.39 | 3.78 | 10.46 | −4.87 |
| ABC_689 | Training | 8.29 | 5.07 | 12.56 | −6.13 |
| ABC_692 | Validation | 8.10 | 5.26 | 11.57 | −5.90 |
| ABC_694 | Validation | 9.67 | 8.15 | 12.41 | −7.09 |
| ABC_700 | Training | 8.37 | 6.75 | 12.10 | −6.36 |
| ABC_702 | Validation | 8.44 | 4.59 | 12.55 | −6.09 |
| ABC_704 | Training | 8.51 | 4.34 | 12.83 | −6.13 |
| ABC_709 | Validation | 7.47 | 4.54 | 13.40 | −5.95 |
| ABC_712 | Validation | 7.12 | 3.99 | 12.02 | −5.46 |
| ABC_714 | Training | 9.57 | 7.03 | 11.97 | −6.77 |
| ABC_717 | Training | 8.33 | 5.54 | 11.34 | −5.98 |
| ABC_725 | Training | 8.04 | 4.40 | 12.76 | −5.97 |
| ABC_726 | Validation | 7.79 | 4.18 | 11.91 | −5.68 |
| ABC_730 | Validation | 8.13 | 7.36 | 12.14 | −6.40 |
| ABC_753 | Training | 9.24 | 6.60 | 13.00 | −6.80 |
| ABC_756 | Training | 9.51 | 5.21 | 12.48 | −6.53 |
| ABC_771 | Training | 8.08 | 4.74 | 12.20 | −5.93 |
| ABC_779 | Training | 8.11 | 4.09 | 9.82 | −5.34 |
| ABC_800 | Validation | 10.34 | 4.83 | 11.91 | −6.61 |
| ABC_807 | Training | 6.58 | 4.44 | 7.56 | −4.44 |
| ABC_809 | Training | 9.29 | 5.72 | 10.83 | −6.21 |
| ABC_816 | Training | 6.36 | 6.36 | 10.64 | −5.35 |
| ABC_820 | Training | 8.10 | 4.79 | 11.98 | −5.90 |
| ABC_823 | Validation | 6.63 | 4.85 | 10.09 | −5.05 |
| ABC_835 | Validation | 9.17 | 7.78 | 12.31 | −6.84 |
| ABC_839 | Training | 8.06 | 4.97 | 11.89 | −5.90 |
| ABC_841 | Validation | 8.05 | 6.24 | 13.19 | −6.39 |
| ABC_858 | Training | 9.02 | 4.86 | 11.74 | −6.16 |
| ABC_872 | Training | 8.67 | 5.85 | 12.47 | −6.37 |
| ABC_875 | Training | 9.60 | 5.59 | 11.26 | −6.37 |
| ABC_912 | Validation | 7.99 | 7.74 | 12.79 | −6.56 |
| ABC_996 | Validation | 6.89 | 6.23 | 10.02 | −5.36 |
| GCB_1005 | Validation | 9.02 | 9.56 | 13.27 | −7.30 |

TABLE 2376-continued

| Sample ID # | Set | Lymph node signature value | Germinal center B-cell signature value | MHC class II signature value | Survival predictor score |
|---|---|---|---|---|---|
| GCB_1008 | Training | 9.27 | 10.49 | 12.83 | −7.46 |
| GCB_1009 | Training | 7.80 | 10.09 | 12.28 | −6.80 |
| GCB_1021 | Validation | 8.73 | 9.20 | 13.20 | −7.13 |
| GCB_1025 | Validation | 9.94 | 9.97 | 12.37 | −7.49 |
| GCB_1026 | Training | 9.54 | 10.20 | 13.52 | −7.63 |
| GCB_1037 | Training | 6.34 | 8.79 | 12.57 | −6.17 |
| GCB_1039 | Training | 8.71 | 9.94 | 13.28 | −7.27 |
| GCB_1049 | Validation | 10.53 | 8.18 | 12.60 | −7.41 |
| GCB_1051 | Validation | 7.63 | 10.18 | 12.76 | −6.86 |
| GCB_1058 | Validation | 8.61 | 9.04 | 12.80 | −6.98 |
| GCB_1060 | Validation | 10.23 | 9.38 | 12.96 | −7.59 |
| GCB_412 | Training | 8.79 | 7.92 | 13.09 | −6.90 |
| GCB_415 | Training | 10.72 | 8.57 | 11.99 | −7.41 |
| GCB_421 | Training | 9.23 | 5.26 | 12.20 | −6.39 |
| GCB_424 | Training | 11.14 | 8.46 | 12.44 | −7.62 |
| GCB_433 | Training | 9.26 | 8.52 | 12.64 | −7.07 |
| GCB_434 | Training | 9.73 | 10.13 | 12.54 | −7.48 |
| GCB_438 | Validation | 9.60 | 9.99 | 12.51 | −7.41 |
| GCB_459 | Validation | 10.51 | 7.75 | 11.37 | −7.07 |
| GCB_470 | Validation | 9.56 | 6.63 | 12.23 | −6.74 |
| GCB_479 | Validation | 7.77 | 4.71 | 13.07 | −6.01 |
| GCB_492 | Training | 8.82 | 9.52 | 12.34 | −7.04 |
| GCB_517 | Validation | 9.92 | 6.96 | 12.76 | −7.03 |
| GCB_523 | Training | 6.59 | 9.17 | 12.77 | −6.35 |
| GCB_524 | Training | 10.00 | 7.83 | 12.51 | −7.16 |
| GCB_529 | Training | 5.61 | 7.93 | 10.77 | −5.41 |
| GCB_533 | Training | 9.55 | 5.54 | 12.44 | −6.59 |
| GCB_537 | Validation | 8.25 | 10.25 | 13.29 | −7.18 |
| GCB_543 | Validation | 9.92 | 8.85 | 12.06 | −7.21 |
| GCB_545 | Training | 9.69 | 4.91 | 12.90 | −6.62 |
| GCB_549 | Validation | 7.86 | 8.88 | 12.15 | −6.58 |
| GCB_550 | Validation | 10.64 | 9.53 | 12.24 | −7.60 |
| GCB_553 | Validation | 10.14 | 9.05 | 12.63 | −7.44 |
| GCB_565 | Validation | 9.08 | 10.80 | 13.42 | −7.57 |
| GCB_572 | Training | 8.93 | 10.03 | 12.58 | −7.21 |
| GCB_617 | Validation | 9.27 | 7.80 | 13.17 | −7.05 |
| GCB_618 | Training | 7.23 | 9.11 | 13.32 | −6.66 |
| GCB_619 | Validation | 9.63 | 9.63 | 12.12 | −7.27 |
| GCB_623 | Training | 8.94 | 9.07 | 12.35 | −7.00 |
| GCB_627 | Validation | 9.72 | 8.33 | 11.85 | −7.02 |
| GCB_654 | Training | 7.04 | 5.60 | 10.00 | −5.30 |
| GCB_661 | Validation | 10.27 | 7.92 | 12.66 | −7.29 |
| GCB_669 | Training | 9.15 | 9.29 | 12.32 | −7.10 |
| GCB_672 | Training | 9.69 | 7.36 | 12.41 | −6.95 |
| GCB_674 | Validation | 9.93 | 6.23 | 12.33 | −6.81 |
| GCB_675 | Validation | 7.48 | 8.46 | 10.12 | −5.97 |
| GCB_681 | Training | 10.77 | 9.52 | 12.59 | −7.72 |
| GCB_688 | Validation | 8.01 | 10.17 | 9.94 | −6.40 |
| GCB_695 | Validation | 10.58 | 9.38 | 12.45 | −7.60 |
| GCB_698 | Validation | 10.44 | 9.00 | 11.99 | −7.39 |
| GCB_701 | Training | 9.38 | 9.27 | 13.10 | −7.33 |
| GCB_710 | Validation | 6.96 | 5.59 | 13.19 | −5.93 |
| GCB_711 | Training | 9.28 | 8.49 | 11.44 | −6.82 |
| GCB_722 | Training | 8.93 | 9.51 | 12.61 | −7.13 |
| GCB_724 | Training | 9.51 | 8.39 | 11.53 | −6.90 |
| GCB_731 | Validation | 8.82 | 9.19 | 12.20 | −6.95 |
| GCB_742 | Validation | 9.95 | 9.37 | 12.95 | −7.50 |
| GCB_744 | Training | 10.23 | 10.11 | 11.85 | −7.49 |
| GCB_745 | Training | 10.29 | 9.71 | 11.95 | −7.46 |
| GCB_747 | Validation | 9.83 | 9.79 | 13.06 | −7.56 |
| GCB_749 | Training | 8.57 | 10.27 | 12.55 | −7.14 |
| GCB_758 | Validation | 6.88 | 5.69 | 12.51 | −5.78 |
| GCB_772 | Validation | 9.92 | 7.28 | 12.25 | −6.98 |
| GCB_777 | Validation | 9.03 | 9.63 | 11.69 | −6.99 |
| GCB_792 | Training | 9.49 | 9.06 | 12.08 | −7.12 |
| GCB_795 | Validation | 11.12 | 9.02 | 11.60 | −7.54 |
| GCB_797 | Validation | 8.42 | 5.90 | 12.84 | −6.38 |
| GCB_803 | Validation | 7.33 | 10.11 | 13.18 | −6.84 |
| GCB_810 | Training | 10.00 | 8.22 | 13.13 | −7.35 |
| GCB_817 | Training | 8.60 | 10.16 | 11.09 | −6.82 |
| GCB_818 | Training | 9.14 | 7.78 | 12.23 | −6.81 |
| GCB_819 | Validation | 9.08 | 8.63 | 13.22 | −7.15 |
| GCB_821 | Validation | 10.05 | 9.81 | 12.41 | −7.50 |
| GCB_832 | Training | 8.83 | 6.91 | 12.47 | −6.61 |
| GCB_836 | Validation | 9.49 | 7.86 | 11.46 | −6.78 |

TABLE 2376-continued

| Sample ID # | Set | Lymph node signature value | Germinal center B-cell signature value | MHC class II signature value | Survival predictor score |
|---|---|---|---|---|---|
| GCB_840 | Training | 9.45 | 5.02 | 11.74 | −6.33 |
| GCB_847 | Training | 9.41 | 8.77 | 12.55 | −7.14 |
| GCB_860 | Training | 9.02 | 6.66 | 11.54 | −6.43 |
| GCB_871 | Training | 6.60 | 4.46 | 11.16 | −5.20 |
| GCB_874 | Training | 10.39 | 9.13 | 11.65 | −7.33 |
| GCB_995 | Validation | 8.52 | 9.35 | 12.22 | −6.89 |
| PMBL_1006 | Validation | 8.72 | 4.67 | 10.94 | −5.86 |
| PMBL_1024 | Validation | 9.30 | 8.47 | 10.89 | −6.71 |
| PMBL_1048 | Validation | 10.30 | 4.98 | 12.18 | −6.68 |
| PMBL_1053 | Training | 8.75 | 9.78 | 11.12 | −6.81 |
| PMBL_484 | Training | 8.25 | 4.96 | 13.62 | −6.32 |
| PMBL_546 | Validation | 9.66 | 6.07 | 11.73 | −6.57 |
| PMBL_570 | Training | 10.58 | 8.54 | 12.70 | −7.50 |
| PMBL_621 | Training | 9.39 | 9.94 | 12.96 | −7.43 |
| PMBL_638 | Training | 9.81 | 8.35 | 11.37 | −6.95 |
| PMBL_691 | Validation | 8.37 | 7.51 | 10.17 | −6.10 |
| PMBL_791 | Validation | 9.29 | 8.65 | 11.56 | −6.88 |
| PMBL_824 | Validation | 9.87 | 7.19 | 13.28 | −7.16 |
| PMBL_994 | Training | 11.27 | 6.73 | 12.43 | −7.35 |
| PMBL_998 | Training | 7.92 | 8.34 | 13.19 | −6.72 |
| UC_DLBCL_1001 | Validation | 8.25 | 5.63 | 12.76 | −6.26 |
| UC_DLBCL_1004 | Validation | 9.01 | 7.01 | 13.09 | −6.81 |
| UC_DLBCL_1007 | Training | 11.42 | 6.73 | 12.97 | −7.51 |
| UC_DLBCL_1018 | Training | 7.77 | 4.58 | 12.71 | −5.91 |
| UC_DLBCL_1041 | Validation | 7.90 | 4.33 | 13.38 | −6.05 |
| UC_DLBCL_1054 | Training | 10.41 | 8.72 | 11.48 | −7.23 |
| UC_DLBCL_306 | Validation | 9.42 | 6.54 | 12.36 | −6.71 |
| UC_DLBCL_310 | Training | 9.97 | 5.50 | 12.27 | −6.69 |
| UC_DLBCL_449 | Validation | 10.01 | 5.37 | 12.17 | −6.65 |
| UC_DLBCL_458 | Training | 7.50 | 5.79 | 9.60 | −5.40 |
| UC_DLBCL_460 | Validation | 10.26 | 8.27 | 12.29 | −7.27 |
| UC_DLBCL_491 | Training | 9.43 | 4.73 | 12.39 | −6.40 |
| UC_DLBCL_528 | Validation | 8.42 | 6.19 | 11.63 | −6.18 |
| UC_DLBCL_615 | Validation | 8.44 | 9.01 | 12.80 | −6.92 |
| UC_DLBCL_625 | Training | 10.43 | 8.27 | 12.62 | −7.39 |
| UC_DLBCL_664 | Training | 9.80 | 8.74 | 12.72 | −7.29 |
| UC_DLBCL_671 | Training | 9.42 | 5.26 | 11.53 | −6.32 |
| UC_DLBCL_682 | Training | 9.01 | 4.73 | 12.33 | −6.26 |
| UC_DLBCL_683 | Training | 8.85 | 8.23 | 12.57 | −6.87 |
| UC_DLBCL_684 | Validation | 9.62 | 8.78 | 12.76 | −7.25 |
| UC_DLBCL_748 | Validation | 7.60 | 5.79 | 9.55 | −5.42 |
| UC_DLBCL_751 | Training | 6.40 | 9.91 | 13.14 | −6.50 |
| UC_DLBCL_808 | Training | 9.44 | 7.01 | 13.09 | −6.95 |
| UC_DLBCL_831 | Validation | 9.45 | 5.81 | 11.58 | −6.43 |
| UC_DLBCL_834 | Training | 8.52 | 7.66 | 11.77 | −6.50 |
| UC_DLBCL_838 | Validation | 8.49 | 4.60 | 12.56 | −6.11 |
| UC_DLBCL_851 | Validation | 7.50 | 4.82 | 8.19 | −4.94 |
| UC_DLBCL_854 | Validation | 8.35 | 5.82 | 12.59 | −6.29 |
| UC_DLBCL_855 | Training | 9.56 | 5.44 | 12.08 | −6.51 |
| UC_DLBCL_856 | Validation | 6.81 | 7.49 | 9.32 | −5.42 |

Figure 12:
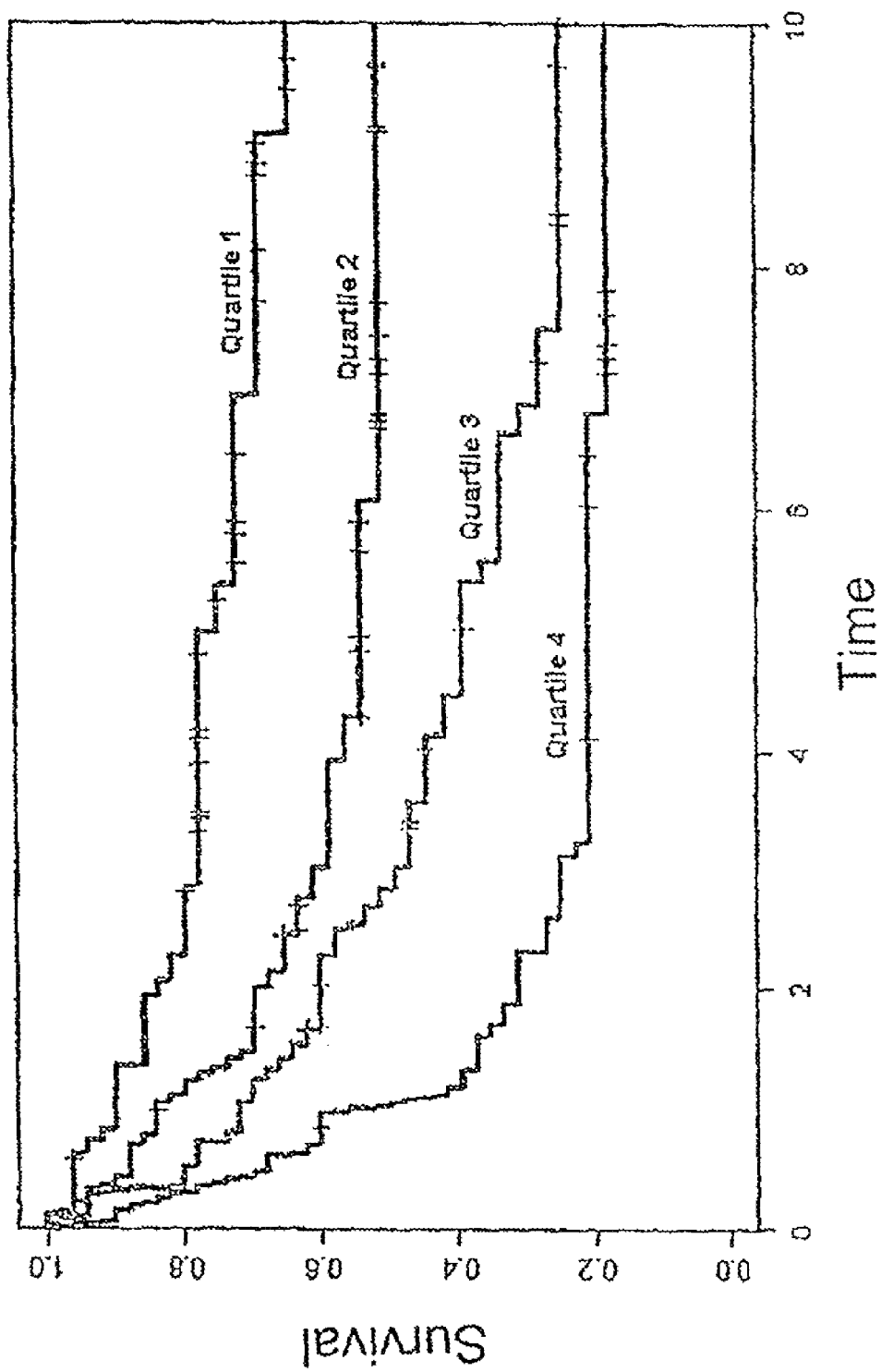
FIG. 12: Kaplan-Meier plot of survival in DLBCL samples based on survival predictor scores. 200 DLBCL samples were divided into quartiles based on their survival predictor scores. The survival predictor scores were calculated by: [−0.32*(lymph node gene expression signature value)]−[0.176*(germinal center B-cell gene expression signature value)]−[0.206*(MHC class II gene expression signature value)].

In order to visualize the predictive power of the model, the 200 samples were ranked according to their survival predictor scores and divided into four quartiles. Kaplan-Meier plots of overall survival probability show clear differences in survival rate between these four quartiles (FIG. 12).

Example 9

Development of an MCL Survival Predictor Using Gene Expression Data from Affymetrix U133A and U133B Microarrays The connection between higher expression of proliferation genes and worse survival in MCL had previously been documented and validated (Rosenwald 2003a). A cluster of proliferation genes had been identified in the DLBCL samples used to create the DLBCL survival predictor described in Example 7. By averaging the expression of these genes, a proliferation gene expression signature value had been developed for the DLBCL samples. The correlation of this signature with each probe set on the U133A and U133B microarrays was determined, and the 22 genes for which the correlation was greater than 0.5 were labeled proliferation genes. The correlation between expression of these proliferation genes and survival in 21 MCL samples was estimated using the Cox proportional hazards model. Table 2377 lists these 21 MCL samples.

TABLE 2377

| Sample ID # | Length of follow-up (years) | Status at follow-up | Used in creating survival predictor? |
|---|---|---|---|
| MCL_1012 | 3.19 | Alive | Yes |
| MCL_1091 | 3.03 | Alive | Yes |
| MCL_1114 | 0.59 | Dead | Yes |

TABLE 2377-continued

| Sample ID # | Length of follow-up (years) | Status at follow-up | Used in creating survival predictor? |
|---|---|---|---|
| MCL_1128 | 0.43 | Dead | Yes |
| MCL_1150 | 3.21 | Dead | Yes |
| MCL_1162 | 0.78 | Alive | Yes |
| MCL_1166 | 0.53 | Dead | Yes |
| MCL_1194 | 0.55 | Alive | Yes |
| MCL_885 | 1.19 | Alive | Yes |
| MCL_918 | 1.95 | Dead | Yes |
| MCL_924 | 5.48 | Dead | Yes |
| MCL_925 | 7.23 | Alive | Yes |
| MCL_926 | 5.18 | Dead | Yes |
| MCL_936 | 2.80 | Alive | Yes |
| MCL_939 | 1.07 | Dead | Yes |
| MCL_953 | 2.31 | Dead | Yes |
| MCL_956 | 1.40 | Dead | Yes |
| MCL_964 | 0.75 | Alive | Yes |
| MCL_966 | 0.21 | Dead | Yes |
| MCL_968 | 1.59 | Dead | Yes |
| MCL_970 | 5.02 | Dead | Yes |

Out of the 22 proliferation genes, 11 were significant at a 0.001 level. The expression level of these 11 genes in each of the 21 MCL samples was averaged to generate a proliferation gene expression signature value. No other genes represented on the U133A or U133B microarrays correlated with MCL survival to an extent greater than would be expected by chance, so the final model included only proliferation genes. The 11 genes used to generate the model are presented in Table 2378.

TABLE 2378

| Signature | UNIQID | Affymetrix probe set ID | GenBank Accession No. | Gene Symbol |
|---|---|---|---|---|
| Proliferation | 1097290 | 224903_at | NM_032830 | CIRH1A |
| Proliferation | 1101295 | 229610_at | NM_152515 | FLJ40629 |
| Proliferation | 1119729 | 202338_at | NM_003258 | TK1 |
| Proliferation | 1120153 | 203276_at | NM_005573 | LMNB1 |
| Proliferation | 1120494 | 203967_at | NM_001254 | CDC6 |
| Proliferation | 1124745 | 212789_at | NM_015261 | KIAA0056 |
| Proliferation | 1126148 | 215143_at | NM_173812 | DKFZp586E1120 |
| Proliferation | 1130618 | 200822_x_at | NM_000365 | TPI1 |
| Proliferation | 1134753 | 209053_s_at | NM_133330 | WHSC1 |
| Proliferation | 1139654 | 219787_s_at | NM_018098 | ECT2 |
| Proliferation | 1140632 | 222036_s_at | NM_005914 | MCM4 |

A survival predictor score for MCL was generated using the following equation:

Survival predictor score=1.66*(proliferation gene expression signature value).

Figure 13:
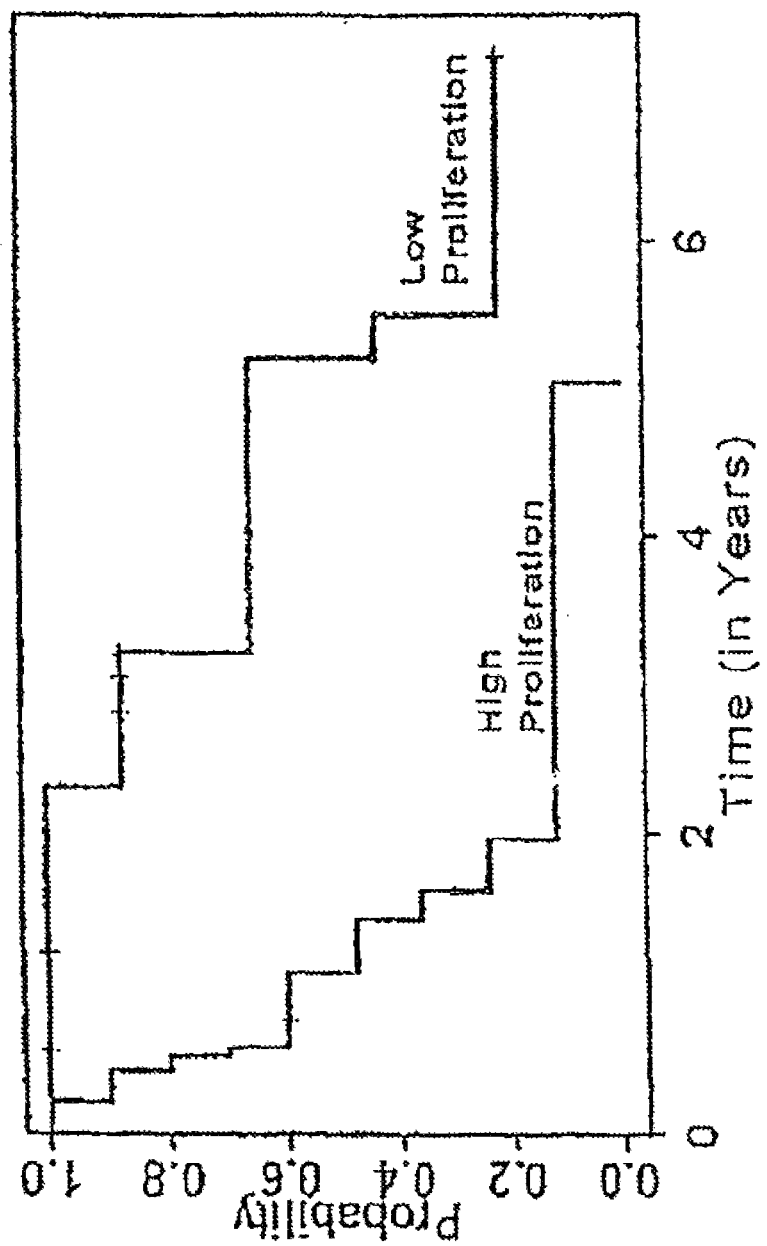
FIG. 13: Kaplan-Meier plot of survival in MCL samples based on survival predictor scores. 21 MCL samples were divided into two equivalent groups based on their survival predictor scores. The survival predictor scores were calculated by: 1.66*(proliferation gene expression signature value).

This model was associated with survival in a statistically significant manner (p=0.00018). To illustrate the significance of the model in predicting survival, the 21 MCL samples were divided into two equivalent groups based on their survival predictor scores. Those samples with survival predictor scores above the median were placed in the high proliferation group, while those with survival predictor scores below the median were placed in the low proliferation group. FIG. 13 illustrates the Kaplan Meier survival estimates for these two groups. Median survival for the high proliferation group was 1.07 years, while median survival for the low proliferation group was 5.18 years.

Example 10

Development of an MCL Survival Predictor Using Gene Expression Data from the Lymph Dx Microarray A set of 21 genes associated with proliferation and poor prognosis in MCL had been identified previously (Rosenwald 2003a). Of these 21 genes, only four were represented on the Lymph Dx microarray. In order to find a larger set of genes on the Lymph Dx microarray associated with survival in MCL, Lymphochip expression data (Rosenwald 2003a) was re-analyzed and another set of proliferation genes whose expression levels were correlated with poor survival in MCL were identified. Thirteen of these genes were represented on the Lymph Dx microarray (median expression>6 on $\log_2$ scale). These 13 genes are listed in Table 2379.

TABLE 2379

| Signature | UNIQID | Unigene ID Build 167 | Affymetrix probe set ID | GenBank Accession No. | Gene symbol |
|---|---|---|---|---|---|
| Proliferation | 1119294 | 156346 | 201292_at | NM_001067 | TOP2A |
| Proliferation | 1119729 | 164457 | 202338_at | NM_003258 | TK1 |
| Proliferation | 1120153 | 89497 | 203276_at | NM_005573 | LMNB1 |
| Proliferation | 1121276 | 24529 | 306394_at | NM_001274 | CHEK1 |
| Proliferation | 1123358 | 442658 | 209464_at | NM_004217 | AURKB |
| Proliferation | 1124178 | 446579 | 211969_at | NM_005348 | HSPCA |
| Proliferation | 1124563 | 249441 | 212533_at | NM_003390 | WEE1 |
| Proliferation | 1130799 | 233952 | 201114_x_at | NM_002792 | PSMA7 |
| Proliferation | 1131274 | 374378 | 201897_s_at | NM_001826 | CKS1B |
| Proliferation | 1131778 | 396393 | 202779_s_at | NM_014501 | UBE2S |
| Proliferation | 1132449 | 250822 | 204092_s_at | NM_003600 | STK6 |

TABLE 2379-continued

| Signature | UNIQID | Unigene ID Build 167 | Affymetrix probe set ID | GenBank Accession No. | Gene symbol |
|---|---|---|---|---|---|
| Proliferation | 1135229 | 367676 | 209932_s_at | NM_001948 | DUT |
| Proliferation | 1136585 | 80976 | 212022_s_at | NM_002417 | MKI67 |

The expression levels of the 13 genes listed in Table 2379 on the Lymph Dx microarray were transformed into the $\log_2$ scale and averaged to form a proliferation gene expression signature value. This was used to generate a survival predictor score using the following equation:

Survival predictor score=1.66*(proliferation gene expression signature value).

For the 21 MCL samples analyzed, the survival predictor score had a mean of 14.85 and a standard deviation of 1.13. Even in this limited sample set, the survival predictor score was significantly associated with prognosis (p=0.0049), with each unit increase in the score corresponding to a 2.7 fold increase in the relative risk of death. Data for all 21 samples is shown in Table 2380.

TABLE 2380

| Sample ID # | Proliferation signature value | Survival predictor score |
|---|---|---|
| MCL_1012 | 8.83 | 14.658 |
| MCL_1091 | 8.81 | 14.625 |
| MCL_1114 | 10.39 | 17.247 |
| MCL_1128 | 10.12 | 16.799 |
| MCL_1150 | 8.33 | 13.828 |
| MCL_1162 | 8.15 | 13.529 |
| MCL_1166 | 9.40 | 15.604 |
| MCL_1194 | 7.44 | 12.350 |
| MCL_885 | 8.68 | 14.409 |
| MCL_918 | 9.33 | 15.488 |
| MCL_924 | 8.35 | 13.861 |
| MCL_925 | 8.86 | 14.708 |
| MCL_926 | 8.14 | 13.512 |
| MCL_936 | 8.56 | 14.21 |
| MCL_939 | 9.14 | 15.172 |
| MCL_953 | 9.25 | 15.355 |
| MCL_956 | 9.35 | 15.521 |
| MCL_964 | 9.74 | 16.168 |
| MCL_966 | 8.76 | 14.542 |
| MCL_968 | 9.10 | 15.106 |
| MCL_970 | 9.27 | 15.388 |

Figure 14:
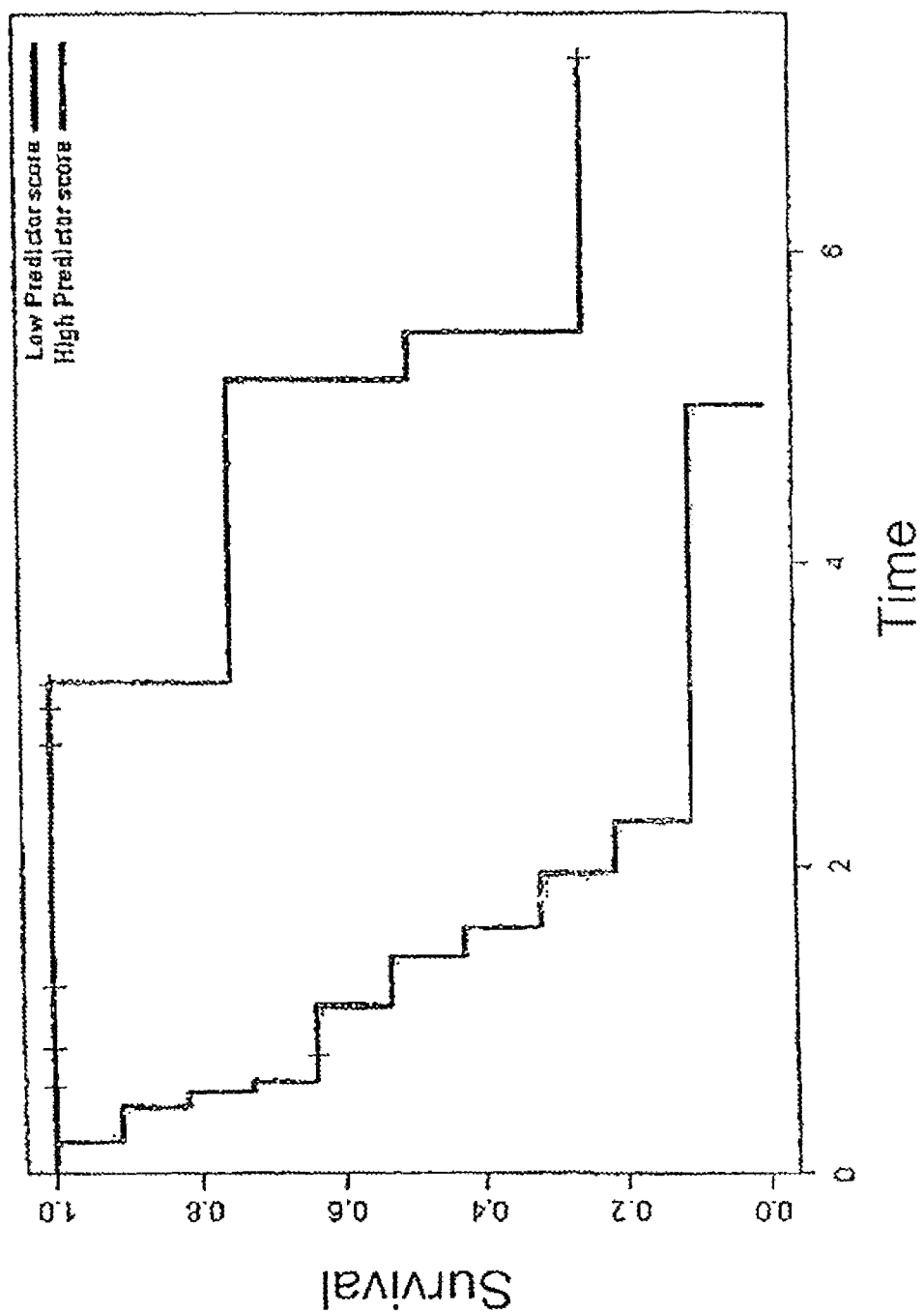
FIG. 14: Kaplan-Meier plot of survival in MCL samples based on survival predictor scores. 21 MCL samples were divided into two equivalent groups based on their survival predictor scores. The survival predictor scores were calculated by: 1.66*(proliferation gene expression signature value).

To illustrate the significance of the model in predicting survival, the 21 MCL samples were divided into two equivalent groups based on their survival predictor scores. Those samples with survival predictor scores above the median were placed in the high proliferation group, while those with survival predictor scores below the median were placed in the low proliferation group. FIG. 14 illustrates the Kaplan Meier survival estimates for these two groups.

Example 11

Identification of Lymphoma Samples as MCL Based on Bayesian Analysis of Gene Expression Data from Affymetrix U133A and U133B Microarrays A statistical method based on Bayesian analysis was developed to distinguish MCL samples from samples belonging to other lymphoma types based on gene expression profiling. This method was developed using the gene expression data obtained in Example 1 for the following lymphoma types: ABC, GCB, PMBL, BL, FH, FL, MALT, MCL, PTLD, SLL, and splenic marginal zone lymphoma (splenic). Tables 1707-1741 (discussed in Example 1) provide gene expression data for samples within each of these lymphoma types, including the expression level of each gene and the difference in expression of each gene between types. Tables 1710, 1715, and 1723 (corresponding to FL, MCL, and DLBCL, respectively) include the correlation between expression of each gene and survival.

To determine the lymphoma type of a sample, a series of predictor models are generated. Each predictor model calculates the probability that the sample belongs to a first lymphoma type rather than a second lymphoma type. A method was developed to determine whether a sample was MCL, or one of the following lymphoma types: ABC, BL, FH, FL, GCB, MALT, PMBL, PTLD, SLL, or splenic. This method required ten different predictor models, each designed to determine whether the sample belonged to MCL or one of the other ten lymphoma types (e.g., MCL vs. ABC, MCL vs. BL, etc.).

Several of the lymphoma samples analyzed displayed a tendency towards elevated or reduced expression of genes from the lymph node and proliferation gene expression signatures. These genes are likely to be highly differentially expressed between the lymphoma types, but they do not serve as good predictor genes because they are often variably expressed within a single lymphoma type. For this reason, any gene that displayed a correlation with the proliferation or lymph node signatures was eliminated from consideration.

For each lymphoma type pair (e.g., MCL vs. ABC, MCL vs. FL, etc.), 20 genes were identified that exhibited the greatest difference in expression between MCL and the second lymphoma type according to a Student's t-test. The choice to use 20 genes was arbitrary. For each sample X, the 20 genes were used to generate a linear predictor score (LPS) according to the following formula:

$$LPS(X) = \sum_{j=1}^{20} t_j X_j,$$

where $X_j$ is the expression of gene j in sample X and $t_j$ is the t-statistic for the difference in expression of gene j between a first lymphoma type and a second lymphoma type. This is merely one method for generating an LPS. Others methods include linear discriminant analysis (Dudoit 2002), support vector machines (Furey 2000), or shrunken centroids (Tibshirani 2002). In addition, there is no requirement that a t-statistic be used as the scaling factor.

Figure 15:
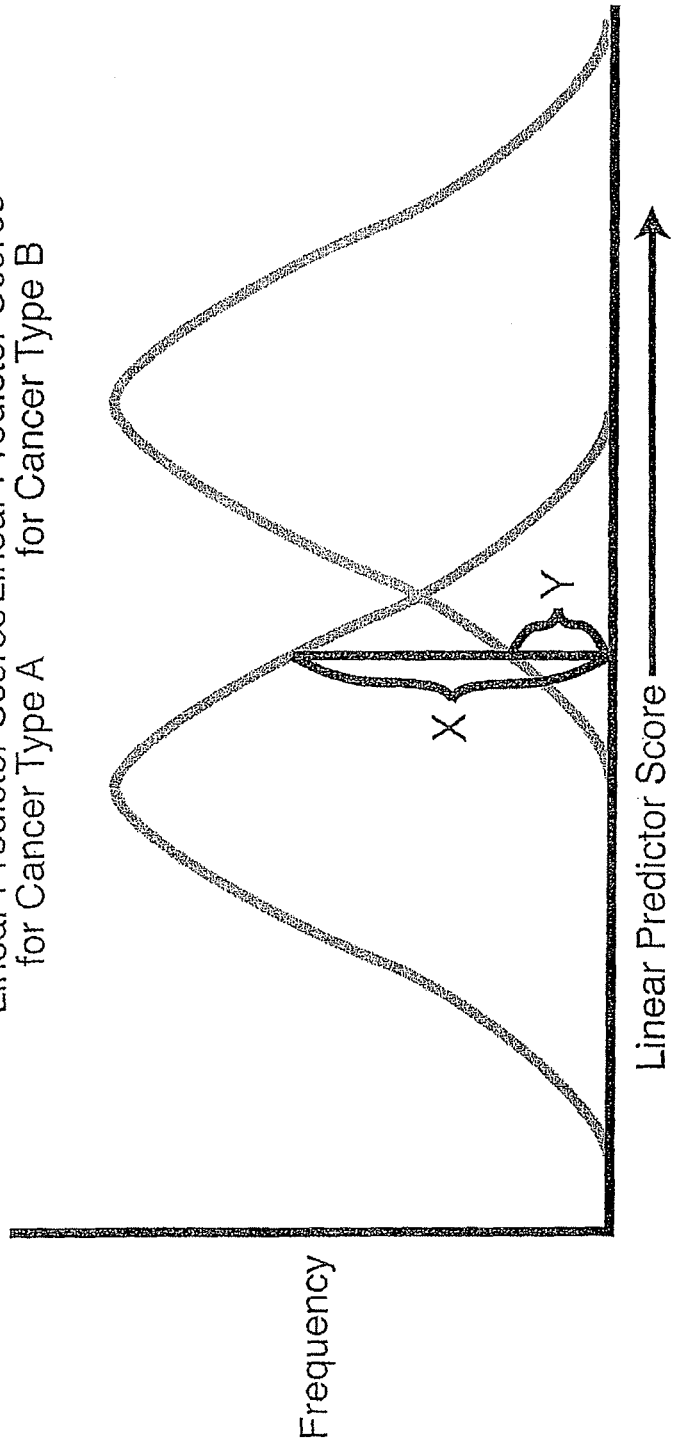
FIG. 15: Predicting lymphoma type using Bayesian analysis. Bayes' rule can be used to determine the probability that an unknown sample belongs to a first lymphoma type rather than a second lymphoma type. A linear predictor score is generated for the sample, and the probability that the sample belongs to the first lymphoma type is determined based on the distribution of linear predictor scores within the first and second lymphoma type.

After an LPS had been formulated for each lymphoma sample, the mean and standard deviation of these LPS's was calculated for each lymphoma type. For a new sample X, Bayes' rule can be used to estimate the probability that the sample belongs to a first lymphoma type rather than a second lymphoma type (FIG. 15). In this example, Bayes' rule was used to calculate the probability q that sample X was MCL rather than a second lymphoma type using the following equation:

$$q(X \text{ is type } 1) = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

where type 1 is MCL, type 2 is one of the other nine lymphoma types, $\phi(x; \mu, \sigma)$ is the normal density function with mean $\mu$ and standard deviation $\sigma$, $\hat{\mu}_1$ and $\hat{\sigma}_1$ are the sample mean and variance of the LPS values for lymphoma type 1, and $\hat{\mu}_2$ and $\hat{\sigma}_2$ are the sample mean and variance of the LPS values for lymphoma type 2.

This method was used to develop ten predictor models, one for each pairing of MCL and a second lymphoma type. A sample was classified as MCL if each of the ten predictors generated at least a 90% probability that the sample was MCL. If any of the ten predictors indicated a probability of less than 90%, the sample was classified as non-MCL.

The 10 sets of 20 genes that were included in these models and the t-statistics for each gene are presented in Tables 2381-2490.

TABLE 2381

MCL vs. ABC predictor genes

| UNIQID | Gene name | Scale Factor |
|---|---|---|
| 1103711 | *Homo sapiens* cDNA FLJ11833 fis, clone HEMBA1006579. | 17.88496416 |
| 1133111 | PDE9A—phosphodiesterase 9A | 17.61579873 |
| 1137987 | PLXNB1—plexin B1 | 17.47030156 |
| 1132835 | SOX11—SRY (sex determining region Y)-box 11 | 16.89404131 |
| 1109505 | *Homo sapiens*, Similar to LOC168058, clone MGC: 39372 IMAGE: 5089466, mRNA, complete cds | 15.78111902 |
| 1139054 | LOC58486—transposon-derived Buster1 transposase-like protein | 15.77800815 |
| 1119361 | TIA1—TIA1 cytotoxic granule-associated RNA binding protein | 15.68070962 |
| 1115226 | KIAA1683—KIAA1683 protein | 15.67954057 |
| 1101211 | *Homo sapiens* cDNA: FLJ21960 fis, clone HEP05517. | 15.4183527 |
| 1118963 | *Homo sapiens* cDNA FLJ35653 fis, clone SPLEN2013690. | 15.36802586 |
| 1096503 | GL012—hypothetical protein GL012 | 14.64776335 |
| 1127849 | SNN—stannin | 14.54859775 |
| 1099204 | *Homo sapiens* mRNA; cDNA DKFZp586K1922 (from clone DKFZp586K1922) | 14.32724822 |
| 1098840 | C3orf6—chromosome 3 open reading frame 6 | 14.10346944 |
| 1139444 | RABL2B—RAB, member of RAS oncogene family-like 2B | 14.10016196 |
| 1106855 | KIAA1909—KIAA1909 protein | 13.9504946 |
| 1126695 | KIAA0484—KIAA0484 protein | 13.92285415 |
| 1120137 | FCGBP—Fc fragment of IgG binding protein | 13.86147896 |
| 1133011 | TMSNB—thymosin, beta, identified in neuroblastoma cells | 13.74377784 |
| 1133192 | GRP3—guanine nucleotide exchange factor for Rap1 | −17.09085725 |

TABLE 2382

MCL vs. BL predictor genes

| UNIQID | Gene name | Scale Factor |
|---|---|---|
| 1120900 | EPHB6—EphB6 | 13.43582327 |
| 1112061 | *Homo sapiens* cDNA FLJ90513 fis, clone NT2RP3004355. | 12.73065392 |
| 1109505 | *Homo sapiens*, Similar to LOC168058, clone MGC: 39372 IMAGE: 5089466, mRNA, complete cds | 12.63674985 |
| 1133099 | DNASE1L3—deoxyribonuclease I-like 3 | 12.43333984 |
| 1106855 | KIAA1909—KIAA1909 protein | 12.32623489 |
| 1110070 | ESTs | 12.05416064 |
| 1121739 | ZNF135—zinc finger protein 135 (clone pHZ-17) | 11.90460363 |
| 1098840 | C3orf6—chromosome 3 open reading frame 6 | 11.90309143 |
| 1132833 | SOX11—SRY (sex determining region Y)-box 11 | 11.60864812 |
| 1121693 | KIAA0450—KIAA0450 gene product | 11.33634052 |
| 1123760 | ILT7—leukocyte immunoglobulin-like receptor, subfamily A (without TM domain), member 4 | 11.18744726 |
| 1125964 | KIAA0792—KIAA0792 gene product | 11.14762675 |
| 1112306 | ESTs | 11.02434114 |
| 1096070 | DNMT3A—DNA (cytosine-5-)-methyltransferase 3 alpha | 10.98991879 |
| 1129943 | *Homo sapiens*, similar to Zinc finger protein 85 (Zinc finger protein HPF4) (HTF1), clone IMAGE: 3352451, mRNA | 10.72494956 |
| 1118749 | PRKWNK1—protein kinase, lysine deficient 1 | 10.64623382 |
| 1098954 | FLJ13204—hypothetical protein FLJ13204 | 10.46164401 |
| 1134749 | PRKCBP1—protein kinase C binding protein 1 | 10.40948157 |
| 1131860 | BIN1—bridging integrator 1 | 10.31084561 |
| 1123148 | TGFBR2—transforming growth factor, beta receptor II (70/80 kDa) | 10.2956213 |

TABLE 2383

| | MCL vs. FH predictor genes | |
|---|---|---|
| UNIQID | Gene name | Scale Factor |
| 1132834 | SOX11—SRY (sex determining region Y)-box 11 | 24.3531072 |
| 1100873 | ESTs | 16.83342764 |
| 1109603 | ESTs | 13.02401995 |
| 1139411 | OSBPL10—oxysterol binding protein-like 10 | 12.54369577 |
| 1106855 | KIAA1909—KIAA1909 protein | 12.10316361 |
| 1125193 | CNR1—cannabinoid receptor 1 (brain) | 12.070579 |
| 1137450 | ALOX5—arachidonate 5-lipoxygenase | 11.74571823 |
| 1100258 | KIAA1384—KIAA1384 protein | 11.60998697 |
| 1133167 | ZFD25—zinc finger protein (ZFD25) | 11.52931491 |
| 1136831 | PPFIBP2—PTPRF interacting protein, binding protein 2 (liprin beta 2) | 11.50062692 |
| 1138222 | NA | 10.99674674 |
| 1099437 | *Homo sapiens* mRNA; cDNA DKFZp667B1913 (from clone DKFZp667B1913) | 10.90797288 |
| 1140236 | SPAP1—SH2 domain containing phosphatase anchor protein 1 | 10.77082801 |
| 1114109 | DCAL1—dendritic cell-associated lectin-1 | 10.65867119 |
| 1098277 | PRICKLE1—prickle-like 1 (*Drosophila*) | 10.55457068 |
| 1135138 | CD24—CD24 antigen (small cell lung carcinoma cluster 4 antigen) | 10.41999962 |
| 1103304 | *Homo sapiens* clone CDABP0095 mRNA sequence | −10.46625233 |
| 1128460 | RDGBB—retinal degeneration B beta | −10.91106245 |
| 1121953 | KIAA0125—KIAA0125 gene product | −11.22466255 |
| 1129281 | C14orf110—chromosome 14 open reading frame 110 | −15.54465448 |

TABLE 2384

| | MCL vs. FL predictor genes | |
|---|---|---|
| UNIQID | Gene name | Scale Factor |
| 1132835 | SOX11—SRY (sex determining region Y)-box 11 | 22.14208817 |
| 1096070 | DNMT3A—DNA (cytosine-5-)-methyltransferase 3 alpha | 20.53740132 |
| 1103711 | *Homo sapiens* cDNA FLJ11833 fis, clone HEMBA1106579. | 20.49880004 |
| 1137987 | PLXNB1—plexin B1 | 18.38081568 |
| 1109505 | *Homo sapiens*, Similar to LOC168058, clone MGC: 39372 IMAGE: 5089466, mRNA, complete cds | 17.17812448 |
| 1098840 | C3orf6—chromosome 3 open reading frame 6 | 16.32703666 |
| 1130926 | C5orf13—chromosome 5 open reading frame 13 | 15.34261878 |
| 1096396 | SPG3A—spastic paraplegia 3A (autosomal dominant) | 14.75437736 |
| 1132734 | COL9A3—collagen, type IX, alpha 3 | 14.684583 |
| 1139393 | OPN3—opsin 3 (encephalopsin, panopsin) | 14.39118445 |
| 1115537 | LOC84518—protein related with psoriasis | 14.18446144 |
| 1102215 | *Homo sapiens* cDNA FLJ11666 fis, clone HEMBA1004672. | 14.16246426 |
| 1124585 | *Homo sapiens* cDNA: FLJ21930 fis, clone HEP04301, highly similar to HSU90916 Human clone 23815 mRNA sequence. | −14.33315955 |
| 1137561 | HOXA1—homeo box A1 | −15.38404642 |
| 1100581 | *Homo sapiens* mRNA; cDNA DKFZp667A1115 (from clone DKFZp667A1115) | −15.91666634 |
| 1124646 | KIAA0084—KIAA0084 protein | −16.40577696 |
| 1114543 | ESTs | −17.60167863 |
| 1120090 | BCL6—B-cell CLL/lymphoma 6 (zinc finger protein 51) | −17.63091181 |
| 1123731 | RGS13—regulator of G-protein signalling 13 | −22.41602151 |
| 1133192 | GRP3—guanine nucleotide exchange factor for Rap1 | −27.28308723 |

TABLE 2385

| | MCL vs. GCB predictor genes | |
|---|---|---|
| UNIQID | Gene name | Scale Factor |
| 1098840 | C3orf6—chromosome 3 open reading frame 6 | 22.26488562 |
| 1132835 | SOX11—SRY (sex determining region Y)-box 11 | 17.76179754 |
| 1137987 | PLXNB1—plexin B1 | 16.86845147 |
| 1098954 | FLJ13204—hypothetical protein FLJ13204 | 16.65023669 |
| 1103711 | *Homo sapiens* cDNA FLJ11833 fis, clone HEMBA1006579. | 15.64719784 |

TABLE 2385-continued

MCL vs. GCB predictor genes

| UNIQID | Gene name | Scale Factor |
|---|---|---|
| 1096070 | DNMT3A—DNA (cytosine-5-)methyltransferase 3 alpha | 15.22540494 |
| 1139393 | OPN3—opsin 3 (encephalopsin, panopsin) | 14.64030565 |
| 1127849 | SNN—stannin | 14.28242206 |
| 1098156 | Human HeLa mRNA isolated as a false positive in a two-hybrid-screen. | 14.00049272 |
| 1128845 | FLJ20174—hypothetical protein FLJ20174 | 13.96064416 |
| 1129943 | *Homo sapiens*, similar to Zinc finger protein 85 (Zinc finger protein HPF4) (HTF1), clone IMAGE: 3352451, mRNA | 13.85404507 |
| 1140116 | DKFZP564B116—hypothetical protein DKFZp564B1162 | 13.81464172 |
| 1106855 | KIAA1909—KIAA1909 protein | 13.74521849 |
| 1120900 | EPHB6—EphB6 | 13.46567004 |
| 1127371 | *Homo sapiens* cDNA FLJ14046 fis, clone HEMBA1006461. | 13.45735668 |
| 1119361 | TIA1—TIA1 cytotoxic granule-associated RNA binding protein | 13.37376559 |
| 1120854 | EDG1—endothelial differentiation, sphingolipid G-protein-coupled receptor, 1 | 13.1047657 |
| 1098277 | PRICKLE1—prickle-like 1 (*Drosophila*) | 13.04993076 |
| 1140127 | TRIM34—tripartite motif-containing 34 | 12.66260609 |
| 1100581 | *Homo sapiens* mRNA; cDNA DKFZp667A1115 (from clone DKFZp667A1115) | −12.81251689 |

TABLE 2386

MCL vs. MALT predictor genes

| UNIQID | Gene name | Scale Factor |
|---|---|---|
| 1132834 | SOX11—SRY (sex determining region Y)-box 11 | 20.7489202 |
| 1101987 | KIAA1909—KIAA1909 protein | 10.78991326 |
| 1100873 | ESTs | 10.11845036 |
| 1130764 | HNRPA0—heterogeneous nuclear ribonucleoprotein A0 | 9.432459453 |
| 1102178 | *Homo sapiens*, Similar to thymosin, beta, identified in neuroblastoma cells, clone MGC: 39900 IMAGE: 5247537, mRNA, complete cds | 9.035605572 |
| 1098277 | PRICKLE1—prickle-like 1 (*Drosophila*) | 9.003360784 |
| 1130926 | C5orf13—chromosome 5 open reading frame 13 | 8.712830747 |
| 1098694 | LOC112868—hypothetical protein LOC112868 | 8.309789856 |
| 1103711 | *Homo sapiens* cDNA FLJ11833 fis, clone HEMBA1006579. | 8.248526605 |
| 1138099 | NA | 8.107440225 |
| 1120854 | EDG1—endothelial differentiation, sphingolipid G-protein-coupled receptor, 1 | 8.045872672 |
| 1102215 | *Homo sapiens* cDNA FLJ11666 fis, clone HEMBA1004672. | 8.032351578 |
| 1121739 | ZNF135—zinc finger protein 135 (clone pHZ-17) | 8.020919565 |
| 1096070 | DNMT3A—DNA (cytosine-5-)-methyltransferase 3 alpha | 7.964477216 |
| 1101211 | *Homo sapiens* cDNA: FLJ21960 fis, clone HEP05517. | 7.738742472 |
| 1120825 | CHL1—cell adhesion molecule with homology to L1CAM (close homolog of L1) | 7.516130116 |
| 1099437 | *Homo sapiens* mRNA; cDNA DKFZp667B1913 (from clone DKFZp667B1913) | 7.209041652 |
| 1096503 | GL012—hypothetical protein GL012 | 7.171540413 |
| 1135927 | LILRA2—leukocyte immunoglobulin-like receptor, subfamily A (with TM domain), member 2 | 7.134470829 |
| 1120645 | FADS3—fatty acid desaturase 3 | 7.039952979 |

TABLE 2387

MCL vs. PMBL predictor genes

| UNIQID | Gene name | Scale Factor |
|---|---|---|
| 1132834 | SOX11—SRY (sex determining region Y)-box 11 | 28.17593839 |
| 1100873 | ESTs | 17.90004832 |
| 1096503 | GL012—hypothetical protein GL012 | 17.43982729 |
| 1098840 | C3orf6—chromosome 3 open reading frame 6 | 17.37421052 |
| 1124734 | NA | 16.73821457 |
| 1135102 | PRKCB1—protein kinase C, beta 1 | 16.67436366 |
| 1103711 | *Homo sapiens* cDNA FLJ11833 fis, clone HEMBA1006579. | 16.57202026 |

TABLE 2387-continued

MCL vs. PMBL predictor genes

| UNIQID | Gene name | Scale Factor |
|---|---|---|
| 1140416 | TOSO—regulator of Fas-induced apoptosis | 15.64802242 |
| 1121757 | ADRB2—adrenergic, beta-2-, receptor, surface | 15.57336633 |
| 1140236 | SPAP1—SH2 domain containing phosphatase anchor protein 1 | 15.20264513 |
| 1099140 | ESTs, Moderately similar to hypothetical protein FLJ20378 [Homo sapiens] [H. sapiens] | 15.11929571 |
| 1099549 | ESTs | 14.92883027 |
| 1139054 | LOC58486—transposon-derived Buster1 transposase-like protein | 14.63422275 |
| 1138818 | ILF3—interleukin enhancer binding factor 3, 90 kDa | 14.50621028 |
| 1109444 | ESTs, Highly similar to IL24_HUMAN Interleukin-24 precursor (Suppression of tumorigenicity 16 protein) (Melanoma differentiation associated protein 7) (MDA-7) [H. sapiens] | 14.20430672 |
| 1124534 | KIAA0553—KIAA0553 protein | 14.18537487 |
| 1098277 | PRICKLE1—prickle-like 1 (Drosophila) | 13.98526258 |
| 1131687 | TLK1—tousled-like kinase 1 | 13.97468703 |
| 1125112 | PLCL2—phospholipase C-like 2 | 13.85714318 |
| 1125397 | Homo sapiens cDNA FLJ33389 fis, clone BRACE2006871. | 13.85049805 |

TABLE 2388

MCL vs. PTLD predictor genes

| UNIQID | Gene name | Scale Factor |
|---|---|---|
| 1109603 | ESTs | 19.95553782 |
| 1138222 | NA | 15.95397369 |
| 1135138 | CD24—CD24 antigen (small cell lung carcinoma cluster 4 antigen) | 15.89198725 |
| 1134230 | RASGRP2—RAS guanyl releasing protein 2 (calcium and DAG-regulated) | 15.80452978 |
| 1139411 | OSBPL10—oxysterol binding protein-like 10 | 14.32818885 |
| 1140416 | TOSO—regulator of Fas-induced apoptosis | 13.89685188 |
| 1132834 | SOX11—SRY (sex determining region Y)-box 11 | 13.78424818 |
| 1121739 | ZNF135—zinc finger protein 135 (clone pHZ-17) | 13.02195529 |
| 1098156 | Human HeLa mRNA isolated as a false positive in a two-hybrid-screen. | 12.95032505 |
| 1099270 | Homo sapiens cDNA FLJ30555 fis, clone BRAWH2003818. | 12.7877735 |
| 1139012 | FLJ20373—hypothetical protein FLJ20373 | 12.70176225 |
| 1120854 | EDG1—endothelial differentiation, sphingolipid G-protein-coupled receptor, 1 | 12.25264341 |
| 1120985 | KIAA0053—KIAA0053 gene product | 12.04626201 |
| 1115952 | LOC146517—hypothetical protein LOC146517 | 11.96299478 |
| 1120825 | CHL1—cell adhesion molecule with homology to L1CAM (close homolog of L1) | 11.82402907 |
| 1131636 | SPOCK2—sparc/osteonectin, cwcv and kazal-like domains proteoglycan (testican) 2 | 11.80417657 |
| 1136706 | MYT1—myelin transcription factor 1 | 11.74962191 |
| 1113560 | Homo sapiens, clone IMAGE: 5725893, mRNA | 11.72049882 |
| 1133851 | P4HA1—procollagen-proline, 2-oxoglutarate 4-dioxygenase (proline 4-hydroxylase), alpha polypeptide I | −12.59876059 |
| 1137459 | BCAT1—branched chain aminotransferase 1, cytosolic | −14.00465411 |

TABLE 2389

MCL vs. SLL predictor genes

| UNIQID | Gene name | Scale Factor |
|---|---|---|
| 1132834 | SOX11—SRY (sex determining region Y)-box 11 | 23.59602107 |
| 1101987 | KIAA1909—KIAA1909 protein | 14.50254794 |
| 1103711 | Homo sapiens cDNA FLJ11833 fis, clone HEMBA1006579. | 13.31375894 |
| 1096070 | DNMT3A—DNA (cytosine-5-)-methyltransferase 3 alpha | 12.37453972 |
| 1130926 | C5orf13—chromosome 5 open reading frame 13 | 11.27840239 |
| 1120645 | FADS3—fatty acid desaturase 3 | 11.14057287 |

TABLE 2389-continued

MCL vs. SLL predictor genes

| UNIQID | Gene name | Scale Factor |
|---|---|---|
| 1138099 | NA | 10.92729287 |
| 1097887 | KIAA0303—KIAA0303 protein | 10.37913127 |
| 1099941 | ESTs | 10.33953409 |
| 1130373 | KIAA0303—KIAA0303 protein | 10.01524528 |
| 1110957 | SYNE2—spectrin repeat containing, nuclear envelope 2 | 9.865436185 |
| 1130320 | ESTs | 9.807091644 |
| 1124373 | LPIN1—lipin 1 | 9.024985551 |
| 1128813 | KREMEN2—kringle containing transmembrane protein 2 | 8.903791941 |
| 1131130 | MARCKS—myristoylated alanine-rich protein kinase C substrate | 8.688979176 |
| 1120825 | CHL1—cell adhesion molecule with homology to L1CAM (close homolog of L1) | 8.685132271 |
| 1119752 | BASP1—brain abundant, membrane attached signal protein 1 | 8.663402838 |
| 1131854 | GCLC—glutamate-cysteine ligase, catalytic subunit | −8.761521136 |
| 1105801 | *Homo sapiens* mRNA; cDNA DKFZp686H1529 (from clone DKFZp686H1529) | −8.828675125 |
| 1097824 | MAP2—microtubule-associated protein 2 | −9.345688564 |

TABLE 2390

MCL vs. splenic predictor genes

| UNIQID | Gene name | Scale Factor |
|---|---|---|
| 1106855 | KIAA1909—KIAA1909 protein | 14.48278638 |
| 1121739 | ZNF135—zinc finger protein 135 (clone pHZ-17) | 11.95918572 |
| 1111850 | *Homo sapiens* cDNA FLJ36977 fis, clone BRACE2006344. | 11.13464157 |
| 1098024 | KIAA1972—KIAA1972 protein | 10.10869886 |
| 1130764 | HNRPA0—heterogeneous nuclear ribonucleoprotein A0 | 10.06898534 |
| 1135342 | SHOX2—short stature homeobox 2 | 9.565884385 |
| 1097218 | MGC45400—hypothetical protein MGC45400 | 9.187725705 |
| 1117193 | RINZF—zinc finger protein RINZF | 9.12522795 |
| 1139564 | PSMD10—proteasome (prosome, macropain) 26S subunit, non-ATPase, 10 | 9.066714773 |
| 1132834 | SOX11—SRY (sex determining region Y)-box 11 | 8.908574745 |
| 1131130 | MARCKS—myristoylated alanine-rich protein kinase C substrate | 8.732921026 |
| 1131756 | PDCD4—programmed cell death 4 (neoplastic transformation inhibitor] | 8.441424593 |
| 1102187 | DKFZp586C102—hypothetical protein DKFZp586C1021 | 8.391861029 |
| 1098195 | DKFZp762C111—hypothetical protein DKFZp762C1112 | 8.349839204 |
| 1101211 | *Homo sapiens* cDNA: FLJ21960 fis, clone HEP05517. | 8.337208237 |
| 1136673 | GNAS—GNAS complex locus | 8.254076655 |
| 1139116 | USP16—ubiquitin specific protease 16 | 8.179384251 |
| 1098694 | LOC112868—hypothetical protein LOC112868 | 7.935903681 |
| 1120519 | WWP2—Nedd-4-like ubiquitin-protein ligase | −7.881202253 |
| 1114916 | FLJ13993—hypothetical protein FLJ13993 | −8.33683119 |

With so many candidate predictor genes being utilized, it is possible to generate a predictor model that accurately predicts every element of a training set but fails to perform on an independent sample. This occurs because the model incorporates and "learns" the individual characteristics of each sample in the training set. Leave-one-out cross-validation was used to verify that the prediction models generated above would work on independent samples that the models had not encountered previously. In this cross-validation method, a single sample is removed from the training set, and the predictor is developed again using the remaining data. The resulting model is then used to predict the sample that was removed. This method is repeated with each individual sample taken out. Since no sample is predicted from a model that includes that sample, this method provides an unbiased estimate of predictor accuracy.

When the predictors developed above were evaluated by leave-one-out cross-validation, all but one of the 21 MCL samples were correctly identified as MCL and none of the 489 non-MCL samples were mistakenly identified as MCL.

Example 12

Identification of Lymphoma Samples as MCL Based on Bayesian Analysis of Gene Expression Data from a Lymphochip Microarray Lymphoma samples with morphology consistent with MCL were identified by pathological review. Since t(11;14) translocation and cyclin D1 overexpression have been consistently associated with MCL, cyclin D1 mRNA levels were measured in each sample by quantitative RT-PCR. Of the 101 samples analyzed, 92 expressed cyclin D1 mRNA. These 92 samples, which were deemed the "core group" of MCLs, were divided into a training set and a validation set. Gene expression was measured in all 101 samples using a Lymphochip microarray (Alizadeh 1999). For comparison, gene expression was measured in 20 samples identified as SLL. In addition, MCL expression data was compared to expression data obtained previously for GCB (134 cases) and ABC (83 cases) (Rosenwald 2002). Several thousand genes were differentially expressed between cyclin D1-positive MCL and the other lymphoma types with high statistical significance (p<0.001). A complete listing of these genes is available at Rosenwald et al., Cancer Cell, 3: 185-197 (2003), which is referenced therein at page 194 and which is hosted by the Lymphoma/Leukemia Molecular Profiling Project Gateways at the National Institute of Health web site.

Three different binary predictor models were developed: MCL vs. SLL, MCL vs. GCB, and MCL vs. ABC. Each of these models was designed to calculate the probability that a sample was MCL rather than the other lymphoma type in the pair. For each pair, the genes that were most differentially expressed between MCL and the other lymphoma type in the pair were identified, and the difference in expression between the lymphoma types was quantified using a Student's t-test. An LPS was then calculated for each sample using the following formula:

$$LPS(X) = \sum_{j \in G} t_j X_j,$$

where $X_j$ is the expression of gene j in sample X and $t_j$ is the t-statistic for the difference in expression of gene j between the two lymphoma types in the pair. Cyclin D1 was excluded from the calculation of LPS so that the model could be used to identify potential MCL cases that were cyclin D1 negative.

After an LPS had been formulated for each lymphoma sample, the mean and standard deviation of these LPS's was calculated for each lymphoma type. For a new sample X, Bayes' rule can be used to estimate the probability q that the sample belongs to MCL rather than the second lymphoma type in the pair using the following equation:

$$q(X \text{ is } MCL) = \frac{\phi(LPS(X); \hat{\mu}_{MCL}, \hat{\sigma}_{MCL})}{\phi(LPS(X); \hat{\mu}_{MCL}, \hat{\sigma}_{MCL}) + \phi(LPS(X); \hat{\mu}_2, \hat{\sigma}_2)}$$

where $\phi(x; \mu, \sigma)$ is the normal density function with mean $\mu$ and standard deviation $\sigma$, $\hat{\mu}_{MCL}$ and $\hat{\sigma}_{MCL}$ are the sample mean and variance of the LPS values for MCL, and $\hat{\mu}_2$ and $\hat{\sigma}_2$ are the sample mean and variance of the LPS values for the second lymphoma type of the pair. A cut-off point of 90% was selected for assigning a sample to a particular lymphoma type. Every sample in the training set was classified correctly using this model (FIG. 16). When applied to the validation set, the model correctly classified 98% of the cyclin D1-positive MCL cases as MCL (FIG. 16).

This diagnostic test was applied to nine lymphoma cases that were morphologically consistent with MCL, but negative for cyclin D1 expression. Seven of these samples were classified as MCL, one was classified as GCB, and one was not assigned to any lymphoma type because none of the pairs generated a probability of 90% or greater.

Example 13

Classification of DLBCL Samples Based on Bayesian Analysis of Gene Expression Data from the Lymphochip Microarray A statistical method to classify DLBCL samples based on Bayesian analysis was developed using gene expression data obtained using the Lymphochip cDNA microarray (Rosenwald 2002). This data is available at http://llmpp.nih.gov/DLBCL. The data was divided into two sets: a training set used to create and optimize the prediction model, and a validation set to evaluate the performance of the model. The training set consisted of 42 ABC DLBCL samples and 67 GCB DLBCL samples, while the validation set consisted of 41 ABC DLBCL samples, 67 GCB DLBCL samples, and 57 type 3 DLBCL samples (Shipp 2002).

Genes that were listed as present on >50% of the samples were identified, and the signal value for these genes on each microarray was normalized to 1,000. After normalization, all signal values under 50 were set to 50. A $\log_2$ transformation was then performed on all the signal values.

An LPS for distinguishing between two lymphoma types was calculated for each sample X in the training set using an equation:

$$LPS(X) = \sum_j t_j X_j,$$

where $X_j$ represents the expression level of gene j and $t_j$ is a scaling factor whose value depends on the difference in expression of gene j between the two lymphoma types. The scaling factor used in this example was the t-statistic generated by a t test of the difference in gene j expression between two lymphoma types. Only those genes with the largest t-statistics were included when calculating the LPS for each sample. The list of genes used to generate the LPS was narrowed further by including only those genes that were most variably expressed within the training set. Only genes in the top third with respect to variance were included. Genes that displayed a correlation with proliferation or lymph node signatures (Shaffer 2001; Rosenwald 2002) were eliminated from consideration, because these genes are often variably expressed within samples from a single lymphoma type (Rosenwald 2002).

Figure 17:
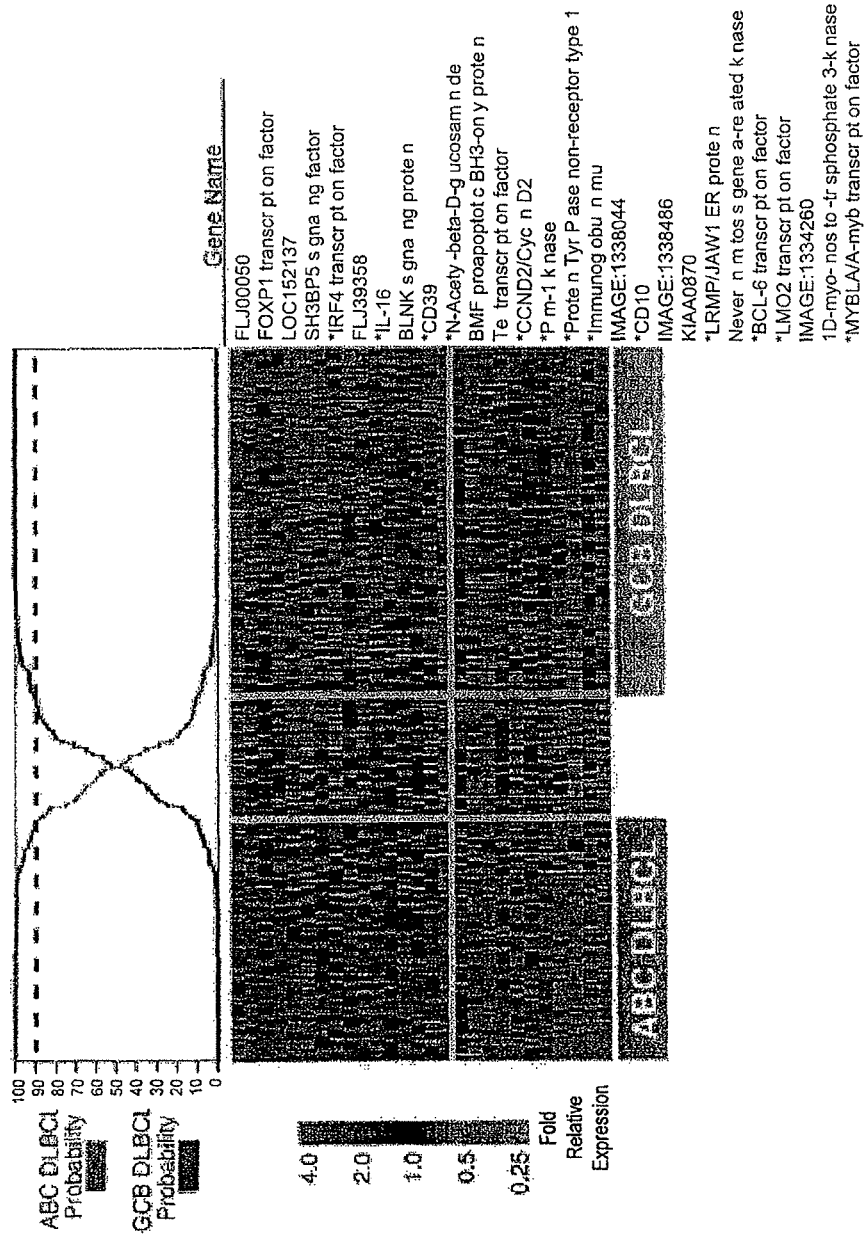
FIG. 17: Gene expression-based identification of DLBCL. Expression levels for 27 genes in a subgroup predictor are shown for 274 DLBCL samples. Expression levels are depicted according to the scale shown at the left. The 14 genes used to predict the DLBCL subgroups in the Affymetrix data set are indicated with asterisks. The probabilities that the DLBCL samples belong to the ABC or GCB subtypes are graphed at the top, and the DLBCL cases are arranged accordingly. Cases belonging to either ABC or GCB with 90% or greater probability are indicated.

Since the LPS is a linear combination of gene expression values, its distribution within each lymphoma type should be approximately normal, provided that it includes a sufficient number of genes and the correlation structure of those genes is not extreme. The mean and variance of these normal distributions within a lymphoma type can then be estimated from the combined LPS's of all samples within the type. The LPS distribution of two lymphoma types can be used to estimate the probability that a new sample belongs to one of the types using Bayes' rule. The probability q that a sample Y belongs to lymphoma type 1 can be determined by an equation:

$$q(Y \text{ is subtype } 1) = \frac{\phi(LPS(Y); \hat{\mu}_1, \hat{\sigma}_1)}{\phi(LPS(Y); \hat{\mu}_1, \hat{\sigma}_1) + \phi(LPS(Y); \hat{\mu}_2, \hat{\sigma}_2)}$$

where $\phi(x; \mu, \sigma)$ is the normal density function with mean $\nu$ and standard deviation $\sigma$, $\hat{\mu}_1$ and $\hat{\sigma}_1$ are the sample mean and variance of the LPS values for lymphoma type 1, and $\hat{\mu}_2$ and $\hat{\sigma}_2$ are the sample mean and variance of the LPS values for lymphoma type 2. This calculation was used to determine the probability that each sample in the training set belonged to GCB or ABC. A sample was classified as a particular type if it had a 90% or greater probability of belonging to that type. The number of genes in the predictor model was optimized based on the accuracy with which the predictor classified samples into the ABC or GCB subtypes defined previously by hierarchical clustering (Rosenwald 2002). The final predictor incorporated 27 genes, and correctly classified 87% of the training set samples into the subtype to which they had been assigned by hierarchical clustering (FIG. 17). The genes included in the predictor are listed in Table 2391.

TABLE 2391

| UNIQID | Unigene ID Build 167 | Gene symbol |
|---|---|---|
| 19375 | 235860 | FOXP1 |
| 19346 | 109150 | SH3BP5 |
| 19227 | 193857 | LOC96597 |
| 16049 | 439852 | IGHM |
| 32529 | 55098 | C3orf6 |
| 24729 | 127686 | IRF4 |
| 24899 | 81170 | PIM1 |
| 19348 | NA | NA |
| 27565 | 444105 | ENTPD1 |
| 17227 | 170359 | IL16 |
| 26919 | 118722 | FUT8 |
| 24321 | 171262 | ETV6 |
| 29385 | 167746 | BLNK |
| 16858 | 376071 | CCND2 |
| 31801 | 386140 | BMF |
| 19234 | 418004 | PTPN1 |
| 26385 | 307734 | MME |
| 24361 | 388737 | NA |
| 24570 | 446198 | NA |
| 24904 | 18166 | KIAA0870 |
| 24429 | 155024 | BCL6 |
| 28224 | 387222 | NEK6 |
| 27673 | 124922 | LRMP |
| 24376 | 317970 | SERPINA11 |
| 17496 | 300592 | MYBL1 |
| 17218 | 283063 | LMO2 |
| 28338 | 78877 | ITPKB |

Since the samples used to estimate the distribution of the LPS's were the same samples used to generate the model, there was a possibility of overfitting. Overfitting would result in a model that indicates a larger separation between the LPS's of two lymphoma types than would be found in independent data. To ensure that overfitting was not taking place, the model was tested on the validation set. The reproducibility of the predictor model was verified by its ability to correctly classify 88% of the samples in the validation set (FIG. 18). Interestingly, 56% of the DLBCL samples that had been placed in the type 3 subtype by hierarchical clustering were classified as either ABC or GCB using this Bayesian model.

Figure 19:
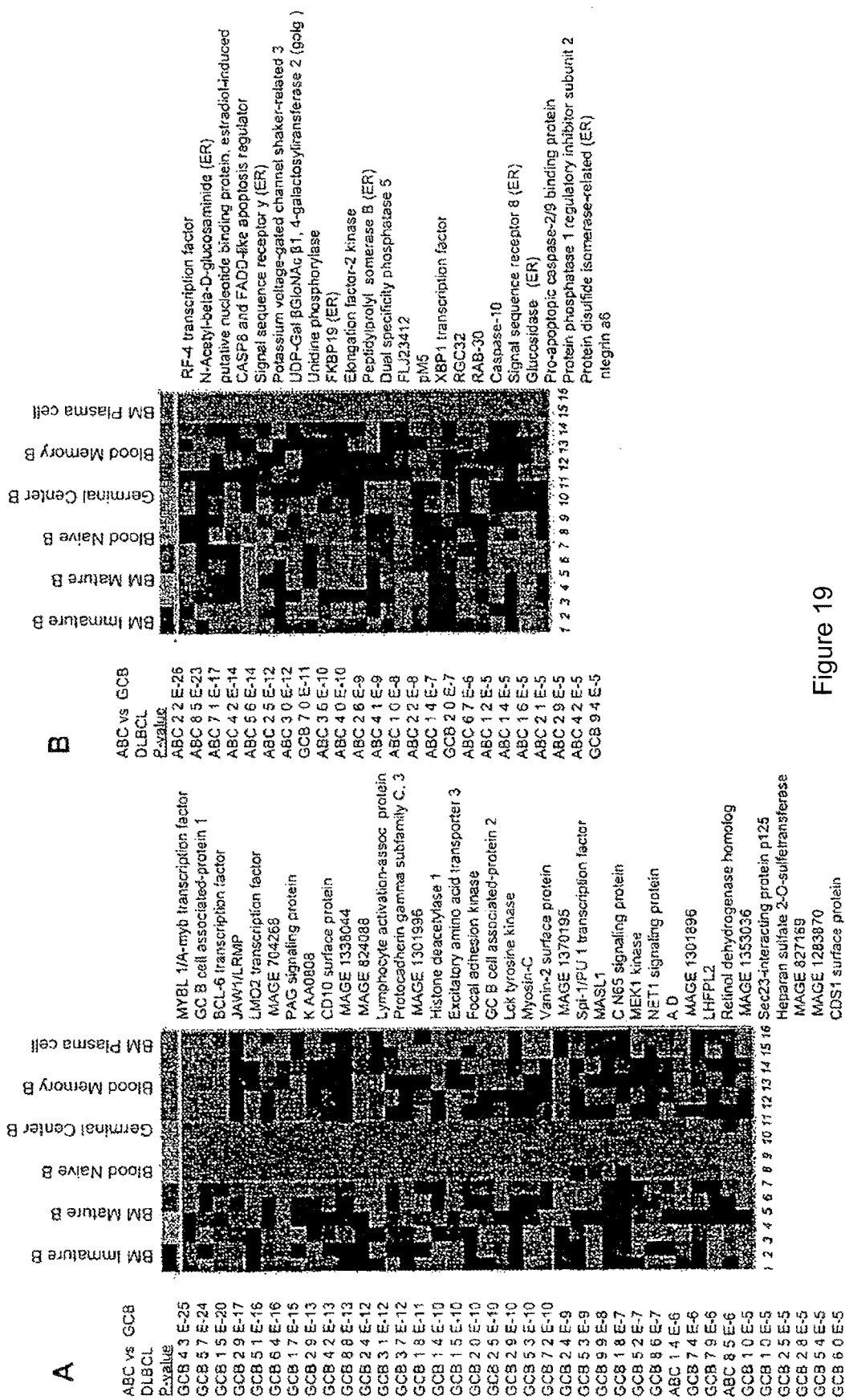
FIG. 19: Relationship of gene expression in normal B cell subpopulations to DLBCL subtypes. Relative gene expression in the indicated purified B cell populations is depicted according to the scale in FIG. 17. The P value of the difference in expression of these genes between the GCB and ABC DLBCL subtypes is shown, and the subtype with the higher expression is indicated. A. DLBCL subtype distinction genes that are more highly expressed in germinal center B cells than at other B cell differentiation stages. B. DLBCL subtype distinction genes that are more highly expressed in plasma cells than at other B cell differentiation stages.

In previous experiments, the genes that were used to distinguish GCB and ABC were deliberately selected to include those that were preferentially expressed in normal GC B cells (Alizadeh 2000; Rosenwald 2002). In the present analysis, the predictor model was not biased a priori to include such genes. The ABC and GCB lymphoma types as defined by the Bayesian model were analyzed for differential expression of GC B cell restricted genes. Thirty seven genes were found to be both more highly expressed in GC B cells than at other stages of differentiation (p<0.001) and differentially expressed between DLBCL subtypes (p<0.001) (FIG. 19A). These 37 genes are listed in Table 2392.

TABLE 2392

| UNIQID | Unigene ID Build 167 | Gene symbol |
|---|---|---|
| 28014 | 300592 | MYBL1 |
| 24376 | 317970 | SERPINA11 |
| 24429 | 155024 | BCL6 |
| 16886 | 124922 | LRMP |
| 27374 | 283063 | LMO2 |
| 29912 | 446198 | |
| 24510 | 266175 | PAG |
| 24854 | 439767 | TOX |
| 32171 | 307734 | MME |
| 24361 | 388737 | |
| 19365 | 171857 | Cyorf15a |
| 27292 | 272251 | KLHL5 |
| 24822 | 283794 | PCDHGC3 |
| 30923 | 446195 | |
| 24825 | 88556 | HDAC1 |
| 31696 | 91139 | SLC1A1 |
| 26976 | 434281 | PTK2 |
| 19279 | 49614 | GCET2 |
| 17866 | 1765 | LCK |
| 24386 | 437459 | MYO1E |
| 33013 | 293130 | VNN2 |
| 25126 | | |
| 30498 | 157441 | SPI1 |
| 26512 | 379414 | MFHAS1 |
| 26582 | 153260 | SH3KBP1 |
| 17840 | 132311 | MAP2K1 |
| 26000 | 25155 | NET1 |
| 24323 | 149342 | AICDA |
| 30922 | 435904 | C21orf107 |
| 30641 | 79299 | LHFPL2 |
| 19308 | 179608 | DHRS9 |
| 24455 | 405387 | |
| 30034 | 300208 | SEC23IP |
| 24977 | 169939 | HS2ST1 |
| 24449 | 206097 | RRAS2 |
| 30763 | 446198 | |
| 27987 | 73792 | CR2 |

All but two (AICDA and DHRS9) of these 37 genes were more highly expressed in GCB than in ABC. This demonstrates that the DLBCL subtypes defined by the Bayesian predictor seem to differ with respect to their cell of origin, with GCB retaining the gene expression program of normal GC B cells.

ABC, on the other hand, displayed higher expression of genes characteristic of plasma cells (FIG. 19B). Twenty four genes were found to be both more highly expressed in plasma cells than in B cells at earlier developmental stages (p<0.001) and differentially expressed between the DLBCL subtypes (p<0.001). These 24 genes are listed in Table 2393.

TABLE 2393

| UNIQID | Unigene ID Build 167 | Gene symbol |
|---|---|---|
| 16614 | 127686 | IRF4 |
| 26907 | 118722 | FUT8 |
| 31104 | 313544 | NS |
| 19219 | 355724 | CFLAR |
| 26174 | 28707 | SSR3 |
| 24566 | 169948 | KCNA3 |
| 34500 | 442808 | B4GALT2 |
| 26991 | 314828 | UPP1 |
| 30191 | 438695 | FKBP11 |
| 27402 | 259855 | EEF2K |
| 26096 | 434937 | PPIB |
| 15887 | 2128 | DUSP5 |
| 32440 | 512686 | C20orf59 |

TABLE 2393-continued

| UNIQID | Unigene ID Build 167 | Gene symbol |
|---|---|---|
| 34827 | 429975 | PM5 |
| 29232 | 437638 | XBP1 |
| 17763 | 76640 | RGC32 |
| 32163 | 445862 | RAB30 |
| 17814 | 5353 | CASP10 |
| 31460 | 409223 | SSR4 |
| 26693 | 83919 | GCS1 |
| 25130 | 409563 | PACAP |
| 16436 | 267819 | PPP1R2 |
| 31610 | 76901 | PDIR |
| 28961 | 212296 | ITGA6 |

The majority of these plasma cell-restricted genes were more highly expressed in ABC than in GCB. Eight of the 32 genes encode proteins that reside and function in the endoplasmic reticulum (ER) or Golgi apparatus, suggesting that ABCs have increased the intracellular machinery for protein secretion. These eight genes are denoted in the above list by the designation "ER" or "golgi" in parentheses. Another gene on this list, XBP-1 transcription factor, encodes a protein that is required for plasma cell differentiation (Reimold 2001) and is involved in the response to unfolded proteins in the ER (Calfon 2002). ABCs have not undergone full plasmacytic differentiation, however, because other key plasma cell genes such as Blimp-1 were not more highly expressed in ABC.

Example 14

Classification of DLBCL Samples Based on Bayesian Analysis of gene Expression Data from the Affymetrix HU6800 Microarray The prediction method described in Example 14 above was applied to gene expression data from 58 DLBCL samples obtained using an Affymetrix HU6800 oligonucleotide microarray (Shipp 2002). This data is available at www.genome.wi.mit.edu/MPR/lymphoma. The first step in analyzing this data was to exclude all microarray features with a median signal value of <200 across the samples. Multiple microarray features representing the same gene were then averaged. Of the 27 genes in the DLBCL subtype predictor developed using the Lymphochip data (above), only 14 were represented on the Affymetrix array and passed this filtering process. These 14 genes are listed in Table 2394.

TABLE 2394

| UNIQID | Unigene ID Build 167 | Gene symbol |
|---|---|---|
| 24729 | 127686 | IRF4 |
| 17227 | 170359 | IL16 |
| 26907 | 118722 | FUT8 |
| 27565 | 444105 | ENTPD1 |
| 16858 | 376071 | CCND2 |
| 24899 | 81170 | PIM1 |
| 16947 | 418004 | PTPN1 |
| 16049 | 439852 | IGHM |
| 26385 | 307734 | MME |
| 27673 | 124922 | LRMP |
| 24429 | 155024 | BCL6 |
| 17218 | 283063 | LMO2 |
| 28338 | 78877 | ITPKB |
| 17496 | 300592 | MYBL1 |

These 14 genes were used to create a new DLBCL subtype predictor in which the LPS scaling coefficients were again calculated based on the DLBCL subtype distinction in the Lymphochip data set (Rosenwald 2002). To account for systematic measuring differences between the Affymetrix and Lymphochip microarrays, the expression value of each gene on the Affymetrix microarray was shifted and scaled to match the mean and variance of the corresponding expression values on the Lymphochip. The adjusted expression values for each of the 14 genes were then used to calculate LPS's for each sample. DLBCL subtype membership was again assigned on a cut-off of 90% certainty. Several observations suggested that the predictor identified ABC and GCB samples within the Affymetrix data set that were comparable to those found in the Lymphochip data set. First, the relative proportions of ABC (29%) and GCB (53%) were very similar to the corresponding proportions in the Lymphochip data set (34% and 49%, respectively). Second, 43 genes were found to be differentially expressed between the two DLBCL subtypes with high significance ($p<0.001$) in the Affymetrix data. This number is substantially higher than would be expected by chance, given that the Affymetrix microarray measures the expression of approximately 5,720 genes. The symbols for these 43 genes were: IGHM; TCF4; IRF4; CCND2; SLA; BATF; KIAA0171; PRKCB1; P2RX5; GOT2; SPIB; CSNK1E; PIM2; MARCKS; PIM1; TPM2; FUT8; CXCR4; SP140; BCL2; PTPN1; KIAA0084; HLA-DMB; ACP1; HLA-DQA1; RTVP1; VCL; RPL21; ITPKB; SLAM; KRT8; DCK; PLEK; SCA1; PSIP2; FAM3C; GPR18; HMG14; CSTB; SPINK2; LRMP; MYBL1; and LMO2. Third, the 43 genes differentially expressed between the types included 22 genes that were not used in the predictor but were represented on Lymphochip arrays. Fourteen of these 22 genes were differentially expressed on the Lymphochip array with high statistical significance ($p<0.001$). Finally, the expression of the c-rel gene was previously found to correspond to amplification of the c-rel genomic locus in DLBCL tumor cells, and oncogenic event occurring in GCB but not ABC (Rosenwald 2002). In the Affymetrix data set, c-rel was differentially expressed between the two subtypes ($p=0.0025$), and was highly expressed only in a subset of GCB's.

Example 15

Identification of DLBCL Samples as PMBL Based on Bayesian Analysis of Gene Expression Data from the Lymphochip Microarray 310 lymphoma biopsy samples identified as DLBCL by a panel of hematopathologists were divided into a 36 sample training set and a 274 sample validation set, with the validation set consisting of the DLBCL samples classified previously in Example 14. All patients from whom the samples were derived had been treated with anthracycline-containing multiagent chemotherapy protocols, with some patients additionally receiving radiation therapy. The training set was profiled for gene expression using Lymphochip microarrays comprising 15,133 cDNA elements as described previously (Alizadeh 2000). This data is available at the web site companion for Rosenwald et al., J. Exp. Med., 198: 851-862 (2003), which is referenced therein at page 852 and which is hosted by Lymphoma/Leukemia Molecular Profiling Project Gateway at the National Institute of Health web site. The validation set had previously been profiled using Lymphochip microarrays comprising 12,196 cDNA elements (Rosenwald 2002). This data is available at the web site companion for Rosenwald et al., New Eng. J. Med., 346: 1937-1947 (2002), which is referenced therein at page 1938 and which is hosted by the Lymphoma/Leukemia Molecular Profiling Project Gateway at the National Institute of Health web site.

Figure 20:
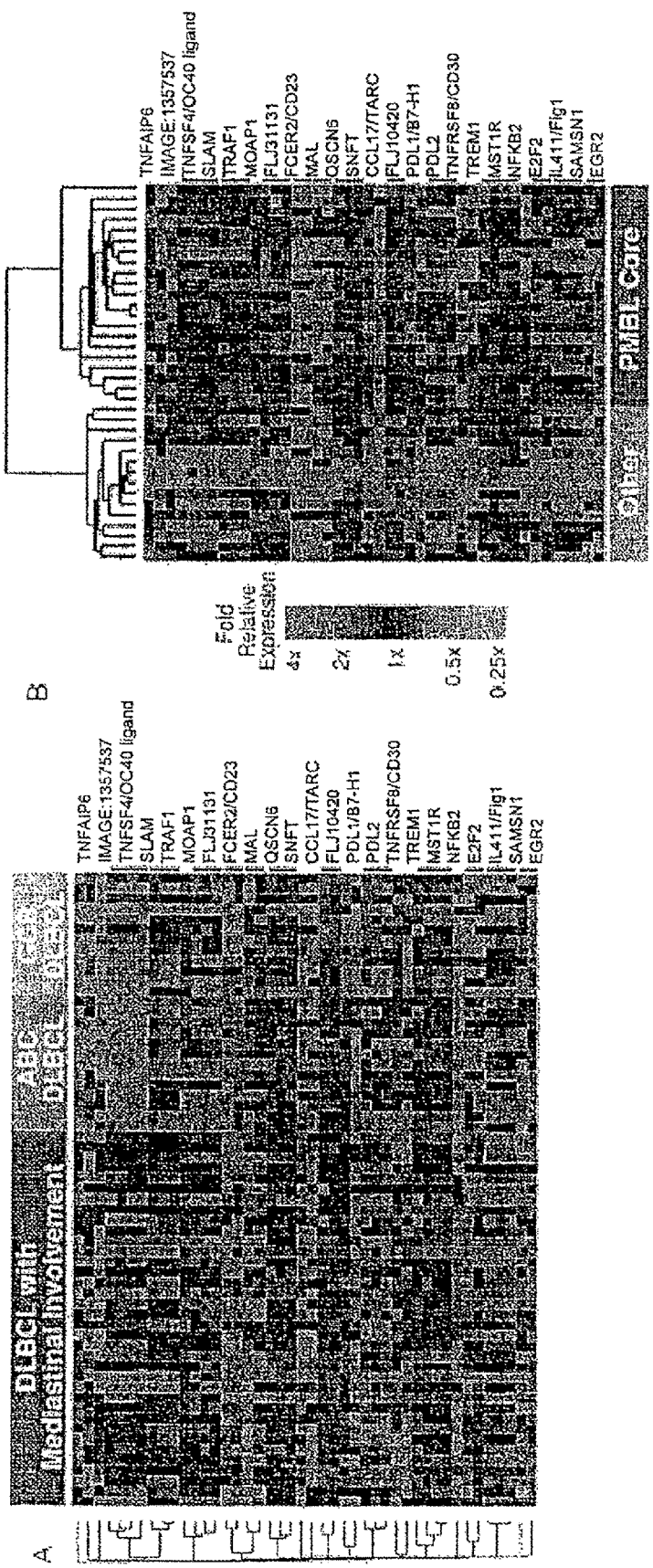
FIG. 20: Identification of a PMBL gene expression signature. A. Hierarchical clustering identified a set of 23 PMBL signature genes that were more highly expressed in most lymphomas with a clinical diagnosis of PMBL than in lymphomas assigned to the GCB or ABC subtypes. Each row presents gene expression measurements from a single Lymphochip microarray feature representing the genes indicated. Each column represents a single lymphoma biopsy sample. Relative gene expression is depicted according to the scale shown. B. Hierarchical clustering of the lymphoma biopsy samples based on expression of the PMBL signature genes identified in (A). A "core" cluster of lymphoma cases was identified that highly expressed the PMBL signature genes.

A hierarchical clustering algorithm (Eisen 1998) was used to organize the genes by their expression patterns across the 36 samples in the training set. A large group of genes that were more highly expressed in lymphomas with mediastinal involvement than in other DLBCLs was shown to be tightly clustered in the resulting dendrogram (FIG. 20A). This cluster of genes included two genes, MAL and FIG1, previously shown to be highly expressed in PMBL (Copie-Bergman 2002; Copie-Bergman 2003). Several of the lymphomas with mediastinal involvement did not express this set of putative PMBL signature genes, and it was suspected that these samples were more likely to be conventional DLBCL than PMBL. Hierarchical clustering was used to organize the samples according to their expression of the PMBL signature genes, resulting in two major clusters of cases (FIG. 20B). One cluster contained 21 samples designated "PMBL core" samples by virtue of their higher expression of PMBL signature genes. The other cluster contained some samples that had virtually no expression of these genes, and other samples that did express these genes but at lower levels than the PMBL core samples.

Figure 21:
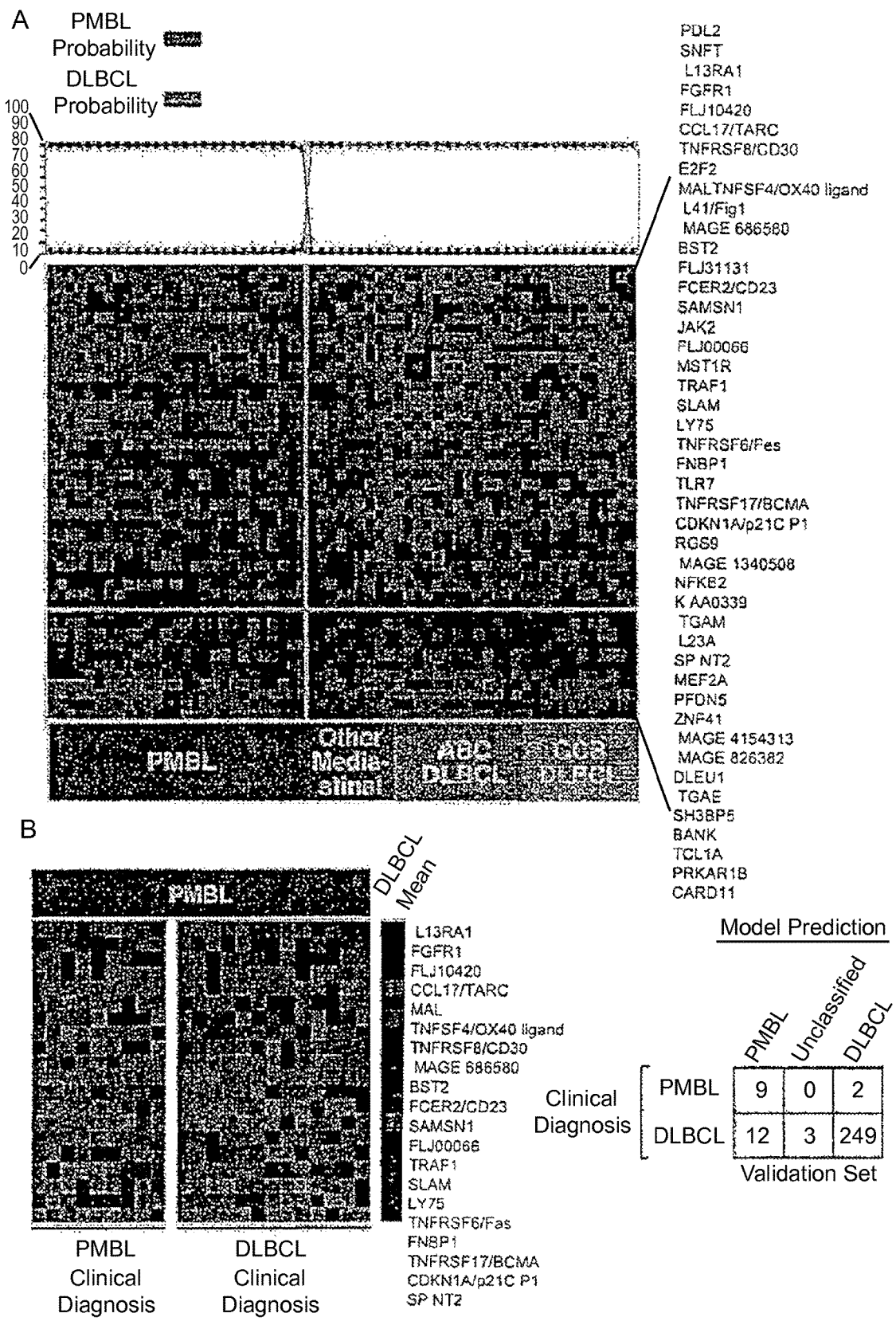
FIG. 21: Development of a gene expression-based molecular diagnosis of PMBL. A. A PMBL predictor was created based on expression of the 46 genes shown. Relative gene expression for each lymphoma biopsy sample is presented according to the color scale shown in FIG. 20. The probability that each sample is PMBL or DLBCL based on gene expression is shown at the top. B. The PMBL predictor was used to classify 274 lymphoma samples as PMBL or DLBCL. Prediction results are summarized on the right, and the relative gene expression for each case that was classified by the predictor as PMBL is shown on the left. Average expression of each gene in samples classified as DLBCL is also shown. The 20 genes listed are those represented on the Lymphochip that were more highly expressed in PMBL than in DLBCL. Not shown are eight genes from the PMBL predictor that were more highly expressed in DLBCL than in PMBL.

A gene expression-based method for distinguishing PMBL core cases from GCB and ABC DLBCL cases based on Bayesian analysis was developed using the methods described in Examples 14 and 15. A set of genes were selected that were differentially expressed between the PMBL core samples and both GCB and ABC (p<0.001). This set of genes included all of the PMBL signature genes identified by hierarchical clustering (FIG. 20A), as well as a large number of additional genes. Many of the genes in this set belonged to the lymph node gene expression signature (Alizadeh 2000; Rosenwald 2002). These genes were excluded from the final predictor because they might cause some DLBCL samples with higher expression of lymph node gene expression signature genes to be misclassified as PMBL. The list of PMBL distinction genes was refined by adding a requirement that they also be differentially expressed between the PMBL core samples and a subgroup of six DLBCL samples with higher expression of lymph node gene expression signature genes (p<0.001). The resulting set of 46 genes included 35 genes that were more highly expressed in PMBL and 11 genes that were more highly expressed in DLBCL (FIG. 21A). The 46 genes in this set were PDL2, SNFT, IL13RA1, FGFR1, FLJ10420, CCL17/TARC, TNFRSF8/CD30, E2F2, MAL, TNFSF4/OX40 ligand, IL411/Fig1, IMAGE:686580, BST2, FLJ31131, FCER2/CD23, SAMSN1, JAK2, FLJ00066, MST1R, TRAF1, SLAM, LY75, TNFRSF6/Fas, FNBP1, TLR7, TNFRSF17/BCMA, CDKN1A/p21CIP1, RGS9, IMAGE: 1340506, NFKB2, KIAA0339, ITGAM, IL23A, SPINT2, MEF2A, PFDN5, ZNF141, IMAGE:4154313, IMAGE: 825382, DLEU1, ITGAE, SH3BP5, BANK, TCL1A, PRKAR1B, and CARD11. A series of linear predictor scores were generated based on the expression of this gene set. Based on the distribution of linear predictor scores within a particular lymphoma type, Bayes' rule can be used to estimate the probability that a particular sample belongs to either of the two types. An arbitrary probability cut-off of 90% or greater was used to classify a sample as a particular lymphoma type. All of the PMBL core samples were classified as PMBL using this method, as were six of the other lymphoma samples with mediastinal involvement. However, nine of the lymphoma samples with mediastinal involvement were classified as a DLBCL, as were all of the GCB and ABC samples.

In the validation set, 11 samples were identified on clinical grounds as being consistent with a diagnosis of PMBL, and the Bayesian model classified nine of these as PMBL (FIG. 21B). Interestingly, 12 of the remaining 263 DLBCL samples were classified as PMBL by the predictor. FIG. 21B shows that these cases were indistinguishable by gene expression from the nine cases diagnosed as PMBL on clinical grounds. As expected, the average expression of the PMBL predictor genes in the 249 samples classified as DLBCL was notably lower than in the 22 PMBL cases. Thus, PMBL represents a third subgroup of DLBCL than can be distinguished from ABC and GCB by gene expression profiling.

Table 2395 compares the clinical parameters of patients assigned to the PMBL, ABC, and GCB subgroups of DLBCL using this prediction method.

TABLE 2395

|  | ABC DLBCL | GCB DLBCL | PMBL Training set | PMBL Validation set | PMBL All cases | P value |
|---|---|---|---|---|---|---|
| Median age | 66 | 61 | 33 | 33 | 33 | 4.4E−16 |
| Age <35 | 5% | 10% | 52% | 56% | 53% | 7.2E−14 |
| Age 35-60 | 29% | 38% | 44% | 28% | 37% |  |
| Age >60 | 66% | 52% | 4% | 17% | 9% |  |
| Gender = male | 59% | 53% | 44% | 50% | 47% | 0.38 |
| Female <35 | 2% | 3% | 32% | 39% | 35% | 1.1E−12 |
| Male <35 | 2% | 7% | 20% | 17% | 19% |  |
| Female 35-60 | 6% | 18% | 24% | 6% | 16% |  |
| Male 35-60 | 23% | 19% | 20% | 22% | 21% |  |
| Female >60 | 33% | 25% | 0% | 6% | 2% |  |
| Male >60 | 34% | 27% | 4% | 11% | 7% |  |

PMBL patients were significantly younger than other DLBCL patients, with a median age at diagnosis of 33 years compared with a median age of 66 and 61 years for ABC and GCB patients, respectively. Although there was no significant difference in gender distribution among the DLBCL subgroups, young women (<35 years) accounted for 35% of PMBL patients, more than any other DLBCL subgroup. Young men (<35 years) were also more frequently represented in the PMBL subgroup, accounting for 19% of the patients. Correspondingly, older men and women (age >60) were significantly underrepresented in the PMBL subgroup. These clinical characteristics were observed in both the training set and the validation set of PMBL cases, demonstrating that the PMBL predictor reproducibly identified a clinically distinct subgroup of DLBCL patients.

Figure 22:
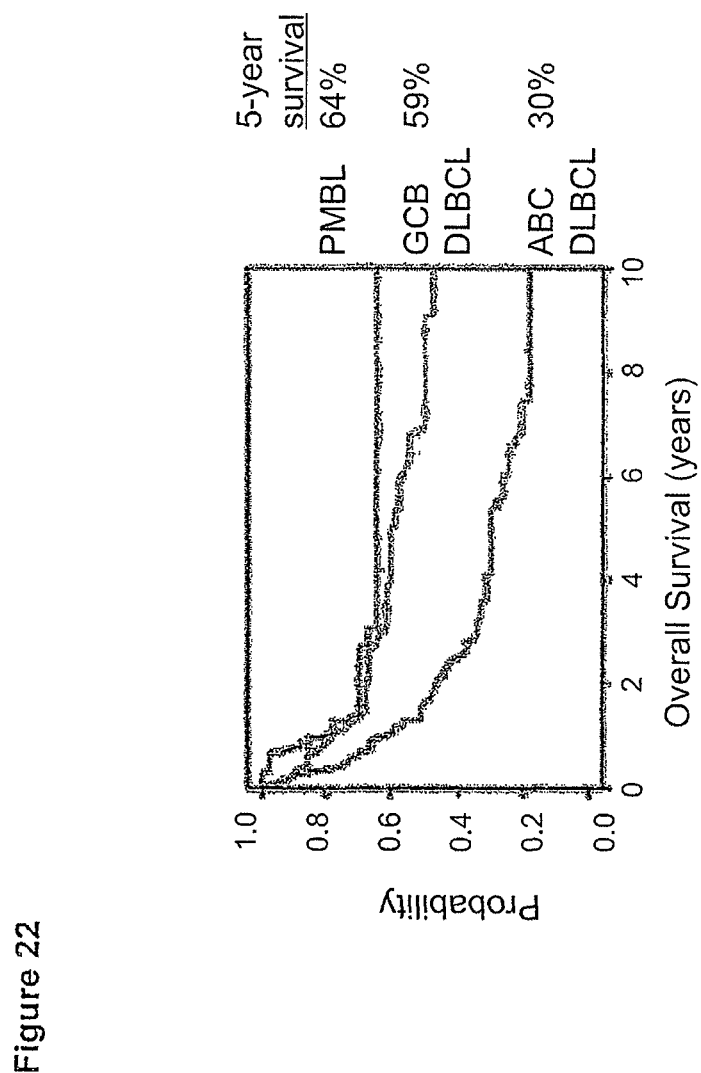
FIG. 22: Clinical characteristics of PMBL patients. Kaplan-Meier plot of overall survival in PMBL, GCB, and ABC patients after chemotherapy.

The PMBL subgroup defined by the PMBL predictor had a relatively favorable overall survival rate after therapy (FIG. 22). PMBL patients had a five-year survival rate of 64%, superior to the 46% rate seen in DLBCL patients as a whole (p=0.0067). The survival of the PMBL subgroup was significantly better than the 30% five-year survival rate of the ABC subgroup (FIG. 22; p=5.8E-5), but only marginally better than the 59% five-year survival rate of the GCB subgroup (p=0.18).

Example 16

Classification of Lymphomas into Types Based on Bayesian Analysis of Gene Expression Data from the Lymph Dx Microarray Based on the clustering of the Lymph Dx microarray signals for the DLBCL samples, a cluster of "proliferation signature" genes and a cluster of "lymph node signature" genes were identified. The expression of these genes was averaged to form a proliferation signature and a lymph node signature. Each gene represented on the Lymph Dx microarray was placed into one of three "gene-list categories" based on its correlation with the proliferation or lymph node gene signatures. "Proliferation" genes were defined as those genes for which the correlation between their expression and the proliferation signature was greater than 0.35. Lymph node genes were defined as those genes for which the correlation between their expression and the lymph node signature was greater than 0.35. The remaining genes on the array were classified as standard genes. This classification resulted in 323 proliferation genes and 375 lymph node genes.

Two stages of lymphoma classification were performed using the gene expression data obtained for the above samples using the Lymph Dx microarray. The general procedure used to classify the samples is presented in flow chart form in FIG. 1.

For the first stage of expression analysis, the samples were divided into five types: FL, MCL, SLL, FH, and a class of aggressive lymphomas that included DLBCL and BL. Samples obtained from subjects with other diagnoses (e.g., MALT, LPC) were omitted from this analysis. Data from the Lymph Dx microarray was then used to compare gene expression in each possible lymphoma type pair (e.g., FH vs. FL, MCL vs. SLL, etc.). This resulted in the creation of ten "pair-wise models" (one for each possible lymphoma type pair) for predicting whether a sample fell into a particular lymphoma type.

For each lymphoma type pair, the difference in expression between the two types for every gene on the microarray was calculated, and a t-statistic was generated to represent this difference. Within each gene-list category (proliferation, lymph node, and standard), individual genes were ordered based on the absolute value of their t-statistic. Only those genes that displayed a statistically significant difference in expression between the two types were included in the model. Those genes with largest absolute t-statistics in each gene-list category were then used to generate a linear predictor score (LPS) for each sample. For a sample X and a set of genes G, the LPS was defined as:

$$LPS(X) = \sum_{j \in G} t_j X_j,$$

where $X_j$ is the expression of gene j in the sample and $t_j$ is the t-statistic representing the difference in expression of gene j between the two lymphoma types. This formulation of LPS, known as the compound covariate predictor, has previously been used successfully (Radmacher 2002; Rosenwald 2003a; Wright 2003). Other ways to formulate an LPS include Fisher linear discriminant analysis (Dudoit 2002), weighted voting (Golub 1999), linear support vector machines (Ramaswamy 2001), and nearest shrunken centroids (Tibshirani 2002).

Figure 23:
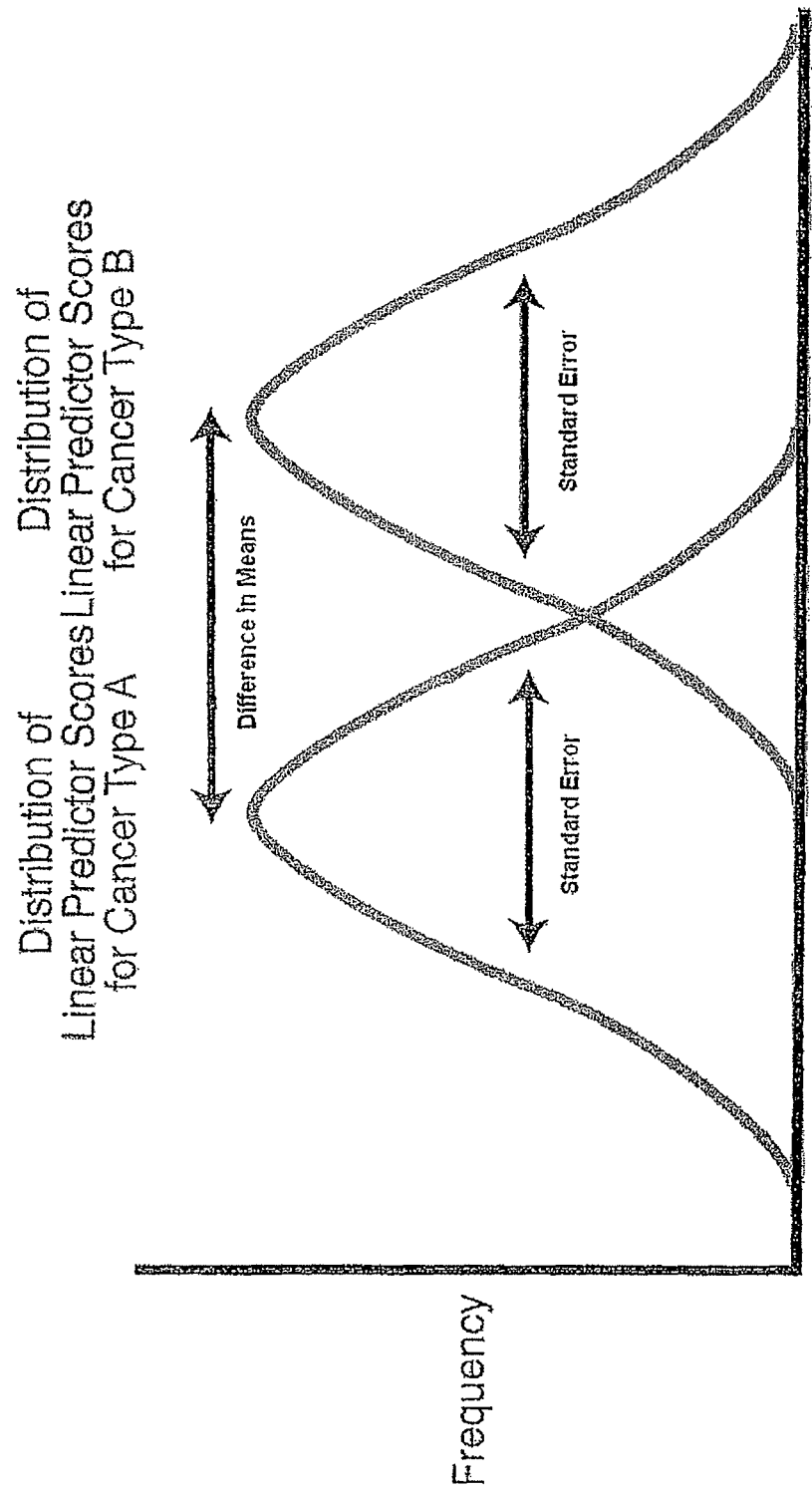
FIG. 23: Optimization of gene number in lymphoma predictor. The optimal number of genes for inclusion in the lymphoma type predictor model is that number which generates a maximum t-statistic when comparing the LPS of two samples from different lymphoma types.

In order to optimize the number of genes used to generate the LPS, a series of LPS's were generated for each sample using between five and 100 genes from each gene-list category. The optimal number of genes is that number which generates a maximum t-statistic when comparing the LPS of two samples from different lymphoma types (FIG. 23). This optimization procedure was repeated for every gene-list category in every pair-wise model, meaning that 30 optimizations were performed in all.

It was recognized that for some pair-wise models, it would be useful to calculate LPS's using different combinations of gene-list categories. LPS's were calculated for each sample using four different combinations. In the first, LPS was calculated using the standard genes only. In the second, LPS's were calculated for both the standard and proliferation genes, but not the lymph node genes. In the third, LPS's were calculated for both the standard and lymph node genes, but not the proliferation genes. In the fourth, LPS's were calculated using all three gene-list categories.

Figure 24:
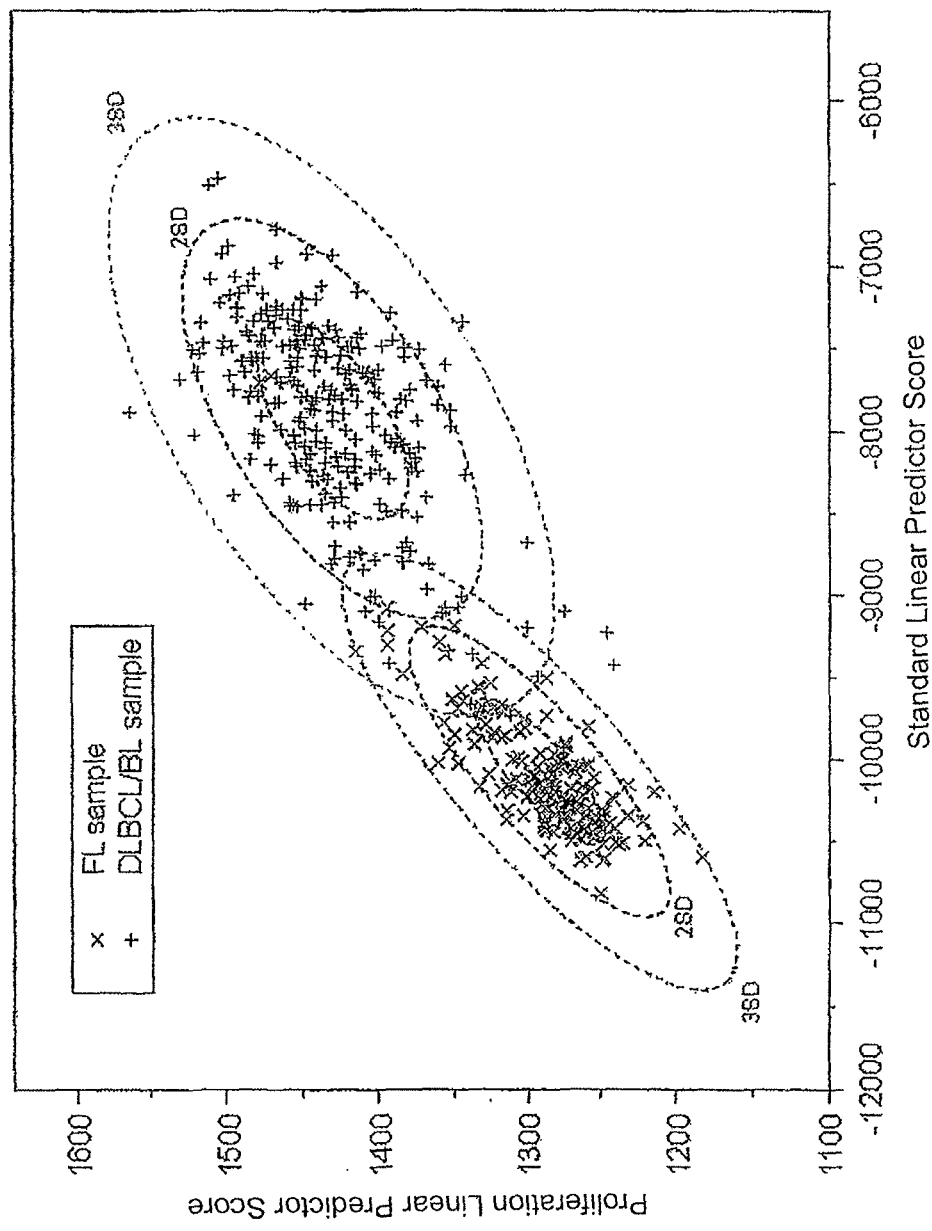
FIG. 24: LPS distribution among FL and DLBCL/BL samples. Standard and proliferation LPSs for FL (x) and DLBCL/BL (+) samples. Dotted lines indicate standard deviations from the fitted multivariate normal distributions.

Depending on the number of gene-list categories included, between one and three LPS's were calculated for each sample in the pair-wise models. Thus, each sample could be thought of as a vector in a space of between one and three dimensions. Since the LPS's were sums of individual expressions, it was reasonable to approximate the distributions as normal. Multivariate normal distributions are defined by two quantities: a mean vector, which indicates the average value of each of the models within a given lymphoma type, and a covariance matrix, which indicates the magnitude and orientation spread of points away from this center. Both of these quantities can be estimated empirically from the observed data. FIG. 24 shows the Standard and Proliferation LPS's for the FL vs. DLBCL/BL pair-wise model. The dotted lines indicate the standard deviations from the fitted multivariate normal distributions.

Once the multidimensional distributions have been estimated, Bayes' rule (Bayes 1763) can be used to estimate the probability that a given sample belongs to one lymphoma type or another. Bayesian analysis of an LPS has been successfully employed in the past to distinguish DLBCL subtypes (Rosenwald 2003a, Wright 2003). For a sample X, the probability q of the sample belonging to a first lymphoma type rather than a second lymphoma type can be calculated using the formula:

$$q = \frac{\phi(LPS(Y); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

where LPS(X) is the linear predictor score for sample X, $\phi(x; \mu, \sigma)$ is the normal density function with mean $\mu$ and standard deviation $\sigma$, $\hat{\mu}_1$ and $\hat{\sigma}_1$ are the mean and variance of the LPS's for the first lymphoma type, and $\hat{\mu}_2$ and $\hat{\sigma}_2$ are the mean and variance of the LPS's for the second lymphoma type. Using this equation, a single probability q value can be developed for each sample and for each of the four LPS combinations. This q value can then be used to classify a sample as a first lymphoma type, a second lymphoma type, or unclassified. Samples with the highest q values are classified as the first lymphoma type, while samples with the lowest q values are classified as the second lymphoma type. Samples with middle range q values are deemed unclassified. Classifying the samples in this manner requires two cut-off points: a lower cut-off point between the second lymphoma type and unclassified, and an upper cut-off point between unclassified and the first lymphoma type. To develop these cut-off points, samples were ordered by their q values, and each possible cut-off point between adjacent samples was considered. To ensure that the cut-off points were reasonable, the lower cut-off point was restricted to between 0.01 and 0.5 and the upper cut-off point was restricted to between 0.5 and 0.99.

Every cut-off point and model combination was analyzed by the following equation:

3.99*[(% of type 1 misidentified as type 2)+(% of type 2 misidentified as type 1)]+[(% of type 1 unclassified)+(% of type 2 misidentified)].

Using this equation, the cut-off point would be adjusted to allow an additional error only if this adjustment resulted in four or more unclassified samples becoming correctly classified. The final model and cut-off point for a given pair-wise analysis was that which minimized this equation. The equation utilizes percentages rather than the actual number of cases in order to account for the different number of samples in each class.

Figure 25:
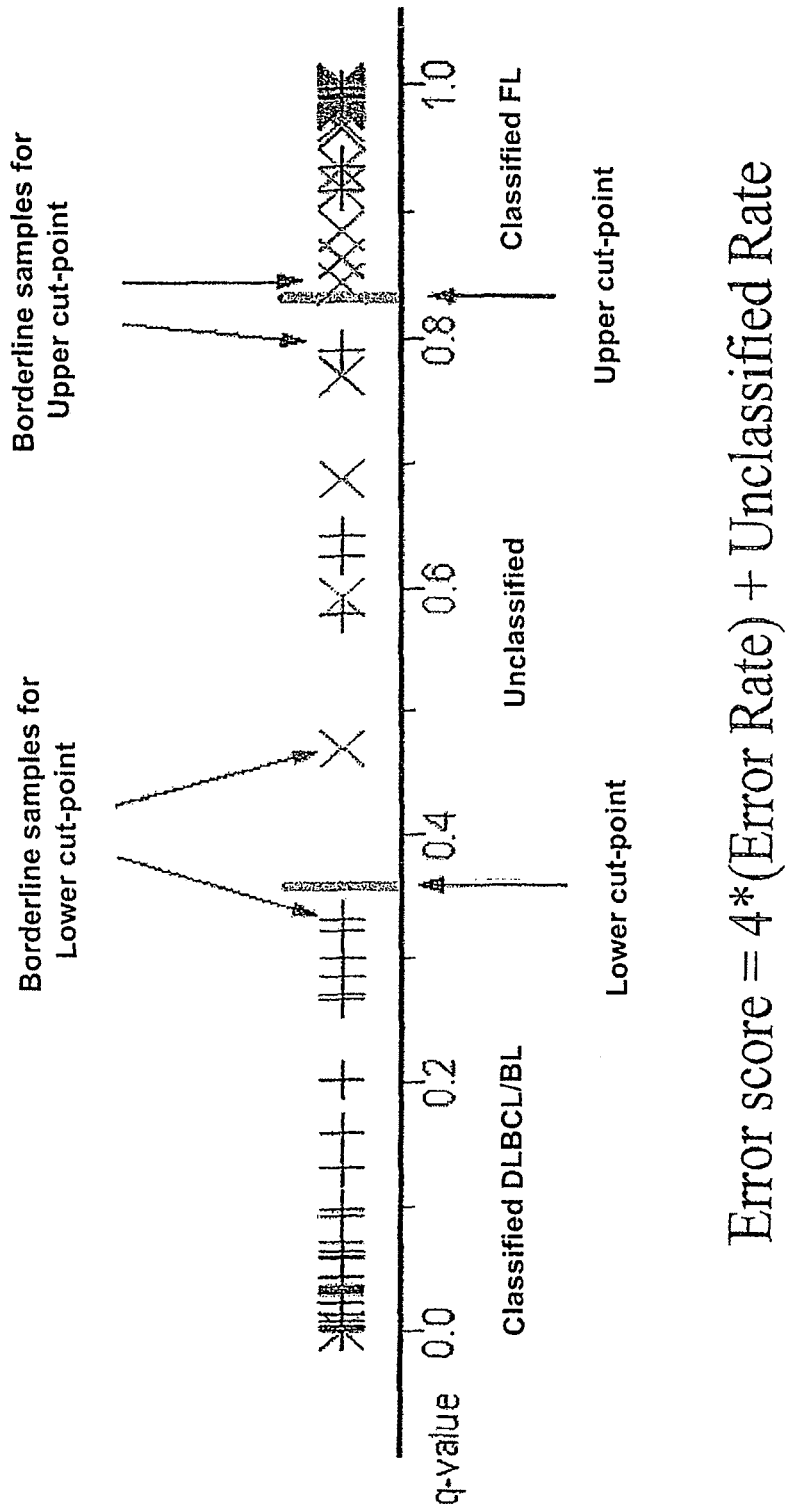
FIG. 25: Determination of cut-off points for lymphoma classification. The cut-off points between samples classified as DLBCL/BL, FL, or unclassified were optimized to minimize the number of samples classified as the wrong lymphoma type. The optimal lower cut-off point was at $q=0.49$, while the optimal upper cut-off point was at $q=0.84$.
Figure 26:
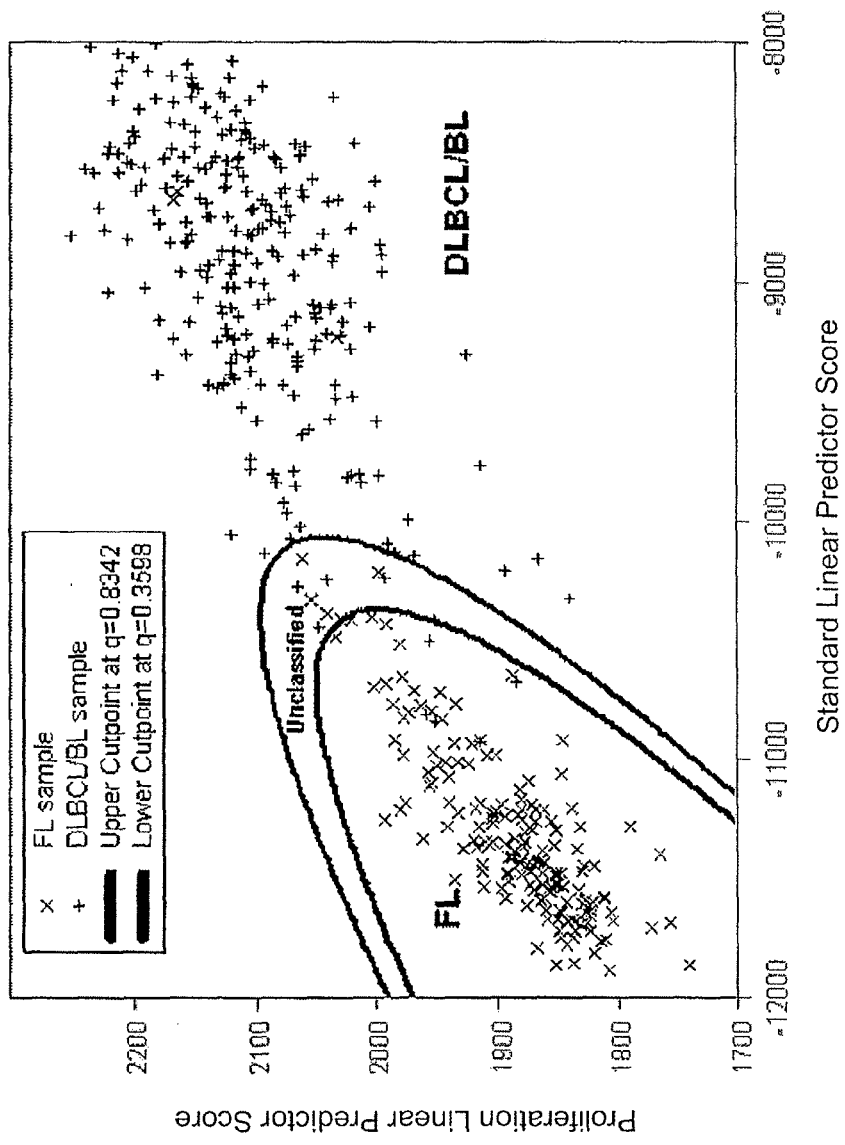
FIG. 26: Division of LPSs among FL and DLBCL/FL samples. Illustration of how the cut-off points described in FIG. 25 divided the space between the LPSs of FL (x) and DLBCL/BL (+) samples.

All cut-off points between a given pair of adjacent q-values will produce the same division of data. Since cut-off point optimality is defined in terms of dividing the data into subtypes, all cut-off points between a pair of borderline cases will be equally optimal. In choosing where to place the actual cut-off point values, values were chosen that would lead to a larger unclassified region. When the lower cut-off point was being defined, a value would be chosen that was ⅕ of the way from the smallest borderline case to the largest. When the upper cut-off point was being defined, a value would be chosen that was ⅘ of the way from the smallest borderline case to the largest. FIG. 25 illustrates the q-results of optimizing the cut-point for the FL versus DLBCL/BL samples. The optimal lower cut-off point for these samples was found at q=0.49, while the optimal upper cut-off point was found at q=0.84. FIG. 26 indicates how this choice of cut-off points divided the space of LPS's.

The above procedures resulted in a series of pair-wise models for comparing every lymphoma type to every other lymphoma type. If there are n types, then there will be n−1 pair-wise models for each type. Since there were five lymphoma types in the stage 1 analysis, each type was involved in 4 pair-wise models. For instance, there were four different pair-wise models for MCL: MCL vs. FH, MCL vs. FL, MCL vs. SLL, and MCL vs. DLBCL/BL. For each sample tested, each pair-wise model will produce one of three possible results: 1) the sample belongs to the first lymphoma type of the pair-wise model, 2) the sample belongs to the second lymphoma type of the pair-wise model, or 3) the sample is unclassified. If each of the n−1 models agrees that the sample belongs to a particular lymphoma type, then the sample is designated as belonging to that type. If the n−1 models do not all agree that the sample belongs to a particular lymphoma type, the sample is designated as unclassified.

To ensure that the above methods did not result in overfitting (i.e., models that fit particular idiosyncrasies of the training set but fail when applied to independent data), the models were validated by leave-one-out cross-validation fashion (Hills 1966). Each sample was removed from the data one at a time, and a predictive model was developed as described above using the remaining data. This model was then used to predict the sample that was removed. Since the model being used to predict a given sample was generated from data that did not include that sample, this method provided an unbiased estimate of the accuracy of the model.

Figure 27:
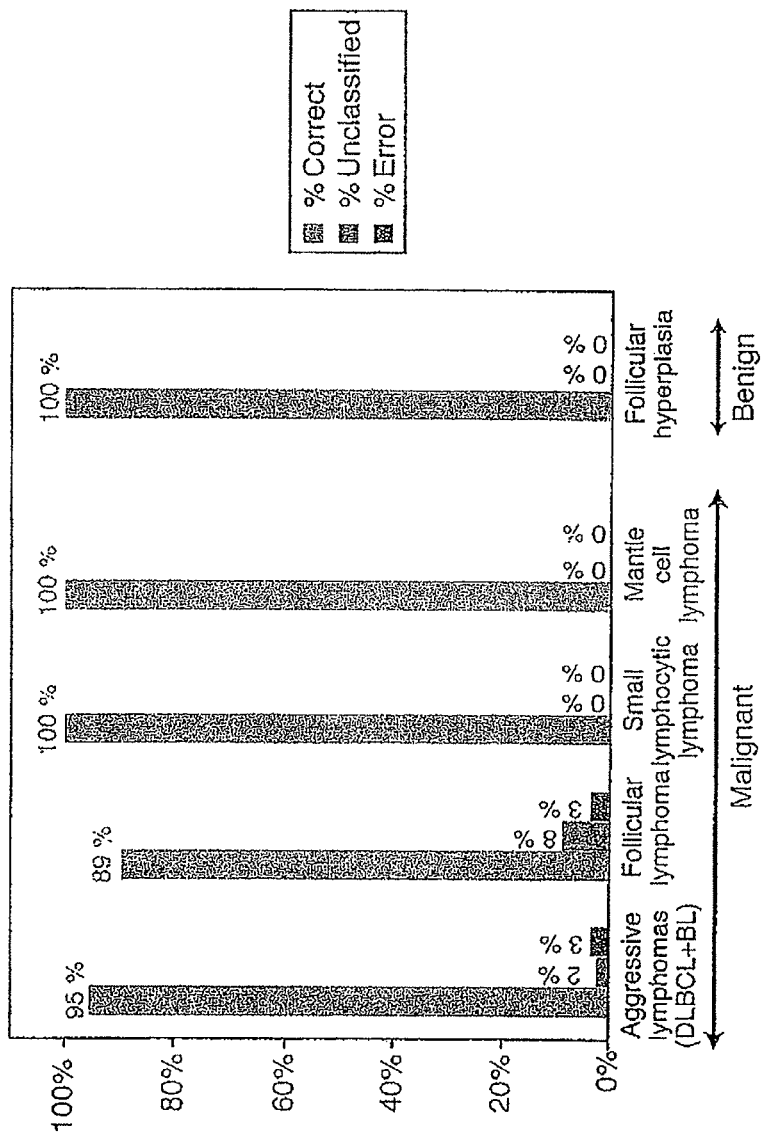
FIG. 27: Lymphoma classification results. Results of lymphoma classification based on gene expression. 100% of SLL, MCL, and FH samples were classified correctly, and only 3% of DLBCL/BL and FL samples were classified incorrectly.

The results of the leave-one-out predictions are set forth in Tables 2396 and 2397, below. The rows in each table correspond to different sample groups, while the columns indicate the prediction results. The standard to which the prediction results were compared in this stage was the diagnoses of a panel of eight expert hematopathologists who used histological morphology and immunohistochemistry to classify the samples. Table 2396 provides classification results for the five lymphoma types tested (DLBCL/BL, FL, FH, MCL, SLL), while Table 2397 provides more specific results for classification of subtypes within these five lymphoma types. The results set forth in Table 2396 are also summarized in FIG. 27.

TABLE 2396

| | DLBCL/BL | FL | FH | MCL | SLL | Unclassified | Total | % Correct | % Unclassified | % Error |
|---|---|---|---|---|---|---|---|---|---|---|
| DLBCL/BL | 249 | 6 | 0 | 0 | 0 | 7 | 262 | 95% | 2% | 3% |
| FL | 5 | 154 | 0 | 0 | 0 | 14 | 173 | 89% | 8% | 3% |
| FH | 0 | 0 | 17 | 0 | 0 | 0 | 17 | 100% | 0% | 0% |
| MCL | 0 | 0 | 0 | 22 | 0 | 0 | 22 | 100% | 0% | 0% |
| SLL | 0 | 0 | 0 | 0 | 14 | 0 | 14 | 100% | 0% | 0% |

TABLE 2397

| | DLBCL/BL | FL | FH | MCL | SLL | Unclassified | Total | % Correct | % Unclassified | % Error |
|---|---|---|---|---|---|---|---|---|---|---|
| ABC | 78 | 0 | 0 | 0 | 0 | 0 | 78 | 100% | 0% | 0% |
| GCB | 77 | 4 | 0 | 0 | 0 | 4 | 85 | 91% | 5% | 5% |
| PMBL | 33 | 0 | 0 | 0 | 0 | 0 | 33 | 100% | 0% | 0% |

TABLE 2397-continued

|  | DLBCL/BL | FL | FH | MCL | SLL | Unclassified | Total | % Correct | % Unclassified | % Error |
|---|---|---|---|---|---|---|---|---|---|---|
| Unclassified DLBCL | 27 | 1 | 0 | 0 | 0 | 2 | 30 | 90% | 7% | 3% |
| DLBCL (not yet subclassed) | 14 | 0 | 0 | 0 | 0 | 1 | 15 | 93% | 7% | 0% |
| BL | 20 | 1 | 0 | 0 | 0 | 0 | 21 | 95% | 0% | 5% |
| FL grade 1 | 1 | 78 | 0 | 0 | 0 | 3 | 82 | 95% | 4% | 1% |
| FL grade 2 | 2 | 58 | 0 | 0 | 0 | 3 | 63 | 92% | 5% | 3% |
| FL grade 3A | 2 | 18 | 0 | 0 | 0 | 8 | 28 | 64% | 29% | 7% |
| Combined FL grades 1, 2, 3A | 5 | 154 | 0 | 0 | 0 | 14 | 173 | 89% | 8% | 3% |
| FL grade 3B | 2 | 1 | 0 | 0 | 0 | 4 | 7 | 14% | 57% | 29% |
| FL unknown grade | 3 | 11 | 0 | 0 | 0 | 0 | 14 | 79% | 0% | 21% |
| FH | 0 | 0 | 17 | 0 | 0 | 0 | 17 | 100% | 0% | 0% |
| MCL | 0 | 0 | 0 | 22 | 0 | 0 | 22 | 100% | 0% | 0% |
| SLL | 0 | 0 | 0 | 0 | 14 | 0 | 14 | 100% | 0% | 0% |

As seen in Table 2396, perfect prediction of SLL, MCL, and FH samples was obtained. The success rate for predicting FL and the aggressive lymphomas (DLBCL/BL) was also very good, with only 3% of the samples being classified incorrectly. As seen in Table 2397, perfect prediction was also obtained for ABC and PMBL samples within the DLBCL samples.

Example 17

Figure 28:
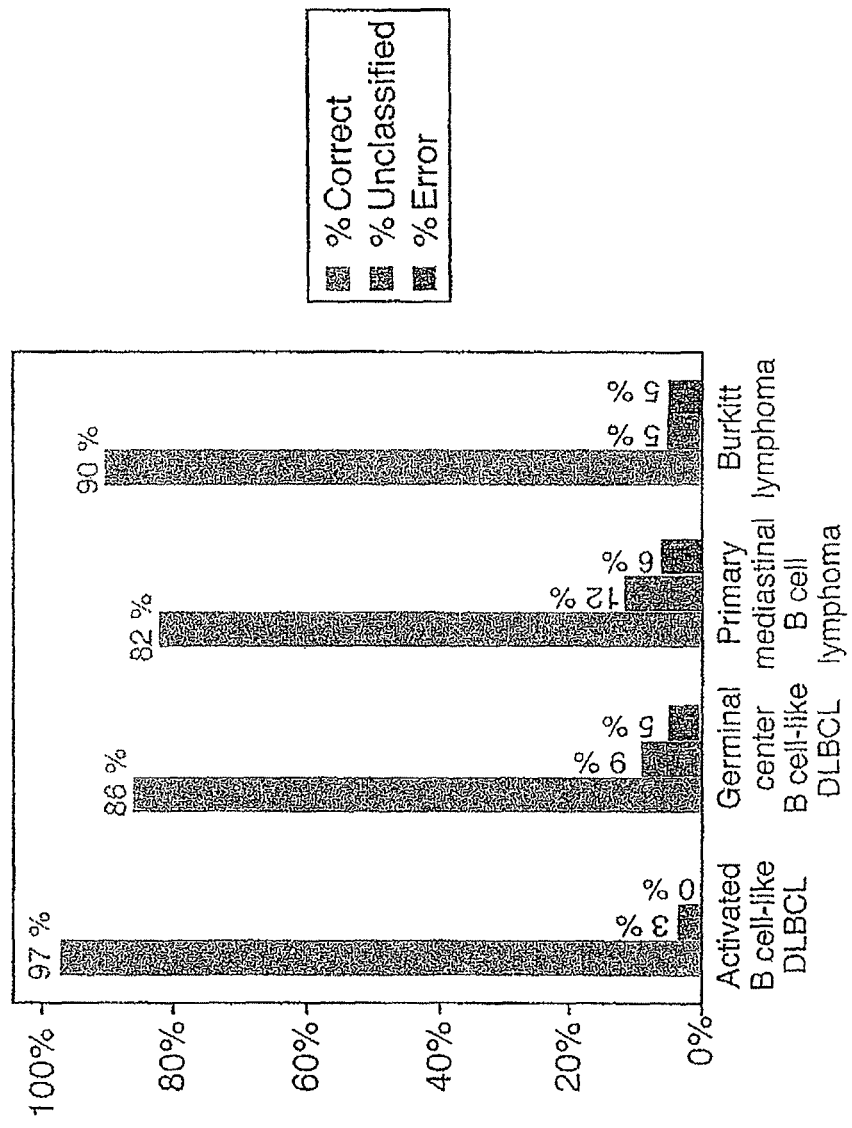
FIG. 28: DLBCL subtype classification based on gene expression. None of the ABC samples were classified as the wrong subtype, while only one of the BL samples was classified incorrectly. Of the GCB and PMBL samples, only 5% and 6%, respectively, were classified incorrectly.

Classification of DLBCL/BL Samples into Subtypes Based on Bayesian Analysis of Gene Expression Data from the Lymph Dx Microarray Samples identified as DLBCL/BL in Example 17 were subdivided into four types: ABC, GCB, PMBL, and BL. These samples were then used to generate six pair-wise models using the same procedure described in Example 17. The results of the leave-one-out predictions using these pair-wise models are set forth in Table 2398, below. These results are also summarized in FIG. 28. The rows in the table correspond to different sample groups, while the columns indicate the prediction results. In this stage, the ability of the prediction method to identify BL was again measured against the diagnoses of hematopathologists. The ability of the prediction method to identify the various DLBCL subtypes, on the other hand, was measured against previous studies in which this distinction between subtypes was based on gene expression data from a Lymphochip microarray (Alizadeh 2000, Rosenwald 2002, Rosenwald 2003a, Wright 2003).

As seen in Table 2398, only 1 of the 20 BL lymphoma samples was classified incorrectly. The classification of DLBCL into subtypes was also quite effective. All previously identified ABC subtype samples were again assigned to the ABC subtype, while only 5% of the GCB samples and 6% of the PMBL samples were assigned to a different subtype than they were assigned to previously.

The above classification was implemented using S+ software and the S+ subtype predictor script contained in the file entitled "Subtype_Predictor.txt," located in the computer program listing appendix contained on CD number 22 of 22. This S+ script implements the lymphoma prediction algorithm. When this script is pasted into an S+ script window and run in a working directory containing the data set files discussed below, it will produce a text file entitled "PredictionResults.txt," which indicates the results of the predictive algorithm. The other files in the computer program listing appendix contain the required data sets, in their required format, for carrying out the lymphoma type identification described above. The file entitled "GeneData.txt" contains the gene expression values for each sample analyzed. This file is included in the working directory when the S+ subtype predictor script is run. The file entitled "GeneID.txt" contains information about the genes in the GeneData.txt file, and is also included in the working directory when the S+ subtype predictor script is run. This file indicates the UNIQID for each gene, as well as the extent to which the gene is associated with the lymph node and proliferation signatures ("LN.cor" and "pro.cor," respectively). The contents of "GeneID.txt" are also set forth in Table 2415 below.

TABLE 2398

|  | ABC | GCB | PMBL | BL | Unclassified | Total | % Correct | % Unclassified | % Error |
|---|---|---|---|---|---|---|---|---|---|
| ABC | 76 | 0 | 0 | 0 | 2 | 78 | 97% | 3% | 0% |
| GCB | 1 | 66 | 2 | 4 | 4 | 77 | 86% | 9% | 5% |
| PMBL | 0 | 2 | 27 | 0 | 4 | 33 | 82% | 12% | 6% |
| Unclassified DLBCL | 5 | 9 | 1 | 1 | 11 | 27 | NA | 41% | 4% |
| DLBCL (not yet subclassed) | 5 | 5 | 0 | 1 | 3 | 14 | NA | 21% | 7% |
| BL | 0 | 1 | 0 | 18 | 1 | 20 | 90% | 5% | 5% |
| FL grade 1 | 0 | 1 | 0 | 0 | 0 | 1 |  |  |  |
| FL grade 2 | 0 | 1 | 0 | 0 | 1 | 2 |  |  |  |
| FL grade 3A | 0 | 2 | 0 | 0 | 0 | 2 |  |  |  |
| Combined FL grades 1, 2, 3A | 0 | 4 | 0 | 0 | 1 | 5 |  |  |  |
| FL grade 3B | 0 | 1 | 0 | 0 | 1 | 2 |  |  |  |
| FL unknown grade | 0 | 1 | 0 | 1 | 1 | 3 |  |  |  |

The file entitled "SampleID.txt" contains information about the samples included in the "GeneData.txt" file, specifically the original classification of all the samples. This file is also included in the working directory when the S+ subtype predictor script is run. The file entitled "PredictionResults.txt" is an example of the productive output of the prediction algorithm.

After the above model was validated using leave-one-out cross-validation, the model was re-fit using all of the data to generate a final predictor that could be applied to a new set of data. Tables 2399-2414 indicate for each of the pair wise models the list of genes used, the weight given to each of those genes, the signature with which each gene was associated, the mean values and covariance matrices associated with the subtypes being compared, and the q-value cut-points of the pair-wise model.

TABLE 2399

ABC vs. BL

| Signature | Scale | UNIQID | Unigene ID Build 167 | Probe set | Gene symbol |
|---|---|---|---|---|---|
| Standard | −18.87 | 1101149 | 517226 | 229437_at | BIC |
| Standard | −17.4 | 1121452 | 227817 | 205681_at | BCL2A1 |
| Standard | −16.42 | 1123163 | 421342 | 208991_at | STAT3 |
| Standard | −16.2 | 1121629 | 41691 | 205965_at | BATF |
| Standard | −15 | 1134095 | 89555 | 208018_s_at | HCK |
| Standard | −14.75 | 1132636 | 306278 | 204490_s_at | CD44 |
| Standard | −14.33 | 1119939 | 170087 | 202820_at | AHR |
| Standard | −14.25 | 1100138 | 278391 | 228234_at | TIRP |
| Standard | −14.02 | 1128626 | 501452 | 219424_at | EB13 |
| Standard | −13.89 | 1132883 | 432453 | 205027_s_at | MAP3K8 |
| Standard | −13.88 | 1134991 | 444105 | 209474_s_at | ENTPD1 |
| Standard | −13.37 | 1109913 | 355724 | 239629_at | CFLAR |
| Standard | −13.25 | 1120389 | 75367 | 203761_at | SLA |
| Standard | −12.99 | 1131497 | 114931 | 202295_s_at | CTSH |
| Standard | −12.71 | 1115071 | 390476 | 223218_s_at | MAIL |
| Standard | −12.46 | 1136329 | 132739 | 211675_s_at | HIC |
| Standard | −12.41 | 1128195 | 115325 | 218699_at | RAB7L1 |
| Standard | −12.37 | 1124381 | 440808 | 212288_at | FNBP1 |
| Standard | −12.30 | 1100562 | 26608 | 228737_at | C20orf100 |
| Standard | −12.24 | 1101272 | 179089 | 229584_at | DKFZp434 |
| Standard | −12.18 | 1128536 | 21126 | 219279_at | DOCK10 |
| Standard | −11.64 | 1098271 | 300670 | 226056_at | CDGAP |
| Standard | −11.41 | 1119566 | 433506 | 201954_at | ARPC1B |
| Standard | −11.11 | 1120651 | 80205 | 204269_at | PIM2 |
| Standard | −10.89 | 1098952 | 62264 | 226841_at | KIAA0937 |
| Standard | −10.80 | 1099939 | 488173 | 227983_at | MGC7036 |
| Standard | −10.67 | 1134270 | 352119 | 208284_x_at | GGT1 |
| Standard | −10.44 | 1134145 | 4750 | 208091_s_at | DKFZP564 |
| Standard | −10.39 | 1123437 | 73090 | 209636_at | NFKB2 |
| Standard | −10.17 | 1119884 | 418004 | 202716_at | PTPM1 |
| Standard | −10.14 | 1129269 | 62919 | 220358_at | SNFT |
| Standard | −10.13 | 1126293 | 504816 | 215346_at | TNFRSF5 |
| Standard | −10.12 | 1112344 | 163242 | 242406_at | |
| Standard | −10.10 | 1135550 | 221811 | 210550_s_at | RASGRF1 |
| Standard | −10.08 | 1135165 | 170359 | 209827_s_at | IL16 |
| Standard | −10.05 | 1120808 | 127686 | 204562_at | IRF4 |
| Standard | −10.01 | 1122087 | 72927 | 206693_at | IL7 |
| Standard | −9.97 | 1132004 | 415117 | 203217_s_at | SIAT9 |
| Standard | −9.88 | 1114824 | 193370 | 222762_x_at | LIMD1 |
| Standard | −9.87 | 1132034 | 410455 | 203271_s_at | UNC119 |
| Standard | −9.87 | 1099680 | 210387 | 227677_at | JAK3 |
| Standard | −9.86 | 1132830 | 31210 | 204908_s_at | BCL3 |
| Standard | −9.79 | 1099631 | 367639 | 227624_at | FLJ20032 |
| Standard | −9.78 | 1120267 | 256278 | 203508_at | TNFRSF1B |
| Standard | −9.77 | 1124187 | 378738 | 211986_at | MGC5395 |
| Standard | −9.73 | 1108970 | 140489 | 238604_at | |
| Standard | −9.71 | 1136216 | 512152 | 211528_x_at | HLA-G |
| Standard | −9.71 | 1120993 | 327 | 204912_at | IL10RA |
| Standard | −9.68 | 1100847 | 97411 | 229070_at | C6orf105 |
| Standard | −9.64 | 1123413 | 418291 | 209575_at | IL10RB |
| Standard | −9.62 | 1115704 | 350268 | 224569_s_at | IRF2BP2 |
| Standard | −9.58 | 1108237 | 126232 | 237753_at | |
| Standard | −9.55 | 1121695 | 511759 | 206082_at | HCP5 |
| Standard | −9.48 | 1101905 | 170843 | 230345_at | |
| Standard | −9.42 | 1119243 | 440165 | 201171_at | ATP6V0E |
| Standard | −9.39 | 1140457 | 210546 | 221658_s_at | IL21R |
| Standard | −9.32 | 1098506 | 193400 | 226333_at | IL6R |
| Standard | −9.31 | 1139805 | 414362 | 220230_s_at | CYB5R2 |
| Standard | −9.30 | 1139037 | 173380 | 218223_s_at | CKIP-1 |
| Standard | −9.28 | 1130533 | 76507 | 200706_s_at | LITAF |
| Standard | −9.15 | 1098678 | 386140 | 226530_at | BMF |
| Standard | −9.04 | 1133210 | 434374 | 205842_s_at | JAK2 |
| Standard | 9.05 | 1116432 | 409362 | 229356_x_at | KIAA1259 |

TABLE 2399-continued

ABC vs. BL

| | | | | | |
|---|---|---|---|---|---|
| Standard | 9.17 | 1097281 | 7037 | 224892_at | PLDN |
| Standard | 9.17 | 1140018 | 438482 | 220917_s_at | PWDMP |
| Standard | 9.30 | 1119997 | 367811 | 202951_at | STK38 |
| Standard | 9.41 | 1119817 | 409194 | 202561_at | TNKS |
| Standard | 9.55 | 1139842 | 133523 | 220367_s_at | SAP130 |
| Standard | 9.64 | 1132122 | 307734 | 203434_s_at | MME |
| Standard | 9.77 | 1119258 | 88556 | 201209_at | HDAC1 |
| Standard | 9.80 | 1128248 | 234149 | 218802_at | FLJ20647 |
| Standard | 10.38 | 1101211 | 287659 | 229513_at | STRBP |
| Standard | 10.52 | 1123419 | 170195 | 209590_at | BMP7 |
| Standard | 10.71 | 1133755 | 404501 | 207318_s_at | CDC2L5 |
| Standard | 10.80 | 1128192 | 102506 | 218696_at | EIF2AK3 |
| Standard | 10.85 | 1124786 | 22370 | 212847_at | NEXN |
| Standard | 10.92 | 1130114 | 445084 | 221965_at | MPHOSPH9 |
| Standard | 11.00 | 1126081 | 309763 | 215030_at | GRSF1 |
| Standard | 11.17 | 1118736 | 96731 | 38340_at | HIP1R |
| Standard | 11.26 | 1124613 | 296720 | 212599_at | AUTS2 |
| Standard | 11.43 | 1125456 | 300592 | 213906_at | MYBL1 |
| Standard | 11.60 | 1097177 | 9691 | 224761_at | GNA13 |
| Standard | 12.11 | 1120400 | 152207 | 203787_at | SSBP2 |
| Standard | 12.12 | 1139266 | 76640 | 218723_s_at | RGC32 |
| Standard | 12.22 | 1100770 | 65578 | 228976_at | |
| Standard | 12.73 | 1131246 | 153752 | 201853_s_at | CDC25B |
| Standard | 13.48 | 1096503 | 21379 | 223522_at | C9orf45 |
| Standard | 14.50 | 1124920 | 6150 | 213039_at | ARHGEF1 |
| Standard | 15.03 | 1128360 | 445043 | 218988_at | SLC35E3 |
| Standard | 15.24 | 1099444 | 434489 | 227407_at | FLJ90013 |
| Standard | 21.03 | 1134582 | 78202 | 208794_s_at | SMARCA4 |

| Standard | | | |
|---|---|---|---|
| Mean ABC | −4179.76 | Cut 1 | 0.20 |
| Mean BL | −1894.68 | Cut 2 | 0.80 |
| Covariance ABC | 53707.58 | | |
| Covariance BL | 194887.5 | | |

TABLE 2400

ABC vs. GCB

| Signature | Scale | UNIQID | Unigene ID Build 167 | Probe set | Gene symbol |
|---|---|---|---|---|---|
| Standard | −15.31 | 1122645 | 158341 | 207641_at | TNFRSF13B |
| Standard | −14.56 | 1120651 | 80205 | 204269_at | PIM2 |
| Standard | −14.18 | 1120808 | 127686 | 204562_at | IRF4 |
| Standard | −13.84 | 1114824 | 193370 | 222762_x_at | LIMD1 |
| Standard | −13.44 | 1136687 | 59943 | 212345_s_at | CREB3L2 |
| Standard | −13.12 | 1139805 | 414362 | 220230_s_at | CYB5R2 |
| Standard | −12.23 | 1104552 | 193857 | 233483_at | LOC96597 |
| Standard | −12.19 | 1097236 | 235860 | 224837_at | FOXP1 |
| Standard | −12.06 | 1121629 | 41691 | 205965_at | BATF |
| Standard | −11.93 | 1128195 | 115325 | 218699_at | RAB7L1 |
| Standard | −11.72 | 1111503 | 502910 | 241383_at | KBRAS2 |
| Standard | −11.66 | 1134991 | 444105 | 209474_s_at | ENTPD1 |
| Standard | −11.27 | 1098678 | 386140 | 226530_at | BMF |
| Standard | −10.9 | 1131074 | 76894 | 201572_x_at | DCTD |
| Standard | −10.82 | 1135165 | 170359 | 209827_s_at | IL16 |
| Standard | −10.7 | 1132396 | 118722 | 203988_s_at | FUT8 |
| Standard | −10.54 | 1131541 | 310230 | 202369_s_at | TRAM2 |
| Standard | −10.47 | 1105759 | 171262 | 235056_at | ETV6 |
| Standard | −10.38 | 1121564 | 437783 | 205865_at | ARID3A |
| Standard | −10.16 | 1130472 | 192374 | 200599_s_at | TRA1 |
| Standard | −10.04 | 1132058 | 161999 | 203313_s_at | TGIF |
| Standard | −10.03 | 1105684 | 195155 | 234973_at | SLC38A5 |
| Standard | −9.95 | 1097735 | 26765 | 225436_at | LOC58489 |
| Standard | −9.94 | 1115071 | 390476 | 223218_s_at | MAIL |
| Standard | −9.85 | 1101149 | 517226 | 229437_at | BIC |
| Standard | −9.83 | 1119884 | 418004 | 202716_at | PTPN1 |
| Standard | −9.71 | 1134095 | 89555 | 208018_s_at | HCK |
| Standard | −9.68 | 1135550 | 221811 | 210550_s_at | RASGRF1 |
| Standard | −9.61 | 1098927 | 356216 | 226811_at | FLJ20202 |
| Standard | −9.6 | 1120389 | 75367 | 203761_at | SLA |
| Standard | −9.58 | 1133910 | 167746 | 207655_s_at | BLNK |
| Standard | 9.56 | 1118736 | 96731 | 38340_at | HIP1R |

TABLE 2400-continued

ABC vs. GCB

| | | | | | |
|---|---|---|---|---|---|
| Standard | 9.58 | 1128860 | 323634 | 219753_at | STAG3 |
| Standard | 9.68 | 1134582 | 78202 | 208794_s_at | SMARCA4 |
| Standard | 9.7 | 1121853 | 98243 | 206310_at | SPINK2 |
| Standard | 10.14 | 1119258 | 88556 | 201209_at | HDAC1 |
| Standard | 10.19 | 1132122 | 307734 | 203434_s_at | MME |
| Standard | 10.23 | 1120400 | 152207 | 203787_at | SSBP2 |
| Standard | 10.48 | 1529344 | 317970 | Lymph_Dx_065_at | SERPINA11 |
| Standard | 10.64 | 1124613 | 296720 | 212599_at | AUTS2 |
| Standard | 10.72 | 1132159 | 147868 | 203521_s_at | ZNF318 |
| Standard | 10.98 | 1097901 | 266175 | 225626_at | PAG |
| Standard | 11.1 | 1128287 | 300063 | 218862_at | ASB13 |
| Standard | 12.26 | 1099686 | 117721 | 227684_at | |
| Standard | 12.45 | 1112674 | 310320 | 242794_at | MAML3 |
| Standard | 13.15 | 1120370 | 78877 | 203723_at | ITPKB |
| Standard | 14.23 | 1125456 | 300592 | 213906_at | MYBL1 |
| Lymph Node | 6.8 | 1097202 | 386779 | 224796_at | DDEF1 |
| Lymph Node | 6.85 | 1131755 | 241257 | 202729_s_at | LTBP1 |
| Lymph Node | 7.27 | 1136273 | 13775 | 211597_s_at | HOP |
| Lymph Node | 7.35 | 1119424 | 75485 | 201599_at | OAT |
| Lymph Node | 7.86 | 1095985 | 83883 | 222450_at | TMEPAI |
| Lymph Node | 8.02 | 1124875 | 18166 | 212975_at | KIAA0870 |
| Lymph Node | 8.32 | 1124655 | 79299 | 212658_at | LHFPL2 |
| Lymph Node | 8.62 | 1115034 | 387222 | 223158_s_at | NEK6 |
| Proliferation | −9.11 | 1120583 | 153768 | 204133_at | RNU3IP2 |
| Proliferation | −7.87 | 1135492 | 408615 | 210448_s_at | P2RX5 |
| Proliferation | −7.68 | 1127756 | 313544 | 217850_at | NS |
| Proliferation | −7.57 | 1097195 | 149931 | 224785_at | MGC29814 |
| Proliferation | −7.31 | 1127813 | 14317 | 217962_at | NOLA3 |
| Proliferation | −7.24 | 1138944 | 84753 | 218051_s_at | FLJ12442 |
| Proliferation | −6.99 | 1139226 | 266514 | 218633_x_at | FLJ11342 |
| Proliferation | −6.7 | 1137486 | 441069 | 214442_s_at | MIZ1 |
| Proliferation | −6.51 | 1133786 | 153591 | 207396_s_at | ALG3 |
| Proliferation | −6.45 | 1131150 | 75514 | 201695_s_at | NP |
| Proliferation | −6.45 | 1119076 | 268849 | 200681_at | GLO1 |
| Proliferation | −6.38 | 1115679 | 8345 | 224523_s_at | MGC4308 |
| Proliferation | −6.34 | 1110223 | 212709 | 239973_at | |
| Proliferation | −6.3 | 1529338 | 284275 | Lymph_Dx_058_s_at | PAK2 |
| Proliferation | −6.24 | 1135164 | 458360 | 209825_s_at | UMPK |
| Proliferation | −6.24 | 1128738 | 335550 | 219581_at | MGC2776 |
| Proliferation | −6.01 | 1099088 | 14355 | 226996_at | |
| Proliferation | −5.98 | 1123192 | 315177 | 209100_at | IFRD2 |
| Proliferation | −5.83 | 1116073 | 146161 | 227103_s_at | MGC2408 |
| Proliferation | 5.79 | 1097388 | 278839 | 225024_at | C20orf77 |
| Proliferation | 6.13 | 1124563 | 249441 | 212533_at | WEE1 |

| | Standard | Lymph Node | Proliferation | | |
|---|---|---|---|---|---|
| Mean ABC | −2226.57 | 476.67 | −1096.34 | Cut 1 | 0.50 |
| Mean GCB | −1352.02 | 547.18 | −1005.72 | Cut 2 | 0.74 |
| Covariance ABC | 33472.10 | 3418.91 | 4347.99 | | |
| | 3418.91 | 1296.05 | 846.32 | | |
| | 4347.99 | 846.32 | 1609.13 | | |
| Covariance GCB | 53751.59 | 466.34 | 751.08 | | |
| | 466.34 | 777.74 | 249.29 | | |
| | 751.08 | 249.29 | 1708.67 | | |

TABLE 2401

ABC vs. PMBL

| Signature | Scale | UNIQID | Unigene ID Build 167 | Probe set | Gene Symbol |
|---|---|---|---|---|---|
| Standard | −14.61 | 1097236 | 235860 | 224837_at | FOXP1 |
| Standard | −14.47 | 1104552 | 193857 | 233483_at | LOC96597 |
| Standard | −13.62 | 1122645 | 158341 | 207641_at | TNFRSF13B |
| Standard | −12.05 | 1135102 | 349845 | 209685_s_at | PRKCB1 |
| Standard | −11.65 | 1096499 | 293867 | 223514_at | CARD11 |
| Standard | −11.26 | 1124770 | 153261 | 212827_at | IGHM |
| Standard | −11.25 | 1125010 | 43728 | 213170_at | GPX7 |
| Standard | −11.13 | 1109545 | 63187 | 239231_at | |
| Standard | −10.99 | 1109220 | 445977 | 238880_at | GTF3A |
| Standard | −10.87 | 1131074 | 76894 | 201572_x_at | DCTD |
| Standard | −10.68 | 1134517 | 75807 | 208690_s_at | PDLIM1 |
| Standard | −10.63 | 1098604 | 32793 | 226444_at | SLC39A10 |

TABLE 2401-continued

ABC vs. PMBL

| | | | | | |
|---|---|---|---|---|---|
| Standard | −10.56 | 1131219 | 109150 | 201810_s_at | SH3BP5 |
| Standard | −10.52 | 1120651 | 80205 | 204269_at | PIM2 |
| Standard | −10.39 | 1133910 | 167746 | 207655_s_at | BLNK |
| Standard | −10.32 | 1099396 | 435949 | 227346_at | ZNFN1A1 |
| Standard | −10.25 | 1529297 | 132335 | Lymph_Dx_015_at | |
| Standard | −10.17 | 1107575 | 424589 | 237033_at | MGC52498 |
| Standard | −10.11 | 1117211 | 356509 | 233955_x_at | HSPC195 |
| Standard | 10.06 | 1129517 | −33 | 220712_at | |
| Standard | 10.29 | 1139950 | 437385 | 220731_s_at | FLJ10420 |
| Standard | 10.35 | 1097553 | 197071 | 225214_at | PSMB7 |
| Standard | 10.41 | 1119516 | 6061 | 201834_at | PRKAB1 |
| Standard | 10.47 | 1122772 | 66742 | 207900_at | CCL17 |
| Standard | 10.55 | 1132762 | 80395 | 204777_s_at | MAL |
| Standard | 10.77 | 1099265 | 375762 | 227193_at | |
| Standard | 10.81 | 1095996 | 288801 | 222482_at | SSBP3 |
| Standard | 11.14 | 1100770 | 65578 | 228976_at | |
| Standard | 11.19 | 1133801 | 181097 | 207426_s_at | TNFSF4 |
| Standard | 11.61 | 1099154 | 97927 | 227066_at | MOBKL2C |
| Standard | 11.63 | 1120370 | 78877 | 203723_at | ITPKB |
| Standard | 11.8 | 1112674 | 310320 | 242794_at | MAML3 |
| Standard | 12.57 | 1105178 | 283961 | 234284_at | GNG8 |
| Standard | 12.63 | 1124613 | 296720 | 212599_at | AUTS2 |
| Standard | 13.28 | 1106415 | 169071 | 235774_at | |
| Standard | 13.3 | 1121762 | 32970 | 206181_at | SLAMF1 |
| Standard | 13.6 | 1121853 | 98243 | 206310_at | SPINK2 |
| Lymph Node | 10.91 | 1105838 | 129837 | 235142_at | ZBTB8 |
| Lymph Node | 10.99 | 1136273 | 13775 | 211597_s_at | HOP |
| Lymph Node | 11.02 | 1099418 | 172792 | 227370_at | KIAA1946 |
| Lymph Node | 11.46 | 1124875 | 18166 | 212975_at | KIAA0870 |
| Lymph Node | 11.99 | 1120299 | 79334 | 203574_at | NFIL3 |
| Lymph Node | 12.49 | 1135871 | 104717 | 211031_s_at | CYLN2 |
| Lymph Node | 13.33 | 1121767 | 458324 | 206187_at | PTGIR |
| Proliferation | −13.17 | 1138944 | 84753 | 218051_s_at | FLJ12442 |
| Proliferation | −11.61 | 1116122 | 42768 | 227408_s_at | DKFZp761O0113 |
| Proliferation | −11.16 | 1110223 | 212709 | 239973_at | |
| Proliferation | −9.93 | 1120717 | 444159 | 204394_at | SLC43A1 |
| Proliferation | −9.54 | 1110099 | 116665 | 239835_at | TA-KRP |
| Proliferation | −9.49 | 1130942 | 445977 | 201338_x_at | GTF3A |
| Proliferation | −9.28 | 1123192 | 315177 | 209100_at | IFRD2 |
| Proliferation | −9.14 | 1135492 | 408615 | 210448_s_at | P2RX5 |
| Proliferation | −9.03 | 1120011 | 3068 | 202983_at | SMARCA3 |
| Proliferation | −9.01 | 1096738 | 87968 | 223903_at | TLR9 |
| Proliferation | −8.91 | 1108961 | 292088 | 238593_at | FLJ22531 |

| | Standard | Lymph Node | Proliferation | | |
|---|---|---|---|---|---|
| Mean ABC | −849.47 | 531.79 | −1027.48 | Cut 1 | 0.20 |
| Mean PMBL | 27.99 | 750.84 | −872.43 | Cut 2 | 0.80 |
| Covariance ABC | 14028.46 | 3705.84 | 3118.60 | | |
| | 3705.84 | 2326.91 | 1083.37 | | |
| | 3118.60 | 1083.37 | 1589.42 | | |
| Covariance PMBL | 19425.29 | 5109.98 | 2199.28 | | |
| | 5109.98 | 2084.28 | 620.86 | | |
| | 2199.28 | 620.86 | 1028.44 | | |

TABLE 2402

BL vs. GCB

| Signature | Scale | UNIQID | Unigene ID Build 167 | Probe set | Gene Symbol |
|---|---|---|---|---|---|
| Standard | −12.78 | 1131246 | 153752 | 201853_s_at | CDC25B |
| Standard | −11.35 | 1099444 | 434489 | 227407_at | FLJ90013 |
| Standard | −10.4 | 1116432 | 409362 | 229356_x_at | KIAA1259 |
| Standard | −10.3 | 1134582 | 78202 | 208794_s_at | SMARCA4 |
| Standard | −10.01 | 1133998 | 76884 | 207826_s_at | ID3 |
| Standard | −9.3 | 1126081 | 309763 | 215030_at | GRSF1 |
| Standard | −9.19 | 1096503 | 21379 | 223522_at | C9orf45 |
| Standard | −8.95 | 1529340 | −99 | Lymph_Dx_061_at | |
| Standard | −8.88 | 1138128 | 390428 | 216199_s_at | MAP3K4 |
| Standard | −8.8 | 1099152 | 351247 | 227064_at | MGC15396 |
| Standard | −8.69 | 1133757 | 6113 | 207320_x_at | STAU |
| Standard | −8.54 | 1116593 | 422889 | 230329_s_at | NUDT6 |
| Standard | −8.4 | 1130926 | 508741 | 201310_s_at | C5orf13 |

TABLE 2402-continued

| | | BL vs. GCB | | | |
|---|---|---|---|---|---|
| Standard | −8.39 | 1135685 | 371282 | 210776_x_at | TCF3 |
| Standard | −8.39 | 1140520 | 11747 | 221741_s_at | C20orf21 |
| Standard | −8.34 | 1119802 | 7370 | 202522_at | PITPNB |
| Standard | −8.31 | 1096149 | 410205 | 222824_at | NUDT5 |
| Standard | −8.23 | 1124786 | 22370 | 212847_at | NEXN |
| Standard | −8.07 | 1098012 | 355669 | 225756_at | CSNK1E |
| Standard | −7.89 | 1116317 | 526415 | 228661_s_at | |
| Standard | −7.86 | 1109195 | 416155 | 238853_at | |
| Standard | −7.71 | 1134880 | 168799 | 209265_s_at | METTL3 |
| Standard | −7.66 | 1529298 | 136707 | Lymph_Dx_016_at | |
| Standard | −7.55 | 1128660 | 413071 | 219471_at | C13orf18 |
| Standard | −7.55 | 1138973 | 11270 | 218097_s_at | C10orf66 |
| Standard | −7.46 | 1127294 | 421986 | 217028_at | CXCR4 |
| Standard | 7.47 | 1134270 | 352119 | 208284_x_at | GGT1 |
| Standard | 7.48 | 1120743 | 79197 | 204440_at | CD83 |
| Standard | 7.5 | 1098179 | 163725 | 225956_at | LOC153222 |
| Standard | 7.55 | 1121400 | 223474 | 205599_at | TRAF1 |
| Standard | 7.59 | 1114967 | 7905 | 223028_s_at | SNX9 |
| Standard | 7.6 | 1122087 | 72927 | 206693_at | IL7 |
| Standard | 7.64 | 1101905 | 170843 | 230345_at | |
| Standard | 7.77 | 1120700 | 410745 | 204362_at | SCAP2 |
| Standard | 7.8 | 1120572 | 84 | 204116_at | IL2RG |
| Standard | 7.84 | 1098271 | 300670 | 226056_at | CDGAP |
| Standard | 7.9 | 1115073 | 131315 | 223220_s_at | BAL |
| Standard | 7.9 | 1133210 | 434374 | 205842_s_at | JAK2 |
| Standard | 8 | 1129269 | 62919 | 220358_at | SNFT |
| Standard | 8.01 | 1131940 | 1103 | 203085_s_at | TGFB1 |
| Standard | 8.07 | 1098506 | 193400 | 226333_at | IL6R |
| Standard | 8.13 | 1120601 | 441129 | 204166_at | KIAA0963 |
| Standard | 8.21 | 1102540 | 434881 | 231093_at | FCRH3 |
| Standard | 8.24 | 1121695 | 511759 | 206082_at | HCP5 |
| Standard | 8.33 | 1136877 | 409934 | 212998_x_at | HLA-DQB1 |
| Standard | 8.37 | 1100138 | 278391 | 228234_at | TIRP |
| Standard | 8.46 | 1126293 | 504816 | 215346_at | TNFRSF5 |
| Standard | 8.46 | 1127805 | 380627 | 217947_at | CKLFSF6 |
| Standard | 8.59 | 1136573 | 914 | 211991_s_at | HLA-DPA1 |
| Standard | 8.62 | 1119111 | 35052 | 200804_at | TEGT |
| Standard | 8.7 | 1136329 | 132739 | 211675_s_at | HIC |
| Standard | 8.74 | 1123690 | 111805 | 210176_at | TLR1 |
| Standard | 8.81 | 1138677 | 390440 | 217436_x_at | |
| Standard | 8.89 | 1113993 | 131811 | 244286_at | |
| Standard | 8.89 | 1132651 | 439767 | 204529_s_at | TOX |
| Standard | 8.91 | 1119566 | 433506 | 201954_at | ARPC1B |
| Standard | 9.01 | 1128626 | 501452 | 219424_at | EBI3 |
| Standard | 9.17 | 1101272 | 179089 | 229584_at | DKFZp434H2111 |
| Standard | 9.33 | 1136777 | 387679 | 212671_s_at | HLA-DQA1 |
| Standard | 9.33 | 1109756 | 530304 | 239453_at | |
| Standard | 9.4 | 1136216 | 512152 | 211528_x_at | HLA-G |
| Standard | 9.4 | 1124381 | 440808 | 212288_at | FNBP1 |
| Standard | 9.46 | 1099680 | 210387 | 227677_at | JAK3 |
| Standard | 9.49 | 1109913 | 355724 | 239629_at | CFLAR |
| Standard | 9.55 | 1132636 | 306278 | 204490_s_at | CD44 |
| Standard | 9.59 | 1119243 | 440165 | 201171_at | ATP6V0E |
| Standard | 9.72 | 1101149 | 517226 | 229437_at | BIC |
| Standard | 9.8 | 1130674 | 381008 | 200905_x_at | HLA-E |
| Standard | 10.34 | 1119939 | 170087 | 202820_at | AHR |
| Standard | 10.44 | 1132883 | 432453 | 205027_s_at | MAP3K8 |
| Standard | 10.74 | 1121452 | 227817 | 205681_at | BCL2A1 |
| Standard | 10.84 | 1137360 | 429658 | 214196_s_at | CLN2 |
| Standard | 12.08 | 1132520 | 283063 | 204249_s_at | LMO2 |
| Standard | 12.33 | 1131497 | 114931 | 202295_s_at | CTSH |
| Standard | 13.58 | 1123163 | 421342 | 208991_at | STAT3 |
| Lymph Node | −9.1 | 1138136 | 433574 | 216215_s_at | RBM9 |
| Lymph Node | 8.78 | 1130121 | 411958 | 221978_at | HLA-F |
| Lymph Node | 9.22 | 1139830 | 221851 | 220330_s_at | SAMSN1 |
| Lymph Node | 9.23 | 1131705 | 386467 | 202638_s_at | ICAM1 |
| Lymph Node | 9.62 | 1130168 | 75626 | 222061_at | CD58 |
| Lymph Node | 9.66 | 1121844 | 83077 | 206295_at | IL18 |
| Lymph Node | 9.68 | 1121000 | 519033 | 204924_at | TLR2 |
| Lymph Node | 9.83 | 1102437 | 437023 | 230966_at | IL4I1 |
| Lymph Node | 10.71 | 1119475 | 296323 | 201739_at | SGK |
| Lymph Node | 11.09 | 1131786 | 375957 | 202803_s_at | ITGB2 |
| Proliferation | −11.07 | 1133141 | 344524 | 205677_s_at | DLEU1 |
| Proliferation | −10.04 | 1138259 | 89525 | 216484_x_at | HDGF |
| Proliferation | −9.74 | 1131578 | 202453 | 202431_s_at | MYC |
| Proliferation | −9.45 | 1137449 | 223745 | 214363_s_at | MATR3 |
| Proliferation | −9.43 | 1130468 | 166463 | 200594_x_at | HNRPU |
| Proliferation | −9.21 | 1138157 | 82563 | 216251_s_at | KIAA0153 |

TABLE 2402-continued

| | | | BL vs. GCB | | | | |
|---|---|---|---|---|---|---|---|
| Proliferation | −9.15 | 1127756 | 313544 | 217850_at | NS | | |
| Proliferation | −9 | 1130433 | 246112 | 200058_s_at | U5-200KD | | |
| Proliferation | −8.76 | 1123108 | 108112 | 208828_at | POLE3 | | |
| Proliferation | −8.75 | 1128738 | 335550 | 219581_at | MGC2776 | | |
| Proliferation | −8.74 | 1122400 | 439911 | 207199_at | TERT | | |
| Proliferation | −8.66 | 1097948 | 69476 | 225684_at | LOC348235 | | |
| Proliferation | −8.6 | 1119460 | 76122 | 201696_at | SFRS4 | | |
| Proliferation | −8.6 | 1136401 | 27258 | 211761_s_at | SIP | | |
| Proliferation | −8.58 | 1099088 | 14355 | 226996_at | | | |
| Proliferation | −8.51 | 1134653 | 253536 | 208901_s_at | TOP1 | | |
| Proliferation | −8.49 | 1140584 | 294083 | 221932_s_at | C14orf87 | | |
| Proliferation | −8.43 | 1121309 | 23642 | 205449_at | HSU79266 | | |
| Proliferation | −8.43 | 1120385 | 36708 | 203755_at | BUB1B | | |
| Proliferation | −8.38 | 1136710 | 75782 | 212429_s_at | GTF3C2 | | |
| Proliferation | −8.36 | 1136605 | 448398 | 212064_x_at | MAZ | | |
| Proliferation | −8.24 | 1120697 | 323462 | 204355_at | DHX30 | | |
| Proliferation | −8.19 | 1127833 | 382044 | 218001_at | MRPS2 | | |
| Proliferation | −8.11 | 1096903 | 437460 | 224185_at | FLJ10385 | | |
| Proliferation | −8.1 | 1120596 | 4854 | 204159_at | CDKN2C | | |
| Proliferation | −8.1 | 1120779 | 28853 | 204510_at | CDC7 | | |
| | | Standard | Lymph Node | Proliferation | | | |
| Mean BL | | 1098.69 | 576.05 | −2392.12 | Cut 1 | 0.09 | |
| Mean GCB | | 2187.37 | 768.53 | −2129.35 | Cut 2 | 0.53 | |
| Covariance BL | | 75263.67 | 12684.43 | 15734.77 | | | |
| | | 12684.43 | 2650.81 | 2358.05 | | | |
| | | 15734.77 | 2358.05 | 4653.00 | | | |
| Covariance GCB | | 50548.22 | 9301.12 | 14182.83 | | | |
| | | 9301.12 | 2602.51 | 3028.21 | | | |
| | | 14182.83 | 3028.21 | 5983.04 | | | |

TABLE 2403

| | | BL vs. PMBL | | | |
|---|---|---|---|---|---|
| Signature | Scale | UNIQID | Unigene ID Build 167 | Probe set | Gene Symbol |
| Standard | −13.54 | 1099444 | 434489 | 227407_at | FLJ90013 |
| Standard | −13.42 | 1096503 | 21379 | 223522_at | C9orf45 |
| Standard | −13.36 | 1130114 | 445084 | 221965_at | MPHOSPH9 |
| Standard | −13.27 | 1124786 | 22370 | 212847_at | NEXN |
| Standard | −13.27 | 1134582 | 78202 | 208794_s_at | SMARCA4 |
| Standard | −12.37 | 1096149 | 410205 | 222824_at | NUDT5 |
| Standard | −11.95 | 1130855 | 77515 | 201189_s_at | ITPR3 |
| Standard | −11.66 | 1529298 | 136707 | Lymph_Dx_016_at | |
| Standard | −11.35 | 1131246 | 153752 | 201853_s_at | CDC25B |
| Standard | −11.17 | 1136925 | 436939 | 213154_s_at | BICD2 |
| Standard | −11.08 | 1124188 | 282346 | 211987_at | TOP2B |
| Standard | −11.06 | 1133998 | 76884 | 207826_s_at | ID3 |
| Standard | −10.76 | 1139266 | 76640 | 218723_s_at | RGC32 |
| Standard | −10.74 | 1134880 | 168799 | 209265_s_at | METTL3 |
| Standard | −10.69 | 1140520 | 11747 | 221741_s_at | C20orf21 |
| Standard | −10.6 | 1109545 | 63187 | 239231_at | |
| Standard | −10.55 | 1106043 | 266331 | 235372_at | FREB |
| Standard | −10.52 | 1110214 | 144519 | 239964_at | TCL6 |
| Standard | −10.49 | 1098592 | 283707 | 226431_at | ALS2CR13 |
| Standard | −10.45 | 1109220 | 445977 | 238880_at | GTF3A |
| Standard | −10.41 | 1131263 | 249955 | 201877_s_at | PPP2R5C |
| Standard | 10.54 | 1122772 | 66742 | 207900_at | CCL17 |
| Standard | 10.59 | 1109913 | 355724 | 239629_at | CFLAR |
| Standard | 10.82 | 1119884 | 418004 | 202716_at | PTPN1 |
| Standard | 10.83 | 1135189 | 137569 | 209863_s_at | TP73L |
| Standard | 10.89 | 1123437 | 73090 | 209636_at | NFKB2 |
| Standard | 11.15 | 1124381 | 440808 | 212288_at | FNBP1 |
| Standard | 11.26 | 1108237 | 126232 | 237753_at | |
| Standard | 11.34 | 1101149 | 517226 | 229437_at | BIC |
| Standard | 11.77 | 1139774 | 15827 | 220140_s_at | SNX11 |
| Standard | 11.87 | 1123163 | 421342 | 208991_at | STAT3 |
| Standard | 11.93 | 1129269 | 62919 | 220358_at | SNFT |
| Standard | 12.03 | 1132636 | 306278 | 204490_s_at | CD44 |
| Standard | 12.1 | 1138677 | 390440 | 217436_x_at | |
| Standard | 12.2 | 1139950 | 437385 | 220731_s_at | FLJ10420 |
| Standard | 12.25 | 1134270 | 352119 | 208284_x_at | GGT1 |

TABLE 2403-continued

BL vs. PMBL

| Signature | Scale | UNIQID | Unigene ID Build 167 | Probe set | Gene Symbol |
|---|---|---|---|---|---|
| Standard | 12.27 | 1136216 | 512152 | 211528_x_at | HLA-G |
| Standard | 12.79 | 1121400 | 223474 | 205599_at | TRAF1 |
| Standard | 12.82 | 1119939 | 170087 | 202820_at | AHR |
| Standard | 13.12 | 1126293 | 504816 | 215346_at | TNFRSF5 |
| Standard | 13.44 | 1100138 | 278391 | 228234_at | TIRP |
| Standard | 13.74 | 1132883 | 432453 | 205027_s_at | MAP3K8 |
| Standard | 13.94 | 1131497 | 114931 | 202295_s_at | CTSH |
| Standard | 14.15 | 1121762 | 32970 | 206181_at | SLAMF1 |
| Standard | 14.51 | 1132520 | 283063 | 204249_s_at | LMO2 |
| Standard | 14.68 | 1121452 | 227817 | 205681_at | BCL2A1 |
| Standard | 15.24 | 1105178 | 283961 | 234284_at | GNG8 |
| Lymph Node | 10.95 | 1121205 | 2488 | 205269_at | LCP2 |
| Lymph Node | 11.22 | 1140845 | 21486 | AFFX-HUMISGF3A/M97935_3_at | STAT1 |
| Lymph Node | 11.45 | 1131068 | 118400 | 201564_s_at | FSCN1 |
| Lymph Node | 11.92 | 1131705 | 386467 | 202638_s_at | ICAM1 |
| Lymph Node | 12.06 | 1131038 | 81328 | 201502_s_at | NFKBIA |
| Lymph Node | 12.49 | 1121444 | 153563 | 205668_at | LY75 |
| Lymph Node | 13.01 | 1123457 | 446304 | 209684_at | RIN2 |
| Lymph Node | 13.19 | 1140404 | 354740 | 221584_s_at | KCNMA1 |
| Lymph Node | 13.26 | 1124875 | 18166 | 212975_at | KIAA0870 |
| Lymph Node | 14.06 | 1102437 | 437023 | 230966_at | IL4I1 |
| Lymph Node | 14.11 | 1132766 | 82359 | 204781_s_at | TNFRSF6 |
| Lymph Node | 15.31 | 1121767 | 458324 | 206187_at | PTGIR |
| Lymph Node | 15.32 | 1135871 | 104717 | 211031_s_at | CYLN2 |
| Lymph Node | 15.34 | 1138652 | 444471 | 217388_s_at | KYNU |
| Lymph Node | 16.01 | 1139830 | 221851 | 220330_s_at | SAMSN1 |

|  | Standard | Lymph Node |  |  |
|---|---|---|---|---|
| Mean BL | −66.97 | 1445.63 | Cut 1 | 0.20 |
| Mean PMBL | 1205.38 | 2041.25 | Cut 2 | 0.80 |
| Covariance BL | 35263.67 | 13424.88 | | |
| | 13424.88 | 7458.56 | | |
| Covariance PMBL | 12064.38 | 5113.74 | | |
| | 5113.74 | 3216.53 | | |

TABLE 2404

FH vs. DLBCL-BL

| Signature | Scale | UNIQID | Unigene ID Build 167 | Probe set | Gene Symbol |
|---|---|---|---|---|---|
| Standard | −12.81 | 1104910 | 458262 | 233969_at | IGL@ |
| Standard | −11.54 | 1102898 | 145519 | 231496_at | FKSG87 |
| Standard | −11.46 | 1117298 | 449586 | 234366_x_at | |
| Standard | −11.46 | 1132973 | 169294 | 205255_x_at | TCF7 |
| Standard | −11.22 | 1133099 | 88646 | 205554_s_at | DNASE1L3 |
| Standard | −10.76 | 1131531 | 153647 | 202350_s_at | MATN2 |
| Standard | −10.59 | 1124283 | 406612 | 212144_at | UNC84B |
| Standard | −10.35 | 1099847 | 36723 | 227867_at | LOC129293 |
| Standard | −10.22 | 1136430 | 102950 | 211798_x_at | IGLJ3 |
| Standard | −10.05 | 1117394 | −13 | 234792_x_at | |
| Standard | −9.95 | 1133047 | 528338 | 205434_s_at | AAK1 |
| Standard | −9.95 | 1098865 | 250905 | 226741_at | LOC51234 |
| Standard | −9.82 | 1108515 | 98132 | 238071_at | LCN6 |
| Standard | −9.8 | 1131407 | 154248 | 202125_s_at | ALS2CR3 |
| Standard | −9.77 | 1128469 | 390817 | 219173_at | FLJ22686 |
| Standard | −9.7 | 1123875 | 428 | 210607_at | FLT3LG |
| Standard | −9.69 | 1131875 | 169172 | 202965_s_at | CAPN6 |
| Standard | −9.69 | 1135173 | 3781 | 209841_s_at | LRRN3 |
| Standard | −9.48 | 1099798 | 411081 | 227811_at | FGD3 |
| Standard | −9.41 | 1119046 | 349499 | 200606_at | DSP |
| Standard | −9.36 | 1122449 | 278694 | 207277_at | CD209 |
| Standard | −9.34 | 1114017 | 133255 | 244313_at | |
| Standard | −9.34 | 1122767 | 652 | 207892_at | TNFSF5 |
| Standard | −9.24 | 1123369 | 79025 | 209481_at | SNRK |
| Standard | −9.16 | 1098954 | 128905 | 226844_at | MOBKL2B |
| Standard | −9.14 | 1135513 | 421437 | 210481_s_at | CD209L |
| Standard | −9.08 | 1100904 | 426296 | 229145_at | LOC119504 |
| Standard | −8.99 | 1122738 | 81743 | 207840_at | CD160 |
| Standard | −8.94 | 1120925 | 204891 | 204773_at | IL11RA |
| Standard | 9.09 | 1123055 | 185726 | 208691_at | TFRC |
| Standard | 9.62 | 1134858 | 405954 | 209226_s_at | TNPO1 |

TABLE 2404-continued

| FH vs. DLBCL-BL | | | | | |
|---|---|---|---|---|---|
| Standard | 10.19 | 1123052 | 180909 | 208680_at | PRDX1 |
| Standard | 10.81 | 1124178 | 446579 | 211969_at | HSPCA |
| Lymph Node | −10.59 | 1137597 | 3903 | 214721_x_at | CDC42EP4 |
| Lymph Node | −9.69 | 1119684 | 439586 | 202242_at | TM4SF2 |
| Lymph Node | −9.25 | 1125593 | 8910 | 214180_at | MAN1C1 |
| Lymph Node | −8.44 | 1124318 | 21858 | 212190_at | SERPINE2 |
| Lymph Node | −8.09 | 1119448 | 212296 | 201656_at | ITGA6 |
| Lymph Node | −8.07 | 1125546 | 125036 | 214081_at | PLXDC1 |
| Lymph Node | −7.7 | 1097683 | 132569 | 225373_at | PP2135 |
| Lymph Node | −7.56 | 1101305 | 112742 | 229623_at | |
| Lymph Node | 7.45 | 1135240 | 436852 | 209955_s_at | FAP |
| Proliferation | 6.97 | 1135101 | 20830 | 209680_s_at | KIFC1 |
| Proliferation | 7.03 | 1130426 | 432607 | 200039_s_at | PSMB2 |
| Proliferation | 7.04 | 1130501 | 2795 | 200650_s_at | LDHA |
| Proliferation | 7.08 | 1130744 | 158688 | 201027_s_at | EIF5B |
| Proliferation | 7.23 | 1137506 | 75258 | 214501_s_at | H2AFY |
| Proliferation | 7.32 | 1131474 | 95577 | 202246_s_at | CDK4 |
| Proliferation | 7.39 | 1130871 | 159087 | 201222_s_at | RAD23B |
| Proliferation | 7.42 | 1119375 | 381072 | 201489_at | PPIF |
| Proliferation | 7.47 | 1136595 | 404814 | 212038_s_at | VDAC1 |
| Proliferation | 7.7 | 1135858 | 90093 | 211015_s_at | HSPA4 |
| Proliferation | 7.78 | 1130527 | 184233 | 200692_s_at | HSPA9B |
| Proliferation | 7.78 | 1130820 | 151777 | 201144_s_at | EIF2S1 |
| Proliferation | 7.83 | 1115829 | 433213 | 225253_s_at | METTL2 |
| Proliferation | 7.84 | 1134699 | 439683 | 208974_x_at | KPNB1 |
| Proliferation | 7.87 | 1120274 | 31584 | 203517_at | MTX2 |
| Proliferation | 7.92 | 1136786 | 63788 | 212694_s_at | PCCB |
| Proliferation | 7.95 | 1097172 | 434886 | 224753_at | CDCA5 |
| Proliferation | 8.4 | 1138537 | −12 | 217140_s_at | |
| Proliferation | 8.53 | 1119488 | 154672 | 201761_at | MTHFD2 |
| Proliferation | 8.58 | 1130799 | 233952 | 201114_x_at | PSMA7 |
| Proliferation | 8.72 | 1135673 | 82159 | 210759_s_at | PSMA1 |
| Proliferation | 9.4 | 1114679 | 16470 | 222503_s_at | FLJ10904 |

| | Standard | Lymph Node | Proliferation | | |
|---|---|---|---|---|---|
| Mean FH | −2193.59 | −588.21 | 1571.78 | Cut 1 | 0.50 |
| Mean DLBCL-BL | −1448.27 | −441.91 | 1735.00 | Cut 2 | 0.92 |
| Covariance FH | 6729.73 | 1223.99 | 2541.22 | | |
| | 1223.99 | 405.22 | 293.72 | | |
| | 2541.22 | 293.72 | 1797.58 | | |
| Covariance DLBCL-BL | 17675.23 | 3642.41 | 4158.43 | | |
| | 3642.41 | 1379.81 | 1066.48 | | |
| | 4158.43 | 1066.48 | 2858.21 | | |

TABLE 2405

| FH vs. FL | | | | | |
|---|---|---|---|---|---|
| Signature | Scale | UNIQID | Unigene ID Build 167 | Probe set | Gene Symbol |
| Standard | −11.23 | 1117298 | 449586 | 234366_x_at | |
| Standard | −10.62 | 1121953 | 38365 | 206478_at | KIAA0125 |
| Standard | −10.6 | 1104910 | 458262 | 233969_at | IGL@ |
| Standard | −10.39 | 1136430 | 102950 | 211798_x_at | IGLJ3 |
| Standard | −9.96 | 1129281 | 395486 | 220377_at | C14orf110 |
| Standard | −9.73 | 1118835 | 102336 | 47069_at | ARHGAP8 |
| Standard | −9.21 | 1127807 | 7236 | 217950_at | NOSIP |
| Standard | −9.05 | 1128377 | 371003 | 219014_at | PLAC8 |
| Standard | −8.85 | 1101004 | 2969 | 229265_at | SKI |
| Standard | 9.06 | 1139411 | 368238 | 219073_s_at | OSBPL10 |
| Standard | 9.07 | 1120789 | 154729 | 204524_at | PDPK1 |
| Standard | 9.21 | 1136464 | 159428 | 211833_s_at | BAX |
| Standard | 9.29 | 1125279 | 445652 | 213575_at | TRA2A |
| Standard | 9.45 | 1529390 | 79241 | Lymph_Dx_120_at | BCL2 |
| Standard | 9.52 | 1132022 | 173911 | 203247_s_at | ZNF24 |
| Standard | 9.57 | 1139645 | 134051 | 219757_s_at | C14orf101 |
| Standard | 9.64 | 1137561 | 67397 | 214639_s_at | HOXA1 |
| Standard | 9.66 | 1114893 | 314623 | 222891_s_at | BCL11A |
| Standard | 10.38 | 1098095 | 131059 | 225852_at | ANKRD17 |
| Standard | 10.4 | 1134858 | 405954 | 209226_s_at | TNPO1 |
| Standard | 12.65 | 1101054 | 173328 | 229322_at | PPP2R5E |

TABLE 2405-continued

FH vs. FL

| Signature | Scale | UNIQID | Unigene ID Build 167 | Probe set | Gene Symbol |
|---|---|---|---|---|---|
| Standard | 12.79 | 1124178 | 446579 | 211969_at | HSPCA |
| Standard | 13.34 | 1135489 | 288178 | 210438_x_at | SSA2 |

| | Standard | | |
|---|---|---|---|
| Mean FH | 136.43 | Cut 1 | 0.50 |
| Mean FL | 640.38 | Cut 2 | 0.99 |
| Covariance FH | 10719.40 | | |
| Covariance FL | 9373.11 | | |

TABLE 2406

FH vs. MCL

| Signature | Scale | UNIQID | Unigene ID Build 167 | Probe set | Gene Symbol |
|---|---|---|---|---|---|
| Standard | 13.05 | 1100258 | 88442 | 228377_at | KIAA1384 |
| Standard | 13.43 | 1529382 | 371468 | Lymph_Dx_111_at | CCND1 |
| Standard | 13.54 | 1106855 | 455101 | 236255_at | KIAA1909 |
| Standard | 13.73 | 1529308 | 193014 | Lymph_Dx_027_x_at | |
| Standard | 14.56 | 1100873 | 445884 | 229103_at | |
| Standard | 21.12 | 1132834 | 432638 | 204914_s_at | SOX11 |
| Lymph Node | −8.44 | 1130378 | 234434 | 44783_s_at | HEY1 |
| Lymph Node | −7.92 | 1123552 | 423077 | 209879_at | SELPLG |
| Lymph Node | −7.7 | 1131218 | 76753 | 201809_s_at | ENG |
| Lymph Node | −7.4 | 1097683 | 132569 | 225373_at | PP2135 |
| Lymph Node | −7.15 | 1136273 | 13775 | 211597_s_at | HOP |
| Lymph Node | 14.16 | 1134532 | 371468 | 208711_s_at | CCND1 |

| | Standard | Lymph Node | | |
|---|---|---|---|---|
| Mean FH | 451.68 | −282.65 | Cut 1 | 0.20 |
| Mean MCFL | 863.16 | −156.82 | Cut 2 | 0.80 |
| Covariance FH | 1617.92 | 222.89 | | |
| | 222.89 | 271.65 | | |
| Covariance MCL | 3154.38 | 917.30 | | |
| | 917.30 | 659.94 | | |

TABLE 2407

FH vs. SLL

| Signature | Scale | UNIQID | Unigene ID Build 167 | Probe set | Gene Symbol |
|---|---|---|---|---|---|
| Standard | −13.14 | 1120765 | 343329 | 204484_at | PIK3C2B |
| Standard | −12.9 | 1097897 | 266175 | 225622_at | PAG |
| Standard | 12.72 | 1133195 | 274243 | 205805_s_at | ROR1 |
| Standard | 12.74 | 1140416 | 58831 | 221601_s_at | TOSO |
| Standard | 13.53 | 1131687 | 369280 | 202606_s_at | TLK1 |
| Standard | 13.57 | 1107044 | 163426 | 236458_at | |
| Standard | 14.43 | 1529389 | 79241 | Lymph_Dx_119_at | BCL2 |
| Standard | 14.51 | 1129026 | 135146 | 220007_at | FLJ13984 |
| Standard | 14.77 | 1136987 | 21695 | 213370_s_at | SFMBT1 |
| Standard | 14.79 | 1137109 | 469653 | 213689_x_at | RPL5 |
| Standard | 15.37 | 1529308 | 193014 | Lymph_Dx_027_x_at | |
| Standard | 15.82 | 1120832 | 57856 | 204604_at | PFTK1 |
| Standard | 17.37 | 1135550 | 221811 | 210550_s_at | RASGRF1 |
| Standard | 18.98 | 1122864 | 434384 | 208195_at | TTN |
| Lymph Node | −12.89 | 1123038 | 119000 | 208636_at | ACTN1 |
| Lymph Node | −12.8 | 1130378 | 234434 | 44783_s_at | HEY1 |
| Lymph Node | −11.59 | 1124875 | 18166 | 212975_at | KIAA0870 |
| Lymph Node | −11.47 | 1103497 | 50115 | 232231_at | |
| Lymph Node | −10.31 | 1099358 | 93135 | 227300_at | |
| Lymph Node | −10.27 | 1121129 | 285401 | 205159_at | CSF2RB |
| Lymph Node | −10.23 | 1100249 | 388674 | 228367_at | HAK |
| Lymph Node | −10.05 | 1132345 | 109225 | 203868_s_at | VCAM1 |
| Lymph Node | −9.93 | 1123401 | 50130 | 209550_at | NDN |

TABLE 2407-continued

FH vs. SLL

| | | | | | |
|---|---|---|---|---|---|
| Lymph Node | −9.75 | 1120500 | 82568 | 203979_at | CYP27A1 |
| Lymph Node | −9.57 | 1124318 | 21858 | 212190_at | SERPINE2 |
| Lymph Node | −9.48 | 1120288 | 17483 | 203547_at | CD4 |
| Lymph Node | −9.45 | 1123372 | 195825 | 209487_at | RBPMS |
| Lymph Node | −9.39 | 1123376 | 37682 | 209496_at | RARRES2 |
| Lymph Node | −9.29 | 1123213 | 12956 | 209154_at | TIP-1 |
| Lymph Node | −9.23 | 1098412 | 409515 | 226225_at | MCC |
| Lymph Node | −9.23 | 1125593 | 8910 | 214180_at | MAN1C1 |
| Lymph Node | −9.17 | 1131786 | 375957 | 202803_s_at | ITGB2 |
| Lymph Node | −9.04 | 1097683 | 132569 | 225373_at | PP2135 |
| Lymph Node | −8.91 | 1097255 | 380144 | 224861_at | |
| Lymph Node | −8.76 | 1131068 | 118400 | 201564_s_at | FSCN1 |
| Lymph Node | −8.7 | 1119074 | 54457 | 200675_at | CD81 |
| Lymph Node | −8.68 | 1125130 | 35861 | 213338_at | RIS1 |
| Lymph Node | −8.59 | 1139661 | 416456 | 219806_s_at | FN5 |

| | Standard | Lymph Node | | |
|---|---|---|---|---|
| Mean FH | 1144.02 | −2223.71 | Cut 1 | 0.20 |
| Mean SLL | 1592.27 | −1798.11 | Cut 2 | 0.80 |
| Covariance FH | 902.56 | 442.69 | | |
| | 442.69 | 809.90 | | |
| Covariance SLL | 2426.26 | 2938.58 | | |
| | 2938.58 | 9435.72 | | |

TABLE 2408

FL vs. DLBCL-BL

| Signature | Scale | UNIQID | Unigene ID Build 167 | Probe set | Gene Symbol |
|---|---|---|---|---|---|
| Standard | −23.03 | 1124833 | 356416 | 212914_at | CBX7 |
| Standard | −22.25 | 1099204 | 193784 | 227121_at | |
| Standard | −22.2 | 1119766 | 93231 | 202423_at | MYST3 |
| Standard | −22.04 | 1099798 | 411081 | 227811_at | FGD3 |
| Standard | −22.01 | 1102898 | 145519 | 231496_at | FKSG87 |
| Standard | −21.79 | 1131197 | 269902 | 201778_s_at | KIAA0494 |
| Standard | −21.69 | 1098415 | 130900 | 226230_at | KIAA1387 |
| Standard | −21.57 | 1120834 | 57907 | 204606_at | CCL21 |
| Standard | −21.39 | 1130155 | 436657 | 222043_at | CLU |
| Standard | −20.98 | 1100904 | 426296 | 229145_at | LOC119504 |
| Standard | −20.8 | 1131531 | 153647 | 202350_s_at | MATN2 |
| Standard | −20.72 | 1137582 | 433732 | 214683_s_at | CLK1 |
| Standard | −20.66 | 1119782 | 155418 | 202478_at | TRB2 |
| Standard | −20.59 | 1122767 | 652 | 207892_at | TNFSF5 |
| Standard | −20.58 | 1125001 | 16193 | 213158_at | |
| Standard | −20.56 | 1134921 | 413513 | 209341_s_at | IKBKB |
| Standard | −20.56 | 1132973 | 169294 | 205255_x_at | TCF7 |
| Standard | −20.53 | 1136984 | 498154 | 213364_at | SNX1 |
| Standard | −20.41 | 1115888 | 35096 | 225629_s_at | ZBTB4 |
| Standard | −20.37 | 1120160 | 436976 | 203288_at | KIAA0355 |
| Standard | −20.36 | 1139054 | 25726 | 218263_s_at | LOC58486 |
| Standard | −20.31 | 1130030 | 301872 | 221834_at | LONP |
| Standard | −20.08 | 1133024 | 436987 | 205383_s_at | ZNF288 |
| Standard | −20.05 | 1124666 | 526394 | 212672_at | ATM |
| Standard | −19.3 | 1529397 | 406557 | Lymph_Dx_127_s_at | CLK4 |
| Standard | −19.16 | 1116056 | 243678 | 226913_s_at | SOX8 |
| Standard | −19.14 | 1098433 | 202577 | 226250_at | |
| Standard | −19.1 | 1123635 | 408614 | 210073_at | SIAT8A |
| Standard | −18.95 | 1138920 | 24395 | 218002_s_at | CXCL14 |
| Standard | −18.84 | 1133099 | 88646 | 205554_s_at | DNASE1L3 |
| Standard | −18.83 | 1098495 | 443668 | 226318_at | TBRG1 |
| Standard | −18.64 | 1100879 | 119983 | 229111_at | MASP2 |
| Standard | −18.59 | 1120695 | 385685 | 204352_at | TRAF5 |
| Standard | −18.55 | 1119983 | 409783 | 202920_at | ANK2 |
| Standard | −18.5 | 1101276 | 1098 | 229588_at | ERdj5 |
| Standard | −18.47 | 1099140 | 500350 | 227052_at | |
| Standard | −18.46 | 1529331 | 374126 | Lymph_Dx_051_s_at | |
| Standard | −18.45 | 1131752 | 170133 | 202724_s_at | FOXO1A |
| Standard | −18.45 | 1099265 | 375762 | 227193_at | |
| Standard | −18.32 | 1098179 | 163725 | 225956_at | LOC153222 |
| Standard | −18.29 | 1119568 | 269777 | 201957_at | PPP1R12B |
| Standard | −18.19 | 1099900 | 444508 | 227934_at | |
| Standard | −18.17 | 1119361 | 391858 | 201448_at | TIA1 |

TABLE 2408-continued

| | | FL vs. DLBCL-BL | | | |
|---|---|---|---|---|---|
| Standard | −18.02 | 1121650 | 421137 | 206002_at | GPR64 |
| Standard | −17.91 | 1100911 | 320147 | 229152_at | C4orf7 |
| Standard | −17.86 | 1529285 | 348929 | Lymph_Dx_002_at | KIAA1219 |
| Standard | −17.47 | 1529357 | 444651 | Lymph_Dx_081_at | |
| Standard | −17.42 | 1131863 | 2316 | 202936_s_at | SOX9 |
| Standard | −17.16 | 1129943 | 512828 | 221626_at | ZNF506 |
| Standard | −17.12 | 1121301 | 449971 | 205437_at | ZNF134 |
| Standard | −17.11 | 1131340 | 437457 | 202018_s_at | LTF |
| Standard | −17.1 | 1124606 | 444324 | 212588_at | PTPRC |
| Standard | −17.08 | 1131407 | 154248 | 202125_at | ALS2CR3 |
| Standard | −16.97 | 1118939 | 198161 | 60528_at | PLA2G4B |
| Standard | −16.91 | 1134738 | 75842 | 209033_s_at | DYRK1A |
| Standard | −16.9 | 1134083 | 285091 | 207996_s_at | C18orf1 |
| Standard | −16.89 | 1120925 | 204891 | 204773_at | IL11RA |
| Standard | −16.86 | 1110070 | −101 | 239803_at | |
| Standard | −16.83 | 1100042 | 351413 | 228113_at | RAB37 |
| Standard | −16.82 | 1120134 | 75545 | 203233_at | IL4R |
| Standard | −16.75 | 1124283 | 406612 | 212144_at | UNC84B |
| Standard | −16.72 | 1109603 | −100 | 239292_at | |
| Standard | −16.71 | 1120509 | 155090 | 204000_at | GNB5 |
| Standard | −16.65 | 1133538 | 1416 | 206760_s_at | FCER2 |
| Standard | −16.64 | 1130735 | 179526 | 201009_s_at | TXNIP |
| Standard | −16.59 | 1100150 | 9343 | 228248_at | MGC39830 |
| Standard | −16.54 | 1124237 | 258855 | 212080_at | MLL |
| Standard | −16.51 | 1124416 | 283604 | 212331_at | RBL2 |
| Standard | −16.48 | 1133091 | 73792 | 205544_s_at | CR2 |
| Standard | −16.46 | 1131263 | 249955 | 201877_s_at | PPP2R5C |
| Standard | −16.44 | 1118347 | 528404 | 243366_s_at | ITGA4 |
| Standard | −16.43 | 1529343 | 521948 | Lymph_Dx_064_at | |
| Standard | −16.43 | 1099549 | 446665 | 227533_at | |
| Standard | 17.05 | 1529453 | 372679 | Lymph_Dx_085_at | FCGR3A |
| Standard | 17.41 | 1097540 | 388087 | 225195_at | |
| Standard | 18.47 | 1140473 | 17377 | 221676_s_at | CORO1C |
| Standard | 18.55 | 1121100 | 301921 | 205098_at | CCR1 |
| Standard | 20.07 | 1124254 | 301743 | 212110_at | SLC39A14 |
| Standard | 20.2 | 1130771 | 61153 | 201068_s_at | PSMC2 |
| Standard | 21.46 | 1137583 | 273415 | 214687_x_at | ALDOA |
| Standard | 21.55 | 1098168 | 22151 | 225943_at | NLN |
| Standard | 24.07 | 1123055 | 185726 | 208691_at | TFRC |
| Standard | 24.09 | 1123052 | 180909 | 208680_at | PRDX1 |
| Lymph Node | −20.5 | 1137597 | 3903 | 214721_x_at | CDC42EP4 |
| Lymph Node | −18.52 | 1124318 | 21858 | 212190_at | SERPINE2 |
| Lymph Node | −18.5 | 1136762 | 380138 | 212624_s_at | CHN1 |
| Lymph Node | −18.07 | 1101305 | 112742 | 229623_at | |
| Lymph Node | −17.75 | 1100249 | 388674 | 228367_at | HAK |
| Lymph Node | −16.1 | 1098412 | 409515 | 226225_at | MCC |
| Lymph Node | −15.51 | 1140464 | 111676 | 221667_s_at | HSPB8 |
| Lymph Node | −15.43 | 1136832 | 434959 | 212842_x_at | RANBP2L1 |
| Lymph Node | −15.37 | 1119684 | 439586 | 202242_at | TM4SF2 |
| Lymph Node | −15.02 | 1097448 | 250607 | 225093_at | UTRN |
| Lymph Node | −14.83 | 1136844 | 16007 | 212875_s_at | C21orf25 |
| Lymph Node | −14.73 | 1135056 | 169946 | 209604_s_at | GATA3 |
| Lymph Node | −14.48 | 1097202 | 386779 | 224796_at | DDEF1 |
| Lymph Node | −14.44 | 1121278 | 21355 | 205399_at | DCAMKL1 |
| Lymph Node | −14.22 | 1125009 | 27621 | 213169_at | |
| Lymph Node | −13.97 | 1100288 | 26981 | 228411_at | ALS2CR19 |
| Lymph Node | −13.51 | 1132462 | 14845 | 204131_s_at | FOXO3A |
| Lymph Node | −13.37 | 1135322 | 450230 | 210095_s_at | IGFBP3 |
| Lymph Node | −13.35 | 1097280 | 423523 | 224891_at | |
| Lymph Node | −12.86 | 1137097 | 20107 | 213656_s_at | KNS2 |
| Lymph Node | −12.85 | 1098809 | 359394 | 226682_at | |
| Lymph Node | −12.28 | 1124875 | 18166 | 212975_at | KIAA0870 |
| Lymph Node | −12.18 | 1132345 | 109225 | 203868_s_at | VCAM1 |
| Lymph Node | −12 | 1097561 | 19221 | 225224_at | DKFZP566G1424 |
| Lymph Node | −11.71 | 1123401 | 50130 | 209550_at | NDN |
| Lymph Node | −11.04 | 1136996 | 283749 | 213397_x_at | RNASE4 |
| Lymph Node | −10.77 | 1136788 | 355455 | 212698_s_at | 36778 |
| Lymph Node | −10.71 | 1098822 | 443452 | 226695_at | PRRX1 |
| Lymph Node | −10.63 | 1134200 | 90786 | 208161_s_at | ABCC3 |
| Lymph Node | −10.47 | 1136427 | 276506 | 211795_s_at | FYB |
| Lymph Node | −10.46 | 1121186 | 100431 | 205242_at | CXCL13 |
| Lymph Node | −10.39 | 1099332 | 32433 | 227272_at | |
| Lymph Node | −10.39 | 1098978 | 124863 | 226869_at | |
| Lymph Node | −10.22 | 1103303 | 49605 | 232000_at | C9orf52 |
| Lymph Node | −10.16 | 1131325 | 13313 | 201990_s_at | CREBL2 |
| Lymph Node | −10.16 | 1098174 | 274401 | 225949_at | LOC340371 |
| Lymph Node | −9.93 | 1124733 | 66762 | 212771_at | LOC221061 |
| Lymph Node | −9.42 | 1123372 | 195825 | 209487_at | RBPMS |

TABLE 2408-continued

| | | FL vs. DLBCL-BL | | | |
|---|---|---|---|---|---|
| Lymph Node | −9.36 | 1132220 | 448805 | 203632_s_at | GPRC5B |
| Lymph Node | −9.29 | 1120703 | 83974 | 204368_at | SLCO2A1 |
| Lymph Node | −9.26 | 1132013 | 434961 | 203232_s_at | SCA1 |
| Lymph Node | −9.25 | 1097307 | 379754 | 224929_at | LOC340061 |
| Lymph Node | −9.18 | 1119251 | 433941 | 201194_at | SEPW1 |
| Lymph Node | −9.08 | 1097609 | 6093 | 225283_at | ARRDC4 |
| Lymph Node | −9.07 | 1136459 | 252550 | 211828_s_at | KIAA0551 |
| Lymph Node | −8.86 | 1132775 | 1027 | 204803_s_at | RRAD |
| Lymph Node | −8.78 | 1098946 | 135121 | 226834_at | ASAM |
| Lymph Node | −8.68 | 1140589 | 433488 | 221942_s_at | GUCY1A3 |
| Lymph Node | −8.44 | 1116966 | 301124 | 232744_x_at | |
| Lymph Node | −8.39 | 1100130 | 76494 | 228224_at | PRELP |
| Lymph Node | −8.36 | 1110019 | −94 | 239744_at | |
| Lymph Node | −8.3 | 1134647 | 298654 | 208892_s_at | DUSP6 |
| Lymph Node | −8.28 | 1125593 | 8910 | 214180_at | MAN1C1 |
| Lymph Node | 7.97 | 1134370 | 1422 | 208438_s_at | FGR |
| Lymph Node | 8.05 | 1123566 | 155935 | 209906_at | C3AR1 |
| Lymph Node | 8.09 | 1131119 | 349656 | 201647_s_at | SCARB2 |
| Lymph Node | 8.11 | 1123586 | 93841 | 209948_at | KCNMB1 |
| Lymph Node | 8.13 | 1128615 | 104800 | 219410_at | FLJ10134 |
| Lymph Node | 8.21 | 1097297 | 166254 | 224917_at | VMP1 |
| Lymph Node | 8.23 | 1120299 | 79334 | 203574_at | NFIL3 |
| Lymph Node | 8.37 | 1128157 | 23918 | 218631_at | VIP32 |
| Lymph Node | 8.4 | 1130054 | 82547 | 221872_at | RARRES1 |
| Lymph Node | 8.41 | 1098152 | 377588 | 225922_at | KIAA1450 |
| Lymph Node | 8.53 | 1101566 | 98558 | 229947_at | |
| Lymph Node | 8.59 | 1135251 | 21486 | 209969_s_at | STAT1 |
| Lymph Node | 8.84 | 1099167 | 381105 | 227080_at | MGC45731 |
| Lymph Node | 9.01 | 1132920 | 753 | 205119_s_at | FPR1 |
| Lymph Node | 9.26 | 1097253 | 77873 | 224859_at | B7H3 |
| Lymph Node | 9.29 | 1120500 | 82568 | 203979_at | CYP27A1 |
| Lymph Node | 9.36 | 1131507 | 172928 | 202311_s_at | COL1A1 |
| Lymph Node | 9.38 | 1096456 | 82407 | 223454_at | CXCL16 |
| Lymph Node | 9.49 | 1136172 | 38084 | 211470_s_at | SULT1C1 |
| Lymph Node | 10.03 | 1138244 | 418138 | 216442_x_at | FN1 |
| Lymph Node | 10.34 | 1134424 | −17 | 208540_x_at | S100A14 |
| Lymph Node | 10.48 | 1136152 | 458436 | 211434_s_at | CCRL2 |
| Lymph Node | 10.51 | 1118708 | 7835 | 37408_at | MRC2 |
| Lymph Node | 10.6 | 1136540 | 179657 | 211924_s_at | PLAUR |
| Lymph Node | 10.63 | 1098278 | 166017 | 226066_at | MITF |
| Lymph Node | 10.76 | 1119477 | 163867 | 201743_at | CD14 |
| Lymph Node | 10.81 | 1096429 | 64896 | 223405_at | NPL |
| Lymph Node | 11.58 | 1123672 | 67846 | 210152_at | LILRB4 |
| Lymph Node | 12 | 1096364 | 29444 | 223276_at | NID67 |
| Lymph Node | 12.16 | 1119070 | 445570 | 200663_at | CD63 |
| Lymph Node | 12.3 | 1133065 | 77274 | 205479_s_at | PLAU |
| Lymph Node | 12.5 | 1135240 | 436852 | 209955_s_at | FAP |
| Lymph Node | 13.09 | 1116826 | 26204 | 231823_at | KIAA1295 |
| Lymph Node | 13.32 | 1119068 | 417004 | 200660_at | S100A11 |
| Lymph Node | 13.45 | 1120266 | 246381 | 203507_at | CD68 |
| Lymph Node | 13.63 | 1133216 | 502577 | 205872_x_at | PDE4DIP |
| Lymph Node | 13.67 | 1131815 | 386678 | 202856_s_at | SLC16A3 |
| Lymph Node | 14.38 | 1132132 | 279910 | 203454_s_at | ATOX1 |
| Lymph Node | 15.25 | 1134682 | 411701 | 208949_s_at | LGALS3 |
| Lymph Node | 15.46 | 1119237 | 389964 | 201141_at | GPNMB |
| Lymph Node | 15.89 | 1137698 | 442669 | 215001_s_at | GLUL |
| Lymph Node | 17.8 | 1137782 | 384944 | 215223_s_at | SOD2 |
| Lymph Node | 20.11 | 1130629 | 135226 | 200839_s_at | CTSB |
| Proliferation | 21.02 | 1119375 | 381072 | 201489_at | PPIF |
| Proliferation | 21.24 | 1119488 | 154672 | 201761_at | MTHFD2 |
| Proliferation | 21.31 | 1119467 | 21635 | 201714_at | TUBG1 |
| Proliferation | 21.68 | 1130820 | 151777 | 201144_s_at | EIF2S1 |
| Proliferation | 21.69 | 1131474 | 95577 | 202246_s_at | CDK4 |
| Proliferation | 22.2 | 1125249 | 244723 | 213523_at | CCNE1 |
| Proliferation | 22.97 | 1130501 | 2795 | 200650_s_at | LDHA |
| Proliferation | 23.12 | 1136913 | 99962 | 213113_s_at | SLC43A3 |
| Proliferation | 24.05 | 1130426 | 432607 | 200039_s_at | PSMB2 |

| | Standard | Lymph Node | Proliferation | | |
|---|---|---|---|---|---|
| Mean FL | −11121.51 | −1603.39 | 1890.60 | Cut 1 | 0.34 |
| Mean DLBCL-BL | −8760.65 | −460.71 | 2101.10 | Cut 2 | 0.94 |
| Covariance FL | 246359.77 | 111505.42 | 28908.20 | | |
| | 111505.42 | 67036.17 | 13130.59 | | |
| | 28908.20 | 13130.59 | 4617.24 | | |

TABLE 2408-continued

| FL vs. DLBCL-BL | | | |
|---|---|---|---|
| Covariance DLBCL-BL | 413069.12 | 178811.32 | 30151.89 |
| | 178811.32 | 106324.53 | 10877.26 |
| | 30151.89 | 10877.26 | 5180.68 |

TABLE 2409

| | | | FL vs. MCL | | |
|---|---|---|---|---|---|
| Signature | Scale | UNIQID | Unigene ID Build 167 | Probe set | Gene Symbol |
| Standard | −24.56 | 1123731 | 17165 | 210258_at | RGS13 |
| Standard | −22.56 | 1133192 | 24024 | 205801_s_at | RASGRP3 |
| Standard | −21.12 | 1114543 | 156189 | 244887_at | |
| Standard | −18.49 | 1120090 | 155024 | 203140_at | BCL6 |
| Standard | −18.07 | 1124646 | 436432 | 212646_at | RAFTLIN |
| Standard | −17.24 | 1132122 | 307734 | 203434_s_at | MME |
| Standard | −16.63 | 1105986 | 49614 | 235310_at | GCET2 |
| Standard | −15.09 | 1120134 | 75545 | 203233_at | IL4R |
| Standard | −14.05 | 1132651 | 439767 | 204529_s_at | TOX |
| Standard | 13.8 | 1098277 | 6786 | 226065_at | PRICKLE1 |
| Standard | 13.85 | 1109560 | 207428 | 239246_at | FARP1 |
| Standard | 13.86 | 1103504 | 142517 | 232239_at | |
| Standard | 13.88 | 1132734 | 126248 | 204724_s_at | COL9A3 |
| Standard | 13.91 | 1115905 | 301478 | 225757_s_at | CLMN |
| Standard | 14.89 | 1098840 | 55098 | 226713_at | C3orf6 |
| Standard | 14.97 | 1100873 | 445884 | 229103_at | |
| Standard | 14.99 | 1139393 | 170129 | 219032_x_at | OPN3 |
| Standard | 16.13 | 1124864 | 411317 | 212960_at | KIAA0882 |
| Standard | 16.36 | 1106855 | 455101 | 236255_at | KIAA1909 |
| Standard | 16.43 | 1120858 | 410683 | 204647_at | HOMER3 |
| Standard | 17.38 | 1130926 | 508741 | 201310_s_at | C5orf13 |
| Standard | 18.3 | 1103711 | 288718 | 232478_at | |
| Standard | 18.62 | 1109505 | 8162 | 239186_at | MGC39372 |
| Standard | 20.31 | 1132834 | 432638 | 204914_s_at | SOX11 |
| Standard | 22.61 | 1096070 | 241565 | 222640_at | DNMT3A |
| Standard | 28.66 | 1529382 | 371468 | Lymph_Dx_111_at | CCND1 |
| Lymph Node | −10.77 | 1097202 | 386779 | 224796_at | DDEF1 |
| Lymph Node | −10.22 | 1119546 | 433898 | 201921_at | GNG10 |
| Lymph Node | −9.89 | 1132766 | 82359 | 204781_s_at | TNFRSF6 |
| Lymph Node | −9.4 | 1138867 | 10706 | 217892_s_at | EPLIN |
| Lymph Node | 9.65 | 1125025 | 301094 | 213196_at | |
| Lymph Node | 10.44 | 1134797 | 433394 | 209118_s_at | TUBA3 |
| Lymph Node | 22.6 | 1529456 | 371468 | Lymph_Dx_113_at | CCND1 |
| Proliferation | −7.36 | 1097948 | 69476 | 225684_at | LOC348235 |
| Proliferation | −7.31 | 1130747 | 234489 | 201030_x_at | LDHB |
| Proliferation | −6.95 | 1130923 | 459987 | 201306_s_at | ANP32B |
| Proliferation | −6.87 | 1120205 | 5198 | 203405_at | DSCR2 |
| Proliferation | −6.64 | 1132468 | 79353 | 204147_s_at | TFDP1 |
| Proliferation | −6.1 | 1119916 | 177584 | 202780_at | OXCT |
| Proliferation | −6.08 | 1119873 | 446393 | 202697_at | CPSF5 |
| Proliferation | −6.08 | 1119488 | 154672 | 201761_at | MTHFD2 |
| Proliferation | −6.04 | 1130658 | 447492 | 200886_s_at | PGAM1 |
| Proliferation | −5.82 | 1132825 | 512813 | 204900_x_at | SAP30 |
| Proliferation | −5.53 | 1115607 | 435733 | 224428_s_at | CDCA7 |
| Proliferation | −5.44 | 1120316 | 63335 | 203611_at | TERF2 |
| Proliferation | −5.34 | 1114970 | 279529 | 223032_x_at | PX19 |
| Proliferation | −5.32 | 1140843 | 169476 | AFFX-HUMGAPDH/ M33197_5_at | GAPD |
| Proliferation | −5.28 | 1131081 | 180610 | 201586_s_at | SFPQ |
| Proliferation | −5.15 | 1121062 | 408658 | 205034_at | CCNE2 |
| Proliferation | 5.15 | 1120986 | 172052 | 204886_at | PLK4 |
| Proliferation | 5.16 | 1097195 | 149931 | 224785_at | MGC29814 |
| Proliferation | 5.2 | 1120011 | 3068 | 202983_at | SMARCA3 |
| Proliferation | 5.47 | 1100183 | 180582 | 228286_at | FLJ40869 |
| Proliferation | 5.67 | 1121012 | 96055 | 204947_at | E2F1 |
| Proliferation | 5.84 | 1115679 | 8345 | 224523_s_at | MGC4308 |
| Proliferation | 5.88 | 1135285 | 449501 | 210024_s_at | UBE2E3 |
| Proliferation | 5.92 | 1120520 | 35120 | 204023_at | RFC4 |
| Proliferation | 6.16 | 1529361 | 388681 | Lymph_Dx_086_s_at | HDAC3 |
| Proliferation | 6.45 | 1096054 | 21331 | 222606_at | FLJ10036 |
| Proliferation | 6.45 | 1096738 | 87968 | 223903_at | TLR9 |
| Proliferation | 6.51 | 1136781 | 120197 | 212680_x_at | PPP1R14B |
| Proliferation | 6.63 | 1119466 | 179718 | 201710_at | MYBL2 |
| Proliferation | 6.65 | 1136285 | 182490 | 211615_s_at | LRPPRC |

TABLE 2409-continued

| FL vs. MCL | | | | |
|---|---|---|---|---|
| Proliferation | 6.67 | 1136853 | 66170 | 212922_s_at | SMYD2 |
| Proliferation | 7.45 | 1119390 | 77254 | 201518_at | CBX1 |
| Proliferation | 8.87 | 1116122 | 42768 | 227408_s_at | DKFZp761O0113 |
| Proliferation | 10.12 | 1119515 | 3352 | 201833_at | HDAC2 |

| | Standard | Lymph Node | Proliferation | | |
|---|---|---|---|---|---|
| Mean FL | −18.82 | −33.90 | 23.53 | Cut 1 | 0.14 |
| Mean MCL | 1558.10 | 113.95 | 165.48 | Cut 2 | 0.58 |
| Covariance FL | 21302.14 | 1098.24 | 678.04 | | |
| | 1098.24 | 226.29 | 75.99 | | |
| | 678.04 | 75.99 | 315.67 | | |
| Covariance MCL | 81008.29 | 5261.37 | 9185.20 | | |
| | 5261.37 | 2047.34 | 875.56 | | |
| | 9185.20 | 875.56 | 1447.43 | | |

TABLE 2410

FL vs. SLL

| Signature | Scale | UNIQID | Unigene ID Build 167 | Probe set | Gene Symbol |
|---|---|---|---|---|---|
| Standard | −21.04 | 1123731 | 17165 | 210258_at | RGS13 |
| Standard | −20.91 | 1124646 | 436432 | 212646_at | RAFTLIN |
| Standard | −18.82 | 1099651 | 120785 | 227646_at | EBF |
| Standard | −18.12 | 1114543 | 156189 | 244887_at | |
| Standard | −17.85 | 1105986 | 49614 | 235310_at | GCET2 |
| Standard | −16.73 | 1100911 | 320147 | 229152_at | C4orf7 |
| Standard | −15.77 | 1132122 | 307734 | 203434_s_at | MME |
| Standard | −15.12 | 1120090 | 155024 | 203140_at | BCL6 |
| Standard | −14.89 | 1097897 | 266175 | 225622_at | PAG |
| Standard | −14.36 | 1529343 | 521948 | Lymph_Dx_064_at | |
| Standard | −14.32 | 1529318 | 291954 | Lymph_Dx_038_at | |
| Standard | −14.06 | 1128694 | 171466 | 219517_at | ELL3 |
| Standard | −13.61 | 1101586 | 187884 | 229971_at | GPR114 |
| Standard | −13.57 | 1119752 | 511745 | 202391_at | BASP1 |
| Standard | −13.13 | 1137561 | 67397 | 214639_s_at | HOXA1 |
| Standard | −12.85 | 1097247 | 388761 | 224851_at | CDK6 |
| Standard | −12.43 | 1529344 | 317970 | Lymph_Dx_065_at | SERPINA11 |
| Standard | −12.4 | 1120765 | 343329 | 204484_at | PIK3C2B |
| Standard | −12.33 | 1130155 | 436657 | 222043_at | CLU |
| Standard | −12.07 | 1529292 | −92 | Lymph_Dx_010_at | |
| Standard | −12.01 | 1119939 | 170087 | 202820_at | AHR |
| Standard | −11.82 | 1119919 | 199263 | 202786_at | STK39 |
| Standard | −11.77 | 1099686 | 117721 | 227684_at | |
| Standard | −11.63 | 1119782 | 155418 | 202478_at | TRB2 |
| Standard | 10.97 | 1529309 | 512797 | Lymph_Dx_028_at | HSH2 |
| Standard | 10.97 | 1139393 | 170129 | 219032_x_at | OPN3 |
| Standard | 11.04 | 1131246 | 153752 | 201853_s_at | CDC25B |
| Standard | 11.07 | 1140391 | 44865 | 221558_s_at | LEF1 |
| Standard | 11.16 | 1140416 | 58831 | 221601_s_at | TOSO |
| Standard | 11.35 | 1127807 | 7236 | 217950_at | NOSIP |
| Standard | 11.67 | 1529317 | −98 | Lymph_Dx_037_at | |
| Standard | 11.81 | 1117343 | 306812 | 234643_x_at | BUCS1 |
| Standard | 11.82 | 1102081 | 506977 | 230551_at | |
| Standard | 11.82 | 1135042 | 79015 | 209582_s_at | MOX2 |
| Standard | 11.96 | 1132734 | 126248 | 204724_s_at | COL9A3 |
| Standard | 12.09 | 1137109 | 469653 | 213689_x_at | RPL5 |
| Standard | 12.14 | 1099939 | 488173 | 227983_at | MGC7036 |
| Standard | 12.19 | 1129103 | 99430 | 220118_at | TZFP |
| Standard | 12.47 | 1135592 | 758 | 210621_s_at | RASA1 |
| Standard | 12.78 | 1108970 | 140489 | 238604_at | |
| Standard | 12.92 | 1097143 | 74335 | 224716_at | HSPCB |
| Standard | 13.18 | 1136865 | 412128 | 212959_s_at | MGC4170 |
| Standard | 13.96 | 1098220 | 80720 | 226002_at | GAB1 |
| Standard | 14.06 | 1100847 | 97411 | 229070_at | C6orf105 |
| Standard | 14.39 | 1098865 | 250905 | 226741_at | LOC51234 |
| Standard | 15.57 | 1136687 | 59943 | 212345_s_at | CREB3L2 |
| Standard | 15.75 | 1107044 | 163426 | 236458_at | |
| Standard | 16.52 | 1123622 | 8578 | 210051_at | EPAC |
| Standard | 17.74 | 1136987 | 21695 | 213370_s_at | SFMBT1 |
| Standard | 19.15 | 1129026 | 135146 | 220007_at | FLJ13984 |
| Standard | 19.65 | 1131854 | 414985 | 202923_s_at | GCLC |
| Lymph Node | −14.99 | 1124875 | 18166 | 212975_at | KIAA0870 |

TABLE 2410-continued

FL vs. SLL

| | | | | |
|---|---|---|---|---|
| Lymph Node | −14.33 | 1099358 | 93135 | 227300_at | |
| Lymph Node | −13.26 | 1121129 | 285401 | 205159_at | CSF2RB |
| Lymph Node | −12.61 | 1119074 | 54457 | 200675_at | CD81 |
| Lymph Node | −12.52 | 1121029 | 412999 | 204971_at | CSTA |
| Lymph Node | −11.48 | 1137247 | 234734 | 213975_s_at | LYZ |
| Lymph Node | −10.97 | 1128781 | 79741 | 219648_at | FLJ10116 |
| Lymph Node | 11.79 | 1119880 | 442844 | 202709_at | FMOD |
| Lymph Node | 14.4 | 1134370 | 1422 | 208438_s_at | FGR |

| | Standard | Lymph Node | | |
|---|---|---|---|---|
| Mean FL | −663.95 | −730.08 | Cut 1 | 0.20 |
| Mean SLL | 1332.84 | −484.93 | Cut 2 | 0.80 |
| Covariance FL | 37097.15 | 1710.73 | | |
| | 1710.73 | 663.78 | | |
| Covariance SLL | 85989.25 | 17661.52 | | |
| | 17661.52 | 4555.06 | | |

TABLE 2411

GCB vs. PMBL

| Signature | Scale | UNIQID | Unigene ID Build 167 | Probe set | Gene Symbol |
|---|---|---|---|---|---|
| Standard | −8.39 | 1096440 | 231320 | 223423_at | GPR160 |
| Standard | −8.13 | 1096108 | 292871 | 222731_at | ZDHHC2 |
| Standard | −8.12 | 1125231 | 446375 | 213489_at | MAPRE2 |
| Standard | −8.02 | 1136759 | 188882 | 212605_s_at | |
| Standard | −7.91 | 1096499 | 293867 | 223514_at | CARD11 |
| Standard | −7.8 | 1099388 | 124024 | 227336_at | DTX1 |
| Standard | −7.71 | 1139623 | 193736 | 219667_s_at | BANK1 |
| Standard | −7.68 | 1098592 | 283707 | 226431_at | ALS2CR13 |
| Standard | −7.67 | 1107575 | 424589 | 237033_at | MGC52498 |
| Standard | −7.63 | 1116829 | 115467 | 231840_x_at | LOC90624 |
| Standard | −7.42 | 1130114 | 445084 | 221965_at | MPHOSPH9 |
| Standard | −7.27 | 1098909 | 446408 | 226789_at | |
| Standard | 7.34 | 1138759 | 396404 | 217707_x_at | SMARCA2 |
| Standard | 7.37 | 1120355 | 80420 | 203687_at | CX3CL1 |
| Standard | 7.4 | 1134270 | 352119 | 208284_x_at | GGT1 |
| Standard | 7.44 | 1115441 | 5470 | 224156_x_at | IL17RB |
| Standard | 7.78 | 1103054 | 341531 | 231690_at | |
| Standard | 7.91 | 1119765 | 81234 | 202421_at | IGSF3 |
| Standard | 7.92 | 1119438 | 118110 | 201641_at | BST2 |
| Standard | 8.09 | 1135645 | 31439 | 210715_s_at | SPINT2 |
| Standard | 8.15 | 1106015 | 96885 | 235343_at | FLJ12505 |
| Standard | 8.18 | 1121400 | 223474 | 205599_at | TRAF1 |
| Standard | 8.38 | 1139950 | 437385 | 220731_s_at | FLJ10420 |
| Standard | 8.73 | 1122112 | 1314 | 206729_at | TNFRSF8 |
| Standard | 8.77 | 1122772 | 66742 | 207900_at | CCL17 |
| Standard | 8.84 | 1132762 | 80395 | 204777_s_at | MAL |
| Standard | 9.64 | 1139774 | 15827 | 220140_s_at | SNX11 |
| Standard | 10.53 | 1133801 | 181097 | 207426_s_at | TNFSF4 |
| Standard | 11.52 | 1106415 | 169071 | 235774_at | |
| Standard | 12.09 | 1129269 | 62919 | 220358_at | SNFT |

| | Standard | | |
|---|---|---|---|
| Mean GCB | 292.76 | Cut 1 | 0.16 |
| Mean PMBL | 725.28 | Cut 2 | 0.50 |
| Covariance GCB | 8538.86 | | |
| Covariance PMBL | 11405.23 | | |

TABLE 2412

MCL vs. DLBCL-BL

| Signature | Scale | UNIQID | Unigene ID Build 167 | Probe set | Gene Symbol |
|---|---|---|---|---|---|
| Standard | −26.11 | 1529382 | 371468 | Lymph_Dx_111_at | CCND1 |
| Standard | −18.35 | 1103711 | 288718 | 232478_at | |
| Standard | −17.03 | 1106855 | 455101 | 236255_at | KIAA1909 |
| Standard | −16.49 | 1098840 | 55098 | 226713_at | C3orf6 |
| Standard | −15.41 | 1109505 | 8162 | 239186_at | MGC39372 |
| Standard | −15.11 | 1098954 | 128905 | 226844_at | MOBKL2B |
| Standard | −14.96 | 1103504 | 142517 | 232239_at | |
| Standard | −14.74 | 1096070 | 241565 | 222640_at | DNMT3A |
| Standard | −13.81 | 1137663 | 247362 | 214909_s_at | DDAH2 |
| Standard | −13.8 | 1124864 | 411317 | 212960_at | KIAA0882 |
| Standard | −13.62 | 1140127 | 125300 | 221044_s_at | TRIM34 |
| Standard | −13.62 | 1119361 | 391858 | 201448_at | TIA1 |
| Standard | −13.37 | 1127849 | 76691 | 218032_at | SNN |
| Standard | 13.72 | 1133192 | 24024 | 205801_s_at | RASGRP3 |
| Standard | 13.85 | 1137583 | 273415 | 214687_x_at | ALDOA |
| Standard | 15.02 | 1123052 | 180909 | 208680_at | PRDX1 |
| Standard | 16.21 | 1097611 | 438993 | 225285_at | BCAT1 |
| Lymph Node | −19.18 | 1529456 | 371468 | Lymph_Dx_113_at | CCND1 |
| Lymph Node | −10.71 | 1098978 | 124863 | 226869_at | |
| Lymph Node | −9.17 | 1097448 | 250607 | 225093_at | UTRN |
| Lymph Node | 8.84 | 1135240 | 436852 | 209955_s_at | FAP |
| Lymph Node | 9.11 | 1119475 | 296323 | 201739_at | SGK |
| Lymph Node | 9.22 | 1119237 | 389964 | 201141_at | GPNMB |
| Lymph Node | 9.46 | 1130629 | 135226 | 200839_s_at | CTSB |
| Lymph Node | 10.1 | 1130054 | 82547 | 221872_at | RARRES1 |

| | Standard | Lymph Node | | |
|---|---|---|---|---|
| Mean MCL | −1417.55 | −25.58 | Cut 1 | 0.50 |
| Mean DLBCL-BL | −756.07 | 202.29 | Cut 2 | 0.88 |
| Covariance MCL | 15347.98 | 3525.48 | | |
| | 3525.48 | 5420.31 | | |
| Covariance DLBCL-BL | 5132.06 | 1007.64 | | |
| | 1007.64 | 991.38 | | |

TABLE 2413

MCL vs. SLL

| Signature | Scale | UNIQID | Unigene ID Build 167 | Probe set | Gene Symbol |
|---|---|---|---|---|---|
| Standard | −20.18 | 1132834 | 432638 | 204914_s_at | SOX11 |
| Standard | −15.17 | 1130926 | 508741 | 201310_s_at | C5orf13 |
| Standard | 13.44 | 1116150 | 16229 | 227606_s_at | AMSH-LP |
| Standard | 14.44 | 1120134 | 75545 | 203233_at | IL4R |
| Standard | 15.18 | 1529437 | 445162 | Lymph_Dx_175_at | BTLA |
| Standard | 15.19 | 1529317 | −98 | Lymph_Dx_037_at | |
| Standard | 16.2 | 1135042 | 79015 | 209582_s_at | MOX2 |

| | Standard | | |
|---|---|---|---|
| Mean MCL | 181.38 | Cut 1 | 0.20 |
| Mean SLL | 564.92 | Cut 2 | 0.80 |
| Covariance MCL | 1734.42 | | |
| Covariance SLL | 910.75 | | |

TABLE 2414

SLL vs. DLBCL-BL

| Signature | Scale | UNIQID | Unigene ID Build 167 | Probe set | Gene Symbol |
|---|---|---|---|---|---|
| Standard | −16.014498 | 1123622 | 8578 | 210051_at | EPAC |
| Standard | −15.26356533 | 1102081 | 506977 | 230551_at | |
| Standard | −14.82150028 | 1107044 | 163426 | 236458_at | |
| Standard | −14.17813266 | 1098865 | 250905 | 226741_at | LOC51234 |
| Standard | −12.92844719 | 1110740 | 416810 | 240538_at | |
| Standard | −12.86520757 | 1129026 | 135146 | 220007_at | FLJ13984 |

TABLE 2414-continued

| | | | SLL vs. DLBCL-BL | | |
|---|---|---|---|---|---|
| Standard | −12.2702748 | 1135592 | 758 | 210621_s_at | RASA1 |
| Standard | −11.87309449 | 1117343 | 306812 | 234643_x_at | BUCS1 |
| Standard | −11.81789137 | 1136987 | 21695 | 213370_s_at | SFMBT1 |
| Standard | −11.78631706 | 1124830 | 9059 | 212911_at | KIAA0962 |
| Standard | −11.39454435 | 1133538 | 1416 | 206760_s_at | FCER2 |
| Standard | −11.39050362 | 1135802 | 439343 | 210944_s_at | CAPN3 |
| Standard | 11.72928644 | 1120770 | 300825 | 204493_at | BID |
| Lymph Node | −12.21593247 | 1119880 | 442844 | 202709_at | FMOD |
| Lymph Node | 9.514704847 | 1135240 | 436852 | 209955_s_at | FAP |
| Lymph Node | 9.739298877 | 1096429 | 64896 | 223405_at | NPL |
| Lymph Node | 10.05087645 | 1119475 | 296323 | 201739_at | SGK |
| Lymph Node | 13.11985922 | 1119237 | 389964 | 201141_at | GPNMB |
| Proliferation | 10.47525875 | 1128106 | 14559 | 218542_at | C10orf3 |
| Proliferation | 10.53295782 | 1132825 | 512813 | 204900_x_at | SAP30 |
| Proliferation | 11.93918891 | 1130501 | 2795 | 200650_s_at | LDHA |
| Proliferation | 11.98738778 | 1123439 | 287472 | 209642_at | BUB1 |
| Proliferation | 11.99741644 | 1115607 | 435733 | 224428_s_at | CDCA7 |

| | Standard | Lymph Node | Proliferation | | |
|---|---|---|---|---|---|
| Mean SLL | −1383.640809 | 177.4452398 | 467.2463569 | Cut 1 | 0.201266305 |
| Mean DLBCL-BL | −926.7275468 | 329.6795845 | 582.9070266 | Cut 2 | 0.799816116 |
| Covariance SLL | 3591.384775 | 1789.7516 | 856.0703202 | | |
| | 1789.7516 | 1421.869535 | 663.4782048 | | |
| | 856.0703202 | 663.4782048 | 965.6470151 | | |
| Covariance DLBCL-BL | 2922.643347 | 473.543487 | 634.3258773 | | |
| | 473.543487 | 931.9845277 | −53.85584619 | | |
| | 634.3258773 | −53.85584619 | 767.3545404 | | |

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

Abbreviations used herein: ABC, activated B-cell-like diffuse large B cell lymphoma; BL, Burkitt lymphoma; CHOP, cyclophosphamide, doxorubicine, vincristine, and prednisone; CI, confidence interval; CNS, central nervous system; DLBCL, diffuse large B-cell lymphoma; ECOG, Eastern Cooperative Oncology Group; EST, expressed sequence tag; FACS, fluorescence-activated cell sorting; FH, follicular hyperplasia; FL, follicular lymphoma; GCB, germinal center B-cell-like diffuse large B cell lymphoma; GI, gastrointestinal; IPI, International Prognostic Index; LPC, lymphoplasmacytic lymphoma; LPS, linear predictor score; MALT, mucosa-associated lymphoid tissue lymphomas; MCL, mantle cell lymphoma; MHC, major histocompatibility complex; NA, not available or not applicable; NK, natural killer; NMZ, nodal marginal zone lymphoma; PCR, polymerase chain reaction; PMBL, primary mediastinal B-cell lymphoma; PTLD, post-transplant lymphoproliferative disorder; REAL, Revised European-American Lymphoma; RPA, RNase protection assay; RR, relative risk of death; RT-PCR, reverse transcriptase polymerase chain reaction; SAGE, serial analysis of gene expression; SLL, small lymphocytic lymphoma; WHO, World Health Organization.

REFERENCES

1. Alizadeh, A. A., et al. 1998. Probing lymphocyte biology by genomic-scale gene expression analysis. J Clin Immunol 18:373-79.
2. Alizadeh, A. A., et al. 1999. The Lymphochip: a specialized cDNA microarray for the genomic-scale analysis of gene expression in normal and malignant lymphocytes. Cold Spring Harbor Symp Quant Biol 64:71-78.
3. Alizadeh, A. A., et al. 2000. Distinct types of diffuse large B-cell lymphoma identified by gene expression profiling. Nature 403:503-511.
4. Alon, U., et al. 1999. Broad patterns of gene expression revealed by clustering analysis of tumor and normal colon tissues probed by oligonucleotide arrays. Proc Natl Acad Sci USA 96:6745-6750.
5. Bayes, T. 1763. An essay towards solving a problem in the doctrine of chances. Phil Trans Roy Soc London 53:370.
6. Chee, M., et al. 1996. Accessing genetic information with high density DNA arrays. Science 274:610-14.
7. Cho, R. J., et al. 1998. A genome-wide transcriptional analysis of the mitotic cell cycle. Mol Cell 2:65-73.
8. Chu, S., et al. 1998. The transcriptional program of sporulation in budding yeast. Science 282:699-705.
9. Copie-Bergman, C., et al. 2002. MAL expression in lymphoid cells: further evidence for MAL as a distinct molecular marker of primary mediastinal large B-cell lymphomas. Mod Pathol 15:1172-1180.
10. Copie-Bergman, C., et al. 2003. Interleukin 4-induced gene 1 is activated in primary mediastinal large B-cell lymphoma. Blood 101:2756-2761.
11. DeRisi, J., et al. 1996. Use of a cDNA microarray to analyze gene expression patterns in human cancer. Nat Genet 14:457-60.
12. DeRisi, J. L., Iyer, V. R., Brown, P. O. 1997. Exploring the metabolic and genetic control of gene expression on a genomic scale. Science 278:680-86.
13. Drapner, H. 1966. Applied regression. Wiley, New York.
14. Dudoit, S., Fridlyand, J., Speed, T. P. 2002. Comparison of discrimination methods for the classification of tumors using gene expression data. J Am Stat Assoc 97:77-87.
15. Eisen, M. B., Spellman, P. T., Brown, P. O., Botstein, D. 1998. Cluster analysis and display of genome-wide expression patterns. Proc Natl Acad Sci USA 95:14863-14868.

16. Fisher, R. I., et al. 1993. Comparison of a standard regimen (CHOP) with three intensive chemotherapy regimens for advanced non-Hodgkin's lymphoma. N Engl J Med 328:1002-1006.
17. Furey, T. S., et al. 2000. Support vector machine classification and validation of cancer tissue samples using microarray expression data. Bioinformatics 16:906-914.
18. Golub, T. R., et al. 1999. Molecular classification of cancer: class discovery and class prediction by gene expression monitoring, Science 286:531-537.
19. Gress, T. M., et al. 1996. A pancreatic cancer-specific expression profile. Oncogene 13:1819-30.
20. Harris, N. L., et al. 1994. A revised European-American classification of lymphoid neoplasms: a proposal from the International Lymphoma Study Group. Blood 84:1361-1392.
21. Heller, R. A., et al. 1997. Discovery and analysis of inflammatory disease-related genes using cDNA microarrays. Proc Natl Acad Sci USA 94:2150-55.
22. Holstege, F. C., et al. 1998. Dissecting the regulatory circuitry of a eukaryotic genome. Cell 95:717-728.
23. Irizarry, R. A., et al. 2003. Exploration, normalization, and summaries of high density oligonucleotide array probe level data. Biostatistics 4:249-264.
24. Hills, M. 1966. Allocation rules and error rates. J Royal Statis Soc Series B 28:1-31.
25. Jaffe, E. S., Harris, N. L., Stein, H., Vardiman, J. W. 2001. Tumors of hematopoietic and lymphoid tissues. IARC Press, Lyon.
26. Khouri, I. F., et al. 1998. Hyper-CVAD and high-dose methotrexate/cytarabine followed by stem-cell transplantation: an active regimen for aggressive mantle-cell lymphoma. J Clin Oncol 12:3803-3809.
27. Kohonen, T. 1997. Self-organizing maps. Springer Press, Berlin.
28. Lashkari, D. A., et al. 1997. Yeast microarrays for genome wide parallel genetic and gene expression analysis. Proc Natl Acad Sci USA 94:13057-62.
29. Li, C., Wong, W. H. 2001. Model-based analysis of oligonucleotide arrays: expression index computation and outlier detection. Proc Natl Acad Sci USA 98:31-36.
30. Lipshutz, R. J., et al. 1995. Using oligonucleotide probe arrays to access genetic diversity. Biotechniques 19:442-47.
31. Lockhart, D. J., et al. 1996. Expression monitoring by hybridization to high-density oligonucleotide arrays. Nat Biotechnol 14:1675-80.
32. Pease, A. C., et al. 1994. Light generated oligonucleotide arrays for rapid DNA sequence analysis. Proc Natl Acad Sci USA 91:5022-26.
33. Pietu, G., et al. 1996. Novel gene transcripts preferentially expressed in human muscles revealed by quantitative hybridization of a high density cDNA array. Genome Res 6:492-503.
34. Radmacher, M. D., McShane, LM., Simon, R. 2002. A paradigm for class prediction using gene expression profiles. J Comput Biol 9:505-511.
35. Ramaswamy, S., et al. 2001. Multiclass cancer diagnosis using tumor gene expression signatures. Proc Natl Acad Sci USA 98:15149-15154.
36. Ransohoff, D. F. 2004. Rules of evidence for cancer molecular-marker discovery and validation. Nat Rev Cancer 4:309-314.
37. Rosenwald, A., et al. 2002. The use of molecular profiling to predict survival after chemotherapy for diffuse large-B-cell lymphoma. New Engl J Med 346:1937-1947.
38. Rosenwald, A., et al. 2003a. The proliferation gene expression signature is a quantitative integrator of oncogenic events that predicts survival in mantle cell lymphoma. Cancer Cell 3:185-197.
39. Schena, M., Shalon, D., Davis, R. W., Brown, P. O. 1995. Quantitative monitoring of gene expression patterns with a complementary DNA microarray. Science 270:467-70.
40. Schena, M., et al. 1996. Parallel human genome analysis: microarray based expression monitoring of 1000 genes. Proc Natl Acad Sci USA 93:10614-19.
41. Shaffer, A. L., et al. 2001. Signatures of the immune response. Immunity 15:375-385.
42. Shalon, D., Smith, S. J., Brown, P. O. 1996. A DNA microarray system for analyzing complex DNA samples using two-color fluorescent probe hybridization. Genome Res 6:639-45.
43. Shipp, M. A., et al. 2002. Diffuse large B-cell lymphoma outcome prediction by gene-expression profiling and supervised machine learning. Nat Med 8: 68-74.
44. Southern, E. M., Maskos, U., Elder, J. K. 1992. Analyzing and comparing nucleic acid sequences by hybridization to arrays of oligonucleotides: evaluation using experimental models. Genomics 13:1008-17.
45. Southern, E. M., et al. 1994. Arrays of complementary oligonucleotides for analysing the hybridisation behaviour of nucleic acids. Nucl Acids Res 22:1368-73.
46. Spellman, P. T., et al. 1998. Comprehensive identification of cell cycle regulated genes of the yeast *Saccharomyces cerevisiae* by microarray hybridization. Mol Biol Cell 9:3273-3297.
47. Tamayo, P., et al. 1999. Interpreting patterns of gene expression with self-organizing maps: methods and application to hematopoietic differentiation. Proc Natl Acad Sci USA 96:2907-2912.
48. Tavazoie, S., et al. 1999. Systematic determination of genetic network architecture. Nat Genet 22:281-285.
49. Tibshirani, R., Hastie, T., Narasimhan, B., Chu, G. 2002. Diagnosis of multiple cancer types by shrunken centroids of gene expression. Proc Natl Acad Sci USA 99:6567-6572.
50. Velculescu, V. E., Zhang, L., Vogelstein, B., Kinzler, K. W. 1995. Serial analysis of gene expression. Science 270:484-87.
51. Wodicka, L., et al. 1997. Genome-wide expression monitoring in *Saccharomyces cerevisiae*. Nat Biotechnol 15:1359-6714.
52. Wright, G., et al. 2003. A gene expression-based method to diagnose clinically distinct subgroups of diffuse large B cell lymphoma. Proc Natl Acad Sci USA 100:9991-9996.

TABLE 2415

GeneID.txt

| Order | UNIQID | NAME | GENEID | LN.cor | Pro.cor |
|---|---|---|---|---|---|
| 1 | 1095985 | TMEPAI :: transmembrane, prostate androgen induced RNA | 83883 | 0.765572912605858 | -0.305829906881871 |
| 2 | 1095996 | SSBP3 :: single stranded DNA binding protein 3 | 288801 | 0.337878824571224 | -0.246570833627667 |
| 3 | 1096028 | STMN3 :: stathmin-like 3 | 285753 | 0.247291930603322 | -0.512359910432692 |
| 4 | 1096035 | UGCGL1 :: UDP-glucose ceramide glucosyltransferase-like 1 | 105794 | -0.044857707563452 | 0.126915353662946 |
| 5 | 1096038 | PPM2C :: protein phosphatase 2C, magnesium-dependent, catalytic subunit | 22265 | 0.059429204462921 | -0.188473830832503 |
| 6 | 1096054 | FLJ10036 :: hypothetical protein FLJ10036 | 21331 | -0.371427712016433 | 0.730940143905553 |
| 7 | 1096070 | DNMT3A :: DNA (cytosine-5-)-methyltransferase 3 alpha | 241565 | 0.065715669272673 | -0.156420432074750 |
| 8 | 1096077 | IPO11 :: importin 11 | 441043 | -0.272220885257140 | 0.497353016437345 |
| 9 | 1096078 | HSU84971 :: fetal hypothetical protein | 284216 | -0.414916213421669 | 0.418061447763775 |
| 10 | 1096085 | HSPC109 :: hypothetical protein HSPC109 | 224137 | -0.293990882168277 | 0.238513282285725 |
| 11 | 1096108 | ZDHHC2 :: zinc finger, DHHC domain containing 2 | 292871 | -0.051768610245872 | 0.113517147008026 |
| 12 | 1096149 | NUDT5 :: nudix (nucleoside diphosphate linked moiety X)-type motif 5 | 410205 | -0.328630578583663 | 0.210623718410482 |
| 13 | 1096152 | IL20RA :: interleukin 20 receptor, alpha | 288240 | -0.082760468199485 | -0.000212236348592 |
| 14 | 1096158 | SLAMF7 :: SLAM family member 7 | 132906 | 0.141965758989601 | -0.400637349397057 |
| 15 | 1096163 | FKSG14 :: leucine zipper protein FKSG14 | 164018 | -0.302881859478226 | 0.709798806284115 |
| 16 | 1096172 | AKT3 :: v-akt murine thymoma viral oncogene homolog 3 (protein kinase B, gamma) | 300642 | 0.079018970053188 | -0.070815586824077 |
| 17 | 1096180 | HSPC065 :: HSPC065 protein | 11614 | -0.248427935178953 | 0.244895011527730 |
| 18 | 1096182 | ITGA11 :: integrin, alpha 11 | 256297 | 0.484784321132005 | -0.141574493942455 |
| 19 | 1096220 | IL22 :: interleukin 22 | 287369 | -0.012202602288250 | 0.102513778017030 |
| 20 | 1096248 | NAT5 :: N-acetyltransferase 5 (ARD1 homolog, S. cerevisiae) | 109253 | -0.179981414304964 | 0.304668080254639 |
| 21 | 1096251 | SLC40A1 :: solute carrier family 40 (iron-regulated transporter), member 1 | 409875 | -0.350169148476026 | -0.039724364810070 |
| 22 | 1096297 | UCK1 :: uridine-cytidine kinase 1 | 9597 | 0.107276488247798 | -0.131638659028410 |
| 23 | 1096300 | MGC2714 :: hypothetical protein MGC2714 | 74284 | -0.293976225239911 | 0.702711029782148 |
| 24 | 1096341 | SNX8 :: sorting nexin 8 | 12169 | 0.143322315228953 | -0.018039018612117 |
| 25 | 1096356 | ALS2CR2 :: amyotrophic lateral sclerosis 2 (juvenile) chromosome region, candidate 2 | 259230 | 0.110280642995490 | -0.020357388828095 |
| 26 | 1096357 | FLJ20432 :: hypothetical protein FLJ20432 | 57898 | -0.498064299913012 | 0.547207855914607 |
| 27 | 1096362 | TCF19 :: transcription factor 19 (SC1) | 512706 | -0.399070415427405 | 0.449227205058841 |
| 28 | 1096364 | NID67 :: putative small membrane protein NID67 | 29444 | 0.683874750520760 | -0.414039064356815 |
| 29 | 1096369 | DERP6 :: S-phase 2 protein | 417029 | -0.344757531355776 | 0.376048402134116 |
| 30 | 1096378 | URP2 :: UNC-112 related protein 2 | 180535 | 0.201631483396441 | -0.176115831847333 |
| 31 | 1096379 | SLC37A3 :: solute carrier family 37 (glycerol-3-phosphate transporter), member 3 | 439590 | 0.381537720604309 | -0.447728614022874 |
| 32 | 1096406 | C6orf115 :: chromosome 6 open reading frame 115 | 238205 | 0.165024207205827 | -0.097834654666083 |
| 33 | 1096429 | NPL :: N-acetylneuraminate pyruvate lyase (dihydrodipicolinate synthase) | 64896 | 0.521727440620009 | -0.359471289677876 |
| 34 | 1096440 | GPR160 :: G protein-coupled receptor 160 | 231320 | -0.270973814036627 | 0.306462668135112 |
| 35 | 1096442 | SIK2 :: salt-inducible serine/threonine kinase 2 | 306864 | -0.062856819831174 | 0.170832425890252 |
| 36 | 1096446 | GBP3 :: guanylate binding protein 3 | 92287 | 0.386684402604806 | -0.494981443515261 |
| 37 | 1096456 | CXCL16 :: chemokine (C-X-C motif) ligand 16 | 82407 | 0.534265409104252 | -0.494680174142867 |
| 38 | 1096460 | CAMKK1 :: calcium/calmodulin-dependent protein kinase kinase 1, alpha | 8417 | 0.063944985869638 | -0.228128654986856 |
| 39 | 1096466 | RASD1 :: RAS, dexamethasone-induced 1 | 25829 | 0.289870036740434 | -0.219151800055010 |
| 40 | 1096469 | RAB3IP :: RAB3A interacting protein (rabin3) | 103267 | -0.332016102837598 | 0.464149286520712 |
| 41 | 1096499 | CARD11 :: caspase recruitment domain family, member 11 | 293867 | -0.436883733442666 | 0.265844768784079 |
| 42 | 1096503 | C9orf45 :: chromosome 9 open reading frame 45 | 21379 | -0.298819325021361 | -0.023184197355755 |
| 43 | 1096530 | PACAP :: proapoptotic caspase adaptor protein | 409563 | -0.314448231660953 | 0.248763654467872 |
| 44 | 1096570 | ANUBL1 :: AN1, ubiquitin-like, homolog (Xenopus laevis) | 409813 | 0.087244086284512 | -0.114499206537960 |
| 45 | 1096579 | HCST :: hematopoietic cell signal transducer | 117339 | 0.191275472761633 | -0.323814264064461 |
| 46 | 1096609 | ARSD :: arylsulfatase D | -35 | 0.501162661333468 | -0.492064259946528 |
| 47 | 1096615 | RPL27A :: ribosomal protein L27a | 356342 | -0.284923968217501 | 0.414116765693771 |

TABLE 2415-continued

GeneID.txt

| Order | UNIQID | NAME | GENEID | LN.cor | Pro.cor |
|---|---|---|---|---|---|
| 48 | 1096616 | 1096616 :: C1QTNF4 :: C1q and tumor necrosis factor related protein 4 | 119302 | 0.245717528496956 | −0.0662117415897l7 |
| 49 | 1096617 | 1096617 :: CCL26 :: chemokine (C-C motif) ligand 26 | 131342 | 0.139107804989950 | −0.111244751036349 |
| 50 | 1096621 | 1096621 :: STK29 :: serine/threonine kinase 29 | 170819 | 0.121643230028416 | 0.0000229063717l6 |
| 51 | 1096690 | 1096690 :: TNFRSF19 :: tumor necrosis factor receptor superfamily, member 19 | 334174 | 0.046446130012764 | −0.106555400562260 |
| 52 | 1096693 | 1096693 :: PDCD1LG1 :: programmed cell death 1 ligand 1 | 443271 | 0.256067109408327 | −0.178200268373170 |
| 53 | 1096719 | 1096719 :: ARP3BETA :: actin-related protein 3-beta | 250153 | 0.245831877624803 | −0.00661529755l808 |
| 54 | 1096738 | 1096738 :: TLR9 :: toll-like receptor 9 | 87968 | −0.454086982168439 | 0.435099752153320 |
| 55 | 1096742 | 1096742 :: ERN2 :: Homo sapiens hypothetical gene supported by NM_033266 (LOC374284), mRNA | 114905 | −0.020800763316815 | 0.082977324102791 |
| 56 | 1096805 | 1096805 :: CCL28 :: chemokine (C-C motif) ligand 28 | 334633 | −0.119965557753727 | −0.076751767859586 |
| 57 | 1096829 | 1096829 :: IL20 :: interleukin 20 | 272373 | 0.000592650321134 | 0.142312268819410 |
| 58 | 1096834 | 1096834 :: IL17C :: interleukin 17C | 278971 | −0.085306904722356 | −0.026275991743137 |
| 59 | 1096877 | 1096877 :: MGC13008 :: hypothetical protein MGC13008 | 326732 | −0.152752641907604 | 0.133576812781343 |
| 60 | 1096903 | 1096903 :: FLJ10385 :: hypothetical protein FLJ10385 | 437460 | −0.363962088997560 | 0.386488614725012 |
| 61 | 1096936 | 1096936 :: IL1F10 :: interleukin 1 family, member 10 (theta) | 306974 | −0.088807796915772 | 0.147815256172852 |
| 62 | 1096965 | 1096965 :: PRO1853 :: hypothetical protein PRO1853 | 433466 | 0.234905061259092 | −0.151522525032889 |
| 63 | 1096981 | 1096981 :: PDCD1LG2 :: programmed cell death 1 ligand 2 | 61929 | 0.411512700132525 | −0.339724398106172 |
| 64 | 1097030 | 1097030 ::: Homo sapiens transcribed sequence with moderate similarity to protein pir:I60307 (E. coli) I60307 beta-galactosidase, alpha peptide - Escherichia coli | 511801 | 0.084096291164457 | −0.211349577111875 |
| 65 | 1097065 | 1097065 :: MAPK1 :: mitogen-activated protein kinase 1 | 324473 | −0.067419611001008 | −0.077605760320246 |
| 66 | 1097096 | 1097096 :: SEPN1 :: selenoprotein N, 1 | 8518 | 0.486311887679975 | −0.324166091574385 |
| 67 | 1097107 | 1097107 :: LENG8 :: leukocyte receptor cluster (LRC) member 8 | −27 | −0.367283482545225 | 0.117896751606288 |
| 68 | 1097109 | 1097109 :: MESDC2 :: mesoderm development candidate 2 | −23 | −0.084057602411658 | 0.123691273481405 |
| 69 | 1097126 | 1097126 :: ANTXR1 :: anthrax toxin receptor 1 | 274520 | 0.872281447063434 | −0.360699565338566 |
| 70 | 1097143 | 1097143 :: HSPCB :: heat shock 90 kDa protein 1, beta | 74335 | −0.329763699311407 | 0.161353868658910 |
| 71 | 1097156 | 1097156 :: CKLFSF3 :: chemokine-like factor superfamily 3 | 298198 | 0.356521698413820 | −0.224978670328984 |
| 72 | 1097161 | 1097161 ::: Homo sapiens cDNA clone IMAGE:5270526, partial cds | 5064 | −0.283919884792974 | 0.245645271796048 |
| 73 | 1097172 | 1097172 :: CDC45 :: cell division cycle associated 5 | 434886 | −0.327278444996126 | 0.823349285555297 |
| 74 | 1097177 | 1097177 :: GNA13 :: guanine nucleotide binding protein (G protein), alpha 13 | 9691 | −0.037330227523842 | 0.164092697479536 |
| 75 | 1097195 | 1097195 :: MGC29814 :: hypothetical protein MGC29814 | −22 | −0.311093569811657 | 0.387394625966569 |
| 76 | 1097202 | 1097202 :: DDEF1 :: development and differentiation enhancing factor 1 | −33 | 0.404219688288097 | −0.239957287582709 |
| 77 | 1097229 | 1097229 :: CPSF5 :: cleavage and polyadenylation specific factor 5, 25 kDa | 446393 | −0.364448004904438 | 0.618328935053735 |
| 78 | 1097236 | 1097236 :: FOXP1 :: forkhead box P1 | 235860 | −0.374617011666339 | 0.219940106264499 |
| 79 | 1097247 | 1097247 ::: Homo sapiens cDNA clone IMAGE:4520413, partial cds | 388761 | 0.078706536819919 | 0.079845030074853 |
| 80 | 1097253 | 1097253 :: BTH3 :: B7 homolog 3 | 77873 | 0.509686941959052 | −0.300155823803531 |
| 81 | 1097255 | 1097255 ::: Homo sapiens, clone IMAGE:5289004, mRNA | 380144 | 0.655182909405963 | −0.480162974610710 |
| 82 | 1097271 | 1097271 :: RALA :: v-ral simian leukemia viral oncogene homolog A (ras related) | 6906 | 0.233158496732894 | 0.116175646014776 |
| 83 | 1097280 | 1097280 ::: Homo sapiens cDNA clone IMAGE:4814010, partial cds | 423523 | 0.425384591076580 | −0.493447794310351 |
| 84 | 1097281 | 1097281 :: PLDN :: pallidin homolog (mouse) | 7037 | 0.173437680009131 | −0.194314449980568 |
| 85 | 1097282 | 1097282 :: LOC283241 :: hypothetical protein LOC283241 | 356719 | −0.025407453597505 | −0.131750092303776 |
| 86 | 1097290 | 1097290 :: CIRH1A :: cirrhosis, autosomal recessive 1A (cirhin) | 151001 | −0.492530933582546 | 0.676549644346020 |
| 87 | 1097297 | 1097297 :: VMP1 :: likely ortholog of rat vacuole membrane protein 1 | 166254 | 0.453085943117571 | −0.244926367026450 |
| 88 | 1097307 | 1097307 :: LOC340061 :: hypothetical protein LOC340061 | 379754 | 0.677098831326282 | −0.583057243877707 |
| 89 | 1097310 | 1097310 :: SMAP-5 :: golgi membrane protein SB140 | 5672 | 0.264429734648259 | −0.148300598780685 |
| 90 | 1097325 | 1097325 :: LASS5 :: LAG1 longevity assurance homolog 5 (S. cerevisiae) | 458450 | 0.077585149886997 | −0.030530283585439 |
| 91 | 1097329 | 1097329 :: TEAD1 :: TEA domain family member 1 (SV40 transcriptional enhancer factor) | 153408 | 0.609915504509915 | −0.330588741531368 |
| 92 | 1097334 | 1097334 :: FLJ10074 :: hypothetical protein FLJ10074 | 71573 | 0.148822092251370 | −0.036195940379043 |
| 93 | 1097359 | 1097359 ::: Homo sapiens transcribed sequence with weak similarity to protein ref:NP_060312.1 (H. sapiens) hypothetical protein FLJ20489 [Homo sapiens] | 518723 | 0.053800334461785 | −0.154524230021900 |
| 94 | 1097365 | 1097365 :: CKLFSF4 :: chemokine-like factor super family 4 | 325825 | 0.519294317954343 | −0.216309380198487 |

TABLE 2415-continued

GeneID.txt

| Order | UNIQID | NAME | GENEID | LN.cor | Pro.cor |
|---|---|---|---|---|---|
| 95 | 1097371 | 1097371 : PHF13 :: PHD finger protein 13 | 7299 | −0.321720660373057 | 0.343670287876139 |
| 96 | 1097383 | 1097383 : CAMK2D :: calcium/calmodulin-dependent protein kinase (CaM kinase) II delta | 111460 | −0.290642761065368 | 0.133360053100389 |
| 97 | 1097388 | 1097388 : C20orf77 :: chromosome 20 open reading frame 77 | 278839 | −0.197750027946280 | 0.376751974725969 |
| 98 | 1097395 | 1097395 : FAD104 :: FAD104 | 299883 | 0.736102004479402 | −0.373635154671711 |
| 99 | 1097424 | 1097424 : DKFZP434C131 :: DKFZP434C131 protein | 7978 | −0.134018331816916 | −0.109225857504428 |
| 100 | 1097441 | 1097441 : FLJ38426 :: hypothetical protein FLJ38426 | 6799 | −0.402273189776746 | 0.543694221269586 |
| 101 | 1097448 | 1097448 : UTRN :: utrophin (homologous to dystrophin) | 250607 | 0.360883799114271 | −0.584276143462886 |
| 102 | 1097540 | 1097540 :: Homo sapiens cDNA FLJ13141 fis, clone NT2RP3003210. | 388087 | −0.061066580853079 | 0.258721848569539 |
| 103 | 1097553 | 1097553 : PSMB7 :: proteasome (prosome, macropain) subunit, beta type, 7 | 197071 | 0.311409341908515 | −0.205155556831752 |
| 104 | 1097561 | 1097561 : C20orf112 :: chromosome 20 open reading frame 112 | 19221 | 0.527162250471833 | −0.440301485246365 |
| 105 | 1097563 | 1097563 : FLJ14743 :: hypothetical protein FLJ14743 | 169577 | −0.168921612398568 | −0.030167777542399 |
| 106 | 1097564 | 1097564 : SKIL :: SKI-like | 272108 | −0.048859117197389 | 0.045546934477234 |
| 107 | 1097600 | 1097600 : SAT2 :: spermidine/spermine N1-acetyltransferase 2 | 10846 | 0.349508117260322 | −0.551195374259974 |
| 108 | 1097609 | 1097609 : LOC91947 :: hypothetical protein LOC91947 | 6093 | 0.698019824770373 | −0.413944744306518 |
| 109 | 1097610 | 1097610 : DNAJC3 :: DnaJ (Hsp40) homolog, subfamily C, member 3 | 6019 | 0.354942495910287 | −0.301478249730580 |
| 110 | 1097611 | 1097611 : BCAT1 :: branched chain aminotransferase 1, cytosolic | 438993 | 0.231503275940178 | 0.054391439403167 |
| 111 | 1097614 | 1097614 : MGC16063 :: hypothetical protein MGC16063 | 410491 | 0.046334195779423 | −0.052886978168640 |
| 112 | 1097637 | 1097637 : ACBD6 :: acyl-Coenzyme A binding domain containing 6 | 63220 | −0.455371733025381 | 0.588517058172155 |
| 113 | 1097665 | 1097665 : HT011 :: uncharacterized hypothalamus protein HT011 | 434241 | 0.302114923194357 | −0.218617058012615 |
| 114 | 1097676 | 1097676 : PGM2 :: phosphoglucomutase 2 | 23363 | −0.105211493496590 | 0.411367274902218 |
| 115 | 1097683 | 1097683 : PP2135 :: PP2135 protein | 132569 | 0.438652292433518 | −0.531837589765522 |
| 116 | 1097684 | 1097684 : MGC45714 :: hypothetical protein MGC45714 | 368878 | −0.262573752576479 | 0.186215149748326 |
| 117 | 1097704 | 1097704 : C1orf19 :: chromosome 1 open reading frame 19 | 440663 | −0.299851016612681 | 0.328280021104323 |
| 118 | 1097707 | 1097707 : C20orf64 :: chromosome 20 open reading frame 64 | 440263 | −0.208966676154304 | 0.237923731267286 |
| 119 | 1097717 | 1097717 : FLJ14681 :: hypothetical protein FLJ14681 | 23317 | 0.125057120164488 | −0.094407570526280 |
| 120 | 1097735 | 1097735 : LOC58489 :: hypothetical protein from EUROIMAGE 588495 | 26765 | −0.152766753795439 | 0.150760192399265 |
| 121 | 1097804 | 1097804 : FLJ10213 :: hypothetical protein FLJ10213 | 446590 | −0.232974145960649 | 0.385796656610468 |
| 122 | 1097814 | 1097814 : CENTB5 :: centaurin, beta 5 | 21446 | 0.025599591925261 | −0.077279249251246 |
| 123 | 1097824 | 1097824 : MAP2 :: microtubule-associated protein 2 | 167 | 0.117548992931937 | −0.120439543060478 |
| 124 | 1097887 | 1097887 : KIAA0303 :: KIAA0303 protein | 212787 | 0.092960318117084 | −0.116573446206172 |
| 125 | 1097897 | 1097897 : PAG :: phosphoprotein associated with glycosphingolipid-enriched microdomains | 266175 | 0.191577241800621 | −0.085455707264803 |
| 126 | 1097899 | 1097899 : LOC92017 :: similar to RIKEN cDNA 4933437K13 | 145047 | 0.096634326522832 | −0.342206059804613 |
| 127 | 1097901 | 1097901 : PAG :: phosphoprotein associated with glycosphingolipid-enriched microdomains | 266175 | 0.204617854117621 | −0.117013400778641 |
| 128 | 1097902 | 1097902 : KIAA1706 :: KIAA1706 protein | 412318 | 0.203615260815970 | −0.140541494164973 |
| 129 | 1097918 | 1097918 : LOC90378 :: atherin | 140309 | −0.379406336299933 | 0.520098002520735 |
| 130 | 1097928 | 1097928 : SEMA6A :: sema domain, transmembrane domain (TM), and cytoplasmic domain, (semaphorin) 6A | 443012 | 0.234759397668220 | −0.219646366867697 |
| 131 | 1097930 | 1097930 : ZAK :: sterile alpha motif and leucine zipper containing kinase AZK | 115175 | 0.108699289989043 | 0.073998196964394 |
| 132 | 1097940 | 1097940 : LOC91663 :: hypothetical protein BC013995 | 380906 | 0.706870503069227 | −0.502093351185603 |
| 133 | 1097948 | 1097948 : LOC348235 :: hypothetical protein LOC348235 | 69476 | −0.269690076470008 | 0.529419096597393 |
| 134 | 1097961 | 1097961 : ACA9 :: Homo sapiens ACA9 snoRNA gene | 25892 | −0.429719438748216 | 0.625988904538759 |
| 135 | 1097966 | 1097966 : KIAA1545 :: KIAA1545 protein | 127270 | 0.027717349383938 | −0.400522062454424 |
| 136 | 1097976 | 1097976 : raptor :: raptor | 218017 | −0.148308861940539 | 0.120470330039901 |
| 137 | 1098012 | 1098012 : CSNK1E :: casein kinase 1, epsilon | 355669 | −0.342068884130279 | 0.262100628123216 |
| 138 | 1098023 | 1098023 : KIAA1972 :: KIAA1972 protein | 181161 | −0.129150683371564 | 0.086536959397880 |
| 139 | 1098065 | 1098065 : FLJ14957 :: hypothetical protein FLJ14957 | 10119 | 0.609772948330722 | −0.373661396100191 |
| 140 | 1098069 | 1098069 :: Homo sapiens mRNA similar to QIL1 (cDNA clone MGC:57483 IMAGE:5288954), complete cds | 356626 | −0.282366680428328 | 0.222535690878294 |
| 141 | 1098095 | 1098095 : ANKRD17 :: ankyrin repeat domain 17 | 131059 | −0.102008011290600 | 0.114467664297043 |
| 142 | 1098103 | 1098103 : NSE2 :: breast cancer membrane protein 101 | 124951 | 0.224301146111536 | −0.418282440606729 |
| 143 | 1098145 | 1098145 : KIAA2002 :: KIAA2002 protein | 9587 | −0.043305517146293 | −0.071453322767335 |

TABLE 2415-continued

| Order | UNIQID | NAME | GeneID.txt | GENEID | LN.cor | Pro.cor |
|---|---|---|---|---|---|---|
| 144 | 1098152 | 1098152 : KIAA1450 :: KIAA1450 protein | | 377588 | 0.582609629394882 | -0.401088162485662 |
| 145 | 1098156 | 1098156 : MAP3K1 :: mitogen-activated protein kinase kinase kinase 1 | | 170610 | -0.393164723370577 | 0.0641836829174630 |
| 146 | 1098168 | 1098168 : NLN :: neurolysin (metallopeptidase M3 family) | | 22151 | -0.0861108896054840 | 0.266365020837430 |
| 147 | 1098174 | 1098174 : LOC340371 :: hypothetical protein LOC340371 | | 274401 | 0.371605420749830 | -0.378069656516850 |
| 148 | 1098179 | 1098179 : LOC153222 :: adult retina protein | | 163725 | 0.113653935807107 | -0.578870218791412 |
| 149 | 1098186 | 1098186 : MGC11349 :: hypothetical protein MGC11349 | | 288697 | -0.411747476151535 | 0.252798351125260 |
| 150 | 1098195 | 1098195 : DKFZp762C1112 :: hypothetical protein DKFZp762C1112 | | 88594 | -0.162948666373984 | 0.0640235089393110 |
| 151 | 1098204 | 1098204 : PRKAA1 :: protein kinase, AMP-activated, alpha 1 catalytic subunit | | 43322 | 0.0824814442293360 | -0.126559120661099 |
| 152 | 1098220 | 1098220 : GAB1 :: GRB2-associated binding protein 1 | | 80720 | -0.270353808866967 | 0.129171526797500 |
| 153 | 1098234 | 1098234 : CD47 :: CD47 antigen (Rh-related antigen, integrin-associated signal transducer) | | 446414 | -0.204808859254960 | -0.130670945404961 |
| 154 | 1098235 | 1098235 : CKLFSF7 :: chemokine-like factor super family 7 | | 440494 | -0.00382063727207917 | -0.213943192132446 |
| 155 | 1098242 | 1098242 : KIAA0379 :: KIAA0379 protein | | 273104 | -0.146990537817309 | 0.382995758727720 |
| 156 | 1098252 | 1098252 : KIAA1203 :: ubiquitin-specific protease KIAA1203 | | 16953 | -0.00661800283423 | 0.0468335913321810 |
| 157 | 1098256 | 1098256 : SVH :: SVH protein | | 431871 | -0.452504903187901 | 0.363026813249536 |
| 158 | 1098258 | 1098258 : AGS3 :: activator of G-protein signaling 3 | | 239370 | 0.310744715383991 | -0.322355508448668 |
| 159 | 1098268 | 1098268 : MAP2K7 :: mitogen-activated protein kinase kinase 7 | | 110299 | -0.298346850539865 | 0.241278514570550 |
| 160 | 1098271 | 1098271 : CDGAP :: KIAA1204 protein | | 300670 | 0.173495129742519 | -0.257241770812174 |
| 161 | 1098277 | 1098277 : PRICKLE1 :: prickle-like 1 (Drosophila) | | 6786 | -0.273817683372350 | 0.0641324444418075 |
| 162 | 1098278 | 1098278 : MITF :: microphthalmia-associated transcription factor | | 166017 | 0.618314859385319 | -0.387872278743441 |
| 163 | 1098303 | 1098303 : FRCP2 :: likely ortholog of mouse fibronectin type III repeat containing protein 2 | | 15463 | 0.010448057045878 | -0.100573117194350 |
| 164 | 1098338 | 1098338 : HRB2 :: HIV-1 rev binding protein 2 | | 269857 | 0.310283160362659 | -0.307858826824513 |
| 165 | 1098405 | 1098405 : IL7R :: interleukin 7 receptor | | 362807 | 0.549494110248763 | -0.263717657392419 |
| 166 | 1098412 | 1098412 : MCC :: mutated in colorectal cancers | | -24 | 0.454236696826577 | -0.310591183271143 |
| 167 | 1098415 | 1098415 : KIAA1387 :: KIAA1387 protein | | 130900 | -0.116869481419355 | -0.122838250620999 |
| 168 | 1098433 | 1098433 : :: Homo sapiens cDNA FLJ10158 fis, clone HEMBA1003463. | | 202577 | 0.136410689468839 | -0.299039669796789 |
| 169 | 1098447 | 1098447 : JDP2 :: jun dimerization protein 2 | | 154095 | -0.141461142027089 | 0.0996022918031270 |
| 170 | 1098459 | 1098459 : SPUVE :: protease, serine, 23 | | 25338 | 0.737264124009213 | -0.334058738968943 |
| 171 | 1098461 | 1098461 : DNER :: delta-notch-like EGF repeat-containing transmembrane | | 234074 | 0.0410201744135690 | -0.0674556257159710 |
| 172 | 1098476 | 1098476 : pknbeta :: protein kinase PKNbeta | | 300485 | -0.194588649952929 | 0.0494904696979650 |
| 173 | 1098495 | 1098495 : TBRG1 :: likely ortholog of mouse transforming growth factor beta regulated gene 1 | | 443668 | 0.0523859163608860 | -0.306318481977251 |
| 174 | 1098506 | 1098506 : IL6R :: interleukin 6 receptor | | 193400 | 0.299704358316571 | -0.483797688597999 |
| 175 | 1098521 | 1098521 : OPN3 :: opsin 3 (encephalopsin, panopsin) | | 170129 | -0.309674653956075 | 0.290934864492843 |
| 176 | 1098548 | 1098548 : NFIC :: nuclear factor I/C (CCAAT-binding transcription factor) | | 436639 | 0.577838108495008 | -0.573059285395985 |
| 177 | 1098550 | 1098550 : :: Homo sapiens cDNA FLJ36584 fis, clone TRACH2013450. | | 355655 | -0.0904794086344668 | -0.00545420784183 |
| 178 | 1098553 | 1098553 : HTPAP :: HTPAP protein | | 437179 | 0.172952993194321 | -0.447010228881662 |
| 179 | 1098574 | 1098574 : KIAA0233 :: KIAA0233 gene product | | 79077 | -0.341045883809633 | 0.355913888061517 |
| 180 | 1098592 | 1098592 : FLJ38771 :: hypothetical protein FLJ38771 | | 283707 | 0.370411569171726 | 0.240153206136564 |
| 181 | 1098604 | 1098604 : SLC39A10 :: solute carrier family 39 (zinc transporter), member 10 | | 32793 | -0.356817082601293 | 0.0395908841152280 |
| 182 | 1098607 | 1098607 : MGC15887 :: hypothetical gene supported by BC009447 | | 38516 | -0.202635338865497 | 0.273499931529896 |
| 183 | 1098611 | 1098611 : PDK1 :: pyruvate dehydrogenase kinase, isoenzyme 1 | | 433611 | 0.0114649726682500 | 0.218494255827149 |
| 184 | 1098613 | 1098613 : RENT1 :: regulator of nonsense transcripts 1 | | 388125 | -0.409061726498054 | 0.340688285828164 |
| 185 | 1098618 | 1098618 : PIK3AP1 :: phosphoinositide-3-kinase adaptor protein 1 | | 374836 | -0.256727551852790 | 0.025741438982940 |
| 186 | 1098629 | 1098629 : :: Homo sapiens mRNA; cDNA DKFZp434B0425 (from clone DKFZp434B0425) | | 103305 | -0.188649329326843 | 0.425239786821600 |
| 187 | 1098658 | 1098658 : PAK1 :: p21/Cdc42/Rac1-activated kinase 1 (STE20 homolog, yeast) | | 64056 | 0.0126585870602080 | -0.114254490164613 |
| 188 | 1098668 | 1098668 : BCAT1 :: branched chain aminotransferase 1, cytosolic | | 438993 | 0.198467154778523 | 0.101188582172517 |
| 189 | 1098669 | 1098669 : KCTD10 :: potassium channel tetramerisation domain containing 10 | | 302746 | -0.0545051676790500 | 0.00595362662953 |
| 190 | 1098678 | 1098678 : BMF :: Bcl-2 modifying factor | | 386140 | -0.340027764754526 | 0.107012841951926 |
| 191 | 1098683 | 1098683 : ITGB6 :: integrin, beta 6 | | 57664 | 0.254592203414043 | -0.200152902993317 |
| 192 | 1098694 | 1098694 : :: Homo sapiens mRNA; cDNA DKFZp547J047 (from clone DKFZp547J047) | | 97837 | 0.128247191609226 | -0.269181101036406 |

TABLE 2415-continued

| Order | UNIQID | NAME | GeneID.txt | GENEID | LN.cor | Pro.cor |
|---|---|---|---|---|---|---|
| 193 | 1098718 | 1098718 : PSPC1 :: paraspeckle component 1 | | 16364 | -0.320538780285753 | 0.522732450579130 |
| 194 | 1098771 | 1098771 : KIAA1501 :: KIAA1501 protein | | 374446 | 0.328061924477626 | -0.168759177690866 |
| 195 | 1098784 | 1098784 : MARK1 :: MAP/microtubule affinity-regulating kinase 1 | | 12808 | 0.0885347954440517 | -0.0933600079546100 |
| 196 | 1098809 | 1098809 ::: Homo sapiens hypothetical protein LOC283666, mRNA (cDNA clone IMAGE:4415549), partial cds | | 359394 | 0.447370410855574 | -0.496179620225829 |
| 197 | 1098821 | 1098821 : PALM2 :: paralemmin 2 | | 42322 | 0.179862598270706 | -0.187856000010376 |
| 198 | 1098822 | 1098822 : PRRX1 :: paired related homeobox 1 | | 443452 | 0.774883481649142 | -0.543483135789053 |
| 199 | 1098832 | 1098832 : FGFR1 :: fibroblast growth factor receptor 1 (fms-related tyrosine kinase 2, Pfeiffer syndrome) | | 748 | 0.543603649322806 | -0.330357417669066 |
| 200 | 1098840 | 1098840 : C3orf6 :: chromosome 3 open reading frame 6 | | 55098 | -0.146221260881764 | -0.090592943233251 |
| 201 | 1098862 | 1098862 : MGC26694 :: hypothetical protein MGC26694 | | 303669 | -0.0348634639750440 | -0.146817360127211 |
| 202 | 1098865 | 1098865 : LOC51234 :: hypothetical protein LOC51234 | | 250905 | 0.159594910624286 | -0.309933221730095 |
| 203 | 1098883 | 1098883 : MBTPS2 :: membrane-bound transcription factor protease, site 2 | | 412014 | 0.360729355144278 | 0.0152385238717091 |
| 204 | 1098893 | 1098893 : ATP8B2 :: ATPase, Class I, type 8B, member 2 | | 43577 | 0.159404272308497 | -0.298738852653094 |
| 205 | 1098898 | 1098898 : ADAM12 :: a disintegrin and metalloproteinase domain 12 (meltrin alpha) | | -36 | 0.763097942064200 | -0.294746482348485 |
| 206 | 1098909 | 1098909 : MGC71745 :: similar to embigin | | 446408 | -0.262428029790519 | -0.0533057151673561 |
| 207 | 1098918 | 1098918 : FYVE6 :: FYVE, RhoGEF and PH domain containing 6 | | 170623 | 0.156113760591959 | 0.0485248126190131 |
| 208 | 1098927 | 1098927 : FLJ20202 :: FLJ20202 protein | | 356216 | -0.0811909018062771 | -0.118355198534421 |
| 209 | 1098946 | 1098946 ::: Homo sapiens transcribed sequence with moderate similarity to protein sp:P39195 (H. sapiens) ALU8_HUMAN Alu subfamily SX sequence contamination warning entry | | 135121 | 0.645970747276803 | -0.478233290280070 |
| 210 | 1098951 | 1098951 : H2AFY :: H2A histone family, member Y | | 75258 | -0.105148799565054 | 0.000183905271443 |
| 211 | 1098952 | 1098952 : KIAA0937 :: KIAA0937 protein | | 62264 | -0.155610228904124 | -0.112321975971408 |
| 212 | 1098954 | 1098954 : MOB3B :: MOB3B protein | | 128905 | 0.141136508773827 | -0.149504432709389 |
| 213 | 1098962 | 1098962 : BMP2K :: BMP2 inducible kinase | | 20137 | 0.286170948451110 | -0.181990310332082 |
| 214 | 1098978 | 1098978 : MAP3K2 :: mitogen-activated protein kinase kinase kinase 2 | | 124863 | 0.619363127968430 | -0.505050387984609 |
| 215 | 1098987 | 1098987 ::: Homo sapiens mRNA; cDNA DKFZp686N20218 (from clone DKFZp686N20218) | | 412559 | 0.0621270704766600 | -0.441644144559950 |
| 216 | 1098991 | 1098991 : FLJ21127 :: hypothetical protein FLJ21127 | | 126085 | 0.069832627264346 | -0.114738890765678 |
| 217 | 1099028 | 1099028 : FNDC1 :: fibronectin type III domain containing 1 | | 334838 | 0.631435118754401 | -0.300213120295103 |
| 218 | 1099032 | 1099032 ::: Homo sapiens cDNA FLJ39934 fis, clone SPLEN2021458, weakly similar to Mus musculus mdgl-1 mRNA. | | 35962 | -0.258137643029524 | 0.696628339145868 |
| 219 | 1099040 | 1099040 : HTRA3 :: serine protease HTRA3 | | 390421 | 0.507829674693844 | -0.252934339568439 |
| 220 | 1099053 | 1099053 ::: Homo sapiens mRNA; cDNA DKFZp761D1624 (from clone DKFZp761D1624) | | 376041 | -0.147877893008140 | -0.132787590083425 |
| 221 | 1099058 | 1099058 ::: Homo sapiens cDNA clone IMAGE:5267224, mRNA | | 425116 | -0.152727197201230 | 0.086705174421553 |
| 222 | 1099072 | 1099072 : MAP3K2 :: mitogen-activated protein kinase kinase kinase 2 | | 28827 | 0.326012687586492 | -0.341129976483760 |
| 223 | 1099088 | 1099088 ::: Homo sapiens mRNA; cDNA DKFZp686N20218 (from clone DKFZp686N20218) | | 14355 | -0.339066628811356 | 0.384877281064520 |
| 224 | 1099105 | 1099105 : LATS2 :: LATS, large tumor suppressor, homolog 2 (Drosophila) | | 78960 | 0.495842158034742 | -0.343366651347192 |
| 225 | 1099112 | 1099112 ::: Homo sapiens cDNA FLJ39934 fis, clone SPLEN2021458, weakly similar to Mus musculus mdgl-1 mRNA. | | 368672 | 0.271313775607110 | -0.552177849009380 |
| 226 | 1099120 | 1099120 ::: Homo sapiens cDNA FLJ46579 fis, clone THYMU3042758 | | 371680 | -0.186112714164960 | 0.122311426949034 |
| 227 | 1099121 | 1099121 : FLJ21870 :: FLJ21870 protein | | 396161 | 0.519619700424312 | -0.453311608748159 |
| 228 | 1099128 | 1099128 : AKAP13 :: A kinase (PRKA) anchor protein 13 | | 350631 | -0.0130338769712500 | -0.132909940435626 |
| 229 | 1099135 | 1099135 : SLC39A11 :: solute carrier family 39 (metal ion transporter), member 11 | | 3402 | 0.326186953473970 | -0.243872317095855 |
| 230 | 1099140 | 1099140 : TNFRSF19L :: tumor necrosis factor receptor superfamily, member 19-like | | 500350 | 0.0656000372561850 | -0.226915577288523 |
| 231 | 1099148 | 1099148 ::: Homo sapiens cDNA FLJ26764 fis, clone PRS02668 | | 434975 | 0.188804128027844 | -0.0860409656003445 |
| 232 | 1099150 | 1099150 ::: Homo sapiens mRNA; cDNA DKFZp686L01105 (from clone DKFZp686L01105) | | 240443 | 0.440961016035862 | -0.370874002114838 |
| 233 | 1099152 | 1099152 : MGC15396 :: hypothetical protein MGC15396 | | 351247 | -0.310898020091843 | 0.293673968871125 |
| 234 | 1099154 | 1099154 : MOB3C :: MOB3C protein | | 97927 | 0.205447190901989 | -0.397423889489784 |
| 235 | 1099167 | 1099167 : MGC45731 :: hypothetical protein MGC45731 | | 381105 | 0.510485627999948 | -0.194298721772200 |
| 236 | 1099204 | 1099204 ::: Homo sapiens mRNA; cDNA DKFZp586K1922 (from clone DKFZp586K1922) | | 193784 | 0.208527885951095 | -0.331184935715711 |
| 237 | 1099265 | 1099265 ::: Homo sapiens mRNA, clone IMAGE:4828750, mRNA | | 375762 | 0.191460172021332 | -0.292819027251602 |
| 238 | 1099291 | 1099291 : FBXO10 :: F-box only protein 10 | | 130774 | -0.241213003745553 | 0.140643790486120 |
| 239 | 1099292 | 1099292 : RNPC2 :: RNA-binding region (RNP1, RRM) containing 2 | | 282901 | -0.0115120278266380 | -0.146104933503048 |
| 240 | 1099299 | 1099299 : EVL :: Enah/Vasp-like | | 241471 | 0.217471121189110 | -0.497486588999731 |

TABLE 2415-continued

| Order | UNIQID | NAME | GeneID.txt | GENEID | LN.cor | Pro.cor |
|---|---|---|---|---|---|---|
| 241 | 1099318 | LOC149420 :: casein kinase | | 29911 | −0.0314516209311163 | 0.0322736075501900 |
| 242 | 1099328 | FLJ35779 :: hypothetical protein FLJ35779 | | 432726 | −0.254822688277176 | 0.160319583944402 |
| 243 | 1099332 | ::: Homo sapiens cDNA FLJ44521 fis, clone UTERU3002786 | | 32433 | 0.353038975004276 | −0.376426689684681 |
| 244 | 1099358 | LOC338773 :: hypothetical protein LOC338773 | | 449718 | 0.813232650418064 | −0.319504511328730 |
| 245 | 1099377 | ADCK4 :: aarF domain containing kinase 4 | | 130712 | −0.0507631399906985 | 0.00476323845278 |
| 246 | 1099388 | DTX1 :: deltex homolog 1 (Drosophila) | | 124024 | −0.194780161074778 | 0.313061833581174 |
| 247 | 1099396 | ZNFN1A1 :: zinc finger protein, subfamily 1A, 1 (Ikaros) | | 435949 | −0.480396437660557 | 0.241771812595989 |
| 248 | 1099403 | PAG :: phosphoprotein associated with glycosphingolipid-enriched microdomains | | 266175 | 0.157815262302368 | −0.138144351639275 |
| 249 | 1099418 | KIAA1946 :: KIAA1946 protein | | 172792 | 0.352518727172842 | −0.221041836869096 |
| 250 | 1099444 | FLJ90013 :: hypothetical protein FLJ90013 | | 434489 | −0.154725204627076 | 0.144181046064220 |
| 251 | 1099510 | ADCK1 :: aarF domain containing kinase 1 | | 15251 | 0.0368230497907738 | −0.189553081209326 |
| 252 | 1099526 | LCHN :: LCHN protein | | 521240 | 0.0598142019158776 | −0.318229548955097 |
| 253 | 1099539 | CXorf15 :: chromosome X open reading frame 15 | | 201624 | −0.159971879950874 | 0.335150972693171 |
| 254 | 1099549 | ::: Homo sapiens transcribed sequences | | −45 | −0.384484470966513 | 0.213030278389421 |
| 255 | 1099563 | ::: Homo sapiens mRNA; cDNA DKFZp686J0156 (from clone DKFZp686J0156) | | 388347 | 0.0910307852113411 | −0.163765026275539 |
| 256 | 1099598 | MGC2452 :: hypothetical protein MGC2452 | | 275711 | −0.347670787807501 | 0.173371242361433 |
| 257 | 1099631 | FLJ20032 :: hypothetical protein FLJ20032 | | 367639 | −0.105513306302497 | −0.0935921942500014 |
| 258 | 1099633 | SGKL :: serum/glucocorticoid regulated kinase-like | | 380877 | 0.366469483816619 | −0.401250676057012 |
| 259 | 1099651 | EBF :: early B-cell factor | | −31 | −0.137184837781477 | 0.247346085114095 |
| 260 | 1099669 | MGC45428 :: hypothetical protein MGC45428 | | 45057 | −0.0943112964766722 | −0.134670571453347 |
| 261 | 1099680 | JAK3 :: Janus kinase 3 (a protein tyrosine kinase, leukocyte) | | 210387 | 0.158713315773940 | −0.344236078856799 |
| 262 | 1099686 | ::: Homo sapiens transcribed sequence with weak similarity to protein ref:NP_060312.1 (H. sapiens) hypothetical protein FLJ20489 [Homo sapiens] | | 117721 | 0.339760641299220 | −0.126834793111279 |
| 263 | 1099699 | SOCS3 :: suppressor of cytokine signaling 3 | | 436943 | 0.458674229868194 | −0.269705172389045 |
| 264 | 1099711 | ::: Homo sapiens mRNA; cDNA DKFZp686I21166 (from clone DKFZp686I21166) | | 243596 | 0.139054816284750 | 0.201358145780389 |
| 265 | 1099734 | KIS :: kinase interacting with leukemia-associated gene (stathmin) | | 127310 | 0.00234142112724100 | −0.0619371880183100 |
| 266 | 1099743 | TRAD :: serine/threonine kinase with Dbl- and pleckstrin homology domains | | 162189 | 0.130663684870377 | −0.0731020997343620 |
| 267 | 1099748 | ::: Homo sapiens mRNA; cDNA DKFZp434N2116 (from clone DKFZp434N2116) | | 356481 | 0.148774754361664 | −0.405219346399157 |
| 268 | 1099760 | CSNK1G3 :: casein kinase 1, gamma 3 | | 129206 | −0.00766604979891600 | −0.109292619399866 |
| 269 | 1099798 | FGD3 :: FGD1 family, member 3 | | 411081 | −0.0159091313608290 | −0.501064586770852 |
| 270 | 1099826 | RAB30 :: RAB30, member RAS oncogene family | | 445862 | −0.294473336045832100 | 0.412965834268278 |
| 271 | 1099830 | EPM2AIP1 :: EPM2A (laforin) interacting protein 1 | | 28020 | −0.358690409532099 | 0.237419003752701 |
| 272 | 1099847 | LOC129293 :: hypothetical protein LOC129293 | | 36723 | 0.029109229364516 | −0.268448964730217 |
| 273 | 1099857 | ::: Homo sapiens annexin II receptor mRNA, complete cds | | 119768 | 0.049788466833904 | −0.291836140756930 |
| 274 | 1099886 | ::: Homo sapiens mRNA; cDNA DKFZp434N2116 (from clone DKFZp434N2116) | | −49 | 0.14877475436164400 | −0.263395070513850 |
| 275 | 1099900 | ::: Homo sapiens transcribed sequences | | 444508 | −0.104446681462296 | −0.145223660017070 |
| 276 | 1099939 | MGC7036 :: hypothetical protein MGC7036 | | 488173 | −0.099560227175285 | −0.171318365358415 |
| 277 | 1099951 | LOC170394 :: hypothetical protein BC011630 | | 157728 | 0.274596536409081 | −0.347843922255294 |
| 278 | 1099953 | C21orf4 :: chromosome 21 open reading frame 4 | | 433668 | 0.047643555151766 | −0.294401060293225 |
| 279 | 1099960 | ::: Homo sapiens cDNA clone IMAGE:3462401, partial cds | | 144583 | −0.127871935602877 | −0.0108215601538530 |
| 280 | 1099965 | LOC138428 :: hypothetical protein LOC138428 | | 71962 | 0.091962882474027 | −0.091249651864211 |
| 281 | 1099978 | STK33 :: serine/threonine kinase 33 | | 148135 | −0.179708365440309 | 0.235587009064294 |
| 282 | 1099995 | LOC115265 :: similar to Smhs1 protein | | 107515 | 0.00732981535710900 | −0.132004117518270 |
| 283 | 1100005 | DUFD1 :: DUF729 domain containing 1 | | 121536 | −0.135976170321747 | 0.601059023563389 |
| 284 | 1100027 | AMICA :: adhesion molecule AMICA | | 16291 | 0.300925302822323 | −0.551597607471469 |
| 285 | 1100040 | RASGRF2 :: Ras protein-specific guanine nucleotide-releasing factor 2 | | 410953 | 0.147596960954750 | −0.215628806283083 |
| 286 | 1100042 | RAB37 :: RAB37, member of RAS oncogene family | | 351413 | 0.165978306204715 | −0.447611622284770 |
| 287 | 1100054 | ::: Homo sapiens cDNA FLJ10641 fis, clone NT2RP2005748. | | 125353 | −0.0938743051519000 | −0.046922285279186 |
| 288 | 1100060 | RIPK3 :: receptor-interacting serine-threonine kinase 3 | | 268551 | −0.0806738912922110 | −0.183740301156722 |

TABLE 2415-continued

GeneID.txt

| Order | UNIQID | NAME | GENEID | LN.cor | Pro.cor |
|---|---|---|---|---|---|
| 289 | 1100071 | 1100071 : IBRDC2 :: IBR domain containing 2 | 432653 | −0.0961395591056040 | 0.0219105301917500 |
| 290 | 1100130 | 1100130 : PRELP :: proline arginine-rich end leucine-rich repeat protein | 76494 | 0.4489035317731970 | −0.4277162603016730 |
| 291 | 1100136 | 1100136 : NUDT1 :: nudix (nucleoside diphosphate linked moiety X)-type motif 1 | 413078 | 0.0569723864221600 | −0.0567025881668040 |
| 292 | 1100138 | 1100138 : CGI-109 :: CGI-109 protein | 278391 | 0.0755253862304140 | −0.0151962409318100 |
| 293 | 1100144 | 1100144 ::: Homo sapiens transcribed sequence with moderate similarity to protein ref:NP_004563.1 (H. sapiens) plakophilin 2 [Homo sapiens] | 436379 | 0.3421206169588520 | −0.3058815115421120 |
| 294 | 1100150 | 1100150 : KIAA1999 :: KIAA1999 protein | 9343 | 0.0439223232928730 | −0.2625479925384780 |
| 295 | 1100159 | 1100159 : FLJ00332 :: FLJ00332 protein | 123164 | −0.1751142769040710 | −0.1512517453986300 |
| 296 | 1100161 | 1100161 : LOC142678 :: skeletrophin | 135805 | −0.2688034082861930 | 0.0430741993990140 |
| 297 | 1100171 | 1100171 : FLJ11029 :: hypothetical protein FLJ11029 | 274448 | −0.3155993695341620 | 0.7766321487278440 |
| 298 | 1100183 | 1100183 : FLJ40869 :: hypothetical protein FLJ40869 | 180582 | −0.3191137074249380 | 0.4072580490701900 |
| 299 | 1100249 | 1100249 : HAK :: heart alpha-kinase | 388674 | 0.4052020295289820 | −0.4229145765729780 |
| 300 | 1100258 | 1100258 : KIAA1384 :: KIAA1384 protein | 88442 | −0.4829274175026830 | 0.2454624307389220 |
| 301 | 1100263 | 1100263 : LOC90268 :: hypothetical protein BC007706 | 406335 | 0.0615491645845740 | 0.0524395793031320 |
| 302 | 1100288 | 1100288 : ALS2CR19 :: amyotrophic lateral sclerosis 2 (juvenile) chromosome region, candidate 19 | 26981 | 0.4288897924282390 | −0.3207128385833900 |
| 303 | 1100290 | 1100290 ::: Homo sapiens cDNA FLJ30800 fis, clone FEBRA2001197. | 4241 | 0.1361961715034170 | −0.2295766696652410 |
| 304 | 1100301 | 1100301 : LLT1 :: lectin-like NK cell receptor | 356250 | −0.0011292590363740 | −0.0999668900578480 |
| 305 | 1100311 | 1100311 : HSPC163 :: HSPC163 protein | 445890 | 0.1053073770707410 | −0.1652667263650810 |
| 306 | 1100335 | 1100335 ::: Homo sapiens transcribed sequence with moderate similarity to protein pir:I60307 (E. coli) I60307 beta-galactosidase, alpha peptide - Escherichia coli | 268474 | −0.1252786493876520 | 0.3165986174457760 |
| 307 | 1100339 | 1100339 : FLJ14813 :: hypothetical protein FLJ14813 | 276905 | −0.2223160269127400 | 0.6076734486988990 |
| 308 | 1100384 | 1100384 : ADCK5 :: aarF domain containing kinase 5 | 283374 | 0.0200593705872460 | 0.0073290961076200 |
| 309 | 1100405 | 1100405 : KIAA0792 :: KIAA0792 gene product | 119387 | 0.2521978258192600 | −0.4422479836568850 |
| 310 | 1100420 | 1100420 : KIAA1804 :: mixed lineage kinase 4 | 50883 | −0.1658516765759380 | 0.2312321393669280 |
| 311 | 1100423 | 1100423 : FLJ30973 :: hypothetical protein FLJ30973 | 50841 | 0.1590037171479200 | −0.1385884372505250 |
| 312 | 1100433 | 1100433 : HTRA3 :: serine protease HTRA3 | 390421 | 0.1631787043814620 | −0.1188712407944970 |
| 313 | 1100443 | 1100443 : MS4A1 :: membrane-spanning 4-domains, subfamily A, member 1 | 438040 | −0.1050675761708440 | 0.0351866106669030 |
| 314 | 1100496 | 1100496 : LOC139886 :: hypothetical protein LOC139886 | 111496 | −0.1247352159948990 | 0.4409818052783880 |
| 315 | 1100538 | 1100538 : PRG4 :: proteoglycan 4, (megakaryocyte stimulating factor, articular superficial zone protein, camptodactyly, arthropathy, coxa vara, pericarditis syndrome) | 432458 | −0.0214887630294264 | −0.1948003475863340 |
| 316 | 1100561 | 1100561 : HEL308 :: DNA helicase HEL308 | 194109 | −0.1854915119875170 | 0.1294097788711180 |
| 317 | 1100562 | 1100562 : C20orf100 :: chromosome 20 open reading frame 100 | 26608 | 0.0593055255011180 | −0.2370950284777750 |
| 318 | 1100581 | 1100581 ::: Homo sapiens mRNA; cDNA DKFZp667A1115 (from clone DKFZp667A1115) | 356307 | 0.1651359337165270 | 0.0261268584373440 |
| 319 | 1100585 | 1100585 : LFNG :: lunatic fringe homolog (Drosophila) | 159142 | 0.3081520827750670 | −0.2958303831490560 |
| 320 | 1100591 | 1100591 : HKR2 :: GLI-Kruppel family member HKR2 | 388162 | −0.2813732604708380 | 0.1423106519626640 |
| 321 | 1100598 | 1100598 ::: Homo sapiens cDNA FLJ40955 fis, clone UTERU2011199. | 438749 | −0.0812728564831470 | 0.3895416532508640 |
| 322 | 1100609 | 1100609 : PPIL2 :: peptidylprolyl isomerase (cyclophilin)-like 2 | 447045 | −0.0100332976685780 | −0.2516264479021450 |
| 323 | 1100625 | 1100625 : RORC :: RAR-related orphan receptor C | 232803 | −0.0175509548431660 | −0.1158014929034450 |
| 324 | 1100721 | 1100721 ::: Homo sapiens cDNA FLJ32207 fis, clone PLACE6003204. | 18713 | 0.3201782629069590 | −0.2946008214461250 |
| 325 | 1100750 | 1100750 ::: Homo sapiens cDNA, clone IMAGE:4753714, mRNA | 280387 | −0.2204189673146020 | 0.3340982405711300 |
| 326 | 1100753 | 1100753 : ZNF19 :: zinc finger protein 19 (KOX 12) | 512717 | −0.0961557463434170 | −0.0735643133382610 |
| 327 | 1100770 | 1100770 ::: Homo sapiens transcribed sequences | 65578 | 0.1264004913811770 | −0.1241404905001880 |
| 328 | 1100847 | 1100847 : C6orf105 :: chromosome 6 open reading frame 105 | 97411 | 0.1016714615976070 | −0.1601543861394870 |
| 329 | 1100849 | 1100849 ::: Homo sapiens cDNA FLJ34866 fis, clone NT2NE2014113. | 184430 | −0.4093551824503650 | 0.3529091742662550 |
| 330 | 1100851 | 1100851 : EHD4 :: EH-domain containing 4 | 55058 | 0.3213390381084030 | −0.2870017672169240 |
| 331 | 1100871 | 1100871 ::: Homo sapiens cDNA FLJ32274 fis, clone PROST2000036. | 48353 | 0.4352066816954380 | −0.5445213877990300 |
| 332 | 1100873 | 1100873 ::: Homo sapiens transcribed sequences | 445884 | −0.2048833517637660 | 0.1577219164751580 |
| 333 | 1100879 | 1100879 : MASP2 :: mannan-binding lectin serine protease 2 | 119983 | −0.1128317838677750 | −0.2906490769350630 |
| 334 | 1100904 | 1100904 : LOC119504 :: hypothetical protein LOC119504 | −25 | −0.0990363422628420 | −0.2564311954741630 |

TABLE 2415-continued

GeneID.txt

| Order | UNIQID | NAME | GENEID | LN.cor | Pro.cor |
|---|---|---|---|---|---|
| 335 | 1100911 | 1100911 : C4orf7 :: chromosome 4 open reading frame 7 | 320147 | 0.060001350276090 | -0.084108354010684 |
| 336 | 1100916 | 1100916 : PRKWNK4 :: protein kinase, lysine deficient 4 | 105448 | 0.108814731820795 | -0.011505711122245 |
| 337 | 1100977 | 1100977 : NRG3 :: neuregulin 3 | -8 | 0.107540349948529 | -0.052860133552450 |
| 338 | 1100995 | 1100995 : FLJ32029 :: hypothetical protein FLJ32029 | 26612 | 0.222494929391081 | -0.247794549127664 |
| 339 | 1101004 | 1101004 : SKI :: v-ski sarcoma viral oncogene homolog (avian) | 2969 | 0.300578623845209 | -0.357871271240017 |
| 340 | 1101023 | 1101023 : EPHA7 :: EphA7 | 73962 | -0.081992625701500 | -0.012091224764700 |
| 341 | 1101054 | 1101054 : PPP2R5E :: protein phosphatase 2, regulatory subunit B (B56), epsilon isoform | 173328 | -0.142239905250465 | 0.091911875646825 |
| 342 | 1101096 | 1101096 ::: Homo sapiens transcribed sequences | 457403 | 0.393655668577862 | -0.355743747889559 |
| 343 | 1101119 | 1101119 : IL17RE :: interleukin 17 receptor E | 390823 | 0.039586216405584 | 0.044022252281821 |
| 344 | 1101128 | 1101128 : MGC45419 :: Similar to calcium/calmodulin-dependent protein kinase 1, beta | 436667 | -0.241815550224320 | 0.169113348318235 |
| 345 | 1101149 | 1101149 ::: Homo sapiens BIC noncoding mRNA, complete sequence | 517226 | 0.029580798362771 | -0.090026984564981 |
| 346 | 1101211 | 1101211 : STRBP :: spermatid perinuclear RNA binding protein | 287659 | -0.250696465092268 | 0.025159511937388 |
| 347 | 1101272 | 1101272 : DKFZp434H2111 :: hypothetical protein DKFZp434H2111 | 179089 | 0.009706674301822 | -0.269132228709153 |
| 348 | 1101276 | 1101276 : ERdj5 :: ER-resident protein ERdj5 | 1098 | 0.006940542351402 | 0.036655849606570 |
| 349 | 1101291 | 1101291 : PPP3CA :: protein phosphatase 3 (formerly 2B), catalytic subunit, alpha isoform (calcineurin A alpha) | 272458 | -0.133666602302100 | 0.284183973397199 |
| 350 | 1101295 | 1101295 : FLJ40629 :: hypothetical protein FLJ40629 | 99807 | -0.205479511626541 | 0.628330940348730 |
| 351 | 1101305 | 1101305 ::: Homo sapiens cDNA clone IMAGE:6301163, containing frame-shift errors | 112742 | 0.473043674581829 | -0.340194063635630 |
| 352 | 1101322 | 1101322 ::: Homo sapiens cDNA clone similar to RIKEN cDNA 2900024C23 (LOC125704), mRNA | 227699 | -0.115836732640888 | 0.157974457392334 |
| 353 | 1101354 | 1101354 : P2RY8 :: purinergic receptor P2Y, G-protein coupled, 8 | 111377 | 0.121615764539941 | -0.111489709931474 |
| 354 | 1101416 | 1101416 : FLJ41238 :: FLJ41238 protein | 338851 | 0.215337920108734 | -0.112373898517407 |
| 355 | 1101430 | 1101430 ::: Homo sapiens transcribed sequences | 418040 | 0.232052953728175 | -0.060942343084998 |
| 356 | 1101439 | 1101439 : TERF2 :: telomeric repeat binding factor 2 | 63335 | -0.043553911594881 | 0.235168237858145 |
| 357 | 1101477 | 1101477 : NUCB2 :: nucleobindin 2 | 423095 | 0.160970742319521 | -0.161034301134445 |
| 358 | 1101478 | 1101478 : MGC45780 :: hypothetical protein MGC45780 | 146246 | 0.560131166008654 | -0.244033722256484 |
| 359 | 1101514 | 1101514 : FLJ32363 :: FLJ32363 protein | 88801 | -0.213383824410450 | 0.584456949856772 |
| 360 | 1101566 | 1101566 ::: Homo sapiens cDNA FLJ26876 fis, clone PRS09003 | 98558 | 0.547923586173589 | -0.120576676385804 |
| 361 | 1101582 | 1101582 : CKLFSF2 :: chemokine-like factor super family 2 | 195685 | -0.164617883959410 | 0.163800631985653 |
| 362 | 1101586 | 1101586 : GPR114 :: G protein-coupled receptor 114 | 187884 | 0.106771558157668 | -0.040640551768368 |
| 363 | 1101628 | 1101628 : LOC374654 :: similar to kinesin family member 21 A; N-5 kinesin | 441708 | -0.301404849554472 | 0.649432137236986 |
| 364 | 1101634 | 1101634 ::: Homo sapiens transcribed sequences | 510588 | -0.187767924798762 | 0.150456533036268 |
| 365 | 1101687 | 1101687 : FNBP1 :: formin binding protein 1 | 440808 | 0.094301262952051 | -0.183143704416937 |
| 366 | 1101708 | 1101708 : MCOLN2 :: mucolipin 2 | 459526 | -0.206286880737142 | 0.089733971257195 |
| 367 | 1101758 | 1101758 : OSM :: oncostatin M | 248156 | 0.427679944948121 | -0.134414873641202 |
| 368 | 1101775 | 1101775 : TTBK1 :: tau tubulin kinase 1 | 343820 | -0.106506268653088 | 0.070427043729278 |
| 369 | 1101777 | 1101777 : MGC33630 :: hypothetical protein MGC33630 | 359981 | 0.095553061289930 | 0.052525796095336 |
| 370 | 1101829 | 1101829 : GPR92 :: G protein-coupled receptor 92 | 155538 | -0.170716626765422 | 0.053271309080346 |
| 371 | 1101892 | 1101892 : CCL27 :: chemokine (C-C motif) ligand 27 | 225948 | 0.090149523471370 | 0.082897675676425 |
| 372 | 1101905 | 1101905 ::: Homo sapiens transcribed sequence with weak similarity to protein pir:I60307 (E. coli) I60307 beta-galactosidase, alpha peptide - Escherichia coli | 170843 | 0.191141074226577 | -0.112946854380485 |
| 373 | 1101944 | 1101944 ::: Homo sapiens transcribed sequences | 439064 | 0.511312767121963 | -0.502590781948196 |
| 374 | 1101948 | 1101948 ::: Homo sapiens mRNA full length insert cDNA clone EUROIMAGE 2138357 | 14411 | 0.109781853161187 | -0.205413488978966 |
| 375 | 1101974 | 1101974 : EPHB1 :: EphB1 | 272311 | -0.151333397001395 | -0.109778955757325 |
| 376 | 1102027 | 1102027 : CD5 :: CD5 antigen (p56-62) | 58685 | 0.051477533952002 | -0.356234543694019 |
| 377 | 1102030 | 1102030 : SLC20A1 :: solute carrier family 20 (phosphate transporter), member 1 | 110855 | 0.320766322780251 | -0.218010866476956 |
| 378 | 1102081 | 1102081 ::: Homo sapiens mRNA; cDNA DKFZp686L0948 (from clone DKFZp686L0948) | 506977 | -0.014999088235277 | -0.142774708354838 |
| 379 | 1102165 | 1102165 ::: Homo sapiens cDNA FLJ12909 fis, clone NT2RP2004400. | 152460 | 0.286482836301455 | -0.254747456654948 |
| 380 | 1102193 | 1102193 ::: Homo sapiens transcribed sequences | 22668 | 0.225058272151899 | 0.014961101827526 |
| 381 | 1102282 | 1102282 : GCNT2 :: glucosaminyl (N-acetyl) transferase 2, I-branching enzyme | 934 | 0.048762986298498 | -0.034402010922042 |
| 382 | 1102350 | 1102350 : MGC42105 :: hypothetical protein MGC42105 | 25845 | -0.026228919079674 | -0.028985150162382 |

TABLE 2415-continued

GeneID.txt

| Order | UNIQID | NAME | GENEID | LN.cor | Pro.cor |
|---|---|---|---|---|---|
| 383 | 102408 | 102408 : RAB3GAP :: RAB3 GTPase-ACTIVATING PROTEIN | 306327 | -0.084819962049070 | 0.075341563718927 |
| 384 | 102415 | 102415 : CKLFSF5 :: chemokine-like factor super family 5 | 99272 | 0.082819335162941 | -0.159143215400658 |
| 385 | 102437 | 102437 : NUP62 :: nucleoporin 62 kDa | 437023 | 0.418912844259920 | -0.394203628829545 |
| 386 | 102470 | 102470 ::: Homo sapiens transcribed sequence with weak similarity to protein ref:NP_060265.1 (*H. sapiens*) hypothetical protein FLJ20378 [*Homo sapiens*] | 292915 | 0.105172178085776 | -0.079629308072535 |
| 387 | 102471 | 102471 : UNC5CL :: unc-5 homolog C (*C. elegans*)-like | 158357 | -0.094907736964586 | -0.227754093321577 |
| 388 | 102479 | 102479 : STK11 :: serine/threonine kinase 11 (Peutz-Jeghers syndrome) | 301772 | 0.037690452961669 | -0.137459558533489 |
| 389 | 102537 | 102537 ::: Homo sapiens transcribed sequences | 202151 | 0.108853907619606 | -0.170270299488847 |
| 390 | 102540 | 102540 : FCRH3 :: Fc receptor-like protein 3 | 434881 | -0.153114207986084 | 0.059006826674309 |
| 391 | 102633 | 102633 ::: Homo sapiens transcribed sequences | 511124 | -0.038532270835624 | 0.067743723935813 |
| 392 | 102652 | 102652 : CKLFSF1 :: chemokine-like factor super family 1 | 343717 | 0.147463476236581 | -0.101172237917063 |
| 393 | 102654 | 102654 : KIAA0350 :: KIAA0350 protein | 380599 | -0.099657744074508 | 0.234041359355527 |
| 394 | 102725 | 102725 : C21orf42 :: chromosome 21 open reading frame 42 | 234016 | 0.122651922822787 | -0.047341180286403 |
| 395 | 102744 | 102744 ::: Homo sapiens transcribed sequences | 198671 | -0.161033129852380 | 0.020948786809089 |
| 396 | 102821 | 102821 ::: Homo sapiens mRNA; cDNA DKFZp686L14188 (from clone DKFZp686L14188) | 202024 | 0.118625008373993 | 0.023472946360875 |
| 397 | 102859 | 102859 ::: Homo sapiens cDNA FLJ42418 fis, clone BLADE2001987 | 446195 | -0.065690917989146 | 0.168415178725098 |
| 398 | 102885 | 102885 : CCNB3 :: cyclin B3 | 130310 | -0.092278455245970 | 0.067527659533562 |
| 399 | 102898 | 102898 : FKSG87 : FKSG87 protein | 145519 | -0.013747221559531 | -0.070588363385651 |
| 400 | 102912 | 102912 : MGC15882 :: hypothetical protein MGC15882 | 194610 | -0.011672180281967 | 0.144165981071462 |
| 401 | 103054 | 103054 ::: Homo sapiens transcribed sequences | 341531 | 0.223445105771884 | -0.188710045144392 |
| 402 | 103107 | 103107 : TAL2 :: T-cell acute lymphocytic leukemia 2 | 247978 | -0.092171941247663 | 0.081590292816983 |
| 403 | 103111 | 103111 : RPC155 :: polymerase (RNA) III (DNA directed) (155 kD) | 436896 | -0.300266776102017 | 0.238379729664432 |
| 404 | 103120 | 103120 : TNFRSF10A :: tumor necrosis factor receptor superfamily, member 10a | 401745 | -0.027192053875555 | 0.031738694361568 |
| 405 | 103124 | 103124 : IRAK2 :: interleukin-1 receptor-associated kinase 2 | 424542 | 0.339830393625871 | -0.235982814260479 |
| 406 | 103134 | 103134 : MYLK2 :: myosin light chain kinase 2, skeletal muscle | 86092 | 0.018064483308290 | -0.026257429266506 |
| 407 | 103137 | 103137 : EPHA8 :: EphA8 | 283613 | -0.127428747463846 | 0.109096457119722 |
| 408 | 103139 | 103139 : NOG :: noggin | 248201 | 0.112737761541130 | -0.019607674631529 |
| 409 | 103224 | 103224 : HOXD8 :: homeo box D8 | 301963 | 0.288364072940970 | -0.201074068135796 |
| 410 | 103264 | 103264 : DKFZP434I0714 :: hypothetical protein DKFZP434I0714 | 142307 | -0.322975964968122 | 0.264079373684896 |
| 411 | 103272 | 103272 ::: Homo sapiens, clone IMAGE:5312754, mRNA | 137206 | -0.100994707504263 | 0.025377105393344 |
| 412 | 103284 | 103284 : TPCN2 :: two pore segment channel 2 | 186655 | 0.345601083093747 | -0.227937096818758 |
| 413 | 103303 | 103303 : C9orf52 :: chromosome 9 open reading frame 52 | 49605 | 0.399198464844216 | -0.466790651317946 |
| 414 | 103304 | 103304 ::: Homo sapiens clone CDABP0095 mRNA sequence | 46919 | 0.065720206673849 | -0.204886670295576 |
| 415 | 103390 | 103390 : BPNT1 :: 3'(2), 5'-bisphosphate nucleotidase 1 | 271752 | 0.136442060214909 | 0.191252082764510 |
| 416 | 103398 | 103398 : FLJ10244 :: Ral-A exchange factor RalGPS2 | 220745 | -0.361204561848680 | 0.406852093691962 |
| 417 | 103420 | 103420 : MBNL2 :: muscleblind-like 2 (*Drosophila*) | 372571 | 0.124346374266239 | -0.191222651743482 |
| 418 | 103475 | 103475 : EBF :: early B-cell factor | 120785 | -0.141391424615001 | 0.266048426373043 |
| 419 | 103497 | 103497 ::: Homo sapiens mRNA; cDNA DKFZp761J1112 (from clone DKFZp761J1112) | 50115 | 0.602843374034205 | -0.450380110586192 |
| 420 | 103504 | 103504 ::: Homo sapiens mRNA; cDNA DKFZp434P0810 (from clone DKFZp434P0810) | 142517 | 0.038856844752532 | -0.192019972011980 |
| 421 | 103540 | 103540 : PRKWNK3 :: protein kinase, lysine deficient 3 | 92423 | 0.079917307313713 | -0.146365124023944 |
| 422 | 103639 | 103639 : KIAA1765 :: KIAA1765 protein | 388304 | -0.021903689889921 | -0.015706254591252 |
| 423 | 103711 | 103711 ::: Homo sapiens cDNA FLJ11833 fis, clone HEMBA1006579. | 288718 | -0.117756771697465 | 0.060550901815652 |
| 424 | 103766 | 103766 : TP73 :: tumor protein p73 | 192132 | -0.202367662929968 | 0.151460770224789 |
| 425 | 103855 | 103855 : LOC153684 :: hypothetical protein LOC153684 | 259625 | 0.089916530004118 | -0.401249389389032 |
| 426 | 103858 | 103858 : PSMA3 :: proteasome (prosome, macropain) subunit, alpha type, 3 | 246240 | 0.036320631564259 | -0.110328564072655 |
| 427 | 103921 | 103921 : MS4A6A :: membrane-spanning 4-domains, subfamily A, member 6A | 371612 | 0.079553258539825 | -0.373450772906280 |
| 428 | 103932 | 103932 ::: Homo sapiens clone HQ0319 | 31330 | 0.132220773211356 | -0.148815074748484 |
| 429 | 103982 | 103982 : MGC26226 :: beta cysteine string protein | 142926 | 0.343337538439363 | -0.063435983118753 |
| 430 | 104072 | 104072 ::: Homo sapiens cDNA FLJ11586 fis, clone HEMBA1003720. | 287429 | -0.084275558872729 | -0.086488630731059 |

TABLE 2415-continued

| Order | UNIQID | NAME GeneID.txt | GENEID | LN.cor | Pro.cor |
|---|---|---|---|---|---|
| 431 | 1104175 | KIAA1639 :: KIAA1639 protein | 287383 | 0.240417880903839 | -0.271486553982473 |
| 432 | 1104195 | DNAH8 :: dynein, axonemal, heavy polypeptide 8 | 172101 | 0.125358396983583 | -0.167980969969610 |
| 433 | 1104254 | ::: Homo sapiens cDNA FLJ12299 fis, clone MAMMA1001851. | 492700 | -0.151297255208119 | 0.0810197298886145 |
| 434 | 1104373 | ::: Homo sapiens cDNA FLJ11709 fis, clone HEMBA1005133. | 295633 | -0.00575606338241S | -0.123990346935139 |
| 435 | 1104545 | ::: Homo sapiens cDNA FLJ20182fis, clone COLF0190 | 254477 | -0.180198148895551 | 0.0146376561 97947 |
| 436 | 1104552 | LOC96597 :: hypothetical protein LOC96597 | 193857 | -0.294998056306420 | 0.136359195898485 |
| 437 | 1104840 | ::: Homo sapiens cDNA FLJ20112 fis, clone COL05405 | 482250 | -0.0575375574 29858 | -0.243362980194851 |
| 438 | 1104870 | KIAA1486 :: KIAA1486 protein | 210958 | -0.077488245043722 | -0.0711740441 11354 |
| 439 | 1104905 | FLJ14753 :: hypothetical protein FLJ14753 | 13453 | 0.046259333205597 | -0.0722722369686S64 |
| 440 | 1104910 | IGL@ :: immunoglobulin lambda locus | -28 | -0.0215913905798S8 | 0.046363051743828 |
| 441 | 1105001 | ::: Homo sapiens transcribed sequence with moderate similarity to protein sp:P39193 (H. sapiens) ALU6_HUMAN Alu subfamily SP sequence contamination warning entry | 296695 | -0.0141921077739% | -0.089068020278894 |
| 442 | 1105178 | GNG8 :: guanine nucleotide binding protein (G protein), gamma 8 | 283961 | 0.242480929979626 | -0.272541916184894 |
| 443 | 1105248 | ::: Homo sapiens similar to Olfactory receptor 1I1 (Olfactory receptor 19-20) (OR19-20) (LOC126370), mRNA | -47 | 0.105352411032661 | -0.0845853154839 32 |
| 444 | 1105668 | ::: Genomic sequence on chromosome 6q23 | -62 | -0.123114691799488 | 0.460907242218706 |
| 445 | 1105684 | SLC38A5 :: solute carrier family 38, member 5 | 195155 | -0.215379417617045 | 0.165670482687 66 |
| 446 | 1105728 | MGC24180 :: hypothetical protein MGC24180 | 13034 | -0.273706962285229 | 0.476949972442765 |
| 447 | 1105732 | FLJ32549 :: hypothetical protein FLJ32549 | 396626 | -0.185773660713166 | 0.331821807671563 |
| 448 | 1105751 | ::: Homo sapiens transcribed sequences | 176376 | 0.282674447127367 | -0.540879875488500 |
| 449 | 1105759 | ETV6 :: ets variant gene 6 (TEL oncogene) | 171262 | -0.063219469536356 | -0.109967146172245 |
| 450 | 1105798 | CKLFSF8 :: chemokine-like factor super family 8 | 154986 | -0.226202356526156 | 0.078083683806646 |
| 451 | 1105814 | ::: Homo sapiens cDNA clone MGC:61554 IMAGE:6174351, complete cds | 105223 | -0.299247057499614 | 0.681904708275970 |
| 452 | 1105832 | GSDML :: gasdermin-like | 306777 | -0.030059243970236 | -0.173576690137134 |
| 453 | 1105838 | ZBTB8 :: zinc finger and BTB domain containing 8 | 129837 | 0.350149587738349 | -0.241921665436000 |
| 454 | 1105842 | KIAA1145 :: KIAA1145 protein | 173392 | 0.181381965671083 | -0.293334666502675 |
| 455 | 1105854 | FLJ14803 :: hypothetical protein FLJ14803 | 267245 | -0.289009334412393 | 0.391432538881942 |
| 456 | 1105866 | ZNF92 :: zinc finger protein 92 (HTF12) | 9521 | -0.217503504116412 | 0.242431438313012 |
| 457 | 1105900 | ::: Homo sapiens transcribed sequence with weak similarity to protein ref:NP_060312.1 (H. sapiens) hypothetical protein FLJ20489 [Homo sapiens] | 525015 | -0.039954870700039 | 0.063846335693864 |
| 458 | 1105915 | ::: Homo sapiens similar to seven transmembrane helix receptor (LOC346170), mRNA | 332649 | 0.355873471451831 | -0.549616497728459 |
| 459 | 1105935 | ::: Homo sapiens cDNA FLJ42786 fis, clone BRAWH3006761 | 444290 | -0.004908164057 7809 | 0.009313018150590 |
| 460 | 1105936 | KSR :: kinase suppressor of ras | 276238 | 0.420303241649637 | -0.508523150659365 |
| 461 | 1105959 | ::: Homo sapiens cDNA FLJ43911 fis, clone TESTI4010928 | -52 | 0.045393922873497 | -0.170316061302771 |
| 462 | 1105986 | GCET2 :: germinal center expressed transcript 2 | 49614 | -0.086493932869463 | 0.206838589089091 |
| 463 | 1106013 | DNAJC3 :: DnaJ (Hsp40) homolog, subfamily C, member 3 | 6019 | 0.151020336613047 | -0.095724381670206 |
| 464 | 1106015 | FLJ12505 :: hypothetical protein FLJ12505 | 96885 | 0.004343352514749 | -0.152871957172409 |
| 465 | 1106025 | KIAA0746 :: KIAA0746 protein | 49500 | 0.096092302067900 | 0.172477760689875 |
| 466 | 1106030 | UNQ3030 :: ELLP3030 | 162185 | -0.141195502114527 | -0.119993933340636 |
| 467 | 1106043 | FREB :: Fc receptor homolog expressed in B cells | 266331 | -0.332541268340366 | 0.343043552564271 |
| 468 | 1106053 | MYO7B :: myosin VIIB | 154578 | 0.0207011177641 10 | -0.030706574277501 |
| 469 | 1106088 | ::: Homo sapiens, clone IMAGE:4689481, mRNA | 499235 | 0.232620601986162 | -0.237498779839844 |
| 470 | 1106110 | FOXP1 :: forkhead box P1 | 235860 | -0.337961967073500 | 0.177654717311019 |
| 471 | 1106124 | HAVCR2 :: hepatitis A virus cellular receptor 2 | 155111 | 0.433718618157491 | -0.387490674695267 |
| 472 | 1106126 | PPIB :: peptidylprolyl isomerase B (cyclophilin B) | 434937 | 0.089296594603901 | -0.151245276102718 |
| 473 | 1106159 | ::: Homo sapiens clone DNA49141 LGLL338 (UNQ338) mRNA, complete cds | 208081 | 0.175796277722861 | -0.190528520520377 |
| 474 | 1106196 | ::: Homo sapiens cDNA FLJ44273 fis, clone TOVAR2001281 | 142074 | 0.260032888023746 | -0.248582710869995 |
| 475 | 1106204 | SDP35 :: cell cycle control protein SDP35 | 445098 | -0.281476076882118 | 0.762743730546786 |
| 476 | 1106230 | FLJ90806 :: hypothetical protein FLJ90806 | 381225 | -0.344498084563556 | 0.748294017497618 |
| 477 | 1106279 | CAMK1D :: calcium/calmodulin-dependent protein kinase ID | 130065 | -0.131837900700824 | -0.026370539273523 |

TABLE 2415-continued

GeneID.txt

| Order | UNIQID | NAME | GENEID | LN.cor | Pro.cor |
|---|---|---|---|---|---|
| 478 | 1106306 | 1106306 :: : Homo sapiens transcribed sequence with weak similarity to protein pir:JC1405 (H. sapiens) JC1405 6-pyruvoyltetrahydropterin synthase - human | 14204 | 0.222510499735753 | -0.0579637846837970 |
| 479 | 1106317 | 1106317 : PRDM1 :: PR domain containing 1, with ZNF domain | 381140 | 0.202422907441878 | -0.278012993914435 |
| 480 | 1106323 | 1106323 :: : Homo sapiens transcribed sequence with moderate similarity to protein ref:NP_056011.1 (H. sapiens) KIAA0922 protein [Homo sapiens] | 442690 | -0.316314328384987 | 0.0853956546738480 |
| 481 | 1106394 | 1106394 :: : Homo sapiens transcribed sequence with moderate similarity to protein ref:NP_060265.1 (H. sapiens) hypothetical protein FLJ20378 [Homo sapiens] | 126932 | 0.0222148155014230 | -0.0372322371499130 |
| 482 | 1106401 | 1106401 : MGC15827 :: hypothetical protein MGC15827 | 11849 | -0.187511903901925 | 0.040102924392511 |
| 483 | 1106415 | 1106415 :: : Homo sapiens cDNA FLJ42409 fis, clone BLADE2000866 | 169071 | 0.211976489947730 | -0.154318192993322 |
| 484 | 1106478 | 1106478 :: : Homo sapiens transcribed sequences | 119898 | -0.094232371717217 | 0.225662520964665 |
| 485 | 1106522 | 1106522 :: : Homo sapiens transcribed sequence with moderate similarity to protein ref:NP_078621.6 (H. sapiens) | 31903 | -0.283587160786216 | 0.127680579514931 |
| 486 | 1106589 | 1106589 : MIST1 :: class II bHLH protein MIST1 | 22627 | -0.047877525130132 | -0.002404261340158 |
| 487 | 1106722 | 1106722 : FLJ14494 :: hypothetical protein FLJ14494 | 150458 | -0.060926027646147 | -0.002462635331184 |
| 488 | 1106781 | 1106781 : LTB4R :: leukotriene B4 receptor | 445013 | 0.007134788675039 | -0.190509701181572 |
| 489 | 1106855 | 1106855 : KIAA1909 :: KIAA1909 protein | 455101 | -0.112998501100632 | -0.030606809310584 |
| 490 | 1106908 | 1106908 : CDKN2B :: cyclin-dependent kinase inhibitor 2B (p15, inhibits CDK4) | 72901 | 0.338895194330555 | -0.124572811365083 |
| 491 | 1106935 | 1106935 : CTLA4 :: cytotoxic T-lymphocyte-associated protein 4 | 247824 | 0.242158855304133 | -0.478804309516501 |
| 492 | 1106990 | 1106990 :: : Homo sapiens transcribed sequences | 369561 | 0.325855303432119 | -0.572765753817467 |
| 493 | 1107044 | 1107044 :: : Homo sapiens transcribed sequences | 163426 | -0.248956419132601 | -0.074083786735442 |
| 494 | 1107076 | 1107076 : BCL2L10 :: BCL2-like 10 (apoptosis facilitator) | 283672 | -0.174263409358457 | 0.142807702201562 |
| 495 | 1107124 | 1107124 :: : Homo sapiens transcribed sequences | 130203 | 0.032157877924701 | -0.055754120038729 |
| 496 | 1107190 | 1107190 : MGC10986 :: hypothetical protein MGC10986 | 50601 | -0.227953163675436 | 0.145694856605193 |
| 497 | 1107197 | 1107197 :: : Homo sapiens transcribed sequence with strong similarity to protein pir:A48045 (H. sapiens) A48045 ribosomal protein S27, cytosolic - human | 40838 | 0.001673335706470 | -0.094560326284670 |
| 498 | 1107329 | 1107329 : LHFPL3 :: lipoma HMGIC fusion partner-like 3 | 439124 | 0.049485671639358 | 0.016357240588240 |
| 499 | 1107348 | 1107348 : SAMD3 :: sterile alpha motif domain containing 3 | 440508 | 0.383635070918944 | -0.539687643012946 |
| 500 | 1107369 | 1107369 :: : Homo sapiens transcribed sequence similar to kinase, Germline helicase-Binding, mitogen/stress activated protein kinase, c-jun N-terminal kinase (kgb-2) (LOC375783), mRNA | 512466 | -0.113783226530150 | 0.145555603342058 |
| 501 | 1107457 | 1107457 : ADAMTS2 :: a disintegrin-like and metalloprotease (reprolysin type) with thrombospondin type 1 motif, 2 | 120330 | 0.311369108148620 | -0.287615459819004 |
| 502 | 1107527 | 1107527 :: : Homo sapiens clone DNA57836 GLPG464 (UNQ464) mRNA, complete cds | 14706 | 0.214235142595632 | -0.115893542930530 |
| 503 | 1107575 | 1107575 : MGC52498 :: hypothetical protein MGC52498 | 424589 | -0.256404584752245 | 0.133592577366628 |
| 504 | 1107637 | 1107637 :: : Homo sapiens transcribed sequences | 135491 | 0.216865140113354 | -0.301141146422204 |
| 505 | 1107762 | 1107762 :: : Homo sapiens transcribed sequences | 58597 | -0.026249400695137 | 0.105000264860588 |
| 506 | 1107838 | 1107838 :: : Homo sapiens cDNA FLJ45323 fis, clone BRHIP3006390 | -51 | 0.259677601688845 | -0.248521794709865 |
| 507 | 1107997 | 1107997 : IL22RA2 :: interleukin 22 receptor, alpha 2 | 126891 | 0.425997734470218 | -0.065713810429864 |
| 508 | 1108088 | 1108088 :: : Homo sapiens cDNA FLJ42957 fis, clone BRSTN2010500 | 441601 | 0.224696534704615 | -0.357079341494018 |
| 509 | 1108200 | 1108200 :: : Homo sapiens transcribed sequences | 156135 | 0.122650831349266 | -0.127800809316600 |
| 510 | 1108237 | 1108237 :: : Homo sapiens transcribed sequence with weak similarity to protein sp:P39189 (H. sapiens) ALU2_HUMAN Alu subfamily SB sequence contamination warning entry | 126232 | 0.150006719613133 | -0.176773524991788 |
| 511 | 1108323 | 1108323 :: : Homo sapiens transcribed sequence with moderate similarity to protein ref:NP_005898.1 (H. sapiens) mannosidase, alpha, class 1A, member 1; Man9-mannosidase [Homo sapiens] | 520353 | -0.056559071242791 | -0.017831032028604 |
| 512 | 1108347 | 1108347 :: : Homo sapiens transcribed sequences | 121476 | 0.042929515389297 | 0.180791027467577 |
| 513 | 1108467 | 1108467 : LOC285016 :: hypothetical protein LOC285016 | 346333 | 0.077616196801139 | -0.053502666868708 |
| 514 | 1108473 | 1108473 : FLJ34389 :: hypothetical protein FLJ34389 | 119878 | 0.154316813062797 | -0.310176893404700 |
| 515 | 1108515 | 1108515 : LCN6 :: lipocalin 6 | 98132 | -0.052695347232417 | -0.116970698134434 |
| 516 | 1108745 | 1108745 : TEAD2 :: TEA domain family member 2 | 166556 | -0.076084681856776 | 0.034540377111740 |
| 517 | 1108776 | 1108776 :: : Homo sapiens cDNA FLJ30967 fis, clone HEART2000309, weakly similar to PTB-ASSOCIATED SPLICING FACTOR. | 513346 | 0.008924647334006 | -0.176389651304266 |

TABLE 2415-continued

GeneID.txt

| Order | UNIQID | NAME | GENEID | LN.cor | Pro.cor |
|---|---|---|---|---|---|
| 518 | 1108910 | 1108910 :: : *Homo sapiens* transcribed sequence with strong similarity to protein ref:NP_542398.1 (*H. sapiens*) hypothetical protein MGC15407 [*Homo sapiens*] | 351848 | 0.0985039997378582 | -0.1073409320535734 |
| 519 | 1108925 | 1108925 : KIAA0853 :: KIAA0853 | 136102 | -0.0673776064440520 | -0.0826185340020208 |
| 520 | 1108961 | 1108961 : FLJ22531 :: hypothetical protein FLJ22531 | 292088 | -0.420239196092467 | 0.357243765247241 |
| 521 | 1108970 | 1108970 :: : *Homo sapiens* cDNA FLJ25559 fis, clone JTH02834 | 140489 | -0.190988477846490 | -0.0891991668039974 |
| 522 | 1108988 | 1108988 : NLK :: nemo-like kinase | 3532 | -0.0306087932535581 | 0.0898825979479955 |
| 523 | 1109058 | 1109058 : FLJ38499 :: hypothetical protein FLJ38499 | 220277 | -0.0893353382777617 | -0.0656101669727742 |
| 524 | 1109107 | 1109107 : FLJ10392 :: hypothetical protein FLJ10392 | 292925 | -0.222666311239519 | 0.361324446901530 |
| 525 | 1109188 | 1109188 : TNFRSF11A :: tumor necrosis factor receptor superfamily, member 11a, activator of NFKB | 204044 | 0.280812113971682 | -0.0793692882513375 |
| 526 | 1109195 | 1109195 :: : *Homo sapiens* cDNA FLJ41734 fis, clone HLUNG2018029 | 416155 | -0.397342842842403 | 0.280143126653589 |
| 527 | 1109210 | 1109210 : KCNK9 :: potassium channel, subfamily K, member 9 | 117010 | -0.0172811359417599 | -0.0836902164306066 |
| 528 | 1109220 | 1109220 : GTF3A :: general transcription factor IIIA | 445977 | -0.429250063896662 | 0.332595945727056 |
| 529 | 1109505 | 1109505 : MGC39372 :: hypothetical protein MGC39372 | 8162 | 0.0753578071054008 | -0.258062753389713 |
| 530 | 1109519 | 1109519 : ALS2CR7 :: amyotrophic lateral sclerosis 2 (juvenile) chromosome region, candidate 7 | 348711 | 0.119836847940248 | -0.0192897862388779 |
| 531 | 1109530 | 1109530 :: : *Homo sapiens* cDNA FLJ25865 fis, clone HEP22218 | 123244 | -0.393536865160815 | 0.464747328088123 |
| 532 | 1109545 | 1109545 :: : *Homo sapiens* cDNA FLJ41910 fis, clone PEBLM2007834 | 63187 | -0.397583692461428 | 0.257403431395117 |
| 533 | 1109557 | 1109557 : NP220 :: NP220 nuclear protein | 444548 | -0.135367039008095 | -0.0874330862578800 |
| 534 | 1109560 | 1109560 : FARP1 :: FERM, RhoGEF (ARHGEF) and pleckstrin domain protein 1 (chondrocyte-derived) | 207428 | 0.0333367430292972 | -0.0860750021059008 |
| 535 | 1109603 | 1109603 :: : *Homo sapiens* transcribed sequences | 317740 | -0.351537059310986 | 0.129233831238711 |
| 536 | 1109732 | 1109732 :: : *Homo sapiens* transcribed sequences | 374124 | 0.300165387297213 | -0.442390304962831 |
| 537 | 1109756 | 1109756 : FNBP1 :: formin binding protein 1 | 191534 | 0.0613729363443499 | -0.209804169980805 |
| 538 | 1109827 | 1109827 : GPR155 :: G protein-coupled receptor 154 | 127196 | 0.242983476822492 | -0.418280288872407 |
| 539 | 1109913 | 1109913 : CFLAR :: CASP8 and FADD-like apoptosis regulator | 355724 | 0.207532726896619 | -0.403624127184567 |
| 540 | 1110019 | 1110019 :: : *Homo sapiens* transcribed sequences | 31444 | 0.360190305256616 | -0.350732887975507 |
| 541 | 1110070 | 1110070 :: : *Homo sapiens* transcribed sequences | 122464 | 0.271451755158904 | -0.436226619954694 |
| 542 | 1110099 | 1110099 : TA-KRP :: T-cell activation kelch repeat protein | 116665 | -0.445325720625770 | 0.477608651819287 |
| 543 | 1110198 | 1110198 :: : *Homo sapiens* transcribed sequences | 189046 | -0.298393216431026 | 0.206436758539511 |
| 544 | 1110214 | 1110214 : TCL6 :: T-cell leukemia/lymphoma 6 | 144519 | -0.228315826191486 | 0.241502528970347 |
| 545 | 1110223 | 1110223 :: : *Homo sapiens* transcribed sequence with moderate similarity to protein ref:NP_060265.1 (*H. sapiens*) hypothetical protein FLJ20378 [*Homo sapiens*] | 212709 | -0.430615107958902 | 0.454780099210 |
| 546 | 1110284 | 1110284 : ELL2 :: elongation factor, RNA polymerase II, 2 | 192221 | 0.191540984442880 | -0.196150763055 |
| 547 | 1110309 | 1110309 :: : *Homo sapiens* transcribed sequences | 105623 | -0.215474752721580 | 0.156976932842674 |
| 548 | 1110313 | 1110313 : FLJ39873 :: hypothetical protein FLJ39873 | 421750 | 0.0697027156008045 | -0.402411470521682 |
| 549 | 1110486 | 1110486 :: : *Homo sapiens* transcribed sequences | 445054 | 0.041319461801742 | -0.116877614471182 |
| 550 | 1110608 | 1110608 : CARD14 :: caspase recruitment domain family, member 14 | 306227 | 0.331483074884149 | -0.441101824343302 |
| 551 | 1110610 | 1110610 :: : *Homo sapiens* transcribed sequences | 436906 | 0.0280134464240267 | -0.137363692502881 |
| 552 | 1110740 | 1110740 :: : *Homo sapiens* transcribed sequences | 416810 | -0.195991680240688 | 0.00783501313426 |
| 553 | 1110852 | 1110852 :: : *Homo sapiens* cDNA FLJ44885 fis, clone BRAMY2039630 | 196026 | 0.195262191447797 | -0.125057253667954 |
| 554 | 1110871 | 1110871 :: : *Homo sapiens* transcribed sequences | 431753 | 0.138463783532811 | -0.121105247114496 |
| 555 | 1111070 | 1111070 :: : *Homo sapiens* transcribed sequence with moderate similarity to protein sp:P39192 (*H. sapiens*) ALU5_HUMAN Alu subfamily SC sequence contamination warning entry | 202201 | -0.0501104773443771 | -0.0342536921388 |
| 556 | 1111478 | 1111478 : ERK8 :: extracellular signal-regulated kinase 8 | 133017 | -0.120958587697857 | -0.0226372059030 |
| 557 | 1111486 | 1111486 :: : *Homo sapiens* cDNA FLJ42259 fis, clone TKIDN2011289 | 33024 | 0.187010000009634 | -0.440447209346948 |
| 558 | 1111494 | 1111494 : IMPDH2 :: IMP (inosine monophosphate) dehydrogenase 2 | 75432 | -0.153973066560439 | 0.069778054724996 |
| 559 | 1111503 | 1111503 : KBRAS2 :: I-kappa-B-interacting Ras-like protein 2 | 502910 | -0.291172996398988 | 0.201225423261566 |
| 560 | 1111694 | 1111694 :: : *Homo sapiens* transcribed sequences | 157302 | 0.134965621816156 | -0.0647330173596334 |
| 561 | 1111807 | 1111807 : OFD1 :: oral-facial-digital syndrome 1 | 6483 | 0.150829248997032 | -0.253651952300585 |
| 562 | 1111946 | 1111946 :: : *Homo sapiens* transcribed sequences | 280881 | -0.159928571994911 | -0.162813334629172 |
| 563 | 1112019 | 1112019 :: : *Homo sapiens* hypothetical LOC148280 (LOC148280), mRNA | 196484 | 0.0718778899993013 | -0.0488272898542663 |

TABLE 2415-continued

GeneID.txt

| Order | UNIQID | NAME | | GENEID | LN.cor | Pro.cor |
|---|---|---|---|---|---|---|
| 564 | 1112052 | 1112052 | ::: Homo sapiens cDNA FLJ31445 fis, clone NT2NE2000864. | 525361 | −0.072202440840592 | 0.020806399380158 |
| 565 | 1112061 | 1112061 | ::: Homo sapiens cDNA FLJ90513 fis, clone NT2RP3004355. | 43410 | 0.261039034660754 | −0.299416343840340 |
| 566 | 1112256 | 1112256 | ::: ING3 :: inhibitor of growth family, member 3 | 143198 | −0.125562046082355 | 0.143701534203396 |
| 567 | 1112344 | 1112344 | ::: Homo sapiens transcribed sequences | 163242 | −0.146713182348301 | 0.093803692880128 |
| 568 | 1112510 | 1112510 | ::: C14orf20 :: chromosome 14 open reading frame 20 | 314432 | 0.104763882180010 | −0.081623532083441 |
| 569 | 1112521 | 1112521 | ::: Homo sapiens transcribed sequence with weak similarity to protein ref:NP_009032.1 (H. sapiens) sarcosine dehydrogenase; dimethylglycine dehydrogenase-like 1 [Homo sapiens] | 244818 | 0.186313001167652 | −0.195394559688516 |
| 570 | 1112552 | 1112552 | ::: Homo sapiens transcribed sequences | 89029 | 0.113342903534869 | −0.150103125377604 |
| 571 | 1112674 | 1112674 | ::: MAML3 :: mastermind-like 3 (Drosophila) | 310320 | 0.342597737627672 | −0.164070058630283 |
| 572 | 1112689 | 1112689 | ::: SERPINB9 :: serine (or cysteine) proteinase inhibitor, clade B (ovalbumin), member 9 | 104879 | 0.143780170116893 | −0.201560350725374 |
| 573 | 1112762 | 1112762 | ::: Homo sapiens mRNA; cDNA DKFZp686G24244 (from clone DKFZp686G24244) | 208179 | 0.150233483486388 | −0.257400669644479 |
| 574 | 1112764 | 1112764 | ::: IFNGR1 :: interferon gamma receptor 1 | 180866 | 0.374189546225726 | −0.308519391383641 |
| 575 | 1112837 | 1112837 | ::: NRD1 :: nardilysin (N-arginine dibasic convertase) | 4099 | −0.128292923629686 | 0.093232911170115 |
| 576 | 1112849 | 1112849 | ::: Homo sapiens cDNA FLJ30333 fis, clone BRACE2007262. | 208965 | 0.195240136859781 | −0.389576368956041 |
| 577 | 1112871 | 1112871 | ::: Homo sapiens transcribed sequences | 269493 | −0.168246902555918 | −0.116751272574924 |
| 578 | 1112935 | 1112935 | ::: NFAM1 :: NFAT activation molecule 1 | 436677 | 0.349529061115025 | −0.429878706483203 |
| 579 | 1112981 | 1112981 | ::: Homo sapiens transcribed sequences | 86650 | −0.347953389898022 | 0.075874931243046 |
| 580 | 1113020 | 1113020 | ::: LOC161577 :: LOC161577 protein | 373484 | 0.135613302187717 | 0.036736840045959 |
| 581 | 1113263 | 1113263 | ::: Homo sapiens cDNA FLJ46553 fis, clone THYMU2000155 | 435736 | −0.148749974226581 | 0.101621280353679 |
| 582 | 1113435 | 1113435 | ::: Homo sapiens cDNA FLJ36210 fis, clone THYMU2000155 | 100636 | 0.034825029929201 | −0.041626982844820 |
| 583 | 1113488 | 1113488 | ::: Homo sapiens cDNA FLJ36210 fis, Similar to Eph receptor A7, clone IMAGE:5273054, mRNA | 129435 | 0.009080742764582 | 0.044989964972229 |
| 584 | 1113500 | 1113500 | ::: Homo sapiens cDNA FLJ37931 fis, clone CTONG2004397. | 165900 | 0.272078126902990 | −0.472804242511080 |
| 585 | 1113545 | 1113545 | ::: Homo sapiens cDNA FLJ46553 fis, clone THYMU3038879 | 435736 | −0.008456873734778 | 0.007667610676891 |
| 586 | 1113555 | 1113555 | ::: Homo sapiens transcribed sequences | 291993 | −0.139176879567708 | −0.125987425138451 |
| 587 | 1113589 | 1113589 | ::: BRAF :: v-raf murine sarcoma viral oncogene homolog B1 | 162967 | −0.121772287050279 | 0.253077019731888 |
| 588 | 1113730 | 1113730 | ::: Homo sapiens transcribed sequences | 293771 | 0.114063697377525 | −0.237457649248006 |
| 589 | 1113769 | 1113769 | ::: Homo sapiens transcribed sequences | 46996 | −0.393658244074914 | 0.080473352209481 |
| 590 | 1113783 | 1113783 | ::: FLJ14431 :: hypothetical protein FLJ14431 | 512793 | −0.222799826904987 | 0.358817889836136 |
| 591 | 1113930 | 1113930 | ::: MGC35521 :: pellino 3 alpha | 24725 | −0.055846303583161 | 0.210050604378661 |
| 592 | 1113972 | 1113972 | ::: IL28RA :: interleukin 28 receptor, alpha (interferon, lambda receptor) | 386334 | −0.185314697287965 | 0.230148638275733 |
| 593 | 1113993 | 1113993 | ::: Homo sapiens transcribed sequence with moderate similarity to protein ref:NP_060265.1 (H. sapiens) hypothetical protein FLJ20378 [Homo sapiens] | 131811 | 0.173371210700442 | −0.239300750059210 |
| 594 | 1114017 | 1114017 | ::: Homo sapiens transcribed sequences | 133255 | 0.308724526786620 | −0.310188543930668 |
| 595 | 1114064 | 1114064 | ::: MYO3A :: myosin IIIA | 148228 | −0.300520026473458 | 0.088707148385397 |
| 596 | 1114109 | 1114109 | ::: DCAL1 :: dendritic cell-associated lectin-1 | 203041 | −0.191231948777420 | 0.183023497372357 |
| 597 | 1114162 | 1114162 | ::: PER1 :: period homolog 1 (Drosophila) | 435736 | 0.258730255563098 | −0.182285726467478 |
| 598 | 1114351 | 1114351 | ::: Homo sapiens cDNA FLJ36210 fis, Similar to Eph receptor A7, clone IMAGE:5273054, mRNA | 514664 | 0.065700609177559 | −0.158512640752179 |
| 599 | 1114503 | 1114503 | ::: Homo sapiens transcribed sequences | 170577 | −0.049779313136241 | −0.022799815868667 |
| 600 | 1114543 | 1114543 | ::: Homo sapiens transcribed sequences | 156189 | 0.089727575328993 | 0.087415478817855 |
| 601 | 1114679 | 1114679 | ::: FLJ10904 :: hypothetical protein FLJ10904 | 16470 | −0.313418247196259 | 0.568840722644661 |
| 602 | 1114715 | 1114715 | ::: PRKCN :: protein kinase C, nu | 434387 | −0.130103404630746 | 0.271352489418930 |
| 603 | 1114726 | 1114726 | ::: NLK :: nemo-like kinase | 3532 | −0.003199898057120 | 0.151365556219048 |
| 604 | 1114766 | 1114766 | ::: RCL1 :: RNA terminal phosphate cyclase-like 1 | 113052 | −0.087555464003998 | 0.217546838114269 |
| 605 | 1114824 | 1114824 | ::: LIMD1 :: LIM domains containing 1 | 193370 | −0.148463864832943 | −0.033916294109501 |
| 606 | 1114853 | 1114853 | ::: ARHF :: ras homolog gene family, member F (in filopodia) | 512618 | 0.016180684058318 | 0.014510688794040 |
| 607 | 1114877 | 1114877 | ::: AK5 :: adenylate kinase 5 | 18268 | 0.232192378472237 | −0.050181060405945 |
| 608 | 1114893 | 1114893 | ::: BCL11A :: B-cell CLL/lymphoma 11A (zinc finger protein) | 314623 | −0.285216070613527 | 0.316813819176734 |
| 609 | 1114913 | 1114913 | ::: KIAA0748 :: KIAA0748 gene product | 33187 | −0.210416126426711 | −0.027114426717208 |
| 610 | 1114967 | 1114967 | ::: SNX9 :: sorting nexin 9 | 7905 | 0.297577356714608 | −0.280214852748554 |

TABLE 2415-continued

| Order | UNIQID | NAME | GeneID.txt | GENEID | LN.cor | Pro.cor |
|---|---|---|---|---|---|---|
| 611 | 1114970 | 1114970 : PX19 :: px19-like protein | | 279529 | -0.259954140140926 | 0.398931866897413 |
| 612 | 1114977 | 1114977 : HSPC182 :: HSPC182 protein | | 30026 | -0.0260936930557321 | 0.0466190409116212 |
| 613 | 1114981 | 1114981 : XPO5 :: exportin 5 | | 203206 | -0.414069207073602 | 0.452995936587216 |
| 614 | 1114988 | 1114988 : IBA2 :: ionized calcium binding adapter molecule 2 | | 4944 | 0.122190372505081 | -0.254155885467689 |
| 615 | 1115008 | 1115008 : USP47 :: ubiquitin specific protease 47 | | 441028 | 0.0610084969555961 | -0.051004028186604 |
| 616 | 1115012 | 1115012 : SFRP2 :: secreted frizzled-related protein 2 | | 31386 | 0.562213196556748 | -0.283291904250779 |
| 617 | 1115034 | 1115034 : NEK6 :: NIMA (never in mitosis gene a)-related kinase 6 | | 387222 | 0.387672292810071 | -0.139523546421676 |
| 618 | 1115052 | 1115052 : MLL5 :: myeloid/lymphoid or mixed-lineage leukemia 5 (trithorax homolog, Drosophila) | | 380021 | 0.0397589974918423 | -0.107953085916089 |
| 619 | 1115071 | 1115071 : MAIL :: molecule possessing ankyrin repeats induced by lipopolysaccharide (MAIL), homolog of mouse | | 390476 | -0.110817987747237 | -0.026034205682165 |
| 620 | 1115073 | 1115073 : BAL :: B aggressive lymphoma gene | | 131315 | 0.175136379072991 | -0.372997453296061 |
| 621 | 1115128 | 1115128 : BOK :: BCL2-related ovarian killer | | 293753 | 0.453574167307278 | -0.255947563977460 |
| 622 | 1115160 | 1115160 : LYAR :: hypothetical protein FLJ20425 | | 425427 | -0.406888533093173 | 0.586797819139025 |
| 623 | 1115176 | 1115176 : CKLF :: chemokine-like factor | | 15159 | 0.192788341170135 | 0.046619194874123 |
| 624 | 1115186 | 1115186 : MRPL47 :: mitochondrial ribosomal protein L47 | | 283734 | -0.420230779755538 | 0.571199396674772 |
| 625 | 1115194 | 1115194 : TNFSF13B :: tumor necrosis factor (ligand) superfamily, member 13b | | 270737 | 0.475174704917625 | -0.577483430130737 |
| 626 | 1115203 | 1115203 : RPS6KL1 :: ribosomal protein S6 kinase-like 1 | | 414481 | 0.0153906978060882 | 0.003703623518892 |
| 627 | 1115226 | 1115226 : KIAA1683 :: KIAA1683 protein | | 279718 | -0.00625573744234 | -0.282909576455325 |
| 628 | 1115253 | 1115253 : BCL2L13 :: BCL2-like 13 (apoptosis facilitator) | | 310922 | -0.183634412043605 | 0.327528714656041 |
| 629 | 1115271 | 1115271 : DKFZp761C169:: vasculin | | 71252 | -0.368758470490713 | 0.067050568022970 |
| 630 | 1115286 | 1115286 : TLR10 :: toll-like receptor 10 | | 120551 | -0.259024464746980 | 0.325663372291740 |
| 631 | 1115290 | 1115290 : GSG2 :: haspin | | 193666 | -0.482306139325171 | 0.619212145708754 |
| 632 | 1115303 | 1115303 : LOC51244 :: hypothetical protein LOC51244 | | 236257 | -0.249657257281461 | 0.132172351643750 |
| 633 | 1115309 | 1115309 : DKFZP434F091 :: DKFZP434F091 protein | | 443081 | -0.240319754851193 | 0.324212477679077 |
| 634 | 1115329 | 1115329 : MGC4796 :: Ser/Thr-like factor | | 439658 | 0.0402081988815129 | -0.018704127839472 |
| 635 | 1115338 | 1115338 : STK31 :: serine/threonine kinase 31 | | 224355 | -0.053536185139454 | -0.107899047198573 |
| 636 | 1115347 | 1115347 : HDAC8 :: histone deacetylase 8 | | 112272 | -0.028339713769977 | 0.390069214505358 |
| 637 | 1115360 | 1115360 : PRO1073 :: PRO1073 protein | | 187199 | 0.0151505780049290 | -0.241074918363573 |
| 638 | 1115441 | 1115441 : IL17RB :: interleukin 17 receptor B | | 5470 | -0.063434193422993 | -0.014102884858889 |
| 639 | 1115519 | 1115519 : MRPS36 :: mitochondrial ribosomal protein S36 | | 408914 | -0.297069852346310 | 0.396251982430131 |
| 640 | 1115566 | 1115566 : SP329 :: hypothetical protein SP329 | | -5 | -0.118697538219683 | -0.0121106218542799 |
| 641 | 1115587 | 1115587 : IRTA1 :: immunoglobulin superfamily receptor translocation associated 1 | | 120260 | -0.0525959866362335 | 0.142155752703307 |
| 642 | 1115589 | 1115589 : IRTA2 :: immunoglobulin superfamily receptor translocation associated 2 | | 415950 | -0.265745174495947 | 0.086115378248171 |
| 643 | 1115591 | 1115591 : SSTK :: serine/threonine protein kinase SSTK | | 367871 | -0.128216622193601 | 0.059300320623737 |
| 644 | 1115607 | 1115607 : CDCA7 :: cell division cycle associated 7 | | 435733 | -0.262295427951373 | 0.573434589773844 |
| 645 | 1115621 | 1115621 : RIOK1 :: RIO kinase 1 (yeast) | | 437474 | -0.229738976454067 | 0.447251600358189 |
| 646 | 1115646 | 1115646 : HECTD1 :: HECT domain containing 1 | | 210850 | -0.167037011541555 | 0.128780114293504 |
| 647 | 1115668 | 1115668 : RTN4IP1 :: reticulon 4 interacting protein 1 | | 155839 | -0.320652767737175 | 0.306593126968738 |
| 648 | 1115673 | 1115673 : IL17RC :: interleukin 17 receptor C | | 129959 | 0.311147392581012 | -0.307737524325344 |
| 649 | 1115679 | 1115679 : MGC4308 :: hypothetical protein MGC4308 | | 8345 | -0.482150529158383 | 0.656200427232135 |
| 650 | 1115695 | 1115695 : TNFRSF18 :: tumor necrosis factor receptor superfamily, member 18 | | 212680 | 0.126824051069217 | -0.342995167264104 |
| 651 | 1115696 | 1115696 : IL1F7 :: interleukin 1 family, member 7 (zeta) | | 166371 | 0.135412621405814 | -0.163355627129065 |
| 652 | 1115704 | 1115704 : IRF2BP2 :: interferon regulatory factor 2 binding protein 2 | | 350268 | 0.258469364814320 | -0.344047490615961 |
| 653 | 1115763 | 1115763 : GPT2 :: glutamic pyruvate transaminase (alanine aminotransferase) 2 | | 355862 | -0.262333353369976 | 0.306381008609851 |
| 654 | 1115800 | 1115800 : RPE :: ribulose-5-phosphate-3-epimerase | | 282260 | -0.0403656293632253 | 0.244729456838177 |
| 655 | 1115812 | 1115812 : EIF2AK4 :: eukaryotic translation initiation factor 2 alpha kinase 4 | | 412102 | 0.0455885109624448 | -0.074238327120572 |
| 656 | 1115813 | 1115813 : CTL2 :: CTL2 gene | | 105509 | -0.221292272952100 | -0.028168066606459 |
| 657 | 1115829 | 1115829 : FLJ12760 :: hypothetical protein FLJ12760 | | 381204 | -0.369293215780449 | 0.627808556684385 |
| 658 | 1115840 | 1115840 : KIAA1728 :: KIAA1728 protein | | 437362 | 0.589217883938435 | -0.416684777312541 |
| 659 | 1115876 | 1115876 : TIMM23 :: translocase of inner mitochondrial membrane 23 homolog (yeast) | | 11866 | -0.381689052923779 | 0.668903617669604 |

TABLE 2415-continued

GeneID.txt

| Order | UNIQID | NAME | GENEID | LN.cor | Pro.cor |
|---|---|---|---|---|---|
| 660 | 1115877 | 1115877 : AKIP :: aurora-A kinase interacting protein | 76239 | −0.207980996336103 | 0.344080166383221 |
| 661 | 1115888 | 1115888 : ZBTB4 :: zinc finger and BTB domain containing 4 | 35096 | 0.298080578428648 | −0.657393520135917 |
| 662 | 1115892 | 1115892 : STK35 :: serine/threonine kinase 35 | 100057 | 0.153696425328605 | −0.057444650366930 |
| 663 | 1115895 | 1115895 : RPC8 :: RNA polymerase III subunit RPC8 | 202505 | −0.354708569266870 | 0.493832792496113 |
| 664 | 1115905 | 1115905 : CLMN :: calmin (calponin-like, transmembrane) | 301478 | 0.091056873434158 | −0.184176927851473 |
| 665 | 1115916 | 1115916 : MGC13204 :: hypothetical protein MGC13204 | 157148 | −0.291511838717354 | 0.401615662719805 |
| 666 | 1115917 | 1115917 : C6orf83 :: chromosome 6 open reading frame 83 | 284265 | 0.270658416402021 | −0.224326090174219 |
| 667 | 1115953 | 1115953 : ZNF385 :: zinc finger protein 385 | 278422 | 0.309580141662476 | −0.371867309369219 |
| 668 | 1115955 | 1115955 : FLJ31434 :: hypothetical protein FLJ31434 | 7988 | −0.153394088626576 | 0.245407623813638 |
| 669 | 1115960 | 1115960 : FRAS1 :: Fraser syndrome 1 | 15420 | 0.273562188785241 | −0.206947496325428 |
| 670 | 1115965 | 1115965 : STK36 :: serine/threonine kinase 36 (fused homolog, Drosophila) | 26996 | 0.076460376343936 | −0.120715477463443 |
| 671 | 1116001 | 1116001 : SON :: SON DNA binding protein | 430541 | −0.038000317919225 | −0.084548879882143 |
| 672 | 1116006 | 1116006 : PTBP1 :: polypyrimidine tract binding protein 1 | 172550 | −0.116461984704372 | 0.168668607063908 |
| 673 | 1116022 | 1116022 : p30 :: nuclear protein p30 | 433422 | −0.040984109576481 | 0.089035758253502 |
| 674 | 1116045 | 1116045 : HEYL :: hairy/enhancer-of-split related with YRPW motif-like | 23823 | 0.298715739339798 | −0.119650323859985 |
| 675 | 1116056 | 1116056 : SOX8 :: SRY (sex determining region Y)-box 8 | 243678 | 0.060190043795450 | −0.181079858440255 |
| 676 | 1116063 | 1116063 : RALBP1 :: ralA binding protein 1 | 75447 | −0.325857678019344 | 0.201375045992707 |
| 677 | 1116071 | 1116071 :: Homo sapiens mRNA; cDNA DKFZp586O031 (from clone DKFZp586O031) | 502564 | 0.326268800212765 | −0.248774088631798 |
| 678 | 1116073 | 1116073 : MGC2408 :: hypothetical protein MGC2408 | 146161 | −0.367109495613606 | 0.473612748294460 |
| 679 | 1116085 | 1116085 : BACH2 :: BTB and CNC homology 1, basic leucine zipper transcription factor 2 | 88414 | −0.246093347541336 | 0.093569752151740 |
| 680 | 1116103 | 1116103 : LTBP3 :: latent transforming growth factor beta binding protein 3 | 289019 | 0.343929273132371 | −0.369780572465803 |
| 681 | 1116122 | 1116122 : DKFZp76lO0113 :: hypothetical protein DKFZp76lO0113 | 42768 | −0.426616095442673 | 0.454893774014263 |
| 682 | 1116126 | 1116126 : INSR :: insulin receptor | 438669 | 0.454454940830311 | −0.265298709888399 |
| 683 | 1116150 | 1116150 : AMSH-LP :: associated molecule with the SH3 domain of STAM (AMSH) like protein | 16229 | −0.266185991205955 | 0.083378166105849 |
| 684 | 1116181 | 1116181 : TAF15 :: TAF15 RNA polymerase II, TATA box binding protein (TBP)-associated factor, 68 kDa | 402752 | −0.062544122751392 | 0.006142039132744 |
| 685 | 1116219 | 1116219 : NAP1L :: napsin B pseudogene | 322854 | −0.189162359230305 | 0.087037800792380 |
| 686 | 1116233 | 1116233 : PAPPA :: pregnancy-associated plasma protein A | 455350 | 0.251466587847966 | −0.234146528669534 |
| 687 | 1116277 | 1116277 : C10orf33 :: chromosome 10 open reading frame 33 | 118210 | 0.094135935217953 | −0.201399654874422 |
| 688 | 1116317 | 1116317 :: Homo sapiens cDNA clone IMAGE:4821863, partial cds | 440776 | −0.349847858207637 | 0.196451295358354 |
| 689 | 1116432 | 1116432 : KIAA1259 :: hypothetical protein KIAA1259 | 525807 | −0.153668990852911 | −0.021062212586290 |
| 690 | 1116445 | 1116445 : C6.1A :: c6.1A | 301927 | −0.091951874829546 | 0.311204877401937 |
| 691 | 1116593 | 1116593 : NUDT6 :: nudix (nucleoside diphosphate linked moiety X)-type motif 6 | 422889 | −0.159193962550566 | 0.195466499750992 |
| 692 | 1116666 | 1116666 : DKFZp564B1162 :: hypothetical protein DKFZp564B1162 | 442801 | −0.383182496994710 | 0.271520439423627 |
| 693 | 1116676 | 1116676 : MSI2 :: musashi homolog 2 (Drosophila) | 185084 | −0.282699630935485 | 0.106190364019197 |
| 694 | 1116715 | 1116715 : FLJ20574 :: hypothetical protein FLJ20574 | 123427 | −0.193791635217953 | 0.316655728293102 |
| 695 | 1116826 | 1116826 : KIAA1295 :: KIAA1295 protein | 26204 | 0.721314629392213 | −0.377963323366939 |
| 696 | 1116829 | 1116829 :: Homo sapiens cDNA clone LOC90624 :: hypothetical protein LOC90624 | 115467 | −0.335027077607960 | 0.336788815470870 |
| 697 | 1116844 | 1116844 : CSNK1G1 :: casein kinase 1, gamma 1 | 405789 | −0.058317444499632 | 0.048781994752368 |
| 698 | 1116854 | 1116854 :: Homo sapiens cDNA FLJ14309 fis, clone PLACE3000221. | 438623 | −0.043460166463994 | −0.054723733397946 |
| 699 | 1116863 | 1116863 : TLR4 :: toll-like receptor 4 | 174312 | 0.475472754697384 | −0.300348466739063 |
| 700 | 1116879 | 1116879 : TNIP2 :: TNFAIP3 interacting protein 2 | 325630 | 0.312285624448172 | −0.214671720019409 |
| 701 | 1116958 | 1116958 : PBF :: papillomavirus regulatory factor PRF-1 | 27410 | −0.229333149413005 | 0.297027698820665 |
| 702 | 1116966 | 1116966 :: Homo sapiens cDNA FLJ11681 fis, clone HEMBA1004865. | 301124 | 0.430855116758033 | −0.468612200509693 |
| 703 | 1117023 | 1117023 : BCL2L12 :: BCL2-like 12 (proline rich) | 289052 | −0.470242230711918 | 0.673594400951872 |
| 704 | 1117211 | 1117211 : HSPC195 :: hypothetical protein HSPC195 | 356509 | −0.350305805203319 | 0.246811696581929 |
| 705 | 1117245 | 1117245 : HARS2 :: histidyl-tRNA synthetase 2 | 444706 | −0.175279674549348 | 0.324254247578305 |
| 706 | 1117278 | 1117278 : ACAS2 :: acetyl-Coenzyme A synthetase 2 (ADP forming) | 14779 | 0.360381976214154 | −0.450784610189096 |
| 707 | 1117298 | 1117298 :: Homo sapiens clone H3 anti-mucin1 light chain variable region mRNA, partial cds | 449586 | 0.190383103967389 | −0.163732239822681 |
| 708 | 1117343 | 1117343 : BUCS1 :: butyryl Coenzyme A synthetase 1 | 306812 | 0.002627195859024 | −0.128596603481639 |

TABLE 2415-continued

| Order | UNIQID | NAME | GeneID.txt | | | |
|---|---|---|---|---|---|---|
| | | | GENEID | LN.cor | Pro.cor | |
| 709 | 1117350 | 1117350 :: FLJ10407 :: hypothetical protein FLJ10407 | 435982 | -0.321428599824394 | 0.748139228339341 | |
| 710 | 1117373 | 1117373 :: SEMA4B :: sema domain, immunoglobulin domain (Ig), transmembrane domain (TM) and short cytoplasmic domain, (semaphorin) 4B | 416077 | 0.0700542664582924 | -0.127801110560990 | |
| 711 | 1117394 | 1117394 :: :: immunoglobulin heavy chain V region | -37 | 0.0773188813S8942 | 0.0373758169003229 | |
| 712 | 1117403 | 1117403 :: FBXO5 :: F-box only protein 5 | 272027 | -0.270275521248700 | 0.472830182511296 | |
| 713 | 1117517 | 1117517 :: Rgr :: Ral-GDS related protein Rgr | 148656 | 0.0850232722566783 | -0.339585977561694 | |
| 714 | 1117555 | 1117555 :: NOD3 :: NOD3 protein | 128357 | 0.0174135521264443 | -0.259854083944416 | |
| 715 | 1117599 | 1117599 :: MGC27085 :: hypothetical protein MGC27085 | 120277 | -0.297300511558719 | 0.294857589419262 | |
| 716 | 1117644 | 1117644 :: :: Homo sapiens transcribed sequence with moderate similarity to protein ref:NP_060312.1 (H. sapiens) hypothetical protein FLJ120489 [Homo sapiens] | 34174 | -0.0438914723767770 | -0.0461767543198 14 | |
| 717 | 1117747 | 1117747 :: :: Homo sapiens hypothetical sequence LOC256686 (LOC256686), mRNA | 158272 | -0.156604323316062 | -0.0334511064388 67 | |
| 718 | 1117800 | 1117800 :: :: Homo sapiens LOH11CR1F gene, loss of heterozygosity, 11, chromosomal region 1 gene F product | 125166 | -0.265166847772953 | -0.0356834237574 95 | |
| 719 | 1117835 | 1117835 :: CR1L :: complement component (3b/4b) receptor 1-like | 89688 | 0.276367621813185 | -0.0535572671658 412 | |
| 720 | 1117853 | 1117853 :: :: Homo sapiens transcribed sequence with strong similarity to protein pdb:1BGM (E. coli) O Chain O, Beta-Galactosidase (Chains I-P) | 268724 | -0.0981307318201 68 | -0.212694005004947 | |
| 721 | 1117977 | 1117977 :: :: Unknown | -40 | -0.0920342850157 09 | -0.0879915776811 70 | |
| 722 | 1118148 | 1118148 :: ZBP1 :: Z-DNA binding protein 1 | -2 | 0.152802746225995 | -0.384059831029427 | |
| 723 | 1118228 | 1118228 :: :: Homo sapiens hypothetical LOC339541 (LOC339541), mRNA | 173679 | -0.201134297495305 | -0.0357744964447 03 | |
| 724 | 1118286 | 1118286 :: MRC2 :: mannose receptor, C type 2 | 147381 | -0.379333390537201 | 0.451785576407 92 | |
| 725 | 1118347 | 1118347 :: ITGA4 :: integrin, alpha 4 (antigen CD49D, alpha 4 subunit of VLA-4 receptor) | 145140 | 0.0556393621714 38 | -0.253900279097663 | |
| 726 | 1118414 | 1118414 :: FCRH1 :: Fc receptor-like protein 1 | 415473 | -0.0929520848068 30 | 0.0805007785880 61 | |
| 727 | 1118573 | 1118573 :: GSK3A :: glycogen synthase kinase 3 alpha | 435970 | -0.351134088845212 | 0.325972671457629 | |
| 728 | 1118612 | 1118612 :: NPR1 :: natriuretic peptide receptor A/guanylate cyclase A (atrionatriuretic peptide receptor A) | 438864 | 0.155470872321411 | -0.159267282520294 | |
| 729 | 1118621 | 1118621 :: CGI-96 :: CGI-96 protein | 239934 | -0.292642395717393 | 0.473939710525280 | |
| 730 | 1118659 | 1118659 :: MAPK7 :: mitogen-activated protein kinase 7 | 150136 | -0.0518838630404 60 | -0.141266790241099 | |
| 731 | 1118681 | 1118681 :: MAFF :: v-maf musculoaponeurotic fibrosarcoma oncogene homolog F (avian) | 460889 | 0.647655603832 26 | -0.362054838189 99 | |
| 732 | 1118684 | 1118684 :: MIPEP :: mitochondrial intermediate peptidase | 68583 | -0.328213532979876 | 0.407014917128267 | |
| 733 | 1118708 | 1118708 :: MRC2 :: mannose receptor, C type 2 | 7835 | 0.754467580767100 | -0.424450710158145 | |
| 734 | 1118736 | 1118736 :: HIP1R :: huntingtin interacting protein-1 -related | 96731 | 0.0399747641245 92 | 0.0661307901553 51 | |
| 735 | 1118772 | 1118772 :: STK10 :: serine/threonine kinase 10 | 16134 | 0.0304026579929 8 | -0.421006503218 50 | |
| 736 | 1118835 | 1118835 :: ARHGAP8 :: Rho GTPase activating protein 8 | 102336 | 0.311235553095650 | -0.396387124788783 | |
| 737 | 1118861 | 1118861 :: PEX16 :: peroxisomal biogenesis factor 16 | 100915 | 0.0298585409701 58 | -0.0431796046517 65 | |
| 738 | 1118939 | 1118939 :: PLA2G4B :: phospholipase A2, group IVB (cytosolic) | 198161 | 0.217116959349918 | -0.409971040705761 | |
| 739 | 1118949 | 1118949 :: IAN4L1 :: immune associated nucleotide 4 like 1 (mouse) | 412331 | 0.142206792172366 | -0.512656283348152 | |
| 740 | 1118963 | 1118963 :: :: Homo sapiens cDNA FLJ42818 fis, clone BRCAN2015371 | -53 | -0.0644318050228 53 | -0.171638599308421 | |
| 741 | 1119003 | 1119003 :: EIF4G2 :: eukaryotic translation initiation factor 4 gamma, 2 | 183684 | -0.133347112654528 | 0.112848239923822 | |
| 742 | 1119007 | 1119007 :: GDI2 :: GDP dissociation inhibitor 2 | 56845 | -0.382242002371 530 | 0.470849494659261 | |
| 743 | 1119015 | 1119015 :: RPS5 :: ribosomal protein S5 | 378103 | -0.384887386329798 | 0.343492082966 66 | |
| 744 | 1119039 | 1119039 :: SMAP :: small acidic protein | 447513 | -0.301459283715944 | 0.321366636007445 | |
| 745 | 1119046 | 1119046 :: DSP :: desmoplakin | 349499 | 0.323961715872806 | -0.285977303076169 | |
| 746 | 1119056 | 1119056 :: UBB :: ubiquitin B | 356190 | 0.028334739217252 | -0.196600028796086 | |
| 747 | 1119061 | 1119061 :: MLP :: MARCKS-like protein | 75061 | 0.00350291622950 | 0.225174791526797 | |
| 748 | 1119068 | 1119068 :: S100A11 :: S100 calcium binding protein A11 (calgizzarin) | 417004 | 0.629923256421890 | -0.515428592835300 | |
| 749 | 1119070 | 1119070 :: CD63 :: CD63 antigen (melanoma 1 antigen) | 445570 | 0.600681920968223 | -0.477615687123999 | |
| 750 | 1119071 | 1119071 :: UBE2D3 :: ubiquitin-conjugating enzyme E2D 3 (UBC4/5 homolog, yeast) | 411826 | -0.159090102348063 | 0.188214633454210 | |
| 751 | 1119072 | 1119072 :: XBP1 :: X-box binding protein 1 | 437638 | -0.0730720237475 63 | 0.0719922504745 92 | |
| 752 | 1119074 | 1119074 :: CD81 :: CD81 antigen (target of antiproliferative antibody 1) | 54457 | 0.460590309714153 | -0.316306331329 744 | |
| 753 | 1119076 | 1119076 :: GLO1 :: glyoxalase I | 268849 | -0.485600996113581 | 0.560563431563 709 | |
| 754 | 1119090 | 1119090 :: FKBP1A :: FK506 binding protein 1A, 12 kDa | 374638 | -0.167154087365112 | 0.256238005345 443 | |

TABLE 2415-continued

| Order | UNIQID | GeneID.txt NAME | GENEID | LN.cor | Pro.cor |
|---|---|---|---|---|---|
| 755 | 1119111 | 1119111 : TEGT :: testis enhanced gene transcript (BAX inhibitor 1) | 35052 | 0.117050432650685 | −0.195242194439661 |
| 756 | 1119139 | 1119139 : DNAJA1 :: DnaJ (Hsp40) homolog, subfamily A, member 1 | 388392 | −0.106484916885441 | 0.145147017992332 |
| 757 | 1119155 | 1119155 : DEK :: DEK oncogene (DNA binding) | 110713 | −0.246967603602159 | 0.515244500061071 |
| 758 | 1119171 | 1119171 : ACTA2 :: actin, alpha 2, smooth muscle, aorta | 208641 | 0.761340632898360 | −0.452825423217664 |
| 759 | 1119173 | 1119173 : MDH1 :: malate dehydrogenase 1, NAD (soluble) | 75375 | −0.127094470887037 | 0.258023826328223 |
| 760 | 1119183 | 1119183 : RBM4 :: RNA binding motif protein 4 | 211203 | 0.381081618660027 | 0.396021571030955 |
| 761 | 1119186 | 1119186 : CD9 :: CD9 antigen (p24) | 387579 | 0.435342892077885 | −0.168246859132740 |
| 762 | 1119202 | 1119202 : TGM2 :: transglutaminase 2 (C polypeptide, protein-glutamine-gamma-glutamyltransferase) | 512708 | 0.571093261465677 | −0.323641083213667 |
| 763 | 1119209 | 1119209 : RCN1 :: reticulocalbin 1, EF-hand calcium binding domain | 167791 | 0.910359724823026 | −0.388503774716019 |
| 764 | 1119212 | 1119212 : MMP2 :: matrix metalloproteinase 2 (gelatinase A, 72 kDa gelatinase, 72 kDa type IV collagenase) | 367877 | 0.610412926669424 | −0.353774466993166 |
| 765 | 1119237 | 1119237 : GPNMB :: glycoprotein (transmembrane) nmb | 389964 | −0.465663098537398 | −0.312616657779815 |
| 766 | 1119239 | 1119239 : HAX1 :: HS1 binding protein | 199625 | 0.250369153999525 | 0.508445219571895 |
| 767 | 1119243 | 1119243 : ATP6V0E :: ATPase, H+ transporting, lysosomal 9 kDa, V0 subunit e | 440165 | −0.231979379939439 | −0.272868162874347 |
| 768 | 1119245 | 1119245 : FBXO7 :: F-box only protein 7 | 5912 | 0.410533826180220 | 0.094393580671121 |
| 769 | 1119251 | 1119251 : SEPW1 :: selenoprotein W, 1 | 433941 | −0.067200590610105 | −0.461863162528100 |
| 770 | 1119258 | 1119258 : HDAC1 :: histone deacetylase 1 | 88556 | −0.000745128042019 | 0.310238210060964 |
| 771 | 1119260 | 1119260 : LGMN :: legumain | 18069 | −0.476370994872774 | −0.229008754509885 |
| 772 | 1119263 | 1119263 : C12orf8 :: chromosome 12 open reading frame 8 | 511762 | 0.333491562996737 | 0.260114831651188 |
| 773 | 1119268 | 1119268 : ILK :: integrin-linked kinase | 6196 | −0.344066595023870 | −0.117810222588527 |
| 774 | 1119294 | 1119294 : TOP2A :: topoisomerase (DNA) II alpha 170 kDa | 156346 | −0.283256434250802 | 0.821915015867740 |
| 775 | 1119300 | 1119300 : STK25 :: serine/threonine kinase 25 (STE20 homolog, yeast) | 155206 | 0.258463564894777 | 0.270411211177143 |
| 776 | 1119311 | 1119311 : ENC1 :: ectodermal-neural cortex (with BTB-like domain) | 104925 | −0.014658638115010 | −0.221825498871520 |
| 777 | 1119317 | 1119317 : SLC9A3R1 :: solute carrier family 9 (sodium/hydrogen exchanger), isoform 3 regulatory factor 1 | 396783 | 0.242847106449200 | −0.191639458116196 |
| 778 | 1119325 | 1119325 : OAZ2 :: ornithine decarboxylase antizyme 2 | 74563 | 0.742369051797669 | −0.190532954990539 |
| 779 | 1119334 | 1119334 : ITGA5 :: integrin, alpha 5 (fibronectin receptor, alpha polypeptide) | 149609 | 0.608086049431527 | −0.374025974512821 |
| 780 | 1119350 | 1119350 : ALDH2 :: aldehyde dehydrogenase 2 family (mitochondrial) | 331141 | −0.026668805173817 | −0.390151454914606 |
| 781 | 1119361 | 1119361 : TIA1 :: TIA1 cytotoxic granule-associated RNA binding protein | 391858 | −0.059278973833658 | 0.189784545154414 |
| 782 | 1119365 | 1119365 : MAPKAPK2 :: mitogen-activated protein kinase-activated protein kinase 2 | 75074 | 0.460486004055358 | −0.035574775797084 |
| 783 | 1119369 | 1119369 : JUNB :: jun B proto-oncogene | 400124 | −0.116077021105342 | −0.369644781391790 |
| 784 | 1119375 | 1119375 : PPIF :: peptidylprolyl isomerase F (cyclophilin F) | 381072 | 0.627827304350395 | 0.359654077539207 |
| 785 | 1119383 | 1119383 : IGFBP4 :: insulin-like growth factor binding protein 4 | 1516 | −0.286085532090585 | −0.357001758702634 |
| 786 | 1119390 | 1119390 : CBX1 :: chromobox homolog 1 (HP1 beta homolog Drosophila) | 77254 | 0.384346199622817 | 0.535476131212779 |
| 787 | 1119400 | 1119400 : DUSP3 :: dual specificity phosphatase 3 (vaccinia virus phosphatase VH1-related) | 181046 | 0.342758824589712 | −0.392842766782088 |
| 788 | 1119401 | 1119401 : FHL1 :: four and a half LIM domains 1 | 421383 | 0.742469575699965 | −0.226789376446408 |
| 789 | 1119417 | 1119417 : FAT :: FAT tumor suppressor homolog 1 (Drosophila) | 166994 | 0.460491519833347 | −0.454543207590739 |
| 790 | 1119424 | 1119424 : OAT :: ornithine aminotransferase (gyrate atrophy) | 75485 | 0.327211434111655 | −0.147080268886920 |
| 791 | 1119438 | 1119438 : BST2 :: bone marrow stromal cell antigen 2 | 118110 | −0.025586939182056 | −0.338002355723367 |
| 792 | 1119443 | 1119443 : JAK1 :: Janus kinase 1 (a protein tyrosine kinase) | 436004 | 0.265474647684479 | 0.025836310250933 |
| 793 | 1119445 | 1119445 : KRT19 :: keratin 19 | 309517 | 0.412797513436557 | −0.137484590496784 |
| 794 | 1119448 | 1119448 : ITGA6 :: integrin, alpha 6 | 212296 | −0.219899785493274 | −0.255244929698541 |
| 795 | 1119460 | 1119460 : SFRS4 :: splicing factor, arginine/serine-rich 4 | 76122 | 0.050393679668880 | 0.375669306197949 |
| 796 | 1119462 | 1119462 : CCND3 :: cyclin D3 | 83173 | −0.410801274991122 | 0.143613724160422 |
| 797 | 1119466 | 1119466 : MYBL2 :: v-myb myeloblastosis viral oncogene homolog (avian)-like 2 | 179718 | −0.430720113786154 | 0.761986466900583 |
| 798 | 1119467 | 1119467 : TUBG1 :: tubulin, gamma 1 | 21635 | 0.458464756569231 | −0.179908409244619 |
| 799 | 1119475 | 1119475 : SGK :: serum/glucocorticoid regulated kinase | 296323 | 0.374658686322277 | −0.449833721869226 |
| 800 | 1119477 | 1119477 : CD14 :: CD14 antigen | 75627 | −0.273520348057380 | 0.189062886154923 |
| 801 | 1119479 | 1119479 : TP53 :: tumor protein p53 (Li-Fraumeni syndrome) | 426890 | −0.190082814208343 | 0.507122961206866 |
| 802 | 1119488 | 1119488 : MTHFD2 :: methylene tetrahydrofolate dehydrogenase (NAD+ dependent), methenyltetrahydrofolate cyclohydrolase | 154672 | | |

TABLE 2415-continued

GeneID.txt

| Order | UNIQID | NAME | GENEID | LN.cor | Pro.cor |
|---|---|---|---|---|---|
| 803 | 1119503 | 1119503 : POLR2B :: polymerase (RNA) II (DNA directed) polypeptide B, 140 kDa | 149353 | -0.276147772083673 | 0.452575668664126 |
| 804 | 1119510 | 1119510 : KRT5 :: keratin 5 (epidermolysis bullosa simplex, Dowling-Meara/Kobner/Weber-Cockayne types) | 433845 | 0.173908847805493 | -0.148894839466960 |
| 805 | 1119515 | 1119515 : HDAC2 :: histone deacetylase 2 | 3352 | -0.296163638102074 | 0.420133073064140 |
| 806 | 1119516 | 1119516 : PRKAB1 :: protein kinase, AMP-activated, beta 1 non-catalytic subunit | 6061 | -0.032255323397443 | 0.048963236579424 |
| 807 | 1119519 | 1119519 : BNIP3 :: BCL2/adenovirus E1B 19 kDa interacting protein 3 | 79428 | 0.070790959573082 | 0.034778072787655 |
| 808 | 1119533 | 1119533 : WDR23 :: WD repeat domain 23 | 283976 | -0.176058140462130 | 0.021248719822432 |
| 809 | 1119537 | 1119537 : ARAF1 :: v-raf murine sarcoma 3611 viral oncogene homolog 1 | 423807 | -0.080697792057249 | 0.107243029276800 |
| 810 | 1119541 | 1119541 : FARP1 :: FERM, RhoGEF (ARHGEF) and pleckstrin domain protein 1 (chondrocyte-derived) | 207428 | 0.319164983800046 | -0.239669774568353 |
| 811 | 1119546 | 1119546 : GNG10 :: guanine nucleotide binding protein (G protein), gamma 10 | 433898 | 0.366292039811560 | -0.247623946731373 |
| 812 | 1119557 | 1119557 : SNK :: serum-inducible kinase | 398157 | 0.703474357008969 | -0.369781265328559 |
| 813 | 1119559 | 1119559 : CPD :: carboxypeptidase D | 5057 | 0.477576763489383 | -0.484691652037264 |
| 814 | 1119561 | 1119561 : FURIN :: furin (paired basic amino acid cleaving enzyme) | 59242 | 0.203389107343861 | -0.194260517260963 |
| 815 | 1119564 | 1119564 : ALCAM :: activated leukocyte cell adhesion molecule | 10247 | -0.174212933203010 | -0.033522636800175 |
| 816 | 1119565 | 1119565 : CIB1 :: calcium and integrin binding 1 (calmyrin) | 135471 | 0.077380378763426 | -0.165969584136888 |
| 817 | 1119566 | 1119566 : ARPC1B :: actin related protein 2/3 complex, subunit 1B, 41 kDa | 433506 | 0.030123569365004 | -0.044674445410727 |
| 818 | 1119568 | 1119568 : PPP1R12B :: protein phosphatase 1, regulatory (inhibitor) subunit 12B | 130760 | 0.031485901809650 | -0.198501575206590 |
| 819 | 1119582 | 1119582 : SIAT1 :: sialyltransferase 1 (beta-galactoside alpha-2,6-sialyltransferase) | 2554 | -0.494168402771241 | 0.205936873075801 |
| 820 | 1119611 | 1119611 : BIRC2 :: baculoviral IAP repeat-containing 2 | 289107 | 0.153685965242011 | -0.064993693037635 |
| 821 | 1119633 | 1119633 : PRPF4B :: PRP4 pre-mRNA processing factor 4 homolog B (yeast) | 198891 | -0.349211361145953 | 0.381772530527532 |
| 822 | 1119636 | 1119636 : RIOK3 :: RIO kinase 3 (yeast) | 209061 | 0.081817545037163 | -0.207039528628000 |
| 823 | 1119639 | 1119639 : BS69 :: adenovirus 5 E1A binding protein | 145894 | 0.220729171963144 | -0.452502889918328 |
| 824 | 1119647 | 1119647 : PRKCL1 :: protein kinase C-like 1 | 2499 | -0.359787604971237 | 0.315822772805629 |
| 825 | 1119652 | 1119652 : CHPF :: chondroitin polymerizing factor | 458374 | 0.231475094432380 | -0.103490870734691 |
| 826 | 1119655 | 1119655 : :: Homo sapiens hypothetical gene supported by NM_018065 (LOC374293), mRNA | 407181 | 0.271438641659253 | -0.320546868315670 |
| 827 | 1119667 | 1119667 : ARL7 :: ADP-ribosylation factor-like 7 | 111554 | 0.344025040053841 | -0.364460171367448 |
| 828 | 1119680 | 1119680 : NNMT :: nicotinamide N-methyltransferase | 364345 | 0.849481601667150 | -0.407473012706719 |
| 829 | 1119683 | 1119683 : C8FW :: phosphoprotein regulated by mitogenic pathways | 444947 | 0.175976631640823 | -0.225708506051835 |
| 830 | 1119684 | 1119684 : TM4SF2 :: transmembrane 4 superfamily member 2 | 439586 | 0.370013597929631 | -0.285991368891065 |
| 831 | 1119694 | 1119694 : BMI1 :: B lymphoma Mo-MLV insertion region (mouse) | 380403 | -0.051029087019197 | -0.238731608205694 |
| 832 | 1119699 | 1119699 : PDGFRB :: platelet-derived growth factor receptor, beta polypeptide | 307783 | 0.727905513250235 | -0.426872032663045 |
| 833 | 1119706 | 1119706 : GAK :: cyclin G associated kinase | 153227 | 0.047312310573583 | -0.212371832168573 |
| 834 | 1119708 | 1119708 : SERPINF1 :: serine (or cysteine) proteinase inhibitor, clade F (alpha-2 antiplasmin, pigment epithelium derived factor), member 1 | 173594 | 0.818127717962518 | -0.494784353536062 |
| 835 | 1119709 | 1119709 : FRAP1 :: FK506 binding protein 12-rapamycin associated protein 1 | 338207 | -0.100924735319417 | 0.123840911452660 |
| 836 | 1119725 | 1119725 : CSK :: c-src tyrosine kinase | 77793 | -0.342193698499374 | 0.386680662501259 |
| 837 | 1119729 | 1119729 : TK1 :: thymidine kinase 1, soluble | 164457 | -0.178159168560846 | 0.621943500601026 |
| 838 | 1119734 | 1119734 : ITGAV :: integrin, alpha V (vitronectin receptor, alpha polypeptide, antigen CD51) | 436873 | 0.880095069226405 | -0.341583015797392 |
| 839 | 1119752 | 1119752 : BASP1 :: brain abundant, membrane attached signal protein 1 | 511745 | 0.039736680045055 | 0.128939385773097 |
| 840 | 1119765 | 1119765 : IGSF3 :: immunoglobulin superfamily, member 3 | 81234 | 0.043154074341915 | -0.220960417200884 |
| 841 | 1119766 | 1119766 : MYST3 :: MYST histone acetyltransferase (monocytic leukemia) 3 | 93231 | -0.201625331472481 | 0.020169749212703 |
| 842 | 1119775 | 1119775 : HDAC5 :: histone deacetylase 5 | 9028 | -0.047258845589192 | -0.144307812706093 |
| 843 | 1119780 | 1119780 : MPI :: mannose phosphate isomerase | 75694 | -0.249376705561104 | 0.265128946611980 |
| 844 | 1119782 | 1119782 : TRB2 :: tribbles homolog 2 | 155418 | 0.015840046216037 | -0.057383709246075 |
| 845 | 1119799 | 1119799 : BCL7B :: B-cell CLL/lymphoma 7B | 408219 | -0.301353371006817 | 0.333515975123573 |
| 846 | 1119802 | 1119802 : PITPNB :: phosphatidylinositol transfer protein, beta | 7370 | -0.279346455254819 | 0.285255269810126 |
| 847 | 1119807 | 1119807 : MAPK14 :: mitogen-activated protein kinase 14 | 79107 | -0.103247521829532 | 0.086030304232384 |
| 848 | 1119808 | 1119808 : IRF1 :: interferon regulatory factor 1 | 80645 | 0.214974139783435 | -0.487005406874141 |
| 849 | 1119813 | 1119813 : PRKCD :: protein kinase C, delta | 155342 | -0.095881893640700 | 0.021482940393706 |
| 850 | 1119817 | 1119817 : TNKS :: tankyrase, TRF1-interacting ankyrin-related ADP-ribose polymerase | 409194 | -0.047999395366169 | 0.021277604032916 |

TABLE 2415-continued

| Order | UNIQID | NAME GeneID.txt | GENEID | LN.cor | Pro.cor |
|---|---|---|---|---|---|
| 851 | 1119820 | CSNK1G2 :: casein kinase 1, gamma 2 | 181390 | 0.101155785845682 | -0.029637775969762 |
| 852 | 1119826 | TYMS :: thymidylate synthetase | 87491 | -0.371762638989175 | 0.732371010652222 |
| 853 | 1119838 | GNAQ :: guanine nucleotide binding protein (G protein), q polypeptide | 469951 | 0.608858917985059 | -0.451610474749559 |
| 854 | 1119841 | LYN :: v-yes-1 Yamaguchi sarcoma viral related oncogene homolog | 80887 | -0.385987016514418 | 0.241969623986561 |
| 855 | 1119846 | POLR2K :: polymerase (RNA) II (DNA directed) polypeptide K, 7.0 kDa | 351475 | -0.144645959994654 | 0.345426430436713 |
| 856 | 1119860 | MAP2K1 :: mitogen-activated protein kinase kinase 1 | 132311 | 0.081523729635758 | 0.107249499092262 |
| 857 | 1119868 | TNFSF10 :: tumor necrosis factor (ligand) superfamily, member 10 | 387871 | 0.361597221904698 | -0.553123293632563 |
| 858 | 1119872 | OSR1 :: oxidative-stress responsive 1 | 95220 | -0.348692541889615 | 0.471254203040539 |
| 859 | 1119873 | CPSF5 :: cleavage and polyadenylation specific factor 5, 25 kDa | 446393 | -0.235700347405962 | 0.584626529399289 |
| 860 | 1119876 | DUSP11 :: dual specificity phosphatase 11 (RNA/RNP complex 1-interacting) | 14611 | -0.190844618983350 | 0.299994415193974 |
| 861 | 1119878 | CCNB2 :: cyclin B2 | 194698 | -0.291964604694904 | 0.784720009084587 |
| 862 | 1119880 | FMOD :: fibromodulin | 442844 | 0.561780493586553 | -0.548252797794380 |
| 863 | 1119884 | PTPN1 :: protein tyrosine phosphatase, non-receptor type 1 | 418004 | -0.007199191487470 | 0.033794205251841 |
| 864 | 1119889 | PDCD4 :: programmed cell death 4 (neoplastic transformation inhibitor) | 257697 | -0.387457805191161 | 0.042363269173874 |
| 865 | 1119894 | ACY1 :: aminoacylase 1 | 334707 | -0.350776535174252 | 0.264656076550105 |
| 866 | 1119895 | PRKACB :: protein kinase, cAMP-dependent, catalytic, beta | 156324 | -0.005364457034190 | -0.120396590491985 |
| 867 | 1119903 | p44S10 :: proteasome regulatory particle subunit p44S10 | 350939 | -0.492672600495662 | 0.540375320876622 |
| 868 | 1119906 | ROCK2 :: Rho-associated, coiled-coil containing protein kinase 2 | 58617 | -0.037457510608621 | 0.095524196892679 |
| 869 | 1119907 | CASP3 :: caspase 3, apoptosis-related cysteine protease | 141125 | -0.261343210354826 | 0.147838406405152 |
| 870 | 1119916 | OXCT :: 3-oxoacid CoA transferase | 177584 | -0.420512115118106 | 0.570427247250647 |
| 871 | 1119919 | STK39 :: serine threonine kinase 39 (STE20/SPS1 homolog, yeast) | 199263 | 0.036380914794334 | 0.137316042469441 |
| 872 | 1119920 | MAPKAPK3 :: mitogen-activated protein kinase-activated protein kinase 3 | 234521 | 0.033224901009291 | -0.290845134954234 |
| 873 | 1119924 | INPP1 :: inositol polyphosphate-1-phosphatase | 32309 | 0.322259775401793 | -0.354327057539113 |
| 874 | 1119928 | CLPP :: ClpP caseinolytic protease, ATP-dependent, proteolytic subunit homolog (*E. coli*) | 317335 | -0.383473848217803 | 0.493264263215279 |
| 875 | 1119936 | AMSH :: associated molecule with the SH3 domain of STAM | 12479 | -0.212970492666360 | 0.177745673538672 |
| 876 | 1119939 | AHR :: aryl hydrocarbon receptor | 170087 | 0.256970446704131 | -0.173340326402877 |
| 877 | 1119946 | AGT :: angiotensinogen (serine (or cysteine) proteinase inhibitor, clade A (alpha-1 antiproteinase, antitrypsin), member 8) | 19383 | -0.083357114522711 | 0.115295274530192 |
| 878 | 1119950 | TAF15 :: TAF15 RNA polymerase II, TATA box binding protein (TBP)-associated factor, 68 kDa | 402752 | -0.306440406993752 | 0.338606484125856 |
| 879 | 1119972 | EPHB4 :: EphB4 | 437008 | 0.213883588482106 | -0.276537888742675 |
| 880 | 1119979 | MSH6 :: mutS homolog 6 (*E. coli*) | 445052 | -0.210797269834120 | 0.563006959737033 |
| 881 | 1119983 | ANK2 :: ankyrin 2, neuronal | 409783 | 0.239718352750997 | -0.362446515998409 |
| 882 | 1119995 | IL1R1 :: interleukin 1 receptor, type I | 82112 | 0.880259393296759 | -0.523750968501772 |
| 883 | 1119997 | STK38 :: serine/threonine kinase 38 | 367811 | 0.116255029911486 | -0.270963700598019 |
| 884 | 1119998 | C1QB :: complement component 1, q subcomponent, beta polypeptide | 8986 | -0.064997812238848 | -0.308036422540148 |
| 885 | 1120008 | DYRK2 :: dual-specificity tyrosine-(Y)-phosphorylation regulated kinase 2 | 173135 | 0.139680495957613 | -0.138798127049231 |
| 886 | 1120011 | SMARCA3 :: SWI/SNF related, matrix associated, actin dependent regulator of chromatin, subfamily a, member 3 | 3068 | -0.393821573018423 | 0.440572225264925 |
| 887 | 1120016 | STARD3 :: START domain containing 3 | 77628 | 0.197664406031218 | -0.216926094278756 |
| 888 | 1120023 | LTBR :: lymphotoxin beta receptor (TNFR superfamily, member 3) | 1116 | 0.449477622659772 | -0.391678588451956 |
| 889 | 1120024 | COG2 :: component of oligomeric golgi complex 2 | 408063 | 0.341869331296081 | -0.211635679580085 |
| 890 | 1120026 | STAT5A :: signal transducer and activator of transcription 5A | 437058 | 0.233594777682906 | -0.490211434372936 |
| 891 | 1120038 | CHSY1 :: carbohydrate (chondroitin) synthase 1 | 110488 | 0.469412842283111 | -0.278608622720236 |
| 892 | 1120044 | BCAS2 :: breast carcinoma amplified sequence 2 | 22960 | -0.118171434304281 | 0.380613118455193 |
| 893 | 1120053 | COQ2 :: component of oligomeric golgi complex 2 | 82309 | -0.322176222203961 | 0.288583667630216 |
| 894 | 1120055 | MADH2 :: MAD, mothers against decapentaplegic homolog 2 (*Drosophila*) | 110741 | -0.198373862314482 | 0.151234655555872 |
| 895 | 1120059 | THBS2 :: thrombospondin 2 | 458354 | 0.823561522648464 | -0.307598472911061 |
| 896 | 1120063 | SDF2 :: stromal cell-derived factor 2 | 118684 | -0.151141188451317 | 0.205246091448918 |
| 897 | 1120069 | CSF1R :: colony stimulating factor 1 receptor, formerly McDonough feline sarcoma viral (v-fms) oncogene homolog | 174142 | 0.586483471012455 | -0.538330757879298 |
| 898 | 1120072 | PTK2B :: PTK2B protein tyrosine kinase 2 beta | 405474 | 0.025565694638970 | -0.081698039331191 |

TABLE 2415-continued

GeneID.txt

| Order | UNIQID | NAME | GENEID | LN.cor | Pro.cor |
|---|---|---|---|---|---|
| 899 | 1120079 | IMPA2 :: inositol(myo)-1(or 4)-monophosphatase 2 | 5753 | -0.142422649698462 | 0.380777710316534 |
| 900 | 1120081 | PDGFRA :: platelet-derived growth factor receptor, alpha polypeptide | 74615 | 0.801797080306997 | -0.363577157808831 |
| 901 | 1120082 | RB1 :: retinoblastoma 1 (including osteosarcoma) | 408528 | -0.092716888870664 | 0.307873154083231 |
| 902 | 1120088 | HAT1 :: histone acetyltransferase 1 | 13340 | -0.233187350154903 | 0.685057151008412 |
| 903 | 1120089 | DAPK1 :: death-associated protein kinase 1 | 244318 | 0.466586639833559 | -0.514289733675279 |
| 904 | 1120090 | BCL6 :: B-cell CLL/lymphoma 6 (zinc finger protein 51) | 155024 | 0.144941230662303 | 0.048693731993595 |
| 905 | 1120108 | ARHG :: ras homolog gene family, member G (rho G) | 75082 | 0.190899533887631 | -0.071434473852746 |
| 906 | 1120120 | ABCC4 :: ATP-binding cassette, sub-family C (CFTR/MRP), member 4 | 307915 | 0.227392907322269 | -0.077875606978302 |
| 907 | 1120121 | CDK9 :: cyclin-dependent kinase 9 (CDC2-related kinase) | 150423 | 0.045051374703949 | -0.071571722929467 |
| 908 | 1120127 | CDC2 :: cell division cycle 2, G1 to S and G2 to M | 334562 | -0.356711902630063 | 0.859586003083525 |
| 909 | 1120128 | MAPK9 :: mitogen-activated protein kinase 9 | 348446 | 0.053836424867107 | 0.050716859954676 |
| 910 | 1120129 | TLE1 :: transducin-like enhancer of split 1 (E(sp1) homolog, Drosophila) | 406491 | -0.147138605178005 | 0.004837891616427 |
| 911 | 1120134 | IL4R :: interleukin 4 receptor | 75545 | -0.046782309391954 | -0.158009856362830 |
| 912 | 1120137 | FCGBP :: Fc fragment of IgG binding protein | 111732 | -0.021179847554413 | 0.084901186125138 |
| 913 | 1120145 | CDH3 :: cadherin 3, type 1, P-cadherin (placental) | 191842 | 0.208811388283192 | -0.196206998994574 |
| 914 | 1120152 | IRF2 :: interferon regulatory factor 2 | 83795 | -0.245349312777798 | -0.021862320330082 |
| 915 | 1120153 | LMNB1 :: lamin B1 | 89497 | -0.349360475211000 | 0.567523295277270 |
| 916 | 1120160 | KIAA0355 :: KIAA0355 gene product | 436976 | -0.006389482890844 | -0.147844881582699 |
| 917 | 1120163 | DCK :: deoxycytidine kinase | 709 | -0.262028531431119 | 0.474753625341165 |
| 918 | 1120191 | SOCS2 :: suppressor of cytokine signaling 2 | 405946 | 0.205081336164991 | -0.120603880465586 |
| 919 | 1120194 | RPS6KA1 :: ribosomal protein S6 kinase, 90 kDa, polypeptide 1 | 149957 | -0.172834971698563 | 0.110172857246101 |
| 920 | 1120196 | TBC1D4 :: TBC1 domain family, member 4 | 173802 | 0.252268611353589 | -0.365300630429192 |
| 921 | 1120205 | MET :: met proto-oncogene (hepatocyte growth factor receptor) | 419124 | -0.341638325826115 | 0.713407022486365 |
| 922 | 1120214 | DSCR2 :: Down syndrome critical region gene 2 | 5198 | -0.152751764379210 | -0.049590054715558 |
| 923 | 1120216 | CD53 :: CD53 antigen | 443057 | -0.324160296081840 | 0.777319506164410 |
| 924 | 1120254 | CCNA2 :: cyclin A2 | 85137 | 0.612541977651677 | -0.539497884538483 |
| 925 | 1120261 | RTN1 :: reticulon 1 | 99947 | 0.217934786713959 | -0.365366022247552 |
| 926 | 1120266 | EPHA2 :: EphA2 | 171596 | 0.451891905380461 | -0.397687894156014 |
| 927 | 1120267 | CD68 :: CD68 antigen | 246381 | 0.233418379708817 | -0.357196376724822 |
| 928 | 1120269 | TNFRSF1B :: tumor necrosis factor receptor superfamily, member 1B | 256278 | 0.095532546067821 | 0.070544177910803 |
| 929 | 1120272 | MAP3K3 :: mitogen-activated protein kinase kinase kinase 3 | 29282 | 0.044758338920690 | -0.191842282997896 |
| 930 | 1120274 | MTX2 :: metaxin 2 | 31584 | -0.329576839455756 | 0.527764199207566 |
| 931 | 1120278 | SEMA4D :: sema domain, immunoglobulin domain (Ig), transmembrane domain (TM) and short cytoplasmic domain, (semaphorin) 4D | 511748 | 0.224371642860400 | -0.290878044536958 |
| 932 | 1120288 | CD4 :: CD4 antigen (p55) | 17483 | 0.453027496723459 | -0.493671880192508 |
| 933 | 1120289 | MAP4K5 :: mitogen-activated protein kinase kinase kinase kinase 5 | 246970 | -0.101195827454930 | 0.110280186060386 |
| 934 | 1120299 | NFIL3 :: nuclear factor, interleukin 3 regulated | 79334 | 0.418150198365747 | -0.353861915577026 |
| 935 | 1120300 | CSNK2A2 :: casein kinase 2, alpha prime polypeptide | 82201 | -0.447144828589450 | 0.441822317864757 |
| 936 | 1120316 | TERF2 :: telomeric repeat binding factor 2 | 63335 | -0.223834288936832 | 0.378657341977871 |
| 937 | 1120317 | BYSL :: bystin-like | 106880 | -0.480611242448932 | 0.673114888210520 |
| 938 | 1120324 | IGF1R :: insulin-like growth factor 1 receptor | 239176 | 0.486016697137607 | -0.246282140833788 |
| 939 | 1120335 | MAP3K11 :: mitogen-activated protein kinase kinase kinase 11 | 432787 | 0.167553983611871 | -0.337924652268674 |
| 940 | 1120350 | IL1RL1LG :: interleukin 1 receptor-like 1 ligand | 446686 | 0.073526046829361 | -0.142883449531743 |
| 941 | 1120353 | BCL2 :: B-cell CLL/lymphoma 2 | 79241 | -0.350722162941236 | -0.216689187537821 |
| 942 | 1120355 | CX3CL1 :: chemokine (C-X3-C motif) ligand 1 | 80420 | 0.096212197388840 | -0.260021871585171 |
| 943 | 1120356 | PKD2 :: polycystic kidney disease 2 (autosomal dominant) | 458291 | 0.604711621900698 | -0.246336204843929 |
| 944 | 1120359 | FRZB :: frizzled-related protein | 128453 | 0.089135535633861 | -0.257118444642874 |
| 945 | 1120361 | PDE4B :: phosphodiesterase 4B, cAMP-specific (phosphodiesterase E4 dunce homolog, Drosophila) | 188 | -0.084837939596466 | -0.104442892301952 |
| 946 | 1120362 | PHKG2 :: phosphorylase kinase, gamma 2 (testis) | 196177 | -0.077059900678308 | -0.191291041020843 |

TABLE 2415-continued

GeneID.txt

| Order | UNIQID | NAME | GENEID | LN.cor | Pro.cor |
|---|---|---|---|---|---|
| 947 | 1120366 | DPP4 :: dipeptidylpeptidase 4 (CD26, adenosine deaminase complexing protein 2) | 44926 | 0.297035769550426 | -0.200947213073117 |
| 948 | 1120370 | ITPKB :: inositol 1,4,5-trisphosphate 3-kinase B | 78877 | 0.190360802060295 | -0.169751144548655 |
| 949 | 1120373 | BAK1 :: BCL2-antagonist/killer 1 | 93213 | -0.200140816613802 | 0.113338862865570 |
| 950 | 1120378 | FLJ11193 :: hypothetical protein FLJ11193 | 151046 | -0.272022865326159 | 0.234783123016162 |
| 951 | 1120385 | BUB1B :: BUB1 budding uninhibited by benzimidazoles 1 homolog beta (yeast) | 36708 | -0.428733600165811 | 0.833405557024467 |
| 952 | 1120387 | CTSO :: cathepsin O | 75262 | 0.374520964899448 | -0.580832415098230 |
| 953 | 1120389 | SLA :: Src-like-adaptor | 75367 | -0.172426216404282 | -0.127234467000589 |
| 954 | 1120400 | SSBP2 :: single-stranded DNA binding protein 2 | 152207 | 0.138133470457960 | 0.041953623299176 |
| 955 | 1120402 | CDC42BPA :: CDC42 binding protein kinase alpha (DMPK-like) | 18586 | 0.342860793681219 | -0.308950300777485 |
| 956 | 1120417 | FLJ10055 :: hypothetical protein FLJ10055 | 9398 | 0.458712245189916 | -0.309562635887674 |
| 957 | 1120419 | NJMU-R1 :: protein kinase Njmu-R1 | 9800 | -0.188573102796126 | 0.435261002793401 |
| 958 | 1120422 | GARP :: glycoprotein A repetitions predominant | 151641 | 0.210134245590657 | 0.098618718300581 |
| 959 | 1120423 | MAP3K5 :: mitogen-activated protein kinase kinase kinase 5 | 151988 | 0.128014378546006 | -0.414691971823296 |
| 960 | 1120425 | RPS6KA3 :: ribosomal protein S6 kinase, 90 kDa, polypeptide 3 | 188361 | 0.280819408584904 | -0.003327617440558 |
| 961 | 1120433 | VRK1 :: vaccinia related kinase 1 | 422662 | -0.298915556379366 | 0.717298406899907 |
| 962 | 1120438 | USP46 :: ubiquitin specific protease 46 | 109268 | -0.301682893848221 | 0.251115921079262 |
| 963 | 1120465 | CXCL9 :: chemokine (C-X-C motif) ligand 9 | 77367 | 0.091216036037422 | -0.424535324487160 |
| 964 | 1120477 | KDR :: kinase insert domain receptor (a type III receptor tyrosine kinase) | 12337 | 0.473056670592013 | -0.203310434691520 |
| 965 | 1120478 | ACVR1 :: activin A receptor, type I | 150402 | 0.691949086102474 | -0.523920470761015 |
| 966 | 1120483 | CSTF3 :: cleavage stimulation factor, 3' pre-RNA, subunit 3, 77 kDa | 180034 | -0.518586670460773 | 0.446361697113926 |
| 967 | 1120484 | MPO :: myeloperoxidase | 458272 | 0.101960994023863 | -0.054587543757020 |
| 968 | 1120494 | CDC6 :: CDC6 cell division cycle 6 homolog (S. cerevisiae) | 405958 | -0.416635429243115 | 0.842295577203676 |
| 969 | 1120500 | CYP27A1 :: cytochrome P450, family 27, subfamily A, polypeptide 1 | 82568 | 0.653610023886872 | -0.304787113463914 |
| 970 | 1120509 | GNB5 :: guanine nucleotide binding protein (G protein), beta 5 | 155090 | -0.267362638918031 | 0.200244247175214 |
| 971 | 1120520 | RFC4 :: replication factor C (activator 1) 4, 37 kDa | 35120 | -0.501231595987143 | 0.789659303959865 |
| 972 | 1120524 | TRIP13 :: thyroid hormone receptor interactor 13 | 436187 | -0.368479048817546 | 0.832946538281856 |
| 973 | 1120529 | CEBPA :: CCAAT/enhancer binding protein (C/EBP), alpha | 76171 | 0.604359145525783 | -0.430431783000636 |
| 974 | 1120538 | ICSBP1 :: interferon consensus sequence binding protein 1 | 14453 | -0.202713033551771 | 0.034802475287723 |
| 975 | 1120544 | STK3 :: serine/threonine kinase 3 (STE20 homolog, yeast) | 166684 | 0.085584173231200 | -0.034446319134313 |
| 976 | 1120553 | PRAME :: preferentially expressed antigen in melanoma | 30743 | 0.096257573354037 | 0.013328837460755 |
| 977 | 1120555 | STK19 :: serine/threonine kinase 19 | 444 | 0.168786958397468 | -0.247788203132821 |
| 978 | 1120562 | CCL4 :: chemokine (C-C motif) ligand 4 | 75703 | 0.281322248691298 | -0.465719953116774 |
| 979 | 1120564 | TESK1 :: testis-specific kinase 1 | 79358 | 0.100723203368127 | -0.228465660577298 |
| 980 | 1120572 | IL2RG :: interleukin 2 receptor, gamma (severe combined immunodeficiency) | 84 | 0.235330936351446 | -0.396807810508209 |
| 981 | 1120574 | CD48 :: CD48 antigen (B-cell membrane protein) | 901 | -0.194668752468389 | -0.098819351341990 |
| 982 | 1120581 | RFC3 :: replication factor C (activator 1) 3, 38 kDa | 115474 | -0.307682737839499 | 0.789291151763360 |
| 983 | 1120583 | BCL9 :: B-cell CLL/lymphoma 9 | 415209 | -0.190510681098454 | 0.148503187654638 |
| 984 | 1120588 | RNU3IP2 :: RNA, U3 small nucleolar interacting protein 2 | 153768 | -0.526724070424994 | 0.500938051852095 |
| 985 | 1120593 | TPST1 :: tyrosylprotein sulfotransferase 1 | 421194 | 0.700549992980495 | -0.302446735476920 |
| 986 | 1120593 | STAB1 :: stabilin 1 | 301989 | 0.315207523101052 | -0.361469709646652 |
| 987 | 1120594 | CDO1 :: cysteine dioxygenase, type I | 442378 | 0.096654329449506 | -0.131902879792736 |
| 988 | 1120595 | KIAA0999 :: KIAA0999 protein | 444909 | -0.158743720518346 | 0.006339680783502 |
| 989 | 1120596 | CDKN2C :: cyclin-dependent kinase inhibitor 2C (p18, inhibits CDK4) | 4854 | -0.277992134637003 | 0.464801755714349 |
| 990 | 1120601 | KIAA0963 :: KIAA0963 protein | 441129 | 0.115377312801900 | -0.173467001738638 |
| 991 | 1120605 | RPS6KB1 :: ribosomal protein S6 kinase, 70 kDa, polypeptide 1 | 86858 | -0.049333332738750 | 0.272123372076907 |
| 992 | 1120615 | IFNAR1 :: interferon (alpha, beta and omega) receptor 1 | 181315 | 0.109452635758577 | -0.098788842929034 |
| 993 | 1120616 | CD37 :: CD37 antigen | 153053 | -0.532314280274716 | 0.308291940284235 |
| 994 | 1120617 | CPT1B :: carnitine palmitoyltransferase 1B (muscle) | 439777 | 0.291222883899948 | -0.467225084628603 |
| 995 | 1120625 | RNGTT :: RNA guanylyltransferase and 5'-phosphatase | 27345 | -0.060185273034959 | -0.030566555399450 |

TABLE 2415-continued

GeneID.txt

| Order | UNIQID | NAME | GENEID | LN.cor | Pro.cor |
|---|---|---|---|---|---|
| 996 | 1120630 | 1120630 : DKFZP564M082 :: DKFZP564M082 protein | 38044 | −0.185687083825884 | 0.335252950655521 |
| 997 | 1120633 | 1120633 : HDAC4 :: histone deacetylase 4 | 222874 | 0.268465157579931 | −0.393330515146740 |
| 998 | 1120637 | 1120637 : FCER1G :: Fc fragment of IgE, high affinity I, receptor for; gamma polypeptide | 433300 | 0.331513918783418 | −0.440800744737435 |
| 999 | 1120643 | 1120643 : CDK2 :: cyclin-dependent kinase 2 | 19192 | −0.293669215593932 | 0.661616741734877 |
| 1000 | 1120645 | 1120645 : FADS3 :: fatty acid desaturase 3 | 21765 | 0.055507218063663 | 0.088445892207464 |
| 1001 | 1120651 | 1120651 : PIM2 :: pim-2 oncogene | 80205 | −0.281220927786929 | 0.185187824043508 |
| 1002 | 1120673 | 1120673 : KIAA0711 :: KIAA0711 gene product | 5333 | 0.068811665106344 | 0.005641795833107 |
| 1003 | 1120695 | 1120695 : TRAF5 :: TNF receptor-associated factor 5 | 385685 | −0.019131171585834 | −0.161636874402010 |
| 1004 | 1120697 | 1120697 : DHX30 :: DEAH (Asp-Glu-Ala-His) box polypeptide 30 | 323462 | −0.471181063703452 | 0.425078805218812 |
| 1005 | 1120700 | 1120700 : SCAP2 :: src family associated phosphoprotein 2 | 410745 | −0.186747716103403 | 0.225355767507172 |
| 1006 | 1120703 | 1120703 : SLCO2A1 :: solute carrier organic anion transporter family, member 2A1 | 83974 | 0.364711626940315 | −0.247170134183657 |
| 1007 | 1120716 | 1120716 : CAMK1 :: calcium/calmodulin-dependent protein kinase I | 512804 | 0.168875956443599 | −0.200055505150205 |
| 1008 | 1120717 | 1120717 : SLC43A1 :: solute carrier family 43, member 1 | 444159 | −0.376807044586730 | 0.520626875405123 |
| 1009 | 1120720 | 1120720 : KCNN4 :: potassium intermediate/small conductance calcium-activated channel, subfamily N, member 4 | 10082 | 0.136091693845411 | −0.076690223326382 |
| 1010 | 1120730 | 1120730 : G1P3 :: interferon, alpha-inducible protein (clone IFI-6-16) | 287721 | 0.310445834508628 | −0.358938894023986 |
| 1011 | 1120743 | 1120743 : CD83 :: CD83 antigen (activated B lymphocytes, immunoglobulin superfamily) | 79197 | 0.016342520267471 | −0.056434824824793 |
| 1012 | 1120750 | 1120750 : LDOC1 :: leucine zipper, down-regulated in cancer 1 | 45231 | 0.348398089655945 | −0.373744732997425 |
| 1013 | 1120755 | 1120755 : CXCL1 :: chemokine (C-X-C motif) ligand 1 (melanoma growth stimulating activity, alpha) | 789 | 0.239712817378015 | −0.227377568731226 |
| 1014 | 1120765 | 1120765 : PIK3C2B :: phosphoinositide-3-kinase, class 2, beta polypeptide | 343329 | 0.099676443902521 | −0.033239919662244 |
| 1015 | 1120770 | 1120770 : BID :: BH3 interacting domain death agonist | 300825 | −0.168931051298000 | 0.231690940935265 |
| 1016 | 1120779 | 1120779 : CDC7 :: CDC7 cell division cycle 7 (S. cerevisiae) | 28853 | −0.364719870070187 | 0.702890401522440 |
| 1017 | 1120780 | 1120780 : FARP2 :: PERM, RhoGEF and pleckstrin domain protein 2 | 301283 | 0.218332541521728 | −0.357637988743606 |
| 1018 | 1120785 | 1120785 : PPIC :: peptidylprolyl isomerase C (cyclophilin C) | 110364 | 0.832325010041904 | −0.364870410416830 |
| 1019 | 1120789 | 1120789 : PDPK1 :: 3-phosphoinositide dependent protein kinase-1 | 154729 | 0.036213766133773 | −0.055531193135830 |
| 1020 | 1120792 | 1120792 : CXCL10 :: chemokine (C-X-C motif) ligand 10 | 413924 | 0.166606940060415 | −0.407303162829402 |
| 1021 | 1120803 | 1120803 : IKBKE :: inhibitor of kappa light polypeptide gene enhancer in B-cells, kinase epsilon | 321045 | 0.173038590863187 | −0.262684854061046 |
| 1022 | 1120808 | 1120808 : IRF4 :: interferon regulatory factor 4 | 127686 | −0.274522690905631 | 0.214443660676563 |
| 1023 | 1120809 | 1120809 : SELL :: selectin L (lymphocyte adhesion molecule 1) | 82848 | −0.034467098542711 | −0.232667176371041 |
| 1024 | 1120813 | 1120813 : KIAA0831 :: KIAA0831 | 414809 | 0.140198507173410 | −0.440539960257267 |
| 1025 | 1120814 | 1120814 : ICK :: intestinal cell (MAK-like) kinase | 417022 | 0.185512034005136 | −0.254094458847882 |
| 1026 | 1120818 | 1120818 : FGFR4 :: fibroblast growth factor receptor 4 | 165950 | −0.173305192411460 | 0.170225481596070 |
| 1027 | 1120824 | 1120824 : ARK5 :: KIAA0537 gene product | 200598 | 0.639988433549215 | −0.342249782851512 |
| 1028 | 1120825 | 1120825 : CHL1 :: cell adhesion molecule with homology to L1CAM (close homolog of L1) | 388344 | 0.116148782379396 | −0.093424425417522 |
| 1029 | 1120828 | 1120828 : EPHB3 :: EphB3 | 2913 | 0.273313344428643 | −0.065126563411831 |
| 1030 | 1120832 | 1120832 : PFTK1 :: PFTAIRE protein kinase 1 | 57856 | 0.168005950948601 | −0.028716212628633 |
| 1031 | 1120834 | 1120834 : CCL21 :: chemokine (C-C motif) ligand 21 | 57907 | −0.035804408078127 | −0.204294856872407 |
| 1032 | 1120838 | 1120838 : PKIA :: protein kinase (cAMP-dependent, catalytic) inhibitor alpha | 433700 | −0.146391280990281 | 0.187658861583021 |
| 1033 | 1120839 | 1120839 : PLCG2 :: phospholipase C, gamma 2 (phosphatidylinositol-specific) | 512298 | −0.460928399830360 | 0.522088964678862 |
| 1034 | 1120846 | 1120846 : RPS6KA4 :: ribosomal protein S6 kinase, 90 kDa, polypeptide 4 | 105584 | 0.045791529310886 | −0.164030593362306 |
| 1035 | 1120847 | 1120847 : NEK4 :: NIMA (never in mitosis gene a)-related kinase 4 | 433008 | −0.162080158681806 | 0.363453471138679 |
| 1036 | 1120853 | 1120853 : NEK2 :: NIMA (never in mitosis gene a)-related kinase 2 | 153704 | −0.257915260526437 | 0.773686557142882 |
| 1037 | 1120854 | 1120854 : EDG1 :: endothelial differentiation, sphingolipid G-protein-coupled receptor, 1 | 154210 | −0.122104475497316 | −0.071633341557146 |
| 1038 | 1120858 | 1120858 : HOMER3 :: homer homolog 3 (Drosophila) | 410683 | 0.335496794625231 | −0.271528013190748 |
| 1039 | 1120863 | 1120863 : CCL5 :: chemokine (C-C motif) ligand 5 | 489044 | 0.542336364272824 | −0.582181977929694 |
| 1040 | 1120875 | 1120875 : LRMP :: lymphoid-restricted membrane protein | 124922 | 0.003183268254248 | 0.168887881459636 |
| 1041 | 1120880 | 1120880 : LTBP2 :: latent transforming growth factor beta binding protein 2 | 105689 | 0.826255058669113 | −0.434328882440352 |
| 1042 | 1120881 | 1120881 : ICAM2 :: intercellular adhesion molecule 2 | 433303 | −0.213253074312284 | −0.041517977663047 |
| 1043 | 1120900 | 1120900 : EPHB6 :: EphB6 | 380089 | 0.013945388707104 | −0.198607193449715 |
| 1044 | 1120918 | 1120918 : HLF :: hepatic leukemia factor | 250692 | 0.013775304997262 | −0.055242216674679 |

TABLE 2415-continued

GeneID.txt

| Order | UNIQID | NAME | GENEID | LN.cor | Pro.cor |
|---|---|---|---|---|---|
| 1045 | 1120923 | ARHGEF5 :: Rho guanine nucleotide exchange factor (GEF) 5 | 334 | 0.209882084442928 | -0.150683350886678 |
| 1046 | 1120925 | IL11RA :: interleukin 11 receptor, alpha | 204891 | 0.273246691313366 | -0.470149289804446 |
| 1047 | 1120946 | MAPK10 :: mitogen-activated protein kinase 10 | 25209 | -0.00292032334190 | 0.154019887369059 |
| 1048 | 1120952 | TTK :: TTK protein kinase | 169840 | -0.236416169728487 | 0.593602839749024 |
| 1049 | 1120955 | MELK :: maternal embryonic leucine zipper kinase | 184339 | -0.208917157762608 | 0.724555232338905 |
| 1050 | 1120958 | CDK8 :: cyclin-dependent kinase 8 | 397734 | -0.039317157762445 | 0.224625838601688 |
| 1051 | 1120976 | GCHFR :: GTP cyclohydrolase I feedback regulatory protein | 245644 | -0.035026457160826 | 0.213041780115649 |
| 1052 | 1120980 | TLE4 :: transducin-like enhancer of split 4 (E(sp1) homolog, *Drosophila*) | 99824 | -0.030677104931693 | -0.067870579035081 |
| 1053 | 1120986 | STK18 :: serine/threonine kinase 18 | 172052 | -0.272148311899732 | 0.739975084000157 |
| 1054 | 1120993 | IL10RA :: interleukin 10 receptor, alpha | 327 | 0.047545601645909 | -0.184922274295712 |
| 1055 | 1121000 | TLR2 :: toll-like receptor 2 | 519033 | 0.249492421868063 | -0.480462743962837 |
| 1056 | 1121005 | TNFRSF11B :: tumor necrosis factor receptor superfamily, member 11b (osteoprotegerin) | 81791 | 0.322049857523582 | -0.151124812823603 |
| 1057 | 1121007 | MAP4K2 :: mitogen-activated protein kinase kinase kinase kinase 2 | 512671 | -0.234244240729329 | 0.375556542684312 |
| 1058 | 1121012 | E2F1 :: E2F transcription factor 1 | 96055 | -0.334386168154563 | 0.678410948823103 |
| 1059 | 1121013 | ICAM3 :: intercellular adhesion molecule 3 | 353214 | -0.297026833246660 | -0.013131917844355 |
| 1060 | 1121021 | CNK :: cytokine-inducible kinase | 153640 | -0.019398263377201 | -0.088470692615038 |
| 1061 | 1121028 | APOM :: apolipoprotein M | 247323 | 0.080461690727297 | -0.173516173118374 |
| 1062 | 1121029 | CSTA :: cystatin A (stefin A) | 412999 | 0.725032558235074 | -0.312936257878748 |
| 1063 | 1121033 | EMP2 :: epithelial membrane protein 2 | 511911 | 0.712789461038450 | -0.289562901195573 |
| 1064 | 1121054 | TGFA :: transforming growth factor, alpha | 170009 | 0.070989900125764 | -0.072416748854938 |
| 1065 | 1121057 | STAT5B :: signal transducer and activator of transcription 5B | 434992 | 0.014885511405709 | -0.076250115454824 |
| 1066 | 1121061 | ITGA2 :: integrin, alpha 2 (CD49B, alpha 2 subunit of VLA-2 receptor) | 387725 | -0.029030779750270 | 0.035897612258061 |
| 1067 | 1121062 | CCNE2 :: cyclin E2 | 408658 | -0.210155943554150 | 0.646944453371192 |
| 1068 | 1121073 | AUH :: AU RNA binding protein/enoyl-Coenzyme A hydratase | 81886 | 0.171546279035464 | -0.332955161867336 |
| 1069 | 1121076 | ITGAE :: integrin, alpha E (antigen CD103, human mucosal lymphocyte antigen 1; alpha polypeptide) | 389133 | -0.431908412475 | 0.301113545375388 |
| 1070 | 1121082 | IL1B :: interleukin 1, beta | 126256 | 0.253563513129184 | -0.274936908342392 |
| 1071 | 1121100 | CCR1 :: chemokine (C-C motif) receptor 1 | 301921 | 0.341958749466600 | -0.274745766841841 |
| 1072 | 1121102 | MHC2TA :: MHC class II transactivator | 126714 | 0.094969874201105 | -0.250509581424846 |
| 1073 | 1121115 | MEF2B :: MADS box transcription enhancer factor 2, polypeptide B (myocyte enhancer factor 2B) | 78881 | -0.260397502438443 | 0.457668819142024 |
| 1074 | 1121117 | VRK2 :: vaccinia related kinase 2 | 82771 | 0.105930454706077 | -0.045187449295500 |
| 1075 | 1121120 | RAGE :: renal tumor antigen | 104119 | 0.011704601675353 | -0.003336985459853 |
| 1076 | 1121129 | CSF2RB :: colony stimulating factor 2 receptor, beta, low-affinity (granulocyte-macrophage) | 285401 | 0.473407369637606 | -0.447047508756504 |
| 1077 | 1121136 | DDR2 :: discoidin domain receptor family, member 2 | 440905 | 0.497410432793414 | -0.341535633908894 |
| 1078 | 1121143 | GNG4 :: guanine nucleotide binding protein (G protein), gamma 4 | 447973 | 0.065124580945373 | -0.114186071226629 |
| 1079 | 1121149 | MAP3K14 :: mitogen-activated protein kinase kinase kinase 14 | 440315 | -0.045622884625820 | -0.157979391580511 |
| 1080 | 1121159 | RELB :: v-rel reticuloendotheliosis viral oncogene homolog B, nuclear factor of kappa light polypeptide gene enhancer in B-cells 3 (avian) | 307905 | -0.014117993609713 | 0.054575676509177 |
| 1081 | 1121161 | IL6 :: interleukin 6 (interferon, beta 2) | 512234 | 0.270707514058880 | -0.160288023175733 |
| 1082 | 1121166 | STK17B :: serine/threonine kinase 17b (apoptosis-inducing) | 88297 | 0.135353436195562 | 0.076356575160992 |
| 1083 | 1121170 | HM74 :: putative chemokine receptor | 458425 | 0.109820599871215 | -0.169065883762500 |
| 1084 | 1121186 | CXCL13 :: chemokine (C-X-C motif) ligand 13 (B-cell chemoattractant) | 100431 | 0.378549805355286 | -0.294769734875808 |
| 1085 | 1121190 | NOTCH4 :: Notch homolog 4 (*Drosophila*) | 436100 | 0.101751050016826 | -0.006262723965488 |
| 1086 | 1121195 | PBX1 :: pre-B-cell leukemia transcription factor 1 | 408222 | -0.095908030808216 | -0.012690445881844 |
| 1087 | 1121201 | BCL10 :: B-cell CLL/lymphoma 10 | 193516 | -0.097298819688125 | 0.262527744599808 |
| 1088 | 1121203 | LIF :: leukemia inhibitory factor (cholinergic differentiation factor) | 2250 | 0.227708415345235 | -0.237257236108422 |
| 1089 | 1121205 | LCP2 :: lymphocyte cytosolic protein 2 (SH2 domain containing leukocyte protein of 76 kDa) | 2488 | 0.509256290000162 | -0.616098101683677 |
| 1090 | 1121217 | IL2RB :: interleukin 2 receptor, beta | 75596 | 0.233728921730338 | -0.367351838583743 |
| 1091 | 1121220 | RBL1 :: retinoblastoma-like 1 (p107) | 87 | -0.254718182068782 | 0.437740141713836 |
| 1092 | 1121228 | SPI1 :: spleen focus forming virus (SFFV) proviral integration oncogene spi1 | 157441 | 0.101862646966026 | -0.078795355216853 |

TABLE 2415-continued

| Order | UNIQID | NAME | GeneID.txt | GENEID | LN.cor | Pro.cor |
|---|---|---|---|---|---|---|
| 1093 | 1121248 | 1121248 :: BARD1 :: BRCA1 associated RING domain 1 | | 54089 | -0.332520033583970 | 0.540409719004797 |
| 1094 | 1121265 | 1121265 :: PLAG1 :: pleiomorphic adenoma gene 1 | | 14968 | -0.055939614174796 | 0.094487218739530 |
| 1095 | 1121276 | 1121276 :: CHEK1 :: CHK1 checkpoint homolog (S. pombe) | | 24529 | -0.352853420627079 | 0.836380563191936 |
| 1096 | 1121278 | 1121278 :: DCAMKL1 :: doublecortin and CaM kinase-like 1 | | 21355 | 0.412883143697658 | -0.298495227861876 |
| 1097 | 1121281 | 1121281 :: IL1R2 :: interleukin 1 receptor, type II | | 25333 | 0.142459721447506 | -0.302261496758997 |
| 1098 | 1121287 | 1121287 :: STK4 :: serine/threonine kinase 4 | | 35140 | -0.141211379313466 | 0.140410355369261 |
| 1099 | 1121290 | 1121290 :: FES :: feline sarcoma oncogene | | 7636 | 0.126479905402088 | -0.115090374078902 |
| 1100 | 1121291 | 1121291 :: EBI2 :: Epstein-Barr virus induced gene 2 (lymphocyte-specific G protein-coupled receptor) | | 784 | 0.235439422364981 | -0.105451694013327 |
| 1101 | 1121301 | 1121301 :: ZNF211 :: zinc finger protein 211 | | 511749 | -0.256995974326506 | -0.116130479767648 |
| 1102 | 1121306 | 1121306 :: SNAPC1 :: small nuclear RNA activating complex, polypeptide 1, 43 kDa | | 179312 | -0.111148822811151 | 0.479702938197036 |
| 1103 | 1121309 | 1121309 :: HSU79266 :: protein predicted by clone 23627 | | 23642 | -0.229837789455481 | 0.499904248128160 |
| 1104 | 1121315 | 1121315 :: MST1R :: macrophage stimulating 1 receptor (c-met-related tyrosine kinase) | | 2942 | 0.207517198765213 | -0.192186835039801 |
| 1105 | 1121316 | 1121316 :: CD3E :: CD3E antigen, epsilon polypeptide (TiT3 complex) | | 3003 | 0.224738515046276 | -0.499493301566731 |
| 1106 | 1121322 | 1121322 :: CASP10 :: caspase 10, apoptosis-related cysteine protease | | 5353 | 0.089986731593722 | -0.314526392551084 |
| 1107 | 1121326 | 1121326 :: CCL20 :: chemokine (C-C motif) ligand 20 | | 75498 | 0.215322214165972 | -0.132607332260028 |
| 1108 | 1121329 | 1121329 :: SIT :: SHP2 interacting transmembrane adaptor | | 88012 | -0.210345828377640 | 0.102148279065859 |
| 1109 | 1121331 | 1121331 :: TESK2 :: testis-specific kinase 2 | | 8980 | -0.039483229481418 | 0.033775496434037 |
| 1110 | 1121343 | 1121343 :: BTK :: Bruton agammaglobulinemia tyrosine kinase | | 159494 | -0.264292738475593 | 0.221493414593700 |
| 1111 | 1121368 | 1121368 :: SV2B :: synaptic vesicle glycoprotein 2B | | 8071 | 0.141032356631520 | -0.147797431288585 |
| 1112 | 1121371 | 1121371 :: TRAF6 :: TNF receptor-associated factor 6 | | 90957 | 0.075399751558709 | -0.168875636897418 |
| 1113 | 1121380 | 1121380 :: LAMP3 :: lysosomal-associated membrane protein 3 | | 10887 | 0.570357891518240 | -0.407916378045071 |
| 1114 | 1121383 | 1121383 :: ANGPT2 :: angiopoietin 2 | | 115181 | 0.217195685938879 | -0.123710120322309 |
| 1115 | 1121387 | 1121387 :: ROR2 :: receptor tyrosine kinase-like orphan receptor 2 | | 208080 | 0.489331037769812 | -0.053435946072310 |
| 1116 | 1121400 | 1121400 :: TRAF1 :: TNF receptor-associated factor 1 | | 438253 | 0.142917780292670 | -0.296365843618807 |
| 1117 | 1121404 | 1121404 :: ANGPT1 :: angiopoietin 1 | | 2463 | 0.374587616111693 | -0.287681985161262 |
| 1118 | 1121406 | 1121406 :: TNFSF12 :: tumor necrosis factor (ligand) superfamily, member 12 | | -4 | 0.458155673630534 | -0.447921783667761 |
| 1119 | 1121408 | 1121408 :: LOC51760 :: B/K protein | | 258326 | 0.108520226350273 | -0.337094362419053 |
| 1120 | 1121414 | 1121414 :: ALKBH :: alkB, alkylation repair homolog (E. coli) | | 94542 | -0.519450896479011 | 0.507278510441829 |
| 1121 | 1121436 | 1121436 :: HDAC9 :: histone deacetylase 9 | | 116753 | -0.062542813471143 | 0.051528289785797 |
| 1122 | 1121444 | 1121444 :: LY75 :: lymphocyte antigen 75 | | 153563 | 0.467870413003146 | -0.334208325739869 |
| 1123 | 1121452 | 1121452 :: BCL2A1 :: BCL2-related protein A1 | | 227817 | 0.047073151548673 | 0.008784276860166 |
| 1124 | 1121468 | 1121468 :: IL17R :: interleukin 17 receptor | | 129751 | 0.254701924480632 | -0.250835608176983 |
| 1125 | 1121473 | 1121473 :: ITGB7 :: integrin, beta 7 | | 1741 | 0.050306964647293 | -0.260994122489540 |
| 1126 | 1121482 | 1121482 :: OSMR :: oncostatin M receptor | | 238648 | 0.287543499924824 | -0.061526651754073 |
| 1127 | 1121497 | 1121497 :: CD8A :: CD8 antigen, alpha polypeptide (p32) | | 85258 | 0.254383170803894 | -0.508843134467300 |
| 1128 | 1121511 | 1121511 :: BIK :: BCL2-interacting killer (apoptosis-inducing) | | 155419 | -0.211383209660163 | 0.261057336302683 |
| 1129 | 1121516 | 1121516 :: CD1D :: CD1D antigen, d polypeptide | | 1799 | -0.172683395640843 | 0.187984153848567 |
| 1130 | 1121518 | 1121518 :: WISP2 :: WNT1 inducible signaling pathway protein 2 | | 194679 | 0.333528312498693 | -0.211973809992181 |
| 1131 | 1121533 | 1121533 :: KLRK1 :: killer cell lectin-like receptor subfamily K, member 1 | | 387787 | 0.170707791965083 | -0.181208812511698 |
| 1132 | 1121542 | 1121542 :: CD2 :: CD2 antigen (p50), sheep red blood cell receptor | | 89476 | 0.302548346747810 | -0.578942684928591 |
| 1133 | 1121546 | 1121546 :: VNN1 :: vanin 1 | | 12114 | 0.567093184662778 | -0.186561364898219 |
| 1134 | 1121554 | 1121554 :: TULP3 :: tubby like protein 3 | | 437046 | -0.056650771210584 | 0.127766542380693 |
| 1135 | 1121558 | 1121558 :: NGFR :: nerve growth factor receptor (TNFR superfamily, member 16) | | 415768 | 0.195753701211791 | -0.227262553501829 |
| 1136 | 1121559 | 1121559 :: LY86 :: lymphocyte antigen 86 | | 184018 | -0.155376905904987 | 0.017075510540213 |
| 1137 | 1121560 | 1121560 :: SPIB :: Spi-B transcription factor (Spi-1/PU.1 related) | | 437905 | -0.289957995332695 | 0.340996439336590 |
| 1138 | 1121564 | 1121564 :: DRIL1 :: dead ringer-like 1 (Drosophila) | | 437783 | -0.163786854286590 | 0.046472888560482 |
| 1139 | 1121572 | 1121572 :: LIFR :: leukemia inhibitory factor receptor | | 446501 | 0.067083275968437 | -0.093535191656365 |
| 1140 | 1121573 | 1121573 :: POU6F1 :: POU domain, class 6, transcription factor 1 | | 2815 | 0.254499733231130 | -0.444889325723879 |
| 1141 | 1121574 | 1121574 :: PRKCM :: protein kinase C, mu | | 2891 | 0.439535360328520 | -0.205359630656177 |

TABLE 2415-continued

GeneID.txt

| Order | UNIQID | NAME | GENEID | LN.cor | Pro.cor |
|---|---|---|---|---|---|
| 1142 | 1121584 | CX3CR1 :: chemokine (C-X-3-C motif) receptor 1 | 78913 | 0.056642673180032 | −0.293821160742612 |
| 1143 | 1121585 | CCNA1 :: cyclin A1 | 417050 | 0.132967965511067 | −0.0905511131678455 |
| 1144 | 1121587 | PNOC :: prepronociceptin | 371809 | −0.282566914984081 | 0.0534689074476172 |
| 1145 | 1121589 | MICA :: MHC class I polypeptide-related sequence A | 90598 | 0.099729225201395 | −0.121123956711348 |
| 1146 | 1121629 | BATF :: basic leucine zipper transcription factor, ATF-like | 41691 | −0.163961627042657 | 0.0589492773380032 |
| 1147 | 1121643 | AATK :: apoptosis-associated tyrosine kinase | 514575 | 0.235022117248436 | −0.174404212348862 |
| 1148 | 1121645 | CD84 :: CD84 antigen (leukocyte antigen) | 398093 | 0.461177430829423 | −0.431475417777315 |
| 1149 | 1121650 | GPR64 :: G protein-coupled receptor 64 | 421137 | 0.107743443918073 | −0.167252293860867 |
| 1150 | 1121655 | ITGA9 :: integrin, alpha 9 | 222 | −0.00329697764285 | −0.0308192070411264 |
| 1151 | 1121680 | SELP :: selectin P (granule membrane protein 140 kDa, antigen CD62) | 73800 | 0.185759516369856 | −0.431934182574265 |
| 1152 | 1121689 | B7 :: B7 gene | 155586 | 0.0265435717156240 | −0.0549490530087915 |
| 1153 | 1121693 | KIAA0450 :: KIAA0450 gene product | 170156 | 0.196900710769728 | −0.124900645118200 |
| 1154 | 1121695 | HCP5 :: HLA complex P5 | 511759 | 0.195273337988109 | −0.381571171508791 |
| 1155 | 1121711 | MAPK12 :: mitogen-activated protein kinase 12 | 432642 | −0.187453008816577 | 0.315641675037325 |
| 1156 | 1121717 | ZNF135 :: zinc finger protein 135 (clone pHZ-17) | 73964 | −0.095018154579005 | 0.154787074255348 |
| 1157 | 1121720 | STAT4 :: signal transducer and activator of transcription 4 | 80642 | 0.218763690606469 | −0.502198054702293 |
| 1158 | 1121722 | CD33 :: CD33 antigen (gp67) | 83731 | 0.276204494664653 | −0.362551394460205 |
| 1159 | 1121726 | BLR1 :: Burkitt lymphoma receptor 1, GTP binding protein (chemokine (C-X-C motif) receptor 5) | 113916 | −0.189249439889998 | 0.258207310335521 |
| 1160 | 1121739 | ADRB2 :: adrenergic, beta-2-, receptor, surface | 85863 | 0.068019769137243 | −0.110406382804294 |
| 1161 | 1121743 | IL3RA :: interleukin 3 receptor, alpha (low affinity) | 460433 | 0.418128176852651 | −0.393074905406381 |
| 1162 | 1121745 | TNFRSF7 :: tumor necrosis factor receptor superfamily, member 7 | 355307 | −0.049393561288948 | −0.199094753107042 |
| 1163 | 1121757 | ADRB2 :: adrenergic, beta-2-, receptor, surface | 2551 | −0.123856836471263 | −0.066380767065075 |
| 1164 | 1121759 | IL13RA2 :: interleukin 13 receptor, alpha 2 | 336046 | 0.096030075479116 | −0.004610449857012 |
| 1165 | 1121760 | BMP6 :: bone morphogenetic protein 6 | 285671 | −0.053975160456425 | −0.004161001141957 |
| 1166 | 1121762 | SLAMF1 :: signaling lymphocytic activation molecule family member 1 | 32970 | 0.321497941850406 | −0.439833541268522 |
| 1167 | 1121767 | PTGIR :: prostaglandin I2 (prostacyclin) receptor (IP) | 458324 | 0.401404596559871 | −0.371573726069884 |
| 1168 | 1121780 | LY64 :: lymphocyte antigen 64 homolog, radioprotective 105 kDa (mouse) | 87205 | −0.166019615235407 | 0.174712903252339 |
| 1169 | 1121783 | SELE :: selectin E (endothelial adhesion molecule 1) | 89546 | 0.501259144636438 | −0.323622231877142 |
| 1170 | 1121788 | STK23 :: serine/threonine kinase 23 | 104865 | 0.096615237663810 | −0.087773525250173 |
| 1171 | 1121792 | TNFRSF10C :: tumor necrosis factor receptor superfamily, member 10c, decoy without an intracellular domain | 119684 | 0.015465407320874 | −0.016309866660398 |
| 1172 | 1121793 | KPI2 :: kinase phosphatase inhibitor 2 | 122708 | 0.010013315668082 | −0.019382995908031 |
| 1173 | 1121809 | MICB :: MHC class I polypeptide-related sequence B | 211580 | −0.140424139371804 | 0.239690343077825 |
| 1174 | 1121814 | BLK :: B lymphoid tyrosine kinase | 389900 | −0.311965481456666 | 0.229138774463185 |
| 1175 | 1121828 | TLR3 :: toll-like receptor 3 | 29499 | 0.342320705636510 | −0.203784020011193 |
| 1176 | 1121834 | PRKY :: protein kinase, Y-linked | 183165 | 0.060119302404676 | −0.023441991964129 |
| 1177 | 1121841 | NTS :: neurotensin | 80962 | −0.147437100102581 | 0.0375733897796696 |
| 1178 | 1121844 | IL18 :: interleukin 18 (interferon-gamma-inducing factor) | 83077 | 0.681064455964660 | −0.401312565491562 |
| 1179 | 1121848 | TEC :: tec protein tyrosine kinase | 278005 | 0.007139144026899 | 0.0777862778989995 |
| 1180 | 1121853 | SPINK2 :: serine protease inhibitor, Kazal type, 2 (acrosin-trypsin inhibitor) | 98243 | 0.231340981766496 | −0.118178578456530 |
| 1181 | 1121854 | GUCY2C :: guanylate cyclase 2C (heat stable enterotoxin receptor) | 171470 | −0.166410484543226 | 0.015691903143909 |
| 1182 | 1121857 | CRLF1 :: cytokine receptor-like factor 1 | 114948 | 0.069617938465999 | 0.053913442948466 |
| 1183 | 1121869 | CXCL6 :: chemokine (C-X-C motif) ligand 6 (granulocyte chemotactic protein 2) | 164021 | 0.144226064872636 | −0.051053576857340 |
| 1184 | 1121870 | CCR7 :: chemokine (C-C motif) receptor 7 | 1652 | −0.067933367028353 | −0.306029747322952 |
| 1185 | 1121874 | IL2RA :: interleukin 2 receptor, alpha | 130058 | −0.051302661595226 | 0.043326548605735 |
| 1186 | 1121887 | MAF :: v-maf musculoaponeurotic fibrosarcoma oncogene homolog (avian) | 134859 | 0.291531644291303 | −0.423337706028555 |
| 1187 | 1121918 | FER :: fer (fps/fes related) tyrosine kinase (phosphoprotein NCP94) | 121558 | −0.081261198422925 | −0.022672401143613 |
| 1188 | 1121947 | BMX :: BMX non-receptor tyrosine kinase | 27372 | −0.045807586018934 | −0.042093914097017 |
| 1189 | 1121953 | KIAA0125 :: KIAA0125 | 38365 | −0.074164934794289 | 0.0939426718632 |
| 1190 | 1121956 | PTK6 :: PTK6 protein tyrosine kinase 6 | 51133 | −0.017027713991015 | −0.158651344799207 |

TABLE 2415-continued

GeneID.txt

| Order | UNIQID | NAME | GENEID | LN.cor | Pro.cor |
|---|---|---|---|---|---|
| 1191 | 1121959 | 1121959 : LAG3 :: lymphocyte-activation gene 3 | 409523 | 0.193959621692431 | −0.437806691232694 |
| 1192 | 1121963 | 1121963 : ITGA2B :: integrin, alpha 2b (platelet glycoprotein IIb of IIb/IIIa complex, antigen CD41B) | 411312 | −0.279619286050182 | 0.284911304714724 |
| 1193 | 1121966 | 1121966 : OCA2 :: oculocutaneous albinism II (pink-eye dilution homolog, mouse) | 82027 | −0.126556699537153 | −0.138777934994851 |
| 1194 | 1121970 | 1121970 : TNFSF7 :: tumor necrosis factor (ligand) superfamily, member 7 | 99899 | −0.052884033648974 | 0.076289357833760 |
| 1195 | 1121996 | 1121996 : CD28 :: CD28 antigen (Tp44) | 1987 | 0.189150158821898 | −0.444718988396679 |
| 1196 | 1122007 | 1122007 : IL24 :: interleukin 24 | 411311 | −0.043959538709898 | −0.038229511247943 |
| 1197 | 1122009 | 1122009 : CDKL5 :: cyclin-dependent kinase-like 5 | 50905 | −0.110217563326053 | 0.038629974027743 |
| 1198 | 1122021 | 1122021 : RAG1 :: recombination activating gene 1 | 73958 | 0.003594546430902 | −0.000989138304343 |
| 1199 | 1122036 | 1122036 : IL18R1 :: interleukin 18 receptor 1 | 159301 | 0.022775763687888 | −0.206454025052186 |
| 1200 | 1122051 | 1122051 : GPR105 :: G protein-coupled receptor 105 | 2465 | 0.059326766092437 | −0.376983837880304 |
| 1201 | 1122053 | 1122053 : TNFRSF17 :: tumor necrosis factor receptor superfamily, member 17 | 2556 | −0.118896791192488 | −0.141169001959615 |
| 1202 | 1122065 | 1122065 : IGLL1 :: immunoglobulin lambda-like polypeptide 1 | 348935 | −0.101518631934236 | 0.138251188755721 |
| 1203 | 1122075 | 1122075 : FLT3 :: fms-related tyrosine kinase 3 | 385 | −0.023290399924544 | −0.134479118790636 |
| 1204 | 1122087 | 1122087 : IL7 :: interleukin 7 | 72927 | −0.054663149358440 | 0.163686002792952 |
| 1205 | 1122091 | 1122091 : TEK :: TEK tyrosine kinase, endothelial (venous malformations, multiple cutaneous and mucosal) | 89640 | 0.405091912365656 | −0.229314036859117 |
| 1206 | 1122104 | 1122104 : LMO1 :: LIM domain only 1 (rhombotin 1) | 1149 | −0.088512856329657 | 0.001423124698225 |
| 1207 | 1122112 | 1122112 : TNFRSF8 :: tumor necrosis factor receptor superfamily, member 8 | 1314 | 0.306311234222199 | −0.257781706040248 |
| 1208 | 1122131 | 1122131 : CHST7 :: carbohydrate (N-acetylglucosamine 6-O) sulfotransferase 7 | 138155 | 0.017714188893945 | −0.187857053179300 |
| 1209 | 1122139 | 1122139 : ITGA10 :: integrin, alpha 10 | 158237 | −0.126540289117975 | −0.102013873270510 |
| 1210 | 1122156 | 1122156 : ERBB4 :: v-erb-a erythroblastic leukemia viral oncogene homolog 4 (avian) | 1939 | −0.201573406555134 | 0.167789413767230 |
| 1211 | 1122165 | 1122165 : CD3G :: CD3G antigen, gamma polypeptide (TiT3 complex) | 2259 | 0.255114685310457 | −0.501702664933897 |
| 1212 | 1122181 | 1122181 : TXK :: TXK tyrosine kinase | 29877 | 0.116717796088994 | −0.338924617001779 |
| 1213 | 1122215 | 1122215 : CCBP2 :: chemokine binding protein 2 | 24286 | −0.095047926225869 | 0.017068598097254 |
| 1214 | 1122217 | 1122217 : IL12RB1 :: interleukin 12 receptor, beta 1 | 223894 | −0.057505725481306 | 0.035649057057820 |
| 1215 | 1122219 | 1122219 : AMHR2 :: anti-Mullerian hormone receptor, type II | 437877 | −0.056887826816452 | −0.019958969581757 |
| 1216 | 1122230 | 1122230 : TNFSF9 :: tumor necrosis factor (ligand) superfamily, member 9 | 1524 | −0.225333682313531 | 0.214293634736012 |
| 1217 | 1122241 | 1122241 : PRKCA :: protein kinase C, alpha | 349611 | −0.004779534344590 | 0.129090253603676 |
| 1218 | 1122253 | 1122253 : TGFBR1 :: transforming growth factor, beta receptor I (activin A receptor type II-like kinase, 53 kDa) | 28805 | 0.014232227032144 | 0.012676202249217 |
| 1219 | 1122274 | 1122274 : CXCR6 :: chemokine (C-X-C motif) receptor 6 | 34526 | 0.291116004542739 | −0.538726060188242 |
| 1220 | 1122275 | 1122275 : LTA :: lymphotoxin alpha (TNF superfamily, member 1) | 36 | 0.272859492127863 | −0.052120311047222 |
| 1221 | 1122277 | 1122277 : CCR2 :: chemokine (C-C motif) receptor 2 | 511794 | 0.312042067191461 | −0.414949503001742 |
| 1222 | 1122281 | 1122281 : CCR6 :: chemokine (C-C motif) receptor 6 | 46468 | −0.003994610054083 | −0.285880226053799 |
| 1223 | 1122284 | 1122284 : CCL25 :: chemokine (C-C motif) ligand 25 | 310511 | −0.011468124459718 | 0.021672293312355 |
| 1224 | 1122288 | 1122288 : IL12RB2 :: interleukin 12 receptor, beta 2 | 413608 | 0.126082647687914 | −0.226273945847826 |
| 1225 | 1122292 | 1122292 : IL8RB :: interleukin 8 receptor, beta | 846 | −0.024711905520565 | −0.102623869064591 |
| 1226 | 1122304 | 1122304 : KITLG :: KIT ligand | 1048 | −0.055609736205835 | 0.138263983925332 |
| 1227 | 1122327 | 1122327 : ERN1 :: ER to nucleus signalling 1 | 137575 | −0.081788789340055 | 0.000256455518645 |
| 1228 | 1122335 | 1122335 : CDKL2 :: cyclin-dependent kinase-like 2 (CDC2-related kinase) | 143241 | −0.064687268142039 | −0.099486553801662 |
| 1229 | 1122344 | 1122344 : IL8RA :: interleukin 8 receptor, alpha | 194778 | 0.010181353539432 | −0.043034622453406 |
| 1230 | 1122353 | 1122353 : EMR1 :: egf-like module containing, mucin-like, hormone receptor-like 1 | 2375 | 0.070191511848735 | −0.358463771479546 |
| 1231 | 1122380 | 1122380 : IL12A :: interleukin 12A (natural killer cell stimulatory factor 1, cytotoxic lymphocyte maturation factor 1, p35) | 673 | −0.156980730012675 | 0.067544361254343 |
| 1232 | 1122382 | 1122382 : HMMR :: hyaluronan-mediated motility receptor (RHAMM) | 72550 | −0.364008235773999 | 0.783745372336510 |
| 1233 | 1122388 | 1122388 : TLX1 :: T-cell leukemia, homeobox 1 | 89583 | −0.006028747857682 | 0.090819031432347 |
| 1234 | 1122394 | 1122394 : CDK3 :: cyclin-dependent kinase 3 | 100009 | −0.109434076904651 | 0.005235741268251 |
| 1235 | 1122400 | 1122400 : TERT :: telomerase reverse transcriptase | 439911 | −0.305126651996366 | 0.360989824065773 |
| 1236 | 1122412 | 1122412 : TNFSF8 :: tumor necrosis factor (ligand) superfamily, member 8 | 177136 | −0.173470362237192 | 0.039366962226564 |
| 1237 | 1122420 | 1122420 : PRKACG :: protein kinase, cAMP-dependent, catalytic, gamma | 158029 | −0.042291694825976 | 0.107568347535975 |
| 1238 | 1122428 | 1122428 : UGT2B17 :: UDP glycosyltransferase 2 family, polypeptide B17 | 183596 | −0.009708775277058 | −0.154853580284755 |

TABLE 2415-continued

GeneID.txt

| Order | UNIQID | NAME | GENEID | LN.cor | Pro.cor |
|---|---|---|---|---|---|
| 1239 | 1122449 | 1122449 :: CD209 :: CD209 antigen | 278694 | -0.054065050435346 | -0.148476591045507 |
| 1240 | 1122471 | 1122471 :: PHKG1 :: phosphorylase kinase, gamma 1 (muscle) | 512612 | 0.0799328560062166 | -0.0810392809982416 |
| 1241 | 1122491 | 1122491 :: CCL16 :: chemokine (C-C motif) ligand 16 | 10458 | -0.182443367350429 | 0.080347048721680 |
| 1242 | 1122537 | 1122537 :: IL10 :: interleukin 10 | 193717 | 0.084051369998383 | -0.014477195723495 |
| 1243 | 1122541 | 1122541 :: CSF3 :: colony stimulating factor 3 (granulocyte) | 2233 | 0.0233780703597223 | -0.012578972648323 |
| 1244 | 1122544 | 1122544 :: TLR6 :: toll-like receptor 6 | 366986 | -0.034908792550942 | -0.117728563898484 |
| 1245 | 1122581 | 1122581 :: PRKG2 :: protein kinase, cGMP-dependent, type II | 41749 | 0.0327015674117012 | 0.012446049249384 |
| 1246 | 1122596 | 1122596 :: CCL1 :: chemokine (C-C motif) ligand 1 | 72918 | 0.016785310093019 | -0.118957054913180 |
| 1247 | 1122599 | 1122599 :: IL4 :: interleukin 4 | 73917 | 0.018527418005221 | -0.024997209419818 |
| 1248 | 1122602 | 1122602 :: MPL :: myeloproliferative leukemia virus oncogene | 84171 | -0.028592483197097 | 0.035730086206858 |
| 1249 | 1122609 | 1122609 :: CHRNA6 :: cholinergic receptor, nicotinic, alpha polypeptide 6 | 103128 | 0.140574731162138 | -0.089510942877138 |
| 1250 | 1122610 | 1122610 :: ROS1 :: v-ros UR2 sarcoma virus oncogene homolog 1 (avian) | 1041 | 0.052118846272900 | -0.039273113315543 |
| 1251 | 1122640 | 1122640 :: PDCD1 :: programmed cell death 1 | 158297 | 0.0378847997009331 | -0.335541082139966 |
| 1252 | 1122645 | 1122645 :: TNFRSF13B :: tumor necrosis factor receptor superfamily, member 13B | 158341 | -0.357072434096211 | 0.193042174649931 |
| 1253 | 1122664 | 1122664 :: CXCR3 :: chemokine (C-X-C motif) receptor 3 | 198252 | 0.247485780222157 | -0.455289533280340 |
| 1254 | 1122680 | 1122680 :: PRKAA2 :: protein kinase, AMP-activated, alpha 2 catalytic subunit | 256067 | 0.129427414307946 | -0.021680077911729 |
| 1255 | 1122710 | 1122710 :: CDKL1 :: cyclin-dependent kinase-like 1 (CDC2-related kinase) | 380788 | -0.130816816182024 | 0.037546570109463 |
| 1256 | 1122738 | 1122738 :: CD160 :: CD160 antigen | 81743 | -0.0804923048119797 | -0.166670719053082 |
| 1257 | 1122740 | 1122740 :: IL13 :: interleukin 13 | 845 | -0.045698316016691 | 0.035475880600793 |
| 1258 | 1122743 | 1122743 :: IL2 :: interleukin 2 | 89679 | -0.018591226450345 | -0.082394388827525 |
| 1259 | 1122744 | 1122744 :: CXCL3 :: chemokine (C-X-C motif) ligand 3 | 89690 | 0.201982112102107 | -0.162220923472979 |
| 1260 | 1122749 | 1122749 :: CCL22 :: chemokine (C-C motif) ligand 22 | 97203 | 0.126129955425322 | -0.113302826242635 |
| 1261 | 1122763 | 1122763 :: GUCY2D :: guanylate cyclase 2D, membrane (retina-specific) | 309958 | 0.092659149259446 | -0.222285418267571 |
| 1262 | 1122767 | 1122767 :: TNFSF5 :: tumor necrosis factor (ligand) superfamily, member 5 (hyper-IgM syndrome) | 652 | 0.094318123549143 | -0.250910889088908 |
| 1263 | 1122772 | 1122772 :: CCL17 :: chemokine (C-C motif) ligand 17 | 66742 | 0.224016681721616 | -0.157484933905442 |
| 1264 | 1122773 | 1122773 :: IL12B :: interleukin 12B (natural killer cell stimulatory factor 2, cytotoxic lymphocyte maturation factor 2, p40) | 674 | 0.157191653410742 | -0.031305411933949 |
| 1265 | 1122774 | 1122774 :: IL5RA :: interleukin 5 receptor, alpha | 68876 | 0.033919120198367 | 0.031505076254719 |
| 1266 | 1122775 | 1122775 :: IL3 :: interleukin 3 (colony-stimulating factor, multiple) | 694 | 0.027509333381645 | 0.004526584546124 |
| 1267 | 1122776 | 1122776 :: TNFSF14 :: tumor necrosis factor (ligand) superfamily, member 14 | 129708 | 0.086682929814505 | -0.077782141454216 |
| 1268 | 1122796 | 1122796 :: IL5 :: interleukin 5 (colony-stimulating factor, eosinophil) | 2247 | 0.031894751519528 | 0.038555120526004 |
| 1269 | 1122824 | 1122824 :: IL1RL2 :: interleukin 1 receptor-like 2 | 416814 | 0.418472381199476 | -0.109242280419714 |
| 1270 | 1122834 | 1122834 :: CCR8 :: chemokine (C-C motif) receptor 8 | 113222 | -0.076673872782458 | -0.054598693128587 |
| 1271 | 1122863 | 1122863 :: IL9 :: interleukin 9 | 960 | 0.063436658685755 | -0.069964371334722 |
| 1272 | 1122864 | 1122864 :: TTN :: titin | 434384 | -0.079878461568367 | 0.057803856684836 |
| 1273 | 1122865 | 1122865 :: IL1A :: interleukin 1, alpha | 1722 | -0.053194591719340 | 0.097988885553944 |
| 1274 | 1122914 | 1122914 :: CCR3 :: chemokine (C-C motif) receptor 3 | 506190 | 0.067137799577373 | -0.079786679856537 |
| 1275 | 1122939 | 1122939 :: CCR4 :: chemokine (C-C motif) receptor 4 | 184926 | 0.000316877107091 | -0.040599986051264 |
| 1276 | 1122956 | 1122956 :: LGALS2 :: lectin, galactoside-binding, soluble, 2 (galectin 2) | 113987 | 0.418472381199476 | -0.449328556890785 |
| 1277 | 1122983 | 1122983 :: TLX3 :: T-cell leukemia, homeobox 3 | 249125 | -0.0326690658625 | -0.023843091659097 |
| 1278 | 1122994 | 1122994 :: GPR15 :: G protein-coupled receptor 15 | 159900 | -0.062091251933203 | -0.043311935732794 |
| 1279 | 1123026 | 1123026 :: SCN10A :: sodium channel, voltage-gated, type X, alpha | 250443 | -0.116973597586132 | 0.070503156564898 |
| 1280 | 1123038 | 1123038 :: ACTN1 :: actinin, alpha 1 | 119000 | 0.873550079736042 | -0.478675322021290 |
| 1281 | 1123039 | 1123039 :: P5 :: protein disulfide isomerase-related protein | 212102 | -0.033833903377211 | 0.140785743381923 |
| 1282 | 1123052 | 1123052 :: PRDX1 :: peroxiredoxin 1 | 180909 | 0.191988590052824 | 0.162925830590233 |
| 1283 | 1123053 | 1123053 :: CAPN2 :: calpain 2, (m/II) large subunit | 350899 | 0.421280597945986 | -0.436423248559518 |
| 1284 | 1123055 | 1123055 :: TFRC :: transferrin receptor (p90, CD71) | 113987 | 0.040040686678309 | 0.144813077262144 |
| 1285 | 1123086 | 1123086 :: CSNK1D :: casein kinase 1, delta | 185726 | -0.155935500932564 | -0.190171534622886 |
| 1286 | 1123105 | 1123105 :: PTK2 :: PTK2 protein tyrosine kinase 2 | 434281 | 0.288913388096928 | -0.065583389930882 |

TABLE 2415-continued

GeneID.txt

| Order | UNIQID | NAME | GENEID | LN.cor | Pro.cor |
|---|---|---|---|---|---|
| 1287 | 1123108 | POLE3 :: polymerase (DNA directed), epsilon 3 (p17 subunit) | 108112 | -0.436072096527712 | 0.682902758497920 |
| 1288 | 1123127 | HLA-DRA :: major histocompatibility complex, class II, DR alpha | 409805 | 0.047143225726272 | -0.242770437918495 |
| 1289 | 1123148 | TGFBR2 :: transforming growth factor, beta receptor II (70/80 kDa) | 82028 | 0.010273158752569 | -0.246551848934111 |
| 1290 | 1123160 | PECAM1 :: platelet/endothelial cell adhesion molecule (CD31 antigen) | 78146 | 0.369552095411465 | -0.455742171741395 |
| 1291 | 1123163 | STAT3 :: signal transducer and activator of transcription 3 (acute-phase response factor) | 421342 | 0.088647677138997 | -0.076284629745413 |
| 1292 | 1123188 | RAB5A :: RAB5A, member RAS oncogene family | 73957 | 0.023479248710834 | -0.110193635053030 |
| 1293 | 1123192 | IFRD2 :: interferon-related developmental regulator 2 | 315177 | -0.486021348173979 | 0.488527458940548 |
| 1294 | 1123193 | CTGF :: connective tissue growth factor | 410037 | 0.729604445971057 | -0.281419391890177 |
| 1295 | 1123198 | CDKN1B :: cyclin-dependent kinase inhibitor 1B (p27, Kip1) | 238990 | 0.042312425837938 | -0.252049352477715 |
| 1296 | 1123213 | TIP-1 :: Tax interaction protein 1 | 12956 | 0.478214019444825 | -0.210865933337574 |
| 1297 | 1123223 | AGR2 :: anterior gradient 2 homolog (Xenopus laevis) | 226391 | 0.144465715233955 | -0.064593480852986 |
| 1298 | 1123231 | FOS :: v-fos FBJ murine osteosarcoma viral oncogene homolog | 25647 | 0.454770929296200 | -0.327994685230221 |
| 1299 | 1123233 | PIM1 :: pim-1 oncogene | 81170 | -0.260781292717673 | 0.122887357920644 |
| 1300 | 1123235 | C6orf11 :: chromosome 6 open reading frame 11 | 436930 | -0.301325588310411 | 0.312607703475414 |
| 1301 | 1123250 | C2F :: C2f protein | 135643 | -0.408607477799746 | 0.542558649958536 |
| 1302 | 1123255 | NFKB1 :: nuclear factor of kappa light polypeptide gene enhancer in B-cells 1 (p105) | 160557 | -0.247639376875525 | 0.307813059694491 |
| 1303 | 1123278 | TNFRSF10B :: tumor necrosis factor receptor superfamily, member 10b | 51233 | 0.231916040100982 | -0.133446996009752 |
| 1304 | 1123286 | BCL2L2 :: BCL2-like 2 | 410026 | 0.430813129995590 | -0.256934797251460 |
| 1305 | 1123289 | POLR1C :: polymerase (RNA) I polypeptide C, 30 kDa | 5409 | -0.439470276015570 | 0.558476803814871 |
| 1306 | 1123293 | ULK1 :: unc-51-like kinase 1 (C. elegans) | 47061 | 0.234598147527924 | -0.243014710846460 |
| 1307 | 1123298 | SIAH2 :: seven in absentia homolog 2 (Drosophila) | 20191 | -0.020735974007859 | 0.251511790730967 |
| 1308 | 1123304 | TNFRSF14 :: tumor necrosis factor receptor superfamily, member 14 (herpesvirus entry mediator) | 279899 | 0.406281787477635 | -0.640800528626002 |
| 1309 | 1123308 | BAD :: BCL2-antagonist of cell death | 76366 | -0.055804103966625 | 0.200577209644432 |
| 1310 | 1123310 | EPHX2 :: epoxide hydrolase 2, cytoplasmic | 212088 | 0.032733558863813 | -0.191468518846761 |
| 1311 | 1123317 | TM4SF1 :: transmembrane 4 superfamily member 1 | 351316 | 0.511959563150185 | -0.296195607797757 |
| 1312 | 1123321 | ENPP2 :: ectonucleotide pyrophosphatase/phosphodiesterase 2 (autotaxin) | 23719 | 0.354323804583203 | -0.255357585629660 |
| 1313 | 1123331 | GRB10 :: growth factor receptor-bound protein 10 | 512218 | 0.546048470195960 | -0.318504437702318 |
| 1314 | 1123346 | SERPINA3 :: serine (or cysteine) proteinase inhibitor, clade A (alpha-1 antiproteinase, antitrypsin), member 3 | 76353 | 0.043287278241036 | 0.026601557579208 |
| 1315 | 1123358 | AURKB :: aurora kinase B | 442658 | -0.383920119898266 | 0.752036804939408 |
| 1316 | 1123369 | SNRK :: SNF-1 related kinase | 79025 | 0.063554265111443 | -0.312500317456464 |
| 1317 | 1123372 | RBPMS :: RNA binding protein with multiple splicing | 195825 | 0.729190743697357 | -0.416042636778450 |
| 1318 | 1123376 | RARRES2 :: retinoic acid receptor responder (tazarotene induced) 2 | 37682 | 0.767753207447146 | -0.419368115432137 |
| 1319 | 1123399 | IGF1 :: insulin-like growth factor 1 (somatomedin C) | 308053 | 0.351339548125761 | -0.181596238406175 |
| 1320 | 1123401 | NDN :: necdin homolog (mouse) | 50130 | 0.666817448656187 | -0.449821627439369 |
| 1321 | 1123413 | IL10RB :: interleukin 10 receptor, beta | 418291 | 0.143751576129052 | -0.265149372827460 |
| 1322 | 1123419 | CD74 :: CD74 antigen (invariant polypeptide of major histocompatibility complex, class II antigen-associated) | 170195 | -0.025788274570143 | 0.099776284015714 |
| 1323 | 1123429 | STK16 :: serine/threonine kinase 16 | 446471 | -0.002859916045464 | -0.296446042702963 |
| 1324 | 1123430 | NFKB2 :: nuclear factor of kappa light polypeptide gene enhancer in B-cells 2 (p49/p100) | 153003 | -0.161361543713864 | 0.064323356701808 |
| 1325 | 1123437 | BMP7 :: bone morphogenetic protein 7 (osteogenic protein 1) | 73090 | 0.219171220578543 | -0.215739729198764 |
| 1326 | 1123439 | BUB1 :: BUB1 budding uninhibited by benzimidazoles 1 homolog (yeast) | 287472 | -0.257755664849282 | 0.734307550843963 |
| 1327 | 1123455 | CBLB :: Cas-Br-M (murine) ecotropic retroviral transforming sequence b | 436986 | -0.033290616456071 | -0.205794640235363 |
| 1328 | 1123457 | RIN2 :: Ras and Rab interactor2 | 446304 | 0.795227551186921 | -0.522963551553488 |
| 1329 | 1123459 | CXCL12 :: chemokine (C-X-C motif) ligand 12 (stromal cell-derived factor 1) | 436042 | 0.338116509418455 | -0.536175354841238 |
| 1330 | 1123470 | M96 :: likely ortholog of mouse metal response element binding transcription factor 2 | 31016 | -0.246647928566614 | 0.506958649157703 |
| 1331 | 1123476 | SLC35D1 :: solute carrier family 35 (UDP-glucuronic acid/UDP-N-acetylgalactosamine dual transporter), member D1 | 82635 | 0.038691099915535 | 0.137047545122540 |
| 1332 | 1123479 | CSF1 :: colony stimulating factor 1 (macrophage) | 173894 | 0.565439636313831 | -0.571152588046333 |
| 1333 | 1123490 | CLECSF2 :: C-type (calcium dependent, carbohydrate-recognition domain) lectin, superfamily member 2 (activation-induced) | 85201 | 0.437423696558292 | -0.418715249984207 |

TABLE 2415-continued

| Order | UNIQID | NAME | GeneID.txt | GENEID | LN.cor | Pro.cor |
|---|---|---|---|---|---|---|
| 1334 | 1123497 | 1123497 : TGFB3 :: transforming growth factor, beta 3 | | 2025 | 0.419181791755442 | -0.341070014629490 |
| 1335 | 1123502 | 1123502 : KIAA0922 :: KIAA0922 protein | | 511944 | -0.430991697827225 | 0.463134135573600 |
| 1336 | 1123507 | 1123507 : BTN3A1 :: butyrophilin, subfamily 3, member A1 | | 284283 | 0.198254555831932 | -0.590128827200630 |
| 1337 | 1123529 | 1123529 : PTCH :: patched homolog (Drosophila) | | 159526 | -0.162582198261289 | 0.118247234101131 |
| 1338 | 1123535 | 1123535 : C6orf32 :: chromosome 6 open reading frame 32 | | 389488 | -0.248332319157757 | 0.033447287747404 |
| 1339 | 1123552 | 1123552 : SELPLG :: selectin P ligand | | 423077 | 0.480246751583851 | -0.619068427619529 |
| 1340 | 1123566 | 1123566 : C3AR1 :: complement component 3a receptor 1 | | 155935 | 0.371658703605566 | -0.442232534412039 |
| 1341 | 1123573 | 1123573 : CCL18 :: chemokine (C-C motif) ligand 18 (pulmonary and activation-regulated) | | 16530 | -0.014202367476697 | -0.100068061738832 |
| 1342 | 1123581 | 1123581 : RIPK1 :: receptor (TNFRSF)-interacting serine-threonine kinase 1 | | 390758 | 0.136323407164192 | -0.285283218731897 |
| 1343 | 1123584 | 1123584 : VEGFC :: vascular endothelial growth factor C | | 79141 | 0.472324986740103 | -0.294475802861250 |
| 1344 | 1123586 | 1123586 : KCNMB1 :: potassium large conductance calcium-activated channel, subfamily M, beta member 1 | | 93841 | 0.508193311461163 | -0.344403736032782 |
| 1345 | 1123587 | 1123587 : NCF2 :: neutrophil cytosolic factor 2 (65 kDa, chronic granulomatous disease, autosomal 2) | | 949 | 0.283363445260573 | -0.264421095224310 |
| 1346 | 1123608 | 1123608 : MALT1 :: mucosa associated lymphoid tissue lymphoma translocation gene 1 | | 180566 | 0.047487079344585 | -0.196154131449671 |
| 1347 | 1123611 | 1123611 : INDO :: indoleamine-pyrrole 2,3 dioxygenase | | 840 | 0.253222128158468 | -0.456068797135009 |
| 1348 | 1123613 | 1123613 : CD2Z :: CD2Z antigen, zeta polypeptide (TiT3 complex) | | 97087 | 0.150625230309775 | -0.337757592132146 |
| 1349 | 1123614 | 1123614 : PRKCQ :: protein kinase C, theta | | 408049 | 0.305157114586210 | -0.562196305322430 |
| 1350 | 1123622 | 1123622 : EPAC :: Rap1 guanine-nucleotide-exchange factor directly activated by cAMP | | 8578 | 0.023864373661857 | -0.205096809629451 |
| 1351 | 1123628 | 1123628 : MAPK13 :: mitogen-activated protein kinase 13 | | 178695 | 0.033235172641225 | -0.074571795620075 |
| 1352 | 1123634 | 1123634 : CCL19 :: chemokine (C-C motif) ligand 19 | | 50002 | 0.237018077209330 | -0.370272180731036 |
| 1353 | 1123635 | 1123635 : SIAT8A :: sialyltransferase 8A (alpha-N-acetylneuraminate: alpha-2,8-sialyltransferase, GD3 synthase) | | 408614 | 0.199110301196979 | -0.415743690175678 |
| 1354 | 1123643 | 1123643 : MAGOH :: mago-nashi homolog, proliferation-associated (Drosophila) | | 421576 | -0.355879676099144 | 0.581734359749056 |
| 1355 | 1123663 | 1123663 : CCL11 :: chemokine (C-C motif) ligand 11 | | 54460 | 0.264138548531733 | -0.204563118558087 |
| 1356 | 1123671 | 1123671 : HIPK3 :: homeodomain interacting protein kinase 3 | | 30148 | 0.047603482330918 | 0.055945015733371 |
| 1357 | 1123672 | 1123672 : LILRB4 :: leukocyte immunoglobulin-like receptor, subfamily B (with TM and ITIM domains), member 4 | | 67846 | 0.478261377044532 | -0.316050786052444 |
| 1358 | 1123679 | 1123679 : CXCL11 :: chemokine (C-X-C motif) ligand 11 | | 103982 | 0.104249322264231 | -0.363739751119532 |
| 1359 | 1123680 | 1123680 : GZMB :: granzyme B (granzyme 2, cytotoxic T-lymphocyte-associated serine esterase 1) | | 1051 | 0.089403932441954 | -0.206108503310258 |
| 1360 | 1123682 | 1123682 : TLR5 :: toll-like receptor 5 | | 114408 | 0.339045664045358 | -0.420163223335381 |
| 1361 | 1123690 | 1123690 : TLR1 :: toll-like receptor 1 | | 111805 | 0.315917942895492 | -0.331871994493504 |
| 1362 | 1123694 | 1123694 : ITGAX :: integrin, alpha X (antigen CD11C (p150), alpha polypeptide) | | 385521 | 0.624065221290532 | -0.401652202104813 |
| 1363 | 1123731 | 1123731 : RGS13 :: regulator of G-protein signalling 13 | | 17165 | 0.094370061595793 | 0.059059084280978 |
| 1364 | 1123744 | 1123744 : GPR18 :: G protein-coupled receptor 18 | | 88269 | -0.051858332062774 | -0.095369670056525 |
| 1365 | 1123760 | 1123760 : ILT7 :: leukocyte immunoglobulin-like receptor, subfamily A (without TM domain), member 4 | | 406708 | -0.202312173039078 | -0.048154927899969 |
| 1366 | 1123762 | 1123762 : FLT4 :: fms-related tyrosine kinase 4 | | 415048 | 0.007820470422523 | 0.029361292237663 |
| 1367 | 1123778 | 1123778 : CAMK4 :: calcium/calmodulin-dependent protein kinase IV | | 440638 | -0.092561842977911 | 0.158012560576592 |
| 1368 | 1123780 | 1123780 : IFNG :: interferon, gamma | | 856 | 0.123476147166574 | -0.362163213194207 |
| 1369 | 1123814 | 1123814 : ICOS :: inducible T-cell co-stimulator | | 56247 | 0.192515826351840 | -0.464793820617578 |
| 1370 | 1123816 | 1123816 : IL1RL1 :: interleukin 1 receptor-like 1 | | 66 | 0.186852010516034 | -0.130615795169223 |
| 1371 | 1123833 | 1123833 : DNTT :: deoxynucleotidyltransferase, terminal | | -32 | -0.056799193445582 | -0.009669825386535 |
| 1372 | 1123842 | 1123842 : FUT7 :: fucosyltransferase 7 (alpha (1,3) fucosyltransferase) | | 457 | 0.137471775731450 | -0.222998236046438 |
| 1373 | 1123847 | 1123847 : BMPR1B :: bone morphogenetic protein receptor, type IB | | 87223 | 0.025637318140648 | -0.036872289193971 |
| 1374 | 1123875 | 1123875 : FLT3LG :: fms-related tyrosine kinase 3 ligand | | 428 | 0.156345539863462 | -0.365585933777951 |
| 1375 | 1123889 | 1123889 : TNFSF11 :: tumor necrosis factor (ligand) superfamily, member 11 | | 333791 | -0.074241864883289 | -0.115085296863344 |
| 1376 | 1123890 | 1123890 : TNFRSF10D :: tumor necrosis factor receptor superfamily, member 10d, decoy with truncated death domain | | 129844 | -0.031223526539161 | -0.058937352170284 |
| 1377 | 1123892 | 1123892 : CMKLR1 :: chemokine-like receptor 1 | | 159553 | 0.322809856731336 | -0.382060391333891 |
| 1378 | 1123938 | 1123938 : FPRL1 :: formyl peptide receptor-like 1 | | 99855 | 0.137586060931396 | -0.155416553108998 |
| 1379 | 1123954 | 1123954 : TNFSF6 :: tumor necrosis factor (ligand) superfamily, member 6 | | 2007 | 0.182530654744065 | -0.397622965632797 |
| 1380 | 1123988 | 1123988 : LAT :: linker for activation of T cells | | 498997 | 0.229116696368979 | -0.579887127104931 |
| 1381 | 1124049 | 1124049 : my048 :: my048 protein | | -1 | -0.037955390490940 | -0.086367167725680 |
| 1382 | 1124132 | 1124132 : PRDX2 :: peroxiredoxin 2 | | 432121 | -0.125199234865877 | 0.288816173026307 |

TABLE 2415-continued

GeneID.txt

| Order | UNIQID | NAME | GENEID | LN.cor | Pro.cor |
|---|---|---|---|---|---|
| 1383 | 1124137 | 1124137 : MGC27165 :: hypothetical protein MGC27165 | 366 | -0.128484811098311 | 0.10051021596324 |
| 1384 | 1124176 | 1124176 : COL4A2 :: collagen, type IV, alpha 2 | 407912 | 0.536181799440743 | -0.067710785250196 |
| 1385 | 1124177 | 1124177 : PORIMIN :: pro-oncosis receptor inducing membrane injury gene | 172089 | 0.0180312566008808 | 0.0285468749246555 |
| 1386 | 1124178 | 1124178 : HSPCA :: heat shock 90 kDa protein 1, alpha | 446579 | -0.115263936938935 | 0.214973051423235 |
| 1387 | 1124187 | 1124187 : MGC5395 :: hypothetical protein MGC5395 | 378738 | 0.349346778708932 | -0.417635861357430 |
| 1388 | 1124188 | 1124188 : TOP2B :: topoisomerase (DNA) II beta 180 kDa | 282346 | -0.195346249007339 | 0.155878107050520 |
| 1389 | 1124192 | 1124192 : PRKWNK1 :: protein kinase, lysine deficient 1 | 275999 | 0.0041404874617065 | -0.0555775339209845 |
| 1390 | 1124195 | 1124195 : H3F3B :: H3 histone, family 3B (H3.3B) | 180877 | 0.0950808149920355 | -0.28030658341766 |
| 1391 | 1124215 | 1124215 : PNN :: pinin, desmosome associated protein | 409965 | -0.441382373300142 | 0.501531516295816 |
| 1392 | 1124237 | 1124237 : MLL :: myeloid/lymphoid or mixed-lineage leukemia (trithorax homolog, Drosophila) | 258855 | -0.0169668250888812 | -0.249537844930093 |
| 1393 | 1124254 | 1124254 : SLC39A14 :: solute carrier family 39 (zinc transporter), member 14 | 301743 | 0.321139013957588 | 0.167246613564032 |
| 1394 | 1124266 | 1124266 : DKFZP564D116 :: DKFZP564D116 protein | 438991 | -0.280125357020864 | 0.287120197674624 |
| 1395 | 1124283 | 1124283 : UNC84B :: unc-84 homolog B (C. elegans) | 406612 | 0.315002331643639 | -0.548815227035707 |
| 1396 | 1124296 | 1124296 : SDC2 :: syndecan 2 (heparan sulfate proteoglycan 1, cell surface-associated, fibroglycan) | 1501 | 0.693813172081440 | -0.342258189120497 |
| 1397 | 1124304 | 1124304 :CPNE1 :: copine I | 166887 | -0.504868086841360 | 0.680830591678959 |
| 1398 | 1124316 | 1124316 : ACACA :: acetyl-Coenzyme A carboxylase alpha | 449863 | -0.181134877886522 | 0.274185965541523 |
| 1399 | 1124318 | 1124318 : SERPINE2 :: serine (or cysteine) proteinase inhibitor, clade E (nexin, plasminogen activator inhibitor type 1), member 2 | 21858 | 0.370324342365429 | -0.211095115024570 |
| 1400 | 1124321 | 1124321 : IL6ST :: interleukin 6 signal transducer (gp130, oncostatin M receptor) | 71968 | 0.278059468191875 | -0.396320310680725 |
| 1401 | 1124342 | 1124342 : PPAP2B :: phosphatidic acid phosphatase type 2B | 432840 | 0.745344693498752 | -0.321206737384094 |
| 1402 | 1124357 | 1124357 : C7orf14 :: chromosome 7 open reading frame 14 | 413636 | -0.402885858524422 | 0.657812900011462 |
| 1403 | 1124362 | 1124362 : CAMKK2 :: calcium/calmodulin-dependent protein kinase kinase 2, beta | 297343 | 0.082047941910144 | 0.0121703226600202 |
| 1404 | 1124365 | 1124365 : TNRC15 :: trinucleotide repeat containing 15 | 334871 | -0.146171232833643 | 0.129612912259863 |
| 1405 | 1124377 | 1124377 : MAC30 :: hypothetical protein MAC30 | 199695 | -0.473824954763453 | 0.767955627108751 |
| 1406 | 1124381 | 1124381 : FNBP1 :: formin binding protein 1 | 440808 | 0.0192309803646461 | -0.207117033691842 |
| 1407 | 1124384 | 1124384 : HIPK1 :: homeodomain interacting protein kinase 1 | 12259 | 0.0385690822877500 | -0.0739897367599850 |
| 1408 | 1124391 | 1124391 : NEK9 :: NIMA (never in mitosis gene a)- related kinase 9 | 7200 | -0.285215409926676 | 0.158971093711156 |
| 1409 | 1124400 | 1124400 : BCL2L1 :: BCL2-like 1 | 305890 | 0.0239764847210147 | -0.0565142913099960 |
| 1410 | 1124411 | 1124411 : FLJ10619 :: hypothetical protein FLJ10619 | 194737 | -0.0189027604908884 | -0.337181044074577 |
| 1411 | 1124416 | 1124416 : RBL2 :: retinoblastoma-like 2 (p130) | 283604 | 0.0437118450900 | -0.322756914235943 |
| 1412 | 1124429 | 1124429 : SULF1 :: sulfatase 1 | 409602 | 0.756874827644649 | -0.200326821232171 |
| 1413 | 1124438 | 1124438 : CLIPR-59 :: CLIP-170-related protein | 7357 | 0.348844827581408 | -0.173908788877715 |
| 1414 | 1124456 | 1124456 : TCF4 :: transcription factor 4 | 359289 | -0.184783079390691 | 0.173790437828407 |
| 1415 | 1124539 | 1124539 : TENC1 :: tensin like C1 domain-containing phosphatase | 6147 | 0.403712878533374 | -0.395953899027013 |
| 1416 | 1124543 | 1124543 : C10orf22 :: chromosome 10 open reading frame 22 | 99821 | -0.0169312323646163 | -0.113380071029849 |
| 1417 | 1124549 | 1124549 : MOAP1 :: modulator of apoptosis 1 | 24119 | -0.176013780064857 | 0.0847454064124491 |
| 1418 | 1124561 | 1124561 : NEK7 :: NIMA (never in mitosis gene a)-related kinase 7 | 24119 | 0.122442978195907 | -0.2099718561273090 |
| 1419 | 1124563 | 1124563 : WEE1 :: WEE1 homolog (S. pombe) | 249441 | -0.173056305348263 | 0.447072813081760 |
| 1420 | 1124577 | 1124577 : HPCAL1 :: hippocalcin-like 1 | 3618 | 0.135165512513168 | -0.2997802558799620 |
| 1421 | 1124583 | 1124583 : GDAP1L1 :: ganglioside-induced differentiation-associated protein 1-like 1 | 20977 | 0.367602161929472 | -0.305814749060591 |
| 1422 | 1124594 | 1124594 : STK38L :: serine/threonine kinase 38 like | 184523 | 0.0193209000966301 | 0.207490282567835 |
| 1423 | 1124606 | 1124606 : PTPRC :: protein tyrosine phosphatase, receptor type, C | 444324 | 0.0453172856935670 | -0.221810375999856 |
| 1424 | 1124610 | 1124610 : IGJ :: immunoglobulin J polypeptide, linker protein for immunoglobulin alpha and mu polypeptides | 381568 | 0.056282104720538 | -0.080088230864314 |
| 1425 | 1124613 | 1124613 : AUTS2 :: autism susceptibility candidate 2 | 296720 | 0.290104164160183 | -0.197864543648102 |
| 1426 | 1124616 | 1124616 : MRPS31 :: mitochondrial ribosomal protein S31 | 154655 | -0.254775558867050 | 0.431147910743260 |
| 1427 | 1124620 | 1124620 : PTPN11 :: protein tyrosine phosphatase, non-receptor type 11 (Noonan syndrome 1) | 83572 | -0.287606650758719 | 0.434137906160620 |

TABLE 2415-continued

GeneID.txt

| Order | UNIQID | NAME | GENEID | LN.cor | Pro.cor |
|---|---|---|---|---|---|
| 1428 | 1124646 | RAFTLIN :: raft-linking protein | 436432 | 0.219635297170966 | −0.099887736967582 |
| 1429 | 1124655 | LHFPL2 :: lipoma HMGIC fusion partner-like 2 | 79299 | 0.364628032268042 | −0.274907028091758 |
| 1430 | 1124658 | K1AA0674 :: K1AA0674 protein | 522351 | 0.289946684284484 | −0.325443854542448 |
| 1431 | 1124666 | ATM :: ataxia telangiectasia mutated (includes complementation groups A, C and D) | 504644 | −0.214240439565213 | −0.133443390905161 |
| 1432 | 1124692 | MFAP4 :: microfibrillar-associated protein 4 | 296049 | 0.330287096674728 | −0.408382477540657 |
| 1433 | 1124705 | DMN :: desmuslin | 381347 | 0.311462686240068 | −0.392006888364421 |
| 1434 | 1124712 | ARHGAP19 :: Rho GTPase activating protein 19 | 80305 | −0.446308155524552 | 0.650257768410998 |
| 1435 | 1124713 | PIK3R4 :: phosphoinositide-3-kinase, regulatory subunit 4, p150 | 306747 | −0.340750199021012 | 0.190039732116352 |
| 1436 | 1124723 | RNF3 :: ring finger protein 3 | 435065 | 0.226995185267053 | −0.232885578590650 |
| 1437 | 1124733 | LOC221061 :: hypothetical protein LOC221061 | 66762 | 0.444250988609368 | −0.296397457839185 |
| 1438 | 1124734 | ZNF238 :: zinc finger protein 238 | 446677 | −0.344114190160318 | 0.037963727929040 |
| 1439 | 1124745 | KIAA0056 :: KIAA0056 protein | 438550 | −0.367374449201276 | 0.681944184031488 |
| 1440 | 1124753 | CIT :: citron (rho-interacting, serine/threonine kinase 21) | 405932 | −0.266684914532091 | 0.597601592399224 |
| 1441 | 1124755 | KIAA0367 :: KIAA0367 protein | 23311 | 0.175438520231790 | −0.161328615677927 |
| 1442 | 1124760 | JAM3 :: junctional adhesion molecule 3 | 419149 | 0.502500588515783 | −0.322402807479759 |
| 1443 | 1124768 | FUBP3 :: far upstream element (FUSE) binding protein 3 | 98751 | 0.043553346616365 | 0.132673344353371 |
| 1444 | 1124770 | IGHM :: Homo sapiens transcribed sequence with moderate similarity to protein sp:P01871 (H. sapiens) MUC_HUMAN Ig MU chain C region | 439852 | −0.264170929427200 | 0.171555883437037 |
| 1445 | 1124782 | NCAM1 :: neural cell adhesion molecule 1 | 78792 | 0.067740345913373 | −0.116287844761153 |
| 1446 | 1124786 | nexilin :: likely ortholog of rat F-actin binding protein nexilin | 22370 | −0.363619385660829 | 0.232945437352754 |
| 1447 | 1124798 | NCOA2 :: nuclear receptor coactivator 2 | 446678 | 0.236699642816994 | −0.309047597110174 |
| 1448 | 1124800 | MAPKAPK5 :: mitogen-activated protein kinase-activated protein kinase 5 | 413901 | −0.193391449305070 | 0.467024572248984 |
| 1449 | 1124806 | PIASY :: protein inhibitor of activated STAT protein PIASy | 105779 | −0.249365264160332 | 0.182499663961299 |
| 1450 | 1124820 | CDK11 :: cyclin-dependent kinase (CDC2-like) 11 | 129836 | 0.171715198585524 | −0.189801012482926 |
| 1451 | 1124830 | KIAA0962 :: KIAA0962 protein | 9059 | −0.239108218809974 | −0.071631456643250 |
| 1452 | 1124831 | RPS6KA2 :: ribosomal protein S6 kinase, 90 kDa, polypeptide 2 | 301664 | 0.542423703800096 | −0.359666198197007 |
| 1453 | 1124833 | CBX7 :: chromobox homolog 7 | 356416 | 0.200522108417050 | −0.597074769576343 |
| 1454 | 1124862 | DYRK4 :: dual-specificity tyrosine-(Y)-phosphorylation regulated kinase 4 | 439530 | −0.185930582424260 | 0.107350511374489 |
| 1455 | 1124864 | KIAA0882 :: KIAA0882 protein | 411317 | 0.230195362925492 | −0.120226438072572 |
| 1456 | 1124875 | KIAA0870 :: KIAA0870 protein | 18166 | 0.381004144174920 | −0.317090511411673 |
| 1457 | 1124889 | BTBD14A :: BTB (POZ) domain containing 14A | 244847 | 0.322548142484688 | −0.483195482115568 |
| 1458 | 1124893 | MARCKS :: myristoylated alanine-rich protein kinase C substrate | 318603 | 0.220998638177546 | −0.233172073523505 |
| 1459 | 1124913 | SSA2 :: Sjogren syndrome antigen A2 (60 kDa, ribonucleoprotein autoantigen SS-A/Ro) | 288178 | −0.317060278822500 | 0.353157816804561 |
| 1460 | 1124920 | P114-RHO-GEF :: Rho-specific guanine nucleotide exchange factor p114 | 6150 | −0.017421135592496 | −0.141829752391113 |
| 1461 | 1124921 | ROCK1 :: Rho-associated, coiled-coil containing protein kinase 1 | 306307 | −0.219106199756838 | 0.167252552911467 |
| 1462 | 1124922 | KIAA0561 :: KIAA0561 protein | 173864 | 0.154513049267643 | −0.226411686845406 |
| 1463 | 1124941 | DPT :: dermatopontin | 80552 | 0.606288990238186 | −0.334437688929020 |
| 1464 | 1124942 | KIAA1237 :: KIAA1237 protein | 433452 | 0.544384575743196 | −0.326311080060450 |
| 1465 | 1124948 | LOC169611 :: hypothetical protein LOC169611 | 357004 | 0.159693541113982 | −0.213890506828779 |
| 1466 | 1124953 | SLC35D2 :: solute carrier family 35, member D2 | 386278 | 0.302215615930412 | −0.532374546381988 |
| 1467 | 1124967 | CAMK2A :: calcium/calmodulin-dependent protein kinase (CaM kinase) II alpha | 143535 | −0.044227814406713 | 0.135835028117236 |
| 1468 | 1124972 | NEK3 :: NIMA (never in mitosis gene a)-related kinase 3 | 2236 | −0.004668815670307 | −0.018473350732855 |
| 1469 | 1125001 | Homo sapiens mRNA; cDNA DKFZp586B211 (from clone DKFZp586B211) | 16193 | 0.309877128137494 | −0.394819111003227 |
| 1470 | 1125009 | SEMA5A :: sema domain, seven thrombospondin repeats (type 1 and type 1-like), transmembrane domain (TM) and short cytoplasmic domain, (semaphorin) 5A | 27621 | 0.570335587773131 | −0.238333324497496 |
| 1471 | 1125010 | GPX6 :: glutathione peroxidase 6 | 43728 | −0.406180476172999 | 0.329255990519276 |
| 1472 | 1125013 | TTC9 :: tetratricopeptide repeat domain 9 | 79170 | 0.203290284926991 | −0.070350427994692 |
| 1473 | 1125025 | Homo sapiens, clone IMAGE:5402962, mRNA | 301094 | 0.373028589705817 | −0.358455467318352 |

TABLE 2415-continued

| Order | UNIQID | NAME | GeneID.txt | | | |
|---|---|---|---|---|---|---|
| | | | | GENEID | LN.cor | Pro.cor |
| 1474 | 1125027 | ACVR1B :: activin A receptor, type IB | 371974 | 0.452094421087183 | -0.406256554874994 |
| 1475 | 1125058 | ATP10D :: ATPase, Class V, type 10D | 437241 | 0.239777925038262 | -0.208589626023053 |
| 1476 | 1125079 | MAP3K12 :: mitogen-activated protein kinase kinase kinase 12 | 211601 | -0.023529974489696 | 0.097742384028628 |
| 1477 | 1125122 | SRC :: v-src sarcoma (Schmidt-Ruppin A-2) viral oncogene homolog (avian) | 436015 | 0.325821834875497 | -0.281566755677791 |
| 1478 | 1125124 | VAMP1 :: vesicle-associated membrane protein 1 (synaptobrevin 1) | 20021 | 0.028033847060342 | -0.030330298910767 |
| 1479 | 1125130 | RIS1 :: Ras-induced senescence 1 | 35861 | 0.707291900474651 | -0.304594771554232 |
| 1480 | 1125132 | FEM1C :: fem-1 homolog c (C. elegans) | 47367 | -0.178267778288773 | 0.251919721452546 |
| 1481 | 1125136 | CDKN1C :: cyclin-dependent kinase inhibitor 1C (p57, Kip2) | 106070 | 0.205535321358345 | -0.417689553467566 |
| 1482 | 1125181 | HSPA6 :: heat shock 70 kDa protein 6 (HSP70B') | 3268 | 0.218052146790839 | -0.175456230712095 |
| 1483 | 1125195 | :: Homo sapiens cDNA FLJ34019 fis, clone FCBBF2002898. | 7309 | 0.062335197338136 | -0.242830127018530 |
| 1484 | 1125231 | MAPRE2 :: microtubule-associated protein, RP/EB family, member 2 | 446375 | -0.258250546492020 | 0.146207410520459 |
| 1485 | 1125245 | DKFZP564J157 :: DKFZP564J157 protein | 132977 | -0.084163299925425 | 0.043797186647820 |
| 1486 | 1125246 | PRKCI :: protein kinase C, iota | 496511 | 0.149649650776333 | -0.029379048720556 |
| 1487 | 1125249 | CCNE1 :: cyclin E1 | 244723 | -0.378533610256387 | 0.582611267644762 |
| 1488 | 1125279 | TRA2A :: transformer-2 alpha | 445652 | -0.039745460274163 | -0.006496641958592 |
| 1489 | 1125305 | MAGED2 :: melanoma antigen, family D, 2 | 376719 | 0.279186046231037 | -0.229412259186242 |
| 1490 | 1125377 | KIAA0298 :: KIAA0298 gene product | 196966 | 0.043538773140655 | -0.083535310053914 |
| 1491 | 1125397 | RABL4 :: RAB, member of RAS oncogene family-like 4 | 415172 | -0.076074155660607 | -0.152334780877398 |
| 1492 | 1125456 | MYBL1 :: v-myb myeloblastosis viral oncogene homolog (avian)-like 1 | 300592 | 0.085358543549403 | 0.119727077539206 |
| 1493 | 1125459 | CPN2 :: carboxypeptidase N, polypeptide 2, 83 kD | 288467 | 0.753834612101326 | -0.275359926533248 |
| 1494 | 1125462 | NKG7 :: natural killer cell group 7 sequence | 10306 | 0.376390754863940 | -0.440135617189111 |
| 1495 | 1125485 | CD6 :: CD6 antigen | 436949 | 0.336912237115247 | -0.602384836873 88 |
| 1496 | 1125516 | ZAP70 :: zeta-chain (TCR) associated protein kinase 70 kDa | 234569 | 0.095543492046246 | -0.451426018665455 |
| 1497 | 1125520 | CCL8 :: chemokine (C-C motif) ligand 8 | 271387 | 0.121752040709514 | -0.288077095465458 |
| 1498 | 1125527 | MGC39900 :: hypothetical protein MGC39900 | 422848 | -0.180192646407023 | 0.262739415756805 |
| 1499 | 1125532 | MYCL1 :: v-myc myelocytomatosis viral oncogene homolog 1, lung carcinoma derived (avian) | -20 | 0.466507304726902 | -0.557697249345758 |
| 1500 | 1125546 | PLXDC1 :: plexin domain containing 1 | 125036 | 0.495158343413 2 | -0.378145766567478 |
| 1501 | 1125593 | MAN1C1 :: mannosidase, alpha, class 1C, member 1 | 8736 | 0.401795734231727 | -0.364401736769574 |
| 1502 | 1125634 | ITGA8 :: integrin, alpha 8 | 171025 | 0.075527959445201 | 0.079267924222490 |
| 1503 | 1125658 | CAMK2G :: calcium/calmodulin-dependent protein kinase (CaM kinase) II gamma | 12436 | -0.135367047257270 | -0.093006589024883 |
| 1504 | 1125685 | STK22B :: serine/threonine kinase 22B (spermiogenesis associated) | 103978 | 0.044261258588761 | -0.051415134140489 |
| 1505 | 1125742 | KLRB1 :: killer cell lectin-like receptor subfamily B, member 1 | 169824 | 0.079711384000230 | -0.301963846541283 |
| 1506 | 1125789 | FPRL2 :: formyl peptide receptor-like 2 | 511953 | 0.380389682365687 | -0.166148068940340 |
| 1507 | 1125818 | PAK3 :: p21 (CDKN1A)-activated kinase 3 | 152663 | 0.225596497818733 | -0.244661698259 961 |
| 1508 | 1125826 | PRF1 :: perforin 1 (pore forming protein) | 103978 | 0.044268240755 40851 | -0.389188823848422 |
| 1509 | 1125852 | ITGA1 :: integrin, alpha 1 | 2200 | 0.124824075540851 | 0.098707633535808 |
| 1510 | 1125854 | KIAA0472 :: KIAA0472 protein | 6874 | 0.110910134647931 | -0.172998186901 32 |
| 1511 | 1125872 | MGC14376 :: hypothetical protein MGC14376 | 417157 | 0.612329640905422 | -0.552935361435317 |
| 1512 | 1125901 | KIAA1069 :: KIAA1069 protein | 193143 | -0.056011672384808 | 0.098707633535808 |
| 1513 | 1125916 | Homo sapiens mRNA, chromosome 1 specific transcript KIAA0507. | 497770 | -0.163266689 46423 | 0.152187955657425 |
| 1514 | 1125917 | CLCN4 :: chloride channel 4 | 417091 | -0.081086279636081 | -0.031095539270792 |
| 1515 | 1125919 | G2 :: G2 protein | 432369 | 0.118135844564772 | -0.183475617606038 |
| 1516 | 1125921 | Homo sapiens immunoglobulin kappa light chain VKJ region mRNA, partial cds | 512124 | 0.054181904837014 | -0.063477080905441 |
| 1517 | 1125927 | IRLB :: c-myc promoter-binding protein | 511742 | 0.007967940915944 | 0.004344525393029 |
| 1518 | 1125928 | SUSP1 :: SUMO1-specific protease | 435628 | 0.126140052656316 | -0.187357956669395 |
| 1519 | 1126047 | MAP3K9 :: mitogen-activated protein kinase kinase kinase 9 | 437214 | -0.123477928740905 | 0.090270515939190 |
| 1520 | 1126081 | GRSF1 :: G-rich RNA sequence binding factor 1 | 309763 | -0.195427410459479 | 0.297879353203236 |
| 1521 | 1126131 | RAG2 :: recombination activating gene 2 | 159376 | 0.018198564132967 | 0.095689042169220 |
| 1522 | 1126148 | FLJ36166 :: hypothetical protein FLJ36166 | 408264 | -0.341178035851254 | 0.550186976150584 |

TABLE 2415-continued

| Order | UNIQID | NAME | GeneID.txt | GENEID | LN.cor | Pro.cor |
|---|---|---|---|---|---|---|
| 1523 | 1126293 | 1126293 : TNFRSF5 :: tumor necrosis factor receptor superfamily, member 5 | | 504816 | 0.123994547059363 | -0.0981929696021 |
| 1524 | 1126387 | 1126387 : MAP2K3 :: mitogen-activated protein kinase kinase 3 | | 180533 | 0.154743211343872 | -0.0977657844491014 |
| 1525 | 1126408 | 1126408 :: Homo sapiens mRNA; cDNA DKFZp586O1318 (from clone DKFZp586O1318) | | 22689 | -0.068959873372587 | 0.0532386275445519 |
| 1526 | 1126540 | 1126540 : KIAA1659 :: KIAA1659 protein | | 474916 | 0.0811085913099987 | -0.0385737312232724 |
| 1527 | 1126554 | 1126554 : LOC91752 :: similar to C630007C17Rik protein | | 159528 | -0.268188912986088 | 0.246488836495623 |
| 1528 | 1126559 | 1126559 : INSRR :: insulin receptor-related receptor | | 248138 | -0.098379843482530 | 0.105773648371041 |
| 1529 | 1126858 | 1126858 : ITGB3 :: integrin, beta 3 (platelet glycoprotein IIIa, antigen CD61) | | 87149 | 0.042983325871373 | -0.144497681552225 |
| 1530 | 1126892 | 1126892 : ITGA7 :: integrin, alpha 7 | | 74369 | 0.0833417388800239 | -0.203924509390271 |
| 1531 | 1127214 | 1127214 : EPHA5 :: EphA5 | | 201920 | -0.0138244701633245 | -0.0366690220251078 |
| 1532 | 1127290 | 1127290 : Homo sapiens ribosomal protein S4-like (RPS4L), mRNA | | -48 | -0.144124961156077 | 0.225161668972163 |
| 1533 | 1127294 | 1127294 : CXCR4 :: chemokine (C-X-C motif) receptor 4 | | 421986 | -0.0893648826272779 | -0.135605829793550 |
| 1534 | 1127371 | 1127371 : TIA1 :: TIA1 cytotoxic granule-associated RNA binding protein | | 444689 | -0.170709900312428 | -0.0690399739378 |
| 1535 | 1127567 | 1127567 : FLJ20013 :: hypothetical protein FLJ20013 | | -29 | -0.192452771538394 | 0.0836186465907 |
| 1536 | 1127576 | 1127576 : Homo sapiens, clone IMAGE:4794941, mRNA | | 172998 | 0.025947000616036 | -0.0644114205717 |
| 1537 | 1127720 | 1127720 : NRBP :: nuclear receptor binding protein | | 272736 | 0.242411931589308 | -0.319823036043122 |
| 1538 | 1127742 | 1127742 : GK001 :: GK001 protein | | 8207 | -0.175524415712497 | 0.253664275070550 |
| 1539 | 1127744 | 1127744 : ARPC4 :: actin related protein 2/3 complex, subunit 4, 20 kDa | | 323342 | 0.0371914971003242 | -0.0333461006968264 |
| 1540 | 1127756 | 1127756 : NS :: nucleostemin | | 313544 | -0.515884078663687 | 0.598986978423638 |
| 1541 | 1127761 | 1127761 : PIAS1 :: protein inhibitor of activated STAT, 1 | | 75251 | 0.0426862019032892 | -0.222289998593937 |
| 1542 | 1127775 | 1127775 : EPS15 :: epidermal growth factor receptor pathway substrate 15 | | 79095 | 0.189507964126997 | -0.127849991253663 |
| 1543 | 1127805 | 1127805 : CKLFSF6 :: chemokine-like factor superfamily 6 | | 380627 | 0.228996715729709 | -0.226964695189832 |
| 1544 | 1127807 | 1127807 : NOSIP :: nitric oxide synthase interacting protein | | 7236 | -0.247563970229520 | 0.168975022386913 |
| 1545 | 1127813 | 1127813 : NOLA3 :: nucleolar protein family A, member 3 (H/ACA small nucleolar RNPs) | | 14317 | -0.267329642981471 | 0.382544204532760 |
| 1546 | 1127822 | 1127822 : SEPX1 :: selenoprotein X, 1 | | 279623 | -0.0435784717256612 | -0.0204275633338161 |
| 1547 | 1127833 | 1127833 : MRPS2 :: mitochondrial ribosomal protein S2 | | 382044 | -0.470025507537828 | 0.585205355806807 |
| 1548 | 1127838 | 1127838 : SE20-4 :: cutaneous T-cell lymphoma-associated tumor antigen se20-4 | | 136164 | -0.103258781815064 | -0.0310955347592986 |
| 1549 | 1127849 | 1127849 : SNN :: stannin | | 76691 | 0.0212665268227127 | -0.236719002607138 |
| 1550 | 1127864 | 1127864 : SLC12A7 :: solute carrier family 12 (potassium/chloride transporters), member 7 | | 172613 | 0.368860530480438 | -0.359243502019673 |
| 1551 | 1127873 | 1127873 : C20orf4 :: chromosome 20 open reading frame 4 | | 11314 | -0.275330975017113 | 0.241185315693476 |
| 1552 | 1127885 | 1127885 : TMEM2 :: transmembrane protein 2 | | 160417 | 0.268288787080805 | -0.265983709009421 |
| 1553 | 1127901 | 1127901 : C20orf97 :: chromosome 20 open reading frame 97 | | 344378 | -0.391732683018817 | 0.394691280966108 |
| 1554 | 1127931 | 1127931 : FLJ22378 :: hypothetical protein FLJ22378 | | 288284 | 0.149298655387153 | -0.194275386943659 |
| 1555 | 1127940 | 1127940 : NUBP2 :: nucleotide binding protein 2 (MinD homolog, E. coli) | | 256549 | -0.300885491703953 | 0.428992853698371 |
| 1556 | 1127943 | 1127943 : C1QA :: complement component 1, q subcomponent, alpha polypeptide | | 9641 | -0.0263353557586648 | -0.341150779315542 |
| 1557 | 1128042 | 1128042 : SIL1 :: endoplasmic reticulum chaperone SIL1, homolog of yeast | | 297875 | 0.393325385452913 | -0.355463933112278 |
| 1558 | 1128066 | 1128066 : HTF9C :: HpaII tiny fragments locus 9C | | 63609 | -0.338428568678676 | 0.192274782223654 |
| 1559 | 1128070 | 1128070 : RRP46 :: exosome component Rrp46 | | 283741 | -0.554229516123466 | 0.607715184909214 |
| 1560 | 1128079 | 1128079 : MST4 :: Mst3 and SOK1-related kinase | | 23643 | -0.195204488353103 | 0.431778599814938 |
| 1561 | 1128095 | 1128095 : TBK1 :: TANK-binding kinase 1 | | 432466 | -0.0353307688412218 | 0.0509272692061200 |
| 1562 | 1128099 | 1128099 : 8D6A :: 8D6 antigen | | 333427 | -0.338346262971788 | 0.398554942958158 |
| 1563 | 1128100 | 1128100 : FHOD1 :: formin homology 2 domain containing 1 | | 95231 | 0.0691725040045891 | 0.0555069532525559 |
| 1564 | 1128106 | 1128106 : C10orf3 :: chromosome 10 open reading frame 3 | | 14559 | -0.301849657377729 | 0.772091150877424 |
| 1565 | 1128111 | 1128111 : FLJ10948 :: hypothetical protein FLJ10948 | | 170915 | 0.136309727475261 | -0.496737872614298 |
| 1566 | 1128125 | 1128125 : ABHD4 :: abhydrolase domain containing 4 | | 445665 | 0.361732950699424 | -0.356070410710610 |
| 1567 | 1128144 | 1128144 : DKFZp761K1423 :: hypothetical protein DKFZp761K1423 | | 236438 | 0.320671799542360 | -0.191684923385100 |
| 1568 | 1128151 | 1128151 : NRN1 :: neuritin 1 | | 103291 | -0.0536551377752169 | -0.122190847084027 |
| 1569 | 1128157 | 1128157 : VIP32 :: vasopressin-induced transcript | | 23918 | 0.450125317312805 | -0.335255101074634 |
| 1570 | 1128164 | 1128164 : FLJ20534 :: hypothetical protein FLJ20534 | | 44344 | -0.136223990395658 | 0.499752179475021 |
| 1571 | 1128167 | 1128167 : SLC25A15 :: solute carrier family 25 (mitochondrial carrier; ornithine transporter) member 15 | | 78457 | -0.292180964755755 | 0.464300618499445 |

TABLE 2415-continued

| Order | UNIQID | NAME | GeneID.txt | GENEID | LN.cor | Pro.cor |
|---|---|---|---|---|---|---|
| 1572 | 1128174 | 1128174 : FZD4 :: frizzled homolog 4 (Drosophila) | | 19545 | 0.417791773620202 | -0.227574007070855 |
| 1573 | 1128192 | 1128192 : EIF2AK3 :: eukaryotic translation initiation factor 2-alpha kinase 3 | | 102506 | 0.0300226579500088 | -0.105794931461638 |
| 1574 | 1128195 | 1128195 : RAB7L1 :: RAB7, member RAS oncogene family-like 1 | | 115325 | -0.0714499348339951 | 0.0017129621056 |
| 1575 | 1128214 | 1128214 : FLJ13848 :: hypothetical protein FLJ13848 | | 408443 | -0.389491187946975 | 0.393766423852120 |
| 1576 | 1128223 | 1128223 : FLJ10307 :: hypothetical protein FLJ10307 | | 55024 | -0.231713872811175 | -0.0364287324453000 |
| 1577 | 1128231 | 1128231 : PRKCH :: protein kinase C, eta | | 315366 | 0.291069538767355 | -0.571782301191371 |
| 1578 | 1128248 | 1128248 : FLJ20647 :: hypothetical protein FLJ20647 | | 234149 | -0.131530675006671 | 0.267271954474071 |
| 1579 | 1128283 | 1128283 : TNFRSF21 :: tumor necrosis factor receptor superfamily, member 21 | | 159651 | 0.338287130511519 | -0.244101265027556 |
| 1580 | 1128287 | 1128287 : ASB13 :: ankyrin repeat and SOCS box-containing 13 | | 300063 | 0.278584506324044 | -0.103554299642182 |
| 1581 | 1128298 | 1128298 : MRPL2 :: mitochondrial ribosomal protein L2 | | 55041 | -0.385624463595324 | 0.416247769862519 |
| 1582 | 1128311 | 1128311 : RPS6KC1 :: ribosomal protein S6 kinase, 52 kDa, polypeptide 1 | | 30352 | 0.0172906064107 | -0.0839490267132884 |
| 1583 | 1128321 | 1128321 : SIGIRR :: single Ig IL-1R-related molecule | | 433036 | 0.155437434081317 | -0.312639809674620 |
| 1584 | 1128341 | 1128341 : BRF2 :: BRF2, subunit of RNA polymerase III transcription initiation factor, BRF1-like | | 274136 | -0.202955230211738 | 0.332040507811259 |
| 1585 | 1128356 | 1128356 : C1RL :: complement component 1, r subcomponent-like | | 415792 | 0.680615686054409 | -0.570295986072283 |
| 1586 | 1128360 | 1128360 : SLC35E3 :: solute carrier family 35, member E2 | | 445043 | -0.0800006858186741 | 0.123127675676569 |
| 1587 | 1128377 | 1128377 : PLAC8 :: placenta-specific 8 | | 371003 | -0.177981381447672 | -0.0904352415581400 |
| 1588 | 1128386 | 1128386 : CD164L1 :: CD164 sialomucin-like 1 | | 195727 | 0.578953125706333 | -0.242872932952950 |
| 1589 | 1128387 | 1128387 : HIPK2 :: homeodomain interacting protein kinase 2 | | 397465 | 0.118459663415695 | -0.299358008077020 |
| 1590 | 1128395 | 1128395 : SEMA4C :: sema domain, immunoglobulin domain (Ig), transmembrane domain (TM) and short cytoplasmic domain, (semaphorin) 4C | | 7188 | 0.385224538166251 | -0.358632797373520 |
| 1591 | 1128401 | 1128401 : ChGn :: chondroitin beta1,4 N-acetylgalactosaminyltransferase | | 341073 | 0.528070744382773 | -0.289776026527080 |
| 1592 | 1128418 | 1128418 : CGI-14 :: CGI-14 protein | | 433499 | -0.127373034363878 | 0.114200478146125 |
| 1593 | 1128435 | 1128435 : PF20 :: PF20 | | 6783 | 0.092087102441032 | 0.063200995949780 |
| 1594 | 1128439 | 1128439 : FKBP11 :: FK506 binding protein 11, 19 kDa | | 438695 | -0.246180835487664 | 0.168972167224322 |
| 1595 | 1128447 | 1128447 : FLJ10287 :: hypothetical protein FLJ10287 | | 40337 | -0.367947704342123 | 0.323692416170365 |
| 1596 | 1128457 | 1128457 : TOPK :: T-LAK cell-originated protein kinase | | 104741 | -0.286232290714309 | 0.809770422276984 |
| 1597 | 1128469 | 1128469 : Homo sapiens similar to hypothetical protein FLJ22686 (LOC374825), mRNA | | -46 | 0.317650902185290 | -0.443676848604039 |
| 1598 | 1128471 | 1128471 : FLJ22555 :: hypothetical protein FLJ22555 | | 3592 | -0.214445966486640 | 0.459159303116971 |
| 1599 | 1128494 | 1128494 : MDA5 :: melanoma differentiation associated protein-5 | | 389539 | 0.381564813967180 | -0.464350966920936 |
| 1600 | 1128506 | 1128506 : CRK7 :: CDC2-related protein kinase 7 | | 416108 | -0.171991120566355 | 0.362497043497882 |
| 1601 | 1128535 | 1128535 : MAP3K6 :: mitogen-activated protein kinase kinase kinase 6 | | 194694 | 0.409909576040118 | -0.416460864199563 |
| 1602 | 1128536 | 1128536 : DOCK10 :: dedicator of cytokinesis 10 | | 21126 | -0.091474581134891 | -0.246286876471628 |
| 1603 | 1128585 | 1128585 : AVEN :: apoptosis, caspase activation inhibitor | | 63168 | -0.185978318974428 | 0.287881726289107 |
| 1604 | 1128615 | 1128615 : FLJ10134 :: hypothetical protein FLJ10134 | | 104800 | 0.750296824306779 | -0.281205969297433 |
| 1605 | 1128626 | 1128626 : EBI3 :: Epstein-Barr virus induced gene 3 | | 501452 | 0.153228999312480 | -0.003441093434900 |
| 1606 | 1128648 | 1128648 : DPEP2 :: dipeptidase 2 | | 499351 | 0.129320687206103 | -0.345905212590144 |
| 1607 | 1128653 | 1128653 : PAK6 :: p21(CDKN1A)-activated kinase 6 | | 21420 | -0.267089728890750 | 0.211427597958234 |
| 1608 | 1128655 | 1128655 : C20orf103 :: chromosome 20 open reading frame 103 | | 22920 | -0.036922789176067 | -0.017091313081673 |
| 1609 | 1128660 | 1128660 : C13orf18 :: chromosome 13 open reading frame 18 | | 413071 | -0.299977691323448 | 0.232152111241391 |
| 1610 | 1128681 | 1128681 : CLC :: cardiotrophin-like cytokine | | 191548 | 0.143956240585398 | -0.053287848623373 |
| 1611 | 1128688 | 1128688 : MYOZ1 :: myozenin 1 | | 238756 | -0.032274730636254 | 0.068290273280881 |
| 1612 | 1128694 | 1128694 : ELL3 :: elongation factor RNA polymerase II-like 3 | | 171466 | -0.107780233344866 | 0.274776739364120 |
| 1613 | 1128705 | 1128705 : HUNK :: hormonally upregulated Neu-associated kinase | | 109437 | -0.156244532976336 | 0.084117298832988 |
| 1614 | 1128710 | 1128710 : NEK11 :: NIMA (never in mitosis gene a)-related kinase 11 | | 159146 | -0.014339677064164 | -0.057185262323488 |
| 1615 | 1128713 | 1128713 : KCTD14 :: potassium channel tetramerisation domain containing 14 | | 17296 | 0.153126487439279 | -0.305451178240051 |
| 1616 | 1128733 | 1128733 : CADPS2 :: Ca2+-dependent activator protein for secretion 2 | | 489847 | 0.517597656273347 | -0.367879060286020 |
| 1617 | 1128738 | 1128738 : MGC2776 :: hypothetical protein MGC2776 | | 335550 | -0.441569943886905 | 0.397227563725956 |
| 1618 | 1128757 | 1128757 : IRAK4 :: interleukin-1 receptor-associated kinase 4 | | 142295 | 0.00548077087186 | -0.089519474289808 |
| 1619 | 1128781 | 1128781 : FLJ10116 :: hypothetical protein FLJ10116 | | 79741 | 0.593995376539243 | -0.326248755475982 |

TABLE 2415-continued

GeneID.txt

| Order | UNIQID | NAME | GENEID | LN.cor | Pro.cor |
|---|---|---|---|---|---|
| 1620 | 1128786 | PTPLA :: protein tyrosine phosphatase-like (proline instead of catalytic arginine), member a | 114062 | -0.173989199888605 | 0.042407369155574 |
| 1621 | 1128787 | C7orf10 :: chromosome 7 open reading frame 10 | 114611 | 0.066883608916300 | 0.135633101298342 |
| 1622 | 1128801 | ZNF435 :: zinc finger protein 435 | 288539 | 0.095389848084550 | -0.186965157005102 |
| 1623 | 1128807 | HSA250839 :: gene for serine/threonine protein kinase | 58241 | 0.148179807102335 | -0.027164856808638 |
| 1624 | 1128845 | FLJ20174 :: hypothetical protein FLJ20174 | 272416 | -0.252885787139230 | -0.168029598476545 |
| 1625 | 1128860 | STAG3 :: stromal antigen 3 | 323634 | 0.166435463482480 | -0.080003410843672 |
| 1626 | 1128900 | STAG3 :: stromal antigen 3 | 323634 | -0.126310620816102 | -0.004486849116136 |
| 1627 | 1128901 | LATS1 :: LATS, large tumor suppressor, homolog 1 (Drosophila) | 487239 | 0.009763439382962 | -0.024911702773039 |
| 1628 | 1128915 | CDKL3 :: cyclin-dependent kinase-like 3 | 105818 | -0.132291718442723 | 0.219964373254252 |
| 1629 | 1128965 | FGD6 :: FYVE, RhoGEF and PH domain containing 6 | 170623 | 0.109709621274018 | 0.168419208192988 |
| 1630 | 1128969 | FLJ10213 :: hypothetical protein FLJ10213 | 446590 | -0.234154512640439 | 0.026794437866472 |
| 1631 | 1129024 | GPR86 :: G protein-coupled receptor 86 | 13040 | 0.305292619286846 | -0.457485905772554 |
| 1632 | 1129026 | FLJ13984 :: hypothetical protein FLJ13984 | 135146 | -0.309743417499126 | -0.013237106043976 |
| 1633 | 1129043 | ACVR2B :: activin A receptor, type IIB | 23994 | 0.068257334337018 | -0.078869667492364 |
| 1634 | 1129049 | IRAK3 :: interleukin-1 receptor-associated kinase 3 | 268552 | 0.295844788432385 | -0.096238995458166 |
| 1635 | 1129059 | IL23A :: interleukin 23, alpha subunit p19 | 98309 | 0.110558875480653 | -0.172783710046595 |
| 1636 | 1129061 | IL22RA1 :: interleukin 22 receptor, alpha 1 | 110915 | -0.049741735912372 | 0.102532093712077 |
| 1637 | 1129064 | BRDG1 :: BCR downstream signaling 1 | 121128 | -0.052914098023446 | 0.083226377510035 |
| 1638 | 1129071 | VPREB3 :: pre-B lymphocyte gene 3 | 136713 | -0.116559035957489 | 0.155519891626767 |
| 1639 | 1129085 | C5R1 :: complement component 5 receptor 1 (C5a ligand) | 2161 | 0.431190714150359 | -0.091961719019167 |
| 1640 | 1129103 | TZFP :: testis zinc finger protein | 99430 | -0.084913089830395 | 0.006324170944062 |
| 1641 | 1129120 | TLR7 :: toll-like receptor 7 | 179152 | 0.189943623624734 | -0.353578222257396 |
| 1642 | 1129151 | MUC16 :: mucin 16 | -21 | 0.088376628477854 | -0.269368537554111 |
| 1643 | 1129203 | IL17B :: interleukin 17B | 110040 | -0.004717127880353 | -0.001612024702046 |
| 1644 | 1129223 | GALNT10 :: UDP-N-acetyl-alpha-D-galactosamine:polypeptide N-acetylgalactosaminyltransferase 10 (GalNAc-T10) | 512728 | -0.024712521451973 | -0.316144966589372 |
| 1645 | 1129228 | MAK :: male germ cell-associated kinase | 148496 | 0.079167291478789 | 0.015734627365448 |
| 1646 | 1129232 | CD244 :: CD244 natural killer cell receptor 2B4 | 157872 | 0.073454393038786 | -0.377710109106282 |
| 1647 | 1129245 | IL1F9 :: interleukin 1 family, member 9 | 211238 | -0.094915764294385 | -0.121817602131821 |
| 1648 | 1129265 | CCRL1 :: chemokine (C-C motif) receptor-like 1 | 310512 | -0.148880028528658 | 0.181608150889073 |
| 1649 | 1129269 | SNFT :: Jun dimerization protein p21 SNFT | 62919 | 0.196502835728553 | -0.241893188568789 |
| 1650 | 1129281 | C14orf110 :: chromosome 14 open reading frame 110 | 395486 | -0.027842501648286 | 0.029163772973386 |
| 1651 | 1129310 | CARK :: cardiac ankyrin repeat kinase | 414091 | -0.106755206423672 | 0.156920333732655 |
| 1652 | 1129336 | KCNK12 :: potassium channel, subfamily K, member 12 | 252617 | 0.256164419250147 | -0.076669190655398 |
| 1653 | 1129419 | GPR2 :: G protein-coupled receptor 2 | 278446 | -0.153560376153935 | 0.073266711206152 |
| 1654 | 1129495 | TBX21 :: T-box 21 | 272409 | 0.099926962762925 | -0.206774112272127 |
| 1655 | 1129517 | FLJ12193 :: FLJ12193 | -63 | 0.268548338717064 | -0.234272075916895 |
| 1656 | 1129535 | RPS6KA6 :: ribosomal protein S6 kinase, 90 kDa, polypeptide 6 | 368153 | -0.060691156845818 | -0.112486779113327 |
| 1657 | 1129537 | IL19 :: interleukin 19 | 71979 | 0.042032462904672 | -0.082637131351126 |
| 1658 | 1129661 | IL17E :: interleukin 17E | 302036 | 0.015759941561729 | -0.147728639632796 |
| 1659 | 1129681 | TNFSF15 :: tumor necrosis factor (ligand) superfamily, member 15 | 241382 | 0.003868440543706 | -0.085807864212777 |
| 1660 | 1129694 | IL26 :: interleukin 26 | 272350 | 0.014873438384474 | -0.150408790090459 |
| 1661 | 1129743 | DKFZp434A0131 :: DKFZp434A0131 protein | 429531 | -0.053337181033571 | -0.096738574513564 |
| 1662 | 1129754 | IL21 :: interleukin 21 | 302014 | 0.101034557454981 | -0.028904887858268 |
| 1663 | 1129760 | RNASEL :: ribonuclease L (2′,5′-oligoisoadenylate synthetase-dependent) | 404277 | -0.076744614539946 | 0.041388715323864 |
| 1664 | 1129812 | CHRNG :: cholinergic receptor, nicotinic, gamma polypeptide | 248101 | -0.094695469974 | 0.198887933475047 |
| 1665 | 1129821 | MOS :: v-mos Moloney murine sarcoma viral oncogene homolog | 248146 | -0.077862620804062 | 0.125245212560540 |
| 1666 | 1129825 | TNFSF18 :: tumor necrosis factor (ligand) superfamily, member 18 | 248197 | -0.075226623664457 | 0.081966056961447 |
| 1667 | 1129874 | CCL24 :: chemokine (C-C motif) ligand 24 | 247838 | -0.009869595016579 | 0.024069346953711 |
| 1668 | 1129879 | XCR1 :: chemokine (C motif) receptor 1 | 248116 | -0.036265621695120 | 0.105554164155718 |

TABLE 2415-continued

| Order | UNIQID | NAME GeneID.txt | GENEID | LN.cor | Pro.cor |
|---|---|---|---|---|---|
| 1669 | 1129887 | 1129887 : B4GALT5 :: UDP-Gal:betaGlcNAc beta 1,4-galactosyltransferase, polypeptide 5 | 107526 | 0.380271891913627 | -0.303897639472657 |
| 1670 | 1129907 | 1129907 : EIF4EBP1 :: eukaryotic translation initiation factor 4E binding protein 1 | 406408 | 0.0367540642144461 | 0.115319060732266 |
| 1671 | 1129911 | 1129911 : GRWD1 :: glutamate-rich WD repeat containing 1 | 400625 | -0.439357897736726 | 0.474210086029623 |
| 1672 | 1129917 | 1129917 : MARK4 :: MAP/microtubule affinity-regulating kinase 4 | 118843 | -0.170633612286300 | -0.0102302717789505 |
| 1673 | 1129923 | 1129923 : TRAF3 :: TNF receptor-associated factor 3 | 297660 | 0.0280903489767656 | -0.0866645961693306 |
| 1674 | 1129943 | 1129943 : ZNF506 :: zinc finger protein 506 | 512828 | -0.101116534668903 | -0.220361168950301 |
| 1675 | 1129967 | 1129967 : C19orf10 :: chromosome 19 open reading frame 10 | 10927 | 0.0490705120808032 | -0.0324875269422485 |
| 1676 | 1129978 | 1129978 : SSH1 :: slingshot 1 | 60377 | 0.219169062430177 | -0.289189938099277 |
| 1677 | 1129993 | 1129993 : FLJ14827 :: hypothetical protein FLJ14827 | 412981 | -0.480749758772810 | 0.554011664313080 |
| 1678 | 1130007 | 1130007 : NTRK2 :: neurotrophic tyrosine kinase, receptor, type 2 | 494313 | 0.120279477549603 | -0.243907629075211 |
| 1679 | 1130030 | 1130030 : LONP :: peroxisomal lon protease | 301872 | -0.0720612927821880 | -0.319246017270642 |
| 1680 | 1130040 | 1130040 : :: Homo sapiens, clone IMAGE:3626627, mRNA | 356460 | -0.3222229909790390 | 0.205828937779337 |
| 1681 | 1130054 | 1130054 : RARRES1 :: retinoic acid receptor responder (tazarotene induced) 1 | 82547 | 0.685839603413505 | -0.362689495840938 |
| 1682 | 1130072 | 1130072 : T1A-2 :: lung type-I cell membrane-associated glycoprotein | 468675 | 0.818831553703874 | -0.294460779566936 |
| 1683 | 1130078 | 1130078 : CYLD :: cylindromatosis (turban tumor syndrome) | 386952 | 0.183694775256214 | -0.419576263991755 |
| 1684 | 1130088 | 1130088 : PCTK2 :: PCTAIRE protein kinase 2 | 258536 | 0.0721528202355180 | -0.107600969822367 |
| 1685 | 1130090 | 1130090 : LGN :: LGN protein | 278338 | 0.00427230168851 | 0.479039312613795 |
| 1686 | 1130114 | 1130114 : MPHOSPH9 :: M-phase phosphoprotein 9 | 445084 | -0.379537586983120 | 0.341620894714238 |
| 1687 | 1130117 | 1130117 : PAX5 :: paired box gene 5 (B-cell lineage specific activator protein) | 22030 | -0.246528946838740 | 0.352341117052491 |
| 1688 | 1130121 | 1130121 : HLA-F :: major histocompatibility complex, class I, F | 411958 | 0.377839466682894 | -0.570631345032229 |
| 1689 | 1130155 | 1130155 : CLU :: clusterin (complement lysis inhibitor, SP-40,40, sulfated glycoprotein 2, testosterone-repressed prostate message 2, apolipoprotein J) | 436657 | 0.161844555045734 | -0.283244372504117 |
| 1690 | 1130168 | 1130168 : CD58 :: CD58 antigen, (lymphocyte function-associated antigen 3) | 75626 | 0.364492432723028 | -0.362266715730823 |
| 1691 | 1130169 | 1130169 : WSX1 :: class I cytokine receptor | 132781 | 0.184454748443662 | -0.424993764533384 |
| 1692 | 1130201 | 1130201 : HRBL :: HIV-1 Rev binding protein-like | 278502 | -0.0756976639930411 | -0.0398216643991790 |
| 1693 | 1130293 | 1130293 : :: Homo sapiens partial mRNA, clone c4-1c6 | 292853 | -0.155443177799334 | 0.0958438890123974 |
| 1694 | 1130337 | 1130337 : ILF2 :: interleukin enhancer binding factor 2, 45 kDa | 75117 | -0.551604865259108 | 0.730250550754830 |
| 1695 | 1130433 | 1130433 : U5-200KD :: U5 snRNP-specific protein, 200-KD | 246112 | -0.366436179521191 | 0.356690965936921 |
| 1696 | 1130446 | 1130446 : MGC2749 :: hypothetical protein MGC2749 | 369785 | -0.162045856993512 | 0.204027835507349 |
| 1697 | 1130447 | 1130447 : OAZ1 :: ornithine decarboxylase antizyme 1 | 446427 | -0.027334049396156 | -0.125481385009298 |
| 1698 | 1130465 | 1130465 : ANAPC5 :: anaphase promoting complex subunit 5 | 7101 | -0.188040952374909 | 0.335757544229032 |
| 1699 | 1130468 | 1130468 : HNRPU :: heterogeneous nuclear ribonucleoprotein U (scaffold attachment factor A) | 166463 | -0.141428315104379 | 0.449595813895559 |
| 1700 | 1130472 | 1130472 : TRA1 :: tumor rejection antigen (gp96) 1 | 192374 | -0.0587704067818450 | 0.008454200316347 |
| 1701 | 1130482 | 1130482 : KIAA0152 :: KIAA0152 gene product | 181418 | -0.013046088161047 | 0.140884826685794 |
| 1702 | 1130483 | 1130483 : CALM3 :: calmodulin 3 (phosphorylase kinase, delta) | 334330 | 0.034506605516631 | 0.070747117402494 |
| 1703 | 1130501 | 1130501 : LDHA :: lactate dehydrogenase A | 2795 | -0.113416716689169 | 0.557153046168620 |
| 1704 | 1130509 | 1130509 : SPARC :: secreted protein, acidic, cysteine-rich (osteonectin) | 111779 | 0.837304026622357 | -0.223436112872554 |
| 1705 | 1130518 | 1130518 : HMGB1 :: high-mobility group box 1 | 434102 | -0.304610144944285 | 0.589052869603598 |
| 1706 | 1130527 | 1130527 : HSPA9B :: heat shock 70 kDa protein 9B (mortalin-2) | 184233 | -0.405952252455406 | 0.580488234077170 |
| 1707 | 1130533 | 1130533 : LITAF :: lipopolysaccharide-induced TNF factor | 76507 | 0.223648867635184 | -0.307782200282530 |
| 1708 | 1130588 | 1130588 : HNRPK :: heterogeneous nuclear ribonucleoprotein K | 307544 | -0.404667709940553 | 0.444695456954984 |

TABLE 2415-continued

GeneID.txt

| Order | UNIQID | NAME | GENEID | LN.cor | Pro.cor |
|---|---|---|---|---|---|
| 1717 | 1130603 | MCL1 :: myeloid cell leukemia sequence 1 (BCL2-related) | 86386 | 0.116326040892859 | −0.411472574543256 |
| 1718 | 1130618 | GRCC9 :: likely ortholog of mouse gene rich cluster, C9 gene | 83848 | −0.105851503751508 | 0.515020841340678 |
| 1719 | 1130622 | ZNF207 :: zinc finger protein 207 | 97128 | −0.352374085161843 | 0.668735280109416 |
| 1720 | 1130624 | SCD :: stearoyl-CoA desaturase (delta-9-desaturase) | 119597 | 0.0684669251311898 | 0.0421101373444519 |
| 1721 | 1130629 | CTSB :: cathepsin B | 135226 | 0.463103175029523 | −0.332067792414087 |
| 1722 | 1130631 | EPRS :: glutamyl-prolyl-tRNA synthetase | 171292 | −0.242075805489007 | 0.343011789857582 |
| 1723 | 1130645 | KIAA1007 :: KIAA1007 protein | 279949 | −0.508837450988830 | 0.647834071617021 |
| 1724 | 1130653 | NOL5A :: nucleolar protein 5A (56 kDa with KKE/D repeat) | 376064 | −0.491441299595535 | 0.618358768431825 |
| 1725 | 1130658 | PGAM1 :: phosphoglycerate mutase 1 (brain) | 447492 | −0.225449863013289 | 0.594965205536490 |
| 1726 | 1130668 | KIAA0992 :: palladin | 194431 | 0.738444332308338 | −0.353184858890758 |
| 1727 | 1130674 | HLA-E :: major histocompatibility complex, class I, E | 381008 | 0.316878271078233 | −0.616553306253961 |
| 1728 | 1130676 | KIAA0992 :: palladin | 194431 | 0.571670266195923 | −0.239239604892387 |
| 1729 | 1130680 | EIF4A2 :: eukaryotic translation initiation factor 4A, isoform 2 | 511904 | −0.406851760364394 | 0.0319284630840635 |
| 1730 | 1130687 | SLC3A2 :: solute carrier family 3 (activators of dibasic and neutral amino acid transport), member 2 | 79748 | 0.00562006879411009 | 0.221535198891908 |
| 1731 | 1130704 | CCND2 :: cyclin D2 | 376071 | −0.0862272130193776 | −0.105185207044404 |
| 1732 | 1130707 | SSRP1 :: structure specific recognition protein 1 | 79162 | −0.478812788644878 | 0.723198294147642 |
| 1733 | 1130712 | ABLIM1 :: actin binding LIM protein 1 | 442540 | 0.0289891080977744 | −0.0247403651809999 |
| 1734 | 1130732 | UBE2V1 :: ubiquitin-conjugating enzyme E2 variant 1 | 381025 | −0.365959820864458 | 0.273619600177731 |
| 1735 | 1130735 | TXNIP :: thioredoxin interacting protein | 179526 | 0.147134141082822 | −0.423880593075217 |
| 1736 | 1130744 | IF2 :: translation initiation factor IF2 | 158688 | −0.436040464525393 | 0.549498651391074 |
| 1737 | 1130746 | CD99 :: CD99 antigen | 283477 | 0.491775584257276 | −0.301267508834440 |
| 1738 | 1130747 | LDHB :: lactate dehydrogenase B | 234489 | −0.474279747751518 | 0.634626298790119 |
| 1739 | 1130755 | ANP32A :: acidic (leucine-rich) nuclear phosphoprotein 32 family, member A | 356089 | −0.531594087149504 | 0.564703678975089 |
| 1740 | 1130771 | PSMC2 :: proteasome (prosome, macropain) 26S subunit, ATPase, 2 | 61153 | −0.0763429185097587 | 0.303662557781198 |
| 1741 | 1130799 | PSMA7 :: proteasome (prosome, macropain) subunit, alpha type, 7 | 233952 | −0.183548593771997 | 0.433457258460047 |
| 1742 | 1130812 | CDH1 :: cadherin 1, type 1, E-cadherin (epithelial) | 194657 | 0.150350262021869 | −0.310581185010029 |
| 1743 | 1130820 | EIF2S1 :: eukaryotic translation initiation factor 2, subunit 1 alpha, 35 kDa | 151777 | −0.248919180836398 | 0.645496589136077 |
| 1744 | 1130835 | IGFBP7 :: insulin-like growth factor binding protein 7 | 435795 | 0.694869060684746 | −0.451635497409526 |
| 1745 | 1130839 | ARHGDIA :: Rho GDP dissociation inhibitor (GDI) alpha | 159161 | −0.287041819068728 | 0.319746037482479 |
| 1746 | 1130852 | CHD4 :: chromodomain helicase DNA binding protein 4 | 74441 | −0.227607888519199 | 0.309877252850406 |
| 1747 | 1130855 | ITPR3 :: inositol 1,4,5-triphosphate receptor, type 3 | 77515 | −0.0900371637524447 | 0.246241985491480 |
| 1748 | 1130871 | RAD23B :: RAD23 homolog B (S. cerevisiae) | 159087 | −0.155432198525978 | 0.354647062606468 |
| 1749 | 1130879 | ENO1 :: enolase 1, (alpha) | 433455 | −0.103238523231766 | 0.472120612291936 |
| 1750 | 1130882 | BTG2 :: BTG family, member 2 | 75462 | −0.401612459640219 | 0.215065673193418 |
| 1751 | 1130888 | RAF1 :: v-raf-1 murine leukemia viral oncogene homolog 1 | 257266 | −0.316699264696602 | 0.210654762972939 |
| 1752 | 1130898 | SYPL :: synaptophysin-like protein | 80919 | −0.0202227914034430 | 0.180749968332613 |
| 1753 | 1130900 | BGN :: biglycan | 821 | 0.433491624346225 | −0.0346657560783871 |
| 1754 | 1130906 | HNRPAB :: heterogeneous nuclear ribonucleoprotein A/B | 81361 | −0.530041416930423 | 0.790305469314572 |
| 1755 | 1130910 | APEH :: N-acylaminoacyl-peptide hydrolase | 221589 | −0.396613250677159 | 0.314489748130245 |
| 1756 | 1130911 | SDC1 :: syndecan 1 | 82109 | 0.257574142041331 | −0.110610745819271 |
| 1757 | 1130914 | WSB1 :: SOCS box-containing WD protein SWiP-1 | 315379 | 0.152566035413182 | −0.130582325128830 |
| 1758 | 1130922 | ANP32B :: acidic (leucine-rich) nuclear phosphoprotein 32 family, member B | 459987 | −0.268323025580090 | 0.586480999073766 |
| 1759 | 1130923 | ANP32B :: acidic (leucine-rich) nuclear phosphoprotein 32 family, member B | 459987 | −0.356618082166821 | 0.545047027556475 |
| 1760 | 1130926 | C5orf13 :: chromosome 5 open reading frame 13 | 508741 | −0.0668934510127013 | 0.226117239200541 |
| 1761 | 1130936 | STAT6 :: signal transducer and activator of transcription 6, interleukin-4 induced | 437475 | −0.187297336007257 | 0.021013107700686 |
| 1762 | 1130942 | GTF3A :: general transcription factor IIIA | 445977 | −0.468852559402542 | 0.503394969496502 |
| 1763 | 1130972 | IGF2R :: insulin-like growth factor 2 receptor | 76473 | 0.214658478470718 | −0.361049786465530 |
| 1764 | 1130977 | ADRBK1 :: adrenergic, beta, receptor kinase 1 | 83636 | −0.0952337350470 | 0.102662710355176 |
| 1765 | 1130994 | DPYSL3 :: dihydropyrimidinase-like 3 | 150358 | 0.809042808419035 | −0.446523381134851 |

TABLE 2415-continued

| Order | UNIQID | NAME | GeneID.txt | GENEID | LN.cor | Pro.cor |
|---|---|---|---|---|---|---|
| 1766 | 1131012 | 1131012 : JUN :: v-jun sarcoma virus 17 oncogene homolog (avian) | | 78465 | 0.457086129845903 | -0.354589691205210 |
| 1767 | 1131019 | 1131019 : ITGA3 :: integrin, alpha 3 (antigen CD49C, alpha 3 subunit of VLA-3 receptor) | | 265829 | 0.0535235818336060 | -0.199397777676044 |
| 1768 | 1131038 | 1131038 : NFKBIA :: nuclear factor of kappa light polypeptide gene enhancer in B-cells inhibitor, alpha | | 81328 | 0.462390024451032 | -0.318458395207705 |
| 1769 | 1131068 | 1131068 : FSCN1 :: fascin homolog 1, actin-bundling protein (Strongylocentrotus purpuratus) | | 118400 | 0.536725531023657 | -0.251210253868377 |
| 1770 | 1131069 | 1131069 : ID2 :: inhibitor of DNA binding 2, dominant negative helix-loop-helix protein | | 180919 | 0.247341922577442 | -0.202808821943620 |
| 1771 | 1131074 | 1131074 : DCTD :: dCMP deaminase | | 76894 | -0.248202975835252 | 0.038410672144689 |
| 1772 | 1131081 | 1131081 : SFPQ :: splicing factor proline/glutamine rich (polypyrimidine tract binding protein associated) | | 180610 | -0.473453393950819 | 0.738837614730302 |
| 1773 | 1131082 | 1131082 : IRAK1 :: interleukin-1 receptor-associated kinase 1 | | 182018 | -0.020262248068331 | 0.232370997542063 |
| 1774 | 1131107 | 1131107 : RRAGA :: Ras-related GTP binding A | | 432330 | 0.325855382913029 | -0.128821612464194 |
| 1775 | 1131110 | 1131110 : IER3 :: immediate early response 3 | | 76095 | 0.516596524226035 | -0.400848458725700 |
| 1776 | 1131119 | 1131119 : SCARB2 :: scavenger receptor class B, member 2 | | 323667 | 0.355068180876334 | -0.357229941974828 |
| 1777 | 1131140 | 1131140 : C14orf92 :: chromosome 14 open reading frame 92 | | 194035 | -0.175581522276715 | 0.264736273192001 |
| 1778 | 1131149 | 1131149 : EGR1 :: early growth response 1 | | 326035 | 0.334773228743566 | -0.223509421726847 |
| 1779 | 1131150 | 1131150 : NP :: nucleoside phosphorylase | | 75514 | -0.354544451710958 | 0.542011939879683 |
| 1780 | 1131181 | 1131181 : LUM :: lumican | | 406475 | 0.892642895727236 | -0.356076175533182 |
| 1781 | 1131197 | 1131197 : KIAA0494 :: KIAA0494 gene product | | 269902 | 0.137090820104737 | -0.390038678127149 |
| 1782 | 1131218 | 1131218 : ENG :: endoglin (Osler-Rendu-Weber syndrome 1) | | 76753 | 0.656737413741246 | -0.520957025407 22 |
| 1783 | 1131219 | 1131219 : SH3BP5 :: SH3-domain binding protein 5 (BTK-associated) | | 109150 | -0.312938579490861 | 0.164418197287064 |
| 1784 | 1131246 | 1131246 : CDC25B :: cell division cycle 25B | | 153752 | -0.153291439533977 | 0.090249162613185 |
| 1785 | 1131260 | 1131260 : ABCE1 :: ATP-binding cassette, sub-family E (OABP), member 1 | | 12013 | -0.388231075478314 | 0.595908004595403 |
| 1786 | 1131263 | 1131263 : PPP2R5C :: protein phosphatase 2, regulatory subunit B (B56), gamma isoform | | 249955 | -0.278824832021527 | -0.010546616084 32 |
| 1787 | 1131268 | 1131268 : IL13RA1 :: interleukin 13 receptor, alpha 1 | | 285115 | 0.603658167 37742 | -0.426475715000783 |
| 1788 | 1131274 | 1131274 : CKS1B :: CDC28 protein kinase regulatory subunit 1B | | 374378 | -0.472115050926466 | 0.804871568180769 |
| 1789 | 1131290 | 1131290 : DAF :: decay accelerating factor for complement (CD55, Cromer blood group system) | | 408864 | -0.021713657405561 | -0.031992085263801 |
| 1790 | 1131321 | 1131321 : EGFR :: epidermal growth factor receptor (erythroblastic leukemia viral (v-erb-b) oncogene homolog, avian) | | 77432 | 0.260851077631343 | -0.225904558910021 |
| 1791 | 1131325 | 1131325 : CREBL2 :: cAMP responsive element binding protein-like 2 | | 13313 | 0.554796719681771 | -0.648770892709224 |
| 1792 | 1131336 | 1131336 : ZNF410 :: zinc finger protein 410 | | 405945 | -0.192290734621065 | 0.122792075 78381 |
| 1793 | 1131340 | 1131340 : LTF :: lactotransferrin | | 437457 | 0.235576626054540 | -0.261846903756942 |
| 1794 | 1131342 | 1131342 : LANCL1 :: LanC lantibiotic synthetase component C-like 1 (bacterial) | | 13351 | -0.017539774281155 | 0.118963845188131 |
| 1795 | 1131379 | 1131379 : PLTP :: phospholipid transfer protein | | 439312 | 0.233879501502951 | -0.271204990365974 |
| 1796 | 1131395 | 1131395 : BRD4 :: bromodomain containing 4 | | 278675 | -0.010421483777346 | 0.015984797307132 |
| 1797 | 1131401 | 1131401 : CPNE3 :: copine III | | 14158 | 0.041142882609723 | -0.055081905354774 |
| 1798 | 1131405 | 1131405 : ABL1 :: v-abl Abelson murine leukemia viral oncogene homolog 1 | | 446504 | -0.221476283909564 | 0.182435762966943 |
| 1799 | 1131407 | 1131407 : ALS2CR3 :: amyotrophic lateral sclerosis 2 (juvenile) chromosome region, candidate 3 | | 154248 | 0.338869376678187 | -0.439596598652341 |
| 1800 | 1131411 | 1131411 : ACTR1B :: ARP1 actin-related protein 1 homolog B, centractin beta (yeast) | | 2477 | 0.077923077119751 | -0.079428496373113 |
| 1801 | 1131414 | 1131414 : CLK3 :: CDC-like kinase 3 | | 511790 | -0.269988760385229 | 0.0826659 28562320 |
| 1802 | 1131450 | 1131450 : SRPK1 :: SFRS protein kinase 1 | | 369358 | -0.461499682598341 | 0.660300221952223 |
| 1803 | 1131473 | 1131473 : PSMB4 :: proteasome (prosome, macropain) subunit, beta type, 4 | | 89545 | -0.520434353958541 | 0.484814019338330 |
| 1804 | 1131474 | 1131474 : CDK4 :: cyclin-dependent kinase 4 | | 95577 | -0.439683564755247 | 0.779895489372238 |
| 1805 | 1131490 | 1131490 : CDKN1A :: cyclin-dependent kinase inhibitor 1A (p21, Cip1) | | 370771 | 0.386435520309 45 | -0.301994028596566 |
| 1806 | 1131497 | 1131497 : CTSH :: cathepsin H | | 114931 | 0.330713175489614 | -0.355002555291128 |
| 1807 | 1131503 | 1131503 : SMARCA5 :: SWI/SNF related, matrix associated, actin dependent regulator of chromatin, subfamily a, member 5 | | 135705 | -0.387527664547821 | 0.543569727624998 |
| 1808 | 1131507 | 1131507 : COL1A1 :: collagen, type I, alpha 1 | | 172928 | 0.748114290829864 | -0.207748584834290 |
| 1809 | 1131531 | 1131531 : MATN2 :: matrilin 2 | | 153647 | 0.325141676021648 | -0.307381647293302 |
| 1810 | 1131541 | 1131541 : TRAM2 :: translocation associated membrane protein 2 | | 310230 | -0.109763921862653 | 0.121260099038360 |
| 1811 | 1131561 | 1131561 : COL1A2 :: collagen, type I, alpha 2 | | 232115 | 0.874692627775946 | -0.334576284522396 |
| 1812 | 1131578 | 1131578 : MYC :: v-myc myelocytomatosis viral oncogene homolog (avian) | | 202453 | -0.473650493201987 | 0.439091538893661 |
| 1813 | 1131584 | 1131584 : IDS :: iduronate 2-sulfatase (Hunter syndrome) | | 303154 | 0.409153834815565 | -0.206704914490955 |
| 1814 | 1131592 | 1131592 : CTSK :: cathepsin K (pycnodysostosis) | | 83942 | 0.848850881019183 | -0.369116963340649 |

TABLE 2415-continued

GeneID.txt

| Order | UNIQID | NAME | GENEID | LN.cor | Pro.cor |
|---|---|---|---|---|---|
| 1815 | 1131594 | ERBB3 :: v-erb-b2 erythroblastic leukemia viral oncogene homolog 3 (avian) | 306251 | -0.0370728165004209 | 0.0141254702226058 |
| 1816 | 1131614 | RANBP1 :: RAN binding protein 1 | 24763 | -0.497718394256005 | 0.861673208863039 |
| 1817 | 1131636 | SPOCK2 :: sparc/osteonectin, cwcv and kazal-like domains proteoglycan (testican) 2 | 436193 | 0.163651135120878 | -0.586216415254260 |
| 1818 | 1131637 | MADH4 :: MAD, mothers against decapentaplegic homolog 4 (Drosophila) | 75862 | -0.296122552295810 | 0.254301505485065 |
| 1819 | 1131640 | DHFR :: dihydrofolate reductase | 83765 | -0.318925662013329 | 0.697984260974183 |
| 1820 | 1131645 | SCYE1 :: small inducible cytokine subfamily E, member 1 (endothelial monocyte-activating) | 105656 | -0.408590686241245 | 0.435284600019574 |
| 1821 | 1131654 | MYLK :: myosin, light polypeptide kinase | 506692 | 0.651782538418739 | -0.499306112068076 |
| 1822 | 1131663 | MARK3 :: MAP/microtubule affinity-regulating kinase 3 | 437625 | -0.127947033428119 | 0.128365431201822 |
| 1823 | 1131687 | TLK1 :: tousled-like kinase 1 | 369280 | -0.497276731283518 | 0.180410183690407 |
| 1824 | 1131705 | ICAM1 :: intercellular adhesion molecule 1 (CD54), human rhinovirus receptor | 386467 | 0.378982406710592 | -0.337971803564004 |
| 1825 | 1131710 | TNFAIP3 :: tumor necrosis factor, alpha-induced protein 3 | 211600 | 0.463815458286967 | -0.506090111158935 |
| 1826 | 1131733 | AXL :: AXL receptor tyrosine kinase | 83341 | 0.378828997894475 | -0.403851757655397 |
| 1827 | 1131737 | STK17A :: serine/threonine kinase 17a (apoptosis-inducing) | 9075 | 0.130652258117317 | -0.103978746190248 |
| 1828 | 1131752 | FOXO1A :: forkhead box O1A (rhabdomyosarcoma) | 170133 | -0.122578273317010 | 0.0403505029977271 |
| 1829 | 1131753 | IFNGR1 :: interferon gamma receptor 1 | 180866 | 0.618517741082226 | -0.417914352213948 |
| 1830 | 1131755 | LTBP1 :: latent transforming growth factor beta binding protein 1 | 241257 | 0.502355072705751 | -0.139333692684381 |
| 1831 | 1131757 | LSM4 :: LSM4 homolog, U6 small nuclear RNA associated (S. cerevisiae) | 76719 | -0.338083430713762 | 0.555861490784508 |
| 1832 | 1131767 | RFXANK :: regulatory factor X-associated ankyrin-containing protein | 296776 | -0.298195363108909 | 0.396266516850386 |
| 1833 | 1131778 | E2-EPF :: ubiquitin carrier protein | 396393 | -0.444812770066341 | 0.811955135871133 |
| 1834 | 1131786 | ITGB2 :: integrin, beta 2 (antigen CD18 (p95), lymphocyte function-associated antigen 1; macrophage antigen 1 (mac-1) beta subunit) | 375957 | 0.558038870974376 | -0.444583848022385 |
| 1835 | 1131806 | DNAJB9 :: DnaJ (Hsp40) homolog, subfamily B, member 9 | 6790 | 0.130968076956592 | -0.29235796758107 |
| 1836 | 1131808 | RALBP1 :: ralA binding protein 1 | 75447 | -0.431671598650297 | 0.449902319020008 |
| 1837 | 1131813 | RYK :: RYK receptor-like tyrosine kinase | 285346 | 0.032808356450494 | -0.176191545516543 |
| 1838 | 1131815 | SLC16A3 :: solute carrier family 16 (monocarboxylic acid transporters), member 3 | 386678 | 0.595720282107956 | -0.261951094065078 |
| 1839 | 1131816 | IL8 :: interleukin 8 | 624 | 0.140264002040061 | -0.022197751307439 |
| 1840 | 1131827 | PSCD1 :: pleckstrin homology, Sec7 and coiled-coil domains 1(cytohesin 1) | 1050 | 0.009086209334830 | -0.326598876849318 |
| 1841 | 1131835 | ANPEP :: alanyl (membrane) aminopeptidase (aminopeptidase N, aminopeptidase M, microsomal aminopeptidase, CD13, p150) | 1239 | 0.560675531752289 | -0.319995337520616 |
| 1842 | 1131839 | SFRS3 :: splicing factor, arginine/serine-rich 3 | 405144 | -0.462771409363554 | 0.757901723793864 |
| 1843 | 1131845 | NBS1 :: Nijmegen breakage syndrome 1 (nibrin) | 25812 | 0.187739986384909 | -0.055483735199348 |
| 1844 | 1131847 | CD97 :: CD97 antigen | 3107 | 0.470642638940702 | -0.594528313613836 |
| 1845 | 1131854 | GCLC :: glutamate-cysteine ligase, catalytic subunit | 414985 | -0.229812122262907 | 0.0336526111878791 |
| 1846 | 1131861 | YES1 :: v-yes-1 Yamaguchi sarcoma viral oncogene homolog 1 | 194148 | 0.404068940647571 | -0.352649679792935 |
| 1847 | 1131863 | SOX9 :: SRY (sex determining region Y)-box 9 (campomelic dysplasia autosomal sex-reversal) | 2316 | 0.023548359459035 | 0.008979903745464 |
| 1848 | 1131868 | GYPC :: glycophorin C (Gerbich blood group) | 81994 | 0.068679003500084 | -0.169866880145741 |
| 1849 | 1131870 | ADAM12 :: a disintegrin and metalloproteinase domain 12 (meltrin alpha) | 8850 | 0.672171616380497 | -0.290298904712172 |
| 1850 | 1131875 | CAPN6 :: calpain 6 | 169172 | 0.053625471376072 | -0.113317658717737 |
| 1851 | 1131916 | PIAS3 :: protein inhibitor of activated STAT3 | 435761 | 0.060317360202652 | -0.119267354100978 |
| 1852 | 1131918 | MTSS1 :: metastasis suppressor 1 | 77694 | 0.126594607748513 | -0.215833382228631 |
| 1853 | 1131925 | TCTA :: T-cell leukemia translocation altered gene | 250894 | -0.140634086253037 | -0.084263934757262 |
| 1854 | 1131940 | TGFB1 :: transforming growth factor, beta 1 (Camurati-Engelmann disease) | 1103 | 0.077307306507790 | -0.219635532756303 |
| 1855 | 1131955 | WHSC2 :: Wolf-Hirschhorn syndrome candidate 2 | 21771 | -0.428553483194901 | 0.522335335717293 |
| 1856 | 1131964 | KIF5C :: kinesin family member 5C | 6641 | 0.178798859283669 | -0.000776060927303 |
| 1857 | 1131972 | PAK4 :: p21(CDKN1A)-activated kinase 4 | 20447 | -0.184120285169395 | 0.182353309770624 |
| 1858 | 1131975 | RNF8 :: ring finger protein (C3HC4 type) 8 | 24439 | -0.246051078343186 | 0.456159857346887 |
| 1859 | 1131998 | RFC5 :: replication factor C (activator 1) 5, 36.5 kDa | 443227 | -0.304105043276485 | 0.580015219267383 |
| 1860 | 1132004 | SIAT9 :: sialyltransferase 9 (CMP-NeuAc:lactosylceramide alpha-2,3-sialyltransferase; GM3 synthase) | 415117 | 0.131829639089957 | -0.357953062221225 |
| 1861 | 1132011 | CLK2 :: CDC-like kinase 2 | 73986 | -0.433221154262639 | 0.333142142452891 |

TABLE 2415-continued

GeneID.txt

| Order | UNIQID | NAME | GENEID | LN.cor | Pro.cor |
|---|---|---|---|---|---|
| 1862 | 1132013 | SCA1 :: spinocerebellar ataxia 1 (olivopontocerebellar ataxia 1, autosomal dominant, ataxin 1) | 434961 | 0.573011124237002 | −0.558158560945881 |
| 1863 | 1132016 | NOTCH3 :: Notch homolog 3 (Drosophila) | 8546 | 0.516342851051717 | −0.283665731808773 |
| 1864 | 1132022 | ZNF24 :: zinc finger protein 24 (KOX 17) | 173911 | −0.132362253139443 | 0.0199397869990243 |
| 1865 | 1132031 | MAP2K4 :: mitogen-activated protein kinase kinase 4 | 134106 | −0.0443266309510000 | 0.0770571869977509 |
| 1866 | 1132034 | UNC119 :: unc-119 homolog (C. elegans) | 410455 | 0.162674778479055 | −0.152850646527214 |
| 1867 | 1132035 | PDAP2 :: PDGFA associated protein 2 | 8186 | −0.351063634678681 | 0.341148418065009 |
| 1868 | 1132058 | TGIF :: TGFB-induced factor (TALE family homeobox) | 161999 | −0.0899543919608 | 0.0129834285775114 |
| 1869 | 1132104 | TBC1D4 :: TBC1 domain family, member 4 | 173802 | 0.174716497125486 | −0.303331906685459 |
| 1870 | 1132122 | MME :: membrane metallo-endopeptidase (neutral endopeptidase, enkephalinase, CALLA, CD10) | 307734 | 0.091058727833380 | 0.213585135607787 |
| 1871 | 1132132 | ATOX1 :: ATX1 antioxidant protein 1 homolog (yeast) | 279910 | 0.371746754962258 | −0.235388977702808 |
| 1872 | 1132159 | ZNF318 :: zinc finger protein 318 | 147868 | 0.039152606400365 | 0.161742423454252 |
| 1873 | 1132178 | PTTG1 :: pituitary tumor-transforming 1 | 350966 | −0.258893293711822 | 0.666347157955608 |
| 1874 | 1132196 | CSF3R :: colony stimulating factor 3 receptor (granulocyte) | 381027 | 0.438613330885891 | −0.418452605605811 |
| 1875 | 1132220 | GPRC5B :: G protein-coupled receptor, family C, group 5, member B | 448805 | 0.366768325666919 | −0.427970742931399 |
| 1876 | 1132223 | FGFR2 :: fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | 404081 | 0.317558427639917 | −0.241289886185299 |
| 1877 | 1132230 | PLA2G2A :: phospholipase A2, group IIA (platelets, synovial fluid) | 76422 | 0.279193056674363 | −0.160817405939559 |
| 1878 | 1132236 | TMOD1 :: tropomodulin 1 | 374849 | 0.324423040844218 | −0.350644740562922 |
| 1879 | 1132256 | KIAA0173 :: KIAA0173 gene product | 169910 | 0.031123896338403 | 0.336046918386896 |
| 1880 | 1132260 | FZD7 :: frizzled homolog 7 (Drosophila) | 173859 | 0.462892817101932 | −0.441381755415042 9 |
| 1881 | 1132288 | STS :: steroid sulfatase (microsomal), arylsulfatase C, isozyme S | 79876 | 0.134794043837710 | 0.0813003460400601 |
| 1882 | 1132292 | BLVRA :: biliverdin reductase A | 435726 | 0.307210356182809 | −0.329095748235412 |
| 1883 | 1132294 | RPS6KB2 :: ribosomal protein S6 kinase, 70 kDa, polypeptide 2 | 103081 | 0.046867241876797 | −0.0314924111847754 |
| 1884 | 1132306 | BCL7A :: B-cell CLL/lymphoma 7A | −34 | −0.145765239332859 | 0.288878301794857 |
| 1885 | 1132329 | ACK1 :: activated p21cdc42Hs kinase | 128392 | 0.015481843347622 | −0.205600218015162 |
| 1886 | 1132336 | GAB2 :: GRB2-associated binding protein 2 | 30687 | 0.279420865222956 | −0.316921655907721 |
| 1887 | 1132345 | VCAM1 :: vascular cell adhesion molecule 1 | 109225 | 0.423122552443272 | −0.521238250710401 |
| 1888 | 1132349 | DMD :: dystrophin (muscular dystrophy, Duchenne and Becker types) | 169470 | 0.015601524791194 | 0.155636775212336 |
| 1889 | 1132353 | THBD :: thrombomodulin | 2030 | 0.319336617488327 | −0.304072866702818 |
| 1890 | 1132354 | DAPK3 :: death-associated protein kinase 3 | 153908 | −0.087408304874834 | 0.169599747878693 |
| 1891 | 1132375 | MARK2 :: MAP/microtubule affinity-regulating kinase 2 | 157199 | 0.008317055906942 | −0.0294390319312 99 |
| 1892 | 1132376 | BTN2A1 :: butyrophilin, subfamily 2, member A1 | 169963 | 0.269826752423953 | −0.381922260724480 |
| 1893 | 1132396 | FUT8 :: fucosyltransferase 8 (alpha (1,6) fucosyltransferase | 118722 | −0.244464243998852 | 0.231749952936851 |
| 1894 | 1132407 | PAWR :: PRKC, apoptosis, WT1, regulator | 406074 | −0.256402843713444 | 0.392482360907927 |
| 1895 | 1132426 | C6orf56 :: chromosome 6 open reading frame 56 | 102471 | 0.075623143391260 | −0.263519720550745 |
| 1896 | 1132428 | SFRP4 :: secreted frizzled-related protein 4 | 105790 | 0.470112484475708 | −0.289073301793498 |
| 1897 | 1132433 | ME1 :: malic enzyme 1, NADP(+)-dependent, cytosolic | 14732 | 0.235924704818424 | −0.341006938347295 |
| 1898 | 1132434 | PRKX :: protein kinase, X-linked | 147996 | 0.082516439464899 | −0.203824608303043 |
| 1899 | 1132435 | ULK2 :: unc-51-like kinase 2 (C. elegans) | 168762 | 0.025216376306500 | −0.043079703646662 |
| 1900 | 1132449 | STK6 :: serine/threonine kinase 6 | 250822 | −0.342484710552208 | 0.854223977659442 |
| 1901 | 1132460 | CDC45L :: CDC45 cell division cycle 45-like (S. cerevisiae) | 114311 | −0.392694067278240 | 0.786127341984203 |
| 1902 | 1132462 | FOXO3A :: forkhead box O3A | 14845 | 0.368591254754925 | −0.433764383288663 |
| 1903 | 1132468 | TFDP1 :: transcription factor Dp-1 | 79353 | −0.281111016450068 | 0.587665041868591 |
| 1904 | 1132479 | CKS2 :: CDC28 protein kinase regulatory subunit 2 | 83738 | −0.336131034183213 | 0.776594329768994 |
| 1905 | 1132485 | ADRBK2 :: adrenergic, beta, receptor kinase 2 | 445563 | 0.026500837215 7 | 0.2121057269571 52 |
| 1906 | 1132498 | PRKR :: protein kinase, interferon-inducible double stranded RNA dependent | 439523 | 0.066840579394694 | −0.087904249089 43 |
| 1907 | 1132504 | GLIPR1 :: GLI pathogenesis-related 1 (glioma) | 511765 | 0.332274083428259 | −0.223318633357 6 |
| 1908 | 1132519 | CDK5 :: cyclin-dependent kinase 5 | 166071 | −0.047271288760870 | 0.233374203627911 |
| 1909 | 1132520 | LMO2 :: LIM domain only 2 (rhombotin-like 1) | 283063 | 0.322555941970676 | −0.133225258835905 |

TABLE 2415-continued

| Order | UNIQID | NAME | GeneID.txt | GENEID | LN.cor | Pro.cor |
|---|---|---|---|---|---|---|
| 1910 | 1132525 | 1132525 : VDR :: vitamin D (1,25-dihydroxyvitamin D3) receptor | | 2062 | 0.433864275074134 | -0.287514297938507 |
| 1911 | 1132529 | 1132529 : C6orf9 :: chromosome 6 open reading frame 9 | | 288316 | 0.0206965375691352 | -0.351700071982180 |
| 1912 | 1132531 | 1132531 : PKMYT1 :: membrane-associated tyrosine- and threonine-specific cdc2-inhibitory kinase | | 77783 | -0.326448359051311 | 0.770085323613511 |
| 1913 | 1132536 | 1132536 : PMAIP1 :: phorbol-12-myristate-13-acetate-induced protein 1 | | 96 | -0.264821671020407 | 0.140274139633261 |
| 1914 | 1132545 | 1132545 : CD151 :: CD151 antigen | | 512857 | 0.484034201302057 | -0.267742723399692 |
| 1915 | 1132547 | 1132547 : NPR2 :: natriuretic peptide receptor B/guanylate cyclase B (atrionatriuretic peptide receptor B) | | 78518 | 0.146399574004803 | -0.263444587844550 |
| 1916 | 1132572 | 1132572 : LIMK1 :: LIM domain kinase 1 | | 36566 | 0.134056222788714 | 0.0420551895011082 |
| 1917 | 1132584 | 1132584 : FGFR3 :: fibroblast growth factor receptor 3 (achondroplasia, thanatophoric dwarfism) | | 1420 | 0.147516952526905 | -0.119140751786612 |
| 1918 | 1132592 | 1132592 : GPRK5 :: G protein-coupled receptor kinase 5 | | 211569 | 0.177329362173847 | -0.0330254038996986 |
| 1919 | 1132614 | 1132614 : ALOX5 :: arachidonate 5-lipoxygenase | | 89499 | 0.253272865281527 | -0.158095339023624 |
| 1920 | 1132628 | 1132628 : TIE :: tyrosine kinase with immunoglobulin and epidermal growth factor homology domains | | 78824 | 0.235417471722526 | -0.0559524418567724 |
| 1921 | 1132636 | 1132636 : CD44 :: CD44 antigen (homing function and Indian blood group system) | | 306278 | 0.170483625093136 | -0.0705352794463917 |
| 1922 | 1132651 | 1132651 : TOX :: thymus high mobility group box protein TOX | | 439767 | 0.118932638076210 | -0.0795464631897911 |
| 1923 | 1132700 | 1132700 : RPS6KA5 :: ribosomal protein S6 kinase, 90 kDa, polypeptide 5 | | 109058 | -0.0173345767062377 | -0.166266630632264 |
| 1924 | 1132726 | 1132726 : MAPK4 :: mitogen-activated protein kinase 4 | | 433628 | 0.00952104891982 | -0.0841756847059911 |
| 1925 | 1132734 | 1132734 : COL9A3 :: collagen, type IX, alpha 3 | | 126248 | -0.101320116382731 | 0.0796973192150944 |
| 1926 | 1132762 | 1132762 : MAL :: mal, T-cell differentiation protein | | 80395 | 0.252541285182322 | -0.443739008375554 |
| 1927 | 1132766 | 1132766 : TNFRSF6 :: tumor necrosis factor receptor superfamily, member 6 | | 82359 | 0.439880140313859 | -0.246840312593953 |
| 1928 | 1132768 | 1132768 : IFNAR2 :: interferon (alpha, beta and omega) receptor 2 | | 512211 | 0.00431987531605 | -0.106811200549353 |
| 1929 | 1132775 | 1132775 : RRAD :: Ras-related associated with diabetes | | 1027 | 0.382640243706838 | -0.245069256965701 |
| 1930 | 1132780 | 1132780 : CACNA2D2 :: calcium channel, voltage-dependent, alpha 2/delta subunit 2 | | 389415 | -0.00881147536046 | -0.0899038219424776 |
| 1931 | 1132787 | 1132787 : BMPR1A :: bone morphogenetic protein receptor, type IA | | 2534 | -0.115173969757864 | 0.228241887165443 |
| 1932 | 1132799 | 1132799 : APAF1 :: apoptotic protease activating factor | | 373575 | 0.108985290832645 | 0.033820592215645 |
| 1933 | 1132809 | 1132809 : PSK :: prostate derived STE20-like kinase PSK | | 122823 | -0.0843703879810833 | 0.063316707183397 |
| 1934 | 1132818 | 1132818 : LCK :: lymphocyte-specific protein tyrosine kinase | | 1765 | 0.166418049475020 | -0.319368734677355 |
| 1935 | 1132825 | 1132825 : SAP30 :: sin3-associated polypeptide, 30 kDa | | 512813 | 0.064474665431520 | 0.408174220850057 |
| 1936 | 1132830 | 1132830 : BCL3 :: B-cell CLL/lymphoma 3 | | 31210 | 0.0122413960978844 | -0.00577089934908 |
| 1937 | 1132834 | 1132834 : SOX11 :: SRY (sex determining region Y)-box 11 | | 432638 | -0.130108520868878 | 0.00893443992576 |
| 1938 | 1132850 | 1132850 : DYRK1B :: dual-specificity tyrosine-(Y)-phosphorylation regulated kinase 1B | | 130988 | -0.150245711405737 | -0.0640378487837788 |
| 1939 | 1132851 | 1132851 : Homo sapiens cDNA FLJ46012 fis, clone SPLEN2007689, highly similar to Neutrophil cytosol factor 1 | | 1583 | -0.105077219223237 | -0.185727977850533 |
| 1940 | 1132852 | 1132852 : CENPA :: centromere protein A, 17 kDa | | 1594 | -0.330307054028778 | 0.834198009135619 |
| 1941 | 1132860 | 1132860 : PSK :: prostate derived STE20-like kinase PSK | | 122823 | -0.140238455355596 | 0.075742960594935 |
| 1942 | 1132862 | 1132862 : ITGB4 :: integrin, beta 4 | | 85266 | -0.0013978053436690 | -0.006702616683621 |
| 1943 | 1132866 | 1132866 : ATF5 :: activating transcription factor 5 | | 9754 | -0.0837400507309572 | -0.030416622263988 |
| 1944 | 1132874 | 1132874 : ADORA2A :: adenosine A2a receptor | | 197029 | -0.171103874940728 | 0.175530614350310 |
| 1945 | 1132883 | 1132883 : MAP3K8 :: mitogen-activated protein kinase kinase kinase 8 | | 432453 | 0.220120953209822 | -0.207562161908588 |
| 1946 | 1132890 | 1132890 : CD79A :: CD79A antigen (immunoglobulin-associated alpha) | | 79630 | -0.337177451882671 | 0.299810735012318 |
| 1947 | 1132892 | 1132892 : KIT :: v-kit Hardy-Zuckerman 4 feline sarcoma viral oncogene homolog | | 81665 | 0.346840521155709 | -0.287525269110642 |
| 1948 | 1132918 | 1132918 : CCL3 :: chemokine (C-C motif) ligand 3 | | 73817 | 0.210200763463909 | -0.379856191443791 |
| 1949 | 1132920 | 1132920 : FPR1 :: formyl peptide receptor 1 | | 753 | 0.450668752553231 | -0.271074665943058 |
| 1950 | 1132953 | 1132953 : ADAM8 :: a disintegrin and metalloproteinase domain 8 | | 86947 | 0.090679204456041 | -0.122432730144956 |
| 1951 | 1132959 | 1132959 : ATP7A :: ATPase, Cu++ transporting, alpha polypeptide (Menkes syndrome) | | 606 | 0.366616137158226 | -0.387610706775942 |
| 1952 | 1132961 | 1132961 : CENTB1 :: centaurin, beta 1 | | 337242 | 0.059851837494540 | -0.278472771716937 |
| 1953 | 1132973 | 1132973 : TCF7 :: transcription factor 7 (T-cell specific, HMG-box) | | 169294 | 0.123121096136518 | -0.447164390873820 |
| 1954 | 1132979 | 1132979 : CCRK :: cell cycle related kinase | | 26322 | 0.207844813354062 | -0.131701392184582 |
| 1955 | 1132990 | 1132990 : CD79B :: CD79B antigen (immunoglobulin-associated beta) | | 89575 | -0.344622456167376 | 0.358039114087407 |
| 1956 | 1132994 | 1132994 : OGG1 :: 8-oxoguanine DNA glycosylase | | 380271 | -0.137099966252423 | 0.320169119840156 |
| 1957 | 1132996 | 1132996 : KMO :: kynurenine 3-monooxygenase (kynurenine 3-hydroxylase) | | 409081 | 0.211990018555365 | -0.291776582897728 |

TABLE 2415-continued

GeneID.txt

| Order | UNIQID | NAME | GENEID | LN.cor | Pro.cor |
|---|---|---|---|---|---|
| 1958 | 1133004 | 1133004 : ACVR2 :: activin A receptor, type II | 389846 | 0.279599795179747 | −0.239731396808758 |
| 1959 | 1133011 | 1133011 : TMSNB :: thymosin, beta, identified in neuroblastoma cells | 56145 | −0.00252006039582 | 0.0718411497761115 |
| 1960 | 1133021 | 1133021 : ACHE :: acetylcholinesterase (YT blood group) | 154495 | 0.402482778770336 | −0.155787254777042 |
| 1961 | 1133024 | 1133024 : ZNF288 :: zinc finger protein 288 | 436987 | 0.265865101259661 | −0.396721785363083 |
| 1962 | 1133030 | 1133030 : CCL15 :: chemokine (C-C motif) ligand 15 | 272493 | 0.057379944824827 | −0.281520577334817 |
| 1963 | 1133042 | 1133042 : ITGBL1 :: integrin, beta-like 1 (with EGF-like repeat domains) | 311054 | 0.622932591813418 | −0.328959959392322 |
| 1964 | 1133047 | 1133047 : AAK1 :: AP2 associated kinase 1 | 135941 | 0.348101012819978 | −0.519349741936085 |
| 1965 | 1133049 | 1133049 : H2AFX :: H2A histone family, member X | 147097 | −0.194779401220227 | 0.611672944781315 |
| 1966 | 1133065 | 1133065 : PLAU :: plasminogen activator, urokinase | 77274 | 0.783707351172337 | −0.379451893760215 |
| 1967 | 1133068 | 1133068 : G1P2 :: interferon, alpha-inducible protein (clone IFI-15K) | 458485 | 0.224134143117873 | −0.313126229936884 |
| 1968 | 1133076 | 1133076 : PDCD8 :: programmed cell death 8 (apoptosis-inducing factor) | 18720 | −0.157569526709521 | 0.402184728488840 |
| 1969 | 1133080 | 1133080 : KATNA1 :: katanin p60 (ATPase-containing) subunit A 1 | 440341 | −0.165970006007139 | 0.181023125522753 |
| 1970 | 1133091 | 1133091 : CR2 :: complement component (3d/Epstein Barr virus) receptor 2 | 73792 | 0.030214844042362 | 0.092058217437685 |
| 1971 | 1133093 | 1133093 : TYK2 :: tyrosine kinase 2 | 75516 | −0.217551973397616 | −0.00242253620170 |
| 1972 | 1133099 | 1133099 : DNASE1L3 :: deoxyribonuclease I-like 3 | 88646 | −0.257980874817348 | −0.166979927446227 |
| 1973 | 1133102 | 1133102 : FRDA :: Friedreich ataxia | 360041 | −0.335514224531287 | 0.492486823001609 |
| 1974 | 1133111 | 1133111 : PDE9A :: phosphodiesterase 9A | 389777 | 0.133104476615309 | −0.019862978252224 |
| 1975 | 1133117 | 1133117 : PACE-1 :: ezrin-binding partner PACE-1 | 435560 | −0.016659594094386 | −0.00295418059327 |
| 1976 | 1133119 | 1133119 : MST1 :: macrophage stimulating 1 (hepatocyte growth factor-like) | 512587 | 0.017059225812341 | −0.167280765698926 |
| 1977 | 1133138 | 1133138 : HLA-DOB :: major histocompatibility complex, class II, DO beta | 1802 | −0.150884123016589 | −0.047034927110652 |
| 1978 | 1133141 | 1133141 : DLEU1 :: deleted in lymphocytic leukemia, 1 | 344524 | −0.476297541441405 | 0.564225643626155 |
| 1979 | 1133148 | 1133148 : CD38 :: CD38 antigen (p45) | 174944 | −0.086274304083668 | −0.258405804308845 |
| 1980 | 1133150 | 1133150 : MAP2K6 :: mitogen-activated protein kinase kinase 6 | 256924 | −0.060625002575886 | 0.143053623586413 |
| 1981 | 1133156 | 1133156 : COMP :: cartilage oligomeric matrix protein | 1584 | 0.441890669117056 | −0.195814414026257 |
| 1982 | 1133184 | 1133184 : ITGAM :: integrin, alpha M (complement component receptor 3, alpha; also known as CD11b (p170), macrophage antigen alpha polypeptide) | 172631 | 0.753289632173116 | −0.438207938207401 |
| 1983 | 1133192 | 1133192 : RASGRP3 :: RAS guanyl releasing protein 3 (calcium and DAG-regulated) | 24024 | −0.227545188050837 | 0.110767187589711 |
| 1984 | 1133195 | 1133195 : ROR1 :: receptor tyrosine kinase-like orphan receptor 1 | 274243 | 0.211158348281962 | −0.095352844765914 |
| 1985 | 1133210 | 1133210 : JAK2 :: Janus kinase 2 (a protein tyrosine kinase) | 434374 | 0.211723154336484 | −0.309565714170364 |
| 1986 | 1133216 | 1133216 : PDE4DIP :: phosphodiesterase 4D interacting protein (myomegalin) | 390449 | 0.469859143755927 | −0.270025422668526 |
| 1987 | 1133219 | 1133219 : RET :: ret proto-oncogene (multiple endocrine neoplasia and medullary thyroid carcinoma 1, Hirschsprung disease) | 350321 | 0.039216692256241 | −0.113466892491905 |
| 1988 | 1133227 | 1133227 : NOLC1 :: nucleolar and coiled-body phosphoprotein 1 | 75337 | −0.467836599715920 | 0.605412542908700 |
| 1989 | 1133232 | 1133232 : CEL :: carboxyl ester lipase (bile salt-stimulated lipase) | 406160 | −0.047643754334538 | 0.004264213209241 |
| 1990 | 1133252 | 1133252 : EPHA1 :: EphA1 | 89839 | 0.291635532708424 | −0.334277608203048 |
| 1991 | 1133260 | 1133260 : IL15 :: interleukin 15 | 168132 | 0.477661261402447 | −0.545949137402680 |
| 1992 | 1133272 | 1133272 : MERTK :: c-mer proto-oncogene tyrosine kinase | 306178 | 0.252944775766872 | −0.308345267333304 |
| 1993 | 1133275 | 1133275 : REL :: v-rel reticuloendotheliosis viral oncogene homolog (avian) | 44313 | −0.085309557979979 | 0.156958739161487 |
| 1994 | 1133296 | 1133296 : EPHA3 :: EphA3 | 123642 | 0.158232174391835 | −0.146669730921844 |
| 1995 | 1133299 | 1133299 : CSNK2A1 :: casein kinase 2, alpha 1 polypeptide | 446484 | −0.402393962409281 | 0.443591691051582 |
| 1996 | 1133300 | 1133300 : CTH :: cystathionase (cystathionine gamma-lyase) | 19904 | −0.174763128546197 | 0.309368945386643 |
| 1997 | 1133355 | 1133355 : MATK :: megakaryocyte-associated tyrosine kinase | 437808 | 0.209013931316900 | −0.223912921475326 |
| 1998 | 1133358 | 1133358 : TAL1 :: T-cell acute lymphocytic leukemia 1 | 73828 | 0.099663664736123 | −0.092238236560719 |
| 1999 | 1133376 | 1133376 : DAPK2 :: death-associated protein kinase 2 | 129208 | 0.312209231371153 | −0.375817373135772 |
| 2000 | 1133388 | 1133388 : MAP3K10 :: mitogen-activated protein kinase kinase kinase 10 | 435014 | −0.085980697049518 | −0.084119677925152 |
| 2001 | 1133389 | 1133389 : XCL1 :: chemokine (C motif) ligand 1 | 174228 | −0.035790980270872 | −0.263917654207473 |
| 2002 | 1133392 | 1133392 : PFC :: properdin P factor, complement | 53155 | 0.101600551414248 | −0.305806420968560 |
| 2003 | 1133397 | 1133397 : PF4 :: platelet factor 4 (chemokine (C-X-C motif) ligand 4) | 81564 | 0.138980500020639 | −0.024818220159783 |
| 2004 | 1133400 | 1133400 : CD19 :: CD19 antigen | 96023 | −0.142433949967589 | 0.163988190753814 |

TABLE 2415-continued

GeneID.txt

| Order | UNIQID | NAME | GENEID | LN.cor | Pro.cor |
|---|---|---|---|---|---|
| 2005 | 1133405 | 1133405 : CCL13 :: chemokine (C-C motif) ligand 13 | 414629 | -0.083416470126778 | -0.088402738547819 |
| 2006 | 1133406 | 1133406 : ABL2 :: v-abl Abelson murine leukemia viral oncogene homolog 2 (arg, Abelson-related gene) | 159472 | 0.022813711233182 | 0.032606347502914 |
| 2007 | 1133407 | 1133407 : TCL1B :: T-cell leukemia/lymphoma 1B | 512850 | -0.174317478777086 | 0.242190379023676 |
| 2008 | 1133408 | 1133408 : DDEF2 :: development and differentiation enhancing factor 2 | 12802 | 0.540194218430208 | -0.416938590146850 |
| 2009 | 1133430 | 1133430 : TNFRSF6B :: tumor necrosis factor receptor superfamily, member 6b, decoy | 348183 | 0.269171054691013 | -0.078298763058308 |
| 2010 | 1133445 | 1133445 : CHC1 :: chromosome condensation 1 | 196769 | -0.388958919390715 | 0.590137912621854 |
| 2011 | 1133453 | 1133453 : RGS9 :: regulator of G-protein signalling 9 | 117149 | 0.120525989789610 | -0.176381127128455 |
| 2012 | 1133476 | 1133476 : MAP4K4 :: mitogen-activated protein kinase kinase kinase kinase 4 | 3628 | 0.186100449709661 | 0.138800618028371 |
| 2013 | 1133515 | 1133515 : PTPN6 :: protein tyrosine phosphatase, non-receptor type 6 | 63489 | 0.012603181388466 | -0.102763121939913 |
| 2014 | 1133538 | 1133538 : FCER2 :: Fc fragment of IgE, low affinity II, receptor for (CD23A) | 1416 | 0.106023153171250 | -0.252188795472937 |
| 2015 | 1133565 | 1133565 : HDAC6 :: histone deacetylase 6 | 6764 | -0.192135925793860 | 0.026151793306868 |
| 2016 | 1133568 | 1133568 : MAP3K7 :: mitogen-activated protein kinase kinase kinase 7 | 290346 | -0.068454670946960 | 0.068695359831212 |
| 2017 | 1133569 | 1133569 : HYAL2 :: hyaluronoglucosaminidase 2 | 76873 | 0.266854829641114 | -0.217117869068044 |
| 2018 | 1133576 | 1133576 : HRK :: harakiri, BCL2 interacting protein (contains only BH3 domain) | 87247 | -0.136002276499443 | 0.126882867488172 |
| 2019 | 1133577 | 1133577 : SLK :: Ste20-related serine/threonine kinase | 105751 | 0.130411355792943 | -0.076955906871234 |
| 2020 | 1133580 | 1133580 : LILRA3 :: leukocyte immunoglobulin-like receptor, subfamily A (without TM domain), member 3 | 113277 | -0.251926329094464 | -0.009994293775648 |
| 2021 | 1133595 | 1133595 : IL11 :: interleukin 11 | 1721 | 0.030444042014686 | -0.107584215640277 |
| 2022 | 1133618 | 1133618 : CCR5 :: chemokine (C-C motif) receptor 5 | 511796 | 0.412073449175704 | -0.559429116658751 |
| 2023 | 1133629 | 1133629 : PTK7 :: PTK7 protein tyrosine kinase 7 | 90572 | 0.437585321386405 | -0.235352422507285 |
| 2024 | 1133652 | 1133652 : ASS :: argininosuccinate synthetase | 160786 | 0.299982247486773 | -0.281306420532693 |
| 2025 | 1133672 | 1133672 : TNF :: tumor necrosis factor (TNF superfamily, member 2) | 241570 | 0.229157733455114 | -0.039984679710739 |
| 2026 | 1133676 | 1133676 : MAPK6 :: mitogen-activated protein kinase 6 | 271980 | -0.053402388955127 | 0.156113673288142 |
| 2027 | 1133694 | 1133694 : AKT1 :: v-akt murine thymoma viral oncogene homolog 1 | 368861 | -0.098441215455632 | 0.210637913631811 |
| 2028 | 1133700 | 1133700 : CDH11 :: cadherin 11, type 2, OB-cadherin (osteoblast) | 443435 | 0.910273241078143 | -0.447714717232453 |
| 2029 | 1133701 | 1133701 : CD80 :: CD80 antigen (CD28 antigen ligand 1, B7-1 antigen) | 838 | 0.234271452338870 | -0.123295283109379 |
| 2030 | 1133702 | 1133702 : FRK :: fyn-related kinase | 89426 | -0.088749786570166 | 0.145490673392961 |
| 2031 | 1133704 | 1133704 : CASP7 :: caspase 7, apoptosis-related cysteine protease | 9216 | 0.150284681291938 | -0.040276646079796 |
| 2032 | 1133708 | 1133708 : ICAM4 :: intercellular adhesion molecule 4, Landsteiner-Wiener blood group | 512159 | 0.072389666623349 | -0.128178472781610 |
| 2033 | 1133724 | 1133724 : PCTK1 :: PCTAIRE protein kinase 1 | 171834 | -0.039172844280366 | 0.183412682054809 |
| 2034 | 1133731 | 1133731 : UBN1 :: ubinuclein 1 | 21479 | -0.233103646285480 | 0.126011351317026 |
| 2035 | 1133753 | 1133753 : KIR3DL2 :: killer cell immunoglobulin-like receptor, three domains, long cytoplasmic tail, 2 | 56328 | 0.057615719536991 | 0.021322335954838 |
| 2036 | 1133755 | 1133755 : CDC2L5 :: cell division cycle 2-like 5 (cholinesterase-related cell division controller) | 404501 | -0.171682635768532 | -0.003512231465868 |
| 2037 | 1133757 | 1133757 : STAU :: staufen, RNA binding protein (Drosophila) | 6113 | -0.285814369623812 | 0.192008922806710 |
| 2038 | 1133766 | 1133766 : LTB :: lymphotoxin beta (TNF superfamily, member 3) | 376208 | 0.229636210128755 | -0.178027816423099 |
| 2039 | 1133778 | 1133778 : IL15RA :: interleukin 15 receptor, alpha | 12503 | 0.411529350916578 | -0.384520065 76836 |
| 2040 | 1133786 | 1133786 : ALG3 :: asparagine-linked glycosylation 3 homolog (yeast, alpha-1,3-mannosyltransferase) | 153590 | -0.379755131485044 | 0.383219707931730 |
| 2041 | 1133801 | 1133801 : TNFSF4 :: tumor necrosis factor (ligand) superfamily, member 4 (tax-transcriptionally activated glycoprotein 1, 34 kDa) | 181097 | 0.137229819751181 | -0.275883435338981 |
| 2042 | 1133802 | 1133802 : CDC2L2 :: cell division cycle 2-like 2 | 402748 | -0.137802379411402 | 0.057863977677410 |
| 2043 | 1133810 | 1133810 : CCR9 :: chemokine (C-C motif) receptor 9 | 225946 | -0.117781028827656 | 0.124533083271088 |
| 2044 | 1133829 | 1133829 : MS4A2 :: membrane-spanning 4-domains, subfamily A, member 2 (Fc fragment of IgE, high affinity I, receptor for; beta polypeptide) | 386748 | 0.177404858682871 | -0.054031419783302 |
| 2045 | 1133834 | 1133834 : LAIR2 :: leukocyte-associated Ig-like receptor 2 | 43803 | 0.226784659149121 | -0.267608718674007 |
| 2046 | 1133846 | 1133846 : TNFRSF9 :: tumor necrosis factor receptor superfamily, member 9 | 193418 | 0.533030357422099 | -0.338024239621130 |
| 2047 | 1133848 | 1133848 : SYK :: spleen tyrosine kinase | 192182 | -0.311059247048826 | 0.343785891142310 |
| 2048 | 1133867 | 1133867 : C1orf38 :: chromosome 1 open reading frame 38 | 10649 | 0.307862904192117 | -0.388823072767907 |
| 2049 | 1133869 | 1133869 : GADD45B :: growth arrest and DNA-damage-inducible, beta | 110571 | 0.223306853942758 | -0.339610292113472 |
| 2050 | 1133901 | 1133901 : MUSK :: muscle, skeletal, receptor tyrosine kinase | 156465 | 0.045285571984218 | 0.076108036762733 |
| 2051 | 1133904 | 1133904 : TNFRSF1A :: tumor necrosis factor receptor superfamily, member 1A | 159 | 0.643710808786366 | -0.596010985742485 |

TABLE 2415-continued

GeneID.txt

| Order | UNIQID | NAME | GENEID | LN.cor | Pro.cor |
|---|---|---|---|---|---|
| 2052 | 1133910 | BLNK :: B-cell linker | 167746 | −0.446169388331319 | 0.329125198490164 |
| 2053 | 1133931 | LILRB2 :: leukocyte immunoglobulin-like receptor, subfamily B (with TM and ITIM domains), member 2 | 306230 | 0.189896569157643 | −0.333536831009256 |
| 2054 | 1133998 | ID3 :: inhibitor of DNA binding 3, dominant negative helix-loop-helix protein | 76884 | −0.231618348471321 | 0.102308599561213 |
| 2055 | 1134069 | CD8B1 :: CD8 antigen, beta polypeptide 1 (p37) | 405667 | 0.225901023201953 | −0.484596706630053 |
| 2056 | 1134076 | ARPC2 :: actin related protein 2/3 complex, subunit 2, 34 kDa | 83583 | 0.136046734918812 | −0.005298188257533 |
| 2057 | 1134083 | C18orf1 :: chromosome 18 open reading frame 1 | 285091 | 0.346451715122800 | −0.373477515568528 |
| 2058 | 1134095 | HCK :: hemopoietic cell kinase | 89555 | −0.014720188541950 | 0.038451469448641 |
| 2059 | 1134109 | MADCAM1 :: mucosal vascular addressin cell adhesion molecule 1 | 102598 | 0.147538030038399 | −0.064881411838308 |
| 2060 | 1134133 | CCL7 :: chemokine (C-C motif) ligand 7 | 251526 | 0.166588295892007 | −0.023081827233061 |
| 2061 | 1134145 | DKFZP564K0822 :: hypothetical protein DKFZp564K0822 | 4750 | −0.071386477041643 | −0.062712005236753 |
| 2062 | 1134200 | ABCC3 :: ATP-binding cassette, sub-family C (CFTR/MRP), member 3 | 90786 | 0.559310932835637 | −0.393423898786516 |
| 2063 | 1134212 | TRIO :: triple functional domain (PTPRF interacting) | 367689 | 0.207746847343388 | −0.222959913655619 |
| 2064 | 1134220 | MYO7A :: myosin VIIA (Usher syndrome 1B (autosomal recessive, severe)) | 370421 | −0.017653358783537 | −0.192603530737153 |
| 2065 | 1134230 | RASGRP2 :: RAS guanyl releasing protein 2 (calcium and DAG-regulated) | 99491 | −0.154642991810068 | 0.051124540138756 |
| 2066 | 1134233 | ALK :: anaplastic lymphoma kinase (Ki-1) | 410680 | 0.186575254434794 | −0.189026699772156 |
| 2067 | 1134270 | GGT1 :: gamma-glutamyltransferase 1 | 352119 | 0.251750587831380 | −0.349120537758305 |
| 2068 | 1134271 | POU5F1 :: POU domain, class 5, transcription factor 1 | 249184 | −0.156623761238959 | 0.029995443126806 |
| 2069 | 1134280 | CRLF2 :: cytokine receptor-like factor 2 | 287729 | −0.035287889475792 | −0.057636116646176 |
| 2070 | 1134296 | FY :: Duffy blood group | 183 | 0.217642615578632 | −0.364345371369456 |
| 2071 | 1134316 | GPRK2L :: G protein-coupled receptor kinase 2-like (Drosophila) | 32959 | 0.033589097434719 | −0.026724476713475 |
| 2072 | 1134361 | KIR2DL4 :: killer cell immunoglobulin-like receptor, two domains, long cytoplasmic tail, 4 | 515605 | −0.064371839816714 | −0.027523138295799 |
| 2073 | 1134370 | FGR :: Gardner-Rasheed feline sarcoma viral (v-fgr) oncogene homolog | 1422 | 0.469902541550403 | −0.371138296962091 |
| 2074 | 1134379 | C4A :: complement component 4A | 150833 | 0.153921754790563 | −0.492982998610867 |
| 2075 | 1134422 | BCL2L11 :: BCL2-like 11 (apoptosis facilitator) | 84063 | −0.167169905260362 | 0.312275568218554 |
| 2076 | 1134424 | S100A14 :: LOC392086: similar to Putative S100 calcium-binding protein A11 pseudogene | −6 | 0.577071499097494 | −0.451549726315866 |
| 2077 | 1134457 | NTRK1 :: neurotrophic tyrosine kinase, receptor, type 1 | 406293 | −0.051929755731206 | −0.076605673516509 |
| 2078 | 1134480 | MACF1 :: microtubule-actin crosslinking factor 1 | 372463 | 0.385302560920052 | −0.489132821439022 |
| 2079 | 1134494 | MSF :: MLL septin-like fusion | 288094 | −0.158164582532209 | 0.094745859172743 |
| 2080 | 1134517 | PDLIM1 :: PDZ and LIM domain 1 (elfin) | 75807 | −0.318932656287507 | 0.223330090652600 |
| 2081 | 1134523 | TKT :: transketolase (Wernicke-Korsakoff syndrome) | 89643 | −0.157519567091726 | 0.331118833432058 |
| 2082 | 1134532 | CCND1 :: cyclin D1 (PRAD1: parathyroid adenomatosis 1) | 371468 | 0.357568571752350 | −0.289354652996340 |
| 2083 | 1134533 | LOC54499 :: putative membrane protein | 93832 | 0.027984409927586 | 0.065539358200285 |
| 2084 | 1134542 | HLA-B :: major histocompatibility complex, class I, B | 77961 | 0.252413302304409 | −0.486244623630763 |
| 2085 | 1134582 | SMARCA4 :: SWI/SNF related, matrix associated, actin dependent regulator of chromatin, subfamily a, member 4 | 78202 | −0.042161334059780 | 0.201113183134652 |
| 2086 | 1134593 | HLA-C :: major histocompatibility complex, class I, C | 274485 | 0.150604563084478 | −0.372850743535715 |
| 2087 | 1134615 | THY1 :: Thy-1 cell surface antigen | 134643 | 0.740295008324578 | −0.289362396064258 |
| 2088 | 1134618 | STK24 :: serine/threonine kinase 24 (STE20 homolog, yeast) | 168913 | −0.302773915211256 | 0.366245931868612 |
| 2089 | 1134647 | DUSP6 :: dual specificity phosphatase 6 | 298654 | 0.506041172080515 | −0.442864261312140 |
| 2090 | 1134653 | TOP1 :: topoisomerase (DNA) I | 253536 | −0.386004901157803 | 0.578538864529316 |
| 2091 | 1134665 | SRI :: sorcin | 422340 | 0.070635339781393 | 0.014029892560073 |
| 2092 | 1134674 | ID1 :: inhibitor of DNA binding 1, dominant negative helix-loop-helix protein | 410900 | 0.315979164228629 | −0.295857070867065 |
| 2093 | 1134676 | TLOC1 :: translocation protein 1 | 158193 | −0.382787060158885 | 0.187687539224563 |
| 2094 | 1134679 | BECN1 :: beclin 1 (coiled-coil, myosin-like BCL2 interacting protein) | 12272 | 0.106604933194899 | −0.102323703391318 |
| 2095 | 1134682 | LGALS3 :: lectin, galactoside-binding, soluble, 3 (galectin 3) | 411701 | 0.499705085052146 | −0.365258666150658 |
| 2096 | 1134687 | TXNDC4 :: thioredoxin domain containing 4 (endoplasmic reticulum) | 154023 | 0.223571308720130 | −0.241073271383677 |
| 2097 | 1134699 | KPNB1 :: karyopherin (importin) beta 1 | 439683 | −0.284720382004117 | 0.534018680230989 |
| 2098 | 1134706 | FBXL11 :: F-box and leucine-rich repeat protein 11 | 219614 | 0.044440389149743 | −0.202122236667693 |
| 2099 | 1134710 | PPIG :: peptidyl-prolyl isomerase G (cyclophilin G) | 77965 | 0.018281322001863 | −0.014383939906630 |
| 2100 | 1134727 | PINK1 :: PTEN induced putative kinase 1 | 439600 | 0.312058012057399 | −0.245134769222099 |

TABLE 2415-continued

GeneID.txt

| Order | UNIQID | NAME | GENEID | LN.cor | Pro.cor |
|---|---|---|---|---|---|
| 2101 | 1134738 | 134738 : DYRK1A :: dual-specificity tyrosine-(Y)-phosphorylation regulated kinase 1A | 75842 | -0.0645685129912211 | -0.100866986311723 |
| 2102 | 1134753 | 134753 : WHSC1 :: Wolf-Hirschhorn syndrome candidate 1 | 110457 | -0.341151329387829 | 0.729975148861719 |
| 2103 | 1134778 | 134778 : RFC1 :: replication factor C (activator 1) 1, 145 kDa | 166563 | -0.336730929289826 | 0.528235750344208 |
| 2104 | 1134797 | 134797 : TUBA3 :: tubulin, alpha 3 | 433394 | 0.405096128352181 | -0.125508822982315 |
| 2105 | 1134837 | 134837 : IRS2 :: insulin receptor substrate 2 | 143648 | 0.449386774571679 | -0.337887011456020 |
| 2106 | 1134843 | 134843 : MEF2C :: MADS box transcription enhancer factor 2, polypeptide C (myocyte enhancer factor 2C) | 368950 | 0.0739715844405973 | 0.121032319047677 |
| 2107 | 1134850 | 134850 : PLEKHC1 :: pleckstrin homology domain containing, family C (with FERM domain) member 1 | 270411 | 0.727857421507228 | -0.375542340871581 |
| 2108 | 1134852 | 134852 : EWSR1 :: Ewing sarcoma breakpoint region 1 | 374477 | -0.370094941491491 | 0.556503015981440 |
| 2109 | 1134858 | 134858 : KPNB2 :: karyopherin (importin) beta 2 | 405954 | -0.133123256535390 | 0.344301361055445 |
| 2110 | 1134865 | 134865 : MINK :: misshapen/NIK-related kinase | 112028 | -0.014360239308387 | -0.031348981802659 |
| 2111 | 1134880 | 134880 : METTL3 :: methyltransferase like 3 | 168799 | -0.501356501976032 | 0.326720755408380 |
| 2112 | 1134888 | 134888 : TFPI2 :: tissue factor pathway inhibitor 2 | 438231 | 0.308231647753657 | -0.273918942666535 |
| 2113 | 1134903 | 134903 : SWAP70 :: SWAP-70 protein | 153026 | 0.0297253973116418 | 0.226883023659028 |
| 2114 | 1134921 | 134921 : IKBKB :: inhibitor of kappa light polypeptide gene enhancer in B-cells, kinase beta | 413513 | 0.101776675617754 | -0.509485574811757 |
| 2115 | 1134928 | 134928 : SIN3B :: SIN3 homolog B, transcriptional regulator (yeast) | 13999 | -0.0953260970287522 | -0.220883061797362 |
| 2116 | 1134933 | 134933 : RUNX1 :: runt-related transcription factor 1 (acute myeloid leukemia 1; aml1 oncogene) | 410774 | 0.136721482617340 | -0.286235883063271 |
| 2117 | 1134945 | 134945 : KIAA1128 :: KIAA1128 protein | 81897 | 0.307874711629927 | -0.456973877209662 |
| 2118 | 1134961 | 134961 : IFI35 :: interferon-induced protein 35 | 50842 | 0.138043455897837 | -0.401306837995058 |
| 2119 | 1134988 | 134988 : MKNK1 :: MAP kinase-interacting serine/threonine kinase 1 | 79516 | 0.226240988283301 | -0.360081299039555 |
| 2120 | 1134991 | 134991 : ENTPD1 :: ectonucleoside triphosphate diphosphohydrolase 1 | 444105 | -0.0671323771128918 | 0.0065277934828675 |
| 2121 | 1135002 | 135002 : TNFSF13 :: tumor necrosis factor (ligand) superfamily, member 13 | 54673 | 0.660500070596942 | -0.623176642780856 |
| 2122 | 1135023 | 135023 : CD34 :: CD34 antigen | 374990 | 0.253442729839205 | -0.0437058764323322 |
| 2123 | 1135024 | 135024 : RIPK2 :: receptor-interacting serine-threonine kinase 2 | 103755 | 0.283145198315740 | -0.0160966513101 |
| 2124 | 1135093 | 135093 : CHUK :: conserved helix-loop-helix ubiquitous kinase | 198998 | 0.109586518187874 | 0.124991404895728 |
| 2125 | 1135028 | 135028 : CD36 :: CD36 antigen (collagen type I receptor, thrombospondin receptor) | 443120 | 0.021104930817611 | 0.007796830614863 |
| 2126 | 1135042 | 135042 : MOX2 :: antigen identified by monoclonal antibody MRC OX-2 | 79015 | 0.0832893199982643 | -0.213987775490654 |
| 2127 | 1135047 | 135047 : EPHB2 :: EphB2 | 125124 | 0.381665736064432 | -0.280685437494666 |
| 2128 | 1135056 | 135056 : GATA3 :: GATA binding protein 3 | 169946 | 0.372973462657120 | -0.616704878063501 |
| 2129 | 1135068 | 135068 : ALP :: alpha-actinin-2-associated LIM protein | 71719 | 0.718732925951149 | -0.283389597854139 |
| 2130 | 1135080 | 135080 : CDKN2A :: cyclin-dependent kinase inhibitor 2A (melanoma, p16, inhibits CDK4) | 421349 | 0.0788280276428553 | 0.161587695324233 |
| 2131 | 1135085 | 135085 : C22orf4 :: chromosome 22 open reading frame 4 | 505862 | -0.0265736210998559 | 0.0164154279639988 |
| 2132 | 1135088 | 135088 : TM4SF10 :: transmembrane 4 superfamily member 10 | 8769 | 0.788275779148947 | -0.406065038614432 |
| 2133 | 1135101 | 135101 : KIFC1 :: kinesin family member C1 | 20830 | -0.215761248668721 | 0.596798091443639 |
| 2134 | 1135102 | 135102 : PRKCB1 :: protein kinase C, beta 1 | 349845 | -0.441119819917753 | 0.127447919616108 |
| 2135 | 1135130 | 135130 : MYCN :: v-myc myelocytomatosis viral related oncogene, neuroblastoma derived (avian) | 25960 | 0.205396780967846 | -0.132247221716385 |
| 2136 | 1135138 | 135138 : CD24 :: CD24 antigen (small cell lung carcinoma cluster 4 antigen) | 375108 | -0.244457507010188 | 0.0478976903112253 |
| 2137 | 1135141 | 135141 : CXCL2 :: chemokine (C-X-C motif) ligand 2 | 75765 | 0.216024020910474 | -0.301155542846476 |
| 2138 | 1135151 | 135151 : CASP6 :: caspase 6, apoptosis-related cysteine protease | 3280 | -0.029027422712854 | 0.0224595329649 |
| 2139 | 1135164 | 135164 : UMPK :: uridine monophosphate kinase | 458360 | -0.281270374505862 | 0.508366629782454 |
| 2140 | 1135165 | 135165 : IL16 :: interleukin 16 (lymphocyte chemoattractant factor) | 170359 | -0.352018704696172 | 0.134294035068052 |
| 2141 | 1135168 | 135168 : DNASE2 :: deoxyribonuclease II, lysosomal | 118243 | 0.356638133348548 | -0.424972558101864 |
| 2142 | 1135173 | 135173 : LRRN3 :: leucine rich repeat neuronal 3 | 3781 | 0.011132687277529 | -0.007027834231566 |
| 2143 | 1135186 | 135186 : ANXA7 :: annexin A7 | 386741 | 0.230842216449984 | -0.125584578249155 |
| 2144 | 1135189 | 135189 : TP73L :: tumor protein p73-like | 137569 | 0.0329386994875300 | -0.029874965045244 |
| 2145 | 1135209 | 135209 : SIAHBP1 :: fuse-binding protein-interacting repressor | 74562 | -0.298973092029240 | 0.426608855649514 |
| 2146 | 1135214 | 135214 : TGFB2 :: transforming growth factor, beta 2 | 169300 | -0.0038377548744404 | 0.033518502051147 |
| 2147 | 1135226 | 135226 : IKBKG :: inhibitor of kappa light polypeptide gene enhancer in B-cells, kinase gamma | 43505 | 0.063215168889229 | -0.006641810511503 |
| 2148 | 1135227 | 135227 : NFE2 :: nuclear factor (erythroid-derived 2), 45 kDa | 75643 | 0.023578319912982 | -0.069183481854815 |
| 2149 | 1135229 | 135229 : DUT :: dUTP pyrophosphatase | 367676 | -0.383694472826659 | 0.644465225193040 |

TABLE 2415-continued

| Order | UNIQID | NAME | GeneID.txt | GENEID | LN.cor | Pro.cor |
|---|---|---|---|---|---|---|
| 2150 | 1135234 | 1135234 :: GSK3B :: glycogen synthase kinase 3 beta | | 282359 | 0.0259397981183179 | 0.093409732601449 |
| 2151 | 1135240 | 1135240 :: FAP :: fibroblast activation protein, alpha | | 436852 | 0.815662355251253 | -0.281574290766028 |
| 2152 | 1135251 | 1135251 :: STAT1 :: signal transducer and activator of transcription 1, 91 kDa | | 21486 | 0.378465896040287 | -0.526929553625389 |
| 2153 | 1135253 | 1135253 :: JTV1 :: JTV1 gene | | 301613 | -0.464197830009685 | 0.642155481384349 |
| 2154 | 1135267 | 1135267 :: TCL1A :: T-cell leukemia/lymphoma 1A | | 2484 | -0.422456471874368 | 0.350212964400887 |
| 2155 | 1135270 | 1135270 :: SOCS1 :: suppressor of cytokine signaling 1 | | 50640 | 0.096514447909570 | -0.088097434161321 |
| 2156 | 1135285 | 1135285 :: UBE2E3 :: ubiquitin-conjugating enzyme E2E 3 (UBC4/5 homolog, yeast) | | 449501 | -0.299207238123007 | 0.432887460519918 |
| 2157 | 1135299 | 1135299 :: LYL1 :: lymphoblastic leukemia derived sequence 1 | | 46446 | -0.060409506735203 | 0.127799805000889 |
| 2158 | 1135322 | 1135322 :: IGFBP3 :: insulin-like growth factor binding protein 3 | | 450230 | 0.451581199548195 | -0.038586544922136 |
| 2159 | 1135328 | 1135328 :: FYN :: FYN oncogene related to SRC, FGR, YES | | 390567 | 0.246026834451783 | -0.483001893866662 |
| 2160 | 1135350 | 1135350 :: DYRK3 :: dual-specificity tyrosine-(Y)-phosphorylation regulated kinase 3 | | 164267 | -0.130079779999979 | 0.204564836502494 |
| 2161 | 1135374 | 1135374 :: BMPR2 :: bone morphogenetic protein receptor, type II (serine/threonine kinase) | | 53250 | 0.021907823889001 | -0.049583428001536 |
| 2162 | 1135379 | 1135379 :: LILRB3 :: leukocyte immunoglobulin-like receptor, subfamily B (with TM and ITIM domains), member 3 | | −26 | 0.242300305886075 | -0.328430462600683 |
| 2163 | 1135380 | 1135380 :: CSF2 :: colony stimulating factor 2 (granulocyte-macrophage) | | 1349 | 0.067243088208555 | -0.044335581523926 |
| 2164 | 1135383 | 1135383 :: CDKN2D :: cyclin-dependent kinase inhibitor 2D (p19, inhibits CDK4) | | 435651 | -0.124512964427258 | 0.064707859522555 |
| 2165 | 1135395 | 1135395 :: GG2-1 :: TNF-induced protein | | 17839 | -0.287358473815222 | 0.057585887401965 |
| 2166 | 1135399 | 1135399 :: ZNF216 :: zinc finger protein 216 | | 406096 | 0.562730843915336 | -0.447012756023576 |
| 2167 | 1135467 | 1135467 :: CAMK2B :: calcium/calmodulin-dependent protein kinase (CaM kinase) II beta | | 321572 | 0.134875231463102 | 0.065771849282309 |
| 2168 | 1135475 | 1135475 :: CHEK2 :: CHK2 checkpoint homolog (S. pombe) | | 146329 | -0.397443511905394 | 0.548880091150802 |
| 2169 | 1135487 | 1135487 :: SCN3A :: sodium channel, voltage-gated, type III, alpha | | 300717 | 0.035229423784445 | -0.077879014673317 |
| 2170 | 1135489 | 1135489 :: SSA2 :: Sjogren syndrome antigen A2 (60 kDa, ribonucleoprotein autoantigen SS-A/Ro) | | 288178 | -0.213090090407771 | 0.262043380399309 |
| 2171 | 1135492 | 1135492 :: P2RX5 :: purinergic receptor P2X, ligand-gated ion channel, 5 | | 408615 | -0.492212038510146 | 0.364853473313676 |
| 2172 | 1135513 | 1135513 :: CD209L :: CD209 antigen-like | | 421437 | -0.269435883536644 | 0.024441295489601 |
| 2173 | 1135526 | 1135526 :: VEGF :: vascular endothelial growth factor | | 73793 | 0.325113508581393 | -0.029534731933042 |
| 2174 | 1135529 | 1135529 :: AKAP12 :: A kinase (PRKA) anchor protein (gravin) 12 | | 197081 | 0.327798628207461 | -0.280667211293206 |
| 2175 | 1135541 | 1135541 :: BIRC3 :: baculoviral IAP repeat-containing 3 | | 127799 | 0.215026966456852 | -0.008057017397116 |
| 2176 | 1135549 | 1135549 :: CCL23 :: chemokine (C-C motif) ligand 23 | | 169191 | 0.169612975596130 | -0.255583009309114 |
| 2177 | 1135550 | 1135550 :: RASGRF1 :: Ras protein-specific guanine nucleotide-releasing factor 1 | | 221811 | -0.174032798373146 | 0.109815766607271 |
| 2178 | 1135571 | 1135571 :: LIMK2 :: LIM domain kinase 2 | | 278027 | 0.228969728759419 | -0.179979819712335 |
| 2179 | 1135583 | 1135583 :: KLRD1 :: killer cell lectin-like receptor subfamily D, member 1 | | 41682 | 0.154767088293625 | -0.291292436228335 |
| 2180 | 1135592 | 1135592 :: RASA1 :: RAS p21 protein activator (GTPase activating protein) 1 | | 758 | -0.128504626836331 | 0.005951003511595 |
| 2181 | 1135593 | 1135593 :: CDK10 :: cyclin-dependent kinase (CDC2-like) 10 | | 77313 | -0.262720735278780 | 0.116291156451995 |
| 2182 | 1135606 | 1135606 :: LAIR1 :: leukocyte-associated Ig-like receptor 1 | | 407964 | 0.367419233997012 | -0.504520192225527 |
| 2183 | 1135622 | 1135622 :: MAPK8 :: mitogen-activated protein kinase 8 | | 445864 | -0.115106896338892 | 0.066131476924408 |
| 2184 | 1135645 | 1135645 :: SPINT2 :: serine protease inhibitor, Kunitz type, 2 | | 31439 | 0.037566720623906 | -0.249380484239846 |
| 2185 | 1135665 | 1135665 :: DDR1 :: discoidin domain receptor family, member 1 | | 423573 | 0.230146680281770 | -0.299775043520402 |
| 2186 | 1135673 | 1135673 :: PSMA1 :: proteasome (prosome, macropain) subunit, alpha type, 1 | | 82159 | 0.281720666174377 | 0.513064897309524 |
| 2187 | 1135684 | 1135684 :: CASP9 :: caspase 9, apoptosis-related cysteine protease | | 329502 | -0.211308620409399 | 0.245352650816304 |
| 2188 | 1135685 | 1135685 :: TCF3 :: transcription factor 3 (E2A immunoglobulin enhancer binding factors E12/E47) | | 371282 | -0.132625532853511 | 0.339380670215153 |
| 2189 | 1135735 | 1135735 :: ACVRL1 :: activin A receptor type II-like 1 | | 410104 | 0.299657105745111 | -0.308198802383384 |
| 2190 | 1135743 | 1135743 :: TNFRSF25 :: tumor necrosis factor receptor superfamily, member 25 | | 299558 | 0.234872487618209 | -0.471593040551215 |
| 2191 | 1135755 | 1135755 :: MCAM :: melanoma cell adhesion molecule | | 511397 | 0.269827609205101 | 0.050044223151702 |
| 2192 | 1135773 | 1135773 :: FCGR2B :: Fc fragment of IgG, low affinity IIb, receptor for (CD32) | | 126384 | -0.094710034742556 | 0.074929655761349 |
| 2193 | 1135778 | 1135778 :: CD86 :: CD86 antigen (CD28 antigen ligand 2, B7-2 antigen) | | 27954 | 0.168916871462908 | -0.289281311109271 |
| 2194 | 1135795 | 1135795 :: Lin10 :: lin-10 protein homolog | | 55923 | 0.528293814614649 | -0.217959944059237 |
| 2195 | 1135801 | 1135801 :: CHS1 :: Chediak-Higashi syndrome 1 | | 130188 | 0.115318364998609 | -0.224257398564241 |
| 2196 | 1135802 | 1135802 :: CAPN3 :: calpain 3, (p94) | | 439343 | 0.164155251202988 | -0.441808712936320 |
| 2197 | 1135826 | 1135826 :: PFKM :: phosphofructokinase, muscle | | 75160 | -0.358643155033839 | 0.498879090538368 |
| 2198 | 1135830 | 1135830 :: GPRK6 :: G protein-coupled receptor kinase 6 | | 235116 | -0.137147395547579 | -0.066956658835406 |

TABLE 2415-continued

GeneID.txt

| Order | UNIQID | NAME | GENEID | LN.cor | Pro.cor |
|---|---|---|---|---|---|
| 2199 | 1135835 | 1135835 : TPM1 :: tropomyosin 1 (alpha) | 133892 | 0.844500075257288 | −0.400650137852855 |
| 2200 | 1135852 | 1135852 : UBE2I :: ubiquitin-conjugating enzyme E2I (UBC9 homolog, yeast) | 302903 | −0.0550216211102330 | 0.0123352990755447 |
| 2201 | 1135858 | 1135858 : HSPA4 :: heat shock 70 kDa protein 4 | 90093 | −0.273737239778974 | 0.470740053479600 |
| 2202 | 1135866 | 1135866 : MGLL :: monoglyceride lipase | 409826 | −0.105545220381370 | −0.152401403416860 |
| 2203 | 1135871 | 1135871 : CYLN2 :: cytoplasmic linker 2 | 104717 | 0.492247783576989 | −0.405561899962111 |
| 2204 | 1135899 | 1135899 : DBI :: diazepam binding inhibitor (GABA receptor modulator, acyl-Coenzyme A binding protein) | 78888 | 0.106730411631004 | 0.0109139900666277 |
| 2205 | 1135925 | 1135925 : LILRB1 :: leukocyte immunoglobulin-like receptor, subfamily B (with TM and ITIM domains), member 1 | 149924 | −0.0228274692554302 | −0.121870105927558 |
| 2206 | 1135929 | 1135929 : NFATC1 :: nuclear factor of activated T-cells, cytoplasmic, calcineurin-dependent 1 | 512591 | −0.230076225407584 | 0.0152639247082688 |
| 2207 | 1135930 | 1135930 : AURKC :: aurora kinase C | 98338 | −0.0156025521095677 | −0.0508526181431340 |
| 2208 | 1135966 | 1135966 : THPO :: thrombopoietin (myeloproliferative leukemia virus oncogene ligand, megakaryocyte growth and development factor) | 1166 | −0.0702400912116135 | 0.0609297970285226 |
| 2209 | 1135968 | 1135968 : ACTN1 :: actinin, alpha 1 | 119000 | 0.803045210914051 | −0.443427303702404 |
| 2210 | 1135974 | 1135974 : RENT1 :: regulator of nonsense transcripts 1 | 388125 | −0.277013571071871 | 0.271498553157074 |
| 2211 | 1135982 | 1135982 : PSTPIP1 :: proline-serine-threonine phosphatase interacting protein 1 | 129758 | 0.263915152962747 | −0.498016545266176 |
| 2212 | 1135994 | 1135994 : ICOSL :: inducible T-cell co-stimulator ligand | 14155 | 0.0959901303080820 | −0.112046453556527 |
| 2213 | 1136002 | 1136002 : CASK :: calcium/calmodulin-dependent serine protein kinase (MAGUK family) | 288196 | 0.101320852559842 | −0.0963674004533437 |
| 2214 | 1136048 | 1136048 : TNFRSF25 :: tumor necrosis factor receptor superfamily, member 25 | 299558 | 0.124716682297827 | −0.408102750362765 |
| 2215 | 1136051 | 1136051 : CSF2RA :: colony stimulating factor 2 receptor, alpha, low-affinity (granulocyte-macrophage) | 520937 | 0.614522954701183 | −0.281145422492197 |
| 2216 | 1136055 | 1136055 : UBC :: ubiquitin C | 183704 | −0.0173909394478490 | −0.243810714198309 |
| 2217 | 1136056 | 1136056 : CDK7 :: cyclin-dependent kinase 7 (MO15 homolog, Xenopus laevis, cdk-activating kinase) | 184298 | −0.204830293446290 | 0.441840876555980 |
| 2218 | 1136087 | 1136087 : ITK :: IL2-inducible T-cell kinase | 211576 | 0.211045649761843 | −0.423904231475203 |
| 2219 | 1136109 | 1136109 : MAP2K5 :: mitogen-activated protein kinase kinase 5 | 436145 | −0.270995770271572 | 0.0453661805734790 |
| 2220 | 1136150 | 1136150 : TYRO3 :: TYRO3 protein tyrosine kinase | 381282 | 0.0692127141835310 | −0.0296713171170980 |
| 2221 | 1136152 | 1136152 : CCRL2 :: chemokine (C-C motif) receptor-like 2 | 458436 | 0.360883312741600 | −0.375561473188188 |
| 2222 | 1136162 | 1136162 : AKT2 :: v-akt murine thymoma viral oncogene homolog 2 | 326445 | −0.208297523200300 | 0.174642196469647 |
| 2223 | 1136172 | 1136172 : SULT1C1 :: sulfotransferase family, cytosolic, 1C, member 1 | 38084 | 0.650163073768228 | −0.258621533863630 |
| 2224 | 1136185 | 1136185 : ITGB8 :: integrin, beta 8 | 355722 | −0.0399295785839420 | −0.0441458162075154 |
| 2225 | 1136193 | 1136193 : MAPK11 :: mitogen-activated protein kinase 11 | 57732 | 0.306565774763432 | −0.328494812564979 |
| 2226 | 1136216 | 1136216 : HLA-G :: HLA-G histocompatibility antigen, class I, G | 512152 | 0.332885800453946 | −0.553560222998666 |
| 2227 | 1136269 | 1136269 : MAST205 :: microtubule associated testis specific serine/threonine protein kinase | 101474 | 0.223412342428654 | 0.138958768884101 |
| 2228 | 1136273 | 1136273 : HOP :: homeodomain-only protein | 13775 | 0.476703368222473 | −0.307711782501049 |
| 2229 | 1136285 | 1136285 : LRPPRC :: leucine-rich PPR-motif containing | 182490 | −0.435679656870025 | 0.601290247138512 |
| 2230 | 1136329 | 1136329 : HIC :: I-mfa domain-containing protein | 132739 | −0.0272886997505700 | −0.117406065312260 |
| 2231 | 1136337 | 1136337 : NCALD :: neurocalcin delta | 90063 | 0.338984738958917 | −0.245462539985130 |
| 2232 | 1136343 | 1136343 : BBC3 :: BCL2 binding component 3 | 87246 | −0.0504051923110055 | −0.0369016889347230 |
| 2233 | 1136357 | 1136357 : OK/SW-cl.56 :: beta 5-tubulin | 512680 | 0.677947187540831 | −0.298730690287187 |
| 2234 | 1136362 | 1136362 : SCGF :: stem cell growth factor; lymphocyte secreted C-type lectin | 356729 | −0.408563420151110 | 0.742172430214216 |
| 2235 | 1136369 | 1136369 : FLJ20323 :: hypothetical protein FLJ20323 | 387140 | −0.262683063661753 | 0.404486726869442 |
| 2236 | 1136371 | 1136371 : FMO2 :: flavin containing monooxygenase 2 | 361155 | 0.0522599650061053 | −0.127270535584830 |
| 2237 | 1136379 | 1136379 : FCER1A :: Fc fragment of IgE, high affinity I, receptor for; alpha polypeptide | 897 | 0.0139366196975110 | −0.0131975575989090 |
| 2238 | 1136391 | 1136391 : PTGDS :: prostaglandin D2 synthase 21 kDa (brain) | 446429 | 0.511480233544877 | −0.435655362037836 |
| 2239 | 1136393 | 1136393 : TUBA6 :: tubulin alpha 6 | 406578 | −0.179227481381745 | 0.374710668827628 |
| 2240 | 1136401 | 1136401 : SIP :: Siah-interacting protein | 27258 | −0.379183284208103 | 0.535722487344917 |
| 2241 | 1136408 | 1136408 : POU2F2 :: POU domain, class 2, transcription factor 2 | 1101 | −0.354137582792841 | 0.429728063769577 |
| 2242 | 1136427 | 1136427 : FYB :: FYN binding protein (FYB-120/130) | 276506 | 0.377966093879180 | −0.441555304919001 |
| 2243 | 1136430 | 1136430 : IGLJ3 :: immunoglobulin lambda joining 3 | 102950 | 0.109778160374844 | −0.098831871658468 |
| 2244 | 1136459 | 1136459 : KIAA0551 :: Traf2 and NCK interacting kinase | 252550 | 0.365508689849397 | −0.430643879731062 |
| 2245 | 1136464 | 1136464 : BAX :: BCL2-associated X protein | 159428 | −0.106161619147764 | 0.0426671340080830 |
| 2246 | 1136540 | 1136540 : PLAUR :: plasminogen activator, urokinase receptor | 179657 | 0.666710687865820 | −0.301093054608278 |

TABLE 2415-continued

| Order | UNIQID | NAME | GeneID.txt | GENEID | LN.cor | Pro.cor |
|---|---|---|---|---|---|---|
| 2247 | 1136573 | 1136573 : HLA-DPA1 :: major histocompatibility complex, class II, DP alpha 1 | | 914 | 0.0939190787666697 | -0.282244466739273 |
| 2248 | 1136585 | 1136585 : MKI67 :: antigen identified by monoclonal antibody Ki-67 | | 80976 | -0.322784784394788 | 0.786209797714773 |
| 2249 | 1136595 | 1136595 : VDAC1 :: voltage-dependent anion channel 1 | | 404814 | -0.329398024691907 | 0.585972473136041 |
| 2250 | 1136599 | 1136599 : MAPK3 :: mitogen-activated protein kinase 3 | | 861 | 0.0795602386803931 | 0.110483410795923 |
| 2251 | 1136601 | 1136601 : KIAA1522 :: KIAA1522 protein | | 322735 | -0.282563015525018 | 0.476574635966113 |
| 2252 | 1136605 | 1136605 : MAZ :: MYC-associated zinc finger protein (purine-binding transcription factor) | | 448398 | -0.375211792940038 | 0.462155982376696 |
| 2253 | 1136620 | 1136620 : COL6A1 :: collagen, type VI, alpha 1 | | 415997 | 0.752399713314935 | -0.294449892879228 |
| 2254 | 1136655 | 1136655 : FBXO9 :: F-box only protein 9 | | 388387 | -0.340363407814236 | 0.444483352898254 |
| 2255 | 1136662 | 1136662 : PIK3R1 :: phosphoinositide-3-kinase, regulatory subunit, polypeptide 1 (p85 alpha) | | 6241 | 0.238423381122479 | -0.289917681487796 |
| 2256 | 1136681 | 1136681 : KHSRP :: KH-type splicing regulatory protein (FUSE binding protein 2) | | 91142 | -0.176274134948602 | 0.237953667245025 |
| 2257 | 1136687 | 1136687 : CREB3L2 :: cAMP responsive element binding protein 3-like 2 | | 59943 | -0.193498113086998 | -0.0606343866685776 |
| 2258 | 1136692 | 1136692 : KIAA0913 :: KIAA0913 protein | | 65135 | 0.157495567129249 | -0.509878413292112 |
| 2259 | 1136702 | 1136702 : KIAA0121 :: KIAA0121 gene product | | 155584 | 0.054990929492512 | 0.0850093193208041 |
| 2260 | 1136710 | 1136710 : GTF3C2 :: general transcription factor IIIC, polypeptide 2, beta 110 kDa | | 75782 | -0.396439011974729 | 0.384390673177142 |
| 2261 | 1136712 | 1136712 : LOC253782 :: hypothetical protein LOC253782 | | 503901 | 0.206133682187914 | -0.355144643398998 |
| 2262 | 1136718 | 1136718 : SUCLG2 :: succinate-CoA ligase, GDP-forming, beta subunit | | 446476 | -0.367316089248735 | 0.168181491783958 |
| 2263 | 1136722 | 1136722 : TPM4 :: tropomyosin 4 | | 250641 | 0.032764759626493 | 0.117199289648095 |
| 2264 | 1136724 | 1136724 : DNAJC8 :: DnaJ (Hsp40) homolog, subfamily C, member 8 | | 433540 | -0.227564371595965 | 0.384799422123307 |
| 2265 | 1136759 | 1136759 : :: Homo sapiens clone 23872 mRNA sequence | | 188882 | -0.246541834783006 | 0.118050545428880 |
| 2266 | 1136762 | 1136762 : CHN1 :: chimerin (chimaerin) 1 | | 380138 | 0.531781776267429 | -0.309684138139920 |
| 2267 | 1136765 | 1136765 : PRKCL2 :: protein kinase C-like 2 | | 69171 | -0.0524497619898850 | 0.002703484646413 |
| 2268 | 1136774 | 1136774 : IL1RN :: interleukin 1 receptor antagonist | | 81134 | 0.198165705307058 | -0.271282824734418 |
| 2269 | 1136777 | 1136777 : HLA-DQA1 :: major histocompatibility complex, class II, DQ alpha 1 | | 387679 | 0.095006436690760 | -0.192356554908310 |
| 2270 | 1136781 | 1136781 : PPP1R14B :: protein phosphatase 1, regulatory (inhibitor) subunit 14B | | 120197 | -0.350667785791036 | 0.599063986397151 |
| 2271 | 1136784 | 1136784 : JMJD1 :: jumonji domain containing 1 | | 321707 | 0.0375076817951980 | 0.042300448176934 |
| 2272 | 1136786 | 1136786 : PCCB :: propionyl Coenzyme A carboxylase, beta polypeptide | | 63788 | -0.589479064855973 | 0.500462229668922 |
| 2273 | 1136788 | 1136788 : SEPT10 :: septin 10 | | 355455 | 0.743385066666469 | -0.472469825174593 |
| 2274 | 1136819 | 1136819 : DKFZP564O043 :: hypothetical protein DKFZp564O043 | | 112605 | -0.108061343689995 | 0.015483574748141 |
| 2275 | 1136831 | 1136831 : PPFIBP2 :: PTPRF interacting protein, binding protein 2 (liprin beta 2) | | 12953 | 0.029792915483790 | -0.00767627865948 |
| 2276 | 1136832 | 1136832 : RANBP2L1 :: RAN binding protein 2-like 1 | | 434959 | 0.482289022689679 | -0.582659344585077 |
| 2277 | 1136844 | 1136844 : C21orf25 :: chromosome 21 open reading frame 25 | | 16007 | 0.360004946699269 | -0.421664849812932 |
| 2278 | 1136853 | 1136853 : SMYD2 :: SET and MYND domain containing 2 | | 66170 | -0.372211589853700 | 0.355510218953968 |
| 2279 | 1136859 | 1136859 : KIAA1199 :: KIAA1199 protein | | 212584 | 0.436417109927428 | -0.218192786328106 |
| 2280 | 1136865 | 1136865 : MGC4170 :: MGC4170 protein | | 412128 | 0.287712752201433 | -0.388421252788627 |
| 2281 | 1136876 | 1136876 : TLK2 :: tousled-like kinase 2 | | 445078 | -0.155319085898057 | 0.204103146968723 |
| 2282 | 1136902 | 1136902 : HLA-DQB2 :: major histocompatibility complex, class II, DQ beta 2 | | 375115 | 0.192355314451624 | -0.319281345548139 |
| 2283 | 1136903 | 1136903 : :: Homo sapiens mRNA; cDNA DKFZp779B1535 (from clone DKFZp779B1535) | | 442592 | 0.037180838679762 | 0.027204468801935 |
| 2284 | 1136913 | 1136913 : EEF1D :: eukaryotic translation elongation factor 1 delta (guanine nucleotide exchange protein) | | 334798 | -0.169515366664499 | 0.121701880331947 |
| 2285 | 1136925 | 1136925 : EEG1 :: likely ortholog of mouse embryonic epithelial gene 1 | | 99962 | -0.120301577698138 | 0.418446911641021 |
| 2286 | 1136938 | 1136938 : BICD2 :: bicaudal D homolog 2 (Drosophila) | | 436939 | -0.290814207335427 | 0.194781442202637 |
| 2287 | 1136939 | 1136939 : MINA53 :: myc-induced nuclear antigen, 53 kDa | | 23394 | -0.417163002239899 | 0.308929563321094 |
| 2288 | 1136971 | 1136971 : :: Homo sapiens T cell receptor beta chain BV20S1 BJ1-5 BC1 mRNA, complete cds | | 419777 | 0.254956828947675 | -0.564468551099593 |
| 2289 | 1136983 | 1136983 : STIP1 :: stress-induced-phosphoprotein 1 (Hsp70/Hsp90-organizing protein) | | 257827 | -0.246439382578630 | 0.490417223621355 |
| 2290 | 1136983 | 1136983 : NEK1 :: NIMA (never in mitosis gene a)-related kinase 1 | | 414410 | -0.231210263189500 | 0.204963384701897 |
| 2291 | 1136983 | 1136983 : :: Homo sapiens similar to Nuclear envelope pore membrane protein POM 121 (Pore membrane protein of 121 kDa) (P145) (LOC340318), mRNA | | 450237 | -0.388641220178648 | 0.487819551534725 |
| 2292 | 1136984 | 1136984 : SNX1 :: sorting nexin 1 | | 498154 | -0.0408803524095611 | -0.263644542525231 |
| 2293 | 1136987 | 1136987 : SFMBT1 :: Scm-like with four mbt domains 1 | | 21695 | -0.302266892109625 | 0.163781928286487 |
| 2294 | 1136988 | 1136988 : CASP8 :: caspase 8, apoptosis-related cysteine protease | | 243491 | 0.135637824443728 | -0.336196763757261 |

TABLE 2415-continued

GeneID.txt

| Order | UNIQID | NAME | GENEID | LN.cor | Pro.cor |
|---|---|---|---|---|---|
| 2295 | 1136996 | 1136996 :: RNASE4 :: ribonuclease, RNase A family, 4 | 283749 | 0.530666527925623 | −0.397210146260416 |
| 2296 | 1137022 | 1137022 :: ITGAL :: integrin, alpha L (antigen CD11A (p180), lymphocyte function-associated antigen 1; alpha polypeptide) | 174103 | 0.205038646441539 | −0.397020451104670 |
| 2297 | 1137026 | 1137026 :: MAP2K2 :: mitogen-activated protein kinase kinase 2 | 366346 | −0.262905023273146 | 0.252101699347407 |
| 2298 | 1137042 | 1137042 :: GOS2 :: putative lymphocyte G0/G1 switch gene | 432132 | 0.538116332321084 | −0.276091529850567 |
| 2299 | 1137097 | 1137097 :: KNS2 :: kinesin 260/70 kDa | 512578 | 0.399642064990379 | −0.453052638372648 |
| 2300 | 1137109 | 1137109 :: RPL5 :: ribosomal protein L5 | 469653 | −0.122252811851800 | 0.006080037924381 |
| 2301 | 1137112 | 1137112 :: MUC1 :: mucin 1, transmembrane | 89603 | 0.317119298256267 | −0.312275797088170 |
| 2302 | 1137137 | 1137137 :: FLNA :: filamin A, alpha (actin binding protein 280) | 195464 | 0.567136331652304 | −0.391193497147128 |
| 2303 | 1137158 | 1137158 :: C14orf120 :: chromosome 14 open reading frame 120 | 9043 | −0.282866289386583 | 0.413058262482048 |
| 2304 | 1137201 | 1137201 :: SRRM2 :: serine/arginine repetitive matrix 2 | 433343 | −0.272530261309250 | 0.320630860600962 |
| 2305 | 1137202 | 1137202 :: SMT3H2 :: SMT3 suppressor of mif two 3 homolog 2 (yeast) | 380973 | −0.234617743279140 | 0.241957518841459 |
| 2306 | 1137247 | 1137247 :: LYZ :: lysozyme (renal amyloidosis) | 234734 | 0.608426386367492 | −0.450067626480979 |
| 2307 | 1137273 | 1137273 :: ITGB5 :: integrin, beta 5 | 149846 | 0.649262426877578 | −0.271621269006555 |
| 2308 | 1137289 | 1137289 :: CD7 :: CD7 antigen (p41) | 36972 | 0.165984784499907 | −0.465353463451909 |
| 2309 | 1137291 | 1137291 :: XTP2 :: HBxAg transactivated protein 2 | 446197 | 0.078785114363620 | −0.149442218814294 |
| 2310 | 1137308 | 1137308 :: FUBP1 :: far upstream element (FUSE) binding protein 1 | 118962 | −0.421138601237465 | 0.248985090248871 |
| 2311 | 1137328 | 1137328 :: PDE4DIP :: phosphodiesterase 4D interacting protein (myomegalin) | 502577 | 0.240910452929125 | −0.201889801334610 |
| 2312 | 1137332 | 1137332 :: PPBP :: pro-platelet basic protein (chemokine (C-X-C motif) ligand 7) | 2164 | 0.006793019489238 | −0.121914777496122 |
| 2313 | 1137343 | 1137343 :: FH :: fumarate hydratase | 391168 | −0.259855496056412 | 0.452895074131933 |
| 2314 | 1137360 | 1137360 :: CLN2 :: ceroid-lipofuscinosis, neuronal 2, late infantile (Jansky-Bielschowsky disease) | 429658 | 0.086740022842950 | −0.125808364812224 |
| 2315 | 1137378 | 1137378 :: TNFRSF4 :: tumor necrosis factor receptor superfamily, member 4 | 129780 | 0.371458297794605 | −0.397187816049941 |
| 2316 | 1137439 | 1137439 :: MAP4K1 :: mitogen-activated protein kinase kinase kinase kinase 1 | 95424 | −0.303418341057957 | 0.261214531356896 |
| 2317 | 1137447 | 1137447 :: HSPCB :: heat shock 90 kDa protein 1, beta | 74335 | −0.458725739759769 | 0.604001646900960 |
| 2318 | 1137449 | 1137449 :: MATR3 :: matrix 3 | 223745 | −0.387281340518201 | 0.358637187063220 |
| 2319 | 1137481 | 1137481 :: C4A :: complement component 4A | 150833 | 0.182892012520496 | −0.507231719813946 |
| 2320 | 1137486 | 1137486 :: MIZ1 :: Msx-interacting-zinc finger | 441069 | −0.443002780855262 | 0.498631456766930 |
| 2321 | 1137488 | 1137488 :: NFKBIB :: nuclear factor of kappa light polypeptide gene enhancer in B-cells inhibitor, beta | 9731 | −0.222344495661454 | 0.244641154107860 |
| 2322 | 1137492 | 1137492 :: HLA-C :: major histocompatibility complex, class I, C | 274485 | 0.197365260701921 | −0.407821263356476 |
| 2323 | 1137506 | 1137506 :: H2AFY :: H2A histone family, member Y | 75258 | −0.149835935606420 | 0.445133707052547 |
| 2324 | 1137512 | 1137512 :: PC4 :: activated RNA polymerase II transcription cofactor 4 | 229641 | −0.082525052793081 | −0.145075136097169 |
| 2325 | 1137534 | 1137534 :: CD7 :: CD7 antigen (p41) | 36972 | 0.107180181166121 | −0.365438064689284 |
| 2326 | 1137539 | 1137539 :: XCL2 :: chemokine (C motif) ligand 2 | 458346 | −0.055308591493161 | −0.246840014028833 |
| 2327 | 1137561 | 1137561 :: HOXA1 :: homeo box A1 | 67397 | −0.150079735454765 | 0.253920313043797 |
| 2328 | 1137582 | 1137582 :: CLK1 :: CDC-like kinase 1 | 433732 | 0.093677520704906 | −0.366781439753622 |
| 2329 | 1137583 | 1137583 :: ALDOA :: aldolase A, fructose-bisphosphate | 273415 | 0.018724212498213 | 0.324301589252045 |
| 2330 | 1137594 | 1137594 :: CCNB1 :: cyclin B1 | 23960 | −0.375043781726022 | 0.836819695371722 |
| 2331 | 1137597 | 1137597 :: CDC42EP4 :: CDC42 effector protein (Rho GTPase binding) 4 | 3903 | 0.425898445808089 | −0.369669790160663 |
| 2332 | 1137601 | 1137601 :: GLG1 :: golgi apparatus protein 1 | 78979 | −0.035094612373837 | 0.009288993829497 |
| 2333 | 1137626 | 1137626 :: PCTK3 :: PCTAIRE protein kinase 3 | 445402 | 0.603150172272823 | −0.262769906333315 |
| 2334 | 1137643 | 1137643 :: GRHPR :: glyoxylate reductase/hydroxypyruvate reductase | 155742 | −0.294353755518062 | 0.291855626208132 |
| 2335 | 1137663 | 1137663 :: DDAH2 :: dimethylarginine dimethylaminohydrolase 2 | 247362 | 0.202876954199153 | −0.290851646277916 |
| 2336 | 1137687 | 1137687 :: CXCL5 :: chemokine (C-X-C motif) ligand 5 | 89714 | 0.150406826331083 | 0.017128841867423 |
| 2337 | 1137698 | 1137698 :: GLUL :: glutamate-ammonia ligase (glutamine synthase) | 442669 | 0.408287031744038 | −0.261423151866599 |
| 2338 | 1137742 | 1137742 :: TSC2 :: transforming growth factor beta-stimulated protein TSC-22 | 433796 | 0.564787776154576 | −0.406101020606446 |
| 2339 | 1137751 | 1137751 :: RBMS1 :: RNA binding motif, single stranded interacting protein 1 | 241567 | 0.433483960928137 | −0.410154493871230 |
| 2340 | 1137760 | 1137760 :: DEDD :: death effector domain containing | 169681 | −0.230491915465838 | 0.225693647285405 |
| 2341 | 1137771 | 1137771 :: HLA-DRB3 :: major histocompatibility complex, class II, DR beta 3 | 308026 | 0.206113521293342 | −0.346477432540799 |
| 2342 | 1137782 | 1137782 :: SOD2 :: superoxide dismutase 2, mitochondrial | 384944 | 0.418904407792592 | −0.306800309295515 |
| 2343 | 1137806 | 1137806 :: HLA-A :: major histocompatibility complex, class I, A | 181244 | 0.201083967413937 | −0.433287362783418 |

TABLE 2415-continued

GeneID.txt

| Order | UNIQID | NAME | GENEID | LN.cor | Pro.cor |
|---|---|---|---|---|---|
| 2344 | 1137809 | 1137809 : CD8B1 :: CD8 antigen, beta polypeptide 1 (p37) | 405667 | 0.185618649145311 | −0.524929307636060 |
| 2345 | 1137838 | 1137838 : C6orf4 :: chromosome 6 open reading frame 4 | 437508 | −0.0119361121563 | 0.009969912053544 |
| 2346 | 1137868 | 1137868 : BTN2A1 :: butyrophilin, subfamily 2, member A1 | 169963 | 0.262408129037849 | −0.396710767904983 |
| 2347 | 1137908 | 1137908 :: *Homo sapiens* similar to Gamma-glutamyltranspeptidase 1 precursor (Gamma-glutamyltransferase 1) (CD224 antigen) (LOC376813), mRNA | 454906 | 0.210979969677693 | −0.256296439980480 |
| 2348 | 1137955 | 1137955 : SNRPA1 :: small nuclear ribonucleoprotein polypeptide A' | 434901 | −0.369156412146049 | 0.608254320273560 |
| 2349 | 1138030 | 1138030 : CD72 :: CD72 antigen | 116481 | −0.294390921816877 | 0.100908549519153 |
| 2350 | 1138048 | 1138048 : LY9 :: lymphocyte antigen 9 | 403857 | 0.073607730059501 | −0.263186409754900 |
| 2351 | 1138120 | 1138120 : ITGB1 :: integrin, beta 1 (fibronectin receptor, beta polypeptide, antigen CD29 includes MDF2, MSK12) | 287797 | 0.160065610900893 | −0.075569646134885 |
| 2352 | 1138128 | 1138128 : MAP3K4 :: mitogen-activated protein kinase kinase kinase 4 | 390428 | −0.049185143371545 | −0.087852800223420 |
| 2353 | 1138132 | 1138132 : IGKV1D-13 :: immunoglobulin kappa variable 1D-13 | 390427 | 0.037120917614071 | −0.136065857206284 |
| 2354 | 1138136 | 1138136 : RBM9 :: RNA binding motif protein 9 | 351478 | 0.378938518577512 | −0.126082972595542 |
| 2355 | 1138147 | 1138147 : PRKACA :: protein kinase, cAMP-dependent, catalytic, alpha | 194350 | −0.053368491488809 | 0.041644135318140 |
| 2356 | 1138150 | 1138150 : MCM5 :: MCM5 minichromosome maintenance deficient 5, cell division cycle 46 (*S. cerevisiae*) | 77171 | −0.444102278229523 | 0.638269533484216 |
| 2357 | 1138157 | 1138157 : KIAA0153 :: KIAA0153 protein | 82563 | −0.391835267746382 | 0.547089312878669 |
| 2358 | 1138192 | 1138192 : NR3C1 :: nuclear receptor subfamily 3, group C, member 1 (glucocorticoid receptor) | 512414 | 0.118279477753652 | −0.092009520189905 |
| 2359 | 1138244 | 1138244 : FN1 :: fibronectin 1 | 418138 | 0.813782327518728 | −0.313203946687403 |
| 2360 | 1138259 | 1138259 : HDGF :: hepatoma-derived growth factor (high-mobility group protein 1-like) | 89525 | −0.214962450182430 | 0.470812643332632 |
| 2361 | 1138279 | 1138279 : TPT1 :: tumor protein, translationally-controlled 1 | 374596 | −0.064219389358256 | −0.167378055599220 |
| 2362 | 1138312 | 1138312 : CCL2 :: chemokine (C-C motif) ligand 2 | 303649 | 0.221948111533212 | −0.350981715150463 |
| 2363 | 1138331 | 1138331 : PS :: protein disulfide isomerase-related protein | −7 | −0.107207026289785 | 0.265506953156497 |
| 2364 | 1138355 | 1138355 : ADA :: adenosine deaminase | 407135 | 0.040541203021177 | −0.080197093953995 |
| 2365 | 1138379 | 1138379 : ERBB2 :: v-erb-b2 erythroblastic leukemia viral oncogene homolog 2, neuro/glioblastoma derived oncogene homolog (avian) | 446352 | 0.283250039386084 | −0.286769120359251 |
| 2366 | 1138392 | 1138392 : MTCP1 :: mature T-cell proliferation 1 | 3548 | −0.004895350279116 | 0.276483111443163 |
| 2367 | 1138400 | 1138400 : IL17 :: interleukin 17 (cytotoxic T-lymphocyte-associated serine esterase 8) | 41724 | −0.032075332580235 | −0.038773611235492 |
| 2368 | 1138417 | 1138417 : ST14 :: suppression of tumorigenicity 14 (colon carcinoma, matriptase, epithin) | 56937 | −0.230444494478436 | 0.279346957925828 |
| 2369 | 1138421 | 1138421 : KIAA0690 :: KIAA0690 protein | 434251 | −0.309130833222402 | 0.403967809571089 |
| 2370 | 1138441 | 1138441 : PASK :: PAS domain containing serine/threonine kinase | 397891 | 0.144733774920620 | −0.188242721745811 |
| 2371 | 1138443 | 1138443 : FCGR1A :: Fc fragment of IgG, high affinity Ia, receptor for (CD64) | 77424 | 0.207475205893738 | −0.341859217621333 |
| 2372 | 1138507 | 1138507 : DMPK :: dystrophia myotonica-protein kinase | 898 | 0.021947645562805 | −0.046183891035291 |
| 2373 | 1138515 | 1138515 : HOMER2 :: homer homolog 2 (*Drosophila*) | 93564 | −0.020645296163426 | −0.133209561135918 |
| 2374 | 1138532 | 1138532 : CAMK1G :: calcium/calmodulin-dependent protein kinase IG | 199068 | −0.012177377795444 | 0.053515660538452 |
| 2375 | 1138537 | 1138537 : VDAC1P :: voltage-dependent anion channel 1 pseudogene | −3 | −0.324102650163308 | 0.516292454706352 |
| 2376 | 1138538 | 1138538 : TRD@ :: T cell receptor delta locus | 2014 | 0.236980853252771 | −0.340030980985647 |
| 2377 | 1138541 | 1138541 : TNK1 :: tyrosine kinase, non-receptor, 1 | 203420 | −0.149408449223409 | −0.017420119646561 |
| 2378 | 1138555 | 1138555 : LTK :: leukocyte tyrosine kinase | 434481 | −0.192632421203761 | 0.079999448729701 |
| 2379 | 1138567 | 1138567 : CYB561 :: cytochrome b-561 | 355264 | 0.218450857044390 | −0.352832586952820 |
| 2380 | 1138645 | 1138645 : MDM2 :: Mdm2, transformed 3T3 cell double minute 2, p53 binding protein (mouse) | 212217 | −0.068650083946957 | 0.108796027856608 |
| 2381 | 1138647 | 1138647 : ETV6 :: ets variant gene 6 (TEL oncogene) | 171262 | −0.010676070319985 | −0.013258155419776 |
| 2382 | 1138652 | 1138652 : KYNU :: kynureninase (L-kynurenine hydrolase) | 444471 | 0.465037916013166 | −0.350613895243343 |
| 2383 | 1138670 | 1138670 : CD22 :: CD22 antigen | 262150 | −0.303837324203375 | 0.291639786954158 |
| 2384 | 1138671 | 1138671 : HIRA :: HIR histone cell cycle regulation defective homolog A (*S. cerevisiae*) | 415735 | −0.234356236620965 | 0.181811279669565 |
| 2385 | 1138677 | 1138677 :: *Homo sapiens* cDNA clone MGC:71446 IMAGE:5420082, complete cds | −50 | 0.334871522054608 | −0.565143538142995 |
| 2386 | 1138721 | 1138721 : CR1 :: complement component (3b/4b) receptor 1, including Knops blood group system | 334019 | 0.213185633461993 | −0.167181671621616 |
| 2387 | 1138759 | 1138759 : SMARCA2 :: SWI/SNF related, matrix associated, actin dependent regulator of chromatin, subfamily a, member 2 | 396404 | 0.239912669361491 | −0.356112384377712 |
| 2388 | 1138765 | 1138765 : SEC61A1 :: Sec61 alpha 1 subunit (*S. cerevisiae*) | 306079 | −0.173564213544419 | 0.042950263600793 |
| 2389 | 1138778 | 1138778 : HRI :: heme-regulated initiation factor 2-alpha kinase | 434986 | −0.436150698025647 | 0.461973052646480 |
| 2390 | 1138780 | 1138780 : PBEF :: pre-B-cell colony-enhancing factor | 293464 | 0.089301913080073 | 0.030231044097990 |

TABLE 2415-continued

| Order | UNIQID | NAME | GeneID.txt | | LN.cor | Pro.cor |
|---|---|---|---|---|---|---|
| | | | | GENEID | | |
| 2391 | 1138783 | 1138783 :: WAC :: WW domain-containing adapter with a coiled-coil region | | 370152 | −0.309940954918134 | 0.313859449051489 |
| 2392 | 1138789 | 1138789 :: FLJ13855 :: hypothetical protein FLJ13855 | | 369120 | 0.086491087161513 | −0.352846239711779 |
| 2393 | 1138801 | 1138801 :: HSPC152 :: hypothetical protein HSPC152 | | 333579 | −0.483341541739176 | 0.490594109811054 |
| 2394 | 1138832 | 1138832 :: USP39 :: ubiquitin specific protease 39 | | 12820 | −0.352268143901638 | 0.421581995099915 |
| 2395 | 1138845 | 1138845 :: CDC42BPB :: CDC42 binding protein kinase beta (DMPK-like) | | 436985 | 0.425134584059284 | −0.387183184478298 |
| 2396 | 1138858 | 1138858 :: MIF :: macrophage migration inhibitory factor (glycosylation-inhibiting factor) | | 407995 | −0.407665306199589 | 0.682825403279751 |
| 2397 | 1138867 | 1138867 :: EPLIN :: epithelial protein lost in neoplasm beta | | 10706 | 0.464814747439025 | −0.363469285796447 |
| 2398 | 1138874 | 1138874 :: TCFL4 :: transcription factor-like 4 | | 383019 | −0.314256250926088 | 0.306346209499633 |
| 2399 | 1138878 | 1138878 :: DNCL2A :: dynein, cytoplasmic, light polypeptide 2A | | 100002 | −0.158303775544263 | −0.051030556926909 |
| 2400 | 1138887 | 1138887 :: HDAC7A :: histone deacetylase 7A | | 200063 | −0.078208993612420 | 0.074601964005980 |
| 2401 | 1138905 | 1138905 :: KIAA1194 :: KIAA1194 | | 437844 | −0.281406606938181 | 0.481911861505412 |
| 2402 | 1138910 | 1138910 :: MORF4L1 :: mortality factor 4 like 1 | | 374503 | 0.034752735498991 | −0.015115740634790 |
| 2403 | 1138920 | 1138920 :: CXCL14 :: chemokine (C-X-C motif) ligand 14 | | 24395 | 0.272782188852422 | −0.301018055660417 |
| 2404 | 1138944 | 1138944 :: FLJ12442 :: hypothetical protein FLJ12442 | | 84753 | −0.388324622909977 | 0.572404037246780 |
| 2405 | 1138959 | 1138959 :: TNKS2 :: tankyrase, TRF1-interacting ankyrin-related ADP-ribose polymerase 2 | | 203605 | −0.433959401052288 | 0.126101372366550 |
| 2406 | 1138973 | 1138973 :: RICH1 :: RhoGAP interacting with CIP4 homologs 1 | | 11270 | −0.252406521349047 | 0.318256960904562 |
| 2407 | 1138994 | 1138994 :: MGC2491 :: hypothetical protein MGC2491 | | 238030 | −0.048843627249750 | −0.056347071925834 |
| 2408 | 1138995 | 1138995 :: SCAMP2 :: secretory carrier membrane protein 2 | | 24956 | 0.312239840661249 | −0.155950823692214 |
| 2409 | 1139005 | 1139005 :: FLJ22056 :: hypothetical protein FLJ22056 | | 273186 | −0.132100329795946 | −0.079271294569867 |
| 2410 | 1139017 | 1139017 :: CABC1 :: chaperone, ABC1 activity of bc1 complex like (S. pombe) | | 274424 | 0.139351446215690 | 0.183979506976574 |
| 2411 | 1139026 | 1139026 :: NANS :: N-acetylneuraminic acid synthase (sialic acid synthase) | | 512094 | −0.060610570736422 | 0.129185990473453 |
| 2412 | 1139037 | 1139037 :: MKNK2 :: MAP kinase-interacting serine/threonine kinase 2 | | 173380 | 0.184289444061499 | −0.394499906002833 |
| 2413 | 1139039 | 1139039 :: CKIP-1 :: CK2 interacting protein 1; HQ0024c protein | | 280776 | −0.153598065351604 | 0.099989367851187 |
| 2414 | 1139048 | 1139048 :: CNOT7 :: CCR4-NOT transcription complex, subunit 7 | | 170553 | −0.298252308752349 | 0.459920880578746 |
| 2415 | 1139054 | 1139054 :: LOC58486 :: transposon-derived Buster1 transposase-like protein | | 25726 | −0.222838320242169 | −0.007560363161300 |
| 2416 | 1139076 | 1139076 :: HERC1 :: hect (homologous to the E6-AP (UBE3A) carboxyl terminus) domain and RCC1 (CHC1)-like domain (RLD) 1 | | 133411 | 0.337597568585952 | −0.434587953268159 |
| 2417 | 1139100 | 1139100 :: GMNN :: geminin, DNA replication inhibitor | | 234896 | −0.318640932117085 | 0.797462309697701 |
| 2418 | 1139105 | 1139105 :: USP21 :: ubiquitin specific protease 21 | | 8015 | −0.434624771827016 | 0.226787372995122 |
| 2419 | 1139106 | 1139106 :: TNFRSF12A :: tumor necrosis factor receptor superfamily, member 12A | | 355899 | 0.499326017992532 | −0.272855576593047 |
| 2420 | 1139127 | 1139127 :: DNAJC1 :: DnaJ (Hsp40) homolog, subfamily C, member 1 | | 13015 | 0.333008884215991 | −0.255818934496613 |
| 2421 | 1139185 | 1139185 :: RIOK2 :: RIO kinase 2 (yeast) | | 27021 | −0.394771749047720 | 0.430516797716350 |
| 2422 | 1139196 | 1139196 :: MAFB :: v-maf musculoaponeurotic fibrosarcoma oncogene homolog B (avian) | | 169487 | 0.439789287104131 | −0.478712508499918 |
| 2423 | 1139202 | 1139202 :: KBTBD4 :: kelch repeat and BTB (POZ) domain containing 4 | | 440695 | −0.139779161280927 | 0.186642624167192 |
| 2424 | 1139215 | 1139215 :: MDS029 :: uncharacterized hematopoietic stem/progenitor cells protein MDS029 | | 43549 | −0.231448151224285 | 0.519061887050639 |
| 2425 | 1139226 | 1139226 :: FBXW7 :: F-box and WD-40 domain protein 7 (archipelago homolog, Drosophila) | | 266514 | −0.505040308522747 | 0.354962950374504 |
| 2426 | 1139230 | 1139230 :: PLEKHF2 :: pleckstrin homology domain containing, family F (with FYVE domain) member 2 | | 29724 | 0.047925608046581 | 0.167450282579172 |
| 2427 | 1139235 | 1139235 :: FLJ11196 :: acheron | | 416755 | 0.518138878363181 | −0.428622150654900 |
| 2428 | 1139265 | 1139265 :: FLJ12436 :: hypothetical protein FLJ12436 | | 187657 | −0.499034983187793 | 0.623313352401062 |
| 2429 | 1139266 | 1139266 :: RGC32 :: RGC32 protein | | 76640 | 0.159027989824428 | −0.087571314039428 |
| 2430 | 1139274 | 1139274 :: CDK5RAP3 :: CDK5 regulatory subunit associated protein 3 | | 20157 | −0.323524477001354 | −0.008936362298060 |
| 2431 | 1139277 | 1139277 :: TAPBP-R :: TAP binding protein related | | 267993 | 0.175034517314223 | −0.361681139356850 |
| 2432 | 1139280 | 1139280 :: FBXW7 :: F-box and WD-40 domain protein 7 (archipelago homolog, Drosophila) | | 312503 | −0.256428453680362 | 0.231741417406240 |
| 2433 | 1139301 | 1139301 :: BSPRY :: B-box and SPRY domain containing | | 108502 | −0.193830915039114 | −0.024241326240483 |
| 2434 | 1139303 | 1139303 :: FLJ20511 :: hypothetical protein FLJ20511 | | 134406 | −0.307110727683744 | 0.247243899636555 |
| 2435 | 1139314 | 1139314 :: FCGRT :: Fc fragment of IgG, receptor, transporter, alpha | | 111903 | 0.263924260656374 | −0.500814050113789 |
| 2436 | 1139360 | 1139360 :: FLJ10486 :: hypothetical protein FLJ10486 | | 173946 | −0.403886709065567 | 0.512692327611680 |
| 2437 | 1139393 | 1139393 :: OPN3 :: opsin 3 (encephalopsin, panopsin) | | 170129 | 0.076789396477269 | −0.141913398593755 |
| 2438 | 1139411 | 1139411 :: OSBPL10 :: oxysterol binding protein-like 10 | | 368238 | −0.417496181839488 | 0.261396462305931 |
| 2439 | 1139444 | 1139444 :: RABL2B :: RAB, member of RAS oncogene family-like 2B | | 355874 | 0.063409117778763 | −0.166237878791748 |

TABLE 2415-continued

GeneID.txt

| Order | UNIQID | NAME | GENEID | LN.cor | Pro.cor |
|---|---|---|---|---|---|
| 2440 | 1139461 | 1139461 : BIN2 :: bridging integrator 2 | 14770 | 0.256527759821467 | −0.339692650263970 |
| 2441 | 1139466 | 1139466 : LOC51762 :: RAB-8b protein | 365655 | 0.231557760181664 | −0.095180733736222 |
| 2442 | 1139483 | 1139483 : FKBP10 :: FK506 binding protein 10, 65 kDa | 3849 | 0.674153797219952 | −0.221743793245193 |
| 2443 | 1139526 | 1139526 : HSPC177 :: hypothetical protein HSPC177 | 415534 | 0.163735980619122 | −0.137102206317660 |
| 2444 | 1139528 | 1139528 : TRPM4 :: transient receptor potential cation channel, subfamily M, member 4 | 31608 | 0.131053770432532 | −0.044594419561590 |
| 2445 | 1139531 | 1139531 : MGC8407 :: hypothetical protein MGC8407 | 145156 | −0.085404256164261 | 0.151455641167260 |
| 2446 | 1139542 | 1139542 : NEIL1 :: nei endonuclease VIII-like 1 (E. coli) | 512732 | 0.026897391209280 | 0.051569026919496 |
| 2447 | 1139552 | 1139552 : FLJ23119 :: hypothetical protein FLJ23119 | 413386 | −0.000301880312722 | −0.058250007576066 |
| 2448 | 1139556 | 1139556 : RIN3 :: Ras and Rab interactor 3 | 413374 | 0.295487317472535 | −0.531057998977965 |
| 2449 | 1139572 | 1139572 : SNCAIP :: synuclein, alpha interacting protein (synphilin) | 24948 | 0.148663268443581 | −0.169804663179603 |
| 2450 | 1139645 | 1139645 : SN :: sialoadhesin | 31869 | −0.010823611694524 | −0.347998166899990 |
| 2451 | 1139579 | 1139579 : BCL11B :: B-cell CLL/lymphoma 11B (zinc finger protein) | 57987 | 0.269001973086771 | −0.570933632618085 |
| 2452 | 1139603 | 1139603 : ZNF226 :: zinc finger protein 226 | 145956 | 0.112382635429707 | −0.194688343434095 |
| 2453 | 1139623 | 1139623 : BANK1 :: B-cell scaffold protein with ankyrin repeats 1 | 193736 | −0.166958172604313 | 0.185243160384443 |
| 2454 | 1139645 | 1139645 : C14orf101 :: chromosome 14 open reading frame 101 | 134051 | −0.193861410475501 | 0.089892119649755 |
| 2455 | 1139654 | 1139654 : ECT2 :: epithelial cell transforming sequence 2 oncogene | 293257 | −0.204091598089242 | 0.656075928375559 |
| 2456 | 1139661 | 1139661 : FN5 :: FN5 protein | 416456 | 0.567268031407027 | −0.473817226590911 |
| 2457 | 1139663 | 1139663 : RNPC4 :: RNA-binding region (RNP1, RRM) containing 4 | 4997 | −0.312001381814897 | 0.310598617201023 |
| 2458 | 1139669 | 1139669 : C17 :: cytokine-like protein C17 | 13872 | 0.224599161272751 | −0.255436447025748 |
| 2459 | 1139767 | 1139767 : FBXL12 :: F-box and leucine-rich repeat protein 12 | 12439 | −0.175973426526743 | 0.041273627872276 |
| 2460 | 1139774 | 1139774 : SNX11 :: sorting nexin 11 | 15827 | 0.021232247766666 | −0.069044004608862 |
| 2461 | 1139805 | 1139805 : CYB5R2 :: cytochrome b5 reductase b5R.2 | 414362 | −0.255806993410501 | 0.209851938563531 |
| 2462 | 1139830 | 1139830 : SAMSN1 :: SAM domain, SH3 domain and nuclear localisation signals, 1 | 221851 | 0.370981356457938 | −0.381164453290482 |
| 2463 | 1139831 | 1139831 : FLJ21736 :: esterase 31 | 268700 | −0.011968075306893 | −0.016434297612474 |
| 2464 | 1139839 | 1139839 : SGK2 :: serum/glucocorticoid regulated kinase 2 | 62863 | 0.241096565067699 | 0.032626900537836 |
| 2465 | 1139842 | 1139842 : SAP130 :: mSin3A-associated protein 130 | 133523 | −0.097742321655318 | 0.266312994370097 |
| 2466 | 1139925 | 1139925 : FAIM :: Fas apoptotic inhibitory molecule | 173438 | −0.124987151146701 | 0.328309523235883 |
| 2467 | 1139949 | 1139949 : DNAH3 :: dynein, axonemal, heavy polypeptide 3 | 375739 | −0.169731374035577 | 0.074225125499242 |
| 2468 | 1139950 | 1139950 : FLJ10420 :: hypothetical protein FLJ10420 | 437385 | 0.236816945983053 | −0.335727361898558 |
| 2469 | 1139955 | 1139955 : SLC12A6 :: solute carrier family 12 (potassium/chloride transporters), member 6 | 4876 | −0.020487054568829 | −0.037480624844835 |
| 2470 | 1139957 | 1139957 : NGLY1 :: N-glycanase 1 | 63657 | −0.525638023143142 | 0.363478080938368 |
| 2471 | 1139962 | 1139962 : C5orf4 :: chromosome 5 open reading frame 4 | 10235 | 0.230250368247300 | −0.233149594377572 |
| 2472 | 1139969 | 1139969 : JIK :: STE20-like kinase | 12040 | −0.197720240185810 | 0.063503215792743 |
| 2473 | 1139971 | 1139971 : LIMS2 :: LIM and senescent cell antigen-like domains 2 | 127273 | −0.023501693605426 | −0.081611153834008 |
| 2474 | 1140007 | 1140007 : TPT :: trans-prenyltransferase | 279865 | −0.267154068193449 | 0.678834620628513 |
| 2475 | 1140018 | 1140018 : PWDMP :: WD repeat membrane protein PWDMP | 438482 | −0.133214603635881 | 0.120024613326089 |
| 2476 | 1140027 | 1140027 : FLJ13409 :: hypothetical protein FLJ13409 | −30 | 0.032352790493303 | −0.421061800596014 |
| 2477 | 1140031 | 1140031 : SIAT7D :: sialyltransferase 7D ((alpha-N-acetylneuraminyl-2,3-beta-galactosyl-1,3)-N-acetyl galactosaminide alpha-2,6-sialyltransferase) | 3972 | −0.255702024856147 | 0.129661591849210 |
| 2478 | 1140072 | 1140072 : SLCO5A1 :: solute carrier organic anion transporter family, member 5A1 | 199750 | 0.242253459635359 | −0.221156982559850 |
| 2479 | 1140075 | 1140075 : SNARK :: likely ortholog of rat SNF1/AMP-activated protein kinase | 172012 | −0.047490349579645 | −0.277054802560530 |
| 2480 | 1140088 | 1140088 : DC-TM4F2 :: tetraspanin similar to TM4SF9 | 509050 | 0.226500769788379 | −0.262234704475871 |
| 2481 | 1140127 | 1140127 : TRIM34 :: tripartite motif-containing 34 | 125300 | −0.166582852111955 | 0.102914711366090 |
| 2482 | 1140151 | 1140151 : FLJ22757 :: hypothetical protein FLJ22757 | 236449 | −0.089956291622834 | −0.171243944377416 |
| 2483 | 1140214 | 1140214 : ANKRD3 :: ankyrin repeat domain 3 | 55565 | −0.135384096304679 | 0.090538047157569 |
| 2484 | 1140236 | 1140236 : SPAP1 :: SH2 domain containing phosphatase anchor protein 1 | 194976 | −0.437940303418959 | 0.326018914273141 |
| 2485 | 1140238 | 1140238 : BCLG :: apoptosis regulator BCL-G | 11962 | −0.042826609936427 | −0.286603480568969 |
| 2486 | 1140344 | 1140344 : BNIP3L :: BCL2/adenovirus E1B 19 kDa interacting protein 3-like | 132955 | 0.217814730487477 | 0.049767573763502 |
| 2487 | 1140370 | 1140370 : CDCA8 :: cell division cycle associated 8 | 48855 | −0.413518820286071 | 0.851402787359892 |

TABLE 2415-continued

GeneID.txt

| Order | UNIQID | NAME | GENEID | LN.cor | Pro.cor |
|---|---|---|---|---|---|
| 2488 | 1140378 | BHLHB3 ::: basic helix-loop-helix domain containing, class B, 3 | 437282 | 0.441953829397093 | −0.128845498205439 |
| 2489 | 1140391 | LEF1 ::: lymphoid enhancer-binding factor 1 | 44865 | −0.102669812122025 | −0.218911457849257 |
| 2490 | 1140399 | PLAB ::: prostate differentiation factor | 296638 | 0.0968631298255444 | −0.118898412519241 |
| 2491 | 1140404 | KCNMA1 ::: potassium large conductance calcium-activated channel, subfamily M, alpha member 1 | 354740 | 0.587653373643620 | −0.452387471739584 |
| 2492 | 1140416 | TOSO ::: regulator of Fas-induced apoptosis | 58831 | −0.227010373770165 | −0.159494002878968 |
| 2493 | 1140457 | IL21R ::: interleukin 21 receptor | 210546 | 0.212002655160102 | −0.176888063733686 |
| 2494 | 1140464 | H11 ::: protein kinase H11 | 111676 | 0.562080363557665 | −0.327453925079561 |
| 2495 | 1140473 | CORO1C ::: coronin, actin binding protein, 1C | 17377 | 0.173358377940601 | −0.047338136392363 |
| 2496 | 1140491 | DKFZp761P1010 ::: hypothetical protein DKFZp761P1010 | 24979 | 0.101756726051739 | −0.183027999855880 |
| 2497 | 1140497 | FLJ12750 ::: hypothetical protein FLJ12750 | 77870 | 0.339043501264461 | −0.382487661946037 |
| 2498 | 1140520 | C20orf21 ::: chromosome 20 open reading frame 21 | 11747 | −0.439383490087482 | 0.339299186966798 |
| 2499 | 1140524 | C6orf37 ::: chromosome 6 open reading frame 37 | 10784 | 0.464548931082200 | −0.451242812457036 |
| 2500 | 1140534 | ARH ::: LDL receptor adaptor protein | 184482 | 0.219197513436446 | −0.333907644050982 |
| 2501 | 1140565 | HLA-F ::: major histocompatibility complex, class I, F | 411958 | 0.384933870287039 | −0.597355642875244 |
| 2502 | 1140567 | CLIC4 ::: chloride intracellular channel 4 | 25035 | 0.0873662138777805 | 0.196012165859917 |
| 2503 | 1140570 | HSPA8 ::: heat shock 70 kDa protein 8 | 180414 | −0.023139338157029 | 0.050939786779129 |
| 2504 | 1140571 | ADCK2 ::: aarF domain containing kinase 2 | 210397 | 0.029868578992176 | 0.158934520479412 |
| 2505 | 1140574 | MGC1203 ::: hypothetical protein MGC1203 | 17987 | 0.086226740004958 | 0.127077044778373 |
| 2506 | 1140584 | C14orf87 ::: chromosome 14 open reading frame 87 | 294083 | −0.335638395822406 | 0.547973957918325 |
| 2507 | 1140589 | GUCY1A3 ::: guanylate cyclase 1, soluble, alpha 3 | 433488 | 0.456463431988372 | −0.374874498826929 |
| 2508 | 1140613 | VRK3 ::: vaccinia related kinase 3 | 443330 | −0.380702233123925 | 0.211440380539557 |
| 2509 | 1140630 | FLT1 ::: fms-related tyrosine kinase 1 (vascular endothelial growth factor/vascular permeability factor receptor) | 347713 | 0.192942882655688 | −0.123277559669215 |
| 2510 | 1140632 | MCM4 ::: MCM4 minichromosome maintenance deficient 4 (S. cerevisiae) | 460184 | −0.376728198824448 | 0.850172826162782 |
| 2511 | 1140729 | IL1F5 ::: interleukin 1 family, member 5 (delta) | 207224 | −0.011674717854802 | 0.027823140475085 |
| 2512 | 1140745 | FER1L4 ::: fer-1-like 4 (C. elegans) | 72222 | −0.172974560266972 | 0.044998775095322 |
| 2513 | 1140781 | NA | −9 | 0.014530846048607 | −0.103093007369487 |
| 2514 | 1140782 | NA | −10 | 0.0062688376287174 | −0.0833289079951826 |
| 2515 | 1140783 | NA | −11 | 0.058336388513323 | −0.094737922344377 |
| 2516 | 1140784 | NA | −12 | 0.0093860862773623 | −0.065007336367840 |
| 2517 | 1140785 | NA | −13 | 0.047643577567512 | −0.140278204847852 |
| 2518 | 1140786 | NA | −14 | 0.016786919443948 | −0.174405991353998 |
| 2519 | 1140787 | NA | −15 | 0.022891073012834 | −0.155713264657076 |
| 2520 | 1140788 | ::: Affy control | −76 | −0.117884908267157 | 0.200102966609546 |
| 2521 | 1140789 | ::: Affy control | −16 | −0.053745102351612 | 0.056855755515683 |
| 2522 | 1140790 | ::: Affy control | −17 | −0.002474950353002 | 0.146778154626489 |
| 2523 | 1140791 | ::: Affy control | −77 | −0.044010031551127 | 0.103181030663411 |
| 2524 | 1140792 | ::: Affy control | −78 | −0.170357382284597 | 0.155867721321911 |
| 2525 | 1140793 | ::: Affy control | −79 | −0.094085257903303 | 0.015739455221676 |
| 2526 | 1140794 | ::: Affy control | −80 | 0.072047623150024 | 0.031147568857574 |
| 2527 | 1140795 | ::: Affy control | −81 | 0.019559904867390 | −0.028763995255638 |
| 2528 | 1140796 | ::: Affy control | −82 | −0.002597758314342 | 0.056810099843959 |
| 2529 | 1140797 | ::: Affy control | −83 | −0.083637785960315 | 0.013222698483578 |
| 2530 | 1140798 | ::: Affy control | −84 | −0.149412058607628 | 0.063774018243496 |
| 2531 | 1140799 | ::: Affy control | −85 | −0.067949626733013 | 0.067189679174101 |
| 2532 | 1140800 | NA | −18 | 0.004654423406066 | −0.073603651584715 |
| 2533 | 1140801 | NA | −19 | 0.007232174980560 | −0.083719225734612 |
| 2534 | 1140802 | ::: Affy control | −86 | −0.041429693151471 | 0.043909563253514 |
| 2535 | 1140803 | ::: Affy control | −87 | −0.016514640117280 | 0.026369412380536 |
| 2536 | 1140804 | ::: Affy control | −88 | −0.031829051168426 | 0.077813697655560 |

TABLE 2415-continued

| Order | UNIQID | NAME | GeneID.txt | GENEID | LN.cor | Pro.cor |
|---|---|---|---|---|---|---|
| 2537 | 1140805 | 1140805 ::: Affy control | | −89 | 0.0208657603678176 | −0.204408613047135 |
| 2538 | 1140806 | 1140806 ::: Affy control | | −90 | −0.023926340232166 | 0.208878284785108 |
| 2539 | 1140807 | 1140807 ::: Affy control | | −91 | 0.113490613013508 | −0.030826444609494 |
| 2540 | 1140808 | 1140808 ::: Affy control | | −92 | 0.0125149823361291 | 0.0752007358866390 |
| 2541 | 1140809 | 1140809 ::: Affy control | | −93 | 0.136504292454269 | −0.119517051436108 |
| 2542 | 1140810 | 1140810 ::: Affy control | | −94 | −0.057422781927538 | 0.086665252476037 |
| 2543 | 1140811 | 1140811 ::: Affy control | | −95 | 0.133189510202426 | −0.101012852018164 |
| 2544 | 1140812 | 1140812 ::: Affy control | | −96 | 0.000122330952000o | 0.0957931806221117 |
| 2545 | 1140813 | 1140813 ::: Affy control | | −97 | −0.009371369059179 | 0.052514206556146 |
| 2546 | 1140814 | 1140814 ::: Affy control | | −98 | −0.027062251510449 | −0.029446918626741 |
| 2547 | 1140815 | 1140815 ::: Affy control | | −99 | −0.019326891464828 | 0.082329569464007 |
| 2548 | 1140816 | 1140816 ::: Affy control | | −100 | −0.016568107211094 | 0.097017805392993 |
| 2549 | 1140817 | 1140817 ::: Affy control | | −101 | −0.006509426539146 | 0.128549591393422 |
| 2550 | 1140818 | 1140818 ::: Affy control | | −102 | 0.027938036404715 | −0.189543315055064 |
| 2551 | 1140819 | 1140819 ::: Affy control | | −103 | −0.021413730370109 | −0.133918701719173 |
| 2552 | 1140820 | 1140820 ::: Affy control | | −104 | 0.001578324636409 | −0.072457711989475 |
| 2553 | 1140821 | 1140821 ::: Affy control | | −105 | −0.006400037365219 | −0.059009456108435 |
| 2554 | 1140822 | 1140822 ::: Affy control | | −106 | −0.023396144647357 | −0.065693911773797 |
| 2555 | 1140823 | 1140823 ::: Affy control | | −107 | 0.011662567339774 | −0.073288829281112 |
| 2556 | 1140824 | 1140824 ::: Affy control | | −108 | 0.012768276145964 | −0.117644303599034 |
| 2557 | 1140825 | 1140825 ::: Affy control | | −109 | −0.009563443665290 | −0.042035406725848 |
| 2558 | 1140826 | 1140826 ::: Affy control | | −110 | −0.000770254451842 | −0.095436504049974 |
| 2559 | 1140827 | 1140827 ::: Affy control | | −111 | −0.019671268603360 | 0.017149224395412 |
| 2560 | 1140828 | 1140828 ::: Affy control | | −112 | −0.001327627906192 | 0.024569651878159 |
| 2561 | 1140829 | 1140829 ::: Affy control | | −113 | −0.166625799047804 | 0.056909535950037 |
| 2562 | 1140834 | 1140834 : ACTB ::: Affy control actin, beta | | 426930 | 0.036626782020363 | −0.206629607105101 |
| 2563 | 1140835 | 1140835 : ACTB ::: Affy control actin, beta | | 426930 | −0.149602339907586 | 0.129812469536959 |
| 2564 | 1140836 | 1140836 : ACTB ::: Affy control actin, beta | | 426930 | −0.091647722342469 | 0.000432322929413 |
| 2565 | 1140837 | 1140837 ::: Affy control actin, beta | | −114 | 0.094646356888252 | 0.037746051614047 |
| 2566 | 1140838 | 1140838 ::: Affy control | | −115 | 0.117428955427767 | 0.062821055865340 |
| 2567 | 1140839 | 1140839 ::: Affy control | | −116 | 0.089772638224071 | 0.092598810615234 |
| 2568 | 1140842 | 1140842 : GAPD ::: Affy control glyceraldehyde-3-phosphate dehydrogenase | | 169476 | −0.081770293481056 | 0.122359836917701 |
| 2569 | 1140843 | 1140843 : GAPD ::: Affy control glyceraldehyde-3-phosphate dehydrogenase | | 169476 | −0.243924592429084 | 0.422918916154454 |
| 2570 | 1140844 | 1140844 : GAPD ::: Affy control glyceraldehyde-3-phosphate dehydrogenase | | 169476 | −0.205317596747236 | 0.311010631943087 |
| 2571 | 1140845 | 1140845 : STAT1 ::: Affy control signal transducer and activator of transcription 1, 91 kDa | | 21486 | 0.377358722885690 | −0.541349128751760 |
| 2572 | 1140846 | 1140846 : STAT1 ::: Affy control signal transducer and activator of transcription 1, 91 kDa | | 21486 | 0.097287175817027 | −0.226153888121370 |
| 2573 | 1140847 | 1140847 : STAT1 ::: Affy control signal transducer and activator of transcription 1, 91 kDa | | 21486 | 0.216947517172567 | −0.391088029796798 |
| 2574 | 1140848 | 1140848 : STAT1 ::: Affy control signal transducer and activator of transcription 1, 91 kDa | | 21486 | 0.222030839773439 | −0.348450257634477 |
| 2575 | 1529284 | 1529284 ::: MCC ::: mutated in colorectal cancers | | 409515 | 0.110972159568218 | −0.072345229884740 |
| 2576 | 1529285 | 1529285 ::: KIAA1219 : KIAA1219 protein | | 348929 | −0.184556459472403 | −0.046992544277234 |
| 2577 | 1529286 | 1529286 ::: MADH5 :: MAD, mothers against decapentaplegic homolog 5 (*Drosophila*) | | 167700 | 0.031685751568576 | 0.146378764529449 |
| 2578 | 1529287 | 1529287 ::: KIAA0303 : KIAA0303 protein | | 212787 | 0.051481011707667 | 0.042849436971698 |
| 2579 | 1529288 | 1529288 ::: CCNG2 :: cyclin G2 | | 13291 | 0.077063799482395 | 0.059768352114886 |
| 2580 | 1529289 | 1529289 ::: *Homo sapiens* cDNA FLJ12727 fis, clone NT2RP2000027. | | 96557 | −0.021365736556446 | −0.015837003083880 |
| 2581 | 1529290 | 1529290 ::: N4BP3 :: Nedd4 binding protein 3 | | 101761 | −0.098254325850797 | 0.157368217757306 |
| 2582 | 1529291 | 1529291 ::: *Homo sapiens* transcribed sequences | | 104450 | −0.076267577734527 | −0.040509704775555 |
| 2583 | 1529292 | 1529292 ::: *Homo sapiens* transcribed sequences | | 105261 | 0.033769033555145 | 0.129433981816277 |
| 2584 | 1529293 | 1529293 ::: *Homo sapiens* hypothetical LOC284134 (LOC284134), mRNA | | 113117 | 0.156492425740869 | −0.366194468589873 |
| 2585 | 1529294 | 1529294 ::: *Homo sapiens* hypothetical LOC284134 (LOC284134), mRNA | | 113117 | 0.182603122401687 | −0.404979176023783 |

TABLE 2415-continued

| Order | UNIQID | NAME GeneID.txt | GENEID | LN.cor | Pro.cor |
|---|---|---|---|---|---|
| 2586 | 1529295 | ::: Homo sapiens transcribed sequences | 116441 | 0.0337057171151087 | 0.117633519020541 |
| 2587 | 1529296 | ::: Homo sapiens transcribed sequences | 122428 | 0.139091174867969 | 0.107806582080154 |
| 2588 | 1529297 | ::: Homo sapiens mRNA; cDNA DKFZp686F08109 (from clone DKFZp686F08109) | 132335 | -0.297312324845849 | 0.119929613672577 |
| 2589 | 1529298 | ::: Homo sapiens mRNA; cDNA DKFZp667B1520 (from clone DKFZp667B1520) | 136707 | -0.314207665564666 | 0.198327056016028 |
| 2590 | 1529299 | ::: Homo sapiens cDNA FLJ42786 fis, clone BRAWH3006761 | 444290 | -0.064690184926136 | 0.011327312833764 |
| 2591 | 1529300 | ::: H. sapiens mRNA for immunoglobulin kappa light chain VJ region (ID POM433) | 449608 | -0.204293297723690 | 0.145878170957971 |
| 2592 | 1529301 | ::: AI281566 | -117 | 0.0717162799105228 | -0.042503405899593 |
| 2593 | 1529302 | ::: ELF3 :: E74-like factor 3 (ets domain transcription factor, epithelial-specific) | 67928 | 0.0299885249272091 | 0.0323051584546580 |
| 2594 | 1529303 | ::: W22811 | -38 | -0.1286403523447951 | -0.0343891818442250 |
| 2595 | 1529304 | ::: W22811 | -38 | -0.0188589264979050 | -0.156626874015480 |
| 2596 | 1529305 | ::: Homo sapiens transcribed sequence with moderate similarity to protein ref:NP_060312.1 (H. sapiens) hypothetical protein FLJ20489 [Homo sapiens] | 173957 | 0.045101000387545 | -0.125823818297820 |
| 2597 | 1529306 | MGC26706 :: hypothetical protein MGC26706 | 190043 | 0.0228630813646400 | 0.0908640144344620 |
| 2598 | 1529307 | ::: Homo sapiens cDNA FLJ46553 fis, clone THYMU3038879 | 435736 | -0.117004050094557 | 0.108321654537967 |
| 2599 | 1529308 | ::: Homo sapiens cDNA FLJ40970 protein | 193014 | -0.194608455512361 | 0.159131057131648 |
| 2600 | 1529309 | HSH2 :: hematopoietic SH2 protein | 512797 | -0.284514425855296 | -0.000918756304083 |
| 2601 | 1529310 | PRKAG1 :: protein kinase, AMP-activated, gamma 1 non-catalytic subunit | 3136 | 0.084646768018470 | -0.094185610330221 |
| 2602 | 1529311 | ::: Homo sapiens transcribed sequences | 251214 | -0.0085621521811595 | 0.207360519494227 |
| 2603 | 1529312 | ::: Homo sapiens cDNA FLJ34500 fis, clone HLUNG2005479. | 255809 | -0.0720562954448426 | -0.259485982293033 |
| 2604 | 1529313 | ::: Homo sapiens transcribed sequences | 271998 | 0.0043833477225770 | 0.265566854529143 |
| 2605 | 1529314 | ::: Homo sapiens transcribed sequences | 276342 | -0.0062273233675800 | 0.0454725237308900 |
| 2606 | 1529315 | ::: Homo sapiens transcribed sequence with weak similarity to protein ref:NP_062553.1 (H. sapiens) hypothetical protein FLJ11267 [Homo sapiens] | 445718 | -0.084112604384647 | 0.019415177758716 |
| 2607 | 1529316 | ZNF198 :: zinc finger protein 198 | 315241 | -0.0863369011114135 | 0.076954907013840 |
| 2608 | 1529317 | ::: AA828425 | -118 | -0.224014424936674 | -0.223856158514235 |
| 2609 | 1529318 | ::: Homo sapiens transcribed sequences | 291954 | 0.073854630491552 | 0.079840492528659 |
| 2610 | 1529319 | KIAA0970 :: KIAA0970 protein | 103329 | -0.0046625990966840 | 0.007684824100232 |
| 2611 | 1529320 | ::: Homo sapiens, clone IMAGE:5222345, mRNA | 309149 | -0.0232964237900600 | -0.0106284843950025 |
| 2612 | 1529321 | IL24 :: interleukin 24 | 411311 | -0.109908045175000 | 0.025765040861020 |
| 2613 | 1529322 | ::: Homo sapiens transcribed sequence with weak similarity to protein ref:NP_038605.1 (M. musculus) L1 repeat, Tf subfamily, member 30 [Mus musculus] | 514291 | 0.030436007092166 | -0.175347477632027 |
| 2614 | 1529323 | ::: Homo sapiens transcribed sequences | 345834 | 0.336779571590933 | -0.359684409503434 |
| 2615 | 1529324 | GZMH :: granzyme H (cathepsin G-like 2, protein h-CCPX) | 348264 | 0.239243227392061 | -0.419048485474577 |
| 2616 | 1529325 | ::: BQ003404 | -75 | -0.140464406043795 | -0.021462938104706 |
| 2617 | 1529326 | HDAC7A :: histone deacetylase 7A | 200063 | -0.109850414890401 | 0.080269797544815 |
| 2618 | 1529327 | SMN2 :: survival of motor neuron 2, centromeric | 288986 | -0.0423842789858200 | 0.248777434604123 |
| 2619 | 1529328 | ::: Homo sapiens transcribed sequences | 369056 | 0.056981262751925 | -0.112051222335899 |
| 2620 | 1529329 | ::: Homo sapiens transcribed sequences | 369101 | -0.135338205033608 | 0.159470087740367 |
| 2621 | 1529330 | LOC153684 :: hypothetical protein LOC153684 | 259625 | -0.105755172392999 | 0.046487888216411 |
| 2622 | 1529331 | ::: Homo sapiens transcribed sequence with weak similarity to protein ref:NP_060312.1 (H. sapiens) hypothetical protein FLJ20489 [Homo sapiens] | 374126 | -0.201436415316463 | 0.127028345378989 |
| 2623 | 1529332 | LOC134492 :: similar to RIKEN cDNA 2700047N05 | 140443 | -0.300773106127023 | 0.228609503612335 |
| 2624 | 1529333 | ::: Homo sapiens cDNA FLJ40549 fis, clone THYMU2001916 | 378849 | -0.016962900796743 | 0.032654218738799 |
| 2625 | 1529334 | ::: Homo sapiens transcribed sequence with moderate similarity to protein ref:NP_071431.1 (H. sapiens) cytokine receptor-like factor 2; cytokine receptor CRL2 precusor [Homo sapiens] | 380255 | -0.073135831632244 | -0.084277957239007 |
| 2626 | 1529335 | ::: Homo sapiens mRNA; cDNA DKFZp586L141 (from clone DKFZp586L141) | 400872 | -0.379618839813305 | 0.435859102100720 |
| 2627 | 1529336 | PTK2B :: PTK2B protein tyrosine kinase 2 beta | 405474 | 0.064169101462340 | -0.102556747779252 |
| 2628 | 1529337 | C6orf166 :: chromosome 6 open reading frame 166 | 201864 | -0.018977987327815 | 0.016958665942910 |
| 2629 | 1529338 | PAK2 :: p21 (CDKN1A)-activated kinase 2 | 284275 | -0.396911297097266 | 0.365705541778953 |

TABLE 2415-continued

| Order | UNIQID | NAME | GENEID | LN.cor | Pro.cor |
|---|---|---|---|---|---|
| 2630 | 1529339 | ::: *Homo sapiens* transcribed sequences | 427710 | -0.126611681377431 | 0.0729495496811158 |
| 2631 | 1529340 | ::: AA827872 | -119 | -0.119915444623348 | 0.179233924660731 |
| 2632 | 1529341 | LY75 : lymphocyte antigen 75 | 153563 | 0.188892498067345 | 0.00132661537281 |
| 2633 | 1529342 | ::: BQ026237 | -74 | 0.158306373307698 | -0.426400997795195 |
| 2634 | 1529343 | ::: *Homo sapiens* transcribed sequence | 521948 | -0.039648581482154 | 0.106009965624923 |
| 2635 | 1529344 | SERPINA11 :: serine proteinase inhibitor A11 | 317970 | 0.238830242521113 | 0.0513948356380566 |
| 2636 | 1529345 | ::: *Homo sapiens* transcribed sequences | 443475 | -0.098204977598259 | 0.0326359385755475 |
| 2637 | 1529346 | ::: *Homo sapiens* transcribed sequences | 443935 | -0.133480744808980 | -0.138767694000192 |
| 2638 | 1529347 | ::: *Homo sapiens* transcribed sequences | 444019 | -0.261867960347880 | 0.0630875174427911 |
| 2639 | 1529348 | SOS1 :: son of sevenless homolog 1 (*Drosophila*) | 326392 | -0.112147722903032 | -0.0173457619152744 |
| 2640 | 1529349 | ::: *Homo sapiens* transcribed sequences | 445500 | 0.0048769404094089 | -0.2935049211599220 |
| 2641 | 1529350 | ::: *Homo sapiens* transcribed sequences | 445884 | -0.196163065913620 | 0.239480015408477 |
| 2642 | 1529351 | ::: *Homo sapiens* transcribed sequences | 445898 | -0.072117447206842 | 0.178173670478469 |
| 2643 | 1529352 | ::: *Homo sapiens* cDNA FLJ42418 fis, clone BLADE2001987 | 446195 | -0.0064982311002315 | 0.089100493043006 |
| 2644 | 1529353 | ::: *Homo sapiens* transcribed sequences | 446198 | -0.054986078590614 | -0.011114342560876 |
| 2645 | 1529354 | BCL11A :: B-cell CLL/lymphoma 11A (zinc finger protein) | 314623 | -0.275592024677063 4 | 0.357053851248126 |
| 2646 | 1529355 | ::: *Homo sapiens* transcribed sequences | 370675 | 0.107276183111680 | -0.141870873747761 |
| 2647 | 1529356 | C14orf170 :: chromosome 14 open reading frame 170 | 303775 | -0.0582353552127145 | -0.001935868254300 |
| 2648 | 1529357 | ::: *Homo sapiens* transcribed sequences | 444651 | -0.169332893572493 | 0.118609634840753 |
| 2649 | 1529358 | ::: *Homo sapiens* transcribed sequence with moderate similarity to protein sp:P39195 (*H. sapiens*) ALU8_HUMAN Alu subfamily SX sequence contamination warning entry | 127178 | 0.185280771017017 | -0.0023410003747225 |
| 2650 | 1529359 | ::: AA832388 | 326173 | 0.185128908116345 | -0.201485649206219 |
| 2651 | 1529360 | ::: *Homo sapiens* transcribed sequences | 443036 | 0.156862502241191 | -0.359190734129611 |
| 2652 | 1529361 | HDAC3 :: histone deacetylase 3 | 388681 | -0.361732180141791 | 0.391019787446920 |
| 2653 | 1529362 | PLK :: polo-like kinase (*Drosophila*) | 329989 | -0.388320346854452 | 0.833326076167866 |
| 2654 | 1529363 | NOTCH1 :: Notch homolog 1, translocation-associated (*Drosophila*) | 311559 | 0.259233913232295 | -0.421434008005552 |
| 2655 | 1529364 | ATM :: ataxia telangiectasia mutated (includes complementation groups A, C and D) | 504644 | -0.118986043194098 | -0.148365566663377 |
| 2656 | 1529365 | TNFRSF13C :: tumor necrosis factor receptor superfamily, member 13C | 344088 | -0.057992715606171 | 0.0527412122283336 |
| 2657 | 1529366 | EBV LMP1 unique | -65 | -0.0821642641386660 | 0.0183697541273422 |
| 2658 | 1529367 | EBV LMP1 3' end | -66 | -0.064572311852911 | -0.0696807931337099 |
| 2659 | 1529368 | EBV EBNA2 3' end | -70 | -0.173444974852027 | 0.2055421044461719 |
| 2660 | 1529369 | EBV EBNA1 CDS | -71 | -0.071747963325640 | 0.065345583125480 |
| 2661 | 1529370 | EBV LPM2A | -64 | -0.001163089708170 | -0.110956119752116 |
| 2662 | 1529371 | EBV BHRFA | -73 | -0.010090518075703 | -0.076381918817641 |
| 2663 | 1529372 | EBV BZLF1 | -72 | -0.221272834194238 | 0.120180577006682 |
| 2664 | 1529373 | EBV EBNA3A | -69 | -0.161072632651006 | 0.055854607395513 |
| 2665 | 1529374 | EBV EBNA3C | -67 | 0.059031065592265 | -0.071182442369590 |
| 2666 | 1529375 | HHV8 K13 | -59 | -0.013660026235568 | -0.085249642533594 |
| 2667 | 1529376 | HHV8 T0.7/P6 | -57 | -0.038217131973910 | -0.030850732712044 |
| 2668 | 1529377 | HHV8 T1.1 | -56 | 0.032597223400267 | -0.067543040593593 |
| 2669 | 1529378 | HHV8 ORF73/LANA | -58 | -0.015664193006648 | 0.006139430844953 |
| 2670 | 1529379 | HHV8 vMIP1b ORFK4.2 KIE-3 | -54 | -0.015626336025217 | -0.056430407873870 |
| 2671 | 1529380 | HHV8 vIL6 | -55 | -0.115982682592600 | 0.085106875881960 |
| 2672 | 1529381 | HHV8 K1-32 Bcb K1 protein | -60 | 0.046238398274642 | 0.0014060075676922 |
| 2673 | 1529382 | CCND1 :: Cyclin D1 coding region; bp 498-1097 of NM_053056 | 371468 | 0.094277437820395 | -0.132713478377930 |
| 2674 | 1529383 | CCND1 :: Cyclin D1 3' end; bp 3691-4290 of NM_053056 | 371468 | 0.555196850752576 | -0.483293591801984 |
| 2675 | 1529384 | CCND1 :: Cyclin D1; bp 2491-3090 of NM_053056 | 371468 | 0.363173664575046 | -0.261555570411604 |
| 2676 | 1529385 | CCND1 :: Cyclin D1; bp 1891-2490 of NM_054056 | 371468 | 0.281719638953775 | -0.208410405004593 |
| 2677 | 1529386 | CCND1 :: Cyclin D1; bp 1291-1890 of NM_054056 | 371468 | 0.429543765430906 | -0.281718193371932 |

TABLE 2415-continued

| Order | UNIQID | NAME | GeneID.txt | GENEID | LN.cor | Pro.cor |
|---|---|---|---|---|---|---|
| 2678 | 1529387 | 1529387 : BCL2 :: BCL-2 MBR bp 2409-3009 of NM_000633 | | 79241 | −0.293554931269457 | −0.116661021933823 |
| 2679 | 1529388 | 1529388 : BCL2 :: BCL-2 coding region end; bp 152-751 of NM_000633 | | 79241 | −0.141729791902808 | −0.017721784560266 |
| 2680 | 1529389 | 1529389 : BCL2 :: BCL-2 3′ end; bp 5431-6030 of NM_000633 | | 79241 | −0.344461791592071 | −0.207115780844928 |
| 2681 | 1529390 | 1529390 : BCL2 :: BCL-2; bp 1401-2000 of NM_000633 | | 79241 | −0.219032917773749 | 0.010350951366667 |
| 2682 | 1529391 | 1529391 : BCL2 :: BCL-2; bp 4431-5030 of NM_000633 | | 79241 | −0.403717253508751 | −0.020031412999953 |
| 2683 | 1529392 | 1529392 : ACVR1C :: activin A receptor, type IC | | 352338 | 0.0545213295010957 | −0.065435713301877 |
| 2684 | 1529393 | 1529393 : KIAA1811 :: KIAA1811 protein | | 182081 | 0.333009117195884 | −0.304901694585517 |
| 2685 | 1529394 | 1529394 : LOC91807 :: myosin light chain kinase (MLCK) | | 339846 | −0.123907032755405 | 0.183602253317435 |
| 2686 | 1529395 | 1529395 ::: Homo sapiens similar to Serine/threonine-protein kinase KKIALRE (Cyclin-dependent kinase-like 1) (LOC344387), mRNA | | 403201 | 0.0281279203838585 | 0.0289662752624666 |
| 2687 | 1529396 | 1529396 : MGC33182 :: casein kinase I alpha S-like | | 512897 | −0.038017413092940 | −0.00461631510152 |
| 2688 | 1529397 | 1529397 : CLK4 :: CDC-like kinase 4 | | 406557 | 0.0862341508802245 | −0.366603829522404 |
| 2689 | 1529398 | 1529398 : HSMDPKIN :: myotonic dystrophy protein kinase like protein | | 293590 | −0.079557360480167 | 0.12019789713621 |
| 2690 | 1529399 | 1529399 : LOC203806 :: hypothetical protein LOC203806 | | 256916 | 0.035952284333729 | −0.030481696710319 |
| 2691 | 1529400 | 1529400 : FLJ32818 :: hypothetical protein FLJ32818 | | 210697 | −0.124775961556475 | 0.094567535746030 |
| 2692 | 1529401 | 1529401 : MAP4K3 :: mitogen-activated protein kinase kinase kinase kinase 3 | | 399752 | 0.277778965134787 | −0.259253792231314 |
| 2693 | 1529402 | 1529402 : KSR2 :: kinase suppressor of Ras-2 | | 375836 | −0.043546893836039 | −0.006927792276891 |
| 2694 | 1529403 | 1529403 : KIAA1883 :: KIAA1883 protein | | 511780 | −0.131034308134048 | 0.103925962598284 |
| 2695 | 1529404 | 1529404 : MAP3K1 :: mitogen-activated protein kinase kinase kinase 1 | | 170610 | −0.109948582091028 | 0.087977859649393 |
| 2696 | 1529405 | 1529405 : SAST :: syntrophin associated serine/threonine kinase | | 227489 | 0.126274276006276 | −0.071352270643548 |
| 2697 | 1529406 | 1529406 : MYO3B :: myosin IIIB | | 409066 | 0.155629369566744 | −0.026270257889408 |
| 2698 | 1529407 | 1529407 : PAK2 :: p21 (CDKN1A)-activated kinase 2 | | 284275 | −0.372590149141074 | 0.355639782047009 |
| 2699 | 1529408 | 1529408 : PSKH2 :: protein kinase PSKH2 | | 336929 | 0.0393763518376211 | −0.003523691344492 |
| 2700 | 1529409 | 1529409 : PRKWNK2 :: protein kinase, lysine deficient 2 | | 351173 | −0.185470415631171 | 0.355295627732664 |
| 2701 | 1529410 | 1529410 : SNF1LK :: SNF1-like kinase | | 380991 | 0.310744319100462 | −0.191354110343142 |
| 2702 | 1529411 | 1529411 : APEG1 :: aortic preferentially expressed protein 1 | | 80181 | −0.0150901558279161 | 0.0493269215829753 |
| 2703 | 1529412 | 1529412 : STK22C :: serine/threonine kinase 22C (spermiogenesis associated) | | 512763 | −0.152113151357401 | 0.144006256228092 |
| 2704 | 1529413 | 1529413 : PRKWNK2 :: protein kinase, lysine deficient 2 | | 232116 | 0.0437075111124126 | −0.024587852541792 |
| 2705 | 1529414 | 1529414 : MGC22688 :: hypothetical protein MGC22688 | | 352370 | 0.129203581496830 | −0.037058867228545 |
| 2706 | 1529415 | 1529415 : DKFZp686A17109 :: hypothetical protein DKFZp686A17109 | | 369523 | −0.148462736251386 | 0.034953320101641 |
| 2707 | 1529416 | 1529416 : CDKN2A :: p14ARF; unique 5′0 region from INK4a locus | | 421349 | 0.0543233634043638 | 0.129218335773114 |
| 2708 | 1529417 | 1529417 : CDKN2A :: INK4a locus common sequence shared by p14ARF and all p16 mRNA isoforms | | 421349 | 0.0421417773814821 | 0.177609611245249 |
| 2709 | 1529418 | 1529418 : CDKN2A :: p16INK4a; p16 unique sequence shared by p16INK4a transcript variants 1 and 3 but not p16INK4a transcript variant 2 and variant 4 (p14ARF) | | 421349 | −0.067908769750351 | 0.020087857642895 |
| 2710 | 1529419 | 1529419 ::: Homo sapiens transcribed sequences | | 104182 | −0.0971461633020226 | 0.131715317478596 |
| 2711 | 1529420 | 1529420 : IL17F :: interleukin 17F | | 272295 | 0.0455254572667832 | −0.000998875712323 |
| 2712 | 1529421 | 1529421 : IL27 :: interleukin 27 | | 375043 | −0.00488367703398 | −0.115384956701855 |
| 2713 | 1529422 | 1529422 : IL23R :: interleukin-23 receptor | | 375184 | 0.0941198546751735 | 0.044609962750620 |
| 2714 | 1529423 | 1529423 : ITGAD :: integrin, alpha D | | 381264 | 0.148608344731398 | −0.198509767943520 |
| 2715 | 1529424 | 1529424 : CCL3L1 :: chemokine (C-C motif) ligand 3-like 1 | | 512683 | 0.205301608020911 | −0.340808318654676 |
| 2716 | 1529425 | 1529425 : IL9R :: interleukin 9 receptor | | 406228 | −0.0455195885988421 | 0.085600863168274 |

TABLE 2415-continued

| Order | UNIQID | NAME | GeneID.txt | | |
|---|---|---|---|---|---|
| | | | GENEID | LN.cor | Pro.cor |
| 2717 | 1529426 | IL28B :: interleukin 28B (interferon, lambda 3) | 406744 | 0.189355610681505 | -0.165534213809855 |
| 2718 | 1529427 | IL29 :: interleukin 29 (interferon, lambda 1) | 406745 | -0.014392642430728 | -0.0708056570346400 |
| 2719 | 1529428 | NGFR :: nerve growth factor receptor (TNFR superfamily, member 16) | 415768 | 0.0353245312277484 | -0.128267249447899 |
| 2720 | 1529429 | IL17D :: interleukin 17D | 434103 | -0.0698106916566676 | 0.0699973071160626 |
| 2721 | 1529430 | SPHK2 :: sphingosine kinase 2 | 444484 | -0.321834026215950 | 0.170461543915022 |
| 2722 | 1529431 | :: Homo sapiens transcribed sequences | 446193 | -0.168353154209300 | 0.128224145113833 |
| 2723 | 1529432 | :: IgG1 constant region | -41 | 0.0768131190211455 | -0.105760779150212 |
| 2724 | 1529433 | :: IgG1 constant region | -41 | 0.0704176472312055 | -0.0752672225590524 |
| 2725 | 1529434 | FLJ27099 :: IgG4 constant region | 103995 | 0.0182305962959647 | -0.0772146395444862 |
| 2726 | 1529435 | :: IgA1 constant region | -44 | 0.186737460085977 | -0.317208744354907 |
| 2727 | 1529436 | :: IgE constant region | -43 | 0.101726014546358 | -0.187640538570034 |
| 2728 | 1529437 | BTLA :: B and T lymphocyte associated | 445162 | -0.318763487600451 | 0.0109894758892377 |
| 2729 | 1529443 | :: Homo sapiens transcribed sequences | 88886 | -0.0260127209140663 | 0.0767870808472003 |
| 2730 | 1529444 | :: Homo sapiens transcribed sequences | 126905 | 0.0102280555161144 | 0.0327132062782911 |
| 2731 | 1529445 | :: BE675157 | 159050 | -0.262325467861960 | 0.149553276873531 |
| 2732 | 1529446 | :: Homo sapiens transcribed sequences | 190626 | -0.0258630596717530 | -0.0657937375687666 |
| 2733 | 1529447 | :: Homo sapiens transcribed sequences | 291886 | -0.0358072489222759 | 0.126157477853033 |
| 2734 | 1529448 | :: Homo sapiens transcribed sequences | 369101 | -0.1224485734444494 | 0.135610608469673 |
| 2735 | 1529449 | :: BQ710740 | 428762 | -0.140372978110498 | 0.0614754087286522 |
| 2736 | 1529450 | :: AA255658 | -120 | -0.077793575103323 | -0.0966017457073011 |
| 2737 | 1529451 | JMY :: junction-mediating and regulatory protein | 396853 | -0.070253972528956 | 0.0014815002678255 |
| 2738 | 1529452 | AIM1 :: absent in melanoma 1 | 422550 | -0.0475767876284588 | 0.0221440764887099 |
| 2739 | 1529453 | FCGR3A :: Fc fragment of IgG, low affinity IIIa, receptor for (CD16) | 372679 | 0.105750028795122 | -0.221420850072347 |
| 2740 | 1529454 | :: EBV EBNA3B | -68 | 0.0252376456299577 | -0.0497526345906388 |
| 2741 | 1529455 | :: HHV8 BCL2 homologue | -61 | -0.0538317105983111 | 0.124768914047081 |
| 2742 | 1529456 | CCND1 :: Cyclin D1; bp 3091-3690 of NM_053056 | 371468 | 0.563476075442490 | -0.453521864341999 |
| 2743 | 1529457 | GPRK7 :: G protein-coupled receptor kinase 7 | 351818 | -0.113143362958157 | 0.0500092066170263 |
| 2744 | 1529458 | NEK8 :: NIMA (never in mitosis gene a)- related kinase 8 | 448468 | -0.258903564937414 | 0.0400640796850566 |
| 2745 | 1529459 | SRMS :: src-related kinase lacking C-terminal regulatory tyrosine and N-terminal myristylation sites | 411061 | -0.0382277119013711 | 0.147063354283128 |

The invention claimed is:

1. A method of treating a subject suffering from diffuse large B cell lymphoma (DLBCL), the method comprising:
   (1) determining a first survival predictor score for the subject comprising the steps of a) through f:
   a) isolating gene expression product from a biopsy sample from the subject;
   b) obtaining gene expression data from the isolated gene expression product by detecting expression levels for genes in an ABC DLBCL high gene expression signature, a lymph node gene expression signature, and an MHC class II gene expression signature;
   c) obtaining an average gene expression level for the genes in the ABC DLBCL high gene expression signature to thereby obtain an ABC DLBCL high gene expression signature value;
   d) obtaining an average gene expression level for the genes in the lymph node gene expression signature to thereby obtain a lymph node gene expression signature value;
   e) obtaining an average gene expression level for the genes in the MHC class II gene expression signature to thereby obtain an MHC class II gene expression signature value; and
   f) calculating a survival predictor score using an equation: [0.586*(ABC DLBCL high gene expression signature value)] - [0.468*(lymph node gene expression signature value)] - [0.336*(MHC class II gene expression signature)];
   wherein a higher survival predictor score is associated with worse survival;
   (2) determining a second survival predictor score for the subject comprising the steps of a) through f) of (1);
   (3) comparing the first and second survival predictor scores of (1) and (2);
   (4) determining the subject has a poor prognosis by determining the second survival predictor score is higher than the first survival predictor score; and
   (5) treating the subject.

2. The method of claim 1 wherein the step of obtaining gene expression data comprises use of a microarray.

3. The method of claim 1 wherein the ABC DLBCL gene expression signature comprises at least one gene selected from the group consisting of (listed by UNIQID): 1134271, 1121564, 1119889, 1133300, 1106030, 1139301, 1122131, 1114824, 1100161, and 1120129.

4. The method of claim 1 wherein the lymph node gene expression signature comprises at least one gene selected from the group consisting of (listed by UNIQID): 1097126, 1120880, 1098898, 1123376, 1128945, 1130994, 1124429, 1099358, 1130509, 1095985, 1123038, 1133700, 1122101, and 1124296.

5. The method of claim 1 wherein the MHC class II gene expression signature comprises at least one gene selected from the group consisting of (listed by UNIQID): 1123127, 1136777, 1137771, 1134281, 1136573, and 1132710.

* * * * *